United States Patent
Xiong et al.

(10) Patent No.: US 10,954,202 B2
(45) Date of Patent: Mar. 23, 2021

(54) PROTEIN TYROSINE PHOSPHATASE INHIBITORS AND METHODS OF USE THEREOF

(71) Applicants: Calico Life Sciences LLC, South San Francisco, CA (US); AbbVie Inc., North Chicago, IL (US)

(72) Inventors: Zhaoming Xiong, Buffalo Grove, IL (US); Jennifer M. Frost, Gurnee, IL (US); Philip R. Kym, Libertyville, IL (US); Xueqing Wang, San Carlos, CA (US); Shuang Chen, Gurnee, IL (US); Dennie Welch, Gurnee, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 17/025,644

(22) Filed: Sep. 18, 2020

(65) Prior Publication Data
US 2021/0009542 A1    Jan. 14, 2021

Related U.S. Application Data

(63) Continuation of application No. PCT/US2019/038459, filed on Jun. 21, 2019.

(60) Provisional application No. 62/688,226, filed on Jun. 21, 2018.

(51) Int. Cl.
C07D 285/10    (2006.01)

(52) U.S. Cl.
CPC ................... C07D 285/10 (2013.01)

(58) Field of Classification Search
None
See application file for complete search history.

(56) References Cited

U.S. PATENT DOCUMENTS

| | | | |
|---|---|---|---|
| 8,252,820 B2 | 8/2012 | Barnes et al. | |
| 9,217,012 B2 | 12/2015 | Zhang et al. | |
| 9,828,399 B2 | 11/2017 | Tremblay et al. | |
| 10,005,804 B2 | 6/2018 | Tremblay et al. | |
| 10,072,043 B2 | 9/2018 | Zhang et al. | |
| 10,150,787 B2 | 12/2018 | Tremblay et al. | |
| 2010/0160228 A1 | 6/2010 | Ivaska et al. | |
| 2010/0168101 A1 | 7/2010 | Bombrun et al. | |
| 2013/0202577 A1 | 8/2013 | Tiganis et al. | |
| 2017/0224731 A1 | 8/2017 | Tiganis et al. | |
| 2018/0325925 A1 | 11/2018 | Suk et al. | |

FOREIGN PATENT DOCUMENTS

| WO | WO-2007/067612 A1 | 6/2007 |
|---|---|---|
| WO | WO-2008/142198 A2 | 11/2008 |
| WO | WO-2010/008852 A2 | 1/2010 |
| WO | WO-2010/118241 A2 | 10/2010 |
| WO | WO-2011/057331 A1 | 5/2011 |
| WO | WO-2011/094806 A1 | 8/2011 |
| WO | WO-2015/127548 A1 | 9/2015 |
| WO | WO-2015/188228 A1 | 12/2015 |
| WO | WO-2017/078499 A2 | 5/2017 |
| WO | WO-2018/148378 A1 | 8/2018 |
| WO | WO-2018/227248 A1 | 12/2018 |
| WO | WO-2019/036815 A1 | 2/2019 |

OTHER PUBLICATIONS

Asante-Appiah et al. "Conformation-assisted Inhibition of Protein-tyrosine Phosphatase-1B Elicits Inhibitor Selectivity over T-cell Protein-tyrosine Phosphatase" The Journal of Biological Chemistry vol. 281, No. 12, Mar. 24, 2006, pp. 8010-8015.

Barluenga et al. "Novel PTP1B inhibitors identified by DNA display of fragment pairs" Bioorg. Med. Chem. Lett. 26 (2016) pp. 1080-1085.

Bourdeau et al. "10 Structure and function of the T-cell protein tyrosine phosphatase" Topics in Current Genetics, vol. 5, 2004, pp. 185-200.

Bourdeau et al. "Inhibition of T Cell Protein Tyrosine Phosphatase Enhances Interleukin-18-Dependent Hematopoietic Stem Cell Expansion" Stem Cells 2013;31: pp. 293-304.

Chen et al. "Investigation of selective binding of inhibitors to PTP1B and TCPTP by accelerated molecular dynamics simulations" Journal of Biomolecular Structure and Dynamics, 2018, pp. 1-11.

Chen et al. "Virtual Screening of Novel and Selective Inhibitors of Protein Tyrosine Phosphatase 1B over T?Cell Protein Tyrosine Phosphatase Using a Bidentate Inhibition Strategy" J. Chem. Inf. Model. 2018, 58, pp. 837?847.

Chen et al. "Wedelolactone, a Naturally Occurring Coumestan, Enhances Interferon-γ Signaling through Inhibiting STAT1 Protein Dephosphorylation" The Journal of Biological Chemistry vol. 288, No. 20, pp. 14417-14427, May 17, 2013.

Deng et al. "Identification of 2-substituted ethenesulfonic acid ester derivatives as novel, potent and selective inhibitors of protein tyrosine phosphatase 1B" Pharmazie 70: pp. 777-783 (2015).

Fang et al. "Studies of the Mechanism of Selectivity of Protein Tyrosine Phosphatase 1B (PTP1B) Bidentate Inhibitors Using Molecular Dynamics Simulations and Free Energy Calculations" J. Chem. Inf. Model. 2008, 48, pp. 2030-2041.

Haftchenary et al. "Identification of a potent salicylic acid-based inhibitor of tyrosine phosphatase PTP1B" Med. Chem. Commun., 2013, pp. 987-992.

He et al. "Small molecule tools for function al interrogation of protein tyrosine phosphatases" FEBS Journal 280 (2013) pp. 731-750, 2012.

International Search Report and Written Opinion of the International Searching Authority for International Application No. PCT/US2019/038459 dated Nov. 8, 2019 (18 pages).

International Search Report and Written Opinion of the International Searching Authority for International Application No. PCT/US2020/022717 dated May 27, 2020 (18 pages).

(Continued)

Primary Examiner — Zinna Northington Davis
(74) Attorney, Agent, or Firm — Goodwin Procter LLP

(57) ABSTRACT

Provided herein are compounds, compositions, and methods useful for inhibiting protein tyrosine phosphatase, e.g., protein tyrosine phosphatase non-receptor type 2 (PTPN2) and/or protein tyrosine phosphatase non-receptor type 1 (PTPN1), and for treating related diseases, disorders and conditions favorably responsive to PTPN1 or PTPN2 inhibitor treatment, e.g., a cancer or a metabolic disease.

4 Claims, No Drawings

Specification includes a Sequence Listing.

(56) References Cited

OTHER PUBLICATIONS

Iversen et al. "Steric Hindrance as a Basis for Structure-Based Design of Selective Inhibitors of Protein-Tyrosine Phosphatases" American Chemical Society, Biochemistry 2001, 40, pp. 14812-14820.

Iverson et al. "Structure Determination of T Cell Protein-tyrosine Phosphatase" The Journal of Biological Chemistry, vol. 277, No. 22, Issue of May 31, pp. 19982-19990, 2002.

Khavrienko et al. "α,α-Difluoro-β-ketophosphonates on a tetraazamacrocyclic platform: Synthesis and inhibitory activity against protein tyrosine phosphatases" 2014, 9; pp. 109-115.

Kim et al. "Inhibition of PTPN2 by PTP inhibitor V" Bull. Korean Chem. Soc. 2013, vol. 34, No. 12, pp. 3874-3876.

Le et al. "Inhibition of protein tyrosine phosphatase non-receptor type 2 by PTP inhibitor XIX: Its role as a multiphosphatase inhibitor" BMB Rep. 2017; 50(6): pp. 329-334.

Liu et al. "Design, synthesis, and biological evaluation of 2-substituted ethenesulfonic acid ester derivatives as selective PTP1B inhibitors" Pharmazie 70 (2015), pp. 446-451.

Liu et al. "Function-Oriented Synthesis of Marine Phidianidine Derivatives as Potential PTP1B Inhibitors with Specific Selectivity" marine drugs, 2018, 16, 97, pp. 1-14.

Loh et al. "Elevated Hypothalamic TCPTP in Obesity Contributes to Cellular Leptin Resistance" Cell Metabolism 14, Nov. 2, 2011, 2011 Elsevier Inc., pp. 684-699.

Ma et al. "The Discovery of a Novel and Selective Inhibitor of PTP1B Over TCPTP: 3D QSAR Pharmacophore Modeling, Virtual Screening, Synthesis, and Biological Evaluation" Chem Biol Drug Des 2014; 83: pp. 697-709.

Mattila et al. "Inhibition of receptor tyrosine kinase signalling by small molecule agonist of T-cell protein tyrosine phosphatase" BMC Cancer 2010, 10:7, pp. 1-12.

Parker et al. "Development of High Throughout Screening Assays Using Fluorescence Polarization: Nuclear Receptor-Ligand-Binding and Kinase*/Phosphatase Assays" Journal of Biomolecular Screening, vol. 5, No. 2, 2000, pp. 77-88.

Penafuerte et al. "Downregulation of PTP1B and TC-PTP phosphatases potentiate dendritic cell-based immunotherapy through IL-12/IFN© signaling" Oncoimmunology 2017, vol. 6, No. 6, e1321185 (14 pages).

Qin et al. "Identification of flavonolignans from *Silybum marianum* seeds as allosteric protein tyrosine phosphatase 1B inhibitors" Journal of Enzyme Inhibition and Medicinal Chemistry, 2018, vol. 33, No. 1, pp. 1283-1291.

Qing et al. "PTPs Inhibition by Zinc(II) Complexes with Multi-benzimidazole Derivatives" Chinese Journal of Inorganic Chemistry, vol. 32, No. 6, pp. 1001-1008, (2016).

Reddy et al. "Developing Selective Inhibitors of PTP1B Over TCPTP" Journal of Global Trends in Pharmaceutical Sciences, vol. 3, Issue 1, pp -558-563, Jan.-Mar. 2012.

Reddy et al. "Diphenylether Derivative as Selective Inhibitor of Protein Tyrosine Phosphatase 1B (PTP1B) Over T-cell Protein Tyrosine Phosphatase (TCPTP) Identified through Virtual Screening" Mini-Reviews in Medicinal Chemistry, 2013, 13, pp. 1-5.

Reddy et al. "Small Molecule Inhibitors of PTP1B and TCPTP" *Int.J.Pharm.Phytopharmacol.Res.* 2012, 1(5): pp. 287-291.

Scrivens et al. "Cdc25A-inhibitory properties and antineoplastic activity of bisperoxovanadium analogues" American Association for Cancer Research, Molecular Cancer Therapeutics, 2003, pp. 1053-1059.

Seo et al. "Ethyl-3,4-dephostatin Inhibits PTPN2 and Induces ERK Activation" Bull. Korean Chem. Soc. 2011, vol. 32, No. 7; pp. 2476-2478.

Wakuda et al. "Manzamenones Inhibit T-Cell Protein Tyrosine Phosphatase" Mar. Drugs 2006, 4, pp. 9-14.

Xie et al. "A Two Stage Click-Based Library of Protein Tyrosine Phosphatase Inhibitors" Bioorg Med Chem. Jan. 1, 2007; 15(1): pp. 458-473.

Yanhong et al. "Synthesis, Crystal Structure and Protein Tyrosine Photopastase Inhibitiion of a Copper (II) Complex with N-(2-Pyridylmethyl)-L-serine" Chemical Journal of Chinese Universities, 2016, pp. 2138-2143.

Zhang et al. "A Combinatorial Strategy for the Acquisition of Potent and Speci fi c Protein Tyrosine Phosphatase Inhibitors" *Rational Drug Design: Methods and Protocols*, Methods in Molecular Biology, vol. 928, 2012, pp. 53-65.

Zhang et al. "Acquisition of a Potent and Selective TC-PTP Inhibitor via a Stepwise Fluorophore-Tagged Combinatorial Synthesis and Screening Strategy" J. Am. Chem. Soc. 2009, 131, pp. 13072-13079.

Zhang et al. "Protein tyrosine phosphatases in hypothalamic insulin and leptin signaling" Protein Tyrosine Phosphatases in Hypothalamic Insulin and Leptin Signaling. Trends in Pharmacological Sciences, 36(10), 2005, pp. 661-674.

Zhang et al. "The development of protein tyrosine phosphatase1B inhibitors defined by binding sites in crystalline complexes" Future Med. Chem. (2018) 10(19), pp. 2345-2367.

U.S. Appl. No. 16/892,786, Protein Tyrosine Phosphate Inhibitors and Methods of Use Thereof, filed Jun. 4, 2020, Notice of Allowance dated Jul. 15, 2020.

SEQUENCE LISTING

```
<160> NUMBER OF SEQ ID NOS: 3

<210> SEQ ID NO 1
<211> LENGTH: 404
<212> TYPE: PRT
<213> ORGANISM: Artificial
<220> FEATURE:
<223> OTHER INFORMATION: synthetic peptide

<400> SEQUENCE: 1

Met Ala Met Pro Thr Thr Ile Glu Arg Glu Phe Glu Glu Leu Asp Thr
1               5                   10                  15

Gln Arg Arg Trp Gln Pro Leu Tyr Leu Glu Ile Arg Asn Glu Ser His
            20                  25                  30

Asp Tyr Pro His Arg Val Ala Lys Phe Pro Glu Asn Arg Asn Arg Asn
        35                  40                  45

Arg Tyr Arg Asp Val Ser Pro Tyr Asp His Ser Arg Val Lys Leu Gln
    50                  55                  60

Asn Ala Glu Asn Asp Tyr Ile Asn Ala Ser Leu Val Asp Ile Glu Glu
65                  70                  75                  80

Ala Gln Arg Ser Tyr Ile Leu Thr Gln Gly Pro Leu Pro Asn Thr Cys
                85                  90                  95

Cys His Phe Trp Leu Met Val Trp Gln Gln Lys Thr Lys Ala Val Val
            100                 105                 110

Met Leu Asn Arg Ile Val Glu Lys Glu Ser Val Lys Cys Ala Gln Tyr
        115                 120                 125

Trp Pro Thr Asp Gln Glu Met Leu Phe Lys Glu Thr Gly Phe Ser
    130                 135                 140

Val Lys Leu Leu Ser Glu Asp Val Lys Ser Tyr Tyr Thr Val His Leu
145                 150                 155                 160

Leu Gln Leu Glu Asn Ile Asn Ser Gly Glu Thr Arg Thr Ile Ser His
                165                 170                 175

Phe His Tyr Thr Thr Trp Pro Asp Phe Gly Val Pro Glu Ser Pro Ala
            180                 185                 190

Ser Phe Leu Asn Phe Leu Phe Lys Val Arg Glu Ser Gly Ser Leu Asn
        195                 200                 205

Pro Asp His Gly Pro Ala Val Ile His Cys Ser Ala Gly Ile Gly Arg
    210                 215                 220

Ser Gly Thr Phe Ser Leu Val Asp Thr Cys Leu Val Leu Met Glu Lys
225                 230                 235                 240
```

```
Gly Asp Asp Ile Asn Ile Lys Gln Val Leu Leu Asn Met Arg Lys Tyr
            245                 250                 255

Arg Met Gly Leu Ile Gln Thr Pro Asp Gln Leu Arg Phe Ser Tyr Met
        260                 265                 270

Ala Ile Ile Glu Gly Ala Lys Cys Ile Lys Gly Asp Ser Ser Ile Gln
        275                 280                 285

Lys Arg Trp Lys Glu Leu Ser Lys Glu Asp Leu Ser Pro Ala Phe Asp
290                 295                 300

His Ser Pro Asn Lys Ile Met Thr Glu Lys Tyr Asn Gly Asn Arg Ile
305                 310                 315                 320

Gly Leu Glu Glu Lys Leu Thr Gly Asp Arg Cys Thr Gly Leu Ser
            325                 330                 335

Ser Lys Met Gln Asp Thr Met Glu Glu Asn Ser Glu Ser Ala Leu Arg
            340                 345                 350

Lys Arg Ile Arg Glu Asp Arg Lys Ala Thr Thr Ala Gln Lys Val Gln
            355                 360                 365

Gln Met Lys Gln Arg Leu Asn Glu Asn Glu Arg Lys Arg Lys Arg Pro
            370                 375                 380

Arg Leu Thr Asp Thr Glu Asn Leu Tyr Phe Gln Ser His His His
385                 390                 395                 400

His His His His
```

```
<210> SEQ ID NO 2
<211> LENGTH: 13
<212> TYPE: PRT
<213> ORGANISM: Artificial
<220> FEATURE:
<223> OTHER INFORMATION: synthetic peptide
<220> FEATURE:
<221> NAME/KEY: X
<222> LOCATION: (1)..(1)
<223> OTHER INFORMATION: (Oregon Green)-(NH-CH2-CH2-O-CH2-CH2-O-CH2-CO)-
      L-threonine
<220> FEATURE:
<221> NAME/KEY: X
<222> LOCATION: (5)..(5)
<223> OTHER INFORMATION: O-phospho-L-tyrosine
<220> FEATURE:
<221> NAME/KEY: X
<222> LOCATION: (13)..(13)
<223> OTHER INFORMATION: L-lysine-NH2

<400> SEQUENCE: 2

Xaa Arg Asp Ile Xaa Glu Thr Asp Tyr Tyr Arg Lys Xaa
1               5                   10

<210> SEQ ID NO 3
<211> LENGTH: 339
<212> TYPE: PRT
<213> ORGANISM: Artificial
<220> FEATURE:
<223> OTHER INFORMATION: synthetic peptide

<400> SEQUENCE: 3

Met Ala His His His His His His Ser Ser Gly Leu Val Pro Arg Gly
1               5                   10                  15

Ser His Met Glu Met Glu Lys Glu Phe Glu Gln Ile Asp Lys Ser Gly
            20                  25                  30

Ser Trp Ala Ala Ile Tyr Gln Asp Ile Arg His Glu Ala Ser Asp Phe
        35                  40                  45

Pro Cys Arg Val Ala Lys Leu Pro Lys Asn Lys Asn Arg Asn Arg Tyr
    50                  55                  60
```

```
Arg Asp Val Ser Pro Phe Asp His Ser Arg Ile Lys Leu His Gln Glu
 65                  70                  75                  80

Asp Asn Asp Tyr Ile Asn Ala Ser Leu Ile Lys Met Glu Glu Ala Gln
                 85                  90                  95

Arg Ser Tyr Ile Leu Thr Gln Gly Pro Leu Pro Asn Thr Cys Gly His
                100                 105                 110

Phe Trp Glu Met Val Trp Glu Gln Lys Ser Arg Gly Val Val Met Leu
            115                 120                 125

Asn Arg Val Met Glu Lys Gly Ser Leu Lys Cys Ala Gln Tyr Trp Pro
        130                 135                 140

Gln Lys Glu Glu Lys Glu Met Ile Phe Glu Asp Thr Asn Leu Lys Leu
145                 150                 155                 160

Thr Leu Ile Ser Glu Asp Ile Lys Ser Tyr Tyr Thr Val Arg Gln Leu
                165                 170                 175

Glu Leu Glu Asn Leu Thr Thr Gln Glu Thr Arg Glu Ile Leu His Phe
            180                 185                 190

His Tyr Thr Thr Trp Pro Asp Phe Gly Val Pro Glu Ser Pro Ala Ser
        195                 200                 205

Phe Leu Asn Phe Leu Phe Lys Val Arg Glu Ser Gly Ser Leu Ser Pro
    210                 215                 220

Glu His Gly Pro Val Val Val His Cys Ser Ala Gly Ile Gly Arg Ser
225                 230                 235                 240

Gly Thr Phe Cys Leu Ala Asp Thr Cys Leu Leu Leu Met Asp Lys Arg
                245                 250                 255

Lys Asp Pro Ser Ser Val Asp Ile Lys Lys Val Leu Leu Glu Met Arg
            260                 265                 270

Lys Phe Arg Met Gly Leu Ile Gln Thr Ala Asp Gln Leu Arg Phe Ser
        275                 280                 285

Tyr Leu Ala Val Ile Glu Gly Ala Lys Phe Ile Met Gly Asp Ser Ser
    290                 295                 300

Val Gln Asp Gln Trp Lys Glu Leu Ser His Glu Asp Leu Glu Pro Pro
305                 310                 315                 320

Pro Glu His Ile Pro Pro Pro Arg Pro Pro Lys Arg Ile Leu Glu
                325                 330                 335

Pro His Asn
```

PROTEIN TYROSINE PHOSPHATASE INHIBITORS AND METHODS OF USE THEREOF

CROSS-REFERENCE TO RELATED APPLICATIONS

This application is a continuation of International Patent Application No. PCT/US2019/038459, filed on Jun. 21, 2019, which claims the benefit of, and priority to, U.S. Provisional Application No. 62/688,226, filed on Jun. 21, 2018, the contents of each of which are incorporated herein by reference in their entirety.

BACKGROUND

Cancer immunotherapy regimens targeting immune evasion mechanisms including checkpoint blockade (e.g. PD-1/PD-L1 and CTLA-4 blocking antibodies) have been shown to be effective in treating in a variety of cancers, dramatically improving outcomes in some populations refractory to conventional therapies. However, incomplete clinical responses and the development of intrinsic or acquired resistance will continue to limit the patient populations who could benefit from checkpoint blockade.

Protein tyrosine phosphatase non-receptor type 2 (PTPN2), also known as T cell protein tyrosine phosphatase (TC-PTP), is an intracellular member of the class 1 subfamily of phospho-tyrosine specific phosphatases that control multiple cellular regulatory processes by removing phosphate groups from tyrosine substrates. PTPN2 is ubiquitously expressed, but expression is highest in hematopoietic and placental cells (Mosinger, B. Jr. et al., *Proc Natl Acad Sci USA* 89:499-503; 1992). In humans, PTPN2 expression is controlled post-transcriptionally by the existence of two splice variants: a 45 kDa form that contains a nuclear localization signal at the C-terminus upstream of the splice junction, and a 48 kDa canonical form which has a C-terminal ER retention motif (Tillmann U. et al., *Mol Cell Biol* 14:3030-3040; 1994). The 45 kDa isoform can passively transfuse into the cytosol under certain cellular stress conditions. Both isoforms share an N-terminal phospho-tyrosine phosphatase catalytic domain. PTPN2 negatively regulates signaling of non-receptor tyrosine kinases (e.g. JAK1, JAK3), receptor tyrosine kinases (e.g. INSR, EGFR, CSF1R, PDGFR), transcription factors (e.g. STAT1, STAT3, STAT5a/b), and Src family kinases (e.g. Fyn, Lck). As a critical negative regulator of the JAK-STAT pathway, PTPN2 functions to directly regulate signaling through cytokine receptors, including IFNγ. The PTPN2 catalytic domain shares 74% sequence homology with PTPN1 (also called PTP1B), and shares similar enzymatic kinetics (Romsicki Y. et al., *Arch Biochem Biophys* 414:40-50; 2003).

Data from a loss of function in vivo genetic screen using CRISPR/Cas9 genome editing in a mouse B16F10 transplantable tumor model show that deletion of Ptpn2 gene in tumor cells improved response to the immunotherapy regimen of a GM-CSF secreting vaccine (GVAX) plus PD-1 checkpoint blockade (Manguso R. T. et al., *Nature* 547:413-418; 2017). Loss of Ptpn2 sensitized tumors to immunotherapy by enhancing IFNγ-mediated effects on antigen presentation and growth suppression. The same screen also revealed that genes known to be involved in immune evasion, including PD-L1 and CD47, were also depleted under immunotherapy selective pressure, while genes involved in the IFNγ signaling pathway, including IFNGR, JAK1, and STAT1, were enriched. These observations point to a putative role for therapeutic strategies that enhance IFNγ sensing and signaling in enhancing the efficacy of cancer immunotherapy regimens.

Protein tyrosine phosphatase non-receptor type 1 (PTPN1), also known as protein tyrosine phosphatase-1B (PTP1B), has been shown to play a key role in insulin and leptin signaling and is a primary mechanism for down-regulating both the insulin and leptin receptor signaling pathways (Kenner K. A. et al., *J Biol Chem* 271: 19810-19816, 1996). Animals deficient in PTP1B have improved glucose regulation and lipid profiles and are resistant to weight gain when treated with a high fat diet (Elchebly M. et al., *Science* 283: 1544-1548, 1999). Thus, PTP1B inhibitors are expected to be useful for the treatment of type 2 diabetes, obesity, and metabolic syndrome.

SUMMARY

The present disclosure is directed, at least in part, to compounds, compositions, and methods for the inhibition of protein tyrosine phosphatase, e.g., protein tyrosine phosphatase non-receptor type 2 (PTPN2) and/or protein tyrosine phosphatase non-receptor type 1 ((PTPN1), also known as protein tyrosine phosphatase-1B (PTP1B)). In some embodiments, disclosed herein is an inhibitor of protein tyrosine phosphatase, e.g., PTPN2 and/or PTP1B, comprising a compound disclosed herein, e.g., a compound of Formula (I), Formula (II) or Formula (III). In other embodiments, disclosed herein are methods of treating a disease or disorder, e.g., cancer, type-2 diabetes, obesity, a metabolic disease, or any other disease, disorder or ailment favorably responsive to PTPN2 or PTP1B inhibitor treatment, comprising administering an effective amount of a compound disclosed herein, e.g., a compound of Formula (I), Formula (II) or Formula (III).

For example, disclosed herein is a compound represented by Formula (I):

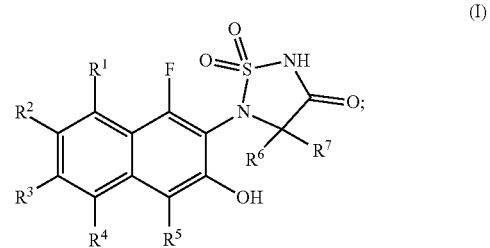

(I)

or a pharmaceutically acceptable salt, solvate, hydrate, tautomer, ester, N-oxide, stereoisomer or isotopically enriched variant thereof, wherein:

$R^1$ is selected from the group consisting of hydrogen, halogen, $C_{1-6}$ alkyl, $C_{3-6}$cycloalkyl, —O—$C_{1-6}$ alkyl, —N($R^a$)—$C_{1-6}$alkyl and —$C_{1-6}$alkylene-5-6 membered heterocyclyl;

wherein $C_{1-6}$alkyl, $C_{3-6}$ cycloalkyl, —O—$C_{1-6}$alkyl, —N($R^a$)—$C_{1-6}$alkyl and —$C_{1-6}$alkylene-5-6 membered heterocyclyl may optionally be substituted on one or more available carbons by one, two, three or more substituents each independently selected from $R^g$; and wherein if —$C_{1-6}$ alkylene-5-6 membered heterocyclyl contains a substitutable ring nitrogen atom, that ring nitrogen atom may optionally be substituted by $R^h$;

$R^2$ is selected from the group consisting of hydrogen, hydroxyl, —$CHF_2$, —$CH_2OH$, —$CH_2CN$, —$CH_2$—O—

$C_{1-6}$ alkyl, —$CH_2$—N(R$^a$)—$C_{1-6}$alkyl, $C_{2-6}$alkyl, $C_{2-6}$alkenyl, —O—$C_{1-6}$alkyl, —N(R$^a$)—$C_{1-6}$ alkyl, —C(O)—N(R$^a$)—$C_{1-6}$alkyl, —N(R$^a$)—C(O)—$C_{1-6}$alkyl, —O—C(O)—N(R$^a$)—$C_{1-6}$alkyl, —N(R$^a$)—C(O)—O—$C_{1-6}$alkyl, —$C_{3-6}$ cycloalkyl, —O—$C_{3-6}$cycloalkyl, $C_{1-6}$alkylene-$C_{3-6}$ cycloalkyl, —$C_{1-6}$alkenylene-$C_{3-6}$cycloalkyl, —O—$C_{1-6}$alkylene-$C_{3-6}$cycloalkyl, 5-6 membered heteroaryl, 4-6 membered heterocyclyl, —O—$C_{1-6}$ alkylene-5-6 membered heteroaryl, —O-4-6 membered heterocyclyl, —N(R$^a$)-4-6 membered heterocyclyl, —$C_{1-6}$alkylene-4-6 membered heterocyclyl and —O—$C_{1-6}$ alkylene-4-6 membered heterocyclyl;

wherein —$CH_2$—O—$C_{1-6}$alkyl, —$CH_2$—N(R$^a$)—$C_{1-6}$ alkyl, $C_{2-6}$alkyl, $C_{2-6}$alkenyl, —O—$C_{1-6}$alkyl, —N(R$^a$)—$C_{1-6}$alkyl, —C(O)—N(R$^a$)—$C_{1-6}$alkyl, —N(R$^a$)—C(O)—$C_{1-6}$alkyl, —O—C(O)—N(R$^a$)—$C_{1-6}$alkyl, —N(R$^a$)—C(O)—O—$C_{1-6}$alkyl, —$C_{3-6}$cycloalkyl, —O—$C_{3-6}$cycloalkyl, —$C_{1-6}$alkylene-$C_{3-6}$cycloalkyl, —$C_{1-6}$alkenylene-$C_{3-6}$cycloalkyl, —O—$C_{1-6}$alkylene-$C_{3-6}$cycloalkyl, 5-6 membered heteroaryl, —O—$C_{1-6}$ alkylene-5-6 membered heteroaryl, 4-6 membered heterocyclyl, —O-4-6 membered heterocyclyl, —N(R$^a$)-4-6 membered heterocyclyl, —$C_{1-6}$ alkylene-4-6 membered heterocyclyl and —O—$C_{1-6}$ alkylene-4-6 membered heterocyclyl may optionally be substituted on one or more available carbons by one, two, three or more substituents each independently selected from R$^g$; and wherein if 5-6 membered heteroaryl, 4-6 membered heterocyclyl, —N(R$^a$)-4-6 membered heterocyclyl, —$C_{1-6}$ alkylene-4-6 membered heterocyclyl or —O—$C_{1-6}$ alkylene-4-6 membered heterocyclyl contains a substitutable ring nitrogen atom, that ring nitrogen atom may optionally be substituted by R$^h$;

or R$^1$ and R$^2$ taken together with the atoms to which they are attached form a 5-6 membered aryl or heteroaryl; wherein aryl or heteroaryl may optionally be substituted by one or more substituents each independently selected from the group consisting of halogen, hydroxyl, cyano, $C_{1-6}$ alkyl and $C_{1-6}$ alkoxy; wherein $C_{1-6}$ alkyl and $C_{1-6}$ alkoxy may optionally be substituted by one, two three or more substituents each independently selected from R$^P$;

R$^3$ is selected from the group consisting of hydrogen, —$C_{1-6}$ alkyl, —O—$C_{1-6}$alkyl, —N(R$^a$)—$C_{1-6}$alkyl, —C(O)—N(R$^a$)—$C_{1-6}$alkyl, —N(R$^a$)—C(O)—$C_{1-6}$alkyl and —$C_{1-6}$alkylene-4-6 membered heterocyclyl;

wherein —$C_{1-6}$alkyl, —O—$C_{1-6}$alkyl, —C(O)—N(R$^a$)—$C_{1-6}$ alkyl, —N(R$^a$)—C(O)—$C_{1-6}$alkyl and —$C_{1-6}$alkylene-4-6 membered heterocyclyl may optionally be substituted on one or more available carbons by one, two, three or more substituents each independently selected from Rg; and wherein if —$C_{1-6}$alkylene$_{-4-6}$ membered heterocyclyl contains a substitutable ring nitrogen atom, that ring nitrogen atom may optionally be substituted by R$^h$;

R$^4$ is selected from the group consisting of hydrogen, halogen, $C_{1-6}$ alkyl, $C_{3-6}$cycloalkyl and —$C_{1-6}$ alkylene-4-6 membered heterocyclyl; wherein $C_{1-6}$ alkyl, $C_{3-6}$ cycloalkyl and —$C_{1-6}$alkylene-4-6 membered heterocyclyl may optionally be substituted on one or more available carbons by one, two, three or more substituents each independently selected from Rg; and wherein if —$C_{1-6}$ alkylene-4-6 membered heterocyclyl contains a substitutable ring nitrogen atom, that ring nitrogen atom may optionally be substituted by R$^h$;

wherein at least one of R$^1$, R$^2$, R$^3$ and R$^4$ is not hydrogen;

R$^5$ is selected from the group consisting of hydrogen, halogen, $C_{1-6}$ alkyl, $C_{3-6}$cycloalkyl and —$C_{1-6}$ alkylene-4-6 membered heterocyclyl; wherein $C_{1-6}$ alkyl, $C_{3-6}$ cycloalkyl and —$C_{1-6}$alkylene-4-6 membered heterocyclyl may optionally be substituted on one or more available carbons by one, two, three or more substituents each independently selected from Rg; and wherein if —$C_{1-6}$ alkylene-4-6 membered heterocyclyl contains a substitutable ring nitrogen atom, that ring nitrogen atom may optionally be substituted by R$^h$;

R$^6$ is hydrogen;

R$^7$ is hydrogen;

R$^g$ is independently selected for each occurrence from the group consisting of hydrogen, halogen, hydroxyl, cyano, nitro, oxo, —C(O)OH, R$^a$R$^b$N—, R$^a$R$^b$N—C(O)—, R$^a$R$^b$N—C(O)—N(R$^a$)—, $C_{1-6}$alkyl, $C_{2-6}$alkenyl, $C_{2-6}$alkynyl, $C_{3-6}$cycloalkyl, phenyl, $C_{1-6}$alkylene-$C_{3-6}$cycloalkyl, —O—$C_{1-6}$alkylene-$C_{3-6}$cycloalkyl, —(CO)—(NR$^a$)—$C_{1-6}$alkylene-$C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$ alkyl-C(O)—, $C_{1-6}$alkyl-O—C(O)—, $C_{1-6}$ alkyl-C(O)—O—, $C_{1-6}$ alkyl-N(R$^a$)—C(O)—, $C_{1-6}$alkyl-C(O)—N(R$^a$), $C_{1-6}$ alkyl-N(R$^a$)—C(O)—N(R$^a$)—, $C_{3-6}$cycloalkyl-N(R$^a$)—SO$_w$—, $C_{1-6}$ alkyl-SO$_w$—N(R$^a$)—, $C_{3-6}$cycloalkyl-SO$_w$—N(R$^a$)—, 4-6 membered heterocyclyl-SO$_w$—N(R$^a$)—, $C_{1-6}$alkoxy-C(O)—N(R$^a$)—, $C_{1-6}$alkyl-N(R$^a$)—C(O)—$C_{1-6}$alkyl-, —P(O)($C_{1-3}$alkyl)$_2$ and $C_{1-6}$ alkoxy-$C_{1-6}$alkyl-; wherein $C_{1-6}$alkyl, $C_{2-6}$alkenyl, $C_{2-6}$alkynyl, $C_{3-6}$cycloalkyl, phenyl, $C_{1-6}$ alkylene-$C_{3-6}$ cycloalkyl, —O—$C_{1-6}$alkylene-$C_{3-6}$cycloalkyl, —(CO)—(NR$^a$)—$C_{1-6}$alkylene-$C_{3-6}$cycloalkyl, $C_{1-6}$alkoxy, $C_{3-6}$alkenyloxy, $C_{3-6}$ alkynyloxy, $C_{3-6}$cycloalkoxy, $C_{1-6}$alkyl-O—C(O)—, $C_{1-6}$alkyl-N(R$^a$)—, $C_{1-6}$alkyl-C(O)—O—, $C_{1-6}$alkyl-S(O)$_w$—N(R$^a$)—, $C_{1-6}$alkyl-N(R$^a$)—C(O)—, $C_{1-6}$alkyl-C(O)—N(R$^a$), $C_{1-6}$alkyl-N(R$^a$)—C(O)—N(R$^a$)—, $C_{3-6}$ cycloalkyl-N(R$^a$)—SO$_w$—, $C_{1-6}$alkyl-SO$_w$—N(R$^a$)—, $C_{3-6}$ cycloalkyl-SO$_w$—N(R$^a$)—, 4-6 membered heterocyclyl-SO$_w$N(R$^a$)—, $C_{1-6}$alkoxy-C(O)—N(R$^a$)—, $C_{1-6}$alkyl-C(O)—N(R$^a$)—$C_{1-6}$alkyl-, $C_{1-6}$ alkyl-N(R$^a$)—C(O)—$C_{1-6}$alkyl-, —P(O)($C_{1-3}$alkyl)$_2$ and $C_{1-6}$alkoxy-$C_{1-6}$alkyl- may optionally be substituted by one, two three or more substituents each independently selected from R$^P$;

R$^h$ is independently selected for each occurrence from the group consisting of $C_{1-6}$alkyl, $C_{3-6}$ alkenyl, $C_{3-6}$alkynyl, $C_{3-6}$ cycloalkyl, —$C_{1-6}$alkyl-$C_{3-6}$ cycloalkyl, $C_{1-6}$alkyl-S(O)$_2$—, $C_{3-6}$cycloalkyl-S(O)$_2$—, 4-6 membered heterocyclyl-S(O)$_2$—, 4-6 membered heterocyclyl-$C_{1-6}$ alkyl-S(O)$_2$—, 5-6 membered heteroaryl-S(O)$_2$—, phenyl-S(O)$_2$—, phenyl-$C_{1-6}$alkyl-S(O)$_2$—, $C_{1-6}$alkyl-C(O)—, $C_{1-6}$ cycloalkyl-C(O)—, $C_{1-6}$ alkoxy-C(O)—, R$^a$R$^b$N—C(O)—, R$^a$R$^b$N—SO$_2$— and —P(O)($C_{1-3}$alkyl)$_2$; wherein $C_{1-6}$alkyl, $C_{3-6}$alkenyl, $C_{3-6}$alkynyl, $C_{3-6}$ cycloalkyl, —$C_{1-6}$alkyl-$C_{3-6}$ cycloalkyl, $C_{1-6}$ alkyl-S(O)$_2$—, $C_{3-6}$cycloalkyl-S(O)$_2$—, 4-6 membered heterocyclyl-S(O)$_2$—, 4-6 membered heterocyclyl-$C_{1-6}$alkyl-S(O)$_2$—, 5-6 membered heteroaryl-S(O)$_2$—, phenyl-S(O)$_2$—, phenyl-$C_{1-6}$alkyl-S(O)$_2$—, $C_{1-6}$ alkyl-C(O)—, $C_{1-6}$ cycloalkyl-C(O)—, $C_{1-6}$ alkoxy-C(O)—, R$^a$R$^b$N—C(O)—, R$^a$R$^b$N—SO$_2$— and —P(O)($C_{1-3}$alkyl)$_2$ may optionally be substituted by one, two three or more substituents each independently selected from R$^P$;

R$^P$ is independently selected for each occurrence from the group consisting of halogen, hydroxyl, cyano, $C_{1-6}$alkyl, $C_{1-6}$ alkoxy, $C_{3-6}$cycloalkyl, 4-6 membered heterocyclyl, R$^a$R$^b$N—, R$^a$R$^b$N-carbonyl-, R$^a$R$^b$N—SO$_2$—, and R$^a$R$^b$N-carbonyl-N(R$^a$)—;

R$^a$ and R$^b$ are independently selected, for each occurrence, from the group consisting of hydrogen, $C_{1-6}$ alkyl and $C_{3-6}$cycloalkyl; wherein $C_{1-6}$alkyl may optionally be substituted by one or more substituents each independently selected from the group consisting of halogen, cyano, oxo, hydroxyl and $C_{1-6}$ alkoxy (optionally substituted by one, two or three fluorine atoms);

or $R^a$ and $R^b$ together with the nitrogen to which they are attached form a 4-6 membered heterocyclyl, wherein the heterocyclyl may optionally be substituted by one or more substituents each independently selected from the group consisting of halogen, cyano, oxo and hydroxyl; and w is 0, 1 or 2.

Also disclosed herein is a compound represented by Formula (II):

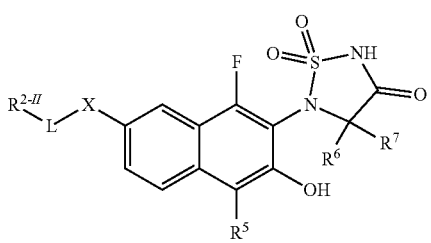

(II)

or a pharmaceutically acceptable salt, solvate, hydrate, tautomer, ester, N-oxide or stereoisomer thereof, wherein:

X is selected from the group consisting of —O— and —N($R^a$)—;

L is straight or branched $C_{1-6}$ alkylene;

$R^{2-II}$ is selected from the group consisting of hydrogen, cyano, —N$R^aR^b$, $C_{1-2}$alkoxy, $C_{3-6}$cycloalkyl-SO$_2$—N($R^a$)—, $C_{1-6}$alkyl-SO$_2$—N($R^a$)—, phenyl, 5-6 membered heteroaryl, 4-6 membered heterocyclyl and $C_{3-6}$cycloalkyl; wherein phenyl, 5-6 membered heteroaryl, 4-6 membered heterocyclyl and $C_{3-6}$ cycloalkyl may optionally be substituted on one or more available carbons by one, two or three substituents each independently selected from the group consisting of halogen, hydroxyl, —N$R^aR^b$, $C_{1-2}$alkyl (optionally substituted by one, two or three halogens) and $C_{1-2}$ alkoxy (optionally substituted by one, two or three halogens); and wherein if 5-6 membered heteroaryl or 4-6 membered heterocyclyl contains a substitutable ring nitrogen atom, that ring nitrogen atom may optionally be substituted by $C_{1-3}$alkyl;

$R^5$ is selected from the group consisting of hydrogen, deuterium and halogen;

$R^6$ is selected from the group consisting of hydrogen and deuterium;

$R^7$ is selected from the group consisting of hydrogen and deuterium; and $R^a$ and $R^b$ are each independently selected for each occurrence from the group consisting of hydrogen and $C_{1-3}$alkyl.

Also disclosed herein is a compound represented by Formula (III):

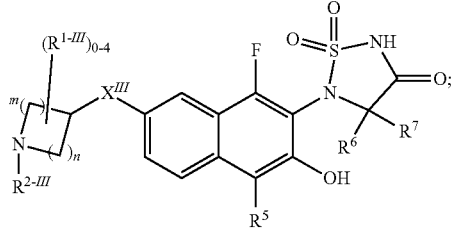

(III)

or a pharmaceutically acceptable salt, solvate, hydrate, tautomer, ester, N-oxide or stereoisomer thereof, wherein:

$X^{III}$ is selected from the group consisting of a bond, —CH$_2$—, —N$R^a$—, —O—, —O—CH$_2$— and —OCH$_2$—CH$_2$— m is 1, 2, or 3;

n is 1, 2, or 3;

$R^{1-III}$ is selected from the group consisting of hydrogen, halogen, hydroxyl, cyano, —N$R^aR^b$, $C_{1-2}$alkyl (optionally substituted by one, two or three halogens) and $C_{1-2}$alkoxy (optionally substituted by one, two or three halogens);

$R^{2-III}$ is selected from the group consisting of hydrogen, $C_{1-4}$ alkyl, C(O)—O—$C_{1-4}$alkyl, —C(O)—N($R^a$)—$C_{1-4}$alkyl, —S(O)$_2$—$C_{1-4}$alkyl and —S(O)$_2$—$C_{3-6}$cycloalkyl; wherein $C_{1-4}$ alkyl, —C(O)—N($R^a$)—$C_{1-4}$alkyl, —S(O)$_2$—$C_{1-4}$alkyl and —S(O)$_2$—$C_{3-6}$ cycloalkyl may optionally be substituted by one, two or three substituents each independently selected from the group consisting of halogen, hydroxyl, cyano, $C_{1-2}$ alkyl (optionally substituted by one, two or three halogens) and $C_{1-2}$ alkoxy (optionally substituted by one, two or three halogens);

$R^5$ is selected from the group consisting of hydrogen, deuterium and halogen;

$R^6$ is selected from the group consisting of hydrogen and deuterium;

$R^7$ is selected from the group consisting of hydrogen and deuterium; and $R^a$ and $R^b$ are each independently selected for each occurrence from the group consisting of hydrogen and $C_{1-3}$alkyl.

Further disclosed herein is a compound selected from the group consisting of:

5-{1-fluoro-3-hydroxy-7-[2-(morpholin-4-yl)ethoxy]naphthalen-2-yl}-1$\lambda^6$,2,5-thiadiazolidine-1,1,3-trione;

5-{7-[1-(cyclopropanesulfonyl)pyrrolidin-3-yl]-1-fluoro-3-hydroxynaphthal-2-yl}-1$\lambda^6$,2,5-thiadiazolidine-1,1,3-trione;

5-[1-fluoro-3-hydroxy-7-(pyrrolidin-3-yl)naphthalen-2-yl]-1$\lambda^6$,2,5-thiadiazolidine-1,1,3-trione; 8-fluoro-6-hydroxy-7-(1,1,4-trioxo-1$\lambda^6$,2,5-thiadiazolidin-2-yl)naphthalen-2-yl propan-2-ylcarbamate;

5-(9-fluoro-7-hydroxynaphtho[2,1-b]furan-8-yl)-1$\lambda^6$,2,5-thiadiazolidine-1,1,3-trione;

5-{7-[2-(azetidin-1-yl)ethoxy]-1-fluoro-3-hydroxynaphthalen-2-yl}-1$\lambda^6$,2,5-thiadiazolidine-1,1,3-trione;

5-[1-fluoro-3-hydroxy-7-methoxy(4-$^2$H)naphthalen-2-yl](4,4-$^2$H$_2$)-1$\lambda^6$,2,5-thiadiazolidine-1,1,3-trione;

5-[1-fluoro-3-hydroxy-7-(methylamino)naphthalen-2-yl] adiazolidine-1,1,3-trione; 5-{1-fluoro-3-hydroxy-7-[2-(piperidin-4-yl)ethoxy]naphthalen-2-yl}trione;

5-(1-fluoro-7-{[3-fluoro-1-(propan-2-yl)pyrrolidin-3-yl]methoxy}-3-hydroxynaphthalen-2-yl)-1$\lambda^6$,2,5-thiadiazolidine-1,1,3-trione;

5-{1-fluoro-7-[(3-fluoropyrrolidin-3-yl)methoxy]-3-hydroxynaphthalen-2-yl}-1$\lambda^6$,2,5-thiadiazolidine-1,1,3-trione;

5-{[8-fluoro-6-hydroxy-7-(1,1,4-trioxo-1$\lambda^6$,2,5-thiadiazolidin-2-yl)naphthalen-2-yl]oxy}pentanenitrile;

5-{1-fluoro-3-hydroxy-7-[2-(piperidin-1-yl)ethoxy]naphthalen-2-yl}-1$\lambda^6$,2,5-thiadiazolidine-1,1,3-trione;

5-{7-[1-(cyclopropanesulfonyl)-2,5-dihydro-1H-pyrrol-3-yl]-1-fluoro-3-hydroxynaphthalen-2-yl}-1$\lambda^6$,2,5-thiadiazolidine-1,1,3-trione;

5-{1-fluoro-3-hydroxy-7-[(piperidin-4-yl)methoxy]naphthalen-2-yl}-1$\lambda^6$,2,5-thiadiazolidine-1,1,3-trione;

5-{[8-fluoro-6-hydroxy-7-(1,1,4-trioxo-1λ$^6$,2,5-thiadiazolidin-2-yl)naphthalen-2-yl]oxy}-3,3-dimethylpentanenitrile;

5-{7-[(3,3-dimethylbutyl)amino]-1-fluoro-3-hydroxynaphthalen-2-yl}-1λ$^6$,2,5-thiadiazolidine-1,1,3-trione;

5-(1,4-difluoro-3-hydroxy-7-methoxynaphthalen-2-yl)-1λ$^6$,2,5-thiadiazolidine-1,1,3-trione;

5-{1-fluoro-3-hydroxy-7-[($^2$H$_3$)methyl oxy]naphthalen-2-yl}-1λ$^6$,2,5-thiadiazolidine-1,1,3-trione;

5-[1-fluoro-3-hydroxy-7-(2-methoxyethoxy)naphthalen-2-yl]-1λ$^6$,2,5-thiadiazolidine-1,1,3-trione;

4-{[8-fluoro-6-hydroxy-7-(1,1,4-trioxo-1λ$^6$,2,5-thiadiazolidin-2-yl)naphthalen-2-yl]oxy}-2,2-dimethylbutanenitrile;

5-{7-[2-(3-aminobicyclo[1.1.1]pentan-1-yl)ethoxy]-1-fluoro-3-hydroxynaphthalen-2-yl}-1λ$^6$,2,5-thiadiazolidine-1,1,3-trione;

5-{7-[2-(dimethylamino)ethyl]amino}-1-fluoro-3-hydroxynaphthalen-2-yl)-1λ$^6$,2,5-thiadiazolidine-1,1,3-trione;

5-(1-fluoro-3-hydroxy-7-methoxynaphthalen-2-yl)(4,4-$^2$H$_2$)-1λ$^6$,2,5-thiadiazolidine-1,1,3-trione;

5-(1-fluoro-3-hydroxy-7-methoxynaphthalen-2-yl)-1λ$^6$,2,5-thiadiazolidine-1,1,3-trione;

N-(2-{[8-fluoro-6-hydroxy-7-(1,1,4-trioxo-1λ$^6$,2,5-thiadiazolidin-2-yl)naphthalen-2-yl]amino}ethyl)cyclopropanesulfonamide;

5-(1-fluoro-3-hydroxy-7-{[1-(methanesulfonyl)pyrrolidin-3-yl]amino}naphthalen-2-yl)-1λ$^6$,2,5-thiadiazolidine-1,1,3-trione;

N-(2-{[8-fluoro-6-hydroxy-7-(1,1,4-trioxo-1λ$^6$,2,5-thiadiazolidin-2-yl)naphthalen-2-yl]oxy}ethyl)cyclopropanesulfonamide5-(1-fluoro-3-hydroxy-7-{[1-(methanesulfonyl)azetidin-3-yl]amino}naphthalen-2-yl)-1λ$^6$,2,5-thiadiazolidine-1,1,3-trione;

4-{[8-fluoro-6-hydroxy-7-(1,1,4-trioxo-1λ$^6$,2,5-thiadiazolidin-2-yl)naphthalen-2-yl]oxy}butanenitrile;

[1-({[8-fluoro-6-hydroxy-7-(1,1,4-trioxo-1λ$^6$,2,5-thiadiazolidin-2-yl)naphthalen-2-yl]oxy}methyl)cyclopropyl]acetonitrile;

5-{7-[2-(dimethylamino)ethoxy]-1-fluoro-3-hydroxynaphthalen-2-yl}-1λ$^6$,2,5-thiadiazolidine-1,1,3-trione;

5-{7-[1-(cyclopropylmethyl)-1H-pyrazol-4-yl]-1-fluoro-3-hydroxynaphthal-2-yl}-1λ$^6$,2,5-thiadiazolidine-1,1,3-trione;

5-{1-fluoro-3-hydroxy-7-[(1H-pyrazol-4-yl)methoxy]naphthalen-2-yl}-1λ$^6$,2,5-thiadiazolidine-1,1,3-trione;

5-[1-fluoro-3-hydroxy-7-(2-methylpropoxy)naphthalen-2-yl]adiazolidine-1,1,3-trione;

5-[1-fluoro-3-hydroxy-7-(2-hydroxypropoxy)naphthalen-2-yl]adiazolidine-1,1,3-trione;

N-(cyclopropylmethyl)-8-fluoro-6-hydroxy-7-(1,1,4-trioxo-1λ$^6$,2,5-thiadiazolidin-2-yl)naphthalene-2-carboxamide;

5-[1-fluoro-3-hydroxy-7-(2-{[2-(trifluoromethoxy)ethyl]amino}ethoxy)naphthalen-2-yl]-1λ$^6$,2,5-thiadiazolidine-1,1,3-trione;

5-(1-fluoro-3-hydroxy-7-{2-[(2-methoxyethyl)amino]ethoxy}naphthalen-2-yl)-1λ$^6$,2,5-thiadiazolidine-1,1,3-trione;

5-{1-fluoro-3-hydroxy-7-[3-(methylamino)propyl]naphthalen-2-yl}-1λ$^6$,2,5-thiadiazolidine-1,1,3-trione;

5-{7-[3-(ethylamino)propyl]-1-fluoro-3-hydroxynaphthalen-2-yl}-1λ$^6$,2,5-thiadiazolidine-1,1,3-trione;

5-{7-[5-(dimethylphosphoryl)thiophen-2-yl]-1-fluoro-3-hydroxynaphthalen-2-yl}thiadiazolidine-1,1,3-trione;

5-{7-[2-(cyclopropylamino)ethoxy]-1-fluoro-3-hydroxynaphthalen-2-yl}thiadiazolidine-1,1,3-trione;

5-{1-fluoro-3-hydroxy-7-[2-(methylamino)ethoxy]naphthalen-2-yl}-1λ$^6$,2,5-thiadiazolidine-1,1,3-trione;

5-{7-[2-(ethylamino)ethoxy]-1-fluoro-3-hydroxynaphthalen-2-yl}-1λ$^6$,2,5-thiadiazolidine-1,1,3-trione;

5-(1-fluoro-3-hydroxy-7-{2-[(propan-2-yl)amino]ethoxy}naphthalen-2-yl)-1λ$^6$,2,5-thiadiazolidine-1,1,3-trione;

5-{7-[3-(diethylphosphoryl)propoxy]-1-fluoro-3-hydroxynaphthalen-2-yl}-1λ$^6$,2,5-thiadiazolidine-1,1,3-trione;

5-{1-fluoro-3-hydroxy-7-[(3S)-3-hydroxybutoxy]naphthalen-2-yl}-1λ$^6$,2,5-thiadiazolidine-1,1,3-trione;

5-{1,4-difluoro-3-hydroxy-7-[(3-methylbutyl)amino]naphthalen-2-yl}-1λ$^6$,2,5-thiadiazolidine-1,1,3-trione;

5-{1-fluoro-3-hydroxy-7-[(3R)-3-hydroxybutoxy]naphthalen-2-yl}-1λ$^6$,2,5-thiadiazolidine-1,1,3-trione;

5-{7-(2-cyclopropyl-2-hydroxyethoxy)-1-fluoro-3-hydroxynaphthalen-2-yl]-1λ$^6$,2,5-thiadiazolidine-1,1,3-trione;

5-{1-fluoro-3-hydroxy-7-[(4R)-4-hydroxypentyl]naphthalen-2-yl}-1λ$^6$,2,5-thiadiazolidine-1,1,3-trione;

5-{1-fluoro-3-hydroxy-7-[(4R)-4-hydroxypentyl]naphthalen-2-yl}-1λ$^6$,2,5-thiadiazolidine-1,1,3-trione;

5-{1-fluoro-3-hydroxy-7-[(4S)-4-hydroxypentyl]naphthalen-2-yl}-1λ$^6$,2,5-thiadiazolidine-1,1,3-trione;

5-[1-fluoro-3-hydroxy-7-(4-hydroxy-4-methylpentyl)naphthalen-2-yl]-1λ$^6$,2, 5-thiadiazolidine-1,1,3-trione;

5-{1-fluoro-3-hydroxy-7-[(3-oxopentyl)oxy]naphthalen-2-yl}-1λ$^6$,2,5-thiadiazolidine-1,1,3-trione;

5-[1-fluoro-3-hydroxy-7-(3-hydroxybutoxy)naphthalen-2-yl]-1λ$^6$,2, 5-thiadiazolidine-1,1,3-trione;

N-[8-fluoro-6-hydroxy-7-(1,1,4-trioxo-1λ$^6$,2,5-thiadiazolidin-2-yl)naphthalen-2-yl]-3-methylbutanamide;

5-[1-fluoro-3-hydroxy-7-(4,4,4-trifluorobutoxy)naphthalen-2-yl]-1λ$^6$,2, 5-thiadiazolidine-1,1,3-trione;

1-(2-{[8-fluoro-6-hydroxy-7-(1,1,4-trioxo-1λ$^6$,2,5-thiadiazolidin-2-yl)naphthalen-2-yl]oxy}ethyl)cyclopropane-1-carbonitrile;

5-(1-fluoro-3-hydroxy-7-{2-[1-(methoxymethyl)cyclopropyl]ethoxy}naphthalen-2-yl)-1λ$^6$,2, 5-thiadiazolidine-1,1,3-trione;

5-(7-{[(cyclopropylmethyl)amino]methyl}-1-fluoro-3-hydroxynaphthalen-2-yl)-1λ$^6$,2, 5-thiadiazolidine-1,1,3-trione;

5-{7-[(2,2-difluoropropyl)amino]-1-fluoro-3-hydroxynaphthalen-2-yl}-1λ$^6$,2, 5-thiadiazolidine-1,1,3-trione;

5-{7-[3,3-dimethyl-4-(methylamino)butoxy]-1-fluoro-3-hydroxynaphthalen-2-yl}-1λ$^6$,2, 5-thiadiazolidine-1,1,3-trione;

5-{1-fluoro-3-hydroxy-7-[(2-phenylethyl)amino]naphthalen-2-yl}-1λ$^6$,2, 5-thiadiazolidine-1,1,3-trione;

5-[7-(3-amino-3-methylbutoxy)-1-fluoro-3-hydroxynaphthalen-2-yl]-1λ$^6$,2, 5-thiadiazolidine-1,1,3-trione;

5-{1-fluoro-3-hydroxy-7-[(4,4,4-trifluorobutyl)amino]naphthalen-2-yl}-1λ$^6$,2, 5-thiadiazolidine-1,1,3-trione;

5-{7-(difluoromethyl)-1-fluoro-3-hydroxynaphthalen-2-yl]-1λ$^6$,2, 5-thiadiazolidine-1,1,3-trione;

5-{7-[1-(dimethylphosphoryl)-2,5-dihydro-1H-pyrrol-3-yl]-1-fluoro-3-hydroxynaphthalen-2-yl}-1λ$^6$,2, 5-thiadiazolidine-1,1,3-trione;

5-{1-fluoro-3-hydroxy-7-[(3,3,3-trifluoropropyl)amino]naphthalen-2-yl}-1λ$^6$,2, 5-thiadiazolidine-1,1,3-trione;

5-[1-fluoro-3-hydroxy-7-(3-methoxy-3-methylbutoxy)naphthalen-2-yl]-1λ$^6$,2, 5-thiadiazolidine-1,1,3-trione;

5-[7-(2-cyclopropylpropoxy)-1-fluoro-3-hydroxynaphthalen-2-yl]-1λ$^6$,2,5-thiadiazolidine-1,1,3-trione;

5-[1-fluoro-3-hydroxy-7-({2-[(propan-2-yl)oxy]
ethyl}amino)naphthalen-2-yl]-1$\lambda^6$,2,5-thiadiazolidine-1,
1,3-trione;
5-(1-fluoro-3-hydroxy-7-{[1-(methanesulfonyl)pyrrolidin-
3-yl]methoxy}naphthalen-2-yl)-1$\lambda^6$,2,5-thiadiazolidine-
1,1,3-trione;
4-{[8-fluoro-6-hydroxy-7-(1,1,4-trioxo-1$\lambda^6$,2,5-thiadiazoli-
din-2-yl)naphthalen-2-yl]amino}butanenitrile;
5-[1-fluoro-3-hydroxy-7-(2-hydroxyethyl)naphthalen-2-yl]-
1$\lambda^6$,2,5-thiadiazolidine-1,1,3-trione;
5-[7-(4-amino-3,3-dimethylbutoxy)-1-fluoro-3-hy-
droxynaphthalen-2-yl]-1$\lambda^6$,2,5-thiadiazolidine-1,1,3-tri-
one;
5-(7-{[2-(azetidin-1-yl)ethyl]amino}-1-fluoro-3-hy-
droxynaphthalen-2-yl)-1$\lambda^6$,2,5-thiadiazolidine-1,1,3-tri-
one;
5-(7-{[1-(cyclopropanesulfonyl)azetidin-3-yl]oxy}-1-
fluoro-3-hydroxynaphthalen-2-yl)-1$\lambda^6$,2,5-thiadiazoli-
dine-1,1,3-trione;
5-{1-fluoro-3-hydroxy-7-[(2-methoxyethyl)amino]naphtha-
len-2-yl}-1$\lambda^6$,2,5-thiadiazolidine-1,1,3-trione;
5-[1-fluoro-3-hydroxy-7-(3,3,3-trifluoropropoxy)naphtha-
len-2-yl]-1$\lambda^6$,2,5-thiadiazolidine-1,1,3-trione;
1-({[8-fluoro-6-hydroxy-7-(1,1,4-trioxo-1$\lambda^6$,2,5-thiadiazo-
lidin-2-yl)naphthalen-2-yl]amino}methyl)cyclopropane-
1-carbonitrile;
5-[1-fluoro-3-hydroxy-7-(3-hydroxy-3-methylbutoxy)naph-
thalen-2-yl]-1$\lambda^6$,2,5-thiadiazolidine-1,1,3-trione;
5-{1-fluoro-3-hydroxy-7-[3-(1H-pyrazol-1-yl)propoxy]
naphthalen-2-yl}-1$\lambda^6$,2,5-thiadiazolidine-1,1,3-trione;
5-(7-{1-[(4-aminophenyl)methanesulfonyl]-2,5-dihydro-
1H-pyrrol-3-yl}-1-fluoro-3-hydroxynaphthalen-2-yl)-
1$\lambda^6$,2,5-thiadiazolidine-1,1,3-trione;
5-[1-fluoro-3-hydroxy-7-(hydroxymethyl)naphthalen-2-yl]-
1$\lambda^6$,2,5-thiadiazolidine-1,1,3-trione;
5-{7-[1-(cyclopropanesulfonyl)piperidin-3-yl]-1-fluoro-3-
hydroxynaphthalen-2-yl}-1$\lambda^6$,2,5-thiadiazolidine-1,1,3-
trione;
5-{7-[1-(cyclopropanecarbonyl)pyrrolidin-2-yl]-1-fluoro-3-
hydroxynaphthalen-2-yl}-1$\lambda^6$,2,5-thiadiazolidine-1,1,3-
trione;
5-{1-fluoro-3-hydroxy-7-[2-(1H-pyrazol-1-yl)ethoxy]naph-
thalen-2-yl}-1$\lambda^6$,2,5-thiadiazolidine-1,1,3-trione;
5-{7-[1-(cyclopropanesulfonyl)pyrrolidin-2-yl]-1-fluoro-3-
hydroxynaphthalen-2-yl}-1$\lambda^6$,2,5-thiadiazolidine-1,1,3-
trione;
5-{7-[1-(cyclopropanesulfonyl)pyrrolidin-2-yl]-1-fluoro-3-
hydroxynaphthalen-2-yl}-1$\lambda^6$,2,5-thiadiazolidine-1,1,3-
trione;
5-[1-fluoro-3-hydroxy-7-(piperidin-3-yl)naphthalen-2-yl]-
1$\lambda^6$,2,5-thiadiazolidine-1,1,3-trione;
5-{7-[2-(2,2-difluorocyclopropyl)ethoxy]-1-fluoro-3-hy-
droxynaphthalen-2-yl}-1$\lambda^6$,2,5-thiadiazolidine-1,1,3-tri-
one;
5-{1-fluoro-3-hydroxy-7-[2-(1-methylcyclopropyl)ethoxy]
naphthalen-2-yl}-1$\lambda^6$,2,5-thiadiazolidine-1,1,3-trione;
5-(7-{1-[(3-aminophenyl)methanesulfonyl]-2,5-dihydro-
1H-pyrrol-3-yl}-1-fluoro-3-hydroxynaphthalen-2-yl)-
1$\lambda^6$,2,5-thiadiazolidine-1,1,3-trione;
5-(7-{1-[(2-aminophenyl)methanesulfonyl]-2,5-dihydro-
1H-pyrrol-3-yl}-1-fluoro-3-hydroxynaphthalen-2-yl)-
1$\lambda^6$,2,5-thiadiazolidine-1,1,3-trione;
5-[7-(2,2-difluoroethyl)-1-fluoro-3-hydroxynaphthalen-2-
yl]-1$\lambda^6$,2,5-thiadiazolidine-1,1,3-trione;
5-[1-fluoro-3-hydroxy-7-(2,2,2-trifluoroethoxy)naphthalen-
2-yl]-1$\lambda^6$,2,5-thiadiazolidine-1,1,3-trione;

5-[1-fluoro-7-(2-fluoroethoxy)-3-hydroxynaphthalen-2-yl]-
1$\lambda^6$,2,5-thiadiazolidine-1,1,3-trione;
1-({[8-fluoro-6-hydroxy-7-(1,1,4-trioxo-1$\lambda^6$,2,5-thiadiazo-
lidin-2-yl)naphthalen-2-yl]oxy}methyl)cyclopropane-1-
carbonitrile;
5-{1-fluoro-3-hydroxy-7-[(3-methylbutyl)amino]naphtha-
len-2-yl}-1$\lambda^6$,2,5-thiadiazolidine-1,1,3-trione;
5-{1-fluoro-3-hydroxy-7-[(2-methylpropyl)amino]naphtha-
len-2-yl}-1$\lambda^6$,2,5-thiadiazolidine-1,1,3-trione;
5-{7-[(cyclopropylmethyl)amino]-1-fluoro-3-hydroxynaph-
thalen-2-yl}-1$\lambda^6$,2,5-thiadiazolidine-1,1,3-trione;
{[8-fluoro-6-hydroxy-7-(1,1,4-trioxo-1$\lambda^6$,2,5-thiadiazoli-
din-2-yl)naphthalen-2-yl]oxy}acetonitrile;
5-[1-fluoro-3-hydroxy-7-(3-methylbutoxy)naphthalen-2-
yl]-1$\lambda^6$,2,5-thiadiazolidine-1,1,3-trione;
5-(1,8-difluoro-3-hydroxy-7-methoxynaphthalen-2-yl)-1$\lambda^6$,
2,5-thiadiazolidine-1,1,3-trione;
5-{7-[1-(cyclopropanesulfonyl)azetidin-3-yl]-1-fluoro-3-
hydroxynaphthalen-2-yl}-1$\lambda^6$,2,5-thiadiazolidine-1,1,3-
trione;
5-{7-[1-(cyclopropanecarbonyl)azetidin-3-yl]-1-fluoro-3-
hydroxynaphthalen-2-yl}-1$\lambda^6$,2,5-thiadiazolidine-1,1,3-
trione;
(2E)-3-[8-fluoro-6-hydroxy-7-(1,1,4-trioxo-1$\lambda^6$,2,5-thiadi-
azolidin-2-yl)naphthalen-2-yl]prop-2-enenitrile;
5-[7-(2-cyclopropylethyl)-1-fluoro-3-hydroxynaphthalen-2-
yl]-1$\lambda^6$,2,5-thiadiazolidine-1,1,3-trione;
5-{7-[(2,2-difluorocyclopropyl)methoxy]-1-fluoro-3-hy-
droxynaphthalen-2-yl}-1$\lambda^6$,2,5-thiadiazolidine-1,1,3-tri-
one;
5-[7-(2-cyclopropylethoxy)-1-fluoro-3-hydroxynaphthalen-
2-yl]-1$\lambda^6$,2,5-thiadiazolidine-1,1,3-trione;
5-{7-[2-(cyclopropylmethoxy)ethoxy]-1-fluoro-3-hy-
droxynaphthalen-2-yl}-1$\lambda^6$,2,5-thiadiazolidine-1,1,3-tri-
one;
5-{1-fluoro-3-hydroxy-7-[2-(oxolan-2-yl)ethoxy]naphtha-
len-2-yl}-1$\lambda^6$,2,5-thiadiazolidine-1,1,3-trione;
5-{7-[2-(cyclobutyloxy)ethoxy]-1-fluoro-3-hydroxynaph-
thalen-2-yl}-1$\lambda^6$,2,5-thiadiazolidine-1,1,3-trione;
5-(1-fluoro-3-hydroxy-7-{2-[(propan-2-yl)oxy]
ethoxy}naphthalen-2-yl)-1$\lambda^6$,2,5-thiadiazolidine-1,1,3-
trione;
5-[7-(3-ethoxypropoxy)-1-fluoro-3-hydroxynaphthalen-2-
yl]-1$\lambda^6$,2,5-thiadiazolidine-1,1,3-trione;
5-[7-(2-tert-butoxyethoxy)-1-fluoro-3-hydroxynaphthalen-
2-yl]-1$\lambda^6$,2,5-thiadiazolidine-1,1,3-trione;
5-(7-{[rac-(1R,2R)-2-ethylcyclopropyl]methoxy}-1-fluoro-
3-hydroxynaphthalen-2-yl)-1$\lambda^6$,2,5-thiadiazolidine-1,1,
3-trione;
5-[1-fluoro-3-hydroxy-7-(4-methylpentyl)naphthalen-2-yl]-
1$\lambda^6$,2,5-thiadiazolidine-1,1,3-trione;
5-{7-[3-(2,2-dimethylpropyl)pyrrolidin-1-yl]-1-fluoro-3-
hydroxynaphthalen-2-yl}-1$\lambda^6$,2,5-thiadiazolidine-1,1,3-
trione;
5-[7-(1-chloro-3-hydroxypropan-2-yl)-1-fluoro-3-hy-
droxynaphthalen-2-yl]-1$\lambda^6$,2,5-thiadiazolidine-1,1,3-tri-
one;
5-{7-[1-(cyclopropylmethyl)pyrrolidin-3-yl]-1-fluoro-3-hy-
droxynaphthalen-2-yl}-1$\lambda^6$,2,5-thiadiazolidine-1,1,3-tri-
one;
5-[7-(cyclopropyloxy)-1-fluoro-3-hydroxynaphthalen-2-
yl]-1$\lambda^6$,2,5-thiadiazolidine-1,1,3-trione;
5-{7-[(2-cyclopropylethyl)amino]-1-fluoro-3-hydroxynaph-
thalen-2-yl}-1$\lambda^6$,2,5-thiadiazolidine-1,1,3-trione;
5-[1-fluoro-3-hydroxy-7-(4-methyl-1H-imidazol-2-yl)naph-
thalen-2-yl]-1$\lambda^6$,2,5-thiadiazolidine-1,1,3-trione;

5-[7-(azetidin-3-yl)-1-fluoro-3-hydroxynaphthalen-2-yl]-1λ⁶,2,5-thiadiazolidine-1,1,3-trione;

5-[1-fluoro-3-hydroxy-7-(5-methoxythiophen-2-yl)naphthalen-2-yl]-1λ⁶,2,5-thiadiazolidine-1,1,3-trione;

[8-fluoro-6-hydroxy-7-(1,1,4-trioxo-1λ⁶,2,5-thiadiazolidin-2-yl)naphthalen-2-yl]acetonitrile;

5-[1-fluoro-3-hydroxy-7-(methoxymethyl)naphthalen-2-yl]-1λ⁶,2,5-thiadiazolidine-1,1,3-trione;

5-{1-fluoro-3-hydroxy-7-[(3-methyloxetan-3-yl)methoxy]naphthalen-2-yl}-1λ⁶,2,5-thiadiazolidine-1,1,3-trione;

5-{4-bromo-7-[1-(cyclopropanesulfonyl)-2,5-dihydro-1H-pyrrol-3-yl]-1-fluoro-3-hydroxynaphthalen-2-yl}-1λ⁶,2,5-thiadiazolidine-1,1,3-trione;

5-{4-bromo-7-[1-(cyclopropanesulfonyl)-1H-pyrrol-3-yl]-1-fluoro-3-hydroxynaphthalen-2-yl}-1λ⁶,2,5-thiadiazolidine-1,1,3-trione;

5-{1-fluoro-3-hydroxy-7-[(3S)-pyrrolidin-3-yl]naphthalen-2-yl}-1λ⁶,2,5-thiadiazolidine-1,1,3-trione;

5-{1-fluoro-3-hydroxy-7-[(3R)-pyrrolidin-3-yl]naphthalen-2-yl}-1λ⁶,2,5-thiadiazolidine-1,1,3-trione;

5-(8-chloro-1-fluoro-3-hydroxy-7-methoxynaphthalen-2-yl)-1λ⁶,2,5-thiadiazolidine-1,1,3-trione;

5-{7-[(3,3-difluorocyclobutyl)methoxy]-1-fluoro-3-hydroxynaphthalen-2-yl}-1λ⁶,2,5-thiadiazolidine-1,1,3-trione;

5-(7-cyclopropyl-1-fluoro-3-hydroxynaphthalen-2-yl)-1λ⁶,2,5-thiadiazolidine-1,1,3-trione;

5-{7-[1-(cyclopropanecarbonyl)-2,5-dihydro-1H-pyrrol-3-yl]-1-fluoro-3-hydroxynaphthalen-2-yl}-1λ⁶,2,5-thiadiazolidine-1,1,3-trione;

5-(4-chloro-1-fluoro-3-hydroxy-7-methoxynaphthalen-2-yl)-1λ⁶,2,5-thiadiazolidine-1,1,3-trione;

5-{7-[(E)-2-cyclopropylethenyl]-1-fluoro-3-hydroxynaphthalen-2-yl}-1λ⁶,2,5-thiadiazolidine-1,1,3-trione;

5-{1-fluoro-3-hydroxy-7-[(1E)-4-methylpent-1-en-1-yl]naphthalen-2-yl}-1λ⁶,2,5-thiadiazolidine-1,1,3-trione;

5-{1-fluoro-3-hydroxy-7-[1-(pentamethylphenyl)ethenyl]naphthalen-2-yl}-1λ⁶,2,5-thiadiazolidine-1,1,3-trione;

5-{7-[1-(cyclopropylmethyl)-2,5-dihydro-1H-pyrrol-3-yl]-1-fluoro-3-hydroxynaphthalen-2-yl}-1λ⁶,2,5-thiadiazolidine-1,1,3-trione;

5-(4-bromo-1-fluoro-3-hydroxy-7-methoxynaphthalen-2-yl)-1λ⁶,2,5-thiadiazolidine-1,1,3-trione;

5-{7-[1-(2-cyclopropylethyl)-2,5-dihydro-1H-pyrrol-3-yl]-1-fluoro-3-hydroxynaphthalen-2-yl}-1λ⁶,2,5-thiadiazolidine-1,1,3-trione;

5-{1-fluoro-3-hydroxy-7-[(1E)-3-methoxyprop-1-en-1-yl]naphthalen-2-yl}-1λ⁶,2,5-thiadiazolidine-1,1,3-trione;

5-[7-(2-ethoxyethoxy)-1-fluoro-3-hydroxynaphthalen-2-yl]-1λ⁶,2,5-thiadiazolidine-1,1,3-trione;

5-[1-fluoro-3-hydroxy-7-(3-methoxypropoxy)naphthalen-2-yl]-1λ⁶,2,5-thiadiazolidine-1,1,3-trione;

5-[7-(1,1-dioxo-1λ⁶-thian-4-yl)-1-fluoro-3-hydroxynaphthalen-2-yl]-1λ⁶,2,5-thiadiazolidine-1,1,3-trione;

5-[1-fluoro-3-hydroxy-7-(oxan-3-yl)naphthalen-2-yl]-1λ⁶,2,5-thiadiazolidine-1,1,3-trione;

5-[7-(cyclopropylmethoxy)-1-fluoro-3-hydroxynaphthalen-2-yl]-1λ⁶,2,5-thiadiazolidine-1,1,3-trione;

5-(1-fluoro-3-hydroxy-7-{[1-(2,2,2-trifluoroethyl)pyrrolidin-3-yl]methyl}naphthalen-2-yl)-1λ⁶,2,5-thiadiazolidine-1,1,3-trione;

5-(1-fluoro-3-hydroxy-7-{[1-(2,2,2-trifluoroethyl)piperidin-4-yl]methyl}naphthalen-2-yl)-1λ⁶,2,5-thiadiazolidine-1,1,3-trione;

5-(1-fluoro-3-hydroxy-7-{2-[methyl(2-methylpropyl)amino]ethoxy}naphthalen-2-yl)-1λ⁶,2,5-thiadiazolidine-1,1,3-trione;

5-{1-fluoro-3-hydroxy-7-[(oxolan-2-yl)methoxy]naphthalen-2-yl}-1λ⁶,2,5-thiadiazolidine-1,1,3-trione;

5-[1-fluoro-3-hydroxy-7-(oxolan-3-yl)naphthalen-2-yl]-1λ⁶,2,5-thiadiazolidine-1,1,3-trione;

5-(7-{[1-(cyclopropanesulfonyl)azetidin-3-yl]methyl}-1-fluoro-3-hydroxynaphthalen-2-yl)-1λ⁶,2,5-thiadiazolidine-1,1,3-trione;

5-(7-{[1-(cyclopropanesulfonyl)piperidin-4-yl]methyl}-1-fluoro-3-hydroxynaphthalen-2-yl)-1λ⁶,2,5-thiadiazolidine-1,1,3-trione;

5-[1-fluoro-3-hydroxy-7-(pyrrolidin-2-yl)naphthalen-2-yl]-1λ⁶,2,5-thiadiazolidine-1,1,3-trione;

5-(7-{[1-(cyclopropanesulfonyl)piperidin-3-yl]methyl}-1-fluoro-3-hydroxynaphthalen-2-yl)-1λ⁶,2,5-thiadiazolidine-1,1,3-trione;

5-[7-(difluoromethoxy)-1-fluoro-3-hydroxynaphthalen-2-yl]-1λ⁶,2,5-thiadiazolidine-1,1,3-trione;

5-(7-{[1-(cyclopropanesulfonyl)pyrrolidin-3-yl]methyl}-1-fluoro-3-hydroxynaphthalen-2-yl)-1λ⁶,2,5-thiadiazolidine-1,1,3-trione;

5-{1-fluoro-3-hydroxy-7-[(pyrrolidin-3-yl)methyl]naphthalen-2-yl}-1λ⁶,2,5-thiadiazolidine-1,1,3-trione;

5-[7-(2,5-dihydrofuran-3-yl)-1-fluoro-3-hydroxynaphthalen-2-yl]-1λ⁶,2,5-thiadiazolidine-1,1,3-trione;

5-[7-(3,6-dihydro-2H-pyran-4-yl)-1-fluoro-3-hydroxynaphthalen-2-yl]-1λ⁶,2,5-thiadiazolidine-1,1,3-trione;

5-[7-(2,5-dihydro-1H-pyrrol-3-yl)-1-fluoro-3-hydroxynaphthalen-2-yl]-1λ⁶,2,5-thiadiazolidine-1,1,3-trione;

5-[1-fluoro-3-hydroxy-7-(pyridin-3-yl)naphthalen-2-yl]-1λ⁶,2,5-thiadiazolidine-1,1,3-trione;

5-{7-[(azetidin-3-yl)methyl]-1-fluoro-3-hydroxynaphthalen-2-yl}-1λ⁶,2,5-thiadiazolidine-1,1,3-trione;

N-(2-cyclopropylethyl)-2-{[8-fluoro-6-hydroxy-7-(1,1,4-trioxo-1λ⁶,2,5-thiadiazolidin-2-yl)naphthalen-2-yl]amino}acetamide;

4-{[8-fluoro-6-hydroxy-7-(1,1,4-trioxo-1λ⁶,2,5-thiadiazolidin-2-yl)naphthalen-2-yl]oxy}-N-methylbutanamide;

N-ethyl-N-(2-{[8-fluoro-6-hydroxy-7-(1,1,4-trioxo-1λ⁶,2,5-thiadiazolidin-2-yl)naphthalen-2-yl]oxy}ethyl)urea;

5-{1-fluoro-3-hydroxy-7-[(oxan-3-yl)methoxy]naphthalen-2-yl}-1λ⁶,2,5-thiadiazolidine-1,1,3-trione;

5-{7-[(1-chloro-3-hydroxypropan-2-yl)oxy]-1-fluoro-3-hydroxynaphthalen-2-yl}-1λ⁶,2,5-thiadiazolidine-1,1,3-trione;

5-{1-fluoro-3-hydroxy-7-[(oxan-4-yl)methoxy]naphthalen-2-yl}-1λ⁶,2,5-thiadiazolidine-1,1,3-trione;

5-{1-fluoro-3-hydroxy-7-[(oxetan-3-yl)oxy]naphthalen-2-yl}-1λ⁶,2,5-thiadiazolidine-1,1,3-trione;

5-{1-fluoro-3-hydroxy-7-[1-(2,2,2-trifluoroethyl)-1,2,3,6-tetrahydropyridin-4-yl]naphthalen-2-yl}-1λ⁶,2,5-thiadiazolidine-1,1,3-trione;

5-(1-fluoro-3,7-dihydroxynaphthalen-2-yl)-1λ⁶,2,5-thiadiazolidine-1,1,3-trione;

5-[1-fluoro-3-hydroxy-7-(2-hydroxyethoxy)naphthalen-2-yl]-1λ⁶,2,5-thiadiazolidine-1,1,3-trione;

5-(1-fluoro-3-hydroxy-7-propoxynaphthalen-2-yl)-1λ⁶,2,5-thiadiazolidine-1,1,3-trione;

5-{1-fluoro-3-hydroxy-7-[(propan-2-yl)oxy]naphthalen-2-yl}-1λ⁶,2,5-thiadiazolidine-1,1,3-trione;

{[8-fluoro-6-hydroxy-7-(1,1,4-trioxo-1λ⁶,2,5-thiadiazolidin-2-yl)naphthalen-2-yl]amino}acetic acid;

N-(2-cyclopropylethyl)-2-{[8-fluoro-6-hydroxy-7-(1,1,4-trioxo-1λ⁶,2,5-thiadiazolidin-2-yl)naphthalen-2-yl]oxy}acetamide;

N,N-diethyl-2-{[8-fluoro-6-hydroxy-7-(1,1,4-trioxo-1λ⁶,2,5-thiadiazolidin-2-yl)naphthalen-2-yl]oxy}acetamide;

5-{1-fluoro-3-hydroxy-7-[2-oxo-2-(pyrrolidin-1-yl)ethoxy]naphthalen-2-yl}-1$\lambda^6$,2,5-thiadiazolidine-1,1,3-trione;

5-(1-fluoro-3-hydroxy-7-{[1-(methanesulfonyl)piperidin-4-yl]oxy}naphthalen-2-yl)-1$\lambda^6$,2,5-thiadiazolidine-1,1,3-trione;

5-{1-fluoro-3-hydroxy-7-[1-(oxolane-3-sulfonyl)-2,5-dihydro-1H-pyrrol-3-yl]naphthalen-2-yl}-1$\lambda^6$,2,5-thiadiazolidine-1,1,3-trione;

5-{1-fluoro-3-hydroxy-7-[1-(2-methoxyethanesulfonyl)-2,5-dihydro-1H-pyrrol-3-yl]naphthalen-2-yl}-1$\lambda^6$,2,5-thiadiazolidine-1,1,3-trione;

5-{1-fluoro-3-hydroxy-7-[1-(3,3,3-trifluoropropane-1-sulfonyl)-2,5-dihydro-1H-pyrrol-3-yl]naphthalen-2-yl}-1$\lambda^6$,2,5-thiadiazolidine-1,1,3-trione;

5-{1-fluoro-3-hydroxy-7-[1-(3,3,3-trifluoropropane-1-sulfonyl)-2,5-dihydro-1H-pyrrol-3-yl]naphthalen-2-yl}-1$\lambda^6$,2,5-thiadiazolidine-1,1,3-trione;

5-(1-fluoro-3-hydroxy-7-{1-[(oxan-2-yl)methanesulfonyl]-2,5-dihydro-1H-pyrrol-3-yl}naphthalen-2-yl)-1$\lambda^6$,2,5-thiadiazolidine-1,1,3-trione;

5-{1-fluoro-3-hydroxy-7-[1-(4,4,4-trifluorobutane-1-sulfonyl)-2,5-dihydro-1H-pyrrol-3-yl]naphthalen-2-yl}-1$\lambda^6$,2,5-thiadiazolidine-1,1,3-trione;

5-{7-[1-(butane-1-sulfonyl)-2,5-dihydro-1H-pyrrol-3-yl]-1-fluoro-3-hydroxynaphthalen-2-yl}-1$\lambda^6$,2,5-thiadiazolidine-1,1,3-trione;

5-(7-{1-[(1,4-dioxan-2-yl)methanesulfonyl]-2,5-dihydro-1H-pyrrol-3-yl}-1-fluoro-3-hydroxynaphthalen-2-yl)-1$\lambda^6$,2,5-thiadiazolidine-1,1,3-trione;

5-{3-[8-fluoro-6-hydroxy-7-(1,1,4-trioxo-1$\lambda^6$,2,5-thiadiazolidin-2-yl)naphthalen-2-yl]-2,5-dihydro-1H-pyrrole-1-sulfonyl}pentanenitrile;

5-{1-fluoro-3-hydroxy-7-[1-(pentane-2-sulfonyl)-2,5-dihydro-1H-pyrrol-3-yl]naphthalen-2-yl}-1$\lambda^6$,2,5-thiadiazolidine-1,1,3-trione;

5-{7-[1-(ethanesulfonyl)-2,5-dihydro-1H-pyrrol-3-yl]-1-fluoro-3-hydroxynaphthalen-2-yl}-1$\lambda^6$,2,5-thiadiazolidine-1,1,3-trione;

5-{1-fluoro-3-hydroxy-7-[1-(propane-2-sulfonyl)-2,5-dihydro-1H-pyrrol-3-yl]naphthalen-2-yl}-1$\lambda^6$,2,5-thiadiazolidine-1,1,3-trione;

5-{7-[1-(cyclopropanesulfonyl)-1,2,3,6-tetrahydropyridin-4-yl]-1-fluoro-3-hydroxynaphthalen-2-yl}-1$\lambda^6$,2,5-thiadiazolidine-1,1,3-trione;

N-(2-{[8-fluoro-6-hydroxy-7-(1,1,4-trioxo-1$\lambda^6$,2,5-thiadiazolidin-2-yl)naphthalen-2-yl]oxy}ethyl)oxetane-3-sulfonamide;

5-[1-fluoro-3-hydroxy-7-(piperidin-4-yl)naphthalen-2-yl]-1$\lambda^6$,2,5-thiadiazolidine-1,1,3-trione;

5-{1-fluoro-3-hydroxy-7-[1-(2-methylpropane-1-sulfonyl)-2,5-dihydro-1H-pyrrol-3-yl]naphthalen-2-yl}-1$\lambda^6$,2,5-thiadiazolidine-1,1,3-trione;

5-(7-ethoxy-1-fluoro-3-hydroxynaphthalen-2-yl)-1$\lambda^6$,2,5-thiadiazolidine-1,1,3-trione;

5-[7-(2,2-difluoroethoxy)-1-fluoro-3-hydroxynaphthalen-2-yl]-1$\lambda^6$,2,5-thiadiazolidine-1,1,3-trione;

5-{7-[1-(cyclopropanesulfonyl)-1H-pyrazol-4-yl]-1-fluoro-3-hydroxynaphthalen-2-yl}-1$\lambda^6$,2,5-thiadiazolidine-1,1,3-trione;

5-(1-fluoro-3-hydroxy-7-{[(3R)-1-(methanesulfonyl)pyrrolidin-3-yl]amino}naphthalen-2-yl)-1$\lambda^6$,2,5-thiadiazolidine-1,1,3-trione;

5-(1-fluoro-3-hydroxy-7-{[1-(methanesulfonyl)piperidin-4-yl]amino}naphthalen-2-yl)-1$\lambda^6$,2,5-thiadiazolidine-1,1,3-trione;

5-(7-{[1-(cyclopropanesulfonyl)pyrrolidin-3-yl]amino}-1-fluoro-3-hydroxynaphthalen-2-yl)-1$\lambda^6$,2,5-thiadiazolidine-1,1,3-trione;

5-(1-fluoro-7-{[3-fluoro-1-(methanesulfonyl)pyrrolidin-3-yl]methoxy}-3-hydroxynaphthalen-2-yl)-1$\lambda^6$,2,5-thiadiazolidine-1,1,3-trione;

5-{1-fluoro-3-hydroxy-7-[1-(propane-2-sulfonyl)pyrrolidin-3-yl]naphthalen-2-yl}-1$\lambda^6$,2,5-thiadiazolidine-1,1,3-trione;

5-[7-(2-aminoethoxy)-1-fluoro-3-hydroxynaphthalen-2-yl]-1$\lambda^6$,2,5-thiadiazolidine-1,1,3-trione;

5-{7-[1-(1,3-dimethyl-1H-pyrazole-4-sulfonyl)-2,5-dihydro-1H-pyrrol-3-yl]-1-fluoro-3-hydroxynaphthalen-2-yl}-1$\lambda^6$,2,5-thiadiazolidine-1,1,3-trione;

N-(2-{[8-fluoro-6-hydroxy-7-(1,1,4-trioxo-1$\lambda^6$,2,5-thiadiazolidin-2-yl)naphthalen-2-yl]oxy}ethyl)ethanesulfonamide;

5-{1-fluoro-7-[1-(furan-3-sulfonyl)-2,5-dihydro-1H-pyrrol-3-yl]-3-hydroxynaphthalen-2-yl}-1$\lambda^6$,2,5-thiadiazolidine-1,1,3-trione;

5-{1-fluoro-3-hydroxy-7-[1-(3-methylbutane-1-sulfonyl)-2,5-dihydro-1H-pyrrol-3-yl]naphthalen-2-yl}-1$\lambda^6$,2,5-thiadiazolidine-1,1,3-trione;

5-{1-fluoro-3-hydroxy-7-[1-(thiophene-3-sulfonyl)-2,5-dihydro-1H-pyrrol-3-yl]naphthalen-2-yl}-1$\lambda^6$,2,5-thiadiazolidine-1,1,3-trione;

5-{7-[1-(benzenesulfonyl)-2,5-dihydro-1H-pyrrol-3-yl]-1-fluoro-3-hydroxynaphthalen-2-yl}-1$\lambda^6$,2,5-thiadiazolidine-1,1,3-trione;

5-{7-[1-(cyclobutanesulfonyl)-2,5-dihydro-1H-pyrrol-3-yl]-1-fluoro-3-hydroxynaphthalen-2-yl}-1$\lambda^6$,2,5-thiadiazolidine-1,1,3-trione;

methyl (2S)-2-amino-4-{[8-fluoro-6-hydroxy-7-(1,1,4-trioxo-1$\lambda^6$,2,5-thiadiazolidin-2-yl)naphthalen-2-yl]oxy}butanoate;

5-{7-[(3,5-dimethyl-1H-pyrazol-4-yl)methoxy]-1-fluoro-3-hydroxynaphthalen-2-yl}-1$\lambda^6$,2,5-thiadiazolidine-1,1,3-trione;

5-[7-(3,5-dimethyl-1H-pyrazol-4-yl)-1-fluoro-3-hydroxynaphthalen-2-yl]-1$\lambda^6$,2,5-thiadiazolidine-1,1,3-trione;

5-[7-(2-cyclohexylethoxy)-1-fluoro-3-hydroxynaphthalen-2-yl]-1$\lambda^6$,2,5-thiadiazolidine-1,1,3-trione;

2-[8-fluoro-6-hydroxy-7-(1,1,4-trioxo-1$\lambda^6$,2,5-thiadiazolidin-2-yl)naphthalen-2-yl]-1H-imidazole-4-carbonitrile;

and a pharmaceutically acceptable salt, solvate, hydrate, tautomer, ester, N-oxide or stereoisomer thereof.

In some embodiments, a compound disclosed herein, e.g., a compound of Formula (I), Formula (II) or Formula (III) is formulated as a pharmaceutically acceptable composition comprising a disclosed compound and a pharmaceutically acceptable carrier.

Also disclosed herein is a method of treating cancer in a patient in need thereof, comprising administering to the patient an effective amount of a compound disclosed herein, e.g., a compound of Formula (I), Formula (II) or Formula (III) in combination with an additional therapeutic agent. In some embodiments, the additional therapeutic agent is an immunotherapeutic agent. For example, in some embodiments, the immunotherapeutic agent is selected from the group consisting of an anti-PD-1 antibody, an anti-PD-L1 antibody and an anti-CTLA-4 antibody.

For example, disclosed herein is a method of treating cancer in a patient in need thereof, comprising administering to the patient an effective amount of a compound disclosed herein, e.g., a compound of Formula (I), Formula (II) or Formula (III).

Further provided herein is a method of treating type-2 diabetes in a patient in need thereof, comprising administering to the patient an effective amount of a compound disclosed herein, e.g., a compound of Formula (I), Formula (II) or Formula (III).

Disclosed herein, for example, is a method of treating and/or controlling obesity in a patient in need thereof, comprising administering to the patient an effective amount of a compound disclosed herein, e.g., a compound of Formula (I), Formula (II) or Formula (III).

For example, disclosed herein is a method of inhibiting further weight gain in an overweight or obese patient in need thereof, comprising administering to the patient an effective amount of a compound disclosed herein, e.g., a compound of Formula (I), Formula (II) or Formula (III).

Further disclosed herein is a method of treating a metabolic disease in a patient in need thereof, comprising administering to the patient an effective amount of a compound disclosed herein, e.g., a compound of Formula (I), Formula (II) or Formula (III).

In some embodiments, the method comprises the treatment of cancer. In some embodiments, the cancer comprises pancreatic cancer, breast cancer, multiple myeloma, melanoma, or a cancer of the secretory cells. In some embodiments, the method comprises the treatment of a metabolic disease. In some embodiments, the metabolic disease comprises non-alcoholic steatohepatitis (NASH), non-alcoholic fatty liver disease (NAFLD), liver fibrosis, obesity, type-2 diabetes, heart disease, atherosclerosis, arthritis, cystinosis, phenylketonuria, proliferative retinopathy, metabolic syndrome or Kearns-Sayre disease.

Also disclosed herein is a composition for use in treating cancer in a patient in need thereof, wherein the composition comprises a compound disclosed herein, e.g., a compound of Formula (I), Formula (II) or Formula (III), in combination with an additional therapeutic agent. In some embodiments, the additional therapeutic agent is an immunotherapeutic agent. For example, in some embodiments, the immunotherapeutic agent is selected from the group consisting of an anti-PD-1 antibody, an anti-PD-L1 antibody and an anti-CTLA-4 antibody.

For example, disclosed herein is a composition for use in treating cancer in a patient in need thereof, wherein the composition comprises a compound disclosed herein, e.g., a compound of Formula (I), Formula (II) or Formula (III).

Further provided herein is a composition for use in treating type-2 diabetes in a patient in need thereof, wherein the composition comprises a compound disclosed herein, e.g., a compound of Formula (I), Formula (II) or Formula (III).

Disclosed herein, for example, is a composition for use in treating and/or controlling obesity in a patient in need thereof, wherein the composition comprises a compound disclosed herein, e.g., a compound of Formula (I), Formula (II) or Formula (III).

For example, disclosed herein is a composition for use in inhibiting further weight gain in an overweight or obese patient in need thereof, wherein the composition comprises a compound disclosed herein, e.g., a compound of Formula (I), Formula (II) or Formula (III).

Further disclosed herein is a composition for use in treating a metabolic disease in a patient in need thereof, wherein the composition comprises a compound disclosed herein, e.g., a compound of Formula (I), Formula (II) or Formula (III).

In some embodiments, the cancer comprises pancreatic cancer, breast cancer, multiple myeloma, melanoma, or a cancer of the secretory cells. In some embodiments, the metabolic disease comprises non-alcoholic steatohepatitis (NASH), non-alcoholic fatty liver disease (NAFLD), liver fibrosis, obesity, type-2 diabetes, heart disease, atherosclerosis, arthritis, cystinosis, phenylketonuria, proliferative retinopathy, metabolic syndrome or Kearns-Sayre disease.

BRIEF DESCRIPTION OF THE SEQUENCE LISTING

Incorporated herein by reference in its entirety is a Sequence Listing entitled, "CLS-014WOC1_SEQ_ID_List_ST25", comprising SEQ ID NO: 1 through SEQ ID NO: 3, which includes the amino acid sequences disclosed herein. The Sequence listing has been submitted herewith in ASCII text format via EFS. The Sequence Listing was first created on Sep. 16, 2020 and is 7,319 bytes in size.

DETAILED DESCRIPTION

The present disclosure is directed, at least in part, to compounds, compositions, and methods for the inhibition of protein tyrosine phosphatase, e.g., protein tyrosine phosphatase non-receptor type 2 (PTPN2) and/or protein tyrosine phosphatase non-receptor type 1 ((PTPN1), also known as protein tyrosine phosphatase-1B (PTP1B)).

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

The abbreviations used herein have their conventional meaning within the chemical and biological arts. The chemical structures and formulae set forth herein are constructed according to the standard rules of chemical valency known in the chemical arts.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., Tetrahedron 33:2725 (1977); Eliel, *Stereochemistry of Carbon Compounds* (McGraw-Hill, N Y, 1962); and Wilen, *Tables of Resolving Agents and Optical Resolutions* p. 268 (E.L. Eliel, Ed., Univ. of Notre Dame Press, Notre Dame, Ind. 1972). The disclosure additionally encompasses compounds described herein as individual isomers substantially free of other isomers, and alternatively, as mixtures of various isomers.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 99% by weight, more than 99.5% by weight, or more than 99.9% by weight, of the enantiomer. In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound.

In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

"Isotopically enriched variant" as used herein refers to a disclosed compound having one or more isotopic substitutions, wherein one or more atoms are replaced by an atom having an atomic mass or mass number different from the atomic mass or mass number usually found in nature. Examples of isotopes that can be incorporated into compounds of the disclosure include isotopes of hydrogen, carbon, nitrogen, oxygen, phosphorus, sulfur, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. For example, hydrogen (H) may be in any isotopic form, including $^{1}H$, $^{2}H$ (D or deuterium), and $^{3}H$ (T or tritium); carbon (C) may be in any isotopic form, including $^{12}C$, $^{13}C$, and $^{14}C$; oxygen (O) may be in any isotopic form, including $^{16}O$ and $^{18}O$; and the like. For example, an isotopically enriched variant as disclosed herein may have one or more hydrogen atoms replaced with deuterium.

The articles "a" and "an" may be used herein to refer to one or to more than one (i.e. at least one) of the grammatical objects of the article. By way of example "an analogue" means one analogue or more than one analogue.

When a range of values is listed, it is intended to encompass each value and sub-range within the range. For example "$C_1$-$C_6$ alkyl" is intended to encompass, $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl.

The following terms are intended to have the meanings presented therewith below and are useful in understanding the description and intended scope of the present disclosure.

"Alkyl" refers to a radical of a straight-chain or branched saturated hydrocarbon group having from 1 to 20 carbon atoms ("$C_1$-$C_{20}$ alkyl"). In some embodiments, an alkyl group has 1 to 12 carbon atoms ("$C_1$-$C_{12}$ alkyl"). In some embodiments, an alkyl group has 1 to 8 carbon atoms ("$C_1$-$C_8$ alkyl"). In some embodiments, an alkyl group has 1 to 6 carbon atoms ("$C_1$-$C_6$ alkyl"). In some embodiments, an alkyl group has 1 to 5 carbon atoms ("$C_1$-$C_5$ alkyl"). In some embodiments, an alkyl group has 1 to 4 carbon atoms ("$C_1$-$C_4$ alkyl"). In some embodiments, an alkyl group has 1 to 3 carbon atoms ("$C_1$-$C_3$ alkyl"). In some embodiments, an alkyl group has 1 to 2 carbon atoms ("$C_1$-$C_2$ alkyl"). In some embodiments, an alkyl group has 1 carbon atom ("$C_1$ alkyl"). In some embodiments, an alkyl group has 2 to 6 carbon atoms ("$C_2$-$C_6$ alkyl"). Examples of $C_1$-$C_6$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Each instance of an alkyl group may be independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —$CH_3$). In certain embodiments, the alkyl group is substituted $C_{1-}$ alkyl. Common alkyl abbreviations include Me (—$CH_3$), Et (—$CH_2CH_3$), iPr (—$CH(CH_3)_2$), nPr (—$CH_2CH_2CH_3$), n-Bu (—$CH_2CH_2CH_2CH_3$), or i-Bu (—$CH_2CH(CH_3)_2$).

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred in the present disclosure. The term "alkenylene," by itself or as part of another substituent, means, unless otherwise stated, a divalent radical derived from an alkene. An alkylene group may be described as, e.g., a $C_1$-$C_6$-membered alkylene, wherein the term "membered" refers to the non-hydrogen atoms within the moiety.

"Alkenyl" refers to a radical of a straight-chain or branched hydrocarbon group having from 2 to 20 carbon atoms, one or more carbon-carbon double bonds, and no triple bonds ("$C_2$-$C_{20}$ alkenyl"). In some embodiments, an alkenyl group has 2 to 10 carbon atoms ("$C_2$-$C_{10}$ alkenyl"). In some embodiments, an alkenyl group has 2 to 8 carbon atoms ("$C_2$-$C_8$ alkenyl"). In some embodiments, an alkenyl group has 2 to 6 carbon atoms ("$C_2$-$C_6$ alkenyl"). In some embodiments, an alkenyl group has 2 to 5 carbon atoms ("$C_2$-$C_5$ alkenyl"). In some embodiments, an alkenyl group has 2 to 4 carbon atoms ("$C_2$-$C_4$ alkenyl"). In some embodiments, an alkenyl group has 2 to 3 carbon atoms ("$C_2$-$C_3$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_2$-$C_4$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_2$-$C_6$ alkenyl groups include the aforementioned $C_{2-4}$ alkenyl groups as well as pentenyl (C), pentadienyl ($C_5$), hexenyl ($C_6$), and the like. Additional examples of alkenyl include heptenyl ($C_7$), octenyl ($C_5$), octatrienyl ($C_5$), and the like. Each instance of an alkenyl group may be independently optionally substituted, e.g., unsubstituted (an "unsubstituted alkenyl") or substituted (a "substituted alkenyl") with one or more substituents, e.g., from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-6}$ alkenyl.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_6$-$C_{14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). An aryl group may be described as, e.g., a $C_6$-$C_{10}$-membered aryl, wherein the term "membered" refers to the non-hydrogen ring atoms within the moiety. Aryl groups include, but are not limited to, phenyl, naphthyl, indenyl, and tetrahydronaphthyl. Each instance of an aryl group may be independently optionally substituted, e.g., unsubstituted (an "unsubstituted aryl") or substituted (a "substituted aryl") with one or more substituents. In certain embodiments, the aryl group is unsubstituted $C_6$-$C_{14}$ aryl. In certain embodiments, the aryl group is substituted $C_6$-$C_{14}$ aryl.

In certain embodiments, an aryl group is substituted with one or more of groups selected from halo, $C_1$-$C_5$ alkyl, halo-$C_1$-$C_8$ alkyl, haloxy-$C_1$-$C_8$ alkyl, cyano, hydroxy, alkoxy $C_1$-$C_8$ alkyl, and amino.

Examples of representative substituted aryls include the following

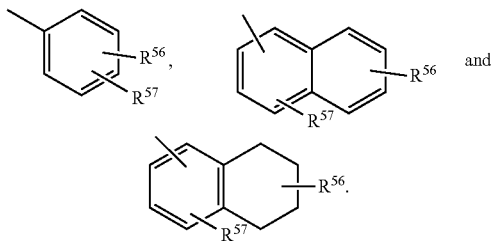

wherein one of $R^{56}$ and $R^{57}$ may be hydrogen and at least one of $R^{56}$ and $R^{57}$ is each independently selected from $C_1$-$C_8$ alkyl, halo-$C_1$-$C_5$ alkyl, 4-10 membered heterocyclyl, alkanoyl, alkoxy-$C_1$-$C_8$ alkyl, heteroaryloxy, alkylamino, arylamino, heteroarylamino, $NR^{58}COR^{59}$, $NR^{58}SOR^{59}NR^{58}SO_2R^{59}$, C(O)Oalkyl, C(O)Oaryl, $CONR^{58}R^{59}$, $CONR^{58}OR^{59}$, $NR^{58}R^{59}$, $SO_2NR^{58}R^{59}$, S-alkyl, S(O)-alkyl, $S(O)_2$-alkyl, S-aryl, S(O)-aryl, $S(O_2)$-aryl; or $R^{56}$ and $R^{57}$ may be joined to form a cyclic ring (saturated or unsaturated) from 5 to 8 atoms, optionally containing one or more heteroatomic groups selected from the group N, O, S, S(O) or $S(O)_2$.

Other representative aryl groups having a fused heterocyclyl group include the following:

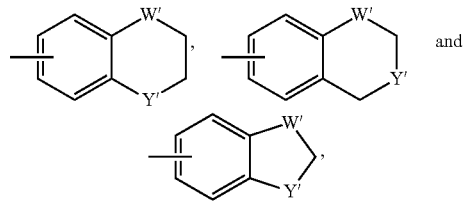

wherein each W' is selected from $C(R^{66})_2$, $NR^{66}$, O, and S; and each Y' is selected from carbonyl, $NR^{66}$, O and S; and $R^{66}$ is independently hydrogen, $C_1$-$C_8$ alkyl, $C_3$-$C_1$ cycloalkyl, 4-10 membered heterocyclyl, $C_6$-$C_{10}$ aryl, and 5-10 membered heteroaryl.

An "arylene" and a "heteroarylene," alone or as part of another substituent, mean a divalent radical derived from an aryl and heteroaryl, respectively. Non-limiting examples of heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene.

"Halo" or "halogen," independently or as part of another substituent, mean, unless otherwise stated, a fluorine (F), chlorine ($C_1$), bromine (Br), or iodine (I) atom. The term "halide" by itself or as part of another substituent, refers to a fluoride, chloride, bromide, or iodide atom. In certain embodiments, the halo group is either fluorine or chlorine.

Additionally, terms such as "haloalkyl" are meant to include monohaloalkyl and polyhaloalkyl. For example, the term "halo-$C_1$-$C_6$ alkyl" includes, but is not limited to, fluoromethyl, difluoromethyl, trifluoromethyl, 2,2,2-trifluoroethyl, 4-chlorobutyl, 3-bromopropyl, and the like.

The term "heteroalkyl," by itself or in combination with another term, means, unless otherwise stated, a non-cyclic stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Exemplary heteroalkyl groups include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —S(O)—$CH_3$, —$S(O)_2$—$CH_3$, —$CH_2$—$CH_2$—S(O)$_2$—$CH_3$, —CH═CH—O—$CH_3$, —Si($CH_3$)$_3$, —$CH_2$—CH═N—$OCH_3$, —CH═CH—N($CH_3$)—$CH_3$, —O—$CH_3$, and —O—$CH_2$—$CH_3$. Up to two or three heteroatoms may be consecutive, such as, for example, —CH$_2$—NH—OCH$_3$ and —CH$_2$—O—Si(CH$_3$)$_3$. Where "heteroalkyl" is recited, followed by recitations of specific heteroalkyl groups, such as —CH$_2$—CH$_3$, —NR$^B$R$^C$, or the like, it will be understood that the terms heteroalkyl and —CH$_2$O—CH$_3$ or —NR$^B$R$^C$ are not redundant or mutually exclusive. Rather, the specific heteroalkyl groups are recited to add clarity. Thus, the term "heteroalkyl" should not be interpreted herein as excluding specific heteroalkyl groups, such as —CH$_2$O—CH$_3$, —NR$^B$R$^C$, or the like.

Similarly, the term "heteroalkylene," by itself or as part of another substituent, means, unless otherwise stated, a divalent radical derived from heteroalkyl, as exemplified, but not limited by, —CH$_2$O— and —CH$_2$CH$_2$O—. A heteroalkylene group may be described as, e.g., a 2-7-membered heteroalkylene, wherein the term "membered" refers to the non-hydrogen atoms within the moiety. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— may represent both —C(O)$_2$R'- and —R'C(O)$_2$—.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). A heteroaryl group may be described as, e.g., a 6-10-membered heteroaryl, wherein the term "membered" refers to the non-hydrogen ring atoms within the moiety.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Each instance of a heteroaryl group may be independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following formulae:

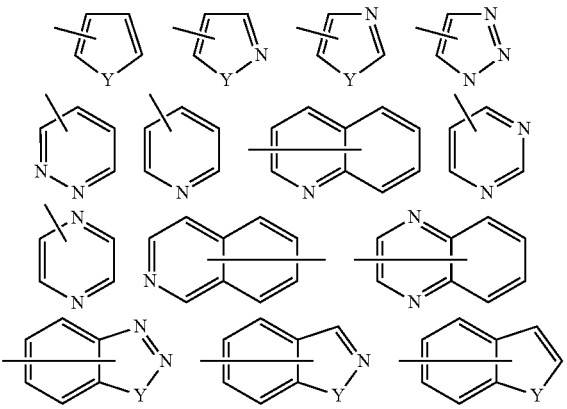

wherein each Y is selected from carbonyl, N, NR$^{65}$, O, and S; and R$^{65}$ is independently hydrogen, C$_1$-C$_8$ alkyl, C$_3$-C$_{10}$ cycloalkyl, 4-10 membered heterocyclyl, C$_6$-C$_{10}$ aryl, and 5-10 membered heteroaryl.

"Cycloalkyl" refers to a radical of a non-aromatic cyclic hydrocarbon group having from 3 to 10 ring carbon atoms ("C$_3$-C$_{10}$ cycloalkyl") and zero heteroatoms in the non-aromatic ring system. In some embodiments, a cycloalkyl group has 3 to 8 ring carbon atoms ("$C_3$-$C_8$cycloalkyl"). In some embodiments, a cycloalkyl group has 3 to 6 ring carbon atoms ("$C_3$-$C_6$ cycloalkyl"). In some embodiments, a cycloalkyl group has 3 to 6 ring carbon atoms ("$C_3$-$C_6$ cycloalkyl"). In some embodiments, a cycloalkyl group has 5 to 10 ring carbon atoms ("$C_5$-$C_{10}$ cycloalkyl"). A cycloalkyl group may be described as, e.g., a $C_4$-$C_7$-membered cycloalkyl, wherein the term "membered" refers to the non-hydrogen ring atoms within the moiety.

Exemplary $C_3$-$C_6$ cycloalkyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl (C), cyclohexenyl ($C_6$), cyclohexadienyl (C), and the like. Exemplary $C_3$-$C_8$ cycloalkyl groups include, without limitation, the aforementioned $C_3$-$C_6$ cycloalkyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), cubanyl (C), bicyclo[1.1.1]pentanyl ($C_5$), bicyclo[2.2.2]octanyl ($C_8$), bicyclo[2.1.1]hexanyl ($C_6$), bicyclo[3.1.1]heptanyl ($C_7$), and the like. Exemplary $C_3$-$C_{10}$ cycloalkyl groups include, without limitation, the aforementioned $C_3$-$C_8$ cycloalkyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the cycloalkyl group is either monocyclic ("monocyclic cycloalkyl") or contain a fused, bridged or spiro ring system such as a bicyclic system ("bicyclic cycloalkyl") and can be saturated or can be partially unsaturated. "Cycloalkyl" also includes ring systems wherein the cycloalkyl ring, as defined above, is fused with one or more aryl groups wherein the point of attachment is on the cycloalkyl ring, and in such instances, the number of carbons continue to designate the number of carbons in the cycloalkyl ring system. Each instance of a cycloalkyl group may be independently optionally substituted, e.g., unsubstituted (an "unsubstituted cycloalkyl") or substituted (a "substituted cycloalkyl") with one or more substituents. In certain embodiments, the cycloalkyl group is unsubstituted $C_3$-$C_{10}$ cycloalkyl. In certain embodiments, the cycloalkyl group is a substituted $C_3$-$C_{10}$ cycloalkyl.

In some embodiments, "cycloalkyl" is a monocyclic, saturated cycloalkyl group having from 3 to 10 ring carbon atoms ("$C_3$-$C_{10}$ cycloalkyl"). In some embodiments, a cycloalkyl group has 3 to 8 ring carbon atoms ("$C_3$-$C_8$ cycloalkyl"). In some embodiments, a cycloalkyl group has 3 to 6 ring carbon atoms ("$C_3$-$C_6$ cycloalkyl"). In some embodiments, a cycloalkyl group has 5 to 6 ring carbon atoms ("$C_5$-$C_6$ cycloalkyl"). In some embodiments, a cycloalkyl group has 5 to 10 ring carbon atoms ("$C_5$-$C_{10}$ cycloalkyl"). Examples of $C_5$-$C_6$ cycloalkyl groups include cyclopentyl ($C_5$) and cyclohexyl ($C_5$). Examples of $C_3$-$C_6$ cycloalkyl groups include the aforementioned $C_5$-$C_6$ cycloalkyl groups as well as cyclopropyl ($C_3$) and cyclobutyl ($C_4$). Examples of $C_3$-$C_8$ cycloalkyl groups include the aforementioned $C_3$-$C_6$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_3$-$C_{10}$ cycloalkyl. In certain embodiments, the cycloalkyl group is substituted $C_3$-$C_{10}$ cycloalkyl.

"Heterocyclyl" or "heterocyclic" refers to a radical of a 3- to 10-membered non-aromatic ring system having ring carbon atoms and 1 to 4 ring heteroatomic groups, wherein each heteroatomic group is independently selected from nitrogen, oxygen, sulfur and oxidized forms of sulfur (for example, S, S(O) and S(O)$_2$), boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more cycloalkyl groups wherein the point of attachment is either on the cycloalkyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. A heterocyclyl group may be described as, e.g., a 3-7-membered heterocyclyl, wherein the term "membered" refers to the non-hydrogen ring atoms, i.e., carbon, nitrogen, oxygen, sulfur and oxidized forms of sulfur (for example, S, S(O) and S(O)$_2$), boron, phosphorus, and silicon, within the moiety. Each instance of heterocyclyl may be independently optionally substituted, e.g., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl. In certain embodiments, the heterocyclyl group is substituted 4-6 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur and oxidized forms of sulfur (for example, S, S(O) and S(O)$_2$), boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, sulfur and oxidized forms of sulfur (for example, S, S(O) and S(O)$_2$) ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, sulfur and oxidized forms of sulfur (for example, S, S(O) and S(O)$_2$) ("5-6 membered heterocyclyl"). In some embodiments, the 5-6 membered heterocyclyl has 1-3 ring heteroatoms selected from nitrogen, oxygen, sulfur and oxidized forms of sulfur (for example, S, S(O) and S(O)$_2$). In some embodiments, the 5-6 membered heterocyclyl has 1-2 ring heteroatoms selected from nitrogen, oxygen, sulfur and oxidized forms of sulfur (for example, S, S(O) and S(O)$_2$). In some embodiments, the 5-6 membered heterocyclyl has one ring heteroatom selected from nitrogen, oxygen, sulfur and oxidized forms of sulfur (for example, S, S(O) and S(O)$_2$).

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl.

Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

Particular examples of heterocyclyl groups are shown in the following illustrative examples:

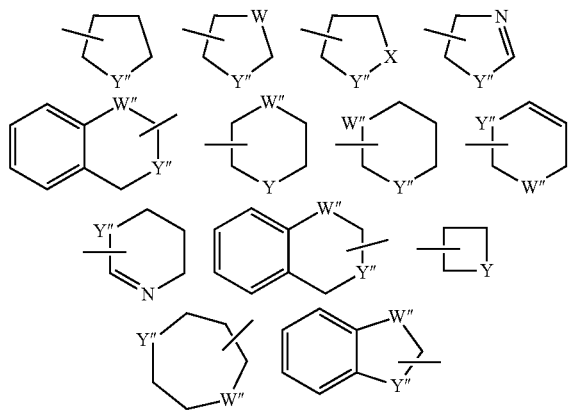

wherein each W" is selected from $CR^{67}$, $C(R^{67})_2$, $NR^{67}$, O, and S; and each Y" is selected from $NR^{67}$, O, and S; and $R^{67}$ is independently hydrogen, $C_1$-$C_8$ alkyl, $C_3$-$C_{10}$ cycloalkyl, 4-10 membered heterocyclyl, $C_6$-$C_{10}$ aryl, and 5-10-membered heteroaryl. These heterocyclyl rings may be optionally substituted with one or more groups selected from the group consisting of acyl, acylamino, acyloxy, alkoxy, alkoxycarbonyl, alkoxycarbonylamino, amino, substituted amino, aminocarbonyl (e.g., amido), aminocarbonylamino, aminosulfonyl, sulfonylamino, aryl, aryloxy, azido, carboxyl, cyano, cycloalkyl, halogen, hydroxy, keto, nitro, thiol, —S-alkyl, —S-aryl, —S(O)-alkyl, —S(O)-aryl, —S(O)$_2$-alkyl, and —S(O)$_2$-aryl. Substituting groups include carbonyl or thiocarbonyl which provide, for example, lactam and urea derivatives.

"Nitrogen-containing heterocyclyl" group means a 4- to 7-membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

"Amino" refers to the radical —$NR^{70}R^{71}$, wherein $R^{70}$ and $R^{71}$ are each independently hydrogen, $C_1$-$C_8$ alkyl, $C_3$-$C_1$ cycloalkyl, 4-10 membered heterocyclyl, $C_6$-$C_{10}$ aryl, and 5-10-membered heteroaryl. In some embodiments, amino refers to $NH_2$.

"Cyano" refers to the radical —CN.

"Hydroxy" or "hydroxyl" refers to the radical —OH.

In some embodiments one or more of the nitrogen atoms of a disclosed compound if present are oxidized to the corresponding N-oxide.

Alkyl, alkenyl, alkynyl, cycloalkyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" cycloalkyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, such as any of the substituents described herein that result in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Two or more substituents may optionally be joined to form aryl, heteroaryl, cycloalkyl, or heterocyclyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

A "counterion" or "anionic counterion" is a negatively charged group associated with a cationic quaternary amino group in order to maintain electronic neutrality. Exemplary counterions include halide ions (e.g., $F^-$, $Cl^-$, $Br^-$, $I^-$), $NO_3^-$, $ClO_4^-$, $OH^-$, $H_2PO_4^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydroiodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66: 1-19 (1977)). Certain specific compounds of the present disclosure contain both basic and acidic functionalities that allow the compounds to be converted into either base or acid addition salts. Other pharmaceutically acceptable carriers known to those of skill in the art are suitable for the present disclosure. Salts tend to be more soluble in aqueous or other protonic solvents that are the corresponding free base forms. In other cases, the preparation may be a lyophilized powder in a first buffer, e.g., in 1 mM-50 mM histidine, 0.1%-2% sucrose, 2%-7% mannitol at a pH range of 4.5 to 5.5, that is combined with a second buffer prior to use.

Thus, the compounds of the present disclosure may exist as salts, such as with pharmaceutically acceptable acids. The present disclosure includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

As used herein, the term "salt" refers to acid or base salts of the compounds used in the methods of the present disclosure. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present disclosure possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)-or (S)- or, as (D)- or (L)-for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

"Treating" or "treatment" includes preventing or delaying the onset of the symptoms, complications, or biochemical indicia of a disease, alleviating or ameliorating the symptoms or arresting or inhibiting further development of the disease, condition, or disorder. "Treating" or "treatment" includes any effect, e.g., lessening, reducing, modulating, or eliminating, that results in the improvement of the condition, disease, disorder and the like. For example, certain methods herein treat cancer by decreasing or reducing or preventing the occurrence, growth, metastasis, or progression of cancer or decreasing a symptom of cancer. The term "treating" and conjugations thereof, include prevention of an injury, pathology, condition, or disease (e.g. preventing the development of one or more symptoms of a disease, disorder, or condition described herein).

An "effective amount" is an amount sufficient to accomplish a stated purpose (e.g. achieve the effect for which it is administered, treat a disease, reduce enzyme activity, increase enzyme activity, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount. "A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

A "reduction" of a symptom or symptoms (and grammatical equivalents of this phrase) means decreasing of the severity or frequency of the symptom(s), or elimination of the symptom(s).

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme, e.g., a protein tyrosine phosphatase, e.g., protein tyrosine phosphatase non-receptor type 2 (PTPN2) or protein tyrosine phosphatase non-receptor type 1 (PTP1B).

As defined herein, the term "inhibition", "inhibit", "inhibiting" and the like in reference to a protein-inhibitor (e.g., antagonist) interaction means negatively affecting (e.g., decreasing) the activity or function of the protein relative to the activity or function of the protein in the absence of the inhibitor. In some embodiments, inhibition refers to reduction of a disease or symptoms of disease. In some embodiments, inhibition refers to a reduction in the activity of a signal transduction pathway or signaling pathway. Thus, inhibition includes, at least in part, partially or totally blocking stimulation, decreasing, preventing, or delaying activation, or inactivating, desensitizing, or down-regulating signal transduction or enzymatic activity or the amount of a protein. In some embodiments, inhibition refers to a decrease in the activity of a protein tyrosine phosphatase, e.g., protein tyrosine phosphatase non-receptor type 2 (PTPN2) or protein tyrosine phosphatase non-receptor type 1 (PTP1B). Thus, inhibition may include, at least in part, partially or totally decreasing stimulation, decreasing or reducing activation, or inactivating, desensitizing, or down-regulating signal transduction or enzymatic activity or the amount of a protein tyrosine phosphatase, e.g., protein tyrosine phosphatase non-receptor type 2 (PTPN2) or protein tyrosine phosphatase non-receptor type 1 (PTP1B).

"Patient" or "subject" in need thereof refers to a living organism suffering from or prone to a disease or condition that can be treated by administration of a compound or pharmaceutical composition, as provided herein. Non-limiting examples include humans, other mammals, bovines, rats, mice, dogs, monkeys, goat, sheep, cows, deer, and other non-mammalian animals. In some embodiments, a patient is human. In some embodiments, a patient is a domesticated animal. In some embodiments, a patient is a dog. In some embodiments, a patient is a parrot. In some embodiments, a patient is livestock animal. In some embodiments, a patient is a mammal. In some embodiments, a patient is a cat. In some embodiments, a patient is a horse. In some embodiments, a patient is bovine. In some embodiments, a patient is a canine. In some embodiments, a patient is a feline. In some embodiments, a patient is an ape. In some embodiments, a patient is a monkey. In some embodiments, a patient is a mouse. In some embodiments, a patient is an experimental animal. In some embodiments, a patient is a rat. In some embodiments, a patient is a hamster. In some embodiments, a patient is a test animal. In some embodiments, a patient is a newborn animal. In some embodiments, a patient is a newborn human. In some embodiments, a patient is a newborn mammal. In some embodiments, a patient is an elderly animal. In some embodiments, a patient is an elderly human. In some embodiments, a patient is an elderly mammal. In some embodiments, a patient is a geriatric patient.

"Disease", "disorder" or "condition" refers to a state of being or health status of a patient or subject capable of being treated with a compound, pharmaceutical composition, or method provided herein. In some embodiments, the compounds and methods described herein comprise reduction or elimination of one or more symptoms of the disease, disorder, or condition, e.g., through administration of a compound disclosed herein, a pharmaceutically acceptable salt thereof, or a pharmaceutical composition comprising a compound disclosed herein, or a pharmaceutically acceptable salt thereof, and a pharmaceutically acceptable carrier.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components.

"Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's solution, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arterial, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a compound or composition described herein is administered at the same time, just prior to, or just after the administration of one or more additional therapies (e.g., anti-cancer agent, chemotherapeutic, or immunotherapeutic agent). The compounds or compositions described herein can be administered alone or can be coadministered to the patient. Coadministration is meant to include simultaneous or sequential administration of the compound or composition individually or in combination (more than one compound or agent). Thus, the preparations can also be combined, when desired, with other active substances (e.g. to reduce metabolic degradation).

The term "PTPN2" as used herein refers to protein tyrosine phosphatase non-receptor type 2. The term "PTPN1" refers to protein tyrosine phosphatase non-receptor type 1 (PTPN1), also known as protein tyrosine phosphatase-1B (PTP1B), Compounds Disclosed herein, for example, is a compound of Formula (I):

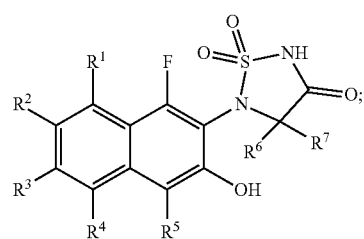

or a pharmaceutically acceptable salt, solvate, hydrate, tautomer, ester, N-oxide, stereoisomer or isotopically enriched variant thereof, wherein:

$R^1$ is selected from the group consisting of hydrogen, halogen, $C_{1-6}$alkyl, $C_{3-6}$cycloalkyl, —O—$C_{1-6}$alkyl, —N($R^a$)—$C_{1-6}$alkyl and —$C_{1-6}$alkylene-5-6 membered heterocyclyl;

wherein $C_{1-6}$alkyl, $C_{3-6}$cycloalkyl, —O—$C_{1-6}$alkyl, —N($R^a$)—$C_{1-6}$alkyl and —$C_{1-6}$alkylene-5-6 membered heterocyclyl may optionally be substituted on one or more available carbons by one, two, three or more substituents each independently selected from $R^g$; and wherein if —$C_{1-6}$alkylene-5-6 membered heterocyclyl contains a substitutable ring nitrogen atom, that ring nitrogen atom may optionally be substituted by $R^h$;

$R^2$ is selected from the group consisting of hydrogen, hydroxyl, —CHF$_2$, —CH$_2$OH, —CH$_2$CN, —CH$_2$—O—$C_{1-6}$ alkyl, —CH$_2$—N($R^a$)—$C_{1-6}$alkyl, $C_{2-6}$alkyl, $C_{2-6}$alkenyl, —O—$C_{1-6}$alkyl, —N($R^a$)—$C_{1-6}$alkyl, —S(O)$_w$—$C_{1-6}$alkyl, —C(O)—N($R^a$)—$C_{1-6}$alkyl, —N($R^a$)—C(O)—$C_{1-6}$alkyl, —O—C(O)—N($R^a$)—$C_{1-6}$ alkyl, —N($R^a$)—C(O)—O—$C_{1-6}$alkyl, —$C_{3-6}$cycloalkyl, —$C_{3-6}$cycloalkyl, $C_{1-6}$alkylene-$C_{3-6}$cycloalkyl, —$C_{1-6}$alkenylene-$C_{3-6}$cycloalkyl, —O—$C_{1-6}$alkylene-$C_{3-6}$cycloalkyl, 5-6 membered heteroaryl, 4-6 membered heterocyclyl, —O—$C_{1-6}$alkylene-5-6 membered heteroaryl, —O-4-6 membered heterocyclyl, —N($R^a$)-4-6 membered heterocyclyl, —$C_{1-6}$alkylene-4-6 membered heterocyclyl and —O—$C_{1-6}$alkylene-4-6 membered heterocyclyl;

wherein —CH$_2$—O—$C_{1-6}$alkyl, —CH$_2$—N($R^a$)—$C_{1-6}$ alkyl, $C_{2-6}$alkyl, $C_{2-6}$alkenyl, —O—$C_{1-6}$ alkyl, —N($R^a$)—$C_{1-6}$alkyl, —S(O)$_w$—$C_{1-6}$alkyl, —C(O)—N($R^a$)—$C_{1-6}$alkyl, —N($R^a$)—C(O)—$C_{1-6}$alkyl, —O—C(O)—N($R^a$)—$C_{1-6}$alkyl, —N($R^a$)—C(O)—O—$C_{1-6}$alkyl, —$C_{3-6}$cycloalkyl, —O—$C_{3-6}$cycloalkyl, —$C_{1-6}$alkylene-$C_{3-6}$cycloalkyl, —$C_{1-6}$alkenylene-$C_{3-6}$cycloalkyl, —O—$C_{1-6}$alkylene-$C_{3-6}$cycloalkyl, 5-6 membered heteroaryl, —O—$C_{1-6}$alkylene-5-6 membered heteroaryl, 4-6 membered heterocyclyl, —O-4-6 membered heterocyclyl, —N($R^a$)-4-6 membered heterocyclyl, —$C_{1-6}$alkylene-4-6 membered heterocyclyl and —O—$C_{1-6}$alkylene-4-6 membered heterocyclyl may optionally be substituted on one or more available carbons by one, two, three or more substituents each independently selected from $R^g$; and wherein if 5-6 membered heteroaryl, 4-6 membered heterocyclyl, —N($R^a$)-4-6 membered heterocyclyl, —$C_{1-6}$alkylene-4-6 membered heterocyclyl or —O—$C_{1-6}$alkylene-4-6 membered heterocyclyl contains a substitutable ring nitrogen atom, that ring nitrogen atom may optionally be substituted by $R^h$;

or $R^1$ and $R^2$ taken together with the atoms to which they are attached form a 5-6 membered aryl or heteroaryl; wherein aryl or heteroaryl may optionally be substituted by one or more substituents each independently selected from the group consisting of halogen, hydroxyl, cyano, $C_{1-6}$alkyl and $C_{1-6}$alkoxy; wherein $C_{1-6}$alkyl and $C_{1-6}$alkoxy may optionally be substituted by one, two three or more substituents each independently selected from $R^P$;

$R^3$ is selected from the group consisting of hydrogen, —$C_{1-6}$alkyl, —$C_{1-6}$alkyl, —N($R^a$)—$C_{1-6}$ alkyl, —S(O)$_w$—$C_{1-6}$alkyl, —C(O)—N($R^a$)—$C_{1-6}$alkyl, —N($R^a$)—C(O)—$C_{1-6}$alkyl and —$C_{1-6}$alkylene-4-6 membered heterocyclyl;
 wherein —$C_{1-6}$alkyl, —O—$C_{1-6}$alkyl, —N($R^a$)—$C_{1-6}$alkyl, —S(O)$_w$—$C_{1-6}$alkyl, —C(O)—N($R^a$)—$C_{1-6}$alkyl, —N($R^a$)—C(O)—$C_{1-6}$alkyl and —$C_{1-6}$alkylene-4-6 membered heterocyclyl may optionally be substituted on one or more available carbons by one, two, three or more substituents each independently selected from $R^g$; and wherein if —$C_{1-6}$alkylene-4-6 membered heterocyclyl contains a substitutable ring nitrogen atom, that ring nitrogen atom may optionally be substituted by $R^h$;

$R^4$ is selected from the group consisting of hydrogen, halogen, $C_{1-6}$alkyl, $C_{3-6}$cycloalkyl and —$C_{1-6}$alkylene-4-6 membered heterocyclyl; wherein $C_{1-6}$alkyl, $C_{3-6}$cycloalkyl and —$C_{1-6}$ alkylene-4-6 membered heterocyclyl may optionally be substituted on one or more available carbons by one, two, three or more substituents each independently selected from $R^g$; and wherein if —$C_{1-6}$alkylene-4-6 membered heterocyclyl contains a substitutable ring nitrogen atom, that ring nitrogen atom may optionally be substituted by $R^h$;

wherein at least one of $R^1$, $R^2$, $R^3$ and $R^4$ is not hydrogen;

$R^5$ is selected from the group consisting of hydrogen, halogen, $C_{1-6}$alkyl, $C_{3-6}$cycloalkyl and —$C_{1-6}$alkylene-4-6 membered heterocyclyl; wherein $C_{1-6}$alkyl, $C_{3-6}$cycloalkyl and —$C_{1-6}$ alkylene-4-6 membered heterocyclyl may optionally be substituted on one or more available carbons by one, two, three or more substituents each independently selected from $R^g$; and wherein if —$C_{1-6}$alkylene-4-6 membered heterocyclyl contains a substitutable ring nitrogen atom, that ring nitrogen atom may optionally be substituted by $R^h$;

$R^6$ is hydrogen;

$R^7$ is hydrogen;

$R^g$ is independently selected for each occurrence from the group consisting of hydrogen, halogen, hydroxyl, cyano, nitro, oxo, —C(O)OH, $R^aR^bN$—, $R^aR^bN$—C(O)—, $R^aR^bN$—SO$_w$—, $R^aR^bN$—C(O)—N($R^a$)—, $C_{1-6}$alkyl, $C_{2-6}$alkenyl, $C_{2-6}$alkynyl, $C_{3-6}$cycloalkyl, phenyl, $C_{1-6}$alkylene-$C_{3-6}$cycloalkyl, —O—$C_{1-6}$alkylene-$C_{3-6}$cycloalkyl, —(CO)—(NR$^a$)—$C_{1-6}$alkylene-$C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-C(O)—, $C_{1-6}$alkyl-O—C(O)—, $C_{1-6}$alkyl-C(O)—O—, $C_{1-6}$alkyl-S(O)$_w$—, $C_{1-6}$alkyl-N($R^a$)—, $C_{1-6}$alkyl-N($R^a$)—C(O)—, $C_{1-6}$alkyl-C(O)—N($R^a$), $C_{1-6}$alkyl-N($R^a$)—C(O)—N($R^a$)—, $C_{1-6}$alkyl-N($R^a$)—SO$_w$—, $C_{3-6}$cycloalkyl-N($R^a$)—SO$_w$—, $C_{1-6}$ alkyl-SO$_w$—N($R^a$)—, $C_{3-6}$cycloalkyl-SO$_w$—N($R^a$)—, 4-6 membered heterocyclyl-SO$_w$—N($R^a$)—, $C_{1-6}$ alkoxy-C(O)—N($R^a$)—, $C_{1-6}$alkyl-C(O)—N($R^a$)—$C_{1-6}$alkyl-, $C_{1-6}$alkyl-N($R^a$)—C(O)—$C_{1-6}$alkyl-, —P(O)($C_{1-3}$alkyl)$_2$ and $C_{1-6}$alkoxy-$C_{1-6}$alkyl-; wherein $C_{1-6}$alkyl, $C_{2-6}$alkenyl, $C_{2-6}$alkynyl, $C_{3-6}$cycloalkyl, phenyl, $C_{1-6}$alkylene-$C_{3-6}$cycloalkyl, —$C_{1-6}$alkylene-$C_{3-6}$cycloalkyl, —(CO)—(NR$^a$)—$C_{1-6}$alkylene-$C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-C(O)—, $C_{1-6}$alkyl-O—C(O)—, $C_{1-6}$alkyl-C(O)—O—, $C_{1-6}$alkyl-S(O)$_w$—, $C_{1-6}$alkyl-N($R^a$)—, $C_{1-6}$ alkyl-N($R^a$)—C(O)—, $C_{1-6}$alkyl-C(O)—N($R^a$), $C_{1-6}$alkyl-N($R^a$)—C(O)—N($R^a$)—, $C_{1-6}$alkyl-N($R^a$)—SO$_w$—, $C_{3-6}$cycloalkyl-N($R^a$)—SO$_w$—, $C_{1-6}$alkyl-SO$_w$—N($R^a$)—, $C_{3-6}$cycloalkyl-SO$_w$—N($R^a$)—, 4-6 membered heterocyclyl-SO$_w$—N($R^a$)—, $C_{1-6}$alkoxy-C(O)—N($R^a$)—, $C_{1-6}$alkyl-C(O)—N($R^a$)—$C_{1-6}$alkyl-, $C_{1-6}$alkyl-N($R^a$)—C(O)—$C_{1-6}$alkyl-, —P(O)($C_{1-3}$alkyl)$_2$ and $C_{1-6}$alkoxy-$C_{1-6}$alkyl- may optionally be substituted by one, two three or more substituents each independently selected from $R^P$;

$R^h$ is independently selected for each occurrence from the group consisting of $C_{1-6}$alkyl, $C_{3-6}$alkenyl, $C_{3-6}$alkynyl, $C_{3-6}$cycloalkyl, —$C_{1-6}$alkyl-$C_{3-6}$cycloalkyl, $C_{1-6}$alkyl-S(O)$_2$—, $C_{3-6}$cycloalkyl-S(O)$_2$—, 4-6 membered heterocyclyl-S(O)$_2$—, 4-6 membered heterocyclyl-$C_{1-6}$alkyl-S(O)$_2$—, 5-6 membered heteroaryl-S(O)$_2$—, phenyl-S(O)$_2$—, phenyl-$C_{1-6}$alkyl-S(O)$_2$—, $C_{1-6}$alkyl-C(O)—, $C_{1-6}$cycloalkyl-C(O)—, $C_{1-6}$alkoxy-C(O)—, $R^aR^bN$—C(O)—, $R^aR^bN$—SO$_2$— and —P(O)($C_{1-3}$alkyl)$_2$; wherein $C_{1-6}$alkyl, $C_{3-6}$alkenyl, $C_{3-6}$alkynyl, $C_{3-6}$cycloalkyl, —$C_{1-6}$alkyl-$C_{3-6}$cycloalkyl, $C_{1-6}$alkyl-S(O)$_2$—, $C_{3-6}$cycloalkyl-S(O)$_2$—, 4-6 membered heterocyclyl-S(O)$_2$—, 4-6 membered heterocyclyl-$C_{1-6}$alkyl-S(O)$_2$—, 5-6 membered heteroaryl-S(O)$_2$—, phenyl-S(O)$_2$—, phenyl-$C_{1-6}$alkyl-S(O)$_2$—, $C_{1-6}$alkyl-C(O)—, $C_{1-6}$cycloalkyl-C(O)—, $C_{1-6}$alkoxy-C(O)—, $R^aR^bN$—C(O)—, $R^aR^bN$—SO$_2$— and —P(O)($C_{1-3}$alkyl)$_2$ may optionally be substituted by one, two three or more substituents each independently selected from $R^P$;

$R^P$ is independently selected for each occurrence from the group consisting of halogen, hydroxyl, cyano, $C_{1-6}$alkyl, $C_{1-6}$alkoxy, $C_{3-6}$cycloalkyl, 4-6 membered heterocyclyl, $R^aR^bN$—, $R^aR^bN$-carbonyl-, $R^aR^bN$—SO$_2$—, and $R^aR^bN$-carbonyl-N($R^a$)—;

$R^a$ and $R^b$ are independently selected, for each occurrence, from the group consisting of hydrogen, $C_{1-6}$alkyl and $C_{3-6}$cycloalkyl; wherein $C_{1-6}$alkyl may optionally be substituted by one or more substituents each independently selected from the group consisting of halogen, cyano, oxo, hydroxyl and $C_{1-6}$alkoxy (optionally substituted by one, two or three fluorine atoms);

or $R^a$ and $R^b$ together with the nitrogen to which they are attached form a 4-6 membered heterocyclyl, wherein the heterocyclyl may optionally be substituted by one or more substituents each independently selected from the group consisting of halogen, cyano, oxo and hydroxyl; and w is 0, 1 or 2.

In some embodiments, one, two, three or more hydrogen atoms of the compound may optionally be deuterium atoms; and wherein all other atoms of the compound are present at their naturally occurring isotopic abundance. For example, in some embodiments, one, two, three or more hydrogen atoms may optionally be deuterium atoms at one, two three or more groups each independently selected from $R^1$, $R^2$, $R^4$, $R^5$, $R^6$, $R^7$, and $R^9$.

In some embodiments, $R^1$ is selected from the group consisting of, e.g., hydrogen, deuterium, chlorine and fluorine.

In some embodiments, $R^2$ is 4-6 membered heterocyclyl; wherein $R^2$ may optionally be substituted on one or more available carbons by one, two or three substituent each independently selected from $R^9$, wherein if 4-6 membered heterocyclyl contains a substitutable ring nitrogen atom, that ring nitrogen atom may optionally be substituted by a substituent selected from $R^h$. For example, in some embodiments $R^2$ is 4-6 membered heterocyclyl; wherein $R^2$ may optionally be substituted on one or more available carbons by one, two or three substituents each independently selected from the group consisting of hydrogen and $C_{1-6}$alkyl; and wherein if $R^2$ contains a substitutable ring nitrogen atom, that ring nitrogen atom may optionally be substituted by a substituent selected from the group consisting of hydrogen, $C_{1-6}$alkyl (optionally substituted by one, two or three fluorine atoms), —$C_{1-6}$alkyl-$C_{3-6}$cycloalkyl, $C_{1-6}$cycloalkyl-C(O)—, $C_{1-6}$alkyl-$S(O)_2$— (optionally substituted by cyano, methoxy or one, two or three fluorine atoms), $C_{3-6}$cycloalkyl-$S(O)_2$—, 4-6 membered heterocyclyl-$S(O)_2$—, 4-6 membered heterocyclyl-$C_{1-6}$alkyl-$S(O)_2$—, 5-6 membered heteroaryl-$S(O)_2$—, phenyl-$S(O)_2$—, phenyl-$C_{1-6}$alkyl-$S(O)_2$-(optionally substituted by $R^aR^bN$—), and —$P(O)(C_{1-3}alkyl)_2$. For example, in some embodiments $R^2$ is selected from the group consisting of, e.g.:

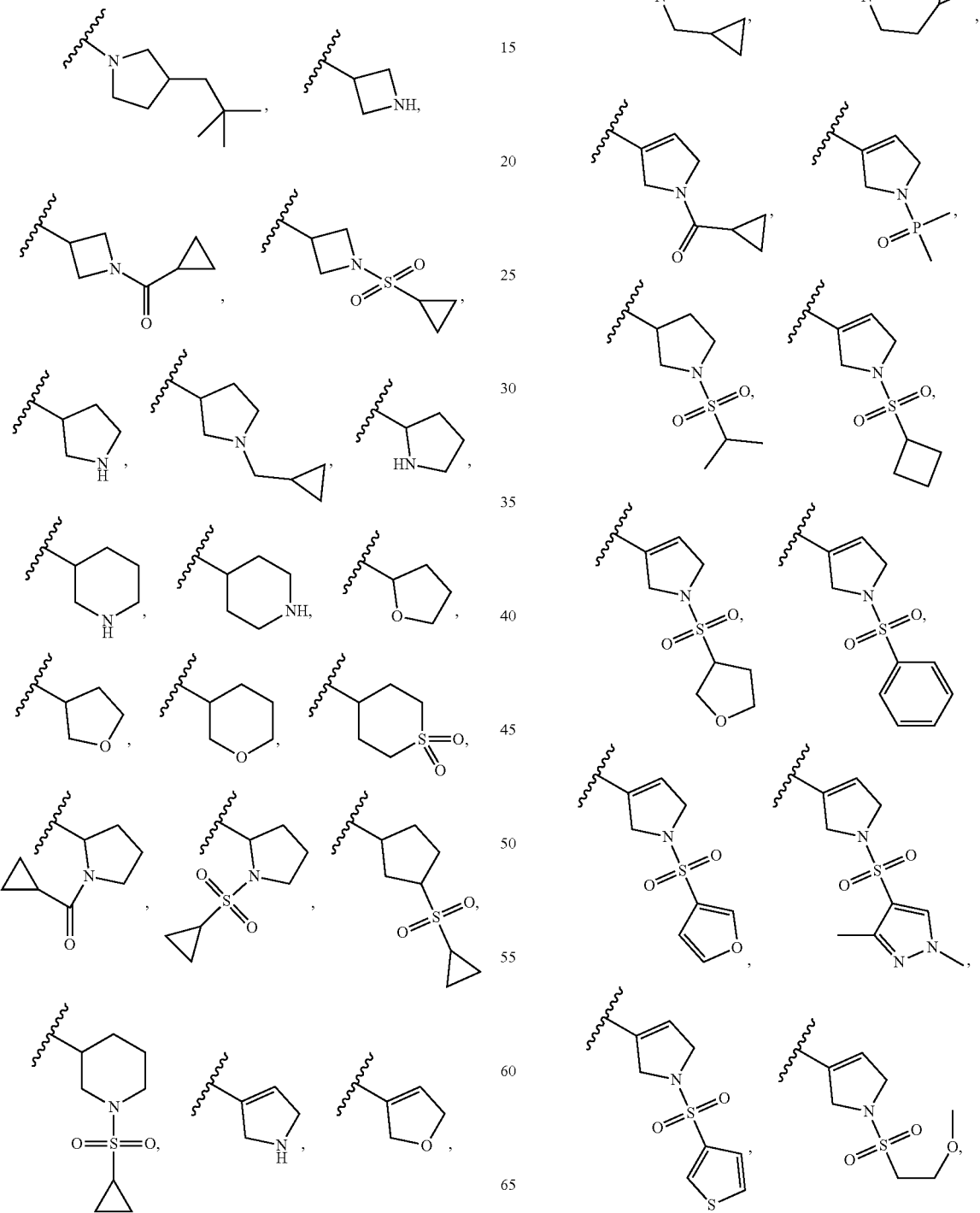

-continued

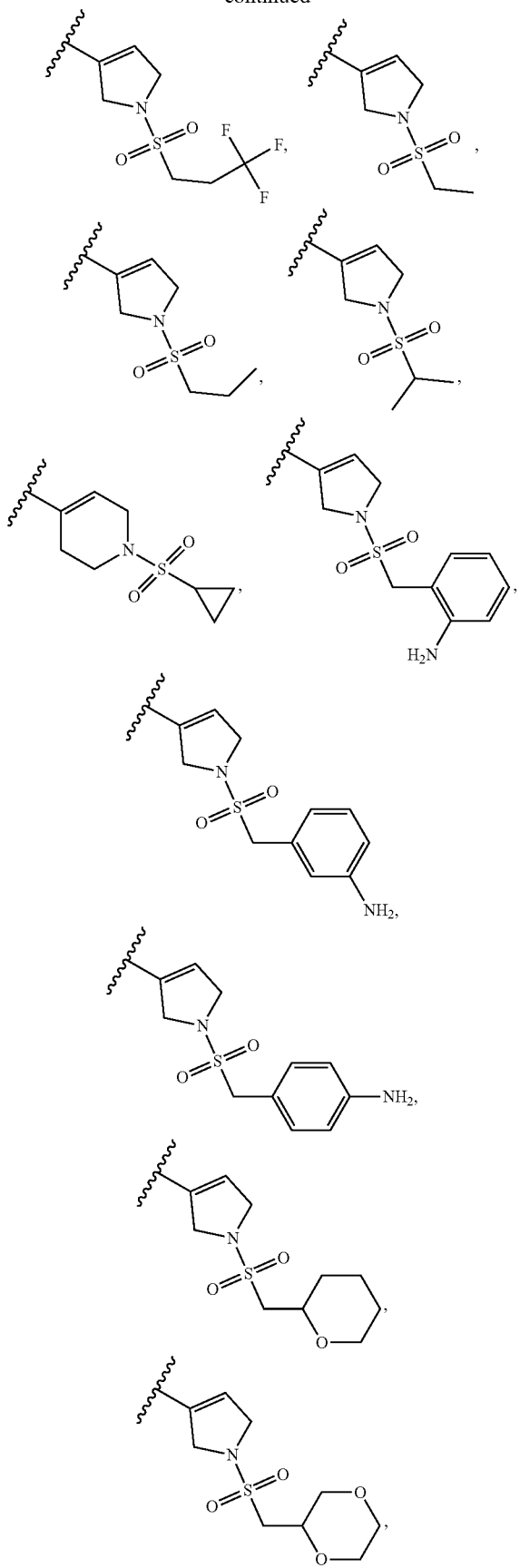
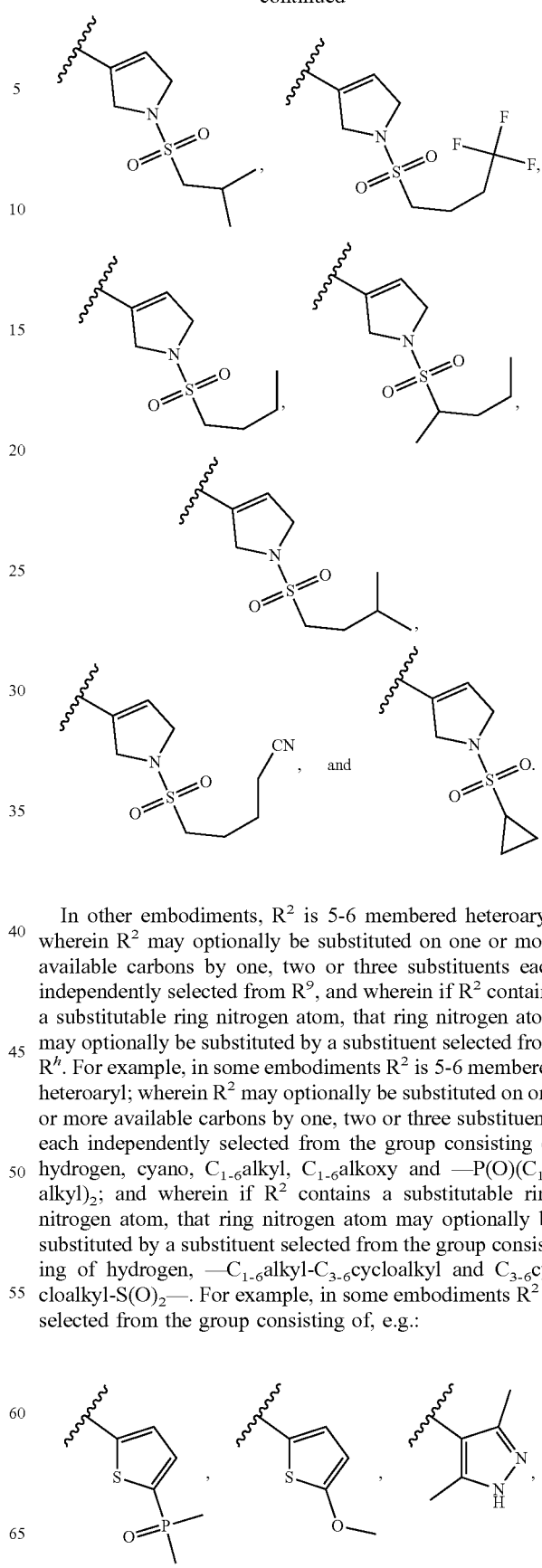

In other embodiments, $R^2$ is 5-6 membered heteroaryl; wherein $R^2$ may optionally be substituted on one or more available carbons by one, two or three substituents each independently selected from $R^9$, and wherein if $R^2$ contains a substitutable ring nitrogen atom, that ring nitrogen atom may optionally be substituted by a substituent selected from $R^h$. For example, in some embodiments $R^2$ is 5-6 membered heteroaryl; wherein $R^2$ may optionally be substituted on one or more available carbons by one, two or three substituents each independently selected from the group consisting of hydrogen, cyano, $C_{1-6}$alkyl, $C_{1-6}$alkoxy and —P(O)($C_{1-3}$ alkyl)$_2$; and wherein if $R^2$ contains a substitutable ring nitrogen atom, that ring nitrogen atom may optionally be substituted by a substituent selected from the group consisting of hydrogen, —$C_{1-6}$alkyl-$C_{3-6}$cycloalkyl and $C_{3-6}$cycloalkyl-S(O)$_2$—. For example, in some embodiments $R^2$ is selected from the group consisting of, e.g.:

-continued

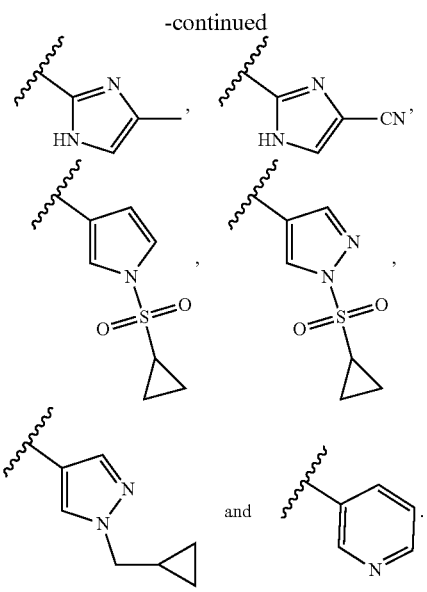

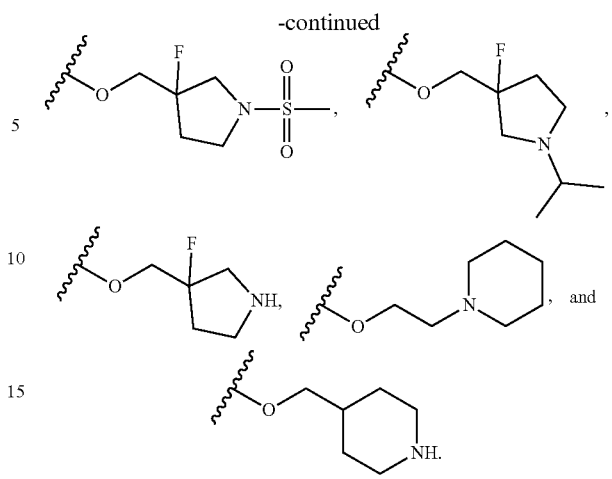

In further embodiments, $R^2$ is —O—$C_{1-6}$alkylene-4-6 membered heterocyclyl, wherein $R^2$ may optionally be substituted on one or more available carbons by one, two or three substituents each independently selected from $R^9$, and wherein if $R^2$ contains a substitutable ring nitrogen atom, that ring nitrogen atom may optionally be substituted by a substituent selected from $R^h$. For example, in some embodiments, $R^2$ is —O—$C_{1-6}$alkylene-4-6 membered heterocyclyl, wherein $R^2$ may optionally be substituted on one or more available carbons by one, two or three substituents each independently selected from the group consisting of hydrogen, halogen and $C_{1-6}$alkyl, and wherein if $R^2$ contains a substitutable ring nitrogen atom, that ring nitrogen atom may optionally be substituted by a substituent selected from the group consisting of hydrogen, $C_{1-6}$alkyl and $C_{1-6}$ alkyl-S(O)$_2$—. For example, in some embodiments $R^2$ is selected from the group consisting of, e.g.:

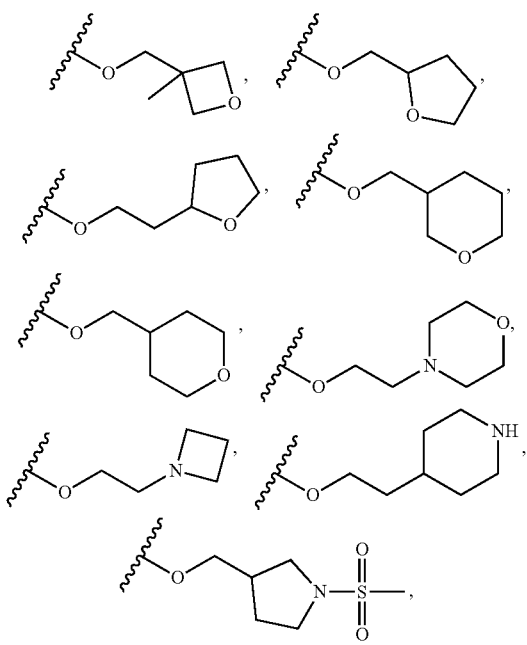

In other embodiments, $R^2$ is —O—$C_{1-6}$alkylene-5-6 membered heteroaryl. For example, in some embodiments $R^2$ is selected from the group consisting of, e.g.:

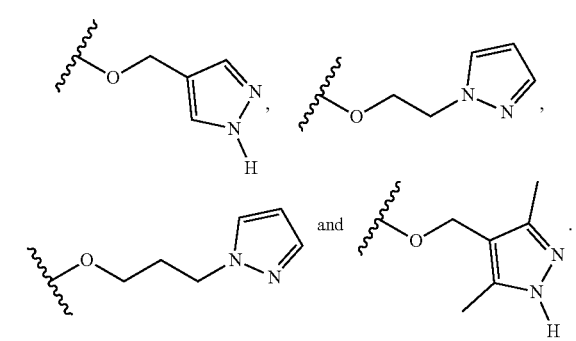

In further embodiments, $R^2$ is selected from the group consisting of —$C_{2-6}$alkyl, $C_{2-6}$alkenyl, and $C_{3-6}$cycloalkyl; wherein $R^2$ may optionally be substituted by one, two, three or more substituents each independently selected from $R^9$. For example, in some embodiments $R^2$ is selected from the group consisting of —$C_{2-6}$alkyl, $C_{2-6}$alkenyl, $C_{3-6}$cycloalkyl, —$C_{1-6}$alkylene-$C_{3-6}$ cycloalkyl and —$C_{1-6}$alkenylene-$C_{3-6}$cycloalkyl; wherein $R^2$ may optionally be substituted by one, two, three or more substituents each independently selected from the group consisting of cyano, chlorine, fluorine, hydroxyl, $C_{1-6}$alkoxy, phenyl, and $R^aR^bN$—. For example, in some embodiments $R^2$ is selected from the group consisting of, e.g.:

—CH$_2$CHF$_2$,

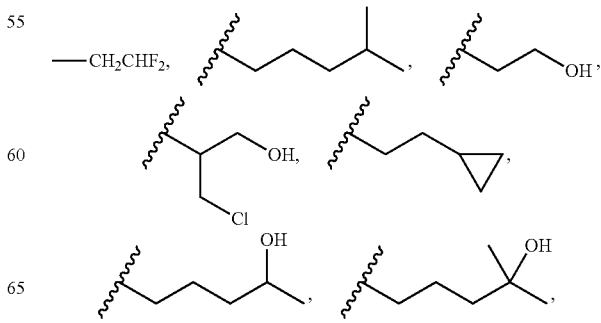

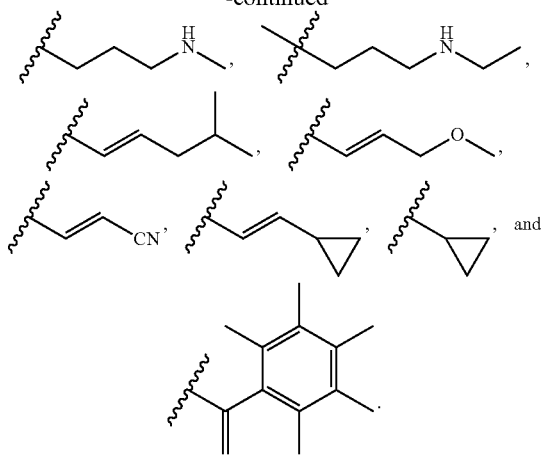

In other embodiments, $R^2$ is —O—$C_{1-6}$alkyl; wherein $R^2$ may optionally be substituted by one, two, three or more substituents each independently selected from $R^9$. For example, in some embodiments $R^2$ is —O—$C_{1-6}$alkyl; wherein $R^2$ may optionally be substituted by one, two, three or more substituents each independently selected from the group consisting of cyano, deuterium, chlorine, fluorine, hydroxyl, oxo, $C_{1-6}$alkoxy, $C_{3-6}$cycloalkoxy, —$C_{1-6}$alkylene-$C_{3-6}$cycloalkyl, —(CO)—(NR$^a$)—$C_{1-6}$alkylene-$C_{3-6}$cycloalkyl, $C_{1-6}$alkyl-O—C(O)—, $R^aR^bN$— (wherein $R^b$ is optionally substituted by —OCH$_3$ or —OCF$_3$), $C_{1-6}$alkyl-N(R$^a$)—, $R^aR^bN$—C(O)—, —P(O)($C_{1-3}$alkyl)$_2$, $C_{1-6}$alkyl-N(R$^a$)—C(O)—, $C_{1-6}$alkyl-N(R$^a$)—C(O)—N(R$^a$)—, $C_{1-6}$alkyl-SO$_2$—N(R$^a$)—, $C_{3-6}$cycloalkyl-SO$_2$—N(R$^a$)— and 4-6 membered heterocyclyl-SO$_2$—N(R$^a$)—. For example, in some embodiments $R^2$ is selected from the group consisting of, e.g.: —OCH$_3$, —OCD$_3$, —OCF$_3$, —OCHF$_2$, —OCH$_2$CH$_3$,

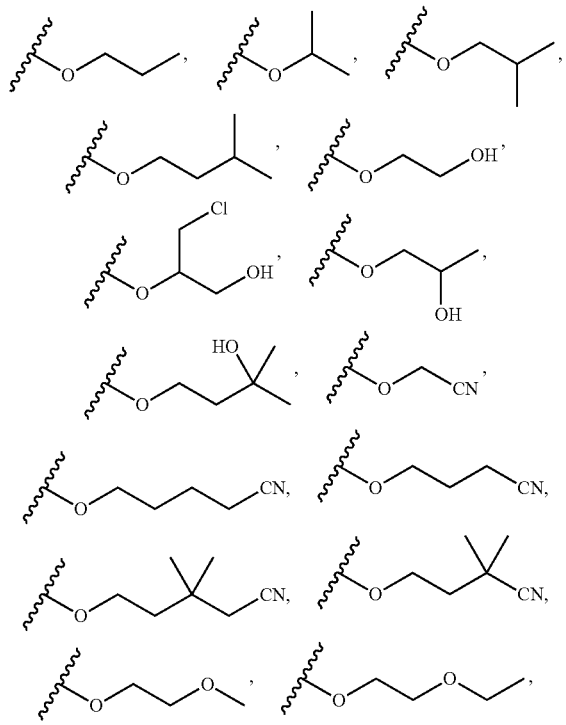

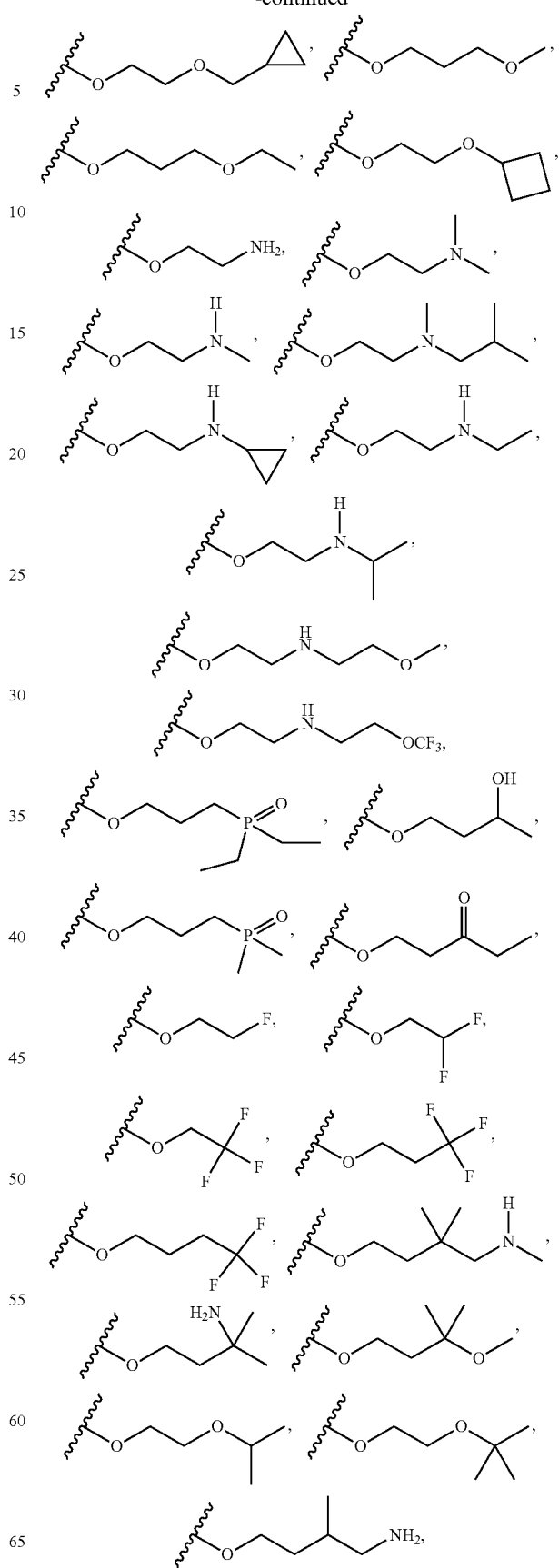

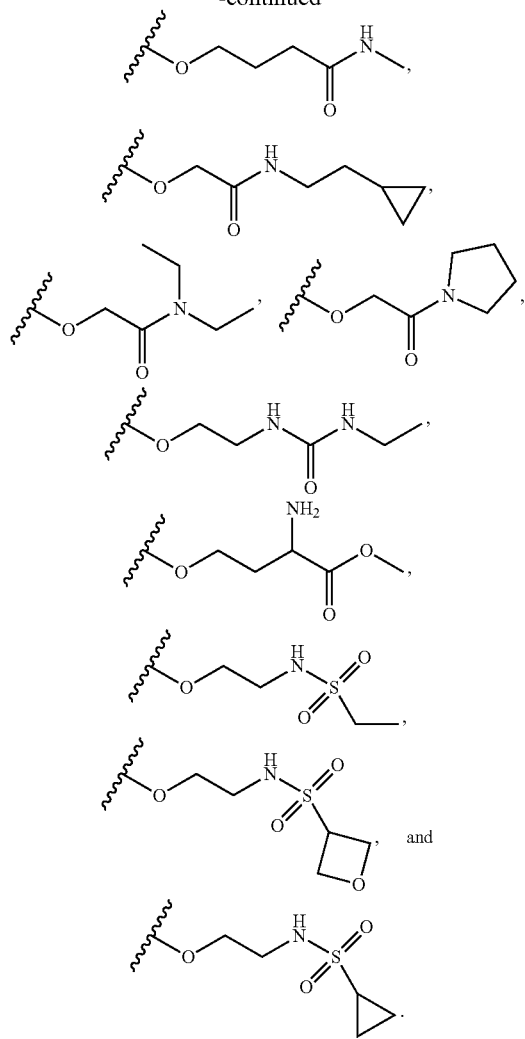

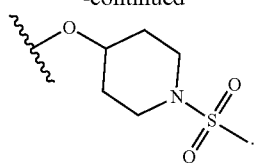

In still further embodiments, $R^2$ is —N($R^a$)—$C_{1-6}$alkyl, wherein $R^2$ may optionally be substituted by one, two or three substituents each independently selected from $R^9$. For example, in some embodiments $R^2$ is —N($R^a$)—$C_{1-6}$alkyl, wherein $R^2$ may optionally be substituted by one, two or three substituents each independently selected from the group consisting of fluoro, —C(O)OH, cyano, oxo, $R^aR^bN$—, $C_{1-6}$alkoxy, phenyl, —$C_{3-6}$cycloalkyl, $C_{3-6}$cycloalkyl-$SO_2$—N($R^a$)—, and —(CO)—(N$R^a$)—$C_{1-6}$alkylene-$C_{3-6}$cycloalkyl. For example, in some embodiments $R^2$ is selected from the group consisting of, e.g.: —N(H)$CH_3$,

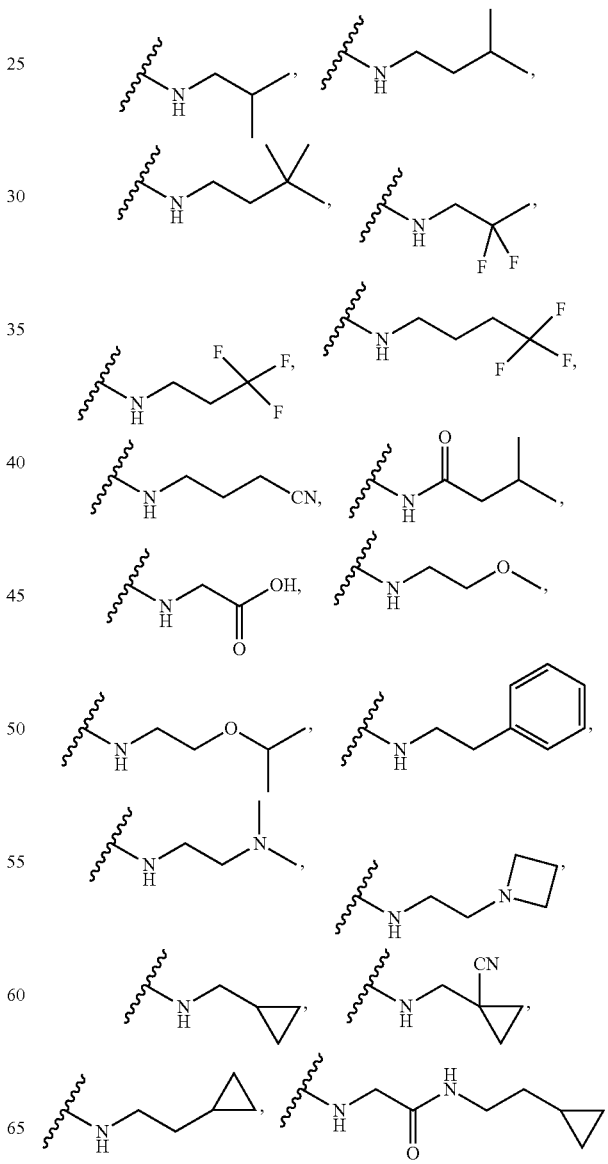

In other embodiments, $R^2$ is —O—$C_{3-6}$cycloalkyl or —O-4-6 membered heterocyclyl; wherein if $R^2$ contains a substitutable ring nitrogen atom, that ring nitrogen atom may optionally be substituted by a substituent selected from $R^h$. For example, in some embodiments $R^2$ is —O—$C_{3-6}$cycloalkyl or —O-4-6 membered heterocyclyl; wherein if $R^2$ contains a substitutable ring nitrogen atom, that ring nitrogen atom may optionally be substituted by a substituent selected from the group consisting of $C_{1-6}$alkyl-$SO_2$—N($R^a$)— and $C_{3-6}$cycloalkyl-$SO_2$—N($R^a$)—. For example, in some embodiments $R^2$ is selected from the group consisting of, e.g.:

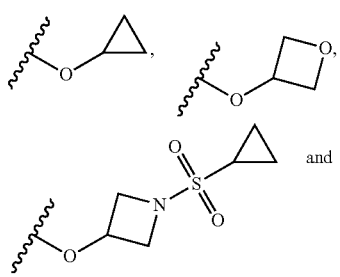

-continued
and

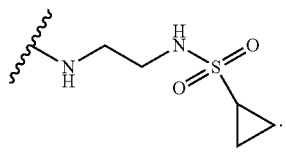

In other embodiments, R² is —O—C₁₋₆alkylene-C₃₋₆cycloalkyl, wherein R² may optionally be substituted by one, two or three substituents each independently selected from R⁹. For example, in some embodiments R² is —O—C₁₋₆alkylene-C₃₋₆cycloalkyl, wherein R² may optionally be substituted by one, two or three substituents each independently selected from the group consisting of fluoro, hydroxyl, R$^a$R$^b$N—, cyano, and C₁₋₃alkyl; wherein C₁₋₃alkyl may be optionally substituted by a substituent selected from the group consisting of cyano and C₁₋₃ alkoxy. For example, in some embodiments R² is selected from the group consisting of, e.g.:

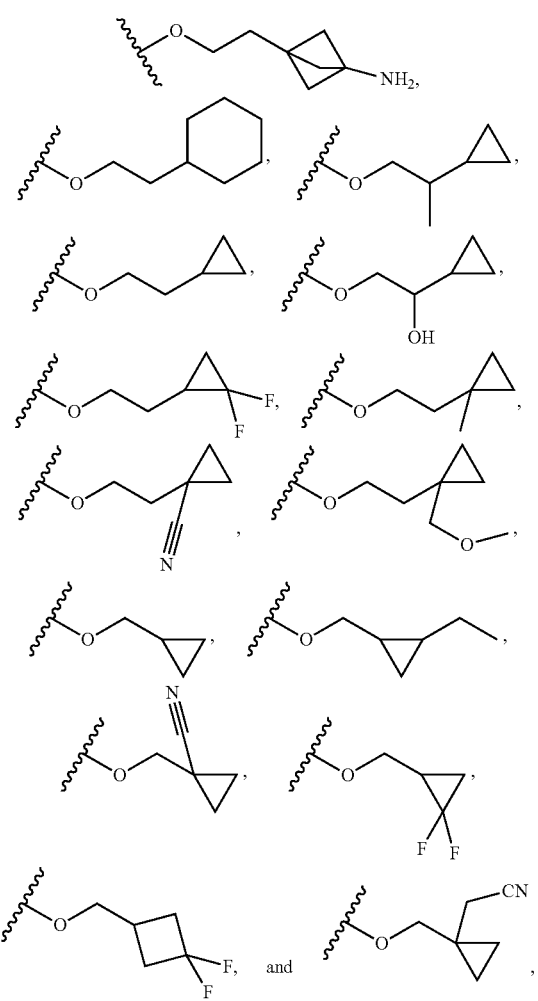

In some embodiments, R² is —O—C(O)—N(R$^a$)—C₁₋₆alkyl. For example, in some embodiments R² is represented by, e.g.:

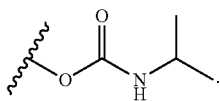

In further embodiments, R² is —N(R$^a$)-4-6 membered heterocyclyl, wherein if R² contains a substitutable ring nitrogen atom, that ring nitrogen atom may optionally be substituted by a substituent selected from R$^h$. For example, in some embodiments R² is —N(R$^a$)-4-6 membered heterocyclyl, wherein if R² contains a substitutable ring nitrogen atom, that ring nitrogen atom may optionally be substituted by a substituent selected from the group consisting of C₁₋₆alkyl-SO₂—N(R$^a$)— and C₃₋₆cycloalkyl-SO₂—N(R$^a$)—. For example, in some embodiments R² is selected from the group consisting of, e.g.:

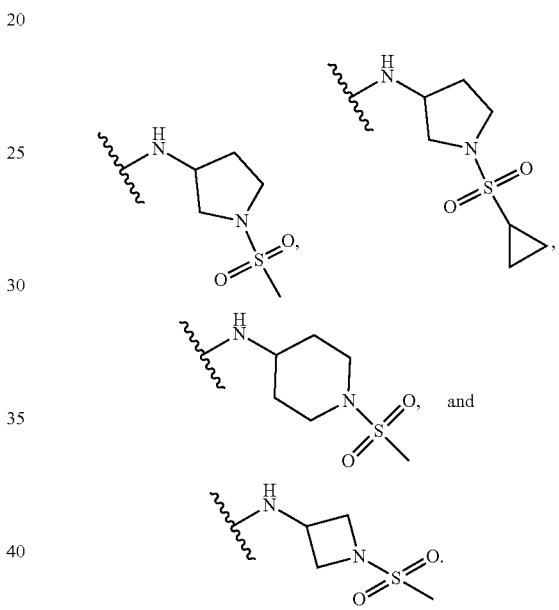

In other embodiments, R² is —C₁₋₆alkylene-4-6 membered heterocyclyl, wherein if R² contains a substitutable ring nitrogen atom, that ring nitrogen atom may optionally be substituted by a substituent selected from R$^h$. For example, in some embodiments R² is —C₁₋₆alkylene-4-6 membered heterocyclyl, wherein if R² contains a substitutable ring nitrogen atom, that ring nitrogen atom may optionally be substituted by a substituent selected from the group consisting of C₁₋₆alkyl, C₁₋₆alkyl-SO₂—N(R$^a$)— and C₃₋₆cycloalkyl-SO₂—N(R$^a$)—, wherein C₁₋₆alkyl may optionally be substituted by one, two or three fluorine atoms. For example, in some embodiments R² is selected from the group consisting of, e.g.:

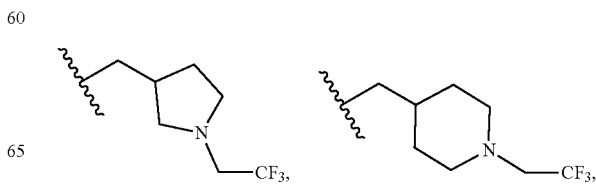

-continued

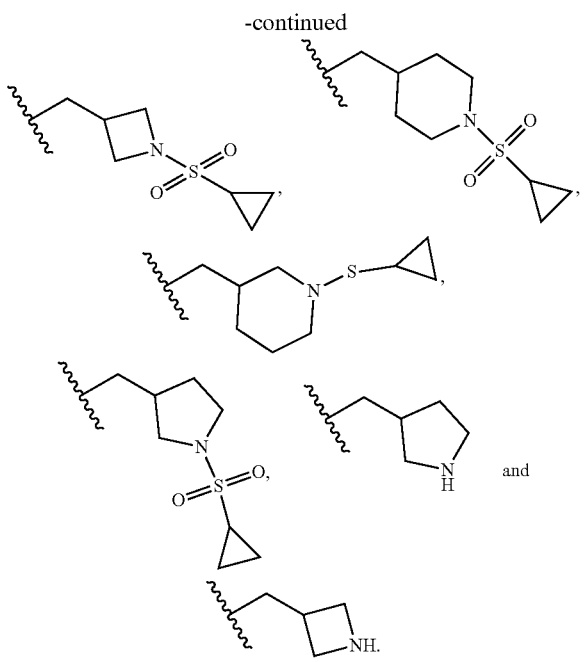

In some embodiments, R² is selected from the group consisting of, for example, —CHF₂, —CH₂OH, —CH₂OCH₃, —CH₂CN, —OH,

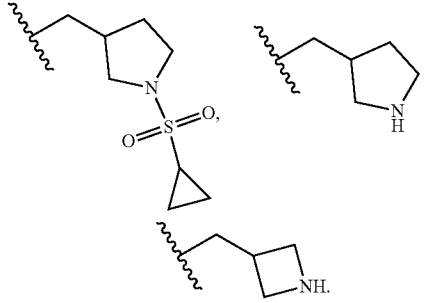

In some embodiments, R¹ and R² taken together with the atoms to which they are attached form a 5 membered heteroaryl. For example, in some embodiments R¹ and R² taken together with the atoms to which they are attached form, e.g., furanyl. For example, in some embodiments the compound of Formula (I) is represented by:

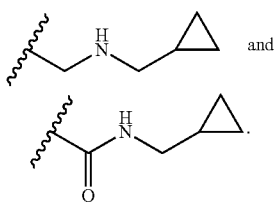

In some embodiments, R³ is hydrogen. In other embodiments, R⁴ is hydrogen. In further embodiments, R⁵ is selected from the group consisting of hydrogen, deuterium, bromine, chlorine, and fluorine. In other embodiments, R⁶ is selected from the group consisting of hydrogen and deuterium. In further embodiments, R⁷ is selected from the group consisting of hydrogen and deuterium. In some embodiments, all atoms of the compound of Formula (I) are present at their naturally occurring isotopic abundance.

Also disclosed herein is compound represented by Formula (II):

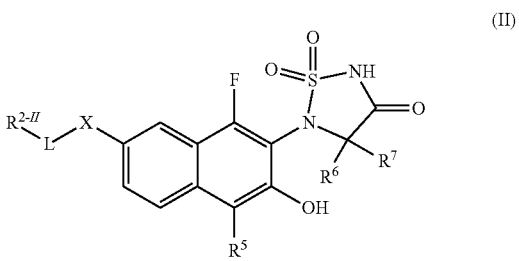

(II)

or a pharmaceutically acceptable salt, solvate, hydrate, tautomer, ester, N-oxide or stereoisomer thereof, wherein:

X is selected from the group consisting of —O— and —N(R$^a$)—;

L is straight or branched $C_{1-6}$alkylene;

$R^{2-II}$ is selected from the group consisting of hydrogen, cyano, —NR$^a$R$^b$, $C_{1-2}$alkoxy, $C_{3-6}$cycloalkyl-SO₂—N(R$^a$)—, $C_{1-6}$alkyl-SO₂—N(R$^a$)—, phenyl, 5-6 membered heteroaryl, 4-6 membered heterocyclyl and $C_{3-6}$cycloalkyl; wherein phenyl, 5-6 membered heteroaryl, 4-6 membered heterocyclyl and $C_{3-6}$cycloalkyl may optionally be substituted on one or more available carbons by one, two or three substituents each independently selected from the group consisting of halogen, hydroxyl, —NR$^a$R$^b$, $C_{1-2}$alkyl (optionally substituted by one, two or three halogens) and $C_{1-2}$alkoxy (optionally substituted by one, two or three halogens); and wherein if 5-6 membered heteroaryl or 4-6 membered heterocyclyl contains a substitutable ring nitrogen atom, that ring nitrogen atom may optionally be substituted by $C_{1-3}$alkyl;

R⁵ is selected from the group consisting of hydrogen, deuterium and halogen;

R⁶ is selected from the group consisting of hydrogen and deuterium;

R⁷ is selected from the group consisting of hydrogen and deuterium; and

R$^a$ and R$^b$ are each independently selected for each occurrence from the group consisting of hydrogen and $C_{1-3}$alkyl.

In some embodiments, X is selected from the group consisting of —O—, —N(H)—, and —N(CH₃)—

In other embodiments, L is selected from the group consisting of

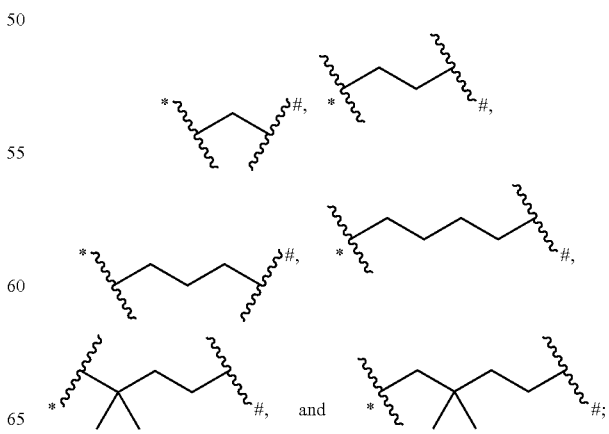

wherein * and # represent the covalent points of attachment to $R^{2-II}$ and X, respectively.

In further embodiments, $R^{2-II}$ is selected from the group consisting of: hydrogen, cyano, —NH$_2$, —N(CH$_3$)$_2$, —OCH$_3$,

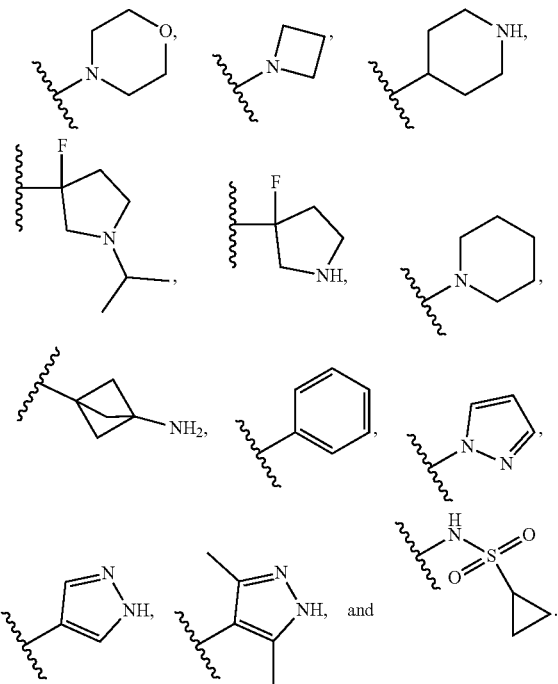

In some embodiments, $R^5$ is selected from the group consisting of hydrogen, deuterium, and fluorine.

Also disclosed herein is a compound represented by Formula (III):

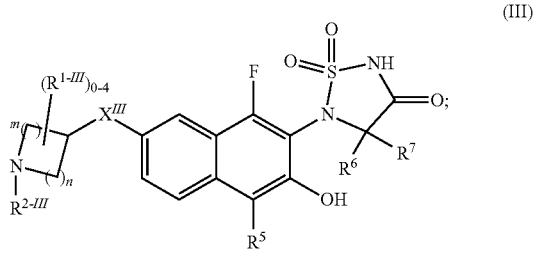

or a pharmaceutically acceptable salt, solvate, hydrate, tautomer, ester, N-oxide or stereoisomer thereof, wherein:

$X^{III}$ is selected from the group consisting of a bond, —CH$_2$—, —NR$^a$—, —O—, —O—CH$_2$— and —OCH$_2$—CH$_2$— m is 1, 2, or 3;

n is 1, 2, or 3;

$R^{1-III}$ is selected from the group consisting of hydrogen, halogen, hydroxyl, cyano, —NR$^a$R$^b$, C$_{1-2}$alkyl (optionally substituted by one, two or three halogens) and C$_{1-2}$alkoxy (optionally substituted by one, two or three halogens);

$R^{2-III}$ is selected from the group consisting of hydrogen, C$_{1-4}$alkyl, —C(O)—C$_{1-4}$alkyl, —C(O)—O—C$_{1-4}$alkyl, —C(O)—N(R$^a$)—C$_{1-4}$alkyl, —S(O)$_2$—C$_{1-4}$alkyl and —S(O)$_2$—C$_{3-6}$cycloalkyl; wherein C$_{1-4}$alkyl, —C(O)—C$_{1-4}$alkyl, —C(O)—O—C$_{1-4}$alkyl, —C(O)—N(R$^a$)—C$_{1-4}$alkyl, —S(O)$_2$—C$_{1-4}$alkyl and —S(O)$_2$—C$_{3-6}$cycloalkyl may optionally be substituted by one, two or three substituents each independently selected from the group consisting of halogen, hydroxyl, cyano, —NR$^a$R$^b$, C$_{1-2}$alkyl (optionally substituted by one, two or three halogens) and C$_{1-2}$alkoxy (optionally substituted by one, two or three halogens);

$R^5$ is selected from the group consisting of hydrogen, deuterium and halogen;

$R^6$ is selected from the group consisting of hydrogen and deuterium;

$R^7$ is selected from the group consisting of hydrogen and deuterium; and $R^a$ and $R^b$ are each independently selected for each occurrence from the group consisting of hydrogen and C$_{1-3}$alkyl.

In some embodiments, $X^{III}$ is selected from the group consisting of a bond, —CH$_2$, —O—, —NH— and —O—CH$_2$—.

In other embodiments, $R^{2-III}$ is selected from the group consisting of hydrogen, isopropyl, —CH$_2$CF$_3$, —S(O)$_2$—CH$_3$ and —S(O)$_2$-cyclopropyl.

In further embodiments, $R^5$ is selected from the group consisting of hydrogen, deuterium, and fluorine.

Further disclosed herein is a compound selected from the group consisting of:

5-{1-fluoro-3-hydroxy-7-[2-(morpholin-4-yl)ethoxy]naphthalen-2-yl}-1λ$^6$,2,5-thiadiazolidine-1,1,3-trione;

5-{7-[1-(cyclopropanesulfonyl)pyrrolidin-3-yl]-1-fluoro-3-hydroxynaphthalen-2-yl}-1λ$^6$,2,5-thiadiazolidine-1,1,3-trione;

5-[1-fluoro-3-hydroxy-7-(pyrrolidin-3-yl)naphthalen-2-yl]-1λ$^6$,2,5-thiadiazolidine-1,1,3-trione;

8-fluoro-6-hydroxy-7-(1,1,4-trioxo-1λ$^6$,2,5-thiadiazolidin-2-yl)naphthalen-2-yl propan-2-ylcarbamate;

5-(9-fluoro-7-hydroxynaphtho[2,1-b]furan-8-yl)-1λ$^6$,2,5-thiadiazolidine-1,1,3-trione; 5-{7-[2-(azetidin-1-yl)ethoxy]-1-fluoro-3-hydroxynaphthalen-2-yl}-1λ$^6$,2,5-thiadiazolidine-1,1,3-trione;

5-[1-fluoro-3-hydroxy-7-methoxy(4-$^2$H)naphthalen-2-yl](4,4-$^2$H$_2$)-1λ$^6$,2,5-thiadiazolidine-1,1,3-trione;

5-[1-fluoro-3-hydroxy-7-(methylamino)naphthalen-2-yl]-1λ$^6$,2,5-thiadiazolidine-1,1,3-trione;

5-{1-fluoro-3-hydroxy-7-[2-(piperidin-4-yl)ethoxy]naphthalen-2-yl}-1λ$^6$,2,5-thiadiazolidine-1,1,3-trione;

5-(1-fluoro-7-{[3-fluoro-1-(propan-2-yl)pyrrolidin-3-yl]methoxy}-3-hydroxynaphthalen-2-yl)-1λ$^6$,2,5-thiadiazolidine-1,1,3-trione;

5-{1-fluoro-7-[(3-fluoropyrrolidin-3-yl)methoxy]-3-hydroxynaphthalen-2-yl}-1λ$^6$,2,5-thiadiazolidine-1,1,3-trione;

5-{[8-fluoro-6-hydroxy-7-(1,1,4-trioxo-1λ$^6$,2,5-thiadiazolidin-2-yl)naphthalen-2-yl]oxy}pentanenitrile;

5-{1-fluoro-3-hydroxy-7-[2-(piperidin-1-yl)ethoxy]naphthalen-2-yl}-1λ$^6$,2,5-thiadiazolidine-1,1,3-trione;

5-{7-[1-(cyclopropanesulfonyl)-2,5-dihydro-1H-pyrrol-3-yl]-1-fluoro-3-hydroxynaphthalen-2-yl}-1λ$^6$,2,5-thiadiazolidine-1,1,3-trione;

5-{1-fluoro-3-hydroxy-7-[(piperidin-4-yl)methoxy]naphthalen-2-yl}-1λ$^6$,2,5-thiadiazolidine-1,1,3-trione;

5-{[8-fluoro-6-hydroxy-7-(1,1,4-trioxo-1λ$^6$,2,5-thiadiazolidin-2-yl)naphthalen-2-yl]oxy}-3,3-dimethylpentanenitrile;

5-{7-[(3,3-dimethylbutyl)amino]-1-fluoro-3-hydroxynaphthalen-2-yl}-1λ$^6$,2,5-thiadiazolidine-1,1,3-trione;

5-(1,4-difluoro-3-hydroxy-7-methoxynaphthalen-2-yl)-1λ$^6$,2,5-thiadiazolidine-1,1,3-trione;

5-{1-fluoro-3-hydroxy-7-[($^2$H3)methyloxy]naphthalen-2-yl}-1λ$^6$,2,5-thiadiazolidine-1,1,3-trione;
5-[1-fluoro-3-hydroxy-7-(2-methoxyethoxy)naphthalen-2-yl]-1λ$^6$,2,5-thiadiazolidine-1,1,3-trione;
4-{[8-fluoro-6-hydroxy-7-(1,1,4-trioxo-1λ$^6$,2,5-thiadiazolidin-2-yl)naphthalen-2-yl]oxy}-2,2-dimethylbutanenitrile;
5-{7-[2-(3-aminobicyclo[1.1.1]pentan-1-yl)ethoxy]-1-fluoro-3-hydroxynaphthalen-2-yl}-1λ$^6$,2,5-thiadiazolidine-1,1,3-trione;
5-(7-{[2-(dimethylamino)ethyl]amino}-1-fluoro-3-hydroxynaphthalen-2-yl)-1λ$^6$,2,5-thiadiazolidine-1,1,3-trione;
5-(1-fluoro-3-hydroxy-7-methoxynaphthalen-2-yl)(4,4-$^2$H$_2$)-1λ$^6$,2,5-thiadiazolidine-1,1,3-trione;
5-(1-fluoro-3-hydroxy-7-methoxynaphthalen-2-yl)-1λ$^6$,2,5-thiadiazolidine-1,1,3-trione;
N-(2-{[8-fluoro-6-hydroxy-7-(1,1,4-trioxo-1λ$^6$,2,5-thiadiazolidin-2-yl)naphthalen-2-yl]amino}ethyl)cyclopropanesulfonamide;
5-(1-fluoro-3-hydroxy-7-{[1-(methanesulfonyl)pyrrolidin-3-yl]amino}naphthalen-2-yl)-1λ$^6$,2,5-thiadiazolidine-1,1,3-trione;
N-(2-{[8-fluoro-6-hydroxy-7-(1,1,4-trioxo-1λ$^6$,2,5-thiadiazolidin-2-yl)naphthalen-2-yl]oxy}ethyl)cyclopropanesulfonamide5-(1-fluoro-3-hydroxy-7-{[1-(methanesulfonyl)azetidin-3-yl]amino}naphthalen-2-yl)-1λ$^6$,2,5-thiadiazolidine-1,1,3-trione;
4-{[8-fluoro-6-hydroxy-7-(1,1,4-trioxo-1λ$^6$,2,5-thiadiazolidin-2-yl)naphthalen-2-yl]oxy}butanenitrile;
[1-({[8-fluoro-6-hydroxy-7-(1,1,4-trioxo-1λ$^6$,2,5-thiadiazolidin-2-yl)naphthalen-2-yl]oxy}methyl)cyclopropyl]acetonitrile;
5-{7-[2-(dimethylamino)ethoxy]-1-fluoro-3-hydroxynaphthalen-2-yl}-1λ$^6$,2,5-thiadiazolidine-1,1,3-trione;
5-{7-[1-(cyclopropylmethyl)-1H-pyrazol-4-yl]-1-fluoro-3-hydroxynaphthalen-2-yl}-1λ$^6$,2,5-thiadiazolidine-1,1,3-trione;
5-{1-fluoro-3-hydroxy-7-[(1H-pyrazol-4-yl)methoxy]naphthalen-2-yl}-1λ$^6$,2,5-thiadiazolidine-1,1,3-trione;
5-[1-fluoro-3-hydroxy-7-(2-methylpropoxy)naphthalen-2-yl]-1λ$^6$,2,5-thiadiazolidine-1,1,3-trione;
5-[1-fluoro-3-hydroxy-7-(2-hydroxypropoxy)naphthalen-2-yl]-1λ$^6$,2,5-thiadiazolidine-1,1,3-trione;
N-(cyclopropylmethyl)-8-fluoro-6-hydroxy-7-(1,1,4-trioxo-1λ$^6$,2,5-thiadiazolidin-2-yl)naphthalene-2-carboxamide;
5-[1-fluoro-3-hydroxy-7-(2-{[2-(trifluoromethoxy)ethyl]amino}ethoxy)naphthalen-2-yl]-1λ$^6$,2,5-thiadiazolidine-1,1,3-trione;
5-(1-fluoro-3-hydroxy-7-{2-[(2-methoxyethyl)amino]ethoxy}naphthalen-2-yl)-1λ$^6$,2,5-thiadiazolidine-1,1,3-trione;
5-{1-fluoro-3-hydroxy-7-[3-(methylamino)propyl]naphthalen-2-yl}-1λ$^6$,2,5-thiadiazolidine-1,1,3-trione;
5-{7-[3-(ethylamino)propyl]-1-fluoro-3-hydroxynaphthalen-2-yl}-1λ$^6$,2,5-thiadiazolidine-1,1,3-trione;
5-{7-[5-(dimethylphosphoryl)thiophen-2-yl]-1-fluoro-3-hydroxynaphthalen-2-yl}-1λ$^6$,2,5-thiadiazolidine-1,1,3-trione;
5-{7-[2-(cyclopropylamino)ethoxy]-1-fluoro-3-hydroxynaphthalen-2-yl}-1λ$^6$,2,5-thiadiazolidine-1,1,3-trione;
5-{1-fluoro-3-hydroxy-7-[2-(methylamino)ethoxy]naphthalen-2-yl}-1λ$^6$,2,5-thiadiazolidine-1,1,3-trione;
5-{7-[2-(ethylamino)ethoxy]-1-fluoro-3-hydroxynaphthalen-2-yl}-1λ$^6$,2,5-thiadiazolidine-1,1,3-trione;
5-(1-fluoro-3-hydroxy-7-{2-[(propan-2-yl)amino]ethoxy}naphthalen-2-yl)-1λ$^6$,2,5-thiadiazolidine-1,1,3-trione;
5-{7-[3-(diethylphosphoryl)propoxy]-1-fluoro-3-hydroxynaphthalen-2-yl}-1λ$^6$,2,5-thiadiazolidine-1,1,3-trione;
5-{1-fluoro-3-hydroxy-7-[(3S)-3-hydroxybutoxy]naphthalen-2-yl}-1λ$^6$,2,5-thiadiazolidine-1,1,3-trione;
5-{1,4-difluoro-3-hydroxy-7-[(3-methylbutyl)amino]naphthalen-2-yl}-1λ$^6$,2,5-thiadiazolidine-1,1,3-trione;
5-{1-fluoro-3-hydroxy-7-[(3R)-3-hydroxybutoxy]naphthalen-2-yl}-1λ$^6$,2,5-thiadiazolidine-1,1,3-trione;
5-[7-(2-cyclopropyl-2-hydroxyethoxy)-1-fluoro-3-hydroxynaphthalen-2-yl]-1λ$^6$,2,5-thiadiazolidine-1,1,3-trione;
5-{1-fluoro-3-hydroxy-7-[(4R)-4-hydroxypentyl]naphthalen-2-yl}-1λ$^6$,2,5-thiadiazolidine-1,1,3-trione;
5-{1-fluoro-3-hydroxy-7-[(4R)-4-hydroxypentyl]naphthalen-2-yl}-1λ$^6$,2,5-thiadiazolidine-1,1,3-trione;
5-{1-fluoro-3-hydroxy-7-[(4S)-4-hydroxypentyl]naphthalen-2-yl}-1λ$^6$,2,5-thiadiazolidine-1,1,3-trione;
5-[1-fluoro-3-hydroxy-7-(4-hydroxy-4-methylpentyl)naphthalen-2-yl]-1λ$^6$,2,5-thiadiazolidine-1,1,3-trione;
5-{1-fluoro-3-hydroxy-7-[(3-oxopentyl)oxy]naphthalen-2-yl}-1λ$^6$,2,5-thiadiazolidine-1,1,3-trione;
5-[1-fluoro-3-hydroxy-7-(3-hydroxybutoxy)naphthalen-2-yl]-1λ$^6$,2,5-thiadiazolidine-1,1,3-trione;
N-[8-fluoro-6-hydroxy-7-(1,1,4-trioxo-1λ$^6$,2,5-thiadiazolidin-2-yl)naphthalen-2-yl]-3-methylbutanamide;
5-[1-fluoro-3-hydroxy-7-(4,4,4-trifluorobutoxy)naphthalen-2-yl]-1λ$^6$,2,5-thiadiazolidine-1,1,3-trione;
1-(2-{[8-fluoro-6-hydroxy-7-(1,1,4-trioxo-1λ$^6$,2,5-thiadiazolidin-2-yl)naphthalen-2-yl]oxy}ethyl)cyclopropane-1-carbonitrile;
5-(1-fluoro-3-hydroxy-7-{2-[1-(methoxymethyl)cyclopropyl]ethoxy}naphthalen-2-yl)-1λ$^6$,2,5-thiadiazolidine-1,1,3-trione;
5-(7-{[(cyclopropylmethyl)amino]methyl}-1-fluoro-3-hydroxynaphthalen-2-yl)-1λ$^6$,2,5-thiadiazolidine-1,1,3-trione;
5-{7-[(2,2-difluoropropyl)amino]-1-fluoro-3-hydroxynaphthalen-2-yl}-1λ$^6$,2,5-thiadiazolidine-1,1,3-trione;
5-{7-[3,3-dimethyl-4-(methylamino)butoxy]-1-fluoro-3-hydroxynaphthalen-2-yl}-1λ$^6$,2,5-thiadiazolidine-1,1,3-trione;
5-{1-fluoro-3-hydroxy-7-[(2-phenylethyl)amino]naphthalen-2-yl}-1λ$^6$,2,5-thiadiazolidine-1,1,3-trione;
5-[7-(3-amino-3-methylbutoxy)-1-fluoro-3-hydroxynaphthalen-2-yl]-1λ$^6$,2,5-thiadiazolidine-1,1,3-trione;
5-{1-fluoro-3-hydroxy-7-[(4,4,4-trifluorobutyl)amino]naphthalen-2-yl}-1λ$^6$,2,5-thiadiazolidine-1,1,3-trione;
5-[7-(difluoromethyl)-1-fluoro-3-hydroxynaphthalen-2-yl]-1λ$^6$,2,5-thiadiazolidine-1,1,3-trione;
5-{7-[1-(dimethylphosphoryl)-2,5-dihydro-1H-pyrrol-3-yl]-1-fluoro-3-hydroxynaphthalen-2-yl}-1λ$^6$,2,5-thiadiazolidine-1,1,3-trione;
5-{1-fluoro-3-hydroxy-7-[(3,3,3-trifluoropropyl)amino]naphthalen-2-yl}-1λ$^6$,2,5-thiadiazolidine-1,1,3-trione;
5-[1-fluoro-3-hydroxy-7-(3-methoxy-3-methylbutoxy)naphthalen-2-yl]-1λ$^6$,2,5-thiadiazolidine-1,1,3-trione;
5-[7-(2-cyclopropylpropoxy)-1-fluoro-3-hydroxynaphthalen-2-yl]-1λ$^6$,2,5-thiadiazolidine-1,1,3-trione;
5-[1-fluoro-3-hydroxy-7-({2-[(propan-2-yl)oxy]ethyl}amino)naphthalen-2-yl]-1λ$^6$,2,5-thiadiazolidine-1,1,3-trione;

5-(1-fluoro-3-hydroxy-7-{[1-(methanesulfonyl)pyrrolidin-3-yl]methoxy}naphthalen-2-yl)-1λ$^6$,2,5-thiadiazolidine-1,1,3-trione;

4-{[8-fluoro-6-hydroxy-7-(1,1,4-trioxo-1λ$^6$,2,5-thiadiazolidin-2-yl)naphthalen-2-yl]amino}butanenitrile;

5-[1-fluoro-3-hydroxy-7-(2-hydroxyethyl)naphthalen-2-yl]-1λ$^6$,2,5-thiadiazolidine-1,1,3-trione;

5-[7-(4-amino-3,3-dimethylbutoxy)-1-fluoro-3-hydroxynaphthalen-2-yl]-1λ$^6$,2,5-thiadiazolidine-1,1,3-trione;

5-(7-{[2-(azetidin-1-yl)ethyl]amino}-1-fluoro-3-hydroxynaphthalen-2-yl)-1λ$^6$,2,5-thiadiazolidine-1,1,3-trione;

5-(7-{[1-(cyclopropanesulfonyl)azetidin-3-yl]oxy}-1-fluoro-3-hydroxynaphthalen-2-yl)-1λ$^6$,2,5-thiadiazolidine-1,1,3-trione;

5-{1-fluoro-3-hydroxy-7-[(2-methoxyethyl)amino]naphthalen-2-yl}-1λ$^6$,2,5-thiadiazolidine-1,1,3-trione;

5-[1-fluoro-3-hydroxy-7-(3,3,3-trifluoropropoxy)naphthalen-2-yl]-1λ$^6$,2,5-thiadiazolidine-1,1,3-trione;

1-({[8-fluoro-6-hydroxy-7-(1,1,4-trioxo-1λ$^6$,2,5-thiadiazolidin-2-yl)naphthalen-2-yl]amino}methyl)cyclopropane-1-carbonitrile;

5-[1-fluoro-3-hydroxy-7-(3-hydroxy-3-methylbutoxy)naphthalen-2-yl]-1λ$^6$,2,5-thiadiazolidine-1,1,3-trione;

5-{1-fluoro-3-hydroxy-7-[3-(1H-pyrazol-1-yl)propoxy]naphthalen-2-yl}-1λ$^6$,2,5-thiadiazolidine-1,1,3-trione;

5-(7-{1-[(4-aminophenyl)methanesulfonyl]-2,5-dihydro-1H-pyrrol-3-yl}-1-fluoro-3-hydroxynaphthalen-2-yl)-1λ$^6$,2,5-thiadiazolidine-1,1,3-trione;

5-[1-fluoro-3-hydroxy-7-(hydroxymethyl)naphthalen-2-yl]-1λ$^6$,2,5-thiadiazolidine-1,1,3-trione;

5-{7-[1-(cyclopropanesulfonyl)piperidin-3-yl]-1-fluoro-3-hydroxynaphthalen-2-yl}-1λ$^6$,2,5-thiadiazolidine-1,1,3-trione;

5-{7-[1-(cyclopropanecarbonyl)pyrrolidin-2-yl]-1-fluoro-3-hydroxynaphthalen-2-yl}-1λ$^6$,2,5-thiadiazolidine-1,1,3-trione;

5-{1-fluoro-3-hydroxy-7-[2-(1H-pyrazol-1-yl)ethoxy]naphthalen-2-yl}-1λ$^6$,2,5-thiadiazolidine-1,1,3-trione;

5-{7-[1-(cyclopropanesulfonyl)pyrrolidin-2-yl]-1-fluoro-3-hydroxynaphthalen-2-yl}-1λ$^6$,2,5-thiadiazolidine-1,1,3-trione;

5-{7-[1-(cyclopropanesulfonyl)pyrrolidin-2-yl]-1-fluoro-3-hydroxynaphthalen-2-yl}-1λ$^6$,2,5-thiadiazolidine-1,1,3-trione;

5-[1-fluoro-3-hydroxy-7-(piperidin-3-yl)naphthalen-2-yl]-1λ$^6$,2,5-thiadiazolidine-1,1,3-trione;

5-{7-[2-(2,2-difluorocyclopropyl)ethoxy]-1-fluoro-3-hydroxynaphthalen-2-yl}-1λ$^6$,2,5-thiadiazolidine-1,1,3-trione;

5-{1-fluoro-3-hydroxy-7-[2-(1-methylcyclopropyl)ethoxy]naphthalen-2-yl}-1λ$^6$,2,5-thiadiazolidine-1,1,3-trione;

5-(7-{1-[(3-aminophenyl)methanesulfonyl]-2,5-dihydro-1H-pyrrol-3-yl}-1-fluoro-3-hydroxynaphthalen-2-yl)-1λ$^6$,2,5-thiadiazolidine-1,1,3-trione;

5-(7-{1-[(2-aminophenyl)methanesulfonyl]-2,5-dihydro-1H-pyrrol-3-yl}-1-fluoro-3-hydroxynaphthalen-2-yl)-1λ$^6$,2,5-thiadiazolidine-1,1,3-trione;

5-[7-(2,2-difluoroethyl)-1-fluoro-3-hydroxynaphthalen-2-yl]-1λ$^6$,2,5-thiadiazolidine-1,1,3-trione;

5-[1-fluoro-3-hydroxy-7-(2,2,2-trifluoroethoxy)naphthalen-2-yl]-1λ$^6$,2,5-thiadiazolidine-1,1,3-trione;

5-[1-fluoro-7-(2-fluoroethoxy)-3-hydroxynaphthalen-2-yl]-1λ$^6$,2,5-thiadiazolidine-1,1,3-trione;

1-({[8-fluoro-6-hydroxy-7-(1,1,4-trioxo-1λ$^6$,2,5-thiadiazolidin-2-yl)naphthalen-2-yl]oxy}methyl)cyclopropane-1-carbonitrile;

5-{1-fluoro-3-hydroxy-7-[(3-methylbutyl)amino]naphthalen-2-yl}-1λ$^6$,2,5-thiadiazolidine-1,1,3-trione;

5-{1-fluoro-3-hydroxy-7-[(2-methylpropyl)amino]naphthalen-2-yl}-1λ$^6$,2,5-thiadiazolidine-1,1,3-trione;

5-{7-[(cyclopropylmethyl)amino]-1-fluoro-3-hydroxynaphthalen-2-yl}-1λ$^6$,2,5-thiadiazolidine-1,1,3-trione;

{[8-fluoro-6-hydroxy-7-(1,1,4-trioxo-1λ$^6$,2,5-thiadiazolidin-2-yl)naphthalen-2-yl]oxy}acetonitrile;

5-[1-fluoro-3-hydroxy-7-(3-methylbutoxy)naphthalen-2-yl]-1λ$^6$,2,5-thiadiazolidine-1,1,3-trione;

5-(1,8-difluoro-3-hydroxy-7-methoxynaphthalen-2-yl)-1λ$^6$,2,5-thiadiazolidine-1,1,3-trione;

5-{7-[1-(cyclopropanesulfonyl)azetidin-3-yl]-1-fluoro-3-hydroxynaphthalen-2-yl}-1λ$^6$,2,5-thiadiazolidine-1,1,3-trione;

5-{7-[1-(cyclopropanecarbonyl)azetidin-3-yl]-1-fluoro-3-hydroxynaphthalen-2-yl}-1λ$^6$,2,5-thiadiazolidine-1,1,3-trione;

(2E)-3-[8-fluoro-6-hydroxy-7-(1,1,4-trioxo-1λ$^6$,2,5-thiadiazolidin-2-yl)naphthalen-2-yl]prop-2-enenitrile;

5-[7-(2-cyclopropylethyl)-1-fluoro-3-hydroxynaphthalen-2-yl]-1λ$^6$,2,5-thiadiazolidine-1,1,3-trione;

5-{7-[(2,2-difluorocyclopropyl)methoxy]-1-fluoro-3-hydroxynaphthalen-2-yl}-1λ$^6$,2,5-thiadiazolidine-1,1,3-trione;

5-[7-(2-cyclopropylethoxy)-1-fluoro-3-hydroxynaphthalen-2-yl]-1λ$^6$,2,5-thiadiazolidine-1,1,3-trione;

5-{7-[2-(cyclopropylmethoxy)ethoxy]-1-fluoro-3-hydroxynaphthalen-2-yl}-1λ$^6$,2,5-thiadiazolidine-1,1,3-trione;

5-{1-fluoro-3-hydroxy-7-[2-(oxolan-2-yl)ethoxy]naphthalen-2-yl}-1λ$^6$,2,5-thiadiazolidine-1,1,3-trione;

5-{7-[2-(cyclobutyloxy)ethoxy]-1-fluoro-3-hydroxynaphthalen-2-yl}-1λ$^6$,2,5-thiadiazolidine-1,1,3-trione;

5-(1-fluoro-3-hydroxy-7-{2-[(propan-2-yl)oxy]ethoxy}naphthalen-2-yl)-1λ$^6$,2,5-thiadiazolidine-1,1,3-trione;

5-[7-(3-ethoxypropoxy)-1-fluoro-3-hydroxynaphthalen-2-yl]-1λ$^6$,2,5-thiadiazolidine-1,1,3-trione;

5-[7-(2-tert-butoxyethoxy)-1-fluoro-3-hydroxynaphthalen-2-yl]-1λ$^6$,2,5-thiadiazolidine-1,1,3-trione;

5-(7-{[rac-(1R,2R)-2-ethylcyclopropyl]methoxy}-1-fluoro-3-hydroxynaphthalen-2-yl)-1λ$^6$,2,5-thiadiazolidine-1,1,3-trione;

5-[1-fluoro-3-hydroxy-7-(4-methylpentyl)naphthalen-2-yl]-1λ$^6$,2,5-thiadiazolidine-1,1,3-trione;

5-{7-[3-(2,2-dimethylpropyl)pyrrolidin-1-yl]-1-fluoro-3-hydroxynaphthalen-2-yl}-1λ$^6$,2,5-thiadiazolidine-1,1,3-trione;

5-[7-(1-chloro-3-hydroxypropan-2-yl)-1-fluoro-3-hydroxynaphthalen-2-yl]-1λ$^6$,2,5-thiadiazolidine-1,1,3-trione;

5-{7-[1-(cyclopropylmethyl)pyrrolidin-3-yl]-1-fluoro-3-hydroxynaphthalen-2-yl}-1λ$^6$,2,5-thiadiazolidine-1,1,3-trione;

5-[7-(cyclopropyloxy)-1-fluoro-3-hydroxynaphthalen-2-yl]-1λ$^6$,2,5-thiadiazolidine-1,1,3-trione;

5-{7-[(2-cyclopropylethyl)amino]-1-fluoro-3-hydroxynaphthalen-2-yl}-1λ$^6$,2,5-thiadiazolidine-1,1,3-trione;

5-[1-fluoro-3-hydroxy-7-(4-methyl-1H-imidazol-2-yl)naphthalen-2-yl]-1λ$^6$,2,5-thiadiazolidine-1,1,3-trione;

5-[7-(azetidin-3-yl)-1-fluoro-3-hydroxynaphthalen-2-yl]-1λ$^6$,2,5-thiadiazolidine-1,1,3-trione;

5-[1-fluoro-3-hydroxy-7-(5-methoxythiophen-2-yl)naphthalen-2-yl]-1λ⁶,2,5-thiadiazolidine-1,1,3-trione;
[8-fluoro-6-hydroxy-7-(1,1,4-trioxo-1λ⁶,2,5-thiadiazolidin-2-yl)naphthalen-2-yl]acetonitrile;
5-[1-fluoro-3-hydroxy-7-(methoxymethyl)naphthalen-2-yl]-1λ⁶,2,5-thiadiazolidine-1,1,3-trione;
5-{1-fluoro-3-hydroxy-7-[(3-methyloxetan-3-yl)methoxy]naphthalen-2-yl}-1λ⁶,2,5-thiadiazolidine-1,1,3-trione;
5-{4-bromo-7-[1-(cyclopropanesulfonyl)-2,5-dihydro-1H-pyrrol-3-yl]-1-fluoro-3-hydroxynaphthalen-2-yl}-1λ⁶,2,5-thiadiazolidine-1,1,3-trione;
5-{4-bromo-7-[1-(cyclopropanesulfonyl)-1H-pyrrol-3-yl]-1-fluoro-3-hydroxynaphthalen-2-yl}-1λ⁶,2,5-thiadiazolidine-1,1,3-trione;
5-{1-fluoro-3-hydroxy-7-[(3S)-pyrrolidin-3-yl]naphthalen-2-yl}-1λ⁶,2,5-thiadiazolidine-1,1,3-trione;
5-{1-fluoro-3-hydroxy-7-[(3R)-pyrrolidin-3-yl]naphthalen-2-yl}-1λ⁶,2,5-thiadiazolidine-1,1,3-trione;
5-(8-chloro-1-fluoro-3-hydroxy-7-methoxynaphthalen-2-yl)-1λ⁶,2,5-thiadiazolidine-1,1,3-trione;
5-{7-[(3,3-difluorocyclobutyl)methoxy]-1-fluoro-3-hydroxynaphthalen-2-yl}-1λ⁶,2,5-thiadiazolidine-1,1,3-trione;
5-(7-cyclopropyl-1-fluoro-3-hydroxynaphthalen-2-yl)-1λ⁶,2,5-thiadiazolidine-1,1,3-trione;
5-{7-[1-(cyclopropanecarbonyl)-2,5-dihydro-1H-pyrrol-3-yl]-1-fluoro-3-hydroxynaphthalen-2-yl}-1λ⁶,2,5-thiadiazolidine-1,1,3-trione;
5-(4-chloro-1-fluoro-3-hydroxy-7-methoxynaphthalen-2-yl)-1λ⁶,2,5-thiadiazolidine-1,1,3-trione;
5-{7-[(E)-2-cyclopropylethenyl]-1-fluoro-3-hydroxynaphthalen-2-yl}-1λ⁶,2,5-thiadiazolidine-1,1,3-trione;
5-{1-fluoro-3-hydroxy-7-[(1E)-4-methylpent-1-en-1-yl]naphthalen-2-yl}-1λ⁶,2,5-thiadiazolidine-1,1,3-trione;
5-{1-fluoro-3-hydroxy-7-[1-(pentamethylphenyl)ethenyl]naphthalen-2-yl}-1λ⁶,2,5-thiadiazolidine-1,1,3-trione;
5-{7-[1-(cyclopropylmethyl)-2,5-dihydro-1H-pyrrol-3-yl]-1-fluoro-3-hydroxynaphthalen-2-yl}-1λ⁶,2,5-thiadiazolidine-1,1,3-trione;
5-(4-bromo-1-fluoro-3-hydroxy-7-methoxynaphthalen-2-yl)-1λ⁶,2,5-thiadiazolidine-1,1,3-trione;
5-{7-[1-(2-cyclopropylethyl)-2,5-dihydro-1H-pyrrol-3-yl]-1-fluoro-3-hydroxynaphthalen-2-yl}-1λ⁶,2,5-thiadiazolidine-1,1,3-trione;
5-{1-fluoro-3-hydroxy-7-[(1E)-3-methoxyprop-1-en-1-yl]naphthalen-2-yl}-1λ⁶,2,5-thiadiazolidine-1,1,3-trione;
5-[7-(2-ethoxyethoxy)-1-fluoro-3-hydroxynaphthalen-2-yl]-1λ⁶,2,5-thiadiazolidine-1,1,3-trione;
5-[1-fluoro-3-hydroxy-7-(3-methoxypropoxy)naphthalen-2-yl]-1λ⁶,2,5-thiadiazolidine-1,1,3-trione;
5-[7-(1,1-dioxo-1λ⁶-thian-4-yl)-1-fluoro-3-hydroxynaphthalen-2-yl]-1λ⁶,2,5-thiadiazolidine-1,1,3-trione;
5-[1-fluoro-3-hydroxy-7-(oxan-3-yl)naphthalen-2-yl]-1λ⁶,2,5-thiadiazolidine-1,1,3-trione;
5-[7-(cyclopropylmethoxy)-1-fluoro-3-hydroxynaphthalen-2-yl]-1λ⁶,2,5-thiadiazolidine-1,1,3-trione;
5-(1-fluoro-3-hydroxy-7-{[1-(2,2,2-trifluoroethyl)pyrrolidin-3-yl]methyl}naphthalen-2-yl)-1λ⁶,2,5-thiadiazolidine-1,1,3-trione;
5-(1-fluoro-3-hydroxy-7-{[1-(2,2,2-trifluoroethyl)piperidin-4-yl]methyl}naphthalen-2-yl)-1λ⁶,2,5-thiadiazolidine-1,1,3-trione;
5-(1-fluoro-3-hydroxy-7-{2-[methyl(2-methylpropyl)amino]ethoxy}naphthalen-2-yl)-1λ⁶,2,5-thiadiazolidine-1,1,3-trione;
5-{1-fluoro-3-hydroxy-7-[(oxolan-2-yl)methoxy]naphthalen-2-yl}-1λ⁶,2,5-thiadiazolidine-1,1,3-trione;
5-[1-fluoro-3-hydroxy-7-(oxolan-3-yl)naphthalen-2-yl]-1λ⁶,2,5-thiadiazolidine-1,1,3-trione;
5-(7-{[1-(cyclopropanesulfonyl)azetidin-3-yl]methyl}-1-fluoro-3-hydroxynaphthalen-2-yl)-1λ⁶,2,5-thiadiazolidine-1,1,3-trione;
5-(7-{[1-(cyclopropanesulfonyl)piperidin-4-yl]methyl}-1-fluoro-3-hydroxynaphthalen-2-yl)-1λ⁶,2,5-thiadiazolidine-1,1,3-trione;
5-[1-fluoro-3-hydroxy-7-(pyrrolidin-2-yl)naphthalen-2-yl]-1λ⁶,2,5-thiadiazolidine-1,1,3-trione;
5-(7-{[1-(cyclopropanesulfonyl)piperidin-3-yl]methyl}-1-fluoro-3-hydroxynaphthalen-2-yl)-1λ⁶,2,5-thiadiazolidine-1,1,3-trione;
5-[7-(difluoromethoxy)-1-fluoro-3-hydroxynaphthalen-2-yl]-1λ⁶,2,5-thiadiazolidine-1,1,3-trione;
5-(7-{[1-(cyclopropanesulfonyl)pyrrolidin-3-yl]methyl}-1-fluoro-3-hydroxynaphthalen-2-yl)-1λ⁶,2,5-thiadiazolidine-1,1,3-trione;
5-{1-fluoro-3-hydroxy-7-[(pyrrolidin-3-yl)methyl]naphthalen-2-yl}-1λ⁶,2,5-thiadiazolidine-1,1,3-trione;
5-[7-(2,5-dihydrofuran-3-yl)-1-fluoro-3-hydroxynaphthalen-2-yl]-1λ⁶,2,5-thiadiazolidine-1,1,3-trione;
5-[7-(3,6-dihydro-2H-pyran-4-yl)-1-fluoro-3-hydroxynaphthalen-2-yl]-1λ⁶,2,5-thiadiazolidine-1,1,3-trione;
5-[7-(2,5-dihydro-1H-pyrrol-3-yl)-1-fluoro-3-hydroxynaphthalen-2-yl]-1λ⁶,2,5-thiadiazolidine-1,1,3-trione;
5-[1-fluoro-3-hydroxy-7-(pyridin-3-yl)naphthalen-2-yl]-1λ⁶,2,5-thiadiazolidine-1,1,3-trione;
5-{7-[(azetidin-3-yl)methyl]-1-fluoro-3-hydroxynaphthalen-2-yl}-1λ⁶,2,5-thiadiazolidine-1,1,3-trione;
N-(2-cyclopropylethyl)-2-{[8-fluoro-6-hydroxy-7-(1,1,4-trioxo-1λ⁶,2,5-thiadiazolidin-2-yl)naphthalen-2-yl]amino}acetamide;
4-{[8-fluoro-6-hydroxy-7-(1,1,4-trioxo-1λ⁶,2,5-thiadiazolidin-2-yl)naphthalen-2-yl]oxy}-N-methylbutanamide;
N-ethyl-N-(2-{[8-fluoro-6-hydroxy-7-(1,1,4-trioxo-1λ⁶,2,5-thiadiazolidin-2-yl)naphthalen-2-yl]oxy}ethyl)urea;
5-{1-fluoro-3-hydroxy-7-[(oxan-3-yl)methoxy]naphthalen-2-yl}-1λ⁶,2,5-thiadiazolidine-1,1,3-trione;
5-{7-[(1-chloro-3-hydroxypropan-2-yl)oxy]-1-fluoro-3-hydroxynaphthalen-2-yl}-1λ⁶,2,5-thiadiazolidine-1,1,3-trione;
5-{1-fluoro-3-hydroxy-7-[(oxan-4-yl)methoxy]naphthalen-2-yl}-1λ⁶,2,5-thiadiazolidine-1,1,3-trione;
5-{1-fluoro-3-hydroxy-7-[(oxetan-3-yl)oxy]naphthalen-2-yl}-1λ⁶,2,5-thiadiazolidine-1,1,3-trione;
5-{1-fluoro-3-hydroxy-7-[1-(2,2,2-trifluoroethyl)-1,2,3,6-tetrahydropyridin-4-yl]naphthalen-2-yl}-1λ⁶,2,5-thiadiazolidine-1,1,3-trione;
5-(1-fluoro-3,7-dihydroxynaphthalen-2-yl)-1λ⁶,2,5-thiadiazolidine-1,1,3-trione;
5-[1-fluoro-3-hydroxy-7-(2-hydroxyethoxy)naphthalen-2-yl]-1λ⁶,2,5-thiadiazolidine-1,1,3-trione;
5-(1-fluoro-3-hydroxy-7-propoxynaphthalen-2-yl)-1λ⁶,2,5-thiadiazolidine-1,1,3-trione;
5-{1-fluoro-3-hydroxy-7-[(propan-2-yl)oxy]naphthalen-2-yl}-1λ⁶,2,5-thiadiazolidine-1,1,3-trione;
{[8-fluoro-6-hydroxy-7-(1,1,4-trioxo-1λ⁶,2,5-thiadiazolidin-2-yl)naphthalen-2-yl]amino}acetic acid;
N-(2-cyclopropylethyl)-2-{[8-fluoro-6-hydroxy-7-(1,1,4-trioxo-1λ⁶,2,5-thiadiazolidin-2-yl)naphthalen-2-yl]oxy}acetamide;
N,N-diethyl-2-{[8-fluoro-6-hydroxy-7-(1,1,4-trioxo-1λ⁶,2,5-thiadiazolidin-2-yl)naphthalen-2-yl]oxy}acetamide;
5-{1-fluoro-3-hydroxy-7-[2-oxo-2-(pyrrolidin-1-yl)ethoxy]naphthalen-2-yl}-1λ⁶,2,5-thiadiazolidine-1,1,3-trione;

5-(1-fluoro-3-hydroxy-7-{[1-(methanesulfonyl)piperidin-4-yl]oxy}naphthalen-2-yl)-1$\lambda^6$,2,5-thiadiazolidine-1,1,3-trione;

5-{1-fluoro-3-hydroxy-7-[1-(oxolane-3-sulfonyl)-2,5-dihydro-1H-pyrrol-3-yl]naphthalen-2-yl}-1$\lambda^6$,2,5-thiadiazolidine-1,1,3-trione;

5-{1-fluoro-3-hydroxy-7-[1-(2-methoxyethanesulfonyl)-2,5-dihydro-1H-pyrrol-3-yl]naphthalen-2-yl}-1$\lambda^6$,2,5-thiadiazolidine-1,1,3-trione;

5-{1-fluoro-3-hydroxy-7-[1-(3,3,3-trifluoropropane-1-sulfonyl)-2,5-dihydro-1H-pyrrol-3-yl]naphthalen-2-yl}-1$\lambda^6$,2,5-thiadiazolidine-1,1,3-trione;

5-{1-fluoro-3-hydroxy-7-[1-(3,3,3-trifluoropropane-1-sulfonyl)-2,5-dihydro-1H-pyrrol-3-yl]naphthalen-2-yl}-1$\lambda^6$,2,5-thiadiazolidine-1,1,3-trione;

5-(1-fluoro-3-hydroxy-7-{1-[(oxan-2-yl)methanesulfonyl]-2,5-dihydro-1H-pyrrol-3-yl}naphthalen-2-yl)-1$\lambda^6$,2,5-thiadiazolidine-1,1,3-trione;

5-{1-fluoro-3-hydroxy-7-[1-(4,4,4-trifluorobutane-1-sulfonyl)-2,5-dihydro-1H-pyrrol-3-yl]naphthalen-2-yl}-1$\lambda^6$,2,5-thiadiazolidine-1,1,3-trione;

5-{7-[1-(butane-1-sulfonyl)-2,5-dihydro-1H-pyrrol-3-yl]-1-fluoro-3-hydroxynaphthalen-2-yl}-1$\lambda^6$,2,5-thiadiazolidine-1,1,3-trione;

5-(7-{1-[(1,4-dioxan-2-yl)methanesulfonyl]-2,5-dihydro-1H-pyrrol-3-yl}-1-fluoro-3-hydroxynaphthalen-2-yl)-1$\lambda^6$,2,5-thiadiazolidine-1,1,3-trione;

5-{3-[8-fluoro-6-hydroxy-7-(1,1,4-trioxo-1$\lambda^6$,2,5-thiadiazolidin-2-yl)naphthalen-2-yl]-2,5-dihydro-1H-pyrrole-1-sulfonyl}pentanenitrile;

5-{1-fluoro-3-hydroxy-7-[1-(pentane-2-sulfonyl)-2,5-dihydro-1H-pyrrol-3-yl]naphthalen-2-yl}-1$\lambda^6$,2,5-thiadiazolidine-1,1,3-trione;

5-{7-[1-(ethanesulfonyl)-2,5-dihydro-1H-pyrrol-3-yl]-1-fluoro-3-hydroxynaphthalen-2-yl}-1$\lambda^6$,2,5-thiadiazolidine-1,1,3-trione;

5-{1-fluoro-3-hydroxy-7-[1-(propane-2-sulfonyl)-2,5-dihydro-1H-pyrrol-3-yl]naphthalen-2-yl}-1$\lambda^6$,2,5-thiadiazolidine-1,1,3-trione;

5-{7-[1-(cyclopropanesulfonyl)-1,2,3,6-tetrahydropyridin-4-yl]-1-fluoro-3-hydroxynaphthalen-2-yl}-1$\lambda^6$,2,5-thiadiazolidine-1,1,3-trione;

N-(2-{[8-fluoro-6-hydroxy-7-(1,1,4-trioxo-1$\lambda^6$,2,5-thiadiazolidin-2-yl)naphthalen-2-yl]oxy}ethyl)oxetane-3-sulfonamide;

5-[1-fluoro-3-hydroxy-7-(piperidin-4-yl)naphthalen-2-yl]-1$\lambda^6$,2,5-thiadiazolidine-1,1,3-trione;

5-{1-fluoro-3-hydroxy-7-[1-(2-methylpropane-1-sulfonyl)-2,5-dihydro-1H-pyrrol-3-yl]naphthalen-2-yl}-1$\lambda^6$,2,5-thiadiazolidine-1,1,3-trione;

5-(7-ethoxy-1-fluoro-3-hydroxynaphthalen-2-yl)-1$\lambda^6$,2,5-thiadiazolidine-1,1,3-trione;

5-[7-(2,2-difluoroethoxy)-1-fluoro-3-hydroxynaphthalen-2-yl]-1$\lambda^6$,2,5-thiadiazolidine-1,1,3-trione;

5-{7-[1-(cyclopropanesulfonyl)-1H-pyrazol-4-yl]-1-fluoro-3-hydroxynaphthalen-2-yl}-1$\lambda^6$,2,5-thiadiazolidine-1,1,3-trione;

5-(1-fluoro-3-hydroxy-7-{[(3R)-1-(methanesulfonyl)pyrrolidin-3-yl]amino}naphthalen-2-yl)-1$\lambda^6$,2,5-thiadiazolidine-1,1,3-trione;

5-(1-fluoro-3-hydroxy-7-{[1-(methanesulfonyl)piperidin-4-yl]amino}naphthalen-2-yl)-1$\lambda^6$,2,5-thiadiazolidine-1,1,3-trione;

5-(7-{[1-(cyclopropanesulfonyl)pyrrolidin-3-yl]amino}-1-fluoro-3-hydroxynaphthalen-2-yl)-1$\lambda^6$,2,5-thiadiazolidine-1,1,3-trione;

5-(1-fluoro-7-{[3-fluoro-1-(methanesulfonyl)pyrrolidin-3-yl]methoxy}-3-hydroxynaphthalen-2-yl)-1$\lambda^6$,2,5-thiadiazolidine-1,1,3-trione;

5-{1-fluoro-3-hydroxy-7-[1-(propane-2-sulfonyl)pyrrolidin-3-yl]naphthalen-2-yl}-1$\lambda^6$,2,5-thiadiazolidine-1,1,3-trione;

5-[7-(2-aminoethoxy)-1-fluoro-3-hydroxynaphthalen-2-yl]-1$\lambda^6$,2,5-thiadiazolidine-1,1,3-trione;

5-{7-[1-(1,3-dimethyl-1H-pyrazole-4-sulfonyl)-2,5-dihydro-1H-pyrrol-3-yl]-1-fluoro-3-hydroxynaphthalen-2-yl}-1$\lambda^6$,2,5-thiadiazolidine-1,1,3-trione;

N-(2-{[8-fluoro-6-hydroxy-7-(1,1,4-trioxo-1$\lambda^6$,2,5-thiadiazolidin-2-yl)naphthalen-2-yl]oxy}ethyl)ethanesulfonamide;

5-{1-fluoro-7-[1-(furan-3-sulfonyl)-2,5-dihydro-1H-pyrrol-3-yl]-3-hydroxynaphthalen-2-yl}-1$\lambda^6$,2,5-thiadiazolidine-1,1,3-trione;

5-{1-fluoro-3-hydroxy-7-[1-(3-methylbutane-1-sulfonyl)-2,5-dihydro-1H-pyrrol-3-yl]naphthalen-2-yl}-1$\lambda^6$,2,5-thiadiazolidine-1,1,3-trione;

5-{1-fluoro-3-hydroxy-7-[1-(thiophene-3-sulfonyl)-2,5-dihydro-1H-pyrrol-3-yl]naphthalen-2-yl}-1$\lambda^6$,2,5-thiadiazolidine-1,1,3-trione;

5-{7-[1-(benzenesulfonyl)-2,5-dihydro-1H-pyrrol-3-yl]-1-fluoro-3-hydroxynaphthalen-2-yl}-1$\lambda^6$,2,5-thiadiazolidine-1,1,3-trione;

5-{7-[1-(cyclobutanesulfonyl)-2,5-dihydro-1H-pyrrol-3-yl]-1-fluoro-3-hydroxynaphthalen-2-yl}-1$\lambda^6$,2,5-thiadiazolidine-1,1,3-trione;

methyl (2S)-2-amino-4-{[8-fluoro-6-hydroxy-7-(1,1,4-trioxo-1$\lambda^6$,2,5-thiadiazolidin-2-yl)naphthalen-2-yl]oxy}butanoate;

5-{7-[(3,5-dimethyl-1H-pyrazol-4-yl)methoxy]-1-fluoro-3-hydroxynaphthalen-2-yl}-1$\lambda^6$,2,5-thiadiazolidine-1,1,3-trione;

5-[7-(3,5-dimethyl-1H-pyrazol-4-yl)-1-fluoro-3-hydroxynaphthalen-2-yl]-1$\lambda^6$,2,5-thiadiazolidine-1,1,3-trione;

5-[7-(2-cyclohexylethoxy)-1-fluoro-3-hydroxynaphthalen-2-yl]-1$\lambda^6$,2,5-thiadiazolidine-1,1,3-trione;

2-[8-fluoro-6-hydroxy-7-(1,1,4-trioxo-1$\lambda^6$,2,5-thiadiazolidin-2-yl)naphthalen-2-yl]-1H-imidazole-4-carbonitrile;

and a pharmaceutically acceptable salt, solvate, hydrate, tautomer, ester, N-oxide or stereoisomer thereof.

In some embodiments, a compound disclosed herein, e.g., a compound of Formula (I), Formula (II) or Formula (III), is formulated as a pharmaceutically acceptable composition comprising a disclosed compound and a pharmaceutically acceptable carrier.

In some embodiments, a compound disclosed herein, e.g., a compound of Formula (I), Formula (II) or Formula (III), is selected from a compound set forth in Table 1.

TABLE 1

Exemplary compounds of the disclosure.

| Compound Number | Structure | Compound Number | Structure |
|---|---|---|---|
| 100 | 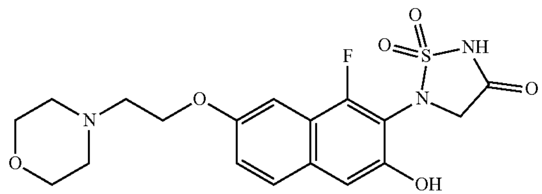 [SMILES: O=C1CN(c2c(O)cc3ccc(OCCN4CCOCC4)cc3c2F)S(=O)(=O)N1] | 101 | 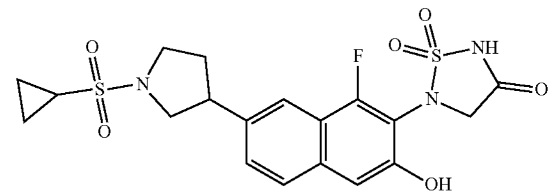 [SMILES: O=C1CN(c2c(O)cc3ccc(C4CCN(S(=O)(=O)C5CC5)C4)cc3c2F)S(=O)(=O)N1] |
| 102 | 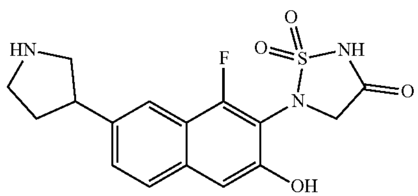 [SMILES: O=C1CN(c2c(O)cc3ccc(C4CCNC4)cc3c2F)S(=O)(=O)N1] | 103 | 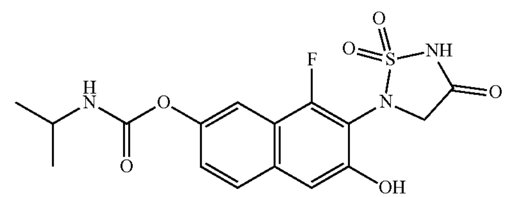 [SMILES: CC(C)NC(=O)Oc1ccc2cc(O)c(N3CC(=O)NS3(=O)=O)c(F)c2c1] |
| 104 | 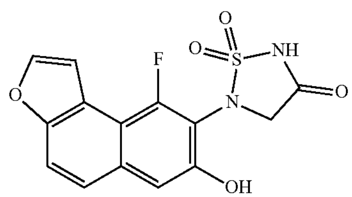 [SMILES: O=C1CN(c2c(O)cc3ccc4occc4c3c2F)S(=O)(=O)N1] | 105 | 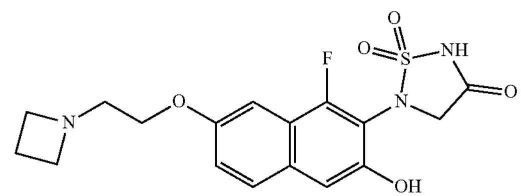 [SMILES: O=C1CN(c2c(O)cc3ccc(OCCN4CCC4)cc3c2F)S(=O)(=O)N1] |
| 106 | 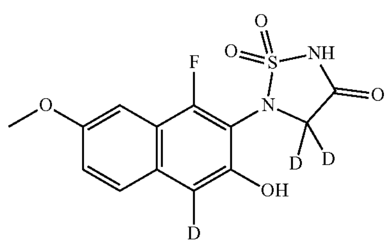 [SMILES: [2H]c1c(O)c(N2C([2H])([2H])C(=O)NS2(=O)=O)c(F)c2cc(OC)ccc12] | 107 | 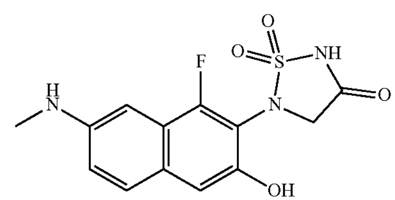 [SMILES: CNc1ccc2cc(O)c(N3CC(=O)NS3(=O)=O)c(F)c2c1] |

TABLE 1-continued

Exemplary compounds of the disclosure.

| Compound Number | Structure | Compound Number | Structure |
|---|---|---|---|
| 108 | 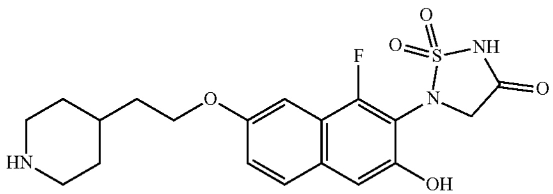 [SMILES: O=C1CN(c2c(O)cc3ccc(OCCC4CCNCC4)cc3c2F)S(=O)(=O)N1] | 109 | 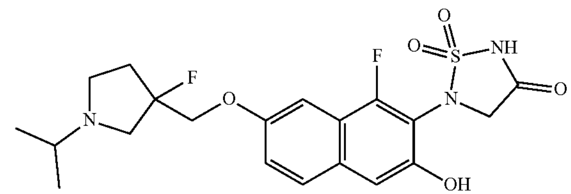 [SMILES: CC(C)N1CCC(F)(COc2ccc3cc(O)c(N4CC(=O)NS4(=O)=O)c(F)c3c2)C1] |
| 110 | 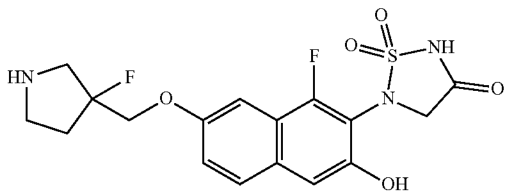 [SMILES: O=C1CN(c2c(O)cc3ccc(OCC4(F)CCNC4)cc3c2F)S(=O)(=O)N1] | 111 | 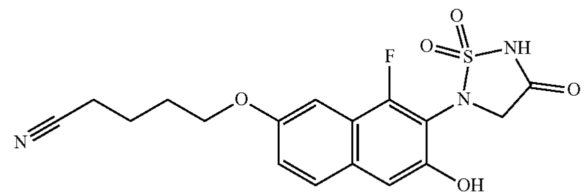 [SMILES: N#CCCCCOc1ccc2cc(O)c(N3CC(=O)NS3(=O)=O)c(F)c2c1] |
| 112 | 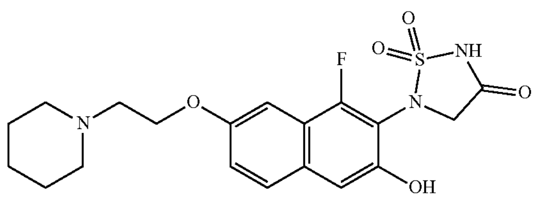 [SMILES: O=C1CN(c2c(O)cc3ccc(OCCN4CCCCC4)cc3c2F)S(=O)(=O)N1] | 113 | 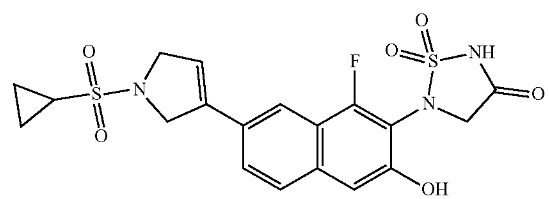 |
| 114 | 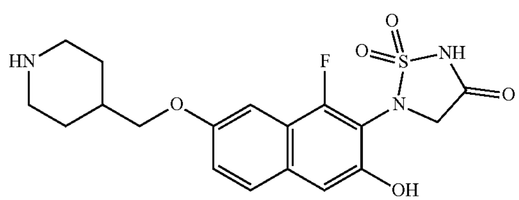 [SMILES: O=C1CN(c2c(O)cc3ccc(OCC4CCNCC4)cc3c2F)S(=O)(=O)N1] | 115 | 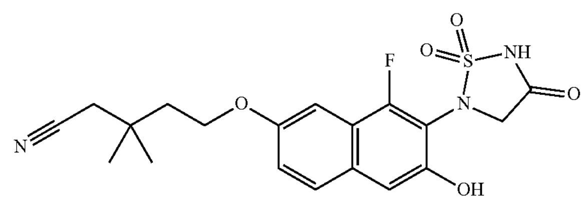 [SMILES: CC(C)(CC#N)CCOc1ccc2cc(O)c(N3CC(=O)NS3(=O)=O)c(F)c2c1] |

TABLE 1-continued

Exemplary compounds of the disclosure.

| Compound Number | Structure | Compound Number | Structure |
|---|---|---|---|
| 116 | 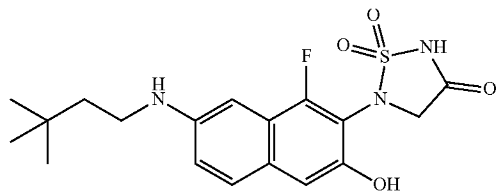 [SMILES: CC(C)(C)CCNc1ccc2cc(O)c(N3CC(=O)NS3(=O)=O)c(F)c2c1] | 117 | 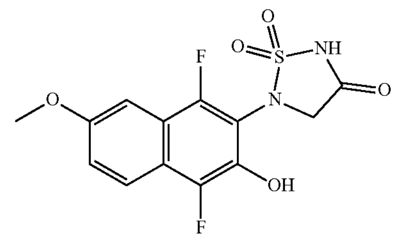 [SMILES: COc1ccc2c(F)c(O)c(N3CC(=O)NS3(=O)=O)c(F)c2c1] |
| 118 | 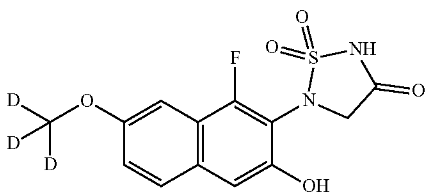 [SMILES: [2H]C([2H])([2H])Oc1ccc2cc(O)c(N3CC(=O)NS3(=O)=O)c(F)c2c1] | 119 | 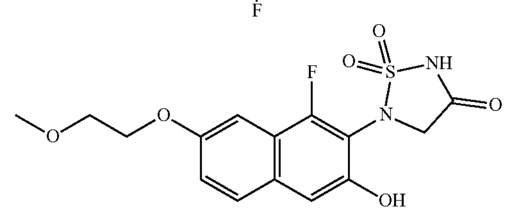 |
| 120 | 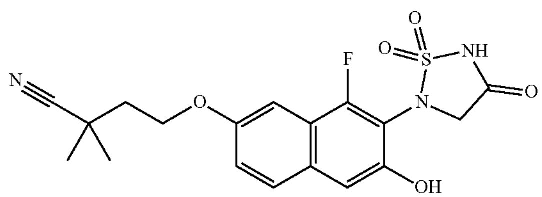 [SMILES: CC(C)(C#N)CCOc1ccc2cc(O)c(N3CC(=O)NS3(=O)=O)c(F)c2c1] | 121 | 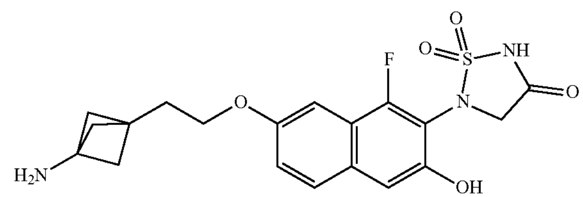 [SMILES: NC12CC(CCOc3ccc4cc(O)c(N5CC(=O)NS5(=O)=O)c(F)c4c3)(C1)C2] |
| 122 | 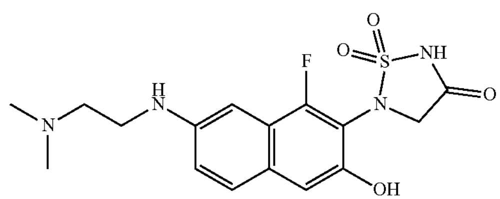 [SMILES: CN(C)CCNc1ccc2cc(O)c(N3CC(=O)NS3(=O)=O)c(F)c2c1] | 123 | 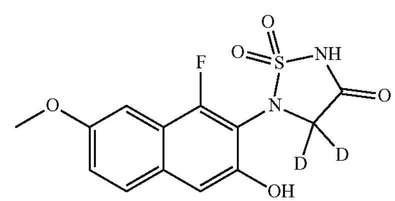 [SMILES: [2H]C1([2H])C(=O)NS(=O)(=O)N1c1c(O)cc2ccc(OC)cc2c1F] |

TABLE 1-continued

Exemplary compounds of the disclosure.

| Compound Number | Structure | Compound Number | Structure |
|---|---|---|---|
| 124 | 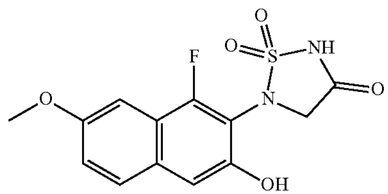 [SMILES: COc1ccc2cc(O)c(N3CC(=O)NS3(=O)=O)c(F)c2c1] | 125 | 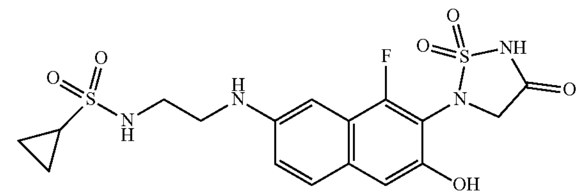 [SMILES: O=C1CN(c2c(O)cc3ccc(NCCNS(=O)(=O)C4CC4)cc3c2F)S(=O)(=O)N1] |
| 126 | 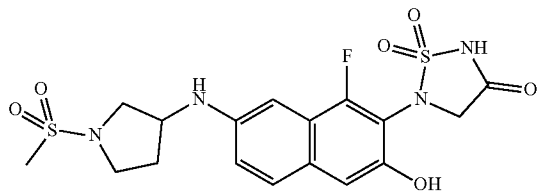 [SMILES: CS(=O)(=O)N1CCC(Nc2ccc3cc(O)c(N4CC(=O)NS4(=O)=O)c(F)c3c2)C1] | 127 | 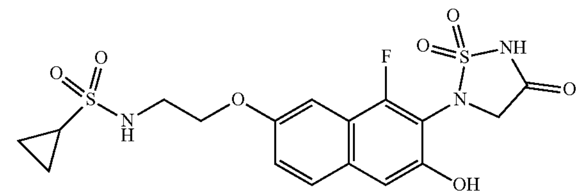 [SMILES: O=C1CN(c2c(O)cc3ccc(OCCNS(=O)(=O)C4CC4)cc3c2F)S(=O)(=O)N1] |
| 218 | 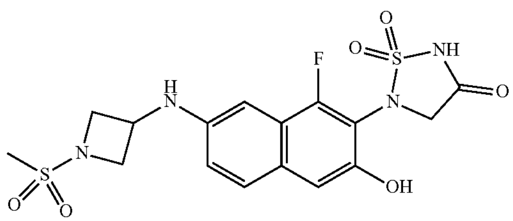 [SMILES: CS(=O)(=O)N1CC(Nc2ccc3cc(O)c(N4CC(=O)NS4(=O)=O)c(F)c3c2)C1] | 129 | 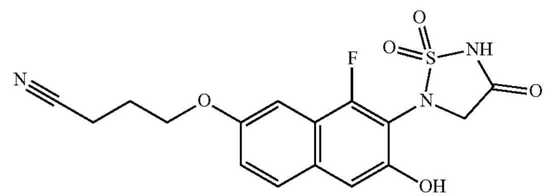 [SMILES: N#CCCCOc1ccc2cc(O)c(N3CC(=O)NS3(=O)=O)c(F)c2c1] |
| 130 | 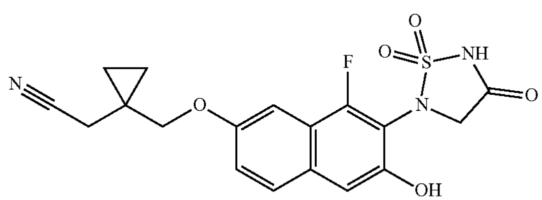 [SMILES: N#CCC1(COc2ccc3cc(O)c(N4CC(=O)NS4(=O)=O)c(F)c3c2)CC1] | 131 | 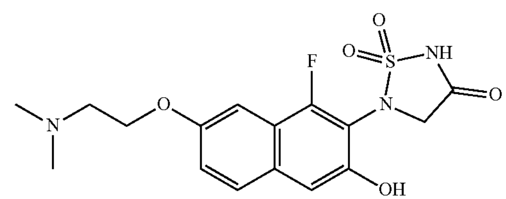 [SMILES: CN(C)CCOc1ccc2cc(O)c(N3CC(=O)NS3(=O)=O)c(F)c2c1] |

TABLE 1-continued

Exemplary compounds of the disclosure.

| Compound Number | Structure | Compound Number | Structure |
|---|---|---|---|
| 132 | 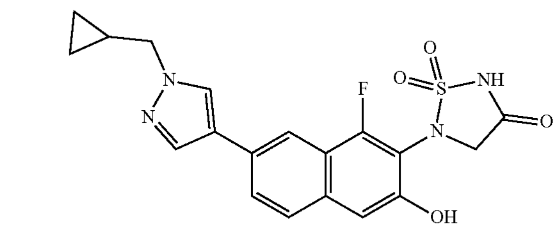 [SMILES: O=C1CN(c2c(O)cc3ccc(-c4cnn(CC5CC5)c4)cc3c2F)S(=O)(=O)N1] | 133 | 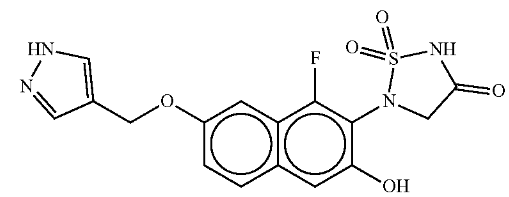 |
| 134 | 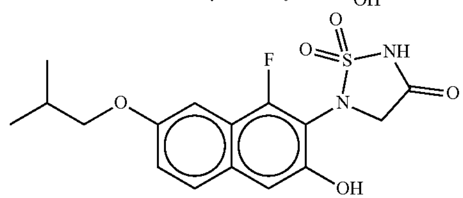 | 135 | 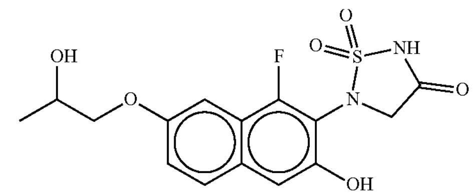 |
| 136 | 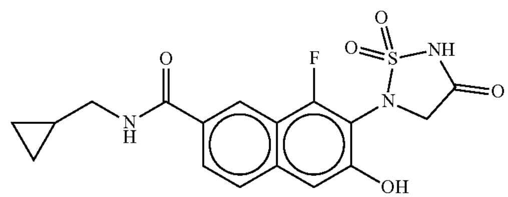 | 137 | 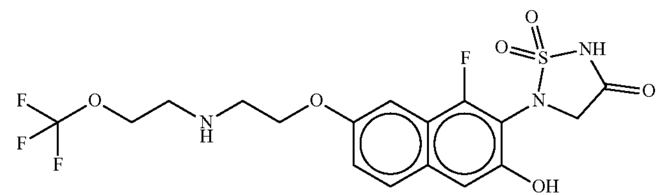 |
| 138 | 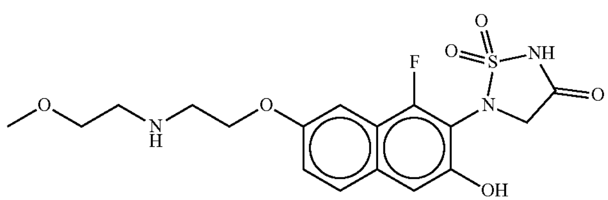 | 139 | 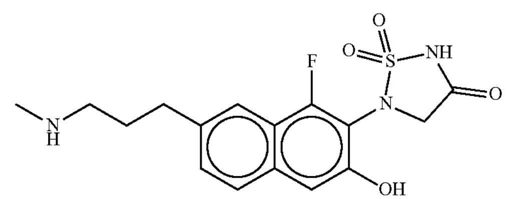 |

TABLE 1-continued

Exemplary compounds of the disclosure.

| Compound Number | Structure | Compound Number | Structure |
|---|---|---|---|
| 140 | 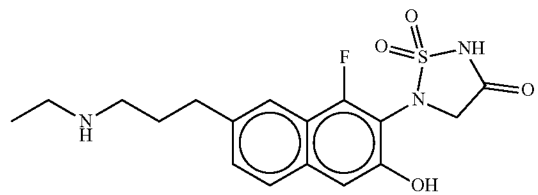 | 141 | 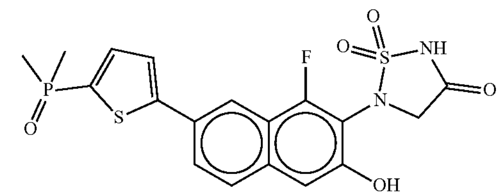 |
| 142 | 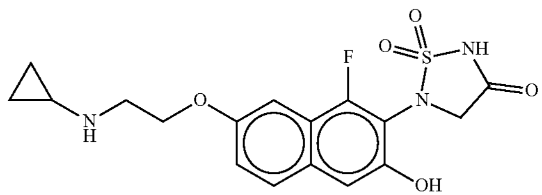 | 143 | 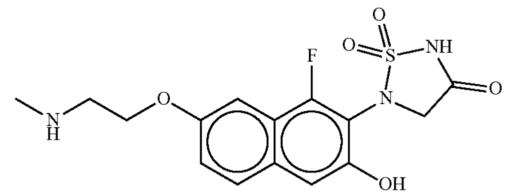 |
| 144 | 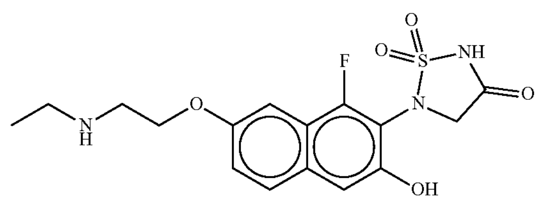 | 145 | 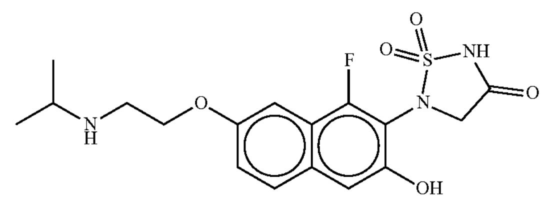 |
| 146 | 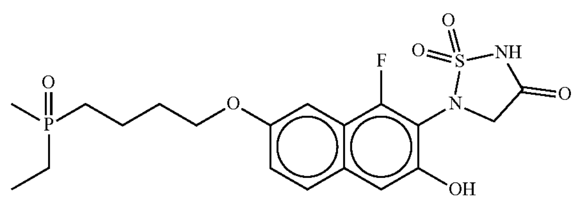 | 147 | 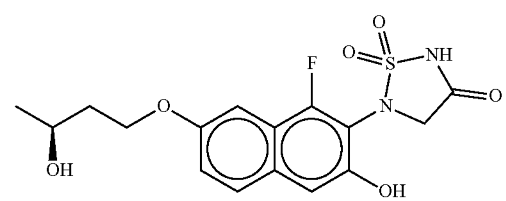 |

TABLE 1-continued

Exemplary compounds of the disclosure.

| Compound Number | Structure | Compound Number | Structure |
|---|---|---|---|
| 148 | 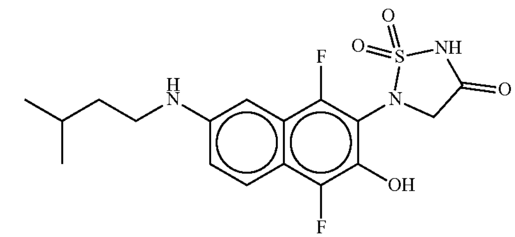 | 149 | 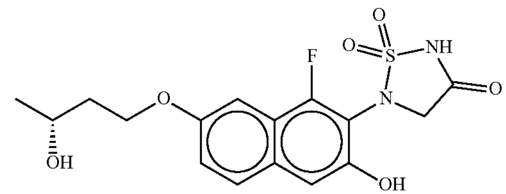 |
| 150 | 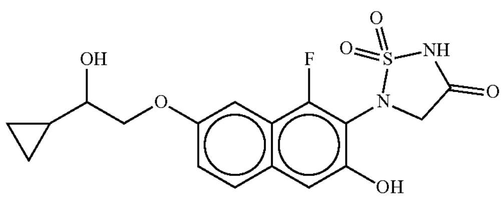 | 151 | 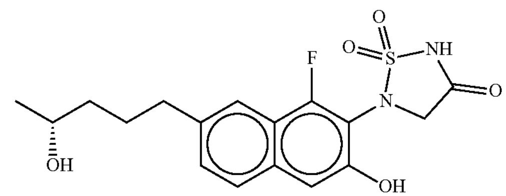 |
| 152 | 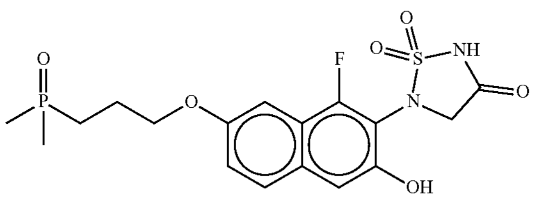 | 153 | 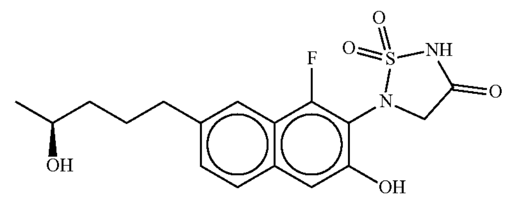 |
| 154 | 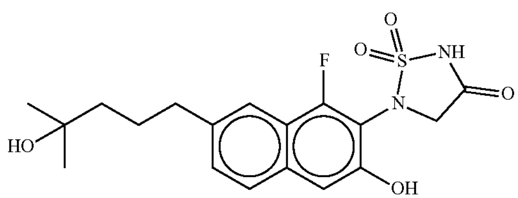 | 155 | 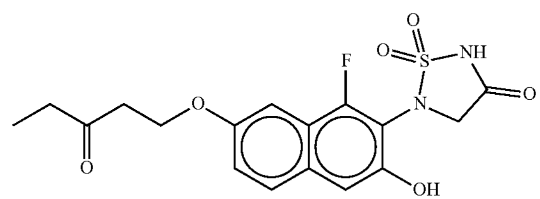 |

TABLE 1-continued

Exemplary compounds of the disclosure.

| Compound Number | Structure | Compound Number | Structure |
|---|---|---|---|
| 156 | 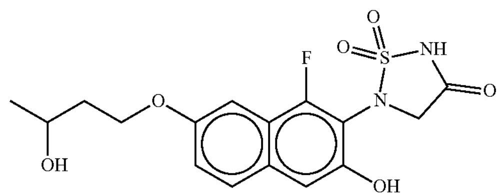 | 157 | 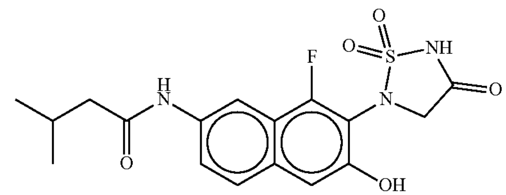 |
| 158 | 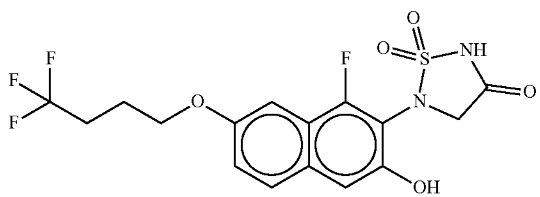 | 159 | 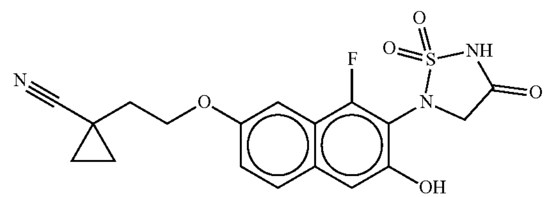 |
| 160 | 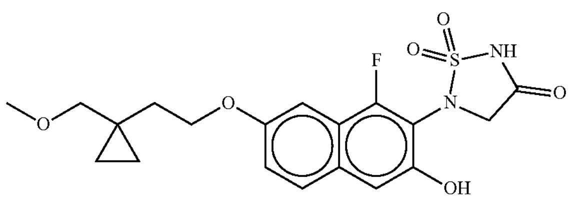 | 161 | 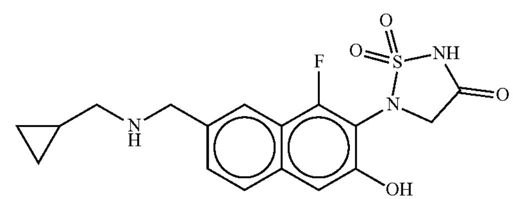 |
| 162 | 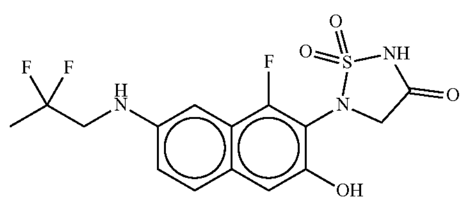 | 163 | 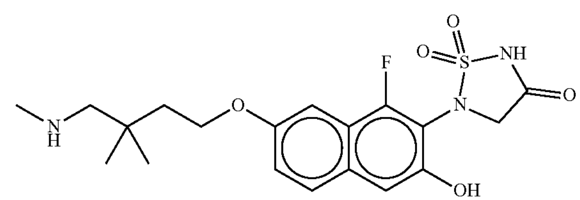 |
| 164 | 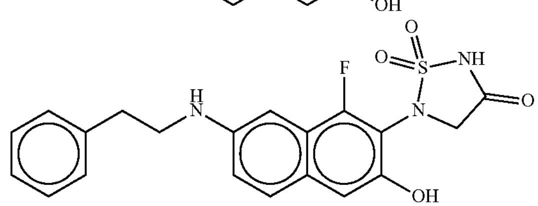 | 165 | 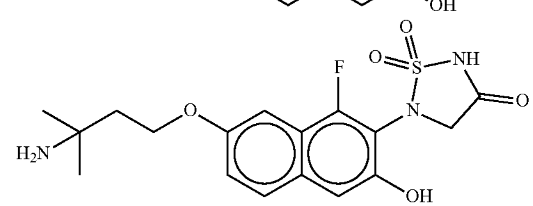 |

TABLE 1-continued

Exemplary compounds of the disclosure.

| Compound Number | Structure |
|---|---|
| 166 | (structure) |
| 167 | (structure) |
| 168 | (structure) |
| 169 | (structure) |
| 170 | (structure) |
| 171 | (structure) |
| 172 | (structure) |
| 173 | (structure) |
| 174 | (structure) |
| 175 | (structure) |

TABLE 1-continued

Exemplary compounds of the disclosure.

| Compound Number | Structure | Compound Number | Structure |
|---|---|---|---|
| 176 | 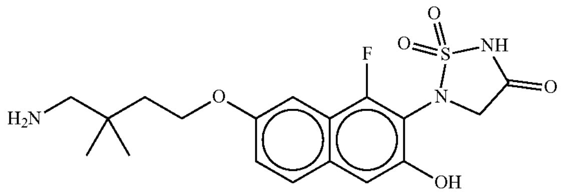 | 177 | 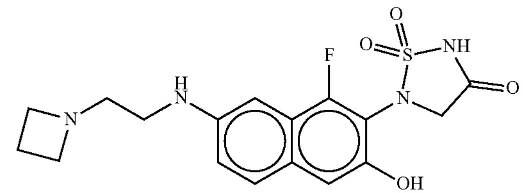 |
| 178 | 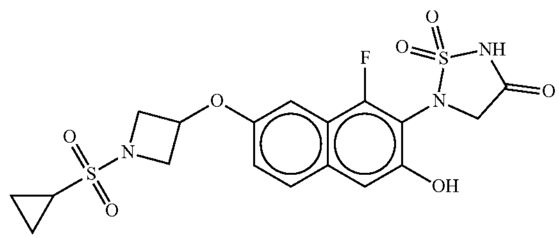 | 179 | 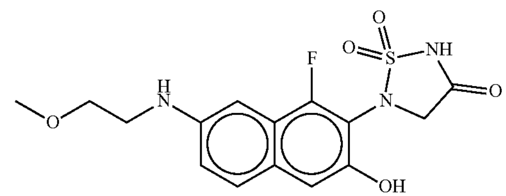 |
| 180 | 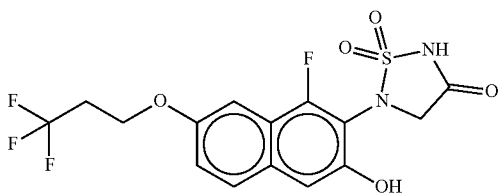 | 181 | 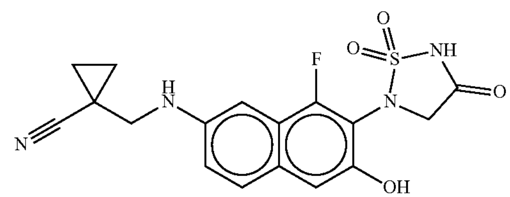 |
| 182 | 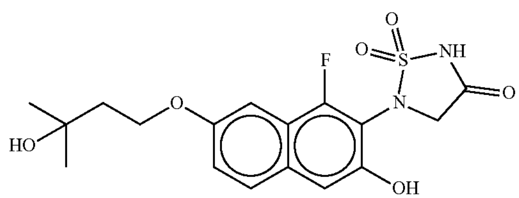 | 183 | 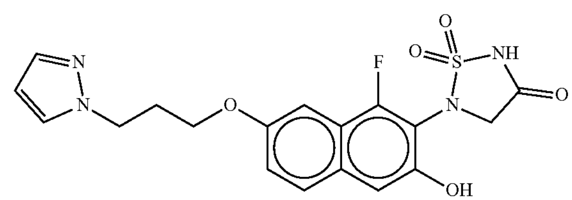 |

TABLE 1-continued

Exemplary compounds of the disclosure.

| Compound Number | Structure | Compound Number | Structure |
|---|---|---|---|
| 184 | 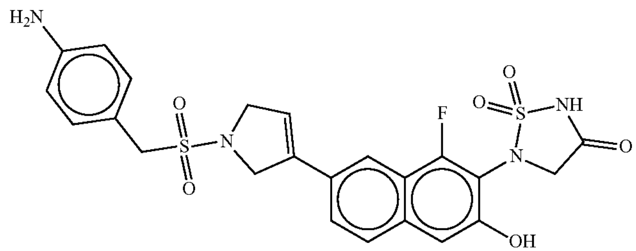 | 185 | 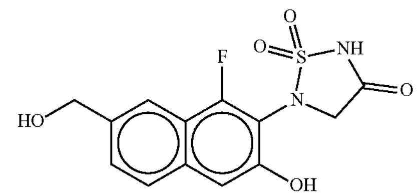 |
| 186 | 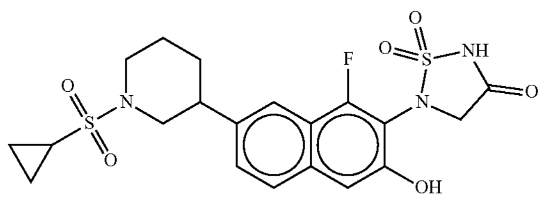 | 187 | 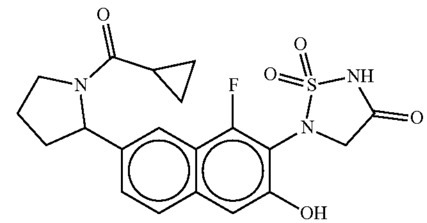 |
| 188 | 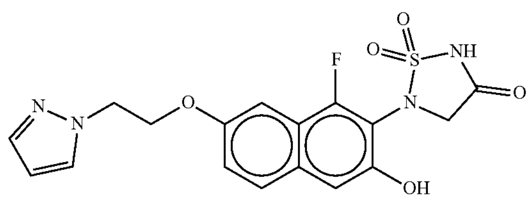 | 189 | 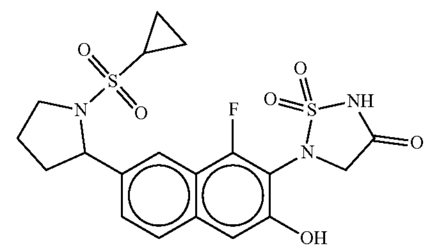 |
| 190 | 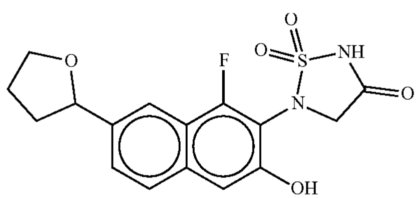 | 191 | 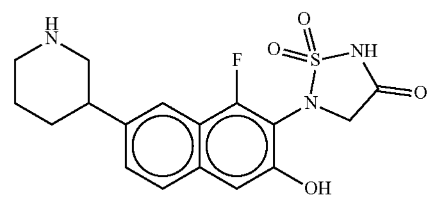 |

TABLE 1-continued

Exemplary compounds of the disclosure.

| Compound Number | Structure | Compound Number | Structure |
|---|---|---|---|
| 192 | 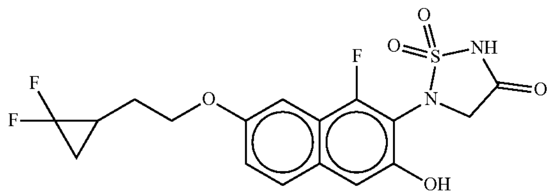 | 193 | 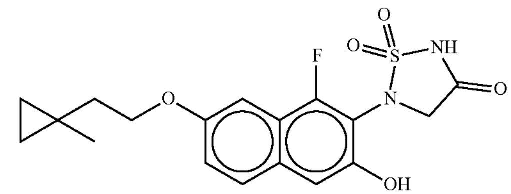 |
| 194 | 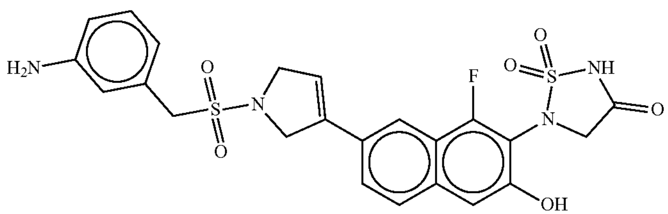 | 195 | 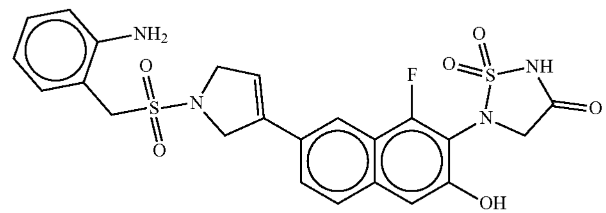 |
| 196 | 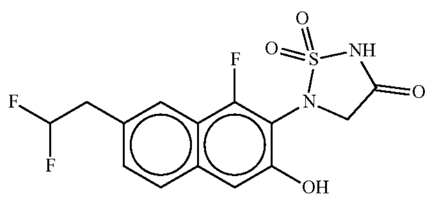 | 197 | 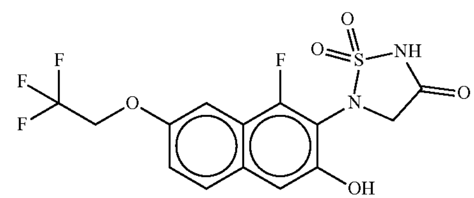 |
| 198 | 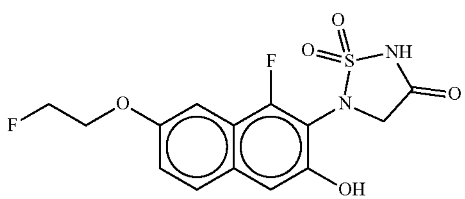 | 199 | 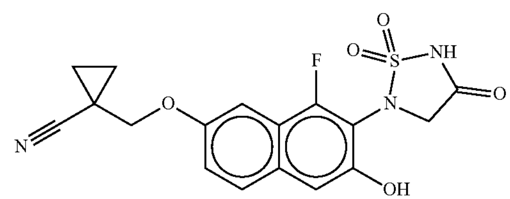 |

TABLE 1-continued

Exemplary compounds of the disclosure.

| Compound Number | Structure | Compound Number | Structure |
|---|---|---|---|
| 200 | 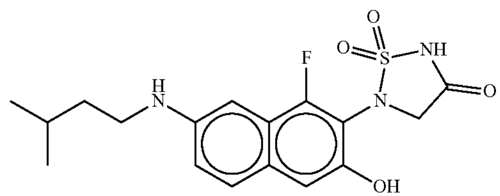 | 201 | 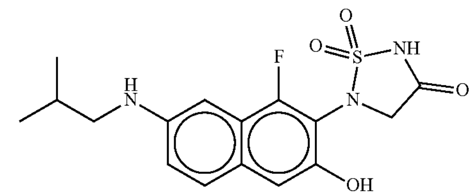 |
| 202 | 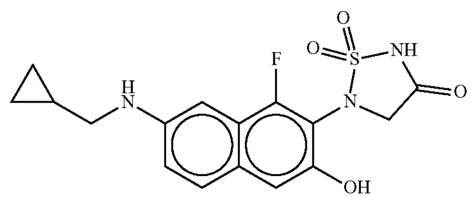 | 203 | 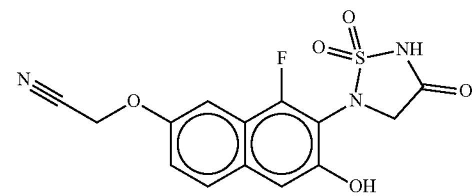 |
| 204 | 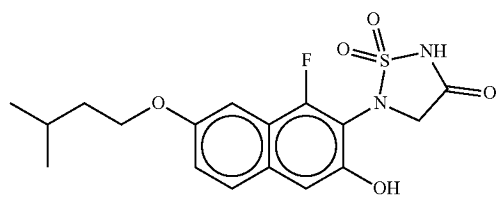 | 205 | 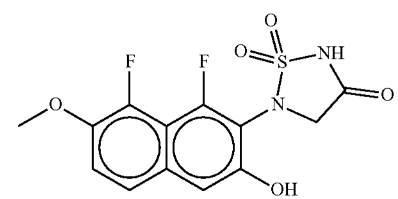 |
| 206 | 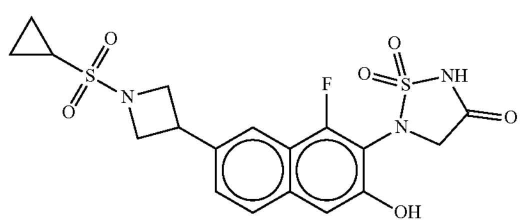 | 207 | 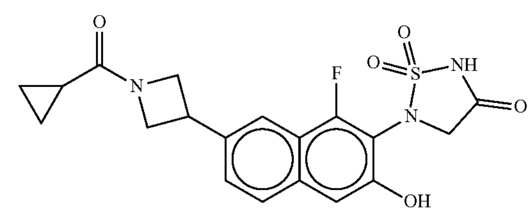 |

TABLE 1-continued

Exemplary compounds of the disclosure.

| Compound Number | Structure | Compound Number | Structure |
|---|---|---|---|
| 208 | (structure) | 209 | (structure) |
| 210 | (structure) | 211 | (structure) |
| 212 | (structure) | 213 | (structure) |
| 214 | (structure) | 215 | (structure) |

TABLE 1-continued

Exemplary compounds of the disclosure.

| Compound Number | Structure | Compound Number | Structure |
|---|---|---|---|
| 216 | 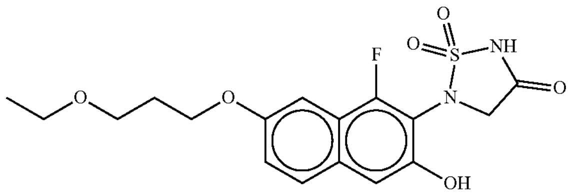 | 217 | 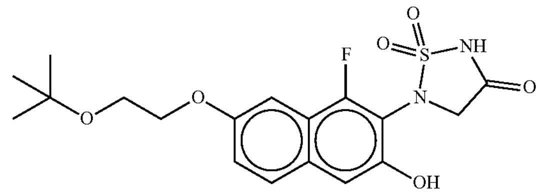 |
| 218 | 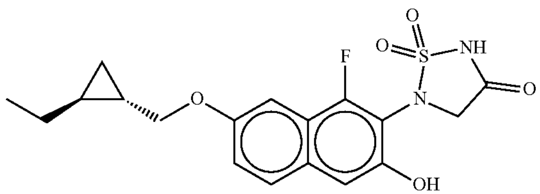 | 219 | 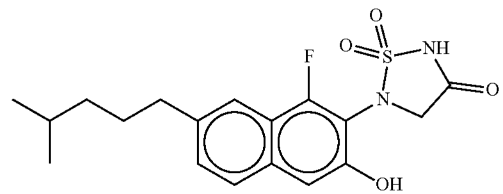 |
| 220 | 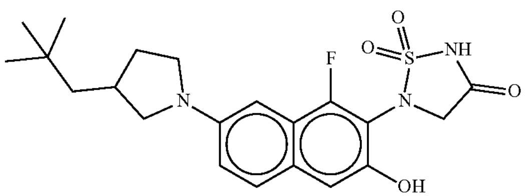 | 221 | 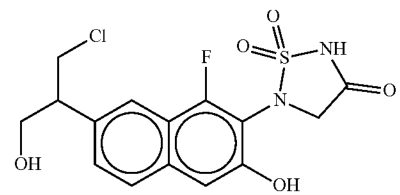 |
| 222 | 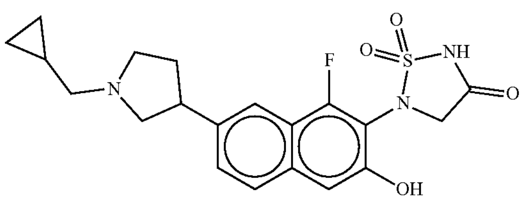 | 223 | 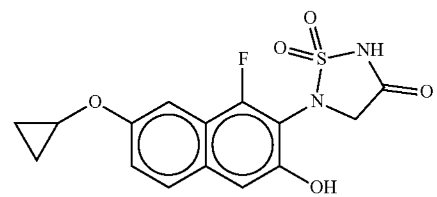 |
| 224 | 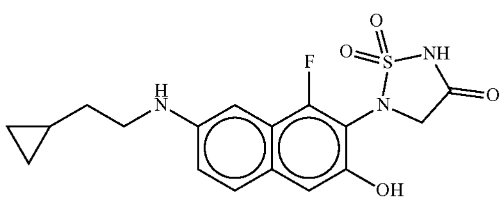 | 225 | 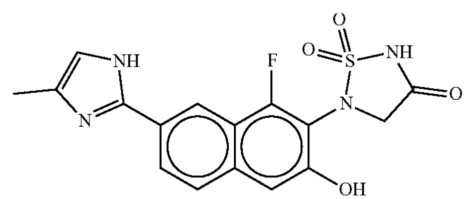 |

TABLE 1-continued

Exemplary compounds of the disclosure.

| Compound Number | Structure | Compound Number | Structure |
|---|---|---|---|
| 226 | 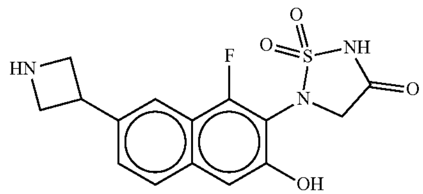 | 227 | 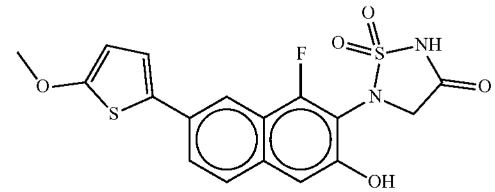 |
| 228 | 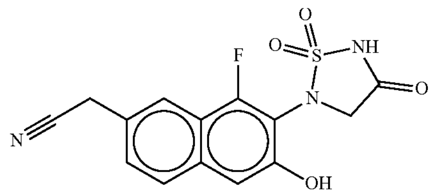 | 229 | 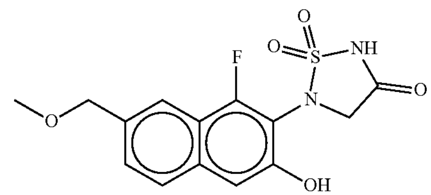 |
| 230 | 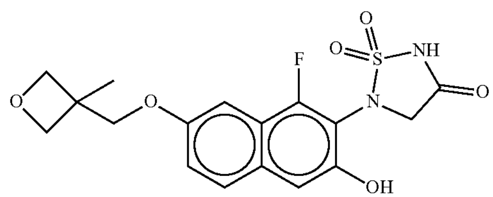 | 231A | 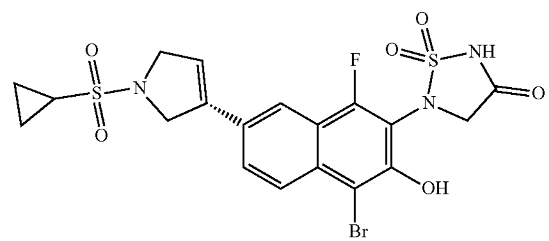 |
| 231B | 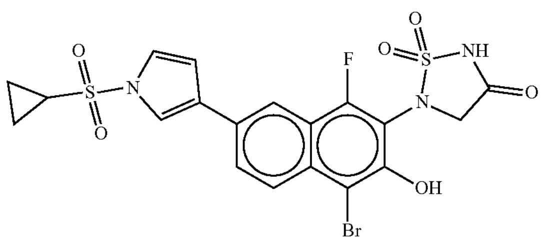 | 232 | 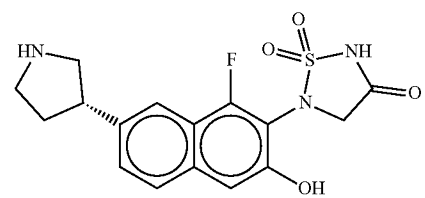 |

TABLE 1-continued

Exemplary compounds of the disclosure.

| Compound Number | Structure | Compound Number | Structure |
|---|---|---|---|
| 233 | 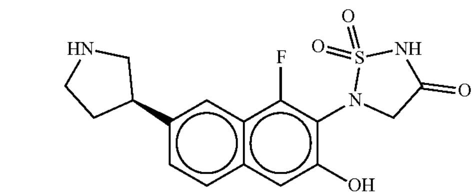 | 234 | 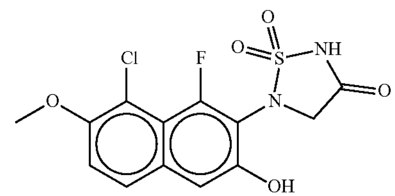 |
| 235 | 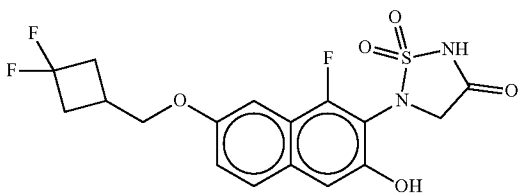 | 236 | 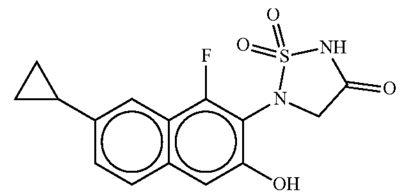 |
| 237 | 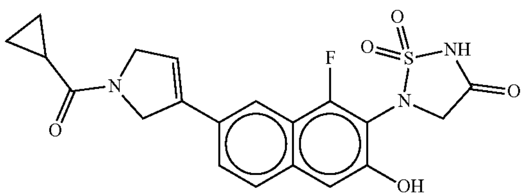 | 238 | 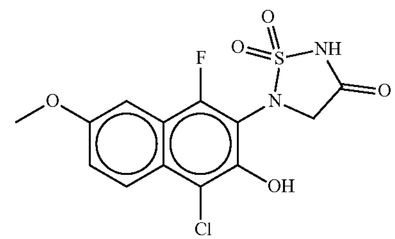 |
| 239 | 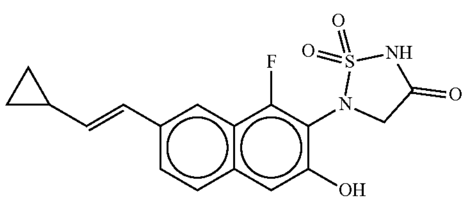 | 240 | 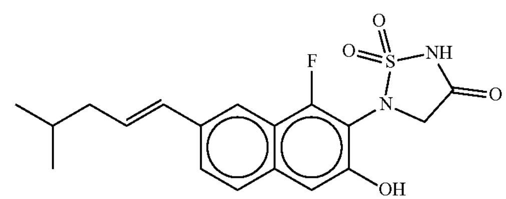 |

TABLE 1-continued

Exemplary compounds of the disclosure.

| Compound Number | Structure | Compound Number | Structure |
|---|---|---|---|
| 241 | 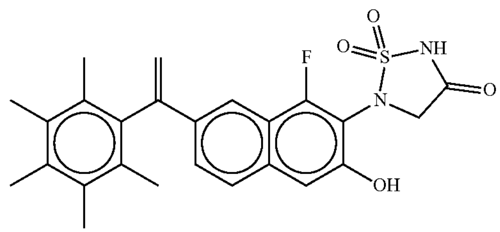 | 242 | 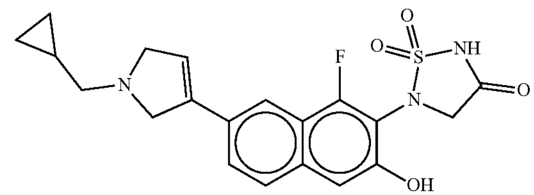 |
| 243 | 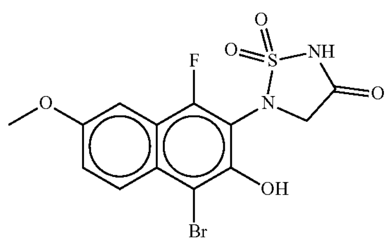 | 244 | 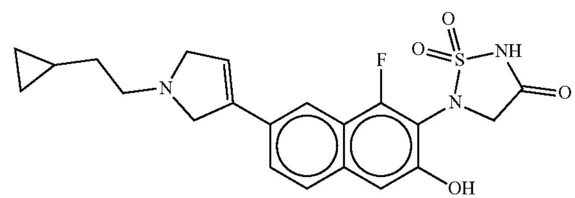 |
| 245 | 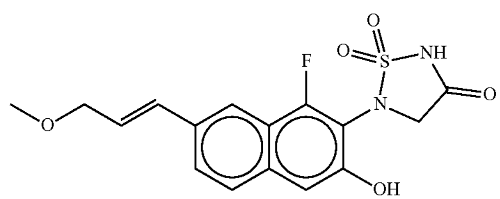 | 246 | 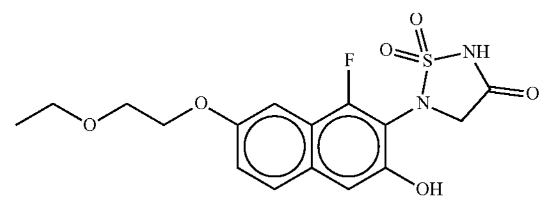 |
| 247 | 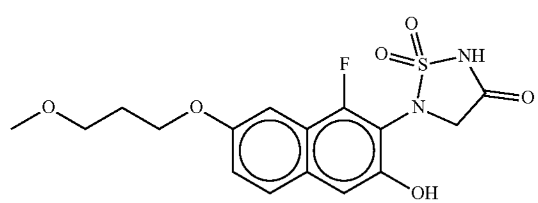 | 248 | 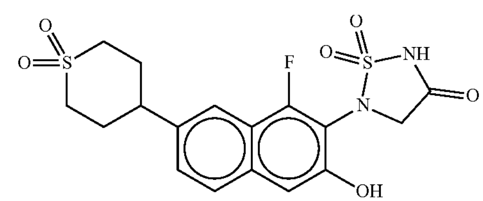 |

TABLE 1-continued

Exemplary compounds of the disclosure.

| Compound Number | Structure | Compound Number | Structure |
|---|---|---|---|
| 249 | 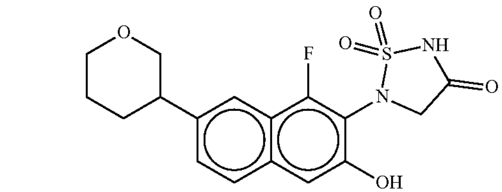 | 250 | 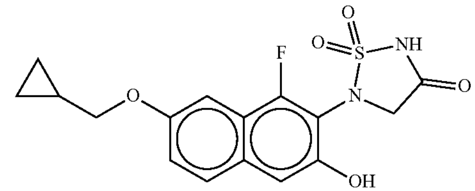 |
| 251 | 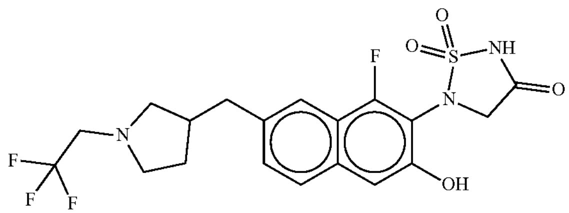 | 252 | 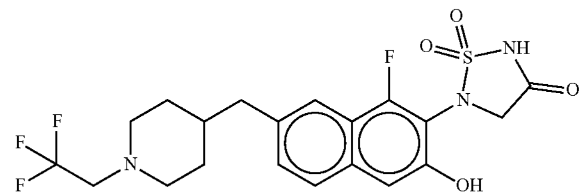 |
| 253 | 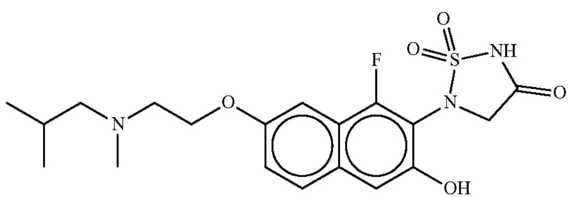 | 254 | 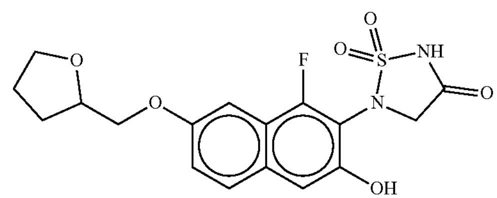 |
| 255 | 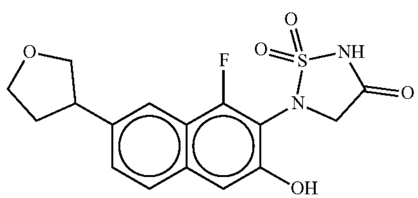 | 256 | 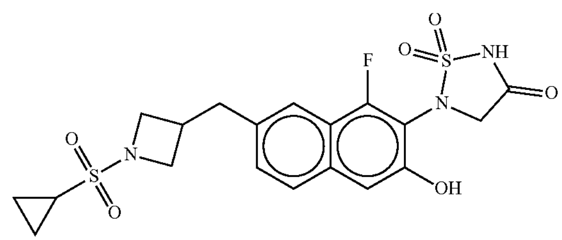 |

TABLE 1-continued

Exemplary compounds of the disclosure.

| Compound Number | Structure | Compound Number | Structure |
|---|---|---|---|
| 257 | 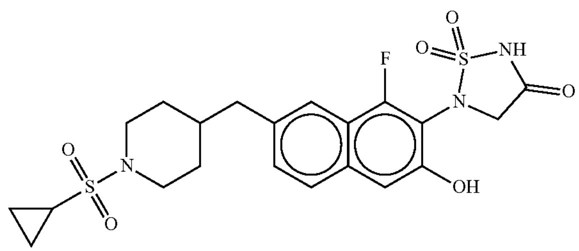 | 258 | 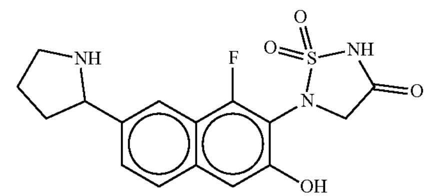 |
| 259 | 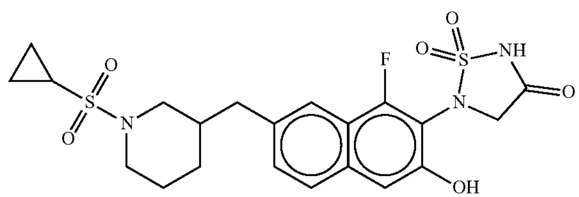 | 260 | 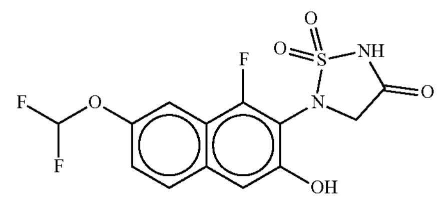 |
| 261 | 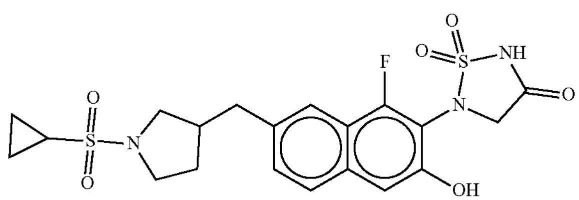 | 262 | 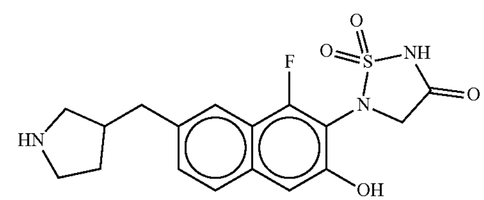 |
| 263 | 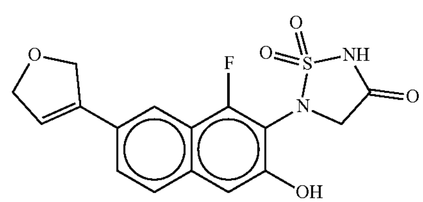 | 264 | 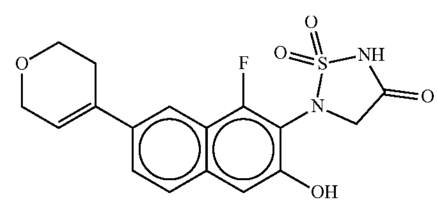 |

TABLE 1-continued

Exemplary compounds of the disclosure.

| Compound Number | Structure | Compound Number | Structure |
|---|---|---|---|
| 265 | 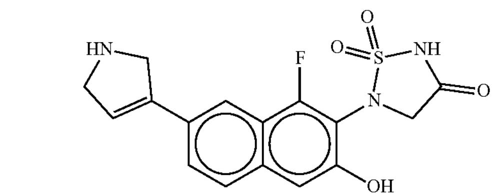 | 266 | 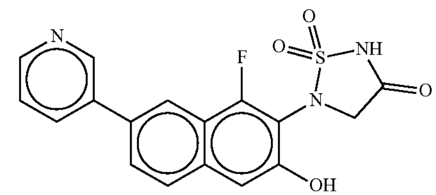 |
| 267 | 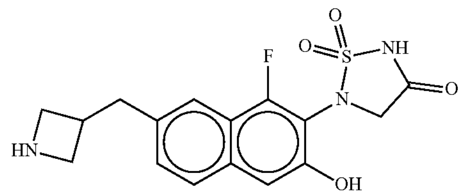 | 268 | 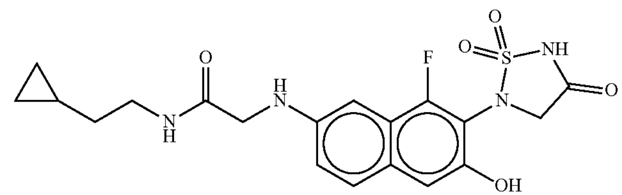 |
| 269 | 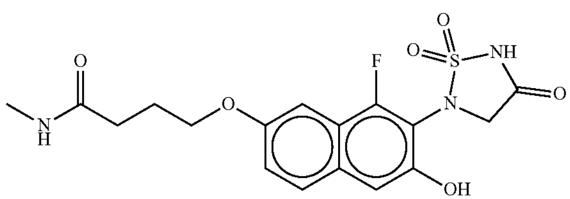 | 270 | 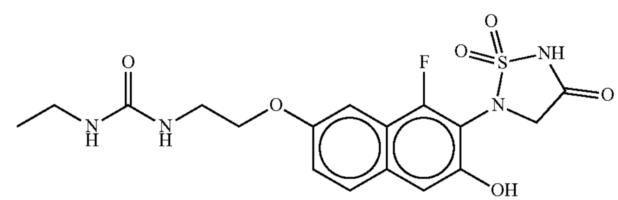 |
| 271 | 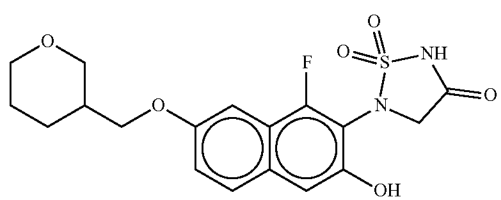 | 272 | 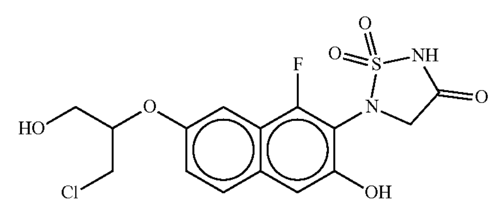 |
| 273 | 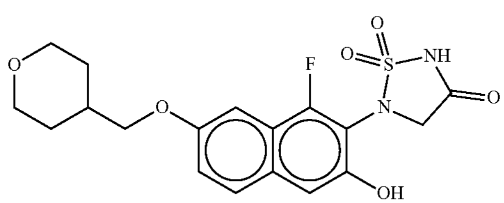 | 274 | 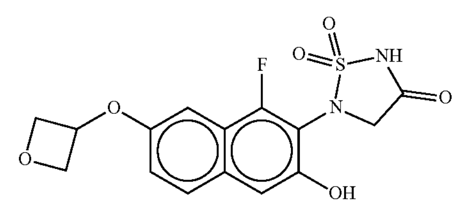 |

TABLE 1-continued

Exemplary compounds of the disclosure.

| Compound Number | Structure |
|---|---|
| 275 | |
| 276 | |
| 277 | |
| 278 | |
| 279 | |
| 280 | |
| 281 | |
| 282 | |

TABLE 1-continued

Exemplary compounds of the disclosure.

| Compound Number | Structure | Compound Number | Structure |
|---|---|---|---|
| 283 | 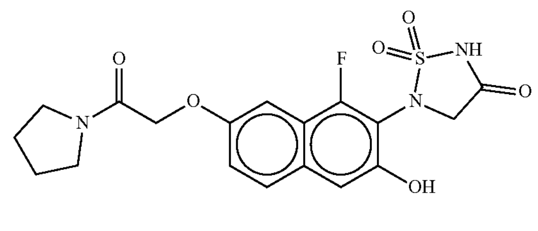 | 284 | 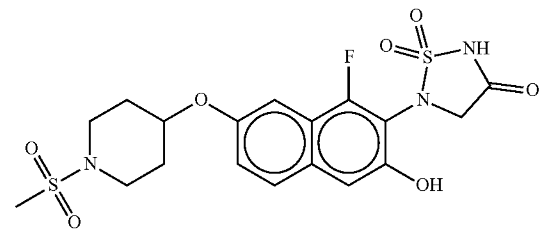 |
| 285 | 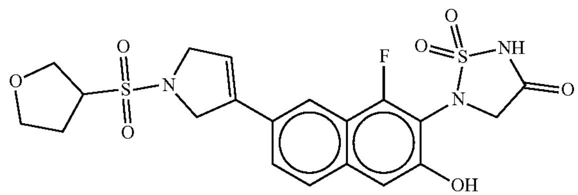 | 286 | 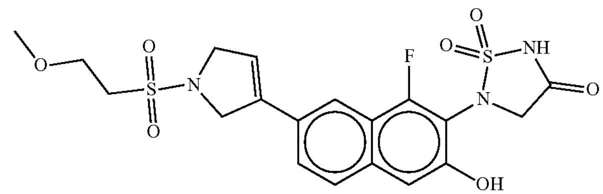 |
| 287 | 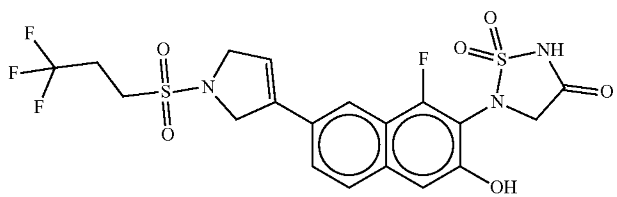 | 288 | 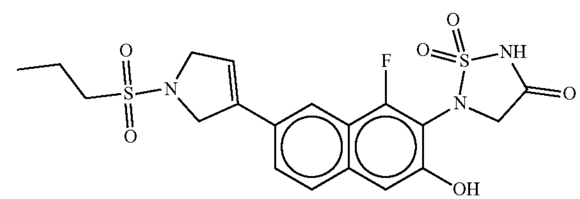 |
| 289 | 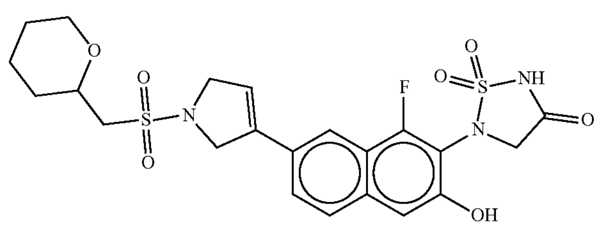 | 290 | 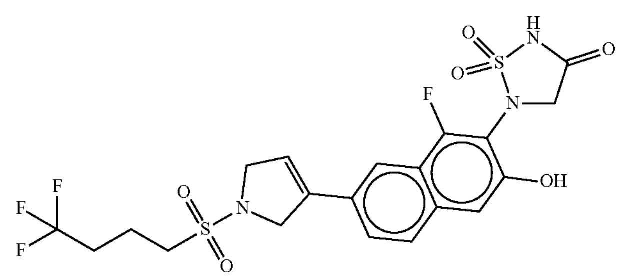 |

TABLE 1-continued

Exemplary compounds of the disclosure.

| Compound Number | Structure |
|---|---|
| 291 | |
| 292 | |
| 293 | |
| 294 | |
| 295 | |
| 296 | |
| 297 | |
| 298 | |

TABLE 1-continued

Exemplary compounds of the disclosure.

| Compound Number | Structure |
|---|---|
| 299 | |
| 300 | |
| 301 | |
| 302 | |
| 303 | |
| 304 | |
| 305 | |
| 306 | |

TABLE 1-continued

Exemplary compounds of the disclosure.

| Compound Number | Structure |
|---|---|
| 307 | |
| 308 | |
| 309 | |
| 310 | |
| 311 | |
| 312 | |
| 313 | |
| 314 | |
| 315 | |
| 316 | |

TABLE 1-continued

Exemplary compounds of the disclosure.

| Compound Number | Structure | Compound Number | Structure |
|---|---|---|---|
| 317 | 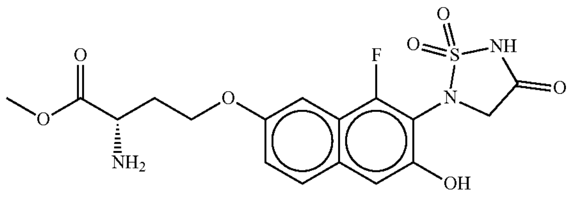 | 318 | 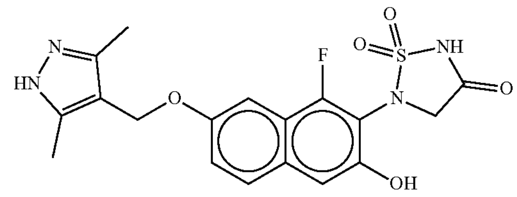 |
| 319 | 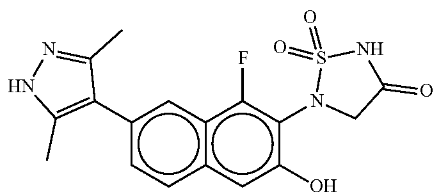 | 320 | 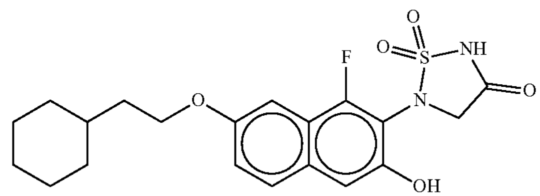 |
| 321 | 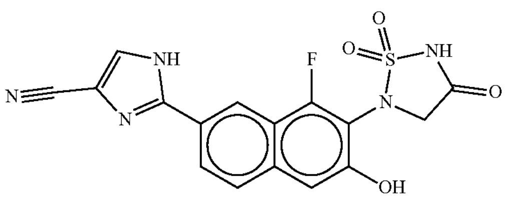 | | |

Methods of Making Exemplary Compounds

The compounds of the present disclosure may be better understood in connection with the following synthetic schemes and methods which illustrate a means by which the compounds can be prepared. The compounds of the present disclosure can be prepared by a variety of synthetic procedures. Representative synthetic procedures are shown in, but not limited to, Schemes 1-7. The variables $R^1$, $R^2$, $R^3$, $R^4$, $R^5$, $R^6$, and $R^7$ are defined as detailed herein, i.e., in the Summary.

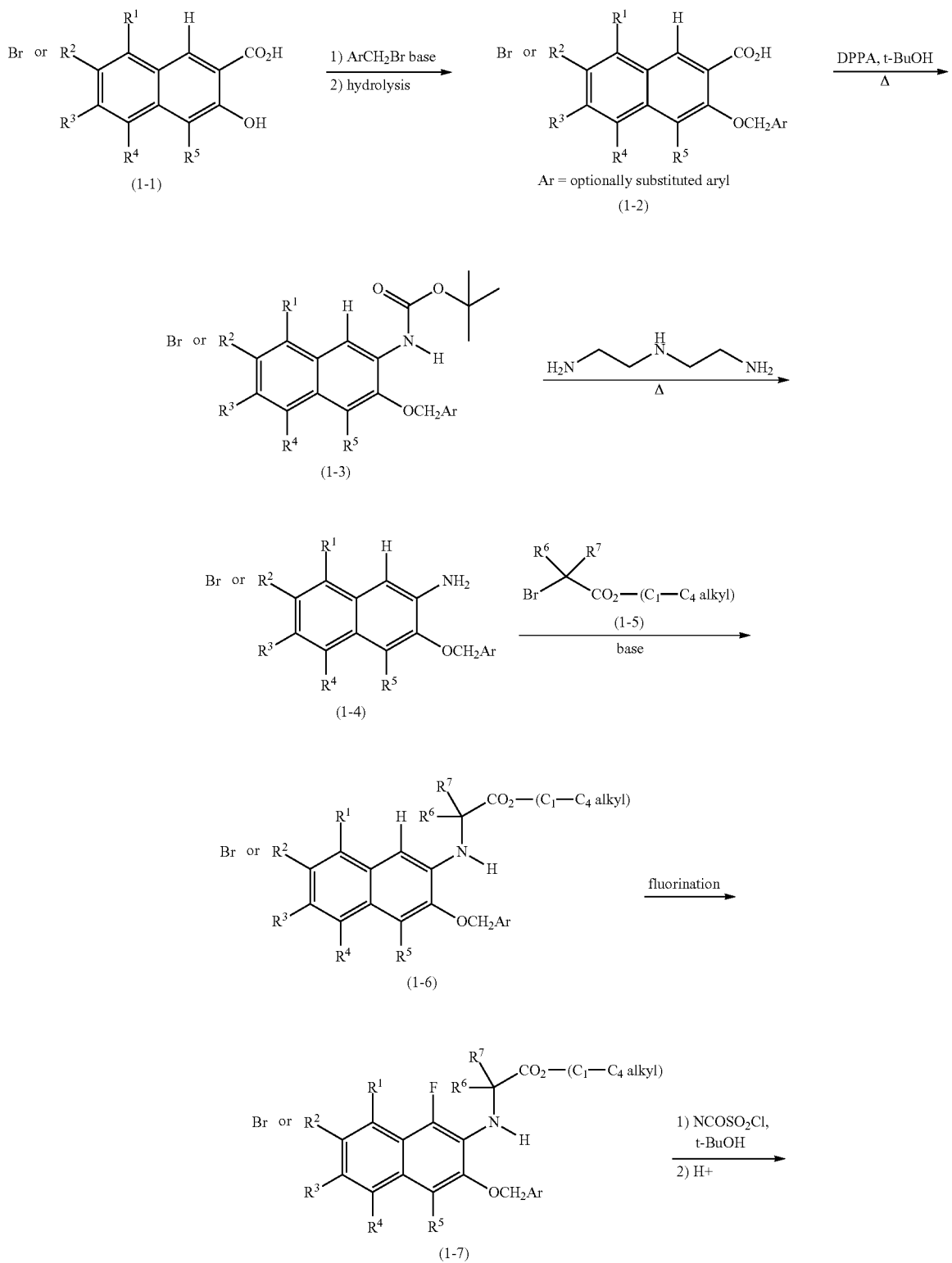

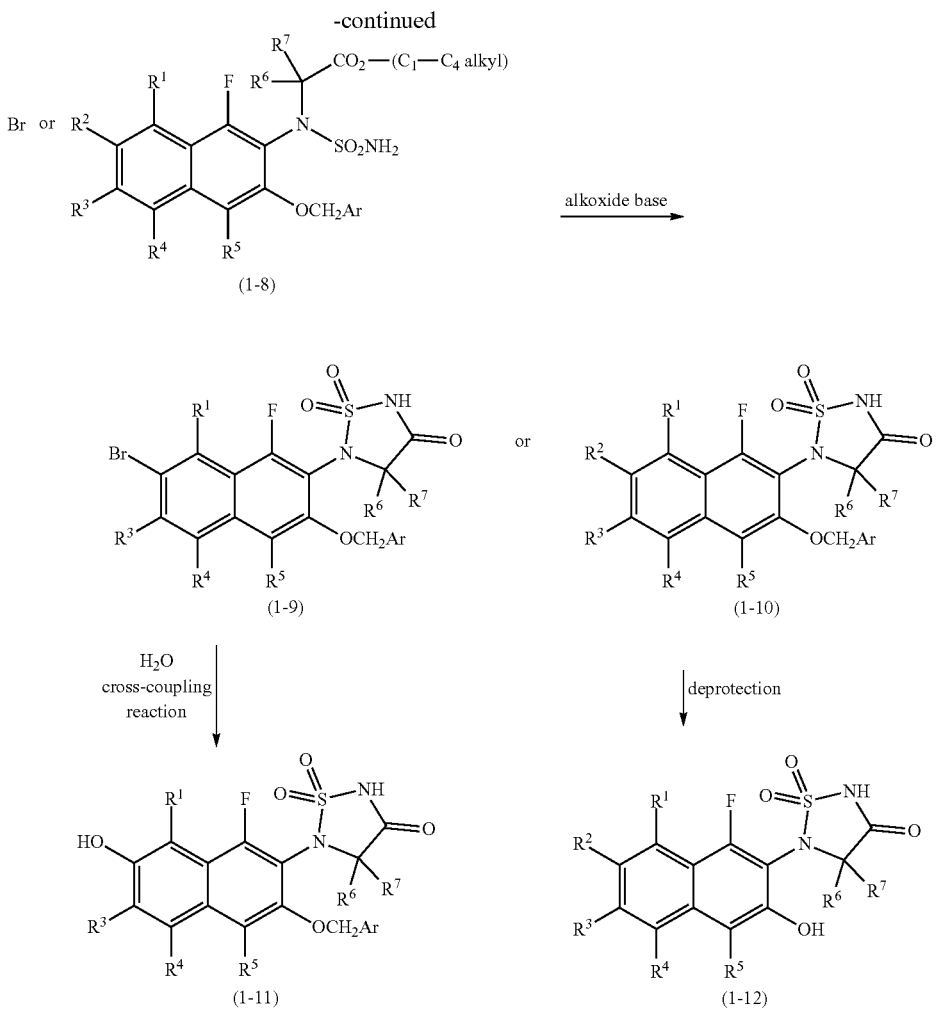

As shown in Scheme 1, compounds of formula (1-9), formula (1-10), formula (1-11), and formula (1-12) can be prepared from compounds of formula (1-1). Compounds of formula (1-1) can be alkylated with an optionally substituted benzyl bromide (e.g., benzyl bromide, 4-methoxybenzyl bromide, or 3,4-dimethoxybenzyl bromide) in the presence of a base such as cesium carbonate in a solvent such as N,N-dimethylformamide. The carboxylic acid group also reacts under these conditions producing a benzyl ester. The benzyl ester can be hydrolyzed with a base such as lithium hydroxide or sodium hydroxide in methanol or a mixture of methanol and water to give compounds of formula (1-2). Compounds of formula (1-2) can be reacted under Curtius reaction conditions (diphenyl phosphorazidate, tert-butanol, triethylamine in heated toluene) to give compounds of formula (1-3). The tert-butoxycarbonyl moiety can be removed from compounds of formula (1-3) by treatment with heated diethylenetriamine to give compounds of formula (1-4). Compounds of formula (1-4) can be reacted with 2-bromoacetates of formula (1-5) in the presence of a base such as potassium carbonate in warmed solvent such as but not limited to a mixture of N,N-dimethylformamide and water to give compounds of formula (1-6). Compounds of formula (1-6) can then be fluorinated with a reagent such as N-fluorobenzenesulfonimide (NFSI) in a solvent such as tetrahydrofuran or Selectfluor® in optionally warmed N,N-dimethylformamide to give compounds of formula (1-7). Compounds of formula (1-7) can be reacted with chlorosulfonyl isocyanate and tert-butanol in the presence of a tertiary amine base such as triethylamine in a solvent such as cooled dichloromethane. Subsequent treatment under acid conditions such as trifluoroacetic acid in dichloromethane to remove the tert-butoxycarbonyl group delivers compounds of formula (1-8). Compounds of formula (1-8) can be reacted with an alkoxide base, e.g., sodium methoxide in optionally warmed methanol or a mixture methanol and water or potassium tert-butoxide in tetrahydrofuran and then quenched with an acid such as 1 M hydrochloric acid to give compounds of formula (1-9) or formula (1-10). Compounds of formula (1-9) can be converted to compounds of formula (1-11) with water under cross-coupling reaction conditions such as water in the presence of a precatalyst, RockPhos Pd G3, a base, cesium carbonate, and a warmed solvent, N,N-dimethylformamide. The optionally substituted benzyl ether of compounds of formula (1-10) can be removed using conditions known to one of skill in the art and dependent on the particular benzyl ether. For example, an unsubstituted benzyl ether can be removed by treatment with trichloroborane in the presence of 1,2,3,4,5-pentamethylbenzene in dichloromethane at −60 to −80° C. to give compounds of formula (1-12). Compounds of formula (1-12) are representative of compounds of formula (I).

Scheme 2:
Representative scheme for synthesis of exemplary compounds of the disclousure.

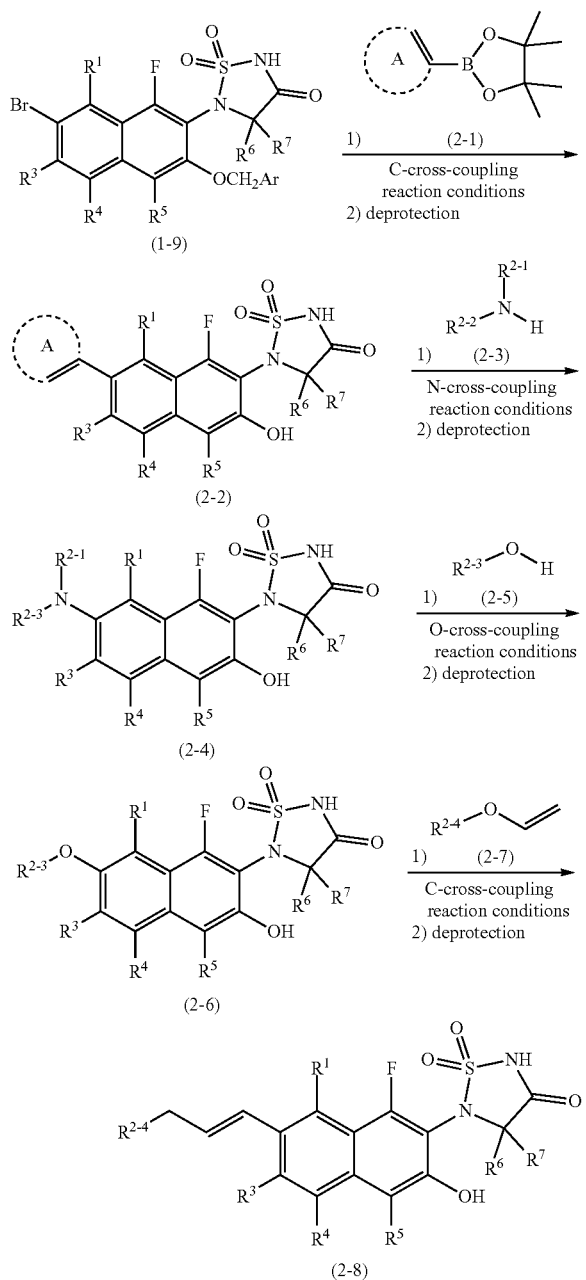

As shown in Scheme 2, compounds of formula (2-2), formula (2-4), formula (2-6), and formula (2-8) can be prepared from compounds of formula (1-9). Compounds of formula (1-9) can be reacted under C-cross-coupling reaction conditions. For example, Suzuki reaction conditions can be used to couple compounds of formula (1-9) with compounds of formula (2-1), wherein A represents an alkene moiety, cyclopropyl or aromatic or partially unsaturated ring. Reaction conditions to couple compounds of formula (1-9) with compounds of formula (2-1) may include a catalyst, (tetrakis(triphenylphosphine)palladium(O), 1,1-bis(diphenylphosphino)ferrocene-palladium(II) dichloride dichloromethane complex, or [1,1'-bis(di-tert-butylphosphino)ferrocene]palladium(II) dichloride), and a base (sodium carbonate, potassium carbonate, or cesium carbonate) in heated dioxane, a mixture of dioxane and water, or a mixture of tetrahydrofuran and water. Subsequently, the optionally substituted benzyl ether protecting group can be removed using conditions known to one of skill in the art and dependent on the particular benzyl ether. For example, an unsubstituted benzyl ether can be removed by treatment with trichloroborane in the presence of 1,2,3,4,5-pentamethylbenzene in dichloromethane at −60 to −80° C. to give compounds of formula (2-2). Additionally, an unsubstituted benzyl ether can be removed by treatment with hydrogen and a palladium catalyst in a solvent such as dioxane or tetrahydrofuran. Compounds of formula (2-2) or the protected precursor can be further modified as known to one of skill in the art and illustrated in the Examples.

Compounds of formula (1-9) can be reacted under N-cross-coupling reaction conditions. For example, Buchwald-Hartwig reaction conditions can be used to couple compounds of formula (1-9) with compounds of formula (2-3). For example, compounds of formula (1-9) and compounds of formula (2-3) can be coupled in the presence of a precatalyst (BrettPhos Pd G3 or RuPhos Pd G3) or catalyst (palladium(II) acetate), a ligand (BrettPhos, RuPhos, or Xantphos), and a base (sodium tert-butoxide or cesium carbonate), in a heated solvent such as dioxane or tert-amyl alcohol. Subsequently, the optionally substituted benzyl ether protecting group can be removed as previously described above to give compounds of formula (2-4), wherein $NR^{2-1}R^{2-2}$ represents a cyclic or acyclic moiety of $R^2$. Compounds of formula (2-4) or the protected precursor can be further modified as known to one of skill in the art and illustrated in the Examples.

Compounds of formula (1-9) can be reacted under O-cross-coupling reaction conditions. For example, cross-coupling reaction conditions can be used to couple compounds of formula (1-9) with compounds of formula (2-5). For example, compounds of formula (1-9) and compounds of formula (2-5) can be coupled in the presence of a precatalyst, RockPhos Pd G3, and a base, cesium carbonate, in a heated solvent such as N,N-dimethylformamide. Subsequently, the optionally substituted benzyl ether protecting group can be removed as previously described above to give compounds of formula (2-6), wherein $OR^{2-3}$ represents an ether moiety of $R^2$. Compounds of formula (2-6) or the protected precursor can be further modified as known to one of skill in the art and illustrated in the Examples.

Compounds of formula (1-9) can be reacted under C-cross-coupling reaction conditions. For example, compounds of formula (1-9) can be coupled with allyl compounds of formula (2-7), wherein $R^{2-4}$ represents the remainder of $R^2$ beyond the allyl moiety. Reaction conditions to couple compounds of formula (1-9) with compounds of formula (2-7) may include a catalyst, such as palladium(II) acetate, a phosphine ligand, such as 2-(di-tert-butylphosphino)biphenyl, 2-dicyclohexylphosphino-2',6'-dimethoxybiphenyl, or 4,5-bis(diphenylphosphino)-9,9-dimethylxanthene, and a base, such as a tertiary amine base, e.g., triethylamine, or cesium carbonate, in a heated solvent, such as N,N-dimethylformamide or dioxane. Subsequently, the optionally substituted benzyl ether protecting group can be removed as previously described above to give compounds of formula to give compounds of formula (2-8). Compounds of formula (2-8) or the protected precursor can be further modified as known to one of skill in the art and illustrated in the Examples.

Compounds of formula (2-2), formula (2-4), formula (2-6), or formula (2-8) are representative of compounds of formula (I) or are precursors to compounds of formula (I).

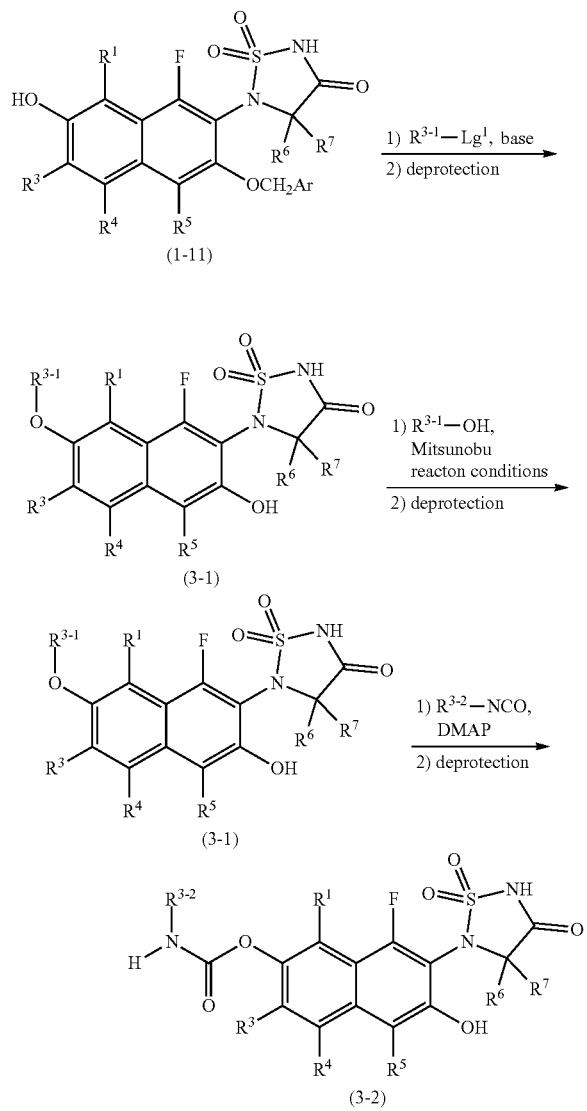

Scheme 3: Representative scheme for synthesis of exemplary compounds of the disclosure.

As shown in Scheme 3, compounds of formula (3-1) and formula (3-2) can be prepared from compounds of formula (1-11). Compounds of formula (1-11) can be alkylated with compounds of formula $R^{3-1}$-$LG^1$, wherein $LG^1$ is a leaving group such as chloro, bromo, iodo or sulfonate and $R^{3-1}$ is an optionally substituted alkyl, optionally substituted heterocyclyl or optionally substituted cycloalkyl. The alkylation conditions can include treatment with a base, such as but not limited to cesium carbonate or sodium hydride, in an optionally heated solvent, such as N,N-dimethylformamide. Subsequently, the optionally substituted benzyl ether protecting group can be removed using conditions known to one of skill in the art and dependent on the particular benzyl ether. For example, an unsubstituted benzyl ether can be removed by treatment with trichloroborane in the presence of 1,2,3,4,5-pentamethylbenzene in dichloromethane at −60 to −80° C. to give compounds of formula (3-1). Compounds of formula (3-1) or the corresponding protected precursors can be further modified as known to one of skill in the art and illustrated in the Examples. The group $OR^{3-1}$ represents an ether moiety of $R^2$.

An alternative preparation of compounds of formula (3-1) involves reacting compounds of formula (1-11) with compounds of formula $R^{3-1}$—OH, wherein $R^{3-1}$ is an optionally substituted alkyl or optionally substituted cycloalkyl, under Mitsunobu reaction conditions. Accordingly, compounds of formula (1-11) and compounds of formula $R^3$-1-OH can be treated with (E)-diazene-1,2-diylbis(piperidin-1-ylmethanone) and tri-n-butylphosphine in a solvent such as warmed tetrahydrofuran. Subsequent removal of the benzyl protecting group as described above gives compounds of formula (3-1). Compounds of formula (3-1) or the corresponding protected precursors can be further modified as known to one of skill in the art and illustrated in the Examples.

Compounds of formula (1-11) can also be transformed to compounds of formula (3-2). Compounds of formula (1-11) can be reacted with compounds of formula of $R^{3-2}$—NCO, wherein $R^3$-2 is an optionally substituted $C_{1-6}$alkyl, in the presence of 4-dimethylaminopyridine in a solvent such as N,N-dimethylformamide to give the corresponding carbamate. Subsequent removal of the benzyl protecting group as described above gives compounds of formula (3-2). The group —OC(O)NHR$^{3-2}$ represents a carbamate moiety of $R^2$. Compounds of formula (3-2) or the corresponding protected precursors can be further modified as known to one of skill in the art and illustrated in the Examples.

Compounds of formula (3-1) and formula (3-2) are representative of compounds of formula (I) or are precursors to compounds of formula (I).

Scheme 4: Representative scheme for synthesis of exemplary compounds of the disclousure.

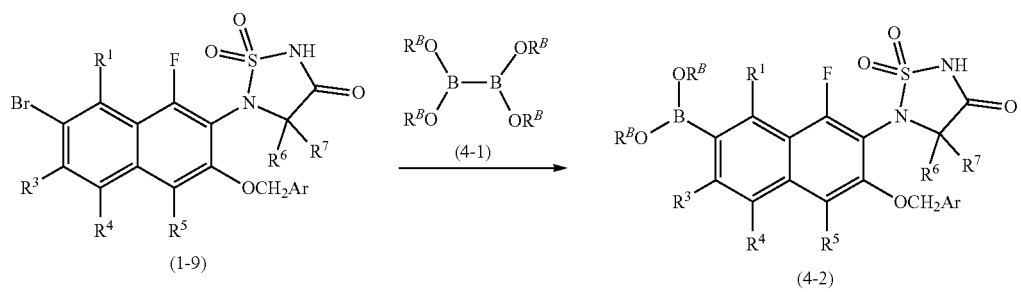

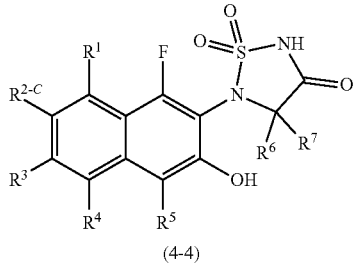

(4-4)

As shown in Scheme 4, compounds of formula (4-4) can be prepared from compounds of formula (1-9). Compounds of formula (1-9) can be reacted under cross-coupling reaction conditions with a boron reagent of formula (4-1), such as bis(pinacolato)diboron, wherein one $R^B$ is connected to another $R^B$, to give compounds of formula (4-2). Reaction conditions to couple compounds of formula (1-9) with compounds of formula (4-1) may include a catalyst ([1,1'-bis(diphenylphosphino)ferrocene]dichloropalladium(II), complex with dichloromethane) and base (potassium acetate or potassium carbonate) in heated dioxane. Compounds of formula (4-2) can be subsequently coupled with compounds of formula (4-3), wherein $R^{2-C}$ represents an aromatic or partially unsaturated ring, an alkyl group, or an alkylene group, and $LG^2$ is a leaving group such as iodine, bromine or chlorine. Reaction conditions to couple compounds of formula (4-4) with compounds of formula (4-3) may include a catalyst (tetrakis(triphenylphosphine)palladium(0), XPhos Pd G2, or meCgpPh Pd G3) and a base (sodium carbonate, potassium phosphate or potassium carbonate) in a heated mixture of toluene and ethanol, or dioxane and water, or N-methyl-2-pyrrolidinone. Subsequently, the optionally substituted benzyl ether protecting group can be removed using conditions known to one of skill in the art and dependent on the particular benzyl ether. For example, an unsubstituted benzyl ether can be removed by treatment with trichloroborane in the presence of 1,2,3,4,5-pentamethyl-benzene in dichloromethane at −60 to −80° C. to give compounds of formula (4-4). Compounds of formula (4-4) or the corresponding protected precursors can be further modified as known to one of skill in the art and illustrated in the Examples.

Compounds of formula (4-4) are representative of compounds of formula (I) or are precursors to compounds of formula (I).

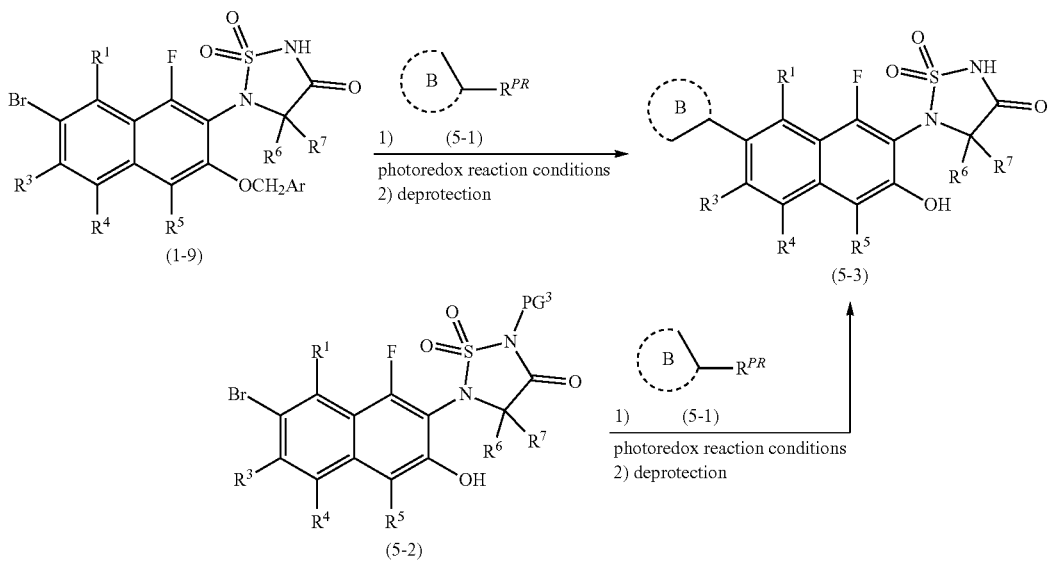

Scheme 5: Representative scheme for synthesis of exemplary compounds of the disclosure.

As shown in Scheme 5, compounds of formula (5-3) can be prepared from compounds of formula (1-9). Compounds of formula (1-9) can be coupled with compounds of formula (5-1), wherein $R^{PR}$ is a potassium trifluoroborate or carboxylic acid moiety and wherein B represents an optionally substituted heterocyclyl or optionally substituted alkyl under photoredox conditions. The conditions to couple compounds of formula (1-9) and compounds of formula (5-1) are treatment with NiCl₂ dimethoxyethane adduct, a ligand (4,4'-di-tert-butyl-2,2'-dipyridyl), a base (cesium carbonate), and bis[3,5-difluoro-2-[5-(trifluoromethyl)-2-pyridyl]phenyl]iridium(1+); 2-(2-pyridyl)pyridine; hexafluorophosphate in solvents such as dioxane with optional N,N-dimethylacetamide in a 450 nm LED photoreactor. Subsequently, the optionally substituted benzyl ether protecting group can be removed using conditions known to one of skill in the art and dependent on the particular benzyl ether. For example, an unsubstituted benzyl ether can be removed by hydrogenation in the presence of a palladium on carbon catalyst in tetrahydrofuran to give compounds of formula (5-3).

Alternatively, the reaction conditions described above also couple compounds of formula (5-1) with compounds of formula (5-2), wherein PG³ is (2-methoxyethoxy)methyl. Deprotection of one or both protecting groups can be achieved by treatment with hydrochloric acid in dioxane to give compounds of formula (5-3).

Compounds of formula (5-3) or the corresponding protected precursors can be further modified as known to one of skill in the art and illustrated in the Examples.

Compounds of formula (5-3) are representative of compounds of formula (I) or are precursors to compounds of formula (I).

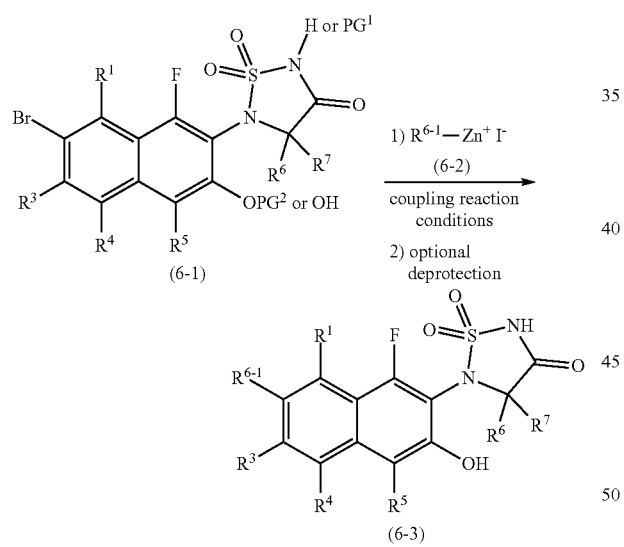

As shown in Scheme 6, compounds of formula (6-3) can be prepared from compounds of formula (6-1). Compounds of formula (6-1), wherein PG¹ is a protecting group such as (2-methoxyethoxy)methyl and PG² is an optionally substituted benzyl group or (2-methoxyethoxy)methyl can be coupled with compounds of formula (6-2), wherein R⁶⁻¹ is an optionally substituted alkyl group, optionally substituted cycloalkyl group or optionally substituted heterocyclyl group. The conditions to couple compounds of formula (6-1) with compounds of formula (6-2) are treatment with a catalyst (Pd SPhos G4) in heated N,N-dimethylacetamide. When present, the optionally substituted benzyl ether protecting group can be removed using conditions known to one of skill in the art and dependent on the particular benzyl ether. For example, an unsubstituted benzyl ether (PG²) can be removed by hydrogenation in the presence of a palladium on carbon catalyst or upon treatment with trichloroborane in dichloromethane to give compounds of formula (6-3). When either PG¹ or PG² is a (2-methoxyethoxy)methyl group, either or both can be removed by treatment with an acid such as hydrochloric acid in dioxane to give compounds of formula (6-3). Compounds of formula (6-3) or the corresponding protected precursors can be further modified as known to one of skill in the art and illustrated in the Examples.

Compounds of formula (6-3) are representative of compounds of formula (I) or are precursors to compounds of formula (I).

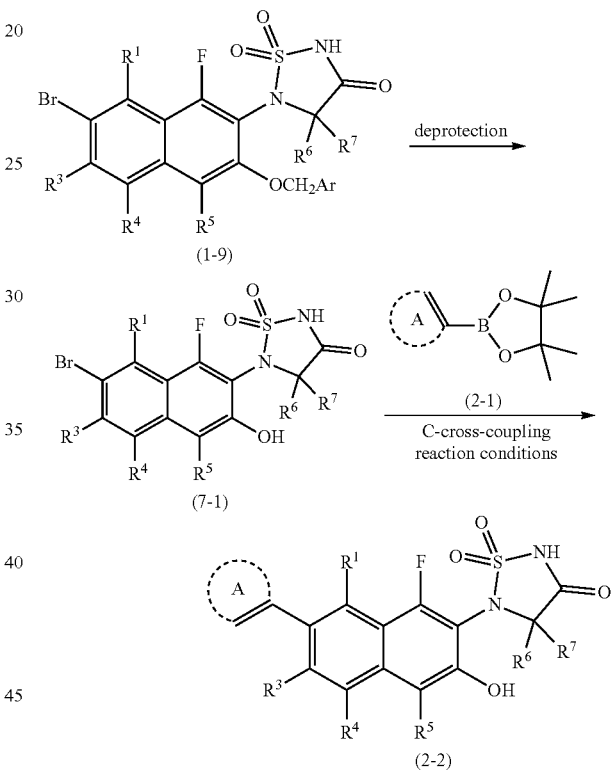

As shown in Scheme 7, compounds of formula (2-2) can be prepared from compounds of formula (1-9) in a reverse synthetic sequence to that described in Scheme 2. In the first step, the optionally substituted benzyl moiety can be removed using conditions known to one of skill in the art and dependent on the particular benzyl ether. For example, an unsubstituted benzyl ether can be removed by treatment with trichloroborane in the presence of 1,2,3,4,5-pentamethylbenzene in dichloromethane at −60 to −80° C. to give compounds of formula (7-1). Compounds of formula (7-1) can be reacted under C-cross-coupling reaction conditions. For example, Suzuki reaction conditions can be used to couple compounds of formula (7-1) with compounds of formula (2-1), wherein A represents an alkene moiety, a cyclopropyl, or an aromatic or a partially unsaturated ring. The corresponding boronic acids of compounds of formula (2-1) are also suitable for the cross-coupling reaction. Reaction conditions to couple compounds of formula (7-1) with compounds of formula (2-1) may include a catalyst (1,1'-bis(di-tert-butylphosphino)ferrocene palladium dichloride), and a base (sodium carbonate or potassium carbonate) in heated dioxane or a mixture of dioxane and water. Compounds of formula (2-2) or the corresponding protected precursors can be further modified as known to one of skill in the art and illustrated in the Examples.

Compounds of formula (2-2) are representative of compounds of formula (I) or are precursors to compounds of formula (I).

Pharmaceutical Compositions

The present disclosure provides pharmaceutical compositions comprising a compound disclosed herein, e.g., a compound of Formula (I), Formula (II) or Formula (III). In some embodiments, the pharmaceutical composition further comprises a pharmaceutically acceptable excipient. In some embodiments, a compound disclosed herein, e.g., a compound of Formula (I), Formula (II) or Formula (III), is provided in an effective amount in the pharmaceutical composition. In some embodiments, the effective amount is a therapeutically effective amount. In certain embodiments, the effective amount is a prophylactically effective amount.

Pharmaceutical compositions described herein can be prepared by any method known in the art of pharmacology. In general, such preparatory methods include the steps of bringing a disclosed compound (the "active ingredient") into association with a carrier and/or one or more other accessory ingredients, and then, if necessary and/or desirable, shaping and/or packaging the product into a desired single- or multi-dose unit. Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of a compound disclosed herein, e.g., a compound of Formula (I), Formula (II) or Formula (III), the pharmaceutically acceptable excipient, and/or any additional ingredients in a pharmaceutical composition of the disclosure will vary, depending upon the identity, size, and/or condition of the subject treated and further depending upon the route by which the composition is to be administered. By way of example, the composition may comprise between 0.1% and 100% (w/w) of a compound disclosed herein.

The term "pharmaceutically acceptable excipient" refers to a non-toxic carrier, adjuvant, diluent, or vehicle that does not destroy the pharmacological activity of the compound with which it is formulated. Pharmaceutically acceptable excipients useful in the manufacture of the pharmaceutical compositions of the disclosure are any of those that are well known in the art of pharmaceutical formulation and include inert diluents, dispersing and/or granulating agents, surface active agents and/or emulsifiers, disintegrating agents, binding agents, preservatives, buffering agents, lubricating agents, and/or oils. Pharmaceutically acceptable excipients useful in the manufacture of the pharmaceutical compositions of the disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present disclosure may be administered orally, parenterally (including subcutaneous, intramuscular, intravenous and intradermal), by inhalation spray, topically, rectally, nasally, buccally, vaginally or via an implanted reservoir. In some embodiments, provided compounds or compositions are administrable intravenously and/or orally.

The term "parenteral" as used herein includes subcutaneous, intravenous, intramuscular, intraocular, intravitreal, intra-articular, intra-synovial, intrasternal, intrathecal, intrahepatic, intraperitoneal intralesional and intracranial injection or infusion techniques. Preferably, the compositions are administered orally, subcutaneously, intraperitoneally or intravenously. Sterile injectable forms of the compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

Pharmaceutically acceptable compositions of this disclosure may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added. In some embodiments, a provided oral formulation is formulated for immediate release or sustained/delayed release. In some embodiments, the composition is suitable for buccal or sublingual administration, including tablets, lozenges and pastilles. A compound disclosed herein may also be in micro-encapsulated form.

The compositions of the present disclosure can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present disclosure may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212, 162; and 4,861,760. The entire contents of these patents are incorporated herein by reference in their entirety for all purposes. The compositions of the present disclosure can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., *Gao Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present disclosure can be delivered by the use of liposomes which fuse with the cellular membrane or are endocytosed, e.g., by employing receptor ligands attached to the liposome that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present disclosure into the target cells in vivo. (See, e.g., Al-Muhammed, J. Microencapsul. 13:293-306, 1996; Chonn, *Curr. Opin. Biotechnol.* 6:698-708, 1995; Ostro, *J. Hosp. Pharm.* 46: 1576-1587, 1989). The compositions of the present disclosure can also be delivered as nanoparticles.

Alternatively, pharmaceutically acceptable compositions of the present disclosure may be administered in the form of suppositories for rectal administration. Pharmaceutically acceptable compositions of this disclosure may also be administered topically, especially when the target of treatment includes areas or organs readily accessible by topical application, including diseases of the eye, the skin, or the lower intestinal tract. Suitable topical formulations are readily prepared for each of these areas or organs.

In some embodiments, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein, e.g., a compound of Formula (I), Formula (II) or Formula (III) are typically formulated in dosage unit form, e.g., single unit dosage form, for ease of administration and uniformity of dosage. It will be understood, however, that the total daily usage of the compositions of the present disclosure will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition disclosed herein can be administered in combination with one or more additional pharmaceutical agents. The compounds or compositions can be administered in combination with additional pharmaceutical agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional pharmaceutical agents, which may be useful as, e.g., combination therapies. Pharmaceutical agents include therapeutically active agents. Pharmaceutical agents also include prophylactically active agents. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the inventive compound with the additional pharmaceutical agents and/or the desired therapeutic and/or prophylactic effect to be achieved. In general, it is expected that the additional pharmaceutical agents utilized in combination be utilized at levels that do not exceed the levels at which they are utilized individually. In some embodiments, the levels utilized in combination will be lower than those utilized individually.

Exemplary additional pharmaceutical agents include, but are not limited to, anti-proliferative agents, anti-cancer agents, anti-diabetic agents, anti-inflammatory agents, immunosuppressant agents, and pain-relieving agents. Pharmaceutical agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

Pharmaceutical compositions provided by the present disclosure include compositions wherein the active ingredient (e.g., compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., inhibiting the activity of a target molecule (e.g. PTPN2 and/or PTPN1), and/or reducing, eliminating, or slowing the progression of disease symptoms. Determination of a therapeutically effective amount of a compound disclosed herein is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods, compounds and compositions disclosed herein. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present disclosure should be sufficient to affect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

Also encompassed by the present are kits (e.g., pharmaceutical packs). The kits provided herein may be useful for preventing and/or treating a disease (e.g., cancer, type-2 diabetes, obesity, a metabolic disease, or other disease or condition described herein).

The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one unit dosage form.

Thus, in one aspect, provided are kits including a first container comprising a compound disclosed herein. In certain embodiments, the kits are useful in preventing and/or treating a proliferative disease in a subject. In certain embodiments, the kits further include instructions for administering a disclosed compound to a subject to prevent and/or treat a disease described herein.

Methods of Treatment

The present disclosure features compounds, compositions, and methods comprising a compound disclosed herein, e.g., a compound of Formula (I), Formula (II) or Formula (III). In some embodiments, the compounds, compositions, and methods disclosed herein are used in the prevention or treatment of a disease, disorder, or condition. Exemplary diseases, disorders, or conditions include, but are not limited to cancer, type-2 diabetes, metabolic syndrome, obesity, or a metabolic disease.

Cancer

In some embodiments, a compound disclosed herein, e.g., a compound of Formula (I), Formula (II) or Formula (III) is used to treat cancer. As used herein, "cancer" refers to human cancers and carcinomas, sarcomas, adenocarcinomas (e.g., papillary adenocarcinomas), lymphomas, leukemias, melanomas, etc., including solid and lymphoid cancers, kidney, breast, lung, bladder, colon, ovarian, prostate, pancreas, stomach, brain, head and neck, skin, uterine, testicular, glioma, esophagus, liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), and/or multiple myeloma. In some further instances, "cancer" refers to lung cancer, breast cancer, ovarian cancer, epithelial ovarian cancer, leukemia, lymphoma, melanoma, pancreatic cancer, sarcoma, bladder cancer, bone cancer, biliary tract cancer, adrenal gland cancer, salivary gland cancer, bronchus cancer, oral cancer, cancer of the oral cavity or pharynx, laryngeal cancer, renal cancer, gynecologic cancers, brain cancer, central nervous system cancer, peripheral nervous system cancer, cancer of the hematological tissues, small bowel or appendix cancer, cervical cancer, colon cancer, esophageal cancer, gastric cancer, liver cancer, head and neck cancer, kidney cancer, myeloma, thyroid cancer, prostate cancer, metastatic cancer, or carcinoma.

As used herein, the term "cancer" refers to all types of cancer, neoplasm or malignant tumors found in mammals, including leukemia, lymphoma, carcinomas and sarcomas. Exemplary cancers that may be treated with a compound, pharmaceutical composition, or method provided herein include lymphoma, B-cell lymphoma, heavy chain disease, alpha chain disease, gamma chain disease, mu chain disease, Waldenstrom's macroglobulinemia, benign monoclonal gammopathy, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g., ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g., hepatocellular carcinoma), lung cancer (e.g., non-small cell lung carcinoma, squamous cell lung carcinoma, adenocarcinoma, large cell lung carcinoma, small cell lung carcinoma, carcinoid, sarcoma), glioblastoma multiforme, acoustic neuroma, retinoblastoma, astrocytoma, craniopharyngioma, hemangioblastoma, pinealoma, ependymoma, oligodendroglioma, meningioma, glioma, or melanoma. Additional examples include, cancer of the thyroid, endocrine system, brain, breast, cervix, colon, head & neck, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, immunocytic amyloidosis, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, chronic leukemia, acute nonlymphocytic leukemia, acute lymphocytic leukemia, B-cell chronic lynipho-cytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, acute myelocytic leukemia, chronic myelocytic leukemia, leukemia cutis, embryonal leukemia, eosinophilic leukemia, erythroleukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocyte leukemia, micromyeloblastic leukemia, monocytic leukemia, myeloblasts leukemia, myelocytic leukemia, myeloid granulocytic leukemia, myelomonocytic leukemia, Naegeli leukemia, plasma cell leukemia, multiple myeloma, plasmacytic leukemia, polycythemia vera, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, leiomyosarcoma, lymphosarcoma, lymphangiosarcoma, lymphangioendotheliosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, endotheliosarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, osteogenic sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bile duct carcinoma, bladder carcinoma, breast carcinoma, Brenner carcinoma, bronchioalveolar carcinoma, bronchiolar carcinoma, bronchiogenic carcinoma, cerebriform carcinoma, cervical carcinoma, cholangiocellular carcinoma, chordoma, chorionic carcinoma, clear cell carcinoma, colloid carcinoma, colon carcinoma, comedo carcinoma, corpus carcinoma, cribriform carcinoma, carcinoma en cuirasse, carcinoma cutaneum, cylindrical carcinoma, cylindrical cell carcinoma, cystadenocarcinoma, duct carcinoma, ductal carcinoma, carcinoma durum, embryonal carcinoma, encephaloid carcinoma, endometrioid carcinoma, epiermoid carcinoma, epithelial carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lung carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, nonpapillary renal cell carcinoma, oat cell carcinoma, carcinoma ossificans, osteoid carcinoma, ovarian carcinoma, pancreati ductal carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, sebaceous gland carcinoma, seminoma, serous carcinoma, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, sweat gland carcinoma, carcinoma telangiectaticum, carcinoma telangiectodes, transitional cell carcinoma, carcinoma tuberosum, tubular carcinoma, tuberous carcinoma, undifferentiated carcinoma, verrucous carcinoma, or carcinoma *villosum*.

In some embodiments, a compound disclosed herein, e.g., a compound of Formula (I), Formula (II) or Formula (III), is used to treat pancreatic cancer, breast cancer, multiple myeloma, cancers of secretory cells. For example, certain methods herein treat cancer by decreasing or reducing or preventing the occurrence, growth, metastasis, or progression of cancer. In some embodiments, the methods described herein may be used to treat cancer by decreasing or eliminating a symptom of cancer. In some embodiments, a compound disclosed herein, e.g., a compound of Formula (I), Formula (II) or Formula (III), may be used as a single agent in a composition or in combination with another agent in a composition to treat a cancer described herein (e.g., pancreatic cancer, breast cancer, multiple myeloma, cancers of secretory cells).

In some embodiments, the compounds (compounds described herein, e.g., a compound of Formula (I), Formula (II) or Formula (III)) and compositions (e.g., compositions comprising a compound described herein, e.g., a compound of Formula (I), Formula (II) or Formula (III)) are used with a cancer immunotherapy (e.g., a checkpoint blocking antibody) to treat a subject (e.g., a human subject), e.g., suffering from a disease or disorder described herein (e.g., abnormal cell growth, e.g., cancer (e.g., a cancer described herein)). The methods described herein comprise administering a compound described herein, e.g., a compound of Formula (I), Formula (II) or Formula (III) and an immunotherapy to a subject having abnormal cell growth such as cancer. Exemplary immunotherapies include but are not limited to the following.

In some embodiments, the immunotherapeutic agent is a compound (e.g., a ligand, an antibody) that inhibits the immune checkpoint blockade pathway. In some embodiments, the immunotherapeutic agent is a compound that inhibits the indoleamine 2,3-dioxygenase (IDO) pathway. In some embodiments, the immunotherapeutic agent is a compound that agonizes the STING pathway. Cancer immunotherapy refers to the use of the immune system to treat cancer. Three groups of immunotherapy used to treat cancer include cell-based, antibody-based, and cytokine therapies. All groups exploit cancer cells' display of subtly different structures (e.g., molecular structure; antigens, proteins, molecules, carbohydrates) on their surface that can be detected by the immune system. Cancer immunotherapy (e.g., anti-tumor immunotherapy or anti-tumor immunotherapeutics) includes but is not limited to, immune checkpoint antibodies (e.g., PD-1 antibodies, PD-L1 antibodies, PD-L2 antibodies, CTLA-4 antibodies, TIM3 antibodies, LAG3 antibodies, TIGIT antibodies); and cancer vaccines (e.g., anti-tumor vaccines or vaccines based on neoantigens such as a peptide or RNA vaccine).

Cell-based therapies (e.g., cancer vaccines), usually involve the removal of immune cells from a subject suffering from cancer, either from the blood or from a tumor. Immune cells specific for the tumor will be activated, grown, and returned to a subject suffering from cancer where the immune cells provide an immune response against the cancer. Cell types that can be used in this way are e.g., natural killer cells, lymphokine-activated killer cells, cytotoxic T-cells, dendritic cells, CAR-T therapies (e.g., chimeric antigen receptor T-cells which are T-cells engineered to target specific antigens), TIL therapy (e.g., administration of tumor-infiltrating lymphocytes), TCR gene therapy, protein vaccines, and nucleic acid vaccines. An exemplary cell-based therapy is Provenge. In some embodiments, the cell-based therapy is a CAR-T therapy.

Interleukin-2 and interferon-alpha are examples of cytokines, proteins that regulate and coordinate the behavior of the immune system.

Cancer Vaccines with Neoantigens

Neoantigens are antigens encoded by tumor-specific mutated genes. Technological innovations have made it possible to dissect the immune response to patient-specific neoantigens that arise as a consequence of tumor-specific mutations, and emerging data suggest that recognition of such neoantigens is a major factor in the activity of clinical immunotherapies. These observations indicate that neoantigen load may form a biomarker in cancer immunotherapy. Many novel therapeutic approaches are being developed that selectively enhance T cell reactivity against this class of antigens. One approach to target neoantigens is via cancer vaccine. These vaccines can be developed using peptides or RNA, e.g., synthetic peptides or synthetic RNA.

Antibody therapies are antibody proteins produced by the immune system and that bind to a target antigen on the surface of a cell. Antibodies are typically encoded by an immunoglobulin gene or genes, or fragments thereof. In normal physiology antibodies are used by the immune system to fight pathogens. Each antibody is specific to one or a few proteins, and those that bind to cancer antigens are used, e.g., for the treatment of cancer. Antibodies are capable of specifically binding an antigen or epitope (Fundamental Immunology, $3^{rd}$ Edition, Paul, W. E, ed., Raven Press, N.Y. (1993). Specific binding occurs to the corresponding antigen or epitope even in the presence of a heterogeneous population of proteins and other biologics. Specific binding of an antibody indicates that it binds to its target antigen or epitope with an affinity that is substantially greater than binding to irrelevant antigens. The relative difference in affinity is often at least 25% greater, more often at least 50% greater, most often at least 100% greater. The relative difference can be at least 2-fold, at least 5-fold, at least 10-fold, at least 25-fold, at least 50-fold, at least 100-fold, or at least 1000-fold, for example.

Exemplary types of antibodies include without limitation human, humanized, chimeric, monoclonal, polyclonal, single chain, antibody binding fragments, and diabodies. Once bound to a cancer antigen, antibodies can induce antibody-dependent cell-mediated cytotoxicity, activate the complement system, prevent a receptor interacting with its ligand or deliver a payload of chemotherapy or radiation, all of which can lead to cell death. Exemplary antibodies for the treatment of cancer include but are not limited to, Alemtuzumab, Bevacizumab, Bretuximab vedotin, Cetuximab, Gemtuzumab ozogamicin, Ibritumomab tiuxetan, Ipilimumab, Ofatumumab, Panitumumab, Rituximab, Tositumomab, Trastuzumab, Nivolumab, Pembrolizumab, Avelumab, durvalumab and pidilizumab.

Checkpoint Blocking Antibodies

The methods described herein comprise, in some embodiments, treating a human subject suffering from a disease or disorder described herein, the method comprising administering a composition comprising a cancer immunotherapy (e.g., an immunotherapeutic agent). In some embodiments, the immunotherapeutic agent is a compound (e.g., an inhibitor or antibody) that inhibits the immune checkpoint blockade pathway. Immune checkpoint proteins, under normal physiological conditions, maintain self-tolerance (e.g., prevent autoimmunity) and protect tissues from damage when the immune system is responding to e.g., pathogenic infection. Immune checkpoint proteins can be dysregulated by tumors as an important immune resistance mechanism (Pardoll, *Nature Rev. Cancer*, 2012, 12, 252-264). Agonists of co-stimulatory receptors or antagonists of inhibitory signals (e.g., immune checkpoint proteins), provide an amplification of antigen-specific T-cell responses. Antibodies that block immune checkpoints do not target tumor cells directly but typically target lymphocyte receptors or their ligands to enhance endogenous antitumor activity.

Exemplary checkpoint blocking antibodies include but are not limited to, anti-CTLA-4, anti-PD-1, anti-LAG3 (e.g., antibodies against lymphocyte activation gene 3), and anti-TIM3 (e.g., antibodies against T-cell membrane protein 3). Exemplary anti-CTLA-4 antibodies include but are not limited to, ipilimumab and tremelimumab. Exemplary anti-PD-1 ligands include but are not limited to, PD-L1 (e.g., B7-H1 and CD274) and PD-L2 (e.g., B7-DC and CD273). Exemplary anti-PD-1 antibodies include but are not limited to, nivolumab (e.g., MDX-1106, BMS-936558, or ONO-4538)), CT-011, AMP-224, pembrolizumab (trade name Keytruda), and MK-3475. Exemplary PD-L1-specific antibodies include but are not limited to, BMS936559 (e.g., MDX-1105), MEDI4736 and MPDL-3280A. Exemplary checkpoint blocking antibodies also include but are not limited to, IMP321 and MGA271.

T-regulatory cells (e.g., CD4+, CD25+, or T-reg) are also involved in policing the distinction between self and non-self (e.g., foreign) antigens, and may represent an important mechanism in suppression of immune response in many cancers. T-reg cells can either emerge from the thymus (e.g., "natural T-reg") or can differentiate from mature T-cells under circumstances of peripheral tolerance induction (e.g., "induced T-reg"). Strategies that minimize the action of T-reg cells would therefore be expected to facilitate the immune response to tumors.

IDO Pathway Inhibitors

The IDO pathway regulates immune response by suppressing T cell function and enabling local tumor immune escape. IDO expression by antigen-presenting cells (APCs) can lead to tryptophan depletion and resulting antigen-specific T cell energy and regulatory T cell recruitment. Some tumors even express IDO to shield themselves from the immune system. A compound that inhibits IDO or the IDO pathway activates the immune system to attack the cancer (e.g., tumor in a subject). Exemplary IDO pathway inhibitors include indoximod, epacadostat and EOS200271.

STING Pathway Agonists

Stimulator of interferon genes (STING) is an adaptor protein that plays an important role in the activation of type I interferons in response to cytosolic nucleic acid ligands. Evidence indicates involvement of the STING pathway in the induction of antitumor immune response. For example, activation of the STING-dependent pathway in cancer cells can result in tumor infiltration with immune cells and modulation of the anticancer immune response. STING agonists are being developed as a class of cancer therapeutics. Exemplary STING agonists include MK-1454 and ADU-S100.

Co-Stimulatory Antibodies

The methods described herein comprise, in some embodiments, treating a human subject suffering from a disease or disorder described herein, the method comprising administering a composition comprising a cancer immunotherapy (e.g., an immunotherapeutic agent). In some embodiments, the immunotherapeutic agent is a co-stimulatory inhibitor or antibody. In some embodiments, the methods described herein comprise depleting or activating anti-4-1BB, anti-OX40, anti-GITR, anti-CD27 and anti-CD40, and variants thereof.

Methods of the present disclosure contemplate single as well as multiple administrations of a therapeutically effective amount of a compound as described herein. Compounds, e.g., a compound as described herein, can be administered at regular intervals, depending on the nature, severity and extent of the subject's condition. In some embodiments, a compound described herein is administered in a single dose. In some embodiments, a compound described herein is administered in multiple doses.

Metabolic Diseases

In some embodiments, a compound disclosed herein, e.g., a compound of Formula (I), Formula (II) or Formula (III), is used to treat a metabolic disease. As used herein, the term "metabolic disease" refers to a disease or condition affecting a metabolic process in a subject. Exemplary metabolic diseases that may be treated with a compound disclosed herein, e.g., a compound of Formula (I), Formula (II) or Formula (III), include non-alcoholic steatohepatitis (NASH), non-alcoholic fatty liver disease (NAFLD), liver fibrosis, obesity, heart disease, atherosclerosis, arthritis, cystinosis, diabetes (e.g., Type I diabetes, Type II diabetes, or gestational diabetes), metabolic syndrome, phenylketonuria, proliferative retinopathy, or Kearns-Sayre disease.

In some embodiments, a compound disclosed herein, e.g., a compound of Formula (I), Formula (II) or Formula (III), is used to treat a metabolic disease (e.g., a metabolic disease described herein) by decreasing or eliminating a symptom of the disease. In some embodiments, the method of treatment comprises decreasing or eliminating a symptom comprising elevated blood pressure, elevated blood sugar level, weight gain, fatigue, blurred vision, abdominal pain, flatulence, constipation, diarrhea, jaundice, and the like. In some embodiments, a compound disclosed herein, e.g., a compound of Formula (I), Formula (II) or Formula (III), may be used as a single agent in a composition or in combination with another agent in a composition to treat a metabolic disease.

Infectious Diseases

In some embodiments, a compound disclosed herein, e.g., a compound of Formula (I), Formula (II) or Formula (III), is used to treat an infectious disease. Exemplary infectious diseases that may be treated with a compound disclosed herein, e.g., a compound of Formula (I), Formula (II) or Formula (III), include bacterial infections, viral infections (e.g., herpes, shingles, influenza, the common cold, encephalitis), and parasitic infections.

In some embodiments, a compound disclosed herein, e.g., a compound of Formula (I), Formula (II) or Formula (III), is used to treat an infectious disease (e.g., an infectious disease described herein) by decreasing or eliminating a symptom of the disease. In some embodiments, a compound disclosed herein, e.g., a compound of Formula (I), Formula (II) or Formula (III), may be used as a single agent in a composition or in combination with another agent in a composition to treat an infectious disease.

Parasitic Infections

In some embodiments, a compound disclosed herein, e.g., a compound of Formula (I), Formula (II) or Formula (III), is used to treat a parasitic infection.

In some embodiments, a compound disclosed herein, e.g., a compound of Formula (I), Formula (II) or Formula (III), is used to treat a parasitic infection by decreasing or eliminating a symptom of the disease. In some embodiments, a compound disclosed herein, e.g., a compound of Formula (I), Formula (II) or Formula (III), may be used as a single agent in a composition or in combination with another agent in a composition to treat a parasitic infection.

Immunosuppressive Diseases

In some embodiments, a compound disclosed herein, e.g., a compound of Formula (I), Formula (II) or Formula (III), is used to treat an immunosuppressive disease.

In some embodiments, a compound disclosed herein, e.g., a compound of Formula (I), Formula (II) or Formula (III), is used to treat an immunosuppressive disease by decreasing or eliminating a symptom of the disease. In some embodiments, a compound disclosed herein, e.g., a compound of Formula (I), Formula (II) or Formula (III), may be used as a single agent in a composition or in combination with another agent in a composition to treat an immunosuppressive disease.

In some embodiments, the compounds disclosed herein are provided as pharmaceutical compositions including a disclosed compound, e.g., of Formula (I), Formula (II) or Formula (III) and a pharmaceutically acceptable excipient. In embodiments of the method, a disclosed compound, e.g., of Formula (I), Formula (II) or Formula (III) is co-administered with a second agent (e.g. therapeutic agent). In other embodiments of the method, a disclosed compound, e.g., of Formula (I), Formula (II) or Formula (III) is co-administered with a second agent (e.g. therapeutic agent), which is administered in a therapeutically effective amount.

Combination Therapy

The present disclosure provides a pharmaceutical composition comprising a compound disclosed herein, e.g., a compound of Formula (I), Formula (II) or Formula (III), as well as a second agent (e.g. a second therapeutic agent). In some embodiments, the pharmaceutical composition includes a second agent (e.g. a second therapeutic agent) in a therapeutically effective amount. In some embodiments, the second agent is an agent for treating cancer, a metabolic disease (e.g., type-2 diabetes or obesity) or a disease or disorder favorably responsive to PTPN2 or PTP1B inhibitor treatment.

The compounds described herein can be used in combination with one another, with other active agents known to be useful in treating cancer, a metabolic disease (e.g., type-2 diabetes or obesity) or a disease or disorder favorably responsive to PTPN2 or PTP1B inhibitor treatment, or with adjunctive agents that may not be effective alone but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In some embodiments, the compounds described herein may be combined with treatments for a cancer, a metabolic disease (e.g., type-2 diabetes or obesity) or a disease or disorder favorably responsive to PTPN2 or PTP1B inhibitor treatment. In embodiments, the second agent is an anti-cancer agent. In embodiments, the second agent is a chemotherapeutic. In embodiments, the second agent is an agent for treating a metabolic disease. In embodiments, the second agent is an anti-diabetic agent. In some embodiments, the second agent is an anti-obesity agent.

Anti-Cancer Agents

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anticancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP 16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 1 1-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone Bl; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin II (including recombinant interleukin II, or rIL.sub.2), interferon alfa-2a; interferon alfa-2b; interferon alfa-n1; interferon alfa-n3; interferon beta-1a; interferon gamma-1b; iprop latin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol, i.e. paclitaxel), Taxotere, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and SC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-1 12378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. TLX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A 1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, Inanocine (i.e. NSC-698666), 3-IAABE (Cytoskeleton/Mt. Sinai School of Medicine), A-204197 (Abbott), T-607 (Tularik, i.e. T-900607), RPR-115781 (Aventis), Eleutherobins (such as Desmethyleleutherobin, Desaetyleleutherobin, isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-25041 1 (Sanofi), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™) vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

Additionally, the compounds described herein can be co-administered with conventional immunotherapeutic agents including, but not limited to, immunostimulants (e.g., *Bacillus* Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), and radioimmunotherapy (e.g., anti-CD20 monoclonal antibody conjugated to $^{111}$In, $^{90}$Y, or $^{131}$I, etc.).

In a further embodiment, the compounds described herein can be co-administered with conventional radiotherapeutic agents including, but not limited to, radionuclides such as $^{47}$Sc, $^{64}$Cu $^{67}$Cu $^{89}$Sr, $^{86}$Y, $^{87}$Y, $^{90}$Y, $^{105}$Rh, $^{m}$Ag, $^{m}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Synthetic Protocols

The compounds provided herein can be prepared from readily available starting materials using modifications to the specific synthesis protocols set forth below that would be well known to those of skill in the art. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures. General scheme relating to methods of making exemplary compounds of the invention are additionally described in the section entitled Methods of Making Exemplary Compounds.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in Greene et al., *Protecting Groups in Organic Synthesis*, Second Edition, Wiley, New York, 1991, and references cited therein.

Abbreviations

APCI for atmospheric pressure chemical ionization; DCI for desorption chemical ionization; DMSO for dimethyl sulfoxide; ESI for electrospray ionization; HPLC for high performance liquid chromatography; LC/MS for liquid chromatography/mass spectrometry; LED for light-emitting diode; MS for mass spectrum; NMR for nuclear magnetic resonance; psi for pounds per square inch; and TLC for thin-layer chromatography.

Example 1: 5-{1-fluoro-3-hydroxy-7-[2-(morpholin-4-yl)ethoxy]naphthalen-2-yl}-1λ⁶,2,5-thiadiazolidine-1,1,3-trione (Compound 100)

Example 1A: benzyl 3-(benzyloxy)-7-bromonaphthalene-2-carboxylate

A mixture of 7-bromo-3-hydroxy-2-naphthoic acid (100 g, 374 mmol) and cesium carbonate (366 g, 1123 mmol) in N,N-dimethylformamide (749 mL) was rapidly stirred for 5 minutes at 23° C. Thereafter, benzyl bromide (89.0 mL, 749 mmol) was added, and the internal temperature rose to 49° C. After 90 minutes, the light yellow mixture was poured into H$_2$O (1.5 L), and the resulting white precipitate was collected via filtration. The collected precipitate was washed sequentially with H$_2$O (3×1 L) and tert-butyl methyl ether/heptanes (1:2, 2×300 mL) and then dried in vacuo (15 mbar) at 45° C. to constant weight to afford the title compound (160.3 g, 358 mmol, 96% yield) as an off-white solid. MS (APCI$^+$) m/z 449 [M+H]$^+$.

Example 1B: 3-(benzyloxy)-7-bromonaphthalene-2-carboxylic acid

To a mixture of the product of Example 1A (150.1 g, 336 mmol), water (746 mL), and methanol (1.49 L) was added lithium hydroxide monohydrate (28.2 g, 671 mmol). The thick slurry was agitated via overhead mechanical stirring and heated to an internal temperature of 70° C. After 3 hours, the mixture was cooled to room temperature in an ice bath and 6 M HCl (168 mL) was added over 5 minutes, causing an off-white solid to precipitate. The solid was collected via filtration and washed with H$_2$O (2×1 L), triturated with tert-butyl methyl ether (2×300 mL), and dried to constant weight in vacuo at 65° C. to afford the title compound (101.5 g, 284 mmol, 85% yield) as a white solid. MS (APCI$^+$) m/z 358 [M+H]$^+$.

Example 1C:
3-(benzyloxy)-7-bromonaphthalen-2-amine

To a suspension of the product of Example 1B (101 g, 283 mmol) in toluene (794 mL) and tert-butanol (794 mL) was added triethylamine (41.8 mL, 300 mmol). The hazy light yellow solution was heated to an internal temperature of 80° C. under nitrogen, and diphenyl phosphorazidate (64.4 mL, 300 mmol) was added dropwise over 90 minutes with the entire reaction behind a blast shield. After 5 hours, the reaction mixture was cooled to room temperature, diluted with H$_2$O (1.5 L), and extracted with ethyl acetate (2×400 mL). The combined organic layers were washed with brine (2×150 mL), dried over sodium sulfate, filtered and concentrated to give a white solid. The solid was carried forward to hydrolysis without further purification.

To the crude intermediate was added diethylenetriamine (253 mL, 2.34 mol). The heterogeneous suspension was heated to an internal temperature of 130° C. under nitrogen, at which time a homogeneous dark orange solution formed. After 13 hours, the mixture was cooled to room temperature in an ice bath, and H$_2$O (800 mL) was added slowly over 3 minutes, resulting in precipitation of a yellow solid and a concomitant exotherm to an internal temperature of 53° C. Once the heterogeneous suspension had cooled to room temperature, the crude solid was dissolved in CH$_2$Cl$_2$ (1.5 L), and the layers were separated. The aqueous layer was back-extracted with CH$_2$Cl$_2$ (3×150 mL). The combined organic layers were washed with brine (3×100 mL), dried over sodium sulfate, filtered, and the volatiles were removed in vacuo to afford an orange solid. The solid was combined with isopropanol (250 mL) to form a slurry that then was filtered. The resulting solid was again combined with isopropanol (2×100 mL), and solids were isolated via filtration. The solid was dried in vacuo (13 mbar) at 35° C. to afford the title compound (68.48 g, 209 mmol, 74% yield over two steps) as a white solid. MS (APCI$^+$) m/z 329 [M+H]$^+$.

Example 1D: methyl {[3-(benzyloxy)-7-bromonaphthalen-2-yl]amino}acetate

To a mixture of the product of Example 1C (67.8 g, 207 mmol) and potassium carbonate (57.1 g, 413 mmol) in N,N-dimethylformamide (354 mL) and H$_2$O (1.861 mL, 103 mmol) was added methyl 2-bromoacetate (29.3 mL, 310 mmol). The suspension was vigorously stirred at room temperature for 5 minutes then heated to an internal temperature of 60° C. After 4 hours, the suspension was cooled to room temperature and partitioned between H$_2$O (400 mL) and ethyl acetate (400 mL). The aqueous layer was extracted with ethyl acetate (2×100 mL), and the combined organic layers were washed with saturated aqueous ammonium chloride (3×60 mL), dried over sodium sulfate, filtered, and concentrated to afford a pale beige solid. The solid was triturated with heptanes (100 mL), and the resulting beige solid was isolated via filtration, washed with additional heptanes (2×30 mL) and dried to constant weight in vacuo (15 mbar) at 35° C. to afford the title compound (68.52 g, 171 mmol, 83% yield) as an off-white solid. MS (APCI$^+$) m/z 401 [M+H]$^+$.

Example 1E: methyl {[3-(benzyloxy)-7-bromo-1-fluoronaphthalen-2-yl]amino}acetate To a solution of the product of Example 1D (15 g, 37.5 mmol) in N,N-dimethylformamide (300 mL) at 2° C. was added a solution of 1-chloromethyl-4-fluoro-1,4-diazoniabicyclo[2.2.2]octane bis(tetrafluoroborate) (15.93 g, 45.0 mmol) in N,N-dimethylformamide (100 mL) over 5 minutes. The resulting solution was stirred for 15 minutes, and then quenched with a 0.33 M solution of sodium thiosulfate (300 mL, exothermic). The mixture was diluted with ethyl acetate (150 mL) and saturated aqueous ammonium chloride (75 mL) and stirred for 15 minutes at room temperature. The layers were separated, and the aqueous layer was extracted with ethyl acetate (3×75 mL). The combined organic layers were washed with saturated aqueous ammonium chloride (4×75 mL) and brine (75 mL), then dried over sodium sulfate, filtered and concentrated in vacuo to give an orange solid. Ethyl acetate (30 mL) was added to the crude solid, and the mixture was sonicated for 30 seconds. Then heptanes (150 mL) were slowly added via an addition funnel over 15 minutes. The resulting yellow solid was collected via filtration and washed with 33% v/v ethyl acetate in heptanes (3×60 mL). The solid was discarded, and the filtrate was concentrated in vacuo to give a yellow/orange solid, which was triturated with anhydrous ethanol (45 mL) heated to an internal temperature of 55° C. and stirred for 30 minutes, then slowly cooled to room temperature. The resulting yellow solid was collected by filtration, then washed with anhydrous ethanol (30 mL), and dried in vacuo (15 mbar) at 50° C. to constant weight to give the title compound (10.1 g, 24.25 mmol, 64.7% yield) as a pale yellow solid. $^1$H NMR (DMSO-d$_6$) δ ppm 7.79 (d, J=2.1 Hz, 1H), 7.65 (dd, J=8.7, 1.7 Hz, 1H), 7.56-7.51 (m, 2H), 7.46-7.35 (m, 3H), 7.38-7.31 (m, 2H), 7.28 (s, 1H), 5.64 (td, J=6.7, 2.5 Hz, 1H), 5.28 (s, 2H), 4.21 (dd, J=6.8, 4.0 Hz, 2H), 3.61 (s, 3H); MS (ESI+) m/z 418, 420 [M+H]$^+$.

Example 1F: methyl {[3-(benzyloxy)-7-bromo-1-fluoronaphthalen-2-yl](sulfamoyl)amino}acetate To a solution of chlorosulfonyl isocyanate (2.26 mL, 26.0 mmol) in dichloromethane (43.5 mL) at 0° C. was added tert-butanol (2.5 mL, 26.0 mmol) slowly so that the internal temperature remained below 10° C. After stirring for 30 minutes at 0° C., a preformed solution of the product of Example 1E (7.25 g, 17.34 mmol) and triethylamine (4.83 mL, 34.7 mmol) in dichloromethane (29.0 mL) was slowly added via addition funnel so that the internal temperature remained below 10° C. Upon complete addition, the addition funnel was rinsed with dichloromethane (12.5 mL). The resulting solution was stirred for 30 minutes at 0° C. and then was allowed to warm to room temperature. After 1 hour, the reaction mixture was quenched with H$_2$O (73 mL). The layers were separated, and the aqueous layer was extracted with dichloromethane (2×36 mL). The combined organic layers were washed with 1 M sodium bisulfate (2×73 mL). The aqueous washes were back extracted with dichloromethane (DCM) (36 mL), and the combined organic layers were dried over sodium sulfate, filtered and concentrated in vacuo to give an orange foam, which was used without purification. MS (APCI$^+$) m/z 541, 543 [M-tert-butyl+H]$^+$.

To a solution of the crude intermediate in dichloromethane (41 mL) was added trifluoroacetic acid (20 mL, 260 mmol), and the resulting dark solution was stirred at room temperature. After 30 minutes, the reaction was quenched by slow addition of saturated aqueous sodium bicarbonate (230 mL) via an addition funnel. The layers were separated, and the aqueous layer was extracted with dichloromethane (2×50 mL). The combined organic layers were concentrated to give an orange foam, which was suspended in dichloromethane (20 mL), and stirred for 5 minutes giving a slurry, which was diluted by dropwise addition of heptanes (40 mL) via an addition funnel. The resulting yellow solid was collected by filtration, washed with 25% v/v dichloromethane in heptanes (2×20 mL) and dried in vacuo (15 mbar) at 50° C. to constant weight to give the title compound (7.5 g, 15.05 mmol, 87% yield). $^1$H NMR (DMSO-$d_6$) δ ppm 8.11 (d, J=2.0 Hz, 1H), 7.84-7.80 (m, 1H), 7.67 (dd, J=8.8, 2.0 Hz, 1H), 7.58-7.53 (m, 2H), 7.44-7.36 (m, 3H), 7.36-7.30 (m, 1H), 7.07 (s, 2H), 5.26 (s, 2H), 4.47 (d, J=17.9 Hz, 1H), 4.31 (d, J=17.8 Hz, 1H), 3.54 (s, 3H); MS (ESI$^+$) m/z 497, 499 [M+H]$^+$.

Example 1G: 5-[3-(benzyloxy)-7-bromo-1-fluoronaphthalen-2-yl]-1λ,2,5-thiadiazolidine-1,1,3-trione To a solution of the product of Example 1F (24.14 g, 48.5 mmol) in tetrahydrofuran (THF) (241 mL) at room temperature was added a solution of sodium methoxide (16.65 mL, 72.8 mmol) (25 weight % in methanol) via syringe, and the resulting solution was stirred at room temperature. After 20 minutes, the reaction was quenched with 1 M hydrochloric acid (240 mL) and diluted with ethyl acetate (120 mL). The layers were separated, and the aqueous layer was extracted with ethyl acetate (2×120 mL). The combined organic layers were washed with a 4:1 mixture of brine and 1 M hydrochloric acid (120 mL), then dried over sodium sulfate, filtered and concentrated to 40 mL total volume to give a dark red solution, which was diluted with dichloromethane (75 mL) and concentrated to 40 mL of total volume. The resulting yellow suspension was diluted with dichloromethane (72 mL), then slowly diluted with heptanes (72 mL). The suspension was sonicated for 30 seconds and stirred for 5 minutes at room temperature. The resulting white solid was collected via filtration, then washed with 25% v/v dichloromethane in heptanes (72 mL) and dried in vacuo (15 mbar) at 50° C. to constant weight to give the title compound (16.4 g, 35.2 mmol, 72.5% yield). $^1$H NMR (DMSO-$d_6$) δ ppm 8.16 (d, J=2.0 Hz, 1H), 7.87 (dd, J=8.9, 1.4 Hz, 1H), 7.74 (dd, J=8.8, 2.0 Hz, 1H), 7.54-7.48 (m, 3H), 7.47-7.29 (m, 3H), 5.28 (s, 2H), 4.54 (s, 2H); MS (ESI$^-$) m/z 463, 465 [M−H]$^-$.

Example 1H: 5-[3-(benzyloxy)-1-fluoro-7-hydroxynaphthalen-2-yl]-1λ,2,5-thiadiazolidine-1,1,3-trione, ammonium salt In a 500 mL round bottom flask were combined the product of Example 1G (9 g, 19.34 mmol), RockPhos Pd G3 precatalyst (0.324 g, 0.387 mmol), and cesium carbonate (18.9 g, 58.0 mmol). The solids were placed under vacuum and stirred for 5 minutes, then the flask was filled with nitrogen and a preformed mixture of N,N-dimethylformamide (90 mL) and H$_2$O (1.045 mL, 58.0 mmol) was added. The resulting suspension was degassed by five vacuum/nitrogen backfills, and then heated to an internal temperature of 80° C. After 3 hours, the reaction mixture was cooled to room temperature, quenched by slow addition of 1 M hydrochloric acid (100 mL), and diluted with ethyl acetate (100 mL). The layers were separated, and the aqueous layer was extracted with ethyl acetate (2×50 mL). The combined organic layers were washed with saturated aqueous ammonium chloride (4×50 mL). The combined aqueous washes were back extracted with ethyl acetate (3×50 mL). The combined organic extracts were washed with a 4:1 mixture of brine and 1 M hydrochloric acid (50 mL), then dried over sodium sulfate, filtered, and concentrated to give a viscous, dark oil. The crude oil was dissolved in acetonitrile (9 mL), then tert-butyl methyl ether (180 mL) was added via addition funnel over 5 minutes with vigorous stirring. The resulting black solid was removed via filtration and washed with 50% v/v tert-butyl methyl ether in ethyl acetate (2×45 mL). The solid was discarded, and the filtrate was concentrated in vacuo. The resulting dark oil was diluted with methanol (9 mL), and then a solution of ammonia in methanol (2.76 mL, 7 M, 19.34 mmol) was added. The resulting solution was diluted by slow addition of 50% v/v ethyl acetate in heptanes (135 mL) via an addition funnel. The resulting solid was collected via filtration, then washed with the cold filtrate, followed by 50% v/v ethyl acetate in heptanes (45 mL), and dried in vacuo (15 mbar) at 50° C. to constant weight to give the title compound as an ammonium salt (6.33 g, 15.10 mmol, 78% yield). $^1$H NMR (DMSO-$d_6$) δ ppm 9.81 (s, 1H), 7.68 (dd, J=8.9, 1.4 Hz, 1H), 7.60-7.49 (m, 2H), 7.39-7.31 (m, 2H), 7.33-7.26 (m, 1H), 7.23 (s, 1H), 7.14 (d, J=2.5 Hz, 1H), 7.10 (dd, J=8.8, 2.5 Hz, 1H), 5.19 (s, 2H), 4.08 (s, 2H); MS (ESI$^-$) m/z 401 [M−H]$^-$.

Example 1I: 5-{3-(benzyloxy)-1-fluoro-7-[2-(morpholin-4-yl)ethoxy]naphthalen-2-yl}-1λ,2,5-thiadiazolidine-1,1,3-trione A mixture of 2-morpholinoethanol (1.69 g, 12.9 mmol), triethylamine (2.70 mL, 19.35 mmol), and anhydrous dichloromethane (71.7 mL) was cooled to 0° C. Thereafter, methanesulfonyl chloride (1.206 mL, 15.48 mmol) was added dropwise over 5 minutes, and after 10 minutes, the reaction was warmed to room temperature and stirred for an additional 30 minutes. The majority of the dichloromethane was removed in vacuo, and the resulting residue was diluted with ethyl acetate (50 mL) and washed with saturated aqueous sodium bicarbonate (2×30 mL), dried over sodium sulfate, filtered, and the volatiles were removed in vacuo at 29° C. to afford 2-morpholinoethyl methanesulfonate (1.71 g, 8.17 mmol, 63.3% yield) as an amorphous yellow residue which was used immediately in the subsequent reaction.

To a solution of the product of Example 1H (120 mg, 0.286 mmol) in N,N-dimethylformamide (954 μL) was added cesium carbonate (186 mg, 0.572 mmol). The suspension was stirred at room temperature for 5 minutes, followed by addition of 2-morpholinoethyl methanesulfonate (114 mg, 0.544 mmol). The reaction was heated to 40° C. After 80 minutes, the mixture was cooled to room temperature. The residual cesium carbonate was collected via filtration, and the cesium carbonate was washed with dimethyl sulfoxide (1×500 μL) to afford a dark yellow filtrate containing the crude product, which was purified via HPLC (Phenomenex® Luna® 10 M C18(2) 100 Å, AXIA™ (00G-4253-U0-AX) column, 250×300 mm, flow rate 50 mL/minute, 5-95% gradient of acetonitrile in buffer (0.025 M aqueous ammonium acetate) to give the title compound (75.5 mg, 0.146 mmol, 51% yield). MS (APCI$^+$) m/z 516 [M+H]$^+$.

Example 1J: 5-{-fluoro-3-hydroxy-7-[2-(morpholin-4-yl)ethoxy]naphthalen-2-yl}-1λ⁶,2,5-thiadiazolidine-1,1,3-trione hydrochloride A mixture of the product of Example 1I (68.2 mg, 0.132 mmol), and pentamethylbenzene (58.8 mg, 0.397 mmol) in dichloromethane (661 μL) was cooled to an internal temperature of −76° C. under an atmosphere of dry nitrogen. Subsequently, a 1 M solution of boron trichloride (1.59 mL, 1.59 mmol) in $CH_2Cl_2$ was added dropwise over 15 minutes, so as not to raise the internal temperature past −72° C. The reaction was warmed to 0° C. and stirred 20 minutes. Thereafter, the mixture was re-cooled to −76° C. and rapidly quenched with anhydrous methanol (2.67 mL, 66.1 mmol). The resulting colorless, homogeneous solution was warmed to room temperature over 20 minutes under nitrogen. The volatiles were removed in vacuo to afford an off-white solid that was purified via HPLC (Phenomenex® Luna® 10 M C18(2) 100 Å, AXIA™ (00G-4253-U0-AX) column, 250× 300 mm, flow rate 50 mL/minute, 5-95% gradient of acetonitrile in buffer (0.025 M aqueous ammonium acetate) to give the title compound as the ammonium salt. This was suspended in methanol/ethyl acetate (1:1, 2 mL) and treated with a freshly-prepared 1 M solution of anhydrous hydrochloric acid in ethyl acetate (66 μL, 0.066 mmol). After stirring 5 minutes at room temperature, the volatiles were removed in vacuo (15 mbar), and the resulting white solid was dried at 35° C. to afford the title compound (22.6 mg, 0.053 mmol, 40% yield). $^1$H NMR (DMSO-$d_6$) δ ppm 9.89 (br s, 1H), 9.57 (s, 1H), 7.73 (dd, J=9.1, 1.1 Hz, 1H), 7.30 (d, J=2.5 Hz, 1H), 7.21 (dd, J=9.1, 2.5 Hz, 1H), 7.06 (s, 1H), 4.47 (t, J=4.8 Hz, 2H), 4.11 (s, 2H), 3.84 (m, 4H), 3.59 (s, 2H), 3.34 (m, 2H); MS (APCI⁺) m/z 426 [M+H]⁺.

Example 2: 5-{7-[1-(cyclopropanesulfonyl)pyrrolidin-3-yl]-1-fluoro-3-hydroxynaphthalen-2-yl}-1λ⁶,2,5-thiadiazolidine-1,1,3-trione (Compound 101)

Example 2A: tert-butyl 3-[6-(benzyloxy)-8-fluoro-7-(1,1,4-trioxo-1λ⁶,2,5-thiadiazolidin-2-yl)naphthalen-2-yl]pyrrolidine-1-carboxylate The product of Example 14A (340 mg, 0.614 mmol) and tetrahydrofuran (THF) (1 mL) were added to 5% Pt/C wet, (100 mg, 0.211 mmol) in a 20 mL Barnstead Hastelloy C reactor and stirred for 0.55 h under 50 psi hydrogen at 25° C. The reaction mixture was filtered, the volatiles were removed under reduced pressure, and the crude residue was subjected to column chromatography ($SiO_2$, dry load with diatomaceous earth, 5% methanol in dichloromethane) to give the title compound (164 mg, 0.295 mmol, 48% yield) as a white solid. $^1$H NMR (501 MHz, DMSO-$d_6$) δ ppm 7.82-7.69 (m, 2H), 7.59-7.52 (m, 2H), 7.54-7.47 (m, 1H), 7.40-7.33 (m, 2H), 7.36-7.27 (m, 2H), 5.25 (s, 2H), 4.08 (s, 2H), 3.76 (dd, J=10.4, 7.5 Hz, 1H), 3.59-3.45 (m, 2H), 3.33-3.23 (m, 2H), 3.17 (s, 1H), 2.26 (s, 1H), 2.04 (q, J=9.9 Hz, 1H), 1.43 (d, J=5.9 Hz, 9H); MS (APCI⁻) m/z 554 [M−H]⁻.

Example 2B: 5-[3-(benzyloxy)-1-fluoro-7-(pyrrolidin-3-yl)naphthalen-2-yl]-1λ⁶,2,5-thiadiazolidine-1,1,3-trione A solution of the product of Example 2A (164 mg, 0.295 mmol) and trifluoroacetic acid (1 mL, 12.98 mmol) in dichloromethane (2 mL) was stirred at room temperature for 1 hour. The volatiles were removed under reduced pressure. Dichloromethane (5 mL) was added, and the volatiles were again removed under reduced pressure. The residue was purified by preparative HPLC [Phenomenex® Luna® C18 (2) 5 μm 100 Å AXIA™ column (250 mm×25 mm); 30-100% gradient of acetonitrile (A) and 0.1% ammonium acetate in water (B) over 15 minutes, at a flow rate of 25 mL/minute] to afford the title compound (77 mg, 0.169 mmol, 57% yield) as a white solid. $^1$H NMR (501 MHz, DMSO-$d_6$) δ ppm 8.77 (s, 2H), 7.87-7.79 (m, 2H), 7.57-7.43 (m, 3H), 7.42-7.25 (m, 5H), 5.24 (s, 2H), 4.07 (s, 2H), 3.70-3.57 (m, 2H), 3.18 (dd, J=10.9, 9.3 Hz, 1H), 2.41 (dtd, J=13.0, 7.1, 3.5 Hz, 1H), 2.02 (dq, J=12.6, 9.5 Hz, 1H); MS (APCI⁻) m/z 454 [M−H]⁻.

Example 2C: 5-{3-(benzyloxy)-7-[1-(cyclopropanesulfonyl)pyrrolidin-3-yl]-1-fluoronaphthalen-2-yl}-1λ⁶,2,5-thiadiazolidine-1,1,3-trione To a solution of product of Example 2B (77 mg, 0.169 mmol) in dichloromethane (5 mL) was added cyclopropanesulfonyl chloride (0.041 mL, 0.338 mmol) at room temperature followed by N-ethyl-N-isopropylpropan-2-amine (0.089 mL, 0.507 mmol). The reaction stirred overnight at room temperature. Additional N-ethyl-N-isopropylpropan-2-amine (0.089 mL, 0.507 mmol) was added which resulted in a clear solution. After 3 hours stirring at room temperature, the volatiles were removed under reduced pressure, and the crude was subjected to column chromatography ($SiO_2$, dry load with diatomaceous earth, 8% $CH_3OH$ in $CH_2C_2$) to afford the title compound (80 mg, 0.143 mmol, 85% yield). MS (APCI⁻) m/z 558 [M−H]⁻.

Example 2D: 5-{7-[1-(cyclopropanesulfonyl)pyrrolidin-3-yl]-1-fluoro-3-hydroxynaphthalen-2-yl}-1λ⁶,2,5-thiadiazolidine-1,1,3-trione The product of Example 2C (80 mg, 0.143 mmol) and 1,2,3,4,5-pentamethylbenzene (63.6 mg, 0.429 mmol) in a 50 mL round bottom flask was flushed with nitrogen for 5 minutes. Dichloromethane (5 mL) was then added, and the heterogeneous suspension was cooled to −78° C. and equilibrated for 5 minutes. Subsequently, a 1 M solution of trichloroborane (0.429 mL, 0.429 mmol) in dichloromethane was added dropwise over 5 minutes. After 20 minutes, the reaction was quenched at −78° C. with dichloromethane:ethanol=9:1 (1 mL) and then slowly warmed to room temperature. The volatiles were removed under reduced pressure, and the residue was subjected to preparative HPLC [Phenomenex® Luna® C18(2) 5 μm 100 Å AXIA™ column (250 mm×25 mm); 30-100% gradient of acetonitrile (A) and 0.1% ammonium acetate in water (B) over 15 minutes, at a flow rate of 25 mL/minute] to afford the title compound (36 mg, 0.077 mmol, 54% yield). $^1$H NMR (501 MHz, DMSO-$d_6$) δ ppm 9.74 (s, 1H), 7.70 (t, J=1.2 Hz, 1H), 7.66 (dd, J=8.8, 1.5 Hz, 1H), 7.41 (dd, J=8.7, 1.8 Hz, 1H), 6.99 (s, 1H), 4.05 (s, 2H), 3.74 (dd, J=9.7, 7.6 Hz, 1H), 3.60-3.46 (m, 2H), 3.42-3.36 (m, 1H), 3.30-3.26 (m, 1H), 3.27-3.17 (m, 1H), 2.77-2.68 (m, 1H), 2.03 (dq, J=12.0, 9.0 Hz, 1H), 0.98-0.85 (m, 4H); MS (APCI⁻) m/z 467 [M−H]⁻.

Example 3: 5-[1-fluoro-3-hydroxy-7-(pyrrolidin-3-yl)naphthalen-2-yl]-1λ⁶,2,5-thiadiazolidine-1,1,3-trione (Compound 102)

Example 3A: tert-butyl 3-[8-fluoro-6-hydroxy-7-(1,1,4-trioxo-1λ⁶,2,5-thiadiazolidin-2-yl)naphthalen-2-yl]pyrrolidine-1-carboxylate The product of Example 14A (300 mg, 0.560 mmol) in tetrahydrofuran (THF) (5 mL) was added to 5% wet Pd/C (500 mg, 2.189 mmol) in a 20 mL Barnstead Hastelloy C reactor, and the mixture was stirred for 6 hours under 50 psi hydrogen at 25° C. The reaction mixture was filtered, and the filtrate was concentrated under reduced pressure. The residue was used in the next step without further purification. MS (APCI⁻) m/z 446 [M–H]⁻.

Example 3B: 5-[1-fluoro-3-hydroxy-7-(pyrrolidin-3-yl)naphthalen-2-yl]-1$\lambda^6$,2,5-thiadiazolidine-1,1,3-trione To a solution of product of Example 3A (20 mg, 0.043 mmol) and in dichloromethane (2 mL) was added trifluoroacetic acid (1 mL, 12.98 mmol), and the reaction mixture was stirred at room temperature for 1 hour. The volatiles were removed under reduced pressure, and the residue was purified by preparative HPLC [Phenomenex® Luna® C18 (2) 5 μm 100 Å AXIA™ column (250 mm×25 mm); 30-100% gradient of acetonitrile (A) and 0.1% ammonium acetate in water (B) over 15 minutes at a flow rate of 25 mL/minute] to afford the title compound (7 mg, 0.019 mmol, 27% yield) as a white solid. ¹H NMR (501 MHz, DMSO-d₆) δ ppm 7.73 (s, 1H), 7.68 (d, J=8.6 Hz, 1H), 7.42-7.36 (m, 1H), 7.00 (s, 1H), 4.03 (s, 2H), 3.62-3.51 (m, 2H), 3.23-3.13 (m, 2H), 3.13-3.05 (m, 1H), 2.34 (ddd, J=12.7, 6.7, 3.5 Hz, 1H), 1.95 (dq, J=12.7, 9.4 Hz, 1H); MS (APCI⁻) m/z 363 [M–H]⁻.

Example 4: 8-fluoro-6-hydroxy-7-(1,1,4-trioxo-1$\lambda^6$,2,5-thiadiazolidin-2-yl)naphthalen-2-yl propan-2-ylcarbamate (Compound 103)

Example 4A: 6-(benzyloxy)-8-fluoro-7-(1,1,4-trioxo-1$\lambda^6$,2,5-thiadiazolidin-2-yl)naphthalen-2-yl propan-2-ylcarbamate To a solution of the product of Example 1H (80 mg, 0.199 mmol) in N,N-dimethylformamide (1 mL) was added 4-dimethylaminopyridine (4.86 mg, 0.040 mmol) and isopropyl isocyanate (22.00 mg, 0.258 mmol). The mixture was stirred at ambient temperature for 14 hours. The reaction mixture was then filtered, purified by preparative HPLC on a Phenomenex® Luna® 10 μm C18 column (30 mm×250 mm) eluted with a gradient of acetonitrile (A) with 0.1% trifluoroacetic acid and water (B) 0.1% with trifluoroacetic acid at a flow rate of 50 mL/minute (0-1 minute 10% A, 1-20 minutes linear gradient 10-100%) to give the title compound (48 mg, 0.098 mmol, 49.5% yield). ¹H NMR (501 MHz, DMSO-d₆) δ ppm 7.93 (d, J=8.9 Hz, 1H), 7.82 (d, J=7.7 Hz, 1H), 7.78 (d, J=2.4 Hz, 1H), 7.68 (s, 1H), 7.56-7.50 (m, 2H), 7.44-7.30 (m, 5H), 5.27 (s, 2H), 4.42 (s, 2H), 3.73-3.66 (m, 1H), 1.16 (d, J=6.6 Hz, 6H); MS (APCI⁻) m/z 486 [M–H]⁺.

Example 4B: 8-fluoro-6-hydroxy-7-(1,1,4-trioxo-1$\lambda^6$,2,5-thiadiazolidin-2-yl)naphthalen-2-yl propan-2-ylcarbamate To a mixture of the product of Example 4A (42 mg, 0.086 mmol) and pentamethylbenzene (63.9 mg, 0.431 mmol) in dichloromethane (2 mL) cooled to –78° C. was added a solution of boron trichloride (1 M, 0.517 mL, 0.517 mmol) in dichloromethane dropwise over 5 minutes. After 30 minutes, the reaction was quenched with 2 N HCl (0.5 mL). The reaction mixture was extracted with ethyl acetate. The organic phase washed with brine, dried over anhydrous Na₂SO₄ and concentrated under reduced pressure. The residue was purified by preparative HPLC using a Phenomenex® Luna® 10 μm C18 column (30 mm×250 mm) eluted with a gradient of acetonitrile (A) with 0.1% trifluoroacetic acid and water (B) 0.1% with trifluoroacetic acid at a flow rate of 50 mL/minute (0-1 minute 10% A, 1-20 minutes linear gradient 10-70%) to give the title compound (28 mg, 0.070 mmol, 82% yield). ¹H NMR (400 MHz, DMSO-d₆) δ ppm 10.59 (s, 1H), 7.78 (dd, J=11.2, 8.3 Hz, 2H), 7.55 (d, J=2.3 Hz, 1H), 7.29 (dd, J=8.9, 2.3 Hz, 1H), 7.14 (s, 1H), 4.48 (s, 2H), 3.73-3.65 (m, 1H), 1.15 (d, J=6.6 Hz, 6H); MS (APCI⁻) m/z 396 [M–H]⁺.

Example 5: 5-(9-fluoro-7-hydroxynaphtho[2,1-b]furan-8-yl)-1$\lambda^6$,2,5-thiadiazolidine-1,1,3-trione (Compound 104)

Example 5A: 5-[3-(benzyloxy)-7-(2,2-dimethoxy-ethoxy)-1-fluoronaphthalen-2-yl]-1$\lambda^6$,2,5-thiadiazolidine-1,1,3-trione To a solution of the product of Example 1H (500 mg, 1.243 mmol) and cesium carbonate (891 mg, 2.73 mmol) in N,N-dimethylformamide (5 mL) was added 2-bromo-1,1-dimethoxyethane (420 mg, 2.485 mmol). The reaction stirred at 75° C. for 5 hours. After cooling down to room temperature, the volatiles were removed under reduced pressure, and the residue was subjected to column chromatography (SiO₂, dry load with diatomaceous earth, 15% CH₃OH in CH₂Cl₂) to afford the title compound (475 mg, 0.968 mmol, 78% yield) as a beige solid. ¹H NMR (501 MHz, DMSO-d₆) δ ppm 7.76 (dd, J=9.1, 1.4 Hz, 1H), 7.56 (dt, J=6.6, 1.4 Hz, 2H), 7.40-7.32 (m, 2H), 7.34-7.26 (m, 3H), 7.22 (dd, J=9.0, 2.6 Hz, 1H), 5.22 (s, 2H), 4.75 (t, J=5.1 Hz, 1H), 4.11 (d, J=5.1 Hz, 2H), 4.09 (s, 2H), 3.38 (s, 6H); MS (APCI⁻) m/z 489 [M–H]⁻.

Example 5B: 5-[7-(2,2-dimethoxyethoxy)-1-fluoro-3-hydroxynaphthalen-2-yl]-1$\lambda^6$,2,5-thiadiazolidine-1,1,3-trione The product of Example 5A (475 mg, 0.968 mmol) in tetrahydrofuran (THF) (10 mL) was added to wet 5% Pd/C (475 mg, 2.080 mmol) in a 20 mL Barnstead Hastelloy C reactor and stirred for 15 minutes under 50 psi of hydrogen at 25° C. The mixture was filtered, and the crude material was subjected to column chromatography (SiO₂ dry load with diatomaceous earth, 15% CH₃OH in CH₂Cl₂) to afford the title compound (182 mg, 0.455 mmol, 47% yield). ¹H NMR (500 MHz, DMSO-d₆) δ ppm 9.50 (s, 1H), 7.68 (dd, J=9.1, 1.4 Hz, 1H), 7.21 (d, J=2.6 Hz, 1H), 7.16 (dd, J=9.0, 2.6 Hz, 1H), 7.03 (s, 1H), 4.74 (t, J=5.1 Hz, 1H), 4.09 (d, J=4.9 Hz, 4H), 3.37 (s, 6H); MS (APCI⁻) m/z 398 [M–H]⁻.

Example 5C: 5-(9-fluoro-7-hydroxynaphtho[2,1-b]furan-8-yl)-1$\lambda^6$,2,5-thiadiazolidine-1,1,3-trione A solution of the product of Example 5B (30 mg, 0.075 mmol) and trifluoroacetic acid (1 mL, 12.98 mmol) in dichloromethane (2 mL) was stirred at room temperature for 1 hour. The volatiles were removed under reduced pressure and the residue was purified by preparative HPLC [Phenomenex® Luna® C18(2) 5 μm 100 Å AXIA™ column (250 mm×25 mm); 30-100% gradient of acetonitrile (A) and 0.1% ammonium acetate in water (B) over 15 minutes at a flow rate of 25 mL/minute] to afford the title compound (12 mg, 0.036 mmol, 48% yield) as a beige solid. ¹H NMR (501 MHz, DMSO-d₆) δ ppm 8.13 (d, J=2.0 Hz, 1H), 7.96 (s, 3H), 7.77 (d, J=8.9 Hz, 1H), 7.66 (dd, J=9.0, 1.7 Hz, 1H), 7.33

(dd, J=3.8, 2.0 Hz, 1H), 7.23 (d, J=1.3 Hz, 1H), 4.13 (s, 2H); MS (APCI⁻) m/z 334 [M−H]⁻.

Example 6: 5-{7-[2-(azetidin-1-yl)ethoxy]-1-fluoro-3-hydroxynaphthalen-2-yl}-1λ⁶,2,5-thiadiazolidine-1,1,3-trione (Compound 105)

Example 6A: 5-{7-[2-(azetidin-1-yl)ethoxy]-3-(benzyloxy)-1-fluoronaphthalen-2-yl}-1λ⁶,2,5-thiadiazolidine-1,1,3-trione A mixture of the product of Example 1H (121 mg, 0.3 mmol), 1-(2-chloroethyl)azetidine, hydrochloric acid (94 mg, 0.600 mmol), cesium carbonate (391 mg, 1.20 mmol) and triethylamine (100 mg, 0.990 mmol) in dimethylformamide (0.8 mL) was stirred at 70° C. for 1.5 hours. The solution was filtered and concentrated under reduced pressure. The residue was purified by flash column chromatography on silica gel eluted with dichloromethane, then dichloromethane/methanol (7:1) to give the title compound (35 mg, 0.072 mmol, 24% yield) as a solid. ¹H NMR (400 MHz, DMSO-d₆) δ ppm 7.80 (d, J=8 Hz, 1H), 7.56 (d, J=8 Hz, 2H), 7.37 (t, J=8 Hz, 2H), 7.31 (m, 3H), 7.23 (dd, J=8, 2 Hz, 1H), 5.23 (s, 2H), 4.28 (t, J=8 Hz, 2H), 4.09 (s, 2H), 4.01 (t, J=8 Hz, 4H), 2.31 (m, 2H); MS (ESI⁻) m/z 484 [M−H]⁻.

Example 6B: 5-{7-[2-(azetidin-1-yl)ethoxy]-1-fluoro-3-hydroxynaphthalen-2-yl}-1λ⁶,2,5-thiadiazolidine-1,1,3-trione To the product of Example 6A (0.034 g, 0.07 mmol) and 1,2,3,4,5-pentamethylbenzene (0.031 g, 0.210 mmol) in dichloromethane (2 mL) at −78° C. was added trichloroborane (0.700 mL, 0.700 mmol, 1.0 M in dichloromethane). The mixture was stirred at −78° C. for 40 minutes. Methanol (3 mL) was added at −78° C. The mixture was stirred for 5 minutes at room temperature and then was concentrated under reduced pressure. The resulting solids were washed with heptane (5 mL×4), then dissolved in methanol (0.5 mL) and N,N-dimethylformamide (3 mL). This material was purified by preparative HPLC [YMC TriArt™ C18 Hybrid 20 μm column, 25×150 mm, flow rate 80 mL/minute, 5-100% gradient of methanol in buffer (0.025 M aqueous ammonium bicarbonate, adjusted to pH 10 with ammonium hydroxide)] to give the title compound (20 mg, 0.051 mmol, 72% yield). ¹H NMR (400 MHz, DMSO-d₆) δ ppm 9.54 (s, 1H), 7.71 (d, J=8 Hz, 1H), 7.25 (d, J=2 Hz, 1H), 7.17 (dd, J=8, 2 Hz, 1H), 7.05 (br s, 1H), 4.28 (t, J=8 Hz, 2H), 4.09 (s, 2H), 4.08 (t, J=8 Hz, 4H), 2.33 (m, 2H); MS (ESI⁻) m/z 394 [M−H]⁻.

Example 7: 5-[1-fluoro-3-hydroxy-7-methoxy(4-²H)naphthalen-2-yl](4,4-2H₂)-1λ⁶,2,5-thiadiazolidine-1,1,3-trione (Compound 106)

To a stirred suspension of the product of Example 25G (0.10 g, 0.306 mmol) in deuterated methanol (methanol-d₄, 99.5%-D) (3.06 mL) was added sodium hydride (0.061 g, 1.532 mmol, 60% in mineral oil). All of solids went into solution, and then the mixture was heated to 60° C. After 72 hours, deuterium enrichment was complete as judged by ¹H NMR. The volatiles were removed, and the solution was treated with DCl in D₂O (1.839 mL, 1.839 mmol, 1 N solution) and ethyl acetate (3 mL). The layers were shaken in a vial and separated, and the organic layer was concentrated under reduced pressure. The resulting organic residue was partitioned between a dimethyl sulfoxide:methanol layer (2 mL 1:1) and a heptane layer (1 mL) to remove any residual mineral oil before purification. Separation of the layers and purification of the dimethyl sulfoxide:methanol layer by reverse phase HPLC [Phenomenex® Luna® C18 (2) 5 μm 100 Å AXIA™ column (150 mm×30 mm); 3-100% gradient of acetonitrile (A) and 10 mM ammonium acetate in water (B) over 17 minutes at a flow rate of 50 mL/minute] yielded a white solid which was dissolved in D₂O:CH₃CN (2 mL, 1:1). The solution was frozen with dry-ice and lyophilized to yield the title compound as a fluffy white powder (19.9 mg, 0.060 mmol, 19.7% yield). ¹H NMR (400 MHz, DMSO-d₆) δ ppm 7.67 (d, J=9.0 Hz, 1H), 7.18 (d, J=2.3 Hz, 1H), 7.13 (dd, J=8.7, 2.7 Hz, 2H), 3.85 (s, 3H); MS (APCI⁻) m/z 328 [M−H]⁻.

Example 8: 5-[1-fluoro-3-hydroxy-7-(methylamino)naphthalen-2-yl]-1λ⁶,2,5-thiadiazolidine-1,1,3-trione (Compound 107)

In a 4 mL vial with a septum screw cap, the product of Example 1G (0.1 g, 0.215 mmol), sodium tert-butoxide (0.062 g, 0.645 mmol), BrettPhos Pd G3 precatalyst (5.84 mg, 6.45 μmol), and BrettPhos (3.46 mg, 6.45 μmol) were combined. The solids were placed under vacuum for 5 minutes with stirring, then the vial was filled with nitrogen, followed by 1,4-dioxane (2 mL) and a solution of methylamine in tetrahydrofuran (0.215 mL, 2 M, 0.430 mmol). The resulting suspension was degassed by five vacuum/nitrogen backfills, was stirred for 10 minutes at room temperature, and then was heated to 100° C. After 30 minutes at 100° C., the reaction mixture was cooled to room temperature, then was quenched with 1 M hydrochloric acid (1 mL) and diluted with ethyl acetate (2 mL). The aqueous layer was extracted with ethyl acetate (2×1 mL). The combined organic layers were washed with a 4:1 mixture of brine and 1 M hydrochloric acid (1 mL), dried over anhydrous sodium sulfate, then filtered and concentrated under reduced pressure to give, 5-[3-(benzyloxy)-1-fluoro-7-(methylamino)naphthalen-2-yl]-1,2,5-thiadiazolidine-1,1,3-trione, a viscous orange oil, which was used for the next reaction without purification. MS (APCI⁻) m/z 414 [M−H]⁻.

To a suspension of the crude intermediate, 5-[3-(benzyloxy)-1-fluoro-7-(methylamino)naphthalen-2-yl]-1λ⁶,2,5-thiadiazolidine-1,1,3-trione, in dichloromethane (2 mL) at −78° C. was added a solution of boron trichloride in dichloromethane (1.29 mL, 1 M, 1.29 mmol) slowly along the side of the flask so that the internal temperature remained below −70° C. The resulting solution was stirred for 5 minutes at −78° C., then the cooling bath was removed, and the reaction mixture was allowed to warm to an internal temperature of 10° C. before cooling back to −78° C. The reaction was quenched by addition of ethyl acetate (1 mL), followed by anhydrous ethanol (0.5 mL). The mixture was warmed to room temperature and then was concentrated under reduced pressure. The crude residue was dissolved in a dimethyl sulfoxide/methanol mixture and was filtered through a glass microfiber frit. The resulting solution was directly purified by preparative HPLC on a Phenomenex® Luna® C8(2) 5 μm 100 Å AXIA column (30 mm×75 mm) with gradient of acetonitrile (A) and 10 mM ammonium acetate in water (B) at a flow rate of 50 mL/minute (0-1.0 minute 5% A, 1.0-8.5 minutes linear gradient 5-100% A, 8.5-11.5 minutes 100% A, 11.5-12.0 minutes linear gradient 95-5% A) to give the title compound (0.0136 g, 0.040 mmol, 18.6% yield). ¹H NMR (400 MHz, DMSO-d₆) δ ppm 7.45 (d, J=8.8 Hz, 1H), 6.93 (dd, J=8.9, 2.3 Hz, 1H), 6.89 (s, 1H), 6.56 (d, J=2.3 Hz, 1H), 5.93-5.80 (m, 1H), 4.07 (s, 2H), 2.76-2.72 (m, 3H); MS (ESI⁻) m/z 324 [M–H]⁻.

Example 9: 5-{1-fluoro-3-hydroxy-7-[2-(piperidin-4-yl)ethoxy]naphthalen-2-yl}-1$\lambda^6$,2,5-thiadiazolidine-1,1,3-trione (Compound 108)

To a solution of the product of Example 1H (0.1 g, 0.249 mmol) and tert-butyl 4-(2-bromoethyl)piperidine-1-carboxylate (0.145 g, 0.497 mmol) in dimethylformamide (1 mL) was added cesium carbonate (0.243 g, 0.0.746 mmol) as a solid, and the resulting suspension was heated to 60° C. After 1 hour, the reaction mixture was cooled to room temperature, quenched with 2 M hydrochloric acid (1 mL), and diluted with ethyl acetate (2 mL). The layers were separated, and the aqueous layer was extracted with ethyl acetate (2×1 mL). The combined organic layers were washed with saturated aqueous ammonium chloride (3×1 mL). The combined aqueous washes were back extracted with ethyl acetate (1 mL), and the combined organic layers were washed with a 4:1 mixture of brine and 1 M hydrochloric acid, then dried over anhydrous sodium sulfate, filtered and concentrated under reduced pressure to give tert-butyl 4-(2-{[6-(benzyloxy)-8-fluoro-7-(1,1,4-trioxo-1$\lambda^6$,2,5-thiadiazolidin-2-yl)naphthalen-2-yl]oxy}ethyl)piperidine-1-carboxylate, a dark gel, which was used for the next reaction without purification. MS (APCI⁻) m/z 612 [M–H]⁻.

To a suspension of the crude intermediate, tert-butyl 4-(2-{[6-(benzyloxy)-8-fluoro-7-(1,1,4-trioxo-1$\lambda^6$,2,5-thiadiazolidin-2-yl)naphthalen-2-yl]oxy}ethyl)piperidine-1-carboxylate, in dichloromethane (2 mL) at –78° C. was added a solution of boron trichloride in dichloromethane (2.49 mL, 1 M, 2.49 mmol) slowly along the side of the vial so that the internal temperature remained below –70° C. The resulting solution was stirred for 5 minutes at –78° C., then the cooling bath was removed, and the reaction mixture was allowed to warm to an internal temperature of 10° C. before cooling back to –78° C. The reaction was quenched by the addition of ethyl acetate (1 mL), followed by anhydrous ethanol (0.5 mL), warmed to room temperature and concentrated under reduced pressure to give a tan solid. The crude solid was dissolved in a dimethyl sulfoxide/methanol mixture and was filtered through a glass microfiber frit. The resulting solution was directly purified by preparative HPLC [Phenomenex® Luna® 10 m C₁₈(2) 250×30 mm column, flow rate 100 mL/minute, a gradient of 5-95% acetonitrile in buffer (0.010 M aqueous ammonium acetate)]. The HPLC purified product was further purified by trituration with a 50% v/v mixture of dichloromethane and acetonitrile (3 mL) to give the title compound (0.066 g, 0.155 mmol, 64.9% yield). ¹H NMR (400 MHz, DMSO-d₆) δ ppm 7.66 (d, J=9.0 Hz, 1H), 7.19 (d, J=2.5 Hz, 1H), 7.11 (dd, J=9.0, 2.5 Hz, 1H), 7.03 (s, 1H), 4.13 (t, J=6.1 Hz, 2H), 4.09 (s, 2H), 2.89-2.76 (m, 1H), 1.90 (s, 3H), 1.86 (s, 2H), 1.82-1.69 (m, 3H), 1.34 (td, J=12.9, 12.1, 8.7 Hz, 2H); MS (ESI⁻) m/z 422 [M–H]⁻.

Example 10: 5-(1-fluoro-7-{[3-fluoro-1-(propan-2-yl)pyrrolidin-3-yl]methoxy}-3-hydroxynaphthalen-2-yl)-1$\lambda^6$,2,5-thiadiazolidine-1,1,3-trione (Compound 109)

Example 10A: 5-[3-(benzyloxy)-1-fluoro-7-{[3-fluoro-1-(propan-2-yl)pyrrolidin-3-yl]methoxy}naphthalen-2-yl]-1$\lambda^6$,2,5-thiadiazolidine-1,1,3-trione To a solution of the product of Example 1H (100 mg, 0.249 mmol) and (3-fluoro-1-isopropylpyrrolidin-3-yl) methanol (120 mg, 0.746 mmol) in tetrahydrofuran (THF) (5 mL) at 0° C. was added (E)-diazene-1,2-diylbis(piperidin-1-ylmethanone) (219 mg, 0.870 mmol). The reaction was flushed with N₂ at 0° C. for 5 minutes followed by addition of tri-n-butylphosphine (0.215 mL, 0.870 mmol). The reaction was stirred at 45° C. for 14 hours. The volatiles were removed under reduced pressure, and the residue was subjected to column chromatography (SiO₂, dry load with diatomaceous earth, 10% methanol in dichloromethane) to afford the title compound (24 mg, 0.044 mmol, 18% yield) as a beige solid. ¹H NMR (400 MHz, DMSO-d₆) δ ppm 7.68 (d, J=9.1 Hz, 1H), 7.25 (d, J=2.6 Hz, 1H), 7.17 (dd, J=9.0, 2.5 Hz, 1H), 7.04 (s, 1H), 4.30 (broad, 1H), 4.24 (broad, 1H), 4.09 (s, 2H), 3.06-2.77 (m, 4H), 2.23-1.98 (m, 2H), 1.46-1.37 (broad, 1H), 1.05 (d, J=6.2 Hz, 6H); MS (APCI⁻) m/z 454.13 [M–CH₂C₆H₅–H]⁻, 544 [M–H]⁻.

Example 10B: 5-(1-fluoro-7-{[3-fluoro-1-(propan-2-yl)pyrrolidin-3-yl]methoxy}-3-hydroxynaphthalen-2-yl)-1$\lambda^6$,2,5-thiadiazolidine-1,1,3-trione The product of Example 10A (22 mg, 0.040 mmol) and 1,2,3,4,5-pentamethylbenzene (17.93 mg, 0.121 mmol) in a 50 mL round bottom flask was flushed with nitrogen for 5 minutes. Dichloromethane (5 mL) was then added, and the heterogeneous suspension was cooled to –78° C. and equilibrated for 5 minutes. Subsequently, a 1 M solution of trichloroborane (0.121 mL, 0.121 mmol) in dichloromethane was added dropwise over 5 minutes. After 30 minutes, the reaction was quenched at –77° C. with dichloromethane:methanol=9:1 (0.5 mL), and then the mixture was slowly warmed to room temperature. The volatiles were removed under reduced pressure, and the residue was subjected to preparative HPLC [Phenomenex® Luna® C18(2) 5 μm 100 Å AXIA™ column (250 mm×25 mm); 30-100% gradient of acetonitrile (A) and 0.1% ammonium acetate in water (B) over 15 minutes, at a flow rate of 25 mL/minute] to afford the title compound (7 mg, 0.015 mmol, 38% yield). ¹H NMR (400 MHz, DMSO-d₆) δ ppm 7.68 (d, J=9.1 Hz, 1H), 7.25 (d, J=2.6 Hz, 1H), 7.17 (dd, J=9.0, 2.5 Hz, 1H), 7.04 (s, 1H), 4.30 (broad, 1H), 4.24 (broad, 1H), 4.09 (s, 2H), 3.06-2.77 (m, 4H), 2.23-1.98 (m, 2H), 1.46-1.37 (broad, 1H), 1.05 (d, J=6.2 Hz, 6H); MS (APCI⁻) m/z 454.13 [M–H]⁻.

Example 11: 5-{1-fluoro-7-[(3-fluoropyrrolidin-3-yl)methoxy]-3-hydroxynaphthalen-2-yl}-1$\lambda^6$,2,5-thiadiazolidine-1,1,3-trione (Compound 110)

Example 1A: tert-butyl 3-({[6-(benzyloxy)-8-fluoro-7-(1,1,4-trioxo-1$\lambda^6$,2,5-thiadiazolidin-2-yl)naphthalen-2-yl]oxy}methyl)-3-fluoropyrrolidine-1-carboxylate To a solution of the product of Example 1H (100 mg, 0.249 mmol) and tert-butyl 3-fluoro-3-(hydroxymethyl)pyrrolidine-1-carboxylate (163 mg, 0.746 mmol) in tetrahydrofuran (THF) (5 mL) at 0° C. was added (E)-diazene-1,2-diylbis(piperidin-1-ylmethanone) (219 mg, 0.870 mmol). The reaction was flushed with N₂ at 0° C. for 5 minutes followed by addition of tri-n-butylphosphine (0.215 mL, 0.870 mmol). The reaction was stirred at 45° C. for 14 hours. The volatiles were removed under reduced pressure, and the residue was subjected to column chromatography (SiO₂, dry load with diatomaceous earth, 10% methanol in dichloromethane) to afford the title compound (48 mg, 0.080 mmol, 32% yield). MS (APCI⁻) m/z 602 [M–H]⁻.

Example 1B: 5-{-fluoro-7-[(3-fluoropyrrolidin-3-yl) methoxy]-3-hydroxynaphthalen-2-yl}-1$\lambda^6$,2,5-thiadiazolidine-1,1,3-trione The product of Example 11A (45 mg, 0.075 mmol) and 1,2,3,4,5-pentamethylbenzene (33.2 mg, 0.224 mmol) in a 50 mL round bottom flask was flushed with nitrogen for 5 minutes. Dichloromethane (5 mL) was then added, and the heterogeneous suspension was cooled to −78° C. and equilibrated for 5 minutes. Subsequently, a 1 M solution of trichloroborane (0.224 mL, 0.224 mmol) in dichloromethane was added dropwise over 5 minutes. After 30 minutes, the reaction was quenched at −77° C. with dichloromethane:methanol=9:1 (0.5 mL) and then slowly warmed to room temperature. The volatiles were removed under reduced pressure, and the residue was subjected to preparative HPLC [Phenomenex® Luna® C18(2) 5 μm 100 Å AXIA™ column (250 mm×25 mm); 30-100% gradient of acetonitrile (A) and 0.1% ammonium acetate in water (B) over 15 minutes, at a flow rate of 25 mL/minute] to afford the title compound (9 mg, 0.022 mmol, 29% yield). $^1$H NMR (501 MHz, DMSO-d$_6$) δ ppm 9.63 (d, J=69.3 Hz, 1H), 7.72 (d, J=9.1 Hz, 1H), 7.28 (d, J=2.6 Hz, 1H), 7.19 (dd, J=9.0, 2.6 Hz, 1H), 7.06 (s, 1H), 4.57-4.41 (s, 2H), 4.10 (s, 2H), 3.73-3.48 (m, 4H), 2.43-2.20 (m, 2H); MS (APCI$^-$) m/z 411.89 [M−H]$^-$.

Example 12: 5-{[8-fluoro-6-hydroxy-7-(1,1,4-trioxo-1$\lambda^6$,2,5-thiadiazolidin-2-yl)naphthalen-2-yl] oxy}pentanenitrile (Compound 111)

Example 12A: 5-{[6-(benzyloxy)-8-fluoro-7-(1,1,4-trioxo-1$\lambda^6$,2,5-thiadiazolidin-2-yl)naphthalen-2-yl] oxy}pentanenitrile A mixture of the product of Example 1H (100 mg, 0.249 mmol), cesium carbonate (162 mg, 0.497 mmol) in N,N-dimethylformamide (2 mL) was stirred at room temperature for 14 hours. The reaction mixture was filtered and purified by preparative HPLC [Phenomenex® Luna® 10 μm C18 column (30 mm×250 mm) eluted with a gradient of acetonitrile (A) with 0.1% trifluoroacetic acid and water (B) 0.1% with trifluoroacetic acid at a flow rate of 50 mL/minute (0-1 minute 10% A, 1-20 minutes linear gradient 10-100%) to give the title compound (80 mg, 0.165 mmol, 67% yield). $^1$H NMR (501 MHz, DMSO-d$_6$) δ ppm 7.86-7.78 (m, 1H), 7.57-7.48 (m, 2H), 7.42 (s, 1H), 7.41-7.36 (m, 2H), 7.36-7.31 (m, 1H), 7.31-7.25 (m, 2H), 5.24 (s, 2H), 4.50 (s, 2H), 4.15 (t, J=6.2 Hz, 2H), 2.61 (t, J=7.1 Hz, 2H), 1.87 (m, 2H), 1.82-1.70 (m, 2H); MS (APCI$^-$) m/z 482 [M−H]$^+$.

Example 12B: 5-{[8-fluoro-6-hydroxy-7-(1,1,4-trioxo-1$\lambda^6$,2,5-thiadiazolidin-2-yl)naphthalen-2-yl] oxy}pentanenitrile To a mixture of the product of Example 12A (75 mg, 0.155 mmol) and pentamethylbenzene (115 mg, 0.776 mmol) in dichloromethane (2 mL) cooled to −78° C. was added a solution of boron trichloride (1 M, 0.931 mL, 0.931 mmol) in dichloromethane dropwise over 5 minutes. After 30 minutes, the reaction mixture was quenched with 2 N HCl (0.5 mL). The mixture was then extracted with ethyl acetate, washed with brine, dried over Na$_2$SO$_4$ and concentrated under reduced pressure. The residue was purified by preparative HPLC on a Phenomenex® Luna® 10 μm C18 column (30 mm×250 mm) eluted with a gradient of acetonitrile (A) with 0.1% trifluoroacetic acid and water (B) 0.1% with trifluoroacetic acid at a flow rate of 50 mL/minute (0-1 minute 10% A, 1-20 minutes linear gradient 10-100%) to give the title compound (40 mg, 0.102 mmol, 65.6% yield). $^1$H NMR (501 MHz, DMSO-d$_6$) δ ppm 10.27 (s, 1H), 7.71 (dd, J=9.1, 1.4 Hz, 1H), 7.25-7.16 (m, 2H), 7.07 (s, 1H), 4.44 (s, 2H), 4.12 (t, J=6.2 Hz, 2H), 2.60 (t, J=7.1 Hz, 2H), 1.87 (dq, J=8.5, 6.4 Hz, 2H), 1.76 (dq, J=9.9, 7.1 Hz, 2H); MS (APCI$^-$) m/z 392 [M−H]$^+$.

Example 13: 5-{1-fluoro-3-hydroxy-7-[2-(piperidin-1-yl)ethoxy]naphthalen-2-yl}-1$\lambda^6$,2,5-thiadiazolidine-1,1,3-trione (Compound 112)

Example 13A: 5-{3-(benzyloxy)-1-fluoro-7-[2-(piperidin-1-yl)ethoxy]naphthalen-2-yl}-1$\lambda^6$,2,5-thiadiazolidine-1,1,3-trione A mixture of the product of Example 1H (84 mg, 0.2 mmol), 1-(2-chloroethyl)piperidine (94 mg, 0.640 mmol), and cesium carbonate (235 mg, 0.720 mmol) in dimethylformamide (1 mL) was stirred at 75° C. for 2 hours. The solution was filtered and concentrated under reduced pressure. The residue was purified by flash column chromatography on silica gel eluted with dichloromethane, then dichloromethane/methanol (10:1) to give the title compound (65 mg, 0.127 mmol, 63% yield) as a solid. MS (ESI$^+$) m/z 514 [M+H]$^+$.

Example 13B: 5-{-fluoro-3-hydroxy-7-[2-(piperidin-1-yl)ethoxy]naphthalen-2-yl}-1$\lambda^6$,2,5-thiadiazolidine-1,1,3-trione To the product of Example 13A (60 mg, 0.117 mmol) and 1,2,3,4,5-pentamethylbenzene (55.4 mg, 0.374 mmol) in dichloromethane (2 mL) at −78° C. was added trichloroborane (1168 μL, 1.168 mmol, 1.0 M in dichloromethane). The mixture was stirred at −78° C. for 40 minutes. Methanol (3 mL) was added at −78° C. The mixture was stirred for 5 minutes at room temperature, then concentrated under reduced pressure. The solid was washed with heptane (4×5 mL), then dissolved in methanol (0.5 mL) and N,N-dimethylformamide (3 mL). The crude material was purified by preparative HPLC [YMC TriArt™ C18 Hybrid 20 m column, 25×150 mm, flow rate 80 mL/minute, 5-100% gradient of methanol in buffer (0.025 M aqueous ammonium bicarbonate, adjusted to pH 10 with ammonium hydroxide)] to give the title compound (30 mg, 0.071 mmol, 61% yield). $^1$H NMR (400 MHz, DMSO-d$_6$) δ ppm 9.52 (br s, 1H), 7.71 (d, J=8 Hz, 1H), 7.28 (d, J=2 Hz, 1H), 7.19 (dd, J=8, 2 Hz, 1H), 7.05 (br s, 1H), 4.42 (m, 2H), 4.09 (s, 2H), 3.46 (m, 4H), 3.00 (m, 2H), 1.72 (m, 4H), 1.47 (m, 2H); MS (ESI$^-$) m/z 422 [M−H]$^-$.

Example 14: 5-{7-[1-(cyclopropanesulfonyl)-2,5-dihydro-1H-pyrrol-3-yl]-1-fluoro-3-hydroxynaphthalen-2-yl}-1$\lambda^6$,2,5-thiadiazolidine-1,1,3-trione (Compound 113)

Example 14A: tert-butyl 3-[6-(benzyloxy)-8-fluoro-7-(1,1,4-trioxo-1$\lambda^6$,2,5-thiadiazolidin-2-yl)naphthalen-2-yl]-2,5-dihydro-1H-pyrrole-1-carboxylate To the product of Example 1G in dioxane (5 mL) was added tert-butyl 3-(4,4,5,5-tetramethyl-1,3,2-dioxaborolan-2-yl)-2,5-dihydro-1H-pyrrole-1-carboxylate (381 mg, 1.290 mmol) and sodium carbonate (1.290 mL, 2.58 mmol). Tetrakis(triphenylphosphine)palladium(0) (99 mg, 0.086 mmol) was added, and the reaction mixture was sparged with N₂ for 5 minutes. The mixture was heated at 100° C. overnight. The reaction was cooled down to room temperature, and the volatiles were removed under reduced pressure. The residue was subjected to column chromatography (dry loading with diatomaceous earth, 5% CH₃OH in CH₂C₂) to afford the title compound (346 mg, 0.625 mmol, 73% yield) as a yellow solid. ¹H (500 MHz, DMSO-d₆) δ ppm 7.87-7.80 (m, 2H), 7.75 (d, J=12.7 Hz, 1H), 7.60-7.52 (m, 2H), 7.41-7.35 (m, 3H), 7.35-7.28 (m, 1H), 6.59-6.52 (m, 1H), 5.27 (s, 2H), 4.53 (d, J=7.7 Hz, 2H), 4.26 (d, J=12.0 Hz, 2H), 4.09 (s, 2H), 1.47 (d, J=10.6 Hz, 9H); MS (APCI⁻) m/z 551 [M–H]⁻.

Example 14B: 5-[3-(benzyloxy)-7-(2,5-dihydro-H-pyrrol-3-yl)-1-fluoronaphthalen-2-yl]-1λ⁶,2,5-thiadiazolidine-1,1,3-trione To a solution of the product of Example 14A (100 mg, 0.181 mmol) in dichloromethane (2 mL) was added 2,2,2-trifluoroacetic acid (1 mL, 3.61 mmol). The mixture was stirred at room temperature for 30 minutes. The volatiles were removed under reduced pressure, and the residue was subjected to preparative HPLC [Phenomenex® Luna® C18 (2) 5 μm 100 Å AXIA™ column (250 mm×25 mm); 30-100% gradient of acetonitrile (A) and 0.1% ammonium acetate in water (B) over 15 minutes at a flow rate of 25 mL/minute] to afford the title compound (60 mg, 0.132 mmol, 73% yield). ¹H NMR (400 MHz, DMSO-d₆) δ ppm 7.86 (d, J=3.7 Hz, 2H), 7.60-7.48 (m, 2H), 7.46-7.27 (m, 5H), 6.60 (t, J=2.2 Hz, 1H), 5.28 (s, 2H), 4.50 (q, J=2.3 Hz, 2H), 4.19 (dt, J=5.0, 2.5 Hz, 2H), 4.10 (s, 2H); MS (APCI⁻) m/z 452 [M–H]⁻.

Example 14C: 5-{3-(benzyloxy)-7-[1-(cyclopropanesulfonyl)-2,5-dihydro-H-pyrrol-3-yl]-1-fluoronaphthalen-2-yl}-1λ⁶,2,5-thiadiazolidine-1,1,3-trione To a solution of the product of Example 14B (88 mg, 0.194 mmol) in dichloromethane (5 mL) was added cyclopropanesulfonyl chloride (0.071 mL, 0.582 mmol) at room temperature followed by N,N-diisopropylethylamine (0.102 mL, 0.582 mmol). The reaction mixture was stirred overnight at room temperature. The volatiles were removed under reduced pressure, and the residue was subjected to column chromatography (SiO₂, dry load with diatomaceous earth, 5% CH₃OH in CH₂C₂) to afford the title compound (77 mg, 0.138 mmol, 71% yield) as a beige solid. MS (APCI⁻) m/z 555 [M–H]⁻.

Example 14D: 5-{7-[1-(cyclopropanesulfonyl)-2,5-dihydro-H-pyrrol-3-yl]-1-fluoro-3-hydroxynaphthalen-2-yl}-1λ⁶,2,5-thiadiazolidine-1,1,3-trione A solution of product of Example 14C (66 mg, 0.118 mmol) and 1,2,3,4,5-pentamethylbenzene (52.6 mg, 0.355 mmol) in dichloromethane (5 mL) was flushed with nitrogen gas for 5 minutes. The solution was cooled to −78° C. and equilibrated for 5 minutes. Subsequently, a 1 M solution of trichloroborane (0.355 mL, 0.355 mmol) in dichloromethane was added dropwise over 5 minutes. After 30 minutes, the reaction was quenched at −77° C. with dichloromethane:methanol=2:1 (0.5 mL) and then slowly warmed to room temperature. The volatiles were removed under reduced pressure, and the residue was subjected to preparative HPLC [Phenomenex® Luna® C18(2) 5 μm 100 Å AXIA™ column (250 mm×25 mm); 30-100% gradient of acetonitrile (A) and 0.1% ammonium acetate in water (B) over 15 minutes at a flow rate of 25 mL/minute] to afford the title compound (25 mg, 0.053 mmol, 45% yield) as a beige solid. ¹H NMR (400 MHz, DMSO-d₆) δ ppm 9.87 (s, 1H), 7.14 (s, 1H), 7.03-6.99 (m, 2H), 6.89 (s, 1H), 6.46 (t, J=2.1 Hz, 1H), 4.62-4.55 (m, 2H), 4.29 (dt, J=6.9, 3.0 Hz, 2H), 4.03 (s, 2H), 2.82-2.71 (m, 1H), 0.97 (dt, J=5.4, 2.8 Hz, 2H), 0.96-0.86 (m, 2H); MS (APCI⁻) m/z 465 [M–H]⁻.

Example 15: 5-{1-fluoro-3-hydroxy-7-[(piperidin-4-yl)methoxy]naphthalen-2-yl}-1λ⁶,2,5-thiadiazolidine-1,1,3-trione (Compound 114)

To a solution of the product of Example 1H (0.1 g, 0.238 mmol) and tert-butyl 4-(2-bromomethyl)piperidine-1-carboxylate (0.133 g, 0.477 mmol) in dimethylformamide (1 mL) was added cesium carbonate (0.311 g, 0.954 mmol) as a solid, and the resulting suspension was heated to 60° C. After 3.5 hours, the reaction was cooled to room temperature, quenched with 2 M hydrochloric acid (1 mL), and diluted with ethyl acetate (2 mL). The layers were separated, and the aqueous layer was extracted with ethyl acetate (2×1 mL). The combined organic layers were washed with saturated aqueous ammonium chloride (3×1 mL). The combined aqueous washes were back extracted with ethyl acetate (1 mL), and the combined organic layers were washed with a 4:1 mixture of brine and 1 M hydrochloric acid, then dried over sodium sulfate, filtered and concentrated under reduced pressure to give tert-butyl 4-({[6-(benzyloxy)-8-fluoro-7-(1,1,4-trioxo-1λ⁶,2,5-thiadiazolidin-2-yl)naphthalen-2-yl]oxy}methyl)piperidine-1-carboxylate which was used for the next reaction without purification. MS (APCI⁻) m/z 598 [M–H]⁻.

To a suspension of tert-butyl 4-({[6-(benzyloxy)-8-fluoro-7-(1,1,4-trioxo-1λ⁶,2,5-thiadiazolidin-2-yl)naphthalen-2-yl]oxy}methyl)piperidine-1-carboxylate in dichloromethane (2 mL) at −78° C. was added a solution of boron trichloride in dichloromethane (2.38 mL, 1 M, 2.38 mmol) slowly along the side of the flask so that the internal temperature remained below −70° C. The resulting solution was stirred for 5 minutes at −78° C., then the cooling bath was removed, and the reaction mixture was allowed to warm to an internal temperature of 10° C. before cooling back to −78° C. The reaction was quenched by addition of ethyl acetate (1 mL) followed by anhydrous ethanol (0.5 mL), was warmed to room temperature, and concentrated under reduced pressure to give a tan solid. The crude solid was suspended in ethyl acetate (5 mL) and sonicated for 30 seconds giving a suspension. The solid was collected via filtration and washed with ethyl acetate (2 mL). The solid was dissolved in a dimethyl sulfoxide/methanol mixture and was filtered through a glass microfiber frit. The resulting solution was directly purified by preparative HPLC [Waters XBridge™ C18 5 μm OBD column, 30×100 mm, flow rate 40 mL/minute, a gradient of 3-30% methanol in buffer (0.025 M aqueous ammonium bicarbonate, adjusted to pH 10 with ammonium hydroxide)] to give the title compound (0.066 g, 0.155 mmol, 65% yield). ¹H NMR (400 MHz, DMSO-d₆) δ ppm 7.65 (dd, J=9.1, 1.5 Hz, 1H), 7.19 (d, J=2.5 Hz, 1H), 7.13 (dd, J=9.0, 2.5 Hz, 1H), 7.02 (s, 1H), 4.11 (s, 2H), 3.96 (s, 2H), 3.27 (s, 2H), 2.90 (td, J=12.8, 3.0 Hz, 2H), 2.08 (d, J=11.0 Hz, 1H), 1.95 (dd, J=14.6, 3.5 Hz, 2H), 1.58-1.37 (m, 2H); MS (ESI⁻) m/z 408 [M–H]⁻.

Example 16: 5-{[8-fluoro-6-hydroxy-7-(1,1,4-tri-oxo-1λ⁶,2,5-thiadiazolidin-2-yl)naphthalen-2-yl]oxy}-3,3-dimethylpentanenitrile (Compound 115)

Example 16A: 5-bromo-3,3-dimethylpentanenitrile

To a solution of 5-bromo-3,3-dimethylpentanoic acid (0.5 g, 2.391 mmol), in dichloromethane (10 mL) was added chlorosulfonyl isocyanate (0.208 mL, 2.391 mmol) dropwise. The resulting solution was stirred for 15 minutes at room temperature, and then heated to an internal temperature of 40° C. After 2 hours, gas evolution had ceased, and the reaction mixture was cooled to 0° C. N,N-Diisopropylethylamine was added slowly via syringe so that the internal temperature remained below 7° C. The resulting solution was then warmed to room temperature and stirred for 1 hour. The reaction was quenched with 1 M sodium bisulfate (5 mL), and the layers were separated. The aqueous layer was extracted with dichloromethane (2×5 mL), and the combined organic layers were dried over anhydrous sodium sulfate, filtered and concentrated in vacuo to give an orange oil. The crude oil was dissolved in a 50% v/v mixture of heptanes and ethyl acetate (5 mL), and the resulting solution was washed with 1 M sodium carbonate (2×5 mL), followed by brine (2 mL), then dried over sodium sulfate, and filtered through silica (2 g). The solid was washed with heptanes (5 mL), and the filtrate was concentrated under reduced pressure to give the title compound (0.33 g, 1.73 mmol, 72.5% yield). ¹H NMR (400 MHz, CDCl₃) δ ppm 3.43-3.29 (m, 2H), 2.28 (s, 2H), 2.08-1.96 (m, 2H), 1.10 (s, 6H); ¹³C NMR (101 MHz, CDCl₃) δ ppm 117.72, 44.58, 34.22, 30.67, 26.39.

Example 16B: 5-{[8-fluoro-6-hydroxy-7-(1,1,4-trioxo-1λ⁶,2,5-thiadiazolidin-2-yl)naphthalen-2-yl]oxy}-3,3-dimethylpentanenitrile To a solution of the product of Example 1H (0.050 g, 0.125 mmol) and the product of Example 16A (0.047 g, 0.249 mmol) in N,N-dimethylformamide (0.5 mL) was added cesium carbonate (0.243 g, 0.746 mmol) as a solid, and the resulting suspension was heated to 60° C. After 3 hours, the reaction was cooled to room temperature, quenched with 2 N hydrochloric acid (1 mL), and diluted with ethyl acetate (2 mL). The layers were separated, and the aqueous layer was extracted with ethyl acetate (2×1 mL). The combined organic layers were washed with saturated aqueous ammonium chloride (3×1 mL). The combined aqueous washes were back extracted with ethyl acetate (1 mL). The combined organic layers were washed with a 4:1 mixture of brine and 1 M hydrochloric acid, then dried over anhydrous sodium sulfate, filtered and concentrated under reduced pressure to give 5-{[6-(benzyloxy)-8-fluoro-7-(1,1,4-trioxo-1λ⁶,2,5-thiadiazolidin-2-yl)naphthalen-2-yl]oxy}-3,3-dimethylpentanenitrile which was used for the next step without purification. MS (APCI⁻) m/z 510 [M−H]⁻.

To a suspension of 5-{[6-(benzyloxy)-8-fluoro-7-(1,1,4-trioxo-1λ⁶,2,5-thiadiazolidin-2-yl)naphthalen-2-yl]oxy}-3,3-dimethylpentanenitrile in dichloromethane (2 mL) at −78° C. was added a solution of boron trichloride in dichloromethane (0.75 mL, 1 M, 0.75 mmol) slowly along the side of the vial so that the internal temperature remained below −70° C. The resulting solution was stirred for 5 minutes at −78° C., then the cooling bath was removed, and the reaction mixture was allowed to warm to an internal temperature of 10° C. before cooling back to −78° C. The reaction was quenched by addition of ethyl acetate (1 mL) followed by anhydrous ethanol (0.5 mL), was warmed to room temperature, and concentrated under reduced pressure to give a tan solid. The residue was dissolved in a dimethyl sulfoxide/methanol mixture and was filtered through a glass microfiber frit. The resulting solution was directly purified by preparative HPLC on a Phenomenex® Luna® C8(2) 5 μm 100 Å AXIA™ column (30 mm×75 mm) with gradient of acetonitrile (A) and 10 mM ammonium acetate in water (B) at a flow rate of 50 mL/minute (0-1.0 minute 5% A, 1.0-8.5 minutes linear gradient 5-100% A, 8.5-11.5 minutes 100% A, 11.5-12.0 minutes linear gradient 95-5% A) to give the title compound (0.0100 g, 0.023 mmol, 18.2% yield). ¹H NMR (400 MHz, DMSO-d₆) δ ppm 7.66 (dd, J=9.1, 1.5 Hz, 1H), 7.23 (d, J=2.6 Hz, 1H), 7.12 (dd, J=9.0, 2.5 Hz, 1H), 7.02 (s, 1H), 4.15 (t, J=6.9 Hz, 2H), 4.09 (s, 2H), 2.59 (s, 2H), 1.84 (t, J=6.9 Hz, 2H), 1.10 (s, 6H); MS (ESI⁻) m/z 420 [M−H]⁻.

Example 17: 5-{7-[(3,3-dimethylbutyl)amino]-1-fluoro-3-hydroxynaphthalen-2-yl}-1λ⁶,2,5-thiadiazolidine-1,1,3-trione (Compound 116)

In a 4 mL vial with a septum screw cap, the product of Example 1G (0.1 g, 0.215 mmol), sodium tert-butoxide (0.062 g, 0.645 mmol), BrettPhos Pd G3 precatalyst (5.84 mg, 6.45 μmol), and BrettPhos (3.46 mg, 6.45 μmol) were combined. The solids were placed under vacuum for 5 minutes with stirring, then the vial was filled with nitrogen, followed by 1,4-dioxane (2 mL) and 3,3-dimethylbutan-1-amine (0.044 g, 0.430 mmol). The resulting suspension was degassed by five vacuum/nitrogen backfills, was stirred for 10 minutes at room temperature, and then was heated to 100° C. After 30 minutes at 100° C., the reaction mixture was cooled to room temperature, then quenched with 1 M hydrochloric acid (1 mL) and diluted with ethyl acetate (2 mL). The aqueous layer was extracted with ethyl acetate (2×1 mL). The combined organic layers were washed with a 4:1 mixture of brine and 1 M hydrochloric acid (1 mL), dried over anhydrous sodium sulfate, then filtered and concentrated under reduced pressure to give 5-{3-(benzyloxy)-7-[(3,3-dimethylbutyl)amino]-1-fluoronaphthalen-2-yl}-1λ⁶,2,5-thiadiazolidine-1,1,3-trione which was used for the next reaction without purification. MS (APCI⁻) m/z 484 [M−H]⁻.

To a suspension of the crude 5-{3-(benzyloxy)-7-[(3,3-dimethylbutyl)amino]-1-fluoronaphthalen-2-yl}-1λ⁶,2,5-thiadiazolidine-1,1,3-trione in dichloromethane (2 mL) at −78° C. was added a solution of boron trichloride in dichloromethane (1.29 mL, 1 M, 1.29 mmol) slowly along the side of the flask so that the internal temperature remained below −70° C. The resulting solution was stirred for 5 minutes at −78° C., then the cooling bath was removed, and the reaction mixture was allowed to warm to an internal temperature of 10° C. before cooling back to −78° C. The reaction was quenched by addition of ethyl acetate (1 mL), followed by anhydrous ethanol (0.5 mL), warmed to room temperature and concentrated under reduced pressure to give a brown solid. The crude product was dissolved in a dimethyl sulfoxide/methanol mixture and was filtered through a glass microfiber frit. The resulting solution was directly purified by preparative HPLC on a Phenomenex® Luna® C8(2) 5 μm 100 Å AXIA™ column (30 mm×75 mm) with gradient of acetonitrile (A) and 10 mM ammonium acetate in water (B) at a flow rate of 50 mL/minute (0-1.0 minute 5% A, 1.0-8.5 minutes linear gradient 5-100% A, 8.5-11.5 minutes 100% A, 11.5-12.0 minutes linear gradient 95-5% A) to give the title compound (0.0165 g, 0.040 mmol, 18.6% yield). ¹H NMR (400 MHz, DMSO-$d_6$) δ ppm 7.44 (dd, J=9.1, 1.7 Hz, 1H), 6.94 (dd, J=9.0, 2.3 Hz, 1H), 6.87 (s, 1H), 6.60 (d, J=2.3 Hz, 1H), 5.74 (t, J=5.4 Hz, 1H), 4.07 (s, 2H), 3.07 (dt, J=10.4, 5.2 Hz, 2H), 1.57-1.49 (m, 2H), 0.97 (s, 9H); MS (ESI$^-$) m/z 394 [M−H]$^-$.

Example 18: 5-(1,4-difluoro-3-hydroxy-7-methoxynaphthalen-2-yl)-1λ$^6$,2,5-thiadiazolidine-1,1,3-trione (Compound 117)

Example 18A: 5-[3-(benzyloxy)-7-bromo-1,4-difluoronaphthalen-2-yl]-1λ$^6$,2,5-thiadiazolidine-1,1,3-trione To a mixture of the product of Example 1F (300 mg, 0.603 mmol) in dimethylformamide (6.73 mL) was added Selectfluor® (256 mg, 0.724 mmol), and the homogeneous light yellow solution was heated to 65° C. After 90 minutes, the mixture was cooled to room temperature, and the excess oxidant was quenched with a solution of sodium thiosulfate pentahydrate (404 mg, 1.63 mmol) in water (3.3 mL). After stirring for 15 minutes, water (10 mL) was added, and the mixture was extracted with ethyl acetate (3×10 mL). The combined organic fractions were washed with saturated aqueous ammonium chloride (2×10 mL) and brine (1×10 mL), dried over sodium sulfate, filtered, and concentrated in vacuo to afford methyl {[3-(benzyloxy)-7-bromo-1,4-difluoronaphthalen-2-yl](sulfamoyl)amino}acetate as a viscous, orange oil that was used in the next step without further purification. MS (APCI$^+$) m/z 516 [M+H]$^+$.

To a solution of methyl {[3-(benzyloxy)-7-bromo-1,4-difluoronaphthalen-2-yl](sulfamoyl)amino}acetate from the previous reaction in tetrahydrofuran (2.69 mL) at room temperature was added a solution of sodium methoxide (207 µL, 0.905 mmol) (25 w % in methanol) via syringe, and the resulting solution was stirred at room temperature. After 5 minutes, the reaction was quenched with 1 M hydrochloric acid (3 mL) and diluted with ethyl acetate (3 mL). The layers were separated, and the aqueous layer was extracted with ethyl acetate (3×1 mL). The combined organic layers were washed with water (2×1 mL), saturated aqueous ammonium chloride (2×1 mL) and brine (1×1 mL) then dried over sodium sulfate, filtered and concentrated. The residue was purified via flash column chromatography (24 g SiO$_2$, CH$_2$Cl$_2$ to 10% methanol/CH$_2$Cl$_2$) to afford the title compound along with minor, inseparable impurities. The product was carried on to the next step without further purification. MS (APCI$^+$) m/z 484 [M+H]$^+$.

Example 18B: 5-[3-(benzyloxy)-1,4-difluoro-7-methoxynaphthalen-2-yl]-1λ$^6$,2,5-thiadiazolidine-1,1,3-trione A mixture of the product of Example 18A (301 mg, 0.623 mmol), RockPhos Pd G3 (16.1 mg, 0.019 mmol), and cesium carbonate (609 mg, 1.87 mmol) were placed under vacuum and stirred for 5 minutes, then the flask was filled with nitrogen and a preformed mixture of N,N-dimethylformamide (3.11 mL) and anhydrous methanol (126 µL, 3.11 mmol) was added. The resulting suspension was degassed by five vacuum/nitrogen backfills, and then heated to an internal temperature of 80° C. After 15 minutes, the reaction mixture was cooled to room temperature, quenched by the slow addition of 1 M hydrochloric acid (5 mL), and diluted with ethyl acetate (5 mL). The layers were separated, and the aqueous layer was extracted with ethyl acetate (2×5 mL). The combined organic layers were washed with saturated aqueous ammonium chloride (4×5 mL), then dried over sodium sulfate, filtered, and concentrated to give a viscous, dark oil. The residue was purified via flash column chromatography (12 g SiO$_2$, CH$_2$Cl$_2$ to 10% methanol/CH$_2$Cl$_2$) to afford the title compound along with minor, inseparable impurities. The product was carried on to the next step without further purification. MS (APCI$^+$) m/z 435 [M+H]$^+$.

Example 18C: 5-(1,4-difluoro-3-hydroxy-7-methoxynaphthalen-2-yl)-1λ$^6$,2,5-thiadiazolidine-1,1,3-trione A mixture of the product of Example 18B (38.7 mg, 0.089 mmol) and pentamethylbenzene (39.6 mg, 0.267 mmol) in dichloromethane (445 µL) was cooled to an internal temperature of −76° C. under an atmosphere of dry nitrogen. Subsequently, a 1 M solution of boron trichloride (178 µL, 0.178 mmol) in CH$_2$Cl$_2$ was added dropwise over 15 minutes, so as not to raise the internal temperature past −72° C. After 15 minutes, the reaction was quenched at −75° C. with CH$_2$Cl$_2$/methanol (10:1, 230 µL) via cannula transfer under nitrogen. The mixture was then slowly warmed to room temperature under nitrogen. The volatiles were removed in vacuo to afford a brown solid that was purified via HPLC (Phenomenex® Luna® 10 M C18(2) 100 Å, AXIA™ (00G-4253-U0-AX) column, 250×300 mm, flow rate 50 mL/minute, 5-95% gradient of acetonitrile in buffer (0.025 M aqueous ammonium acetate) to give the title compound (10.3 mg, 0.030 mmol, 34% yield) as a white solid. $^1$H NMR (CD$_3$OD) δ ppm 7.84 (dd, J=9.3, 1.4 Hz, 1H), 7.30 (t, J=1.5 Hz, 1H), 7.23 (dd, J=9.3, 2.5 Hz, 1H), 4.41 (s, 2H), 3.91 (s, 3H); MS (ESI$^-$) m/z 343 [M−H]$^-$.

Example 19: 5-{1-fluoro-3-hydroxy-7-[($^2$H$_3$)methyloxy]naphthalen-2-yl}-1λ$^6$,2,5-thiadiazolidine-1,1,3-trione (Compound 118)

Example 19A: 5-{3-(benzyloxy)-1-fluoro-7-[($^2$H$_3$)methyloxy]naphthalen-2-yl}-1λ$^6$,2,5-thiadiazolidine-1,1,3-trione A mixture of the product of Example 1H (200 mg, 0.497 mmol), iodomethane-d$_3$ (68.4 mg, 0.472 mmol), and cesium carbonate (324 mg, 0.994 mmol) in N,N-dimethylformamide (2 mL) was stirred at ambient temperature for 2 hours. The reaction mixture was purified by preparative HPLC on a Phenomenex® Luna® 10 µm C$_{18}$ column (30 mm×250 mm) eluted with a gradient of acetonitrile (A) with 0.1% trifluoroacetic acid and water (B) 0.1% with trifluoroacetic acid at a flow rate of 50 mL/minute (0-1 minute 10% A, 1-20 minutes linear gradient 10-75%) to give the title compound (60 mg, 0.143 mmol, 28.8% yield). $^1$H NMR (501 MHz, DMSO-d$_6$) δ ppm 7.81 (dt, J=8.2, 1.4 Hz, 1H), 7.54-7.49 (m, 2H), 7.42 (s, 1H), 7.41-7.36 (m, 2H), 7.37-7.31 (m, 1H), 7.27 (d, J=8.3 Hz, 2H), 5.24 (s, 2H), 4.48 (s, 2H); MS (APCI$^-$) m/z 418 [M−H]$^-$.

Example 19B: 5-{-fluoro-3-hydroxy-7-[($^2$H)methyloxy]naphthalen-2-yl}-1λ$^6$,2,5-thiadiazolidine-1,1,3-trione To a mixture of the product of Example 19A (56 mg, 0.134 mmol) and pentamethylbenzene (99 mg, 0.668 mmol) in dichloromethane (2 mL) cooled to −78° C. was added a solution of boron trichloride (0.801 mL, 0.801 mmol) in dichloromethane dropwise over 5 minutes. After 30 minutes, the reaction was quenched with 2 N HCl (0.5 mL). The reaction mixture was extracted with ethyl acetate. The organic fractions were washed with brine, dried over Na$_2$SO$_4$ and concentrated under reduced pressure. The residue was purified by preparative HPLC on a Phenomenex® Luna® 10 μm C18 column (30 mm×250 mm) eluted with a gradient of acetonitrile (A) with 0.1% trifluoroacetic acid and water (B) 0.1% with trifluoroacetic acid at a flow rate of 50 mL/minute (0-1 minute 10% A, 1-20 minutes linear gradient 10-100%) to give the title compound (30 mg, 0.091 mmol, 68.2% yield). $^1$H NMR (501 MHz, DMSO-d$_6$) δ ppm 7.81 (dt, J=8.2, 1.4 Hz, 1H), 7.54-7.49 (m, 2H), 7.42 (s, 1H), 7.41-7.36 (m, 2H), 7.37-7.31 (m, 1H), 7.27 (d, J=8.3 Hz, 2H), 5.24 (s, 2H), 4.48 (s, 2H); MS (APCI$^-$) m/z 328 [M−H]$^-$.

Example 20: 5-[1-fluoro-3-hydroxy-7-(2-methoxyethoxy)naphthalen-2-yl]-1λ$^6$,2,5-thiadiazolidine-1,1,3-trione (Compound 119)

Example 20A: 5-[3-(benzyloxy)-1-fluoro-7-(2-methoxyethoxy)naphthalen-2-yl]-1λ$^6$,2,5-thiadiazolidine-1,1,3-trione A mixture of the product of Example 1H (97 mg, 0.24 mmol), 1-bromo-2-methoxyethane (66.7 mg, 0.480 mmol) and cesium carbonate (180 mg, 0.552 mmol) in N,N-dimethylformamide (0.8 mL) was stirred at 75° C. for 40 minutes. The solution was filtered and concentrated under reduced pressure. The residue was purified by flash column chromatography on silica gel eluted with dichloromethane, then dichloromethane:methanol (10:1) to give the title compound (100 mg, 0.217 mmol, 90% yield) as a solid. $^1$H NMR (400 MHz, DMSO-d$_6$) δ ppm 7.76 (d, J=8 Hz, 1H), 7.56 (d, J=8 Hz, 2H), 7.37 (t, J=8 Hz, 2H), 7.32 (m, 1H), 7.30 (br s, 1H), 7.25 (d, J=2 Hz, 1H), 7.21 (dd, J=8, 2 Hz, 1H), 5.21 (s, 2H), 4.21 (m, 2H), 4.08 (s, 2H), 3.72 (m, 2H), 3.33 (s, 3H); MS (ESI$^-$) m/z 459 [M−H]$^-$.

Example 20B: 5-[1-fluoro-3-hydroxy-7-(2-methoxyethoxy)naphthalen-2-yl]-1λ$^6$,2,5-thiadiazolidine-1,1,3-trione To the product of Example 20A (100 mg, 0.217 mmol) and 1,2,3,4,5-pentamethylbenzene (97 mg, 0.652 mmol) in dichloromethane (3 mL) at −78° C. was added trichloroborane (869 μl, 0.869 mmol, 1.0 M in dichloromethane). The mixture was stirred at −78° C. for 40 minutes. Methanol (5 mL) was added at −78° C. The mixture was stirred for 5 minutes at room temperature, and then was concentrated under reduced pressure. The resulting solid was washed with heptane (5 mL×4), and then was dissolved in methanol (0.5 mL) and N,N-dimethylformamide (3 mL). The mixture was purified by preparative HPLC [YMC TriArt™ C18 Hybrid 20 μm column, 25×150 mm, flow rate 80 mL/minute, 5-100% gradient of methanol in buffer (0.025 M aqueous ammonium bicarbonate, adjusted to pH 10 with ammonium hydroxide)] to give the title compound (35 mg, 0.095 mmol, 44% yield). $^1$H NMR (400 MHz, DMSO-d$_6$) δ ppm 9.27 (br s, 1H), 7.67 (d, J=8 Hz, 1H), 7.18 (d, J=2 Hz, 1H), 7.14 (dd, J=8, 2 Hz, 1H), 7.03 (br s, 1H), 4.19 (m, 2H), 4.09 (s, 2H), 3.71 (m, 2H), 3.33 (s, 3H); MS (ESI$^-$) m/z 369 [M−H]$^-$.

Example 21: 4-{[8-fluoro-6-hydroxy-7-(1,1,4-trioxo-1λ$^6$,2,5-thiadiazolidin-2-yl)naphthalen-2-yl]oxy}-2,2-dimethylbutanenitrile (Compound 120)

Example 21A: 4-{[6-(benzyloxy)-8-fluoro-7-(1,1,4-trioxo-1λ$^6$,2,5-thiadiazolidin-2-yl)naphthalen-2-yl]oxy}-2,2-dimethylbutanenitrile To a solution of the product of Example 1H (100 mg, 0.249 mmol) in dimethylformamide (3 mL) was added sodium hydride (21.87 mg, 0.547 mmol) at room temperature in three portions. The mixture was stirred for 30 minutes until no gas evolution was observed. A solution of 4-bromo-2,2-dimethylbutanenitrile (96 mg, 0.547 mmol) in N,N-dimethylformamide (2 mL) was slowly added to the reaction mixture. The mixture was stirred overnight at room temperature. Methanol (2 mL) was added, the volatiles were removed under reduced pressure, and the residue was subjected to column chromatography (SiO$_2$, 10% CH$_3$OH in CH$_2$Cl$_2$) to afford the title compound (65 mg, 0.131 mmol, 53% yield). $^1$H NMR (501 MHz, DMSO-d$_6$) δ ppm 7.77 (dd, J=9.1, 1.4 Hz, 1H), 7.59-7.50 (m, 2H), 7.44-7.26 (m, 5H), 7.20 (dd, J=9.0, 2.5 Hz, 1H), 5.22 (s, 2H), 4.28 (t, J=6.5 Hz, 2H), 4.09 (s, 2H), 3.17 (d, J=5.2 Hz, 1H), 2.12-2.05 (m, 2H), 1.41 (s, 6H); MS (APCI$^-$) m/z 496 [M−H]$^-$.

Example 21B: 4-{[8-fluoro-6-hydroxy-7-(1,1,4-trioxo-1λ$^6$,2,5-thiadiazolidin-2-yl)naphthalen-2-yl]oxy}-2,2-dimethylbutanenitrile The product of Example 21A (56 mg, 0.113 mmol) and 1,2,3,4,5-pentamethylbenzene (50.1 mg, 0.338 mmol) in a 50 mL round bottom flask was flushed with nitrogen for 5 minutes. Dichloromethane (5 mL) was then added, and the heterogeneous suspension was cooled to −78° C. and equilibrated for 5 minutes. Subsequently, a 1 M solution of trichloroborane (0.338 mL, 0.338 mmol) in dichloromethane was added dropwise over 5 minutes. After 30 minutes, the reaction was quenched at −77° C. with dichloromethane:methanol=2:1(1 mL), and then the mixture was slowly warmed to room temperature. The volatiles were removed under reduced pressure, and the residue was subjected to preparative HPLC [Phenomenex® Luna® C18(2) 5 μm 100 Å AXIA™ column (250 mm×25 mm). 30-100% gradient of acetonitrile (A) and 0.1% ammonium acetate in water (B) over 15 minutes at a flow rate of 25 mL/minute] to afford the title compound (28 mg, 0.069 mmol, 61% yield) as a white solid. $^1$H NMR (501 MHz, DMSO-d$_6$) δ ppm 7.68 (dd, J=9.1, 1.4 Hz, 1H), 7.25 (d, J=2.6 Hz, 1H), 7.13 (dd, J=9.0, 2.5 Hz, 1H), 7.04 (d, J=1.3 Hz, 1H), 4.29-4.18 (m, 2H), 4.10 (s, 2H), 2.11-2.05 (m, 2H), 1.41 (s, 6H); MS (APCI$^-$) m/z 405 [M−H]$^-$.

Example 22: 5-{7-[2-(3-aminobicyclo[1.1.1]pentan-1-yl)ethoxy]-1-fluoro-3-hydroxynaphthalen-2-yl}-1λ$^6$,2,5-thiadiazolidine-1,1,3-trione (Compound 121)

Example 22A: 2-{3-[(tert-butoxycarbonyl)amino]bicyclo[1.1.1]pentan-1-yl}ethyl methanesulfonate To a mixture of tert-butyl (3-(2-hydroxyethyl)bicyclo[1.1.1]pentan-1-yl)carbamate (0.341 g, 1.5 mmol) and triethylamine (0.304 g, 3.00 mmol) in dichloromethane (4 mL) at 0° C. was added methanesulfonyl chloride (0.180 g, 1.575 mmol) in dichloromethane (1 mL). The mixture was stirred at room temperature for 40 minutes. The mixture was diluted with dichloromethane (60 mL) and washed with water (20 mL×2). The organic phase was dried over anhydrous Na$_2$SO$_4$ and concentrated under reduced pressure to give the title compound (460 mg, 1.50 mmol, 100% yield) as a solid. $^1$H NMR (400 MHz, DMSO-d$_6$) δ ppm 7.39 (br s, 1H), 4.16

(t, J=8 Hz, 2H), 3.15 (s, 3H), 1.89 (t, J=8 Hz, 2H), 1.81 (s, 6H), 1.37 (s, 9H); MS (ESI+) m/z 250 [M−tert−Bu+H]+.

Example 22B: tert-butyl[3-(2-{[6-(benzyloxy)-8-fluoro-7-(1,1,4-trioxo-1λ⁶,2, 5-thiadiazolidin-2-yl)naphthalen-2-yl]oxy}ethyl)bicyclo[0.1.]pentan-1-yl] carbamate A mixture of the product of Example 1H (62.8 mg, 0.15 mmol), the product of Example 22A (110 mg, 0.360 mmol) and cesium carbonate (161 mg, 0.495 mmol) in dimethylformamide (1 mL) was stirred at 75° C. for 1.5 hours. The mixture was filtered and concentrated under reduced pressure. The residue was purified by flash column chromatography on silica gel eluted with dichloromethane, then dichloromethane/methanol (20:1) to give the title compound (70 mg, 0.11 mmol, 74% yield) as a solid. $^1$H NMR (400 MHz, DMSO-$d_6$) δ ppm 7.78 (d, J=8 Hz, 1H), 7.57 (d, J=8 Hz, 2H), 7.49 (s, 1H), 7.42 (d, J=2 Hz, 1H), 7.28-7.38 (m, 4H), 7.21 (dd, J=8, 2 Hz, 1H), 5.21 (br s, 2H), 4.10 (t, J=8 Hz, 2H), 3.93 (br s, 2H), 2.00 (t, J=8 Hz, 2H), 1.84 (s, 6H), 1.37 (s, 9H); MS (ESI⁻) m/z 626 [M−H]⁻.

Example 22C: 5-{7-[2-(3-aminobicyclo[1.1.1]pentan-1-yl)ethoxy]-3-(benzyloxy)-1-fluoronaphthalen-2-yl}-1λ⁶,2,5-thiadiazolidine-1,1,3-trione A mixture of Example 22B (88 mg, 0.144 mmol) and trifluoroacetic acid (1148 mg, 10.07 mmol) in dichloromethane (1.5 mL) was stirred at room temperature for 20 minutes. The mixture was concentrated. The residue was purified by flash column chromatography on silica gel eluted with dichloromethane, then dichloromethane/methanol (7:1) to give the title compound (90 mg, 0.144 mmol, 100 yield) as a trifluoroacetate salt. MS (ESI+) m/z 512 [M+H]+.

Example 22D: 5-{7-[2-(3-aminobicyclo[1.1.1]pentan-1-yl)ethoxy]-1-fluoro-3-hydroxynaphthalen-2-yl}-1λ⁶,2,5-thiadiazolidine-1,1,3-trione To the product of Example 22C (80 mg, 0.128 mmol) and 1,2,3,4,5-pentamethylbenzene (76 mg, 0.512 mmol) in dichloromethane (3 mL) at −78° C. was added trichloroborane (1535 µL, 1.535 mmol, 1.0 M in dichloromethane). The mixture was stirred at −78° C. for 10 minutes, then 0° C. for 20 minutes. Methanol (6 mL) was added at 0° C. The ice-bath was removed, and the mixture was stirred for 5 minutes at room temperature and then was concentrated under reduced pressure. The resulting solid was washed with heptane (5 mL×4) and dichloromethane (2 mL×4) and was purified by flash column chromatography on silica gel eluted with dichloromethane, then dichloromethane/methanol (5:1) to give the title compound (32 mg, 0.076 mmol, 59% yield). $^1$H NMR (400 MHz, DMSO-$d_6$) δ ppm 8.77 9br s, 2H), 7.67 (d, J=8 Hz, 1H), 7.19 (d, J=2 Hz, 1H), 7.12 (dd, J=8, 2 Hz, 1H), 7.16 (s, 1H), 4.14 (br s, 2H), 4.09 (t, J=8 Hz, 2H), 2.04 (t, J=8 Hz, 2H), 1.94 (s, 6H); MS (ESI⁻) m/z 420 [M−H]⁻.

Example 23: 5-(7-{[2-(dimethylamino)ethyl]amino}-1-fluoro-3-hydroxynaphthalen-2-yl)-1λ⁶,2, 5-thiadiazolidine-1,1,3-trione (Compound 122)

In a 4 mL vial with a septum screw cap, the product of Example 1G (0.1 g, 0.215 mmol), sodium tert-butoxide (0.062 g, 0.645 mmol), BrettPhos Pd G3 precatalyst (5.84 mg, 6.45 µmol), and BrettPhos (3.46 mg, 6.45 µmol) were combined. The solids were placed under vacuum for 5 minutes with stirring, then the vial was filled with nitrogen, followed by 1,4-dioxane (2 mL) and N,N-dimethylethylenediamine (0.047 mL, 0.430 mmol). The resulting suspension was degassed by five vacuum/nitrogen backfills, stirred for 10 minutes at room temperature, and then heated to 100° C. After 30 minutes at 100° C., the reaction mixture was cooled to room temperature, then was quenched with 1 M hydrochloric acid (1 mL) and diluted with ethyl acetate (2 mL). The aqueous layer was extracted with ethyl acetate (2×1 mL). The combined organic layers were washed with a 4:1 mixture of brine and 1 M hydrochloric acid (1 mL), dried over anhydrous sodium sulfate, then filtered and concentrated under reduced pressure to give 5-[3-(benzyloxy)-7-{[2-(dimethylamino)ethyl]amino}-1-fluoronaphthalen-2-yl]-1λ⁶,2,5-thiadiazolidine-1,1,3-trione, which was used for the next reaction without purification. MS (APCI⁻) m/z 471 [M−H]⁻.

To a suspension of 5-[3-(benzyloxy)-7-{[2-(dimethylamino)ethyl]amino}-1-fluoronaphthalen-2-yl]-1λ⁶,2,5-thiadiazolidine-1,1,3-trione in dichloromethane (2 mL) at −78° C. was added a solution of boron trichloride in dichloromethane (2.15 mL, 1 M, 2.15 mmol) slowly along the side of the flask so that the internal temperature remained below −70° C. The resulting solution was stirred for 5 minutes at −78° C., then the cooling bath was removed, and the reaction mixture was allowed to warm to an internal temperature of 10° C. before cooling back to −78° C. The reaction was quenched by addition of ethyl acetate (1 mL), followed by anhydrous ethanol (0.5 mL), and warmed to room temperature, giving a suspension. The resulting solid was collected via filtration, then washed with ethyl acetate (2×1 mL) followed by a 50% v/v mixture of acetonitrile and ethyl acetate (1 mL), and dried in vacuo (15 mbar) at 50° C. to constant weight to give the title compound (0.0524 g, 0.125 mmol, 58.7% yield). $^1$H NMR (400 MHz, DMSO-$d_6$) δ ppm 7.53 (d, J=8.8 Hz, 1H), 7.02 (dd, J=9.0, 2.2 Hz, 1H), 6.96 (s, 1H), 6.80 (s, 1H), 4.25 (br s, 2H), 3.49 (t, J=6.2 Hz, 2H), 3.31 (t, J=5.9 Hz, 2H), 2.83 (s, 6H); MS (ESI⁻) m/z 381 [M−H]⁻.

Example 24: 5-(1-fluoro-3-hydroxy-7-methoxynaphthalen-2-yl)(4,4-$^2$H$_2$)-1λ⁶,2,5-thiadiazolidine-1,1,3-trione (Compound 123)

Example 24A: methyl {[3-(benzyloxy)-7-methoxynaphthalen-2-yl]amino}($^2$H$_2$)acetate To a stirred suspension of the product of Example 25C (889.2 mg, 3.18 mmol) and potassium carbonate (880 mg, 6.37 mmol) in N,N-dimethylformamide (8 mL) was added methyl bromoacetate-2,2-$d_2$ (0.452 mL, 4.77 mmol) with 0.5 equivalent of D$_2$O (0.032 mL, 1.592 mmol). The mixture was stirred at 60° C. for 2 hours and then was allowed to cool to ambient temperature. The reaction was quenched with 10% acetic acid-$d_4$ in D$_2$O (3 mL) and was then diluted with extracted with ethyl acetate (50 mL). The organic layer was washed with saturated aqueous NH$_4$Cl (3×50 mL) and brine (1×50 mL) and dried with Na$_2$CO$_3$. The mixture was filtered and concentrated under reduced pressure to give the title compound which was used directly in the following step. MS (APCI+) m/z 354 [M+H]+.

Example 24B: methyl {[3-(benzyloxy)-1-fluoro-7-methoxynaphthalen-2-yl]amino}(H$_2$)acetate To a stirred solution of the product of Example 24A (0.180 g, 0.509 mmol) in tetrahydrofuran (5.1 mL) was added N-fluoro-N-(phenylsulfonyl)benzenesulfonamide (0.169 g, 0.535 mmol). After 2 hours, Na$_2$SO$_3$ (200 mg) was added, and the suspension was stirred for 30 minutes. The tetrahydrofuran was removed under a stream of N$_2$, and residue was purified by column chromatography (SiO$_2$, 0-50% ethyl acetate in heptanes) to yield the title compound (0.160 g, 0.431 mmol, 85%). MS (APCI$^+$) m/z 372 [M+H]$^+$.

Example 24C: methyl {[3-(benzyloxy)-1-fluoro-7-methoxynaphthalen-2-yl][(tert-butoxycarbonyl)sulfamoyl]amino}(H$_2$)acetate A heat-dried 20 mL scintillation vial with a stir bar was charged with CH$_2$C$_2$ (5 mL) followed by chlorosulfonyl isocyanate (0.075 mL, 0.859 mmol)) under nitrogen. Subsequently, 2-methylpropan-2-($^2$H)ol (0.083 mL, 0.859 mmol) was added dropwise over 10 minutes and the reaction was subsequently stirred at ambient temperature for 30 minutes. Thereafter, a freshly-prepared solution of the product of Example 24B (160 mg, 0.430 mmol) and triethylamine (0.180 mL, 1.289 mmol) in dichloromethane (3 mL) was added dropwise over 2 minutes. The reaction was stirred at room temperature. Most of the solvent was then removed under a stream of N$_2$ and 2 mL of toluene was added. The residue was purified by column chromatography (SiO$_2$, 0-50% ethyl acetate in heptanes) to yield the title compound (0.180 g, 0.327 mmol, 76%). MS (APCI$^+$) m/z 451 [M-CO$_2$C(CH$_3$)$_3$+H]$^+$, 495 [M-C(CH$_3$)$_3$+H]$^+$, 569 [M+H$_2$O+H]$^+$.

Example 24D: methyl {[3-(benzyloxy)-1-fluoro-7-methoxynaphthalen-2-yl](sulfamoyl)amino}($^2$H$_2$) acetate To a stirred solution of the product of Example 24C (0.18 g, 0.327 mmol) in CH$_2$C$_2$ (3 mL) was added trifluoroacetic acid-d (0.381 mL, 4.90 mmol) dropwise. The solution was stirred at ambient temperature. After 1 hour, all of the volatiles were removed, and the residue was purified by column chromatography (SiO$_2$, 0-100% ethyl acetate in heptanes) to yield the title compound (0.132 g, 0.293 mmol, 90%). MS (APCI$^+$) m/z 451 [M+H]$^+$.

Example 24E: 5-[3-(benzyloxy)-1-fluoro-7-methoxynaphthalen-2-yl](4,4-$^2$H$_2$)-1λ$^6$,2,5-thiadiazolidine-1,1,3-trione Prior to reaction, a freshly prepared ~1 N solution of DCl was obtained by dissolving 265 uL of 35% (weight in D$_2$O) solution DCl in D$_2$O up to 3 mL. The product of Example 24D (0.02 g, 0.044 mmol) was taken up in deuterated methanol (1 mL) to give a suspension. Sodium hydride (8.79 mg, 0.220 mmol) was added slowly at room temperature; the solution became homogenous and faint yellow in color. The solution was heated to 60° C. and was allowed to stir for 30 minutes. The mixture was carefully quenched with 1 mL DCl in D$_2$O (~1M), and ethyl acetate (1 mL) was added. The organic layer was dried over anhydrous Na$_2$SO$_4$, filtered and concentrated under reduced pressure to yield the title compound (0.013 g, 0.031 mmol, 70.7%). MS (APCI$^+$) m/z 419 [M+H]$^+$.

Example 24F: 5-(1-fluoro-3-hydroxy-7-methoxynaphthalen-2-yl)(4,4-$^2$H$_2$)-1λ$^6$,2,5-thiadiazolidine-1,1,3-trione The product of Example 24E (0.121 g, 0.289 mmol) was dissolved in dichloromethane (5 mL) and 1,2,3,4,5-pentamethylbenzene (0.129 g, 0.868 mmol) was added. The mixture was cooled to −78° C. and was stirred for 5 minutes before adding boron trichloride (0.636 mL, 0.636 mmol) dropwise. The mixture was stirred for 30 minutes and methanol-d$_4$ (0.125 g, 3.47 mmol) in dichloromethane (0.75 mL) was added slowly down the side of the vial. The mixture was stirred for 10 minutes, and the dry-ice bath was removed. The mixture was allowed to warm to ambient temperature (white solid precipitated out of solution) and was stirred for 30 minutes. The solvent was removed under a stream of N$_2$, and the residue was purified by reverse phase-HPLC [Phenomenex® Luna® C18(2) 5 µm 100 Å AXIA™ column (150 mm×30 mm); 3-100% gradient of acetonitrile (A) and 10 mM ammonium acetate in water (B) over 17 minutes at a flow rate of 50 mL/minute] to yield the product which was dissolved in CH$_3$CN:D$_2$O (1:1, 4 mL) and lyophilized to give the title compound as a white powder (44.7 mg, 0.136 mmol, 47%). $^1$H NMR (400 MHz, DMSO-d$_6$) δ ppm 7.67 (d, J=9.3 Hz, 1H), 7.17 (d, J=2.5 Hz, 1H), 7.13 (dd, J=9.0, 2.4 Hz, 1H), 7.03 (d, J=1.3 Hz, 1H), 3.85 (s, 3H); MS (APCI$^−$) m/z 327 [M−H]$^−$.

Example 25: 5-(1-fluoro-3-hydroxy-7-methoxynaphthalen-2-yl)-1λ$^6$,2,5-thiadiazolidine-1,1,3-trione (Compound 124)

Example 25A: benzyl 3-(benzyloxy)-7-methoxynaphthalene-2-carboxylate

A mixture of 3-hydroxy-7-methoxy-2-naphthoic acid (75 g, 344 mmol) and cesium carbonate (336 g, 1031 mmol) in N,N-dimethylformamide (687 mL) was rapidly stirred for 5 minutes at 23° C. Thereafter, benzyl bromide (84 mL, 705 mmol) was added. After 90 minutes, the mixture was poured into H$_2$O (1 L) and extracted with ethyl acetate (4×300 mL). The combined organic layers were washed with saturated aqueous ammonium chloride (3×100 mL), dried over sodium sulfate, filtered, and concentrated in vacuo to afford a brown solid. The crude solid was collected by filtration, slurried with tert-butyl methyl ether/heptanes (1:2, 3×100 mL), then dried in vacuo (12 mbar) at 40° C. to afford the title compound (122.5 g, 307 mmol, 89% yield) as a beige solid. MS (APCI$^+$) m/z 399 [M+H]$^+$.

Example 25B: 3-(benzyloxy)-7-methoxynaphthalene-2-carboxylic acid

To a suspension of the product of Example 25A (122.5 g, 307 mmol) in methanol (780 mL) was added 6 M aqueous sodium hydroxide (154 mL, 922 mmol). The heterogeneous, brown slurry was agitated with an overhead mechanical stirrer and heated to an internal temperature of 68° C. After 15 minutes, the mixture was cooled to room temperature in an ice bath, and 6 M HCl (250 mL) was added over 5 minutes. The off-white solid was collected by filtration, washed with H$_2$O (3×500 mL), and dried to constant weight in vacuo at 65° C. to afford the title compound (84.1 g, 273 mmol, 89% yield) as a white solid. MS (APCI$^+$) m/z 309 [M+H]$^+$.

Example 25C: 3-(benzyloxy)-7-methoxynaphthalen-2-amine

To a suspension of the product of Example 25B (84.1 g, 273 mmol), in toluene (766 mL) and tert-butanol (766 mL) was added triethylamine (40.3 mL, 289 mmol). The homogeneous black solution was heated to an internal temperature of 80° C. under nitrogen, and diphenyl phosphorazidate (62.2 mL, 289 mmol) was added dropwise over 90 minutes with the entire reaction behind a blast shield. After 5 hours, the reaction was cooled to room temperature, diluted with $H_2O$ (1.5 L), and extracted with ethyl acetate (3×150 mL). The combined organic layers were washed with brine (2×100 mL), dried over sodium sulfate, filtered and concentrated to give 180.1 g of a dark brown solid. The solid was carried forward to hydrolysis without further purification.

To the crude intermediate was added diethylenetriamine (475 mL, 4.40 mol). The heterogeneous suspension was heated to an internal temperature of 130° C. under nitrogen, at which time a homogeneous dark orange solution formed. After 16 hours, the mixture was cooled to room temperature in an ice bath, and $H_2O$ (1.5 L) was added slowly over 3 minutes, resulting in precipitation of a yellow solid and a concomitant exotherm to an internal temperature of 62° C. Once the heterogeneous suspension had cooled to room temperature, the crude solid was dissolved in $CH_2Cl_2$ (1.5 L), and the layers were separated. The aqueous layer was back-extracted with $CH_2Cl_2$ (3×150 mL), and the combined organic layers were washed with brine (3×100 mL), dried over sodium sulfate, filtered, and concentrated in vacuo to afford 78.8 g of an orange solid. The solid was slurried with isopropanol (50 mL), collected via filtration, re-slurried with isopropanol (1×50 mL), and dried in vacuo (15 mbar) at 35° C. to afford the title compound (60.12 g, 215 mmol, 79% yield over two steps) as a yellow solid. MS (APCI$^+$) m/z 280 [M+H]$^+$.

Example 25D: methyl {[3-(benzyloxy)-7-methoxynaphthalen-2-yl]amino}acetate

To a mixture of the product of Example 25C (59.2 g, 212 mmol) and potassium carbonate (58.6 g, 424 mmol) in dimethylformamide (363 mL) and $H_2O$ (1.91 mL, 106 mmol) was added methyl 2-bromoacetate (30.1 mL, 318 mmol). The suspension was vigorously stirred at room temperature for 5 minutes and then heated to an internal temperature of 60° C. After 70 minutes, the suspension was cooled to room temperature and diluted with $H_2O$ (600 mL) and ethyl acetate (500 mL). The aqueous layer was extracted with ethyl acetate (2×300 mL), and the combined organic layers were washed with saturated aqueous ammonium chloride (3×60 mL), dried over sodium sulfate, filtered, and concentrated to afford 104.3 g of a pale beige solid. The solid was triturated with heptanes (200 mL). The resulting beige solid was collected via filtration, washed with additional heptanes (2×30 mL), and dried in vacuo (15 mbar) at 35° C. to afford the title compound (72.27 g, 206 mmol, 97% yield) as an off-white solid. MS (APCI$^+$) m/z 352 [M+H]$^+$.

Example 25E: methyl {[3-(benzyloxy)-1-fluoro-7-methoxynaphthalen-2-yl]amino}acetate To a mixture of the product of Example 25D (30.0 g, 85 mmol) and N-fluorobenzenesulfonimide (26.9 g, 85 mmol) was added tetrahydrofuran (THF) (854 mL), and the resulting homogeneous yellow solution was stirred at room temperature. After 90 minutes, residual oxidant was quenched by adding a solution of sodium thiosulfate pentahydrate (10.59 g, 42.7 mmol) in water (150 mL), and the mixture was stirred at room temperature for 30 minutes. Thereafter, ethyl acetate (600 mL) was added, the aqueous layer was separated, and the organic layer was washed with a solution of sodium carbonate (18.10 g, 171 mmol) in water (30 mL), followed by water:brine (1:1, 1×20 mL). The organic fraction was dried over sodium sulfate, filtered, and the concentrated in vacuo to afford a bright yellow/orange solid. The solids were triturated with tert-butyl methyl ether (300 mL), collected via filtration, and the filter cake (N-(phenylsulfonyl)benzenesulfonamide) was washed with tert-butyl methyl ether (2×100 mL). The filtrate was concentrated to afford 34.6 g of a dark red oil that was purified by flash chromatography (750 g $SiO_2$, heptanes to 20% ethyl acetate/heptanes) to afford the title compound (16.07 g, 43.5 mmol, 51% yield) as a yellow solid. MS (APCI$^+$) m/z 370 [M+H]$^+$.

Example 25F: methyl {[3-(benzyloxy)-1-fluoro-7-methoxynaphthalen-2-yl](sulfamoyl)amino}acetate To a solution of chlorosulfonyl isocyanate (5.13 mL, 59.1 mmol) in dichloromethane (83 mL) at 0° C. was added tert-butanol (5.65 mL, 59.1 mmol) slowly so that the internal temperature remained less than 10° C. After stirring for 30 minutes at 0° C., a preformed solution of the product of Example 25E (14.55 g, 39.4 mmol) and triethylamine (10.98 mL, 79 mmol) in dichloromethane (68.9 mL) was added slowly via addition funnel so that the internal temperature remained below 10° C. Upon complete addition, the addition funnel was rinsed with dichloromethane (23 mL). The resulting solution was stirred for 30 minutes at 0° C., and then the reaction mixture was quenched with $H_2O$ (20 mL). The layers were separated, and the aqueous layer was extracted with dichloromethane (2×30 mL). The combined organic layers were washed with brine (1×30 mL), dried over sodium sulfate, filtered and concentrated in vacuo to give an orange oil. The residue was dissolved in ethyl acetate (200 mL) and washed with water:brine (1:1, 2×50 mL) to remove residual triethylamine hydrochloride. The organic layer was dried over sodium sulfate, filtered, and concentrated in vacuo to give methyl {[3-(benzyloxy)-1-fluoro-7-methoxynaphthalen-2-yl][(tert-butoxycarbonyl)sulfamoyl]amino}acetate which was used without purification.

To a solution of methyl {[3-(benzyloxy)-1-fluoro-7-methoxynaphthalen-2-yl][(tert-butoxycarbonyl)sulfamoyl]amino}acetate in dichloromethane (98 mL) was added trifluoroacetic acid (45.5 mL, 591 mmol), and the resulting dark solution was stirred at room temperature. After 20 minutes, the reaction was quenched by slow addition of saturated aqueous sodium bicarbonate (691 mL) via an addition funnel. The layers were separated, and the aqueous layer was extracted with dichloromethane (2×50 mL). The combined organic layers were concentrated to give a dark red oil; upon addition of tert-butyl methyl ether (60 mL), a yellow solid precipitated that was collected via filtration, washed with tert-butyl methyl ether (2×30 mL) and dried in vacuo (15 mbar) at 35° C. to give the title compound (13.23 g, 29.5 mmol, 75% yield over two steps) as a light yellow solid. MS (ESI$^+$) m/z 449 [M+H]$^+$.

Example 25G: 5-(1-fluoro-3-hydroxy-7-methoxynaphthalen-2-yl)-1$\lambda^6$,2,5-thiadiazolidine-1,1,3-trione To a solution of the product of Example 25F (13.23 g, 29.5 mmol) in tetrahydrofuran (THF) (355 mL) at room temperature was added solid potassium tert-butoxide (3.31 g, 29.5 mmol), and the resulting solution was stirred at room temperature. After 10 minutes, the reaction was quenched with 1 M hydrochloric acid (90 mL) and diluted with ethyl acetate (400 mL). The layers were separated, and the aqueous layer was extracted with ethyl acetate (2×120 mL). The combined organic layers were washed with brine (3×50 mL), then dried over sodium sulfate, filtered and concentrated. The crude 5-[3-(benzyloxy)-1-fluoro-7-methoxynaphthalen-2-yl]-1λ$^6$,2,5-thiadiazolidine-1,1,3-trione was used in the subsequent reaction without further purification.

A mixture of crude intermediate, 5-[3-(benzyloxy)-1-fluoro-7-methoxynaphthalen-2-yl]-1λ$^6$,2,5-thiadiazolidine-1,1,3-trione (12.28 g, 29.5 mmol) and pentamethylbenzene (13.11 g, 88 mmol) in dichloromethane (147 mL) was cooled to an internal temperature of −76° C. under an atmosphere of dry nitrogen. Subsequently, a 1 M solution of boron trichloride (59.0 mL, 59.0 mmol) in CH$_2$Cl$_2$ was added dropwise over 15 minutes, so as not to raise the internal temperature past −72° C. Over the course of the addition, the reaction turned dark brown and became homogeneous. Incomplete conversion was observed, and additional boron trichloride (2×5.90 mL, 2×5.90 mmol) was added, resulting in full conversion. The reaction was quenched at −75° C. with CH$_2$Cl$_2$/methanol (10:1, 140 mL) via cannula transfer under nitrogen over 15 minutes, then slowly warmed to room temperature over 20 minutes under nitrogen. The volatiles were removed in vacuo to afford a brown/tan solid, which was collected by filtration, and slurried with heptanes (5×40 mL) and CH$_2$Cl$_2$ (3×40 mL). The crude solid was suspended in isopropanol (75 mL), warmed until the material dissolved, then allowed to cool slowly to room temperature over 1 hour. The solid was collected by filtration, washed with heptanes (2×30 mL), and dried in vacuo (15 mbar) at 60° C. to afford 5.11 g of a white solid. The mother liquor was concentrated, and the process was repeated to give an additional 1.96 g of a white solid. The batches were combined to obtain the title compound (7.07 g, 21.67 mmol, 73.5% yield over two steps). $^1$H NMR (CD$_3$OD) δ ppm 7.60 (dd, J=9.1, 1.5 Hz, 1H), 7.25 (d, J=2.6, 1H), 7.16 (dd, J=9.1, 2.6 Hz, 1H), 7.04 (s, 1H), 4.56 (s, 2H), 3.89 (s, 3H); MS (ESI$^-$) m/z 325 [M−H]$^-$.

Example 26: N-(2-{[8-fluoro-6-hydroxy-7-(1,1,4-trioxo-1λ$^6$,2,5-thiadiazolidin-2-yl)naphthalen-2-yl]amino}ethyl)cyclopropanesulfonamide (Compound 125)

In a 4 mL vial with a septum screw cap, the product of Example 1G (0.15 g, 0.322 mmol), sodium tert-butoxide (0.0.093 g, 0.967 mmol), BrettPhos Pd G3 precatalyst (8.77 mg, 9.67 µmol), and BrettPhos (5.19 mg, 9.67 µmol) were combined. The solids were placed under vacuum for 5 minutes with stirring, then the vial was filled with nitrogen, followed by 1,4-dioxane (3 mL) followed by tert-butyl (2-aminoethyl)carbamate (0.102 mL, 0.645 mmol). The resulting suspension was degassed by five vacuum/nitrogen backfills, stirred for 10 minutes at room temperature, and then heated to 100° C. After 30 minutes at 100° C., the reaction mixture was cooled to room temperature, then quenched with 1 M hydrochloric acid (1 mL) and diluted with ethyl acetate (2 mL). The aqueous layer was extracted with ethyl acetate (2×1 mL). The combined organic layers were washed with a 4:1 mixture of brine and 1 M hydrochloric acid (1 mL), dried over anhydrous sodium sulfate, then filtered and concentrated under reduced pressure to give tert-butyl (2-{[6-(benzyloxy)-8-fluoro-7-(1,1,4-trioxo-1λ$^6$,2,5-thiadiazolidin-2-yl)naphthalen-2-yl]amino}ethyl)carbamat which was used for the next reaction without purification. MS (APCI$^-$) m/z 543 [M−H]$^-$.

To a solution of crude tert-butyl (2-{[6-(benzyloxy)-8-fluoro-7-(1,1,4-trioxo-1λ$^6$,2,5-thiadiazolidin-2-yl)naphthalen-2-yl]amino}ethyl)carbamate in dioxane (0.875 mL) was added a solution of HCl in dioxane (0.35 mL, 1.4 mmol, 4 M), and the resulting solution was stirred for 2 hours at room temperature. The reaction mixture was diluted with tert-butyl methyl ether (1.75 mL), giving a suspension. The resulting solid was collected by filtration, washed with methyl tert-butyl methyl ether (2×0.875 mL) and dried to give a hygroscopic white solid that quickly became a brown tar on standing in the air. The 5-{7-[(2-aminoethyl)amino]-3-(benzyloxy)-1-fluoronaphthalen-2-yl}-1λ$^6$,2,5-thiadiazolidine-1,1,3-trione hydrochloric acid salt was used without further purification for the next reaction. MS (APCI$^+$) m/z 445 [M+H]$^+$.

To a suspension of crude 5-{7-[(2-aminoethyl)amino]-3-(benzyloxy)-1-fluoronaphthalen-2-yl}-1λ$^6$,2,5-thiadiazolidine-1,1,3-trione hydrochloric acid salt in dichloromethane (1.6 mL) was added 1,2,2,6,6-pentamethylpiperidine (0.235 mL, 1.288 mol). The resulting solution was stirred for 5 minutes at room temperature, and then was cooled to 0° C. To the cooled solution was added cyclopropanesulfonyl chloride (0.059 mL, 0.644 mmol) dropwise via syringe. The resulting solution was stirred for 30 minutes and then was quenched with water (2 mL). The layers were separated, and the aqueous layer was extracted with dichloromethane (3×1 mL). The combined organic layers were washed with 1 M sodium bisulfate (1 mL), and the second aqueous layer was back extracted with dichloromethane (2 mL). The combined organic layers were dried over anhydrous sodium sulfate, filtered and concentrated under reduced pressure to give N-(2-{[6-(benzyloxy)-8-fluoro-7-(1,1,4-trioxo-1λ$^6$,2,5-thiadiazolidin-2-yl)naphthalen-2-yl]amino}ethyl)cyclopropanesulfonamide which was used for the next reaction without purification. MS (APCI$^-$) m/z 547 [M−H]$^-$.

To a suspension of the crude N-(2-{[6-(benzyloxy)-8-fluoro-7-(1,1,4-trioxo-1λ$^6$,2,5-thiadiazolidin-2-yl)naphthalen-2-yl]amino}ethyl)cyclopropanesulfonamide in dichloromethane (3.5 mL) at −78° C. was added a solution of boron trichloride in dichloromethane (3.22 mL, 1 M, 3.22 mmol) slowly along the side of the flask so that the internal temperature remained below −70° C. The resulting solution was stirred for 5 minutes at −78° C., then the cooling bath was removed, and the reaction mixture was allowed to warm to an internal temperature of 10° C. before cooling back to −78° C. The reaction was quenched by addition of ethyl acetate (1 mL), followed by anhydrous ethanol (0.5 mL), and then warmed to room temperature and concentrated under reduced pressure giving a tan solid. The crude solid was suspended in heptanes (5 mL) and sonicated for 30 seconds giving a suspension. The solid was collected via filtration and washed with heptanes (2 mL). The solid was then dissolved in a dimethyl sulfoxide/methanol mixture and was filtered through a glass microfiber frit. The resulting solution was directly purified by preparative HPLC [Phenomenex® Luna® 10 µm C18(2) 250×30 mm column, flow rate 100 mL/minute, gradient of 5-60% methanol in buffer (0.010 M aqueous ammonium acetate)] to give the title compound (0.0475 g, 0.100 mmol, 47% yield). $^1$H NMR (400 MHz, DMSO-d$_6$) δ ppm 7.46 (dd, J=9.0, 1.6 Hz, 1H), 6.95 (dd, J=9.0, 2.4 Hz, 1H), 6.88 (d, J=10.3 Hz, 1H), 6.69 (d, J=2.3 Hz, 1H), 4.10 (s, 2H), 3.27-3.21 (m, 2H), 3.21-3.15 (m, 2H), 2.58-2.49 (m, 1H), 0.97-0.85 (m, 4H); MS (ESI$^-$) m/z 457 [M−H]$^-$.

Example 27: 5-(1-fluoro-3-hydroxy-7-{[1-(methanesulfonyl)pyrrolidin-3-yl]amino}naphthalen-2-yl)-1$\lambda^6$,2,5-thiadiazolidine-1,1,3-trione (Compound 126)

In a 4 mL vial with a septum screw cap, 3-amino-1-methanesulfonylpyrrolidine (0.71 g, 0.430 mmol), the product of Example 1G (0.1 g, 0.215 mmol), sodium tert-butoxide (0.062 g, 0.645 mmol), BrettPhos Pd G3 precatalyst (5.84 mg, 6.45 µmol), and BrettPhos (3.46 mg, 6.45 µmol) were combined. The solids were placed under vacuum for 5 minutes with stirring, and then the vial was filled with nitrogen followed by 1,4-dioxane (2 mL). The resulting suspension was degassed by five vacuum/nitrogen backfills, stirred for 10 minutes at room temperature, and then heated to 100° C. After 30 minutes at 100° C., the reaction mixture was cooled to room temperature, then quenched with 1 M hydrochloric acid (1 mL) and diluted with ethyl acetate (2 mL). The aqueous layer was extracted with ethyl acetate (2×1 mL). The combined organic layers were washed with a 4:1 mixture of brine and 1 M hydrochloric acid (1 mL), dried over anhydrous sodium sulfate, then filtered and concentrated under reduced pressure to give 5-[3-(benzyloxy)-1-fluoro-7-{[1-(methanesulfonyl)pyrrolidin-3-yl]amino}naphthalen-2-yl]-1$\lambda^6$,2,5-thiadiazolidine-1,1,3-trione which was used for the next reaction without purification. MS (APCI$^+$) m/z 549 [M+H]$^+$.

To a suspension of the crude 5-[3-(benzyloxy)-1-fluoro-7-{[1-(methanesulfonyl)pyrrolidin-3-yl]amino}naphthalen-2-yl]-1$\lambda^6$,2,5-thiadiazolidine-1,1,3-trione in dichloromethane (2.3 mL) at −78° C. was added a solution of boron trichloride in dichloromethane (2.15 mL, 1 M, 2.15 mmol) slowly along the side of the flask so that the internal temperature remained below −70° C. The resulting solution was stirred for 5 minutes at −78° C., then the cooling bath was removed, and the reaction mixture was allowed to warm to an internal temperature of 10° C., before cooling back to −78° C. The reaction was quenched by addition of ethyl acetate (1 mL), followed by anhydrous ethanol (0.5 mL), and then was warmed to room temperature, and concentrated under reduced pressure giving a tan solid. The crude solid was suspended in heptanes (5 mL), and then sonicated for 30 seconds giving a suspension. The solid was collected via filtration and washed with heptanes (2 mL). The solid was then dissolved in a dimethyl sulfoxide/methanol mixture and was filtered through a glass microfiber frit. The resulting solution was directly purified by preparative HPLC [Phenomenex® Luna® 10 µm C18(2) 250×30 mm column, flow rate 100 mL/minute, gradient of 5-60% methanol in buffer (0.010 M aqueous ammonium acetate)] to give the title compound (0.0475 g, 0.100 mmol, 47% yield). $^1$H NMR (400 MHz, DMSO-d$_6$) δ ppm 7.48 (d, J=8.8 Hz, 1H), 7.04-6.88 (m, 2H), 6.67 (d, J=2.4 Hz, 1H), 4.10 (s, 2H), 3.54 (dt, J=10.4, 5.2 Hz, 1H), 3.41 (dt, J=9.9, 7.3 Hz, 1H), 3.38-3.29 (m, 1H), 3.15 (dd, J=10.3, 3.7 Hz, 1H), 2.84 (s, 3H), 2.25 (dt, J=13.7, 6.8 Hz, 1H), 1.96-1.86 (m, 1H); MS (ESI$^-$) m/z 457 [M−H]$^-$.

Example 28: N-(2-{[8-fluoro-6-hydroxy-7-(1,1,4-trioxo-1$\lambda^6$,2,5-thiadiazolidin-2-yl)naphthalen-2-yl]oxy}ethyl)cyclopropanesulfonamide (Compound 127)

Example 28A: N-(2-bromoethyl)cyclopropanesulfonamide

A mixture of 2-bromoethanamine hydrobromide (266 mg, 1.3 mmol), cyclopropanesulfonyl chloride (192 mg, 1.365 mmol), and triethylamine (395 mg, 3.90 mmol) in dichloromethane (10 mL) was stirred at room temperature for 4 hours. The mixture was diluted with dichloromethane (60 mL), washed with water (20 mL) and brine (20 mL), dried over anhydrous Na$_2$SO$_4$ and concentrated under reduced pressure to give the title compound (200 mg 0.88 mmol, 67% yield) as an oil. $^1$H NMR (400 MHz, DMSO-d$_6$) δ ppm 3.56 (t, J=8 Hz, 2H), 3.55 (m, 2H), 2.62 (m, 1H), 1.01 (m, 4H).

Example 28B: N-(2-{[6-(benzyloxy)-8-fluoro-7-(1,1,4-trioxo-1$\lambda^6$,2,5-thiadiazolidin-2-yl)naphthalen-2-yl]oxy}ethyl)cyclopropanesulfonamide A mixture of the product of Example 1H (89 mg, 0.22 mmol), the product of Example 28A (151 mg, 0.660 mmol), and cesium carbonate (215 mg, 0.660 mmol) in N,N-dimethylformamide (1 mL) was stirred at 75° C. for 2 hours. The solution was filtered. The filtrate was purified by flash column chromatography on silica gel eluted with dichloromethane, then dichloromethane/methanol (10:1) to give the title compound (60 mg 0.11 mmol, 50% yield) as a solid. MS (ESI$^+$) m/z 550 [M+1]$^+$.

Example 28C: N-(2-{[8-fluoro-6-hydroxy-7-(1,1,4-trioxo-1$\lambda^6$,2,5-thiadiazolidin-2-yl)naphthalen-2-yl]oxy}ethyl)cyclopropanesulfonamide To the product of Example 28B (44 mg, 0.080 mmol) and 1,2,3,4,5-pentamethylbenzene (35.6 mg, 0.240 mmol) in dichloromethane (3 mL) at −78° C. was added trichloroborane (1201 µL, 1.201 mmol). The mixture was stirred at −78° C. for 10 minutes and then at 0° C. for 40 minutes. Ethanol (1 mL) was added at 0° C. The mixture was stirred for 20 minutes at room temperature, and then was concentrated under reduced pressure. The resulting solid was washed with heptane (5 mL×4), then dissolved in N,N-dimethylformamide (2.5 mL) and purified by preparative HPLC [YMC TriArt™ C18 Hybrid 20 m column, 25×150 mm, flow rate 80 mL/minute, 5-100% gradient of methanol in buffer (0.025 M aqueous ammonium bicarbonate, adjusted to pH 10 with ammonium hydroxide)] to give the title compound (10 mg, 0.022 mmol, 27% yield). $^1$H NMR (400 MHz, DMSO-d$_6$) δ ppm 9.50 (s, 1H), 7.69 (d, J=8 Hz, 1H), 7.20 (d, J=2 Hz, 1H), 7.16 (dd, J=8, 2 Hz, 1H), 7.04 (s, 1H), 4.15 (t, J=8 Hz, 2H), 4.11 (s, 2H), 3.41 (m, 2H), 2.63 (m, 1H), 0.94 (m, 4H); MS (ESI$^-$) m/z 458 [M−H]$^-$.

Example 29: 5-(1-fluoro-3-hydroxy-7-{[1-(methanesulfonyl)azetidin-3-yl]amino}naphthalen-2-yl)-1$\lambda^6$,2,5-thiadiazolidine-1,1,3-trione (Compound 128)

In a 4 mL vial with a septum screw cap, combined 3-amino-1-(methanesulfonyl)azetidine (0.065 g, 0.430 mmol), the product of Example 1G (0.1 g, 0.215 mmol), sodium tert-butoxide (0.062 g, 0.645 mmol), BrettPhos Pd G3 precatalyst (5.84 mg, 6.45 µmol), and BrettPhos (3.46 mg, 6.45 µmol). The solids were placed under vacuum for 5 minutes with stirring, then the vial was filled with nitrogen followed by 1,4-dioxane (2 mL). The resulting suspension was degassed by five vacuum/nitrogen backfills, stirred for 10 minutes at room temperature, and then was heated to 100° C. After 30 minutes at 100° C., the reaction mixture was cooled to room temperature, then quenched with 1 M hydrochloric acid (1 mL) and diluted with ethyl acetate (2 mL). The aqueous layer was extracted with ethyl acetate (2×1 mL). The combined organic layers were washed with a 4:1 mixture of brine and 1 M hydrochloric acid (1 mL), dried over anhydrous sodium sulfate, then filtered and concentrated under reduced pressure to give 5-[3-(benzyloxy)-1-fluoro-7-{[1-(methanesulfonyl)azetidin-3-yl]amino}naphthalen-2-yl]-1$\lambda^6$,2,5-thiadiazolidine-1,1,3-trione, which was used for the next reaction without purification. MS (APCI$^-$) m/z 533 [M–H]$^-$.

To a suspension of the crude intermediate, 5-[3-(benzyloxy)-1-fluoro-7-{[1-(methanesulfonyl)azetidin-3-yl]amino}naphthalen-2-yl]-1$\lambda^6$,2,5-thiadiazolidine-1,1,3-trione, in dichloromethane (2.3 mL) at –78° C. was added a solution of boron trichloride in dichloromethane (2.15 mL, 1 M, 2.15 mmol) slowly along the side of the flask so that the internal temperature remained below –70° C. The resulting solution was stirred for 5 minutes at –78° C., then the cooling bath was removed, and the reaction mixture was allowed to warm to an internal temperature of 10° C. before cooling back to –78° C. The reaction was quenched by addition of ethyl acetate (1 mL), followed by anhydrous ethanol (0.5 mL), and then warmed to room temperature, and concentrated under reduced pressure giving a tan solid. The crude solid was suspended in heptanes (5 mL) and sonicated for 30 seconds giving a suspension. The solid was collected via filtration and washed with heptanes (2 mL). The solid was dissolved in a dimethyl sulfoxide/methanol mixture and was filtered through a glass microfiber frit. The resulting solution was directly purified by preparative HPLC [Waters XBridge™ C18 5 μm OBD column, 30×100 mm, flow rate 40 mL/minute, a gradient of 3-30% methanol in buffer (0.025 M aqueous ammonium bicarbonate, adjusted to pH 10 with ammonium hydroxide)] to give the title compound (0.0357 g, 0.077 mmol, 36% yield). $^1$H NMR (400 MHz, DMSO-d$_6$) δ ppm 7.51 (dd, J=9.0, 1.5 Hz, 1H), 6.96 (dd, J=8.9, 2.3 Hz, 1H), 6.91 (s, 1H), 6.57 (d, J=2.4 Hz, 1H), 4.32 (dq, J=7.8, 5.8 Hz, 2H), 4.23 (t, J=7.7 Hz, 3H), 4.09 (s, 2H), 3.00 (s, 3H); MS (ESI$^-$) m/z 443 [M–H]$^-$.

Example 30: 4-{[8-fluoro-6-hydroxy-7-(1,1,4-trioxo-1$\lambda^6$,2,5-thiadiazolidin-2-yl)naphthalen-2-yl]oxy}butanenitrile (Compound 129)

A mixture of the product of Example 1H (86 mg, 0.214 mmol), cesium carbonate (139 mg, 0.427 mmol) and 4-bromobutyronitrile (47.4 mg, 0.321 mmol) in N,N-dimethylformamide (1 mL) was stirred at ambient temperature for 2 hours. In a separate vial, a mixture of the product of Example 1H (86 mg, 0.214 mmol), cesium carbonate (139 mg, 0.427 mmol) and 4-bromobutyronitrile (47.4 mg, 0.321 mmol) in dioxane:N,N-dimethylformamide (2:1, 1.5 mL) was stirred at ambient temperature for 2 hours. The reaction mixtures of the reactions were combined, diluted with ethyl acetate, washed with water, brine, dried over anhydrous Na$_2$SO$_4$ and concentrated under reduced pressure to give 4-{[6-(benzyloxy)-8-fluoro-7-(1,1,4-trioxo-1$\lambda^6$,2,5-thiadiazolidin-2-yl)naphthalen-2-yl]oxy}butanenitrile which was used in the next step without purification. MS (APCI$^-$) m/z 468 (M–H)$^-$ To a mixture of the above intermediate, 4-{[6-(benzyloxy)-8-fluoro-7-(1,1,4-trioxo-1$\lambda^6$,2,5-thiadiazolidin-2-yl)naphthalen-2-yl]oxy}butanenitrile (200 mg, 0.426 mmol), and pentamethylbenzene (316 mg, 2.130 mmol) in dichloromethane (3 mL) at –78° C., was added a solution of boron trichloride (2.56 mL, 2.56 mmol) in dichloromethane dropwise over 5 minutes. After 30 minutes, the reaction was quenched with 2 N HCl (0.5 mL) and extracted with ethyl acetate. The organic fraction was washed with brine, dried over anhydrous Na$_2$SO$_4$ and concentrated under reduced pressure. The crude product was triturated with dichloromethane to give the title compound (90 mg, 0.237 mmol, 56%). $^1$H NMR (501 MHz, DMSO-d$_6$) δ ppm 10.35 (s, 1H), 7.73 (d, J=9.0 Hz, 1H), 7.26-7.17 (m, 2H), 7.08 (s, 1H), 4.49 (s, 2H), 4.15 (t, J=6.1 Hz, 2H), 2.69 (t, J=7.2 Hz, 2H), 2.08 (p, J=6.6 Hz, 2H). MS (APCI$^-$) m/z 378 [M–H]$^-$.

Example 31: [1-({[8-fluoro-6-hydroxy-7-(1,1,4-trioxo-1$\lambda^6$,2,5-thiadiazolidin-2-yl)naphthalen-2-yl]oxy}methyl)cyclopropyl]acetonitrile (Compound 130)

A mixture of the product of Example 1H (150 mg, 0.373 mmol), cesium carbonate (243 mg, 0.746 mmol) and 2-(1-(bromomethyl)cyclopropyl)acetonitrile (97 mg, 0.559 mmol) in N,N-dimethylformamide (1.5 mL) was stirred at ambient temperature for 2 hours. The reaction mixture was then partitioned between ethyl acetate (60 mL) and water (15 mL) with 1.5 mL 2 N HCl. The ethyl acetate fraction was separated, washed with water and brine, dried over anhydrous Na$_2$SO$_4$ and concentrated under reduced pressure to give [1-({[6-(benzyloxy)-8-fluoro-7-(1,1,4-trioxo-1$\lambda^6$,2,5-thiadiazolidin-2-yl)naphthalen-2-yl]oxy}methyl)cyclopropyl]acetonitrile, which was used in the next step without purification. MS (APCI$^-$) m/z 494 [M–H]$^-$.

To a mixture of the above intermediate [1-({[6-(benzyloxy)-8-fluoro-7-(1,1,4-trioxo-1$\lambda^6$,2,5-thiadiazolidin-2-yl)naphthalen-2-yl]oxy}methyl)cyclopropyl]acetonitrile (185 mg, 0.373 mmol) and pentamethylbenzene (277 mg, 1.867 mmol) in dichloromethane (3 mL) at –78° C. was added a solution of boron trichloride (2.24 mL, 2.240 mmol) in dichloromethane dropwise over 5 minutes. After 30 minutes, the reaction was quenched with 2 mL of 0.5 N HCl and extracted with ethyl acetate. The organic fraction was washed with brine, dried over anhydrous Na$_2$SO$_4$ and concentrated under reduced pressure. The residue was triturated with dichloromethane to give the title compound (85 mg, 0.210 mmol, 56% yield). $^1$H NMR (501 MHz, DMSO-d$_6$) δ ppm 10.28 (s, 1H), 7.75-7.70 (m, 1H), 7.22 (m, 2H), 7.07 (s, 1H), 4.45 (s, 2H), 4.00 (s, 2H), 2.80 (s, 2H), 0.77-0.70 (m, 2H), 0.72-0.65 (m, 2H); MS (APCI$^-$) m/z 404 [M–H]$^-$.

Example 32: 5-{7-[2-(dimethylamino)ethoxy]-1-fluoro-3-hydroxynaphthalen-2-yl}-1$\lambda^6$,2,5-thiadiazolidine-1,1,3-trione (Compound 131)

Example 32A: 2-(dimethylamino)ethyl methanesulfonate

To the solution of 2-(dimethylamino)ethanol (500 mg, 5.61 mmol) in dichloromethane (25 mL) at 0° C. was added methanesulfonyl chloride (0.523 mL, 6.73 mmol) and triethylamine (1.01 mL, 7.85 mmol). The reaction mixture was stirred 10 minutes at 0° C. and 1 hour at room temperature. Water (5 mL) was then added, and the mixture was extracted with dichloromethane. The organic layers were collected and washed with brine (2 mL) and dried over anhydrous Na$_2$SO$_4$. The volatiles were carefully removed under reduced pressure (bath temperature maintained ~25° C.) to afford the crude title compound which was subjected to the next reaction without purification.

Example 32B: 5-{3-(benzyloxy)-7-[2-(dimethylamino)ethoxy]-1-fluoronaphthalen-2-yl}-1$\lambda^6$,2,5-thiadiazolidine-1,1,3-trione To the product of Example 1H (150 mg, 0.373 mmol) in N,N-dimethylformamide (3 mL) was added sodium hydride (60% dispersed in mineral oil, 32.8 mg, 0.820 mmol) at room temperature in three portions. The reaction was stirred for 30 minutes until no gas evolution was observed. A solution of freshly prepared product of Example 32A (137 mg, 0.820 mmol) in N,N-dimethylformamide (2 mL) was slowly added to the reaction mixture. The reaction was stirred overnight at room temperature. Methanol (1 mL) was added, the volatiles were removed under reduced pressure, and the residue was purified by preparative HPLC [Phenomenex® Luna® C18(2) 5 μm 100 Å AXIA™ column (250 mm×25 mm). 30-100% gradient of acetonitrile (A) and 0.1% ammonium acetate in water (B) over 15 minutes, at a flow rate of 25 mL/minute] to afford the title compound (91 mg, 0.192 mmol, 52% yield) as a white solid. $^1$H NMR (400 MHz, DMSO-$d_6$) δ ppm 9.55 (s, 1H), 7.81 (dd, J=9.1, 1.5 Hz, 1H), 7.60-7.53 (m, 2H), 7.41-7.33 (m, 3H), 7.37-7.27 (m, 2H), 7.26 (dd, J=9.0, 2.5 Hz, 1H), 5.23 (s, 2H), 4.46 (t, J=5.0 Hz, 2H), 4.09 (s, 2H), 3.55 (t, J=5.0 Hz, 2H), 2.87 (s, 6H); MS (APCI$^-$) m/z 472 [M–H]$^-$.

Example 32C: 5-{7-[2-(dimethylamino)ethoxy]-1-fluoro-3-hydroxynaphthalen-2-yl}-1λ$^6$,2,5-thiadiazolidine-1,1,3-trione The product of Example 32B (88 mg, 0.186 mmol) and 1,2,3,4,5-pentamethylbenzene (83 mg, 0.558 mmol) in a 50 mL round bottom flask was flushed with nitrogen for 5 minutes. Dichloromethane (5 mL) was then added, and the heterogeneous suspension was cooled to –78° C. and equilibrated for 5 minutes. Subsequently, a 1 M solution of trichloroborane (0.56 mL, 0.558 mmol) in dichloromethane was added dropwise over 5 minutes. After 20 minutes, the reaction was quenched at –78° C. with dichloromethane:ethanol=9:1 (1 mL) and then slowly warmed to room temperature. The volatiles were removed under reduced pressure, and the residue was purified by preparative HPLC [Phenomenex® Luna® C18(2) 5 μm 100 Å AXIA™ column (250 mm×25 mm); 30-100% gradient of acetonitrile (A) and 0.1% ammonium acetate in water (B) over 15 minutes, at a flow rate of 25 mL/minute] to give the title compound (30 mg, 0.078 mmol, 42% yield) as a white solid. $^1$H NMR (501 MHz, DMSO-$d_6$) δ ppm 9.53 (s, 1H), 7.71 (dd, J=9.0, 1.4 Hz, 1H), 7.28 (d, J=2.6 Hz, 1H), 7.18 (dd, J=9.0, 2.6 Hz, 1H), 7.05 (s, 1H), 4.38 (t, J=5.2 Hz, 2H), 4.10 (s, 2H), 2.75 (s, 6H); MS (APCI) m/z 382 [M–H]$^-$.

Example 33: 5-{7-[1-(cyclopropylmethyl)-1H-pyrazol-4-yl]-1-fluoro-3-hydroxynaphthalen-2-yl}-1λ$^6$,2,5-thiadiazolidine-1,1,3-trione (Compound 132)

Example 33A: 5-{3-(benzyloxy)-7-[1-(cyclopropylmethyl)-1H-pyrazol-4-yl]-1-fluoronaphthalen-2-yl}-1λ$^6$,2,5-thiadiazolidine-1,1,3-trione To the product of Example 1G (100 mg, 0.215 mmol) in dioxane (5 mL) was added 1-(cyclopropylmethyl)-4-(4,4,5,5-tetramethyl-1,3,2-dioxaborolan-2-yl)-1H-pyrazole (80 mg, 0.322 mmol) and sodium carbonate (0.322 mL, 0.645 mmol). Tetrakis(triphenylphosphine)palladium(0) (24.8 mg, 0.021 mmol) was added, and the reaction mixture was sparged with N$_2$ for 5 minutes. The mixture was heated at 100° C. overnight. The reaction was cooled to room temperature, and the volatiles were removed under reduced pressure. The residue was purified by column chromatography (SiO$_2$, dry loading, 5% methanol in dichloromethane) to afford the title compound (68 mg, 0.134 mmol, 63% yield) as a yellow solid. MS (APCI$^-$) m/z 505 [M–H]$^-$.

Example 33B: 5-{7-[1-(cyclopropylmethyl)-H-pyrazol-4-yl]-1-fluoro-3-hydroxynaphthalen-2-yl}-1λ$^6$,2,5-thiadiazolidine-1,1,3-trione The product of Example 33A (50 mg, 0.099 mmol) and 1,2,3,4,5-pentamethylbenzene (43.9 mg, 0.296 mmol) in a 50 mL round bottom flask was flushed with nitrogen for 5 minutes. Dichloromethane (5 mL) was then added, and the heterogeneous suspension was cooled to –78° C. and equilibrated for 5 minutes. Subsequently, a 1 M solution of trichloroborane (0.296 mL, 0.296 mmol) in dichloromethane was added dropwise over 5 minutes. After 20 minutes, the reaction was quenched at –78° C. with dichloromethane:ethanol=9:1 (1 mL) and then slowly warmed to room temperature. The volatiles were removed under reduced pressure, and the residue was purified by preparative HPLC [Phenomenex® Luna® C18(2) 5 μm 100 Å AXIA™ column (250 mm×25 mm) 30-100% gradient of acetonitrile (A) and 0.1% ammonium acetate in water (B) over 15 minutes, at a flow rate of 25 mL/minute] to afford the title compound (18 mg, 0.043 mmol, 44% yield) as a white solid. $^1$H NMR (501 MHz, DMSO-$d_6$) δ ppm 9.71 (s, 1H), 8.34 (s, 1H), 8.00 (d, J=10.7 Hz, 2H), 7.73 (s, 2H), 7.05 (s, 1H), 4.11 (s, 2H), 4.00 (d, J=7.1 Hz, 2H), 1.29 (tt, J=7.6, 4.8 Hz, 1H), 0.60-0.51 (m, 2H), 0.44-0.38 (m, 2H); MS (APCI$^-$) m/z 415 [M–H]$^-$.

Example 34: 5-{1-fluoro-3-hydroxy-7-[(1H-pyrazol-4-yl)methoxy]naphthalen-2-yl}-1λ$^6$,2,5-thiadiazolidine-1,1,3-trione (Compound 133)

Example 34A: tert-butyl 4-(((methylsulfonyl)oxy)methyl)-H-pyrazole-1-carboxylate Methanesulfonyl chloride (202 mg, 1.760 mmol) in dichloromethane (1 mL) was added dropwise to a stirred cold (0° C.) solution of tert-butyl 4-(hydroxymethyl)-1H-pyrazole-1-carboxylate (317 mg, 1.6 mmol) and triethylamine (324 mg, 3.20 mmol) in dichloromethane (6 mL). The reaction mixture was allowed to warm to ambient temperature and maintained at ambient temperature for 30 minutes. The reaction mixture was diluted with ethyl acetate (30 mL) and quenched with 0.2 N HCl aqueous solution (10 mL). The organic layer was separated and washed with brine (10 mL), dried over sodium sulfate, filtered and concentrated to give the title compound (415 mg, 1.502 mmol, 94% yield). $^1$H NMR (500 MHz, DMSO-$d_6$) δ ppm 8.44 (s, 1H), 7.91 (s, 1H), 5.21 (s, 2H), 2.32 (s, 3H), 1.58 (s, 9H).

Example 34B: tert-butyl 4-({[6-(benzyloxy)-8-fluoro-7-(1,1,4-trioxo-1λ$^6$,2,5-thiadiazolidin-2-yl)naphthalen-2-yl]oxy}methyl)-1H-pyrazole-1-carboxylate A mixture of Example 1H (150 mg, 0.373 mmol), Example 34A (206 mg, 0.746 mmol), and cesium carbonate (202 mg, 0.621 mmol) in N,N-dimethylformamide (1 mL) was stirred at 70° C. for 40 minutes. The mixture was cooled to ambient temperature and diluted with ethyl acetate (50 mL). The organic phase was washed with 0.2 N HCl aqueous solution (10 mL) and brine (10 mL), dried over sodium sulfate, filtered and concentrated to give the title compound (215 mg, 0.369 mmol, 99% yield). MS (ESI$^-$) m/z 581 (M–H)$^-$.

Example 34C: 5-{t-fluoro-3-hydroxy-7-[(1H-pyrazol-4-yl)methoxy]naphthalen-2-yl}-1λ⁶,2,5-thiadiazolidine-1,1,3-trione To a mixture of 1,2,3,4,5-pentamethylbenzene (115 mg, 0.772 mmol) and Example 34B (150 mg, 0.257 mmol) in dichloromethane (3 mL) at −78° C. was added trichloroborane (2.832 mL, 2.83 mmol, 1 M in dichloromethane). The mixture was stirred at −78° C. for 10 minutes, then at −20° C. for 30 minutes. The mixture was quenched with ethanol (6 mL) and concentrated. The residue was washed with heptane (4×4 mL) and dichloromethane (6×3 mL) and concentrated to give the crude product. The crude product was dissolved in N,N-dimethylformamide (3 mL), filtered through a glass microfiber frit and purified by preparative HPLC [YMC TriArt™ C18 Hybrid 5 μm column, 50×100 mm, flow rate 140 mL/minute, 5-55% gradient of acetonitrile in buffer (0.025 M aqueous ammonium bicarbonate, adjusted to pH 10 with ammonium hydroxide)] to give the title compound (34 mg, 0.087 mmol, 33.7% yield). $^1$H NMR (500 MHz, DMSO-$d_6$) δ ppm 12.85 (br s, 1H), 7.87 (br s, 1H), 7.66 (dd, J=8, 2 Hz, 1H), 7.60 (br s, 1H), 7.29 (d, J=2 Hz, 1H), 7.13 (dd, J=8, 2 Hz, 1H), 7.02 (s, 1H), 5.08 (s, 2H), 4.11 (m, 1H), 4.09 (s, 2H); MS (ESI$^-$) m/z 391 (M−H)$^-$.

Example 35: 5-[1-fluoro-3-hydroxy-7-(2-methylpropoxy)naphthalen-2-yl]-1λ⁶,2,5-thiadiazolidine-1,1,3-trione (Compound 134)

Example 35A: 5-[3-(benzyloxy)-1-fluoro-7-(2-methylpropoxy)naphthalen-2-yl]-1λ⁶,2,5-thiadiazolidine-1,1,3-trione 1-Iodo-2-methylpropane (0.09 mL, 0.77 mmol, 1.6 equivalents) was added to a suspension of cesium carbonate (362 mg, 1.11 mmol, 2.2 equivalents) and the product of Example 1H (201 mg, 0.5 mmol, 1 equivalent) in N,N-dimethylformamide (1.0 mL) at 23° C. The reaction vessel (4 mL vial) was sealed, and the sealed vessel was placed in a heating block that had been preheated to 60° C. The reaction mixture was stirred for 2 hours at 60° C. The reaction mixture was cooled to 23° C. over 5 minutes. Additional 1-iodo-2-methylpropane (0.09 mL, 0.77 mmol, 1.6 equivalents) was added at 23° C. The reaction vessel was sealed, and the sealed vessel was placed in a heating block that had been preheated to 100° C. The reaction mixture was stirred for 3 hours at 100° C. The reaction mixture was cooled to 23° C. over 5 minutes. Additional 1-iodo-2-methylpropane (0.09 mL, 0.77 mmol, 1.6 equivalents) was added at 23° C. The reaction vessel was sealed, and the sealed vessel was placed in a heating block that had been preheated to 100° C. The reaction mixture was stirred for 1 hour at 100° C. The product mixture was cooled to 23° C. over 15 minutes. The cooled mixture was diluted with water (0.5 mL) and dimethyl sulfoxide (5.0 mL). The diluted mixture was purified by reverse-phase flash-column chromatography (100 g RediSep® Gold $C_{18}$ column, eluted with a gradient from 10-100% [v/v] methanol-0.025 M aqueous ammonium bicarbonate solution [acidified with solid carbon dioxide] over 10 column volumes, then isocratic elution with 100% methanol for 3 column volumes, flow rate=60 mL/minute) to furnish the title compound as a yellow solid (59.0 mg, 25%). $^1$H NMR (400 MHz, DMSO-$d_6$) δ ppm 7.77 (dd, J=9.6, 4.0 Hz, 1H), 7.49-7.32 (m, 6H), 7.23-7.17 (m, 2H), 5.17 (d, J=17.4 Hz, 2H), 7.73 (s, 1H), 4.66 (s, 1H), 3.93 (d, J=6.7 Hz, 1H), 3.27 (d, J=7.6 Hz, 1H), 1.88 (dq, J=13.4, 6.7 Hz, 1H), 0.86 (d, J=6.7 Hz, 2H), 0.79 (d, J=6.7 Hz, 2H); MS (APCI$^+$) m/z 459 [M+H]$^+$.

Example 35B: 5-[1-fluoro-3-hydroxy-7-(2-methylpropoxy)naphthalen-2-yl]-1λ⁶,2,5-thiadiazolidine-1,1,3-trione A solution of boron trichloride in dichloromethane (1.0 M, 0.80 mL, 0.80 mmol, 6.2 equivalents) was added to a suspension of the product of Example 35A (59.0 mg, 0.13 mmol, 1 equivalent) in dichloromethane (1.5 mL) at −78° C. The reaction mixture was stirred for 10 minutes at −78° C. (dry-ice/acetone bath). The reaction vessel was then transferred to an ice bath. The reaction mixture was stirred for 10 minutes at 0° C. The reaction vessel was then returned to the dry-ice/acetone bath. The reaction mixture was stirred for 5 minutes at −78° C. The product mixture was then diluted slowly with ethanol (2.0 mL) at −78° C. The diluted mixture was warmed to 23° C. and the warmed mixture was concentrated. The residue obtained was triturated with heptanes (5 mL). The residue obtained was dissolved in 10% acetone-dichloromethane (2.0 mL), and the solution was diluted with heptanes (10.0 mL). A precipitate formed, and the mother liquor was decanted. The residue obtained was triturated with heptanes (1.0 mL) to furnish the title compound (10.2 mg, 22%). $^1$H NMR (400 MHz, DMSO-$d_6$) δ ppm 7.65 (dd, J=11.9, 9.2 Hz, 1H), 7.14-7.09 (m, 2H), 7.03 (d, J=13.4 Hz, 1H), 4.80 (s, 1H), 4.63 (s, 1H), 4.26 (d, J=6.6 Hz, 1H), 3.43 (d, J=7.6 Hz, 1H), 2.13-2.04 (m, 1H), 0.99 (d, J=6.7 Hz, 3H), 0.94 (d, J=6.7 Hz, 3H); MS (APCI$^+$) m/z 369 [M+H]$^+$.

Example 36: 5-[1-fluoro-3-hydroxy-7-(2-hydroxypropoxy)naphthalen-2-yl]-1λ⁶,2,5-thiadiazolidine-1,1,3-trione (Compound 135)

Example 36A: 5-[3-(benzyloxy)-1-fluoro-7-(2-hydroxypropoxy)naphthalen-2-yl]-1λ⁶,2,5-thiadiazolidine-1,1,3-trione To a solution of Example 1H (120 mg, 0.298 mmol) in N,N-dimethylformamide (2 mL), was added cesium carbonate (214 mg, 0.656 mmol) and 1-bromo-2-propanol (41.4 mg, 0.298 mmol). The mixture was heated to 80° C. overnight. After cooling, the mixture was filtered by passing through diatomaceous earth, the volatiles were removed under reduced pressure, and the residue was subjected to preparative HPLC [Phenomenex® Luna® C18(2) 5 μm 100 Å AXIA™ column (250 mm×25 mm). 30-100% gradient of acetonitrile (A) and 0.1% trifluoroacetic acid in water (B) over 15 minutes, at a flow rate of 25 mL/minute] to give the title compound (30 mg, 0.065 mmol, 22% yield). MS (APCI$^-$) m/z 459 [M−H]$^-$.

Example 36B: 5-[l-fluoro-3-hydroxy-7-(2-hydroxypropoxy)naphthalen-2-yl]-1λ⁶,2,5-thiadiazolidine-1,1,3-trione The product of Example 36A (30 mg, 0.065 mmol) and tetrahydrofuran (3 mL) were added to 10% Pd (OH)$_2$/C (wet, 60 mg, 0.214 mmol) in a 20 mL Barnstead Hast C reactor with glass liner, and the mixture was stirred at 25° C. for 21.1 hours under 113 psi of hydrogen. The mixture was filtered through a pad of diatomaceous earth, the volatiles were removed under reduced pressure, and the residue was subjected to preparative HPLC [Phenomenex® Luna® C18 (2) 5 μm 100 Å AXIA™ column (250 mm×25 mm). 30-100% gradient of acetonitrile (A) and 0.1% trifluoroacetic acid in water (B) over 15 minutes, at a flow rate of 25 mL/minute] to give the title compound (6 mg, 0.016 mmol, 25% yield). $^1$H NMR (400 MHz, DMSO-d$_6$) δ ppm 10.31 (s, 1H), 7.75-7.68 (m, 1H), 7.27-7.18 (m, 1H), 7.19 (s, 1H), 7.07 (s, 1H), 4.48 (s, 2H), 4.00 (p, J=5.9 Hz, 1H), 3.99-3.86 (m, 2H), 1.19 (d, J=6.3 Hz, 3H); MS (APCI$^-$) m/z 369 [M−H]$^-$.

Example 37: N-(cyclopropylmethyl)-8-fluoro-6-hydroxy-7-(1,1,4-trioxo-1λ$^6$,2,5-thiadiazolidin-2-yl)naphthalene-2-carboxamide (Compound 136)

Example 37A: methyl 6-(benzyloxy)-8-fluoro-7-(1,1,4-trioxo-1λ$^6$, 2,5-thiadiazolidin-2-yl)naphthalene-2-carboxylate To a mixture of Example 1G (2.5 g, 5.37 mmol), [1,1'-bis(diphenylphosphino)ferrocene]dichloropalladium(II) (0.079 g, 0.107 mmol) in a 50 mL stainless steel pressure reactor were added methanol (25 mL) and triethylamine (1.498 mL, 10.75 mmol). The reactor was degassed with nitrogen gas several times followed by refilling with carbon monoxide gas to 60 psi. The mixture was heated to 80° C. and stirred for 10 hours under 60 psi of carbon monoxide. The mixture was filtered, and the filtrate was concentrated under reduced pressure, and the residue was subjected to column chromatography (SiO$_2$, 5% methanol in dichloromethane) to afford the title compound (1.5 g, 3.38 mmol, 63% yield). $^1$H NMR (400 MHz, DMSO-d$_6$) δ ppm 8.97 (s, 3H), 8.55 (d, J=1.6 Hz, 1H), 8.05-7.91 (m, 2H), 7.60-7.55 (m, 2H), 7.47 (s, 1H), 7.42-7.28 (m, 3H), 5.31 (s, 2H), 4.10 (s, 2H), 3.92 (s, 3H); MS (APCI$^-$) m/z 443 [M−H]$^-$.

Example 37B: 6-(benzyloxy)-8-fluoro-7-(1,1,4-trioxo-1λ$^6$,2,5-thiadiazolidin-2-yl)naphthalene-2-carboxylic acid To the solution of Example 37A (200 mg, 0.450 mmol) in methanol (1 mL), tetrahydrofuran (1 mL) and water (1 mL) was added LiOH (32.3 mg, 1.350 mmol) at ambient temperature, and the mixture was stirred overnight at ambient temperature. The pH of the reaction mixture was adjusted to neutral by addition of HCl (2 N). The mixture was extracted with ethyl acetate (3×3 mL), volatiles were removed under reduced pressure and the residue was subjected to preparative HPLC [Phenomenex® Luna® C18(2) 5 µm 100 Å AXIA™ column (250 mm×25 mm). 30-100% gradient of acetonitrile (A) and 0.1% trifluoroacetic acid in water (B) over 15 minutes, at a flow rate of 25 mL/minute] to afford the title compound (150 mg, 0.349 mmol, 77% yield). MS (APCI$^-$) m/z 429 [M−H]$^-$.

Example 37C: N-(cyclopropylmethyl)-8-fluoro-6-hydroxy-7-(1,1,4-trioxo-1λ$^6$,2,5-thiadiazolidin-2-yl)naphthalene-2-carboxamide To a solution of Example 37B (150 mg, 0.349 mmol) in N,N-dimethylformamide (2 mL) was added cyclopropylmethanamine (49.6 mg, 0.697 mmol), (1-[bis(dimethylamino)methylene]-1H-1,2,3-triazolo[4,5-b]pyridinium 3-oxid hexafluorophosphate (139 mg, 0.366 mmol), and triethylamine (106 mg, 1.046 mmol) and the mixture was stirred at 60° C. overnight. After cooling, water (10 mL) was added and the mixture was extracted with ethyl acetate (3×5 mL). The organic layers were combined, dried over sodium sulfate, and concentrated under reduced pressure to give 6-(benzyloxy)-N-(cyclopropylmethyl)-8-fluoro-7-(1,1,4-trioxo-1λ$^6$,2,5-thiadiazolidin-2-yl)naphthalene-2-carboxamide that was subjected to the next step without purification. MS (APCI$^-$) m/z 482 [M−H]$^-$.

The 6-(benzyloxy)-N-(cyclopropylmethyl)-8-fluoro-7-(1,1,4-trioxo-1λ$^6$,2,5-thiadiazolidin-2-yl)naphthalene-2-carboxamide and tetrahydrofuran (2 mL) were added to 5% Pd/C (120 mg, 0.525 mmol) in a 20 mL Barnstead reactor with a glass liner. The mixture was stirred at 25° C. for 18 hours under 50 psi of hydrogen. The mixture was filtered, volatiles were removed under reduced pressure, and the residue was subjected to preparative HPLC [Phenomenex® Luna® C18(2) 5 µm 100 Å AXIA™ column (250 mm×25 mm). 30-100% gradient of acetonitrile (A) and 0.1% trifluoroacetic acid in water (B) over 15 minutes, at a flow rate of 25 mL/minute] to give the title compound (46 mg, 0.117 mmol, 47% yield over two steps). $^1$H NMR (500 MHz, DMSO-d$_6$) δ ppm 10.96 (s, 1H), 8.78 (t, J=5.7 Hz, 1H), 8.49 (d, J=1.8 Hz, 1H), 7.96 (dd, J=8.7, 1.8 Hz, 1H), 7.85 (dd, J=8.8, 1.4 Hz, 1H), 7.16 (s, 1H), 4.52 (s, 2H), 3.19 (dd, J=6.8, 5.7 Hz, 2H), 1.12-1.01 (m, 1H), 0.49-0.40 (m, 2H), 0.29-0.22 (m, 2H); MS (APCI$^-$) m/z 392 [M−H]$^-$.

Example 38: 5-[1-fluoro-3-hydroxy-7-(2-{[2-(trifluoromethoxy)ethyl]amino}ethoxy)naphthalen-2-yl]-1λ$^6$,2,5-thiadiazolidine-1,1,3-trione (Compound 137)

The title compound was prepared using the methodologies described in Example 46 substituting 2-(trifluoromethoxy)ethanamine for propan-2-amine. $^1$H NMR (500 MHz, DMSO-d$_6$) δ ppm 9.56 (s, 1H), 8.71 (br s, 2H), 7.73 (d, J=8, Hz, 1H), 7.26 (d, J=2, Hz, 1H), 7.20 (dd, J=8, 2 Hz, 1H), 7.05 (s, 1H), 4.37 (m, 4H), 4.11 (t, J=6 Hz, 2H), 4.10 (s, 2H), 3.42 (m, 2H); MS (ESI$^-$) m/z 466 (M−H)$^-$.

Example 39: 5-(1-fluoro-3-hydroxy-7-{2-[(2-methoxyethyl)amino]ethoxy}naphthalen-2-yl)-1λ$^6$,2,5-thiadiazolidine-1,1,3-trione (Compound 138)

The title compound was prepared using the methodologies described in Example 46 substituting 2-methoxyethanamine for propan-2-amine. $^1$H NMR (500 MHz, DMSO-d$_6$) δ ppm 9.51 (s, 1H), 8.25 (br s, 2H), 7.72 (d, J=8, Hz, 1H), 7.25 (d, J=2, Hz, 1H), 7.19 (dd, J=8, 2 Hz, 1H), 7.05 (s, 1H), 4.32 (t, J=6 Hz, 2H), 4.09 (s, 2H), 3.59 (t, J=6 Hz, 2H), 3.35 (m, 2H), 3.29 (s, 3H), 3.17 (m, 2H); MS (ESI$^-$) m/z 412 (M−H); MS (ESI$^-$) m/z 366 (M−H)$^-$.

Example 40: 5-{1-fluoro-3-hydroxy-7-[3-(methylamino)propyl]naphthalen-2-yl}-1λ$^6$,2,5-thiadiazolidine-1,1,3-trione (Compound 139)

The title compound was prepared using the methodologies described in Example 41 substituting methanamine for ethanamine. $^1$H NMR (500 MHz, DMSO-d$_6$) δ ppm 10.44 (s, 1H), 8.51 (br s, 2H), 7.74 (d, J=8, Hz, 1H), 7.73 (d, J=2, Hz, 1H), 7.40 (dd, J=8, 2 Hz, 1H), 7.10 (s, 1H), 4.42 (s, 2H), 2.87 (m, 2H), 2.81 (t, J=7, Hz, 2H), 2.54 (m, 3H), 1.96 (m, 2H).

Example 41: 5-{7-[3-(ethylamino)propyl]-1-fluoro-3-hydroxynaphthalen-2-yl}-1λ$^6$,2,5-thiadiazolidine-1,1,3-trione (Compound 140)

Example 41A: 3-[6-(benzyloxy)-8-fluoro-7-(1,1,4-trioxo-1λ$^6$,2,5-thiadiazolidin-2-yl)naphthalen-2-yl]propanal A mixture of Example 1G (0.60 g, 1.290 mmol), 2-(di-tert-butylphosphino)biphenyl (0.058 g, 0.193 mmol), palladium(II) acetate (0.043 g, 0.193 mmol), prop-2-en-1-ol (0.225 g, 3.87 mmol) and triethylamine (0.261 g, 2.58 mmol) in N,N-dimethylformamide (4 mL) was placed under nitrogen and heated to 120° C. for 1.5 hours. The mixture was cooled to ambient temperature and diluted with ethyl acetate (60 mL). The organic phase was washed with 0.5 N HCl aqueous solution (10 mL) and brine (10 mL×3), dried over sodium sulfate, filtered and concentrated to give the title compound (520 mg, 1.175 mmol, 92% yield). MS (ESI$^-$) m/z 441 (M–H)$^-$.

Example 41B: 5-{3-(benzyloxy)-7-[3-(ethylamino) propyl]-1-fluoronaphthalen-2-yl}-1$\lambda^6$,2,5-thiadiazolidine-1,1,3-trione A mixture of Example 41A (100 mg, 0.226 mmol), triethylamine (114 mg, 1.130 mmol), ethanamine (0.339 mL, 0.678 mmol) and sodium triacetoxyborohydride (192 mg, 0.904 mmol) in acetonitrile/methanol (4:1, 3 mL) was stirred at ambient temperature for 18 hours. Then methanol/water (1:2, 2 mL) was added. The solution was filtered, and the filtrate was purified by preparative HPLC [YMC Tri-Art™ C18 Hybrid 5 µm column, 50×100 mm, flow rate 140 mL/minute, 5-70% gradient of methanol in buffer (0.025 M aqueous ammonium bicarbonate, adjusted to pH 10 with ammonium hydroxide)] to give the title compound (35 mg, 0.074 mmol, 32.8% yield). MS (ESI$^-$) m/z 470 (M–H)$^-$.

Example 41C: 5-{7-[3-(ethylamino)propyl]-1-fluoro-3-hydroxynaphthalen-2-yl}-1$\lambda^6$,2,5-thiadiazolidine-1,1,3-trione To a mixture of 1,2,3,4,5-pentamethylbenzene (38.5 mg, 0.260 mmol) and Example 41B (35 mg, 0.074 mmol) in dichloromethane (3 mL) at −78° C. was added trichloroborane (0.816 mL, 0.816 mmol, 1 M in dichloromethane). The mixture was stirred at −78° C. for 10 minutes, then −20° C. for 20 minutes. The mixture was quenched with ethanol (3 mL) and concentrated.

The residue was washed with heptane (4×4 mL) and dichloromethane (6×3 mL) and concentrated to give the title compound (27 mg, 0.071 mmol, 95% yield). $^1$H NMR (500 MHz, DMSO-d$_6$) δ ppm 10.51 (s, 1H), 8.63 (br s, 2H), 7.74 (d, J=8, Hz, 1H), 7.73 (d, J=2, Hz, 1H), 7.42 (dd, J=8, 2 Hz, 1H), 7.11 (s, 1H), 4.45 (s, 2H), 2.90 (m, 4H), 2.82 (t, J=7, Hz, 2H), 1.98 (m, 2H), 1.17 (t, J=7 Hz, 3H); MS (ESI$^-$) m/z 380 (M–H)$^-$.

Example 42: 5-{7-[5-(dimethylphosphoryl)thiophen-2-yl]-1-fluoro-3-hydroxynaphthalen-2-yl}-1$\lambda^6$, 2,5-thiadiazolidine-1,1,3-trione (Compound 141)

Example 42A: (5-bromothiophen-2-yl)(dimethyl)oxo-1-phosphane

To a solution of 2-bromo-5-iodothiophene (407 mg, 1.409 mmol), dimethylphosphine oxide (100 mg, 1.281 mmol) and triethylamine (0.214 mL, 1.537 mmol) in 1,4-dioxane (5 mL) was added tris(dibenzylideneacetone)dipalladium(0) (Pd$_2$(dba)$_3$, 11.73 mg, 0.013 mmol) and (9,9-dimethyl-9H-xanthene-4,5-diyl)bis(diphenylphosphine) (Xantphos, 14.83 mg, 0.026 mmol) at 20° C. under nitrogen. Then the mixture was stirred for 12 hours at 20° C. The reaction mixture was concentrated under reduced pressure. The residue was purified by preparative HPLC [Agela-SNAP 20-35 µm, 100 Å C18 flash column, 120 g, flow rate 20 mL/minute, monitor wavelength: 220&254 nm, 0-35% gradient of acetonitrile in water] to give the title compound (220 mg, 0.874 mmol, 68.2% yield). $^1$H NMR (400 MHz, CDCl$_3$) δ ppm 7.32 (dd, J=7.88, 3.75 Hz, 1H), 7.13-7.16 (m, 1H), 1.79 (d, J=13.26 Hz, 6H).

Example 42B: 5-[3-(benzyloxy)-1-fluoro-7-(4,4,5,5-tetramethyl-1,3,2-dioxaborolan-2-yl)naphthalen-2-yl]-1$\lambda^6$,2,5-thiadiazolidine-1,1,3-trione and [6-(benzyloxy)-8-fluoro-7-(1,1,4-trioxo-1$\lambda^6$,2,5-thiadiazolidin-2-yl)naphthalen-2-yl]boronic acid To a solution of Example 1G (400 mg, 0.860 mmol), potassium acetate (253 mg, 2.58 mmol) and bis(pinacolato) diboron (437 mg, 1.719 mmol) in 1,4-dioxane (7 mL) was added [1,1'-bis(diphenylphosphino)ferrocene]dichloropalladium(II), complex with dichloromethane (PdCl$_2$(dppf)-CH$_2$Cl$_2$ adduct, 140 mg, 0.172 mmol) at 20° C. under nitrogen. Then the mixture was stirred for 4 hours at 80° C. Then the mixture was concentrated under reduced pressure. The residue was purified by preparative HPLC [Agela-SNAP C18 20~35 µm, 100 Å flash column, 120 g, flow rate 120 mL/minute, 0-45% gradient of acetonitrile in water, monitor wavelength: 220&254 nm] and the solution was concentrated under reduced pressure to give a mixture of the title compounds (300 mg, 0.577 mmol, yield 67.1%). $^1$H NMR (400 MHz, DMSO-d$_6$) δ ppm 8.50 (s, 1H), 8.30 (s, 1H), 7.95 (d, J=8.25 Hz, 1H), 7.85-7.89 (m, 1H), 7.78-7.84 (m, 2H), 7.53 (br d, J=7.38 Hz, 4H), 7.30-7.44 (m, 8H), 5.29 (br s, 4H), 4.50 (br d, J=6.50 Hz, 4H), 1.34 (s, 9H), 1.15-1.17 (m, 3H).

Example 42C: 5-{3-(benzyloxy)-7-[5-(dimethylphosphoryl)thiophen-2-yl]-1-fluoronaphthalen-2-yl}-1$\lambda^6$,2,5-thiadiazolidine-1,1,3-trione Tetrakis[triphenylphosphine]palladium(0) (Pd(Ph$_3$P)$_4$, 17.40 mg, 0.015 mmol) was added to a mixture of the compounds of Example 42B (86 mg, 0.181 mmol), sodium carbonate (Na$_2$CO$_3$, 31.9 mg, 0.301 mmol) and the compound of Example 42A (40 mg, 0.151 mmol) in toluene (2 mL), ethanol (1 mL) and water (0.5 mL) under nitrogen at 20° C. The mixture was stirred for 2 hours at 100° C. under nitrogen. Then the mixture was cooled to 25° C. One additional vial in 10 mg scale and one additional vial in 40 mg scale were set up as described above. These three reactions were combined and diluted with water (50 mL). The resulting mixture was extracted with ethyl acetate (3×20 mL). The aqueous solution was acidified with aqueous 1 M hydrochloric acid to pH=3. The resulting mixture was extracted with ethyl acetate (3×30 mL). The combined organic phases were washed with brine (50 mL), dried over anhydrous sodium sulfate and concentrated under reduced pressure. The residue was purified by preparative HPLC [Welch Xtimate™ C18 150×25 mm, 5 µm column, flow rate 25 mL/minute, 30-50% gradient over 15 minutes of acetonitrile in aqueous ammonium bicarbonate (10 mM), wavelength: 220&254 nm]. The resulting solution was acidified with aqueous 1 M hydrochloric acid to pH=3 and extracted with ethyl acetate (3×30 mL). The combined organic phases were washed with brine (30 mL), dried over anhydrous sodium sulfate and concentrated under reduced pressure to give the title compound (40 mg, 0.070 mmol, 20.60% yield). $^1$H NMR (400 MHz, DMSO-d$_6$) δ ppm 7.97 (s, 2H), 7.82 (dd, J=3.69, 1.69 Hz, 1H), 7.63 (dd, J=7.13, 3.75 Hz, 1H), 7.47-7.58 (m, 3H), 7.30-7.44 (m, 3H), 5.30 (s, 2H), 4.49 (s, 2H), 1.78 (d, J=13.76 Hz, 6H); MS (ESI$^-$) m/z 543 (M–H)$^-$.

Example 42D: 5-{7-[5-(dimethylphosphoryl)thiophen-2-yl]-1-fluoro-3-hydroxynaphthalen-2-yl}-1λ⁶,2,5-thiadiazolidine-1,1,3-trione, ammonium salt To a mixture of the compound of Example 42C (35 mg, 0.061 mmol) in anhydrous dichloromethane (10 mL) was added trichloroborane (0.366 mL, 0.366 mmol) dropwise at 0° C. Then the mixture was stirred for 2 hours at 20° C. One additional vial in 5 mg scale was set up as described above. These two reaction mixtures were combined, quenched with 5 mL of methanol, and concentrated under reduced pressure. The residue was dissolved with N,N-dimethylformamide and purified by preparative HPLC [Gilson 281 semi-preparative HPLC system, Welch Xtimate™ C18 column, 150×25 mm, 5 μm, flow rate 25 mL/minute, 30-50% gradient of acetonitrile in buffer (10 mM aqueous ammonium bicarbonate), wavelength: 220&254 nm] and lyophilization to give the title compound (15 mg, 0.030 mmol, 43.2% yield) as an ammonium salt. $^1$H NMR (400 MHz, DMSO-d$_6$) δ ppm 8.13 (s, 1H), 7.83 (s, 2H), 7.77 (dd, J=3.50, 1.50 Hz, 1H), 7.61 (dd, J=7.07, 3.69 Hz, 1H), 7.34-7.56 (m, 3H), 7.10 (s, 1H), 4.11 (s, 2H), 1.77 (d, J=13.76 Hz, 6H); MS (ESI⁻) m/z 453 (M−H)⁻.

Example 43: 5-{7-[2-(cyclopropylamino)ethoxy]-1-fluoro-3-hydroxynaphthalen-2-yl}-1λ⁶,2,5-thiadiazolidine-1,1,3-trione (Compound 142)

The title compound was prepared using the methodologies described in Example 46 substituting cyclopropanamine for propan-2-amine. $^1$H NMR (500 MHz, DMSO-d$_6$) δ ppm 9.99 (s, 1H), 8.95 (br s, 2H), 7.75 (d, J=8, Hz, 1H), 7.29 (d, J=2, Hz, 1H), 7.27 (dd, J=8, 2 Hz, 1H), 7.09 (s, 1H), 4.38 (t, J=5 Hz, 2H), 4.30 (s, 2H), 3.49 (m, 2H), 2.83 (m, 1H), 0.87 (m, 2H), 0.79 (m, 2H); MS (ESI⁻) m/z 394 (M−H)⁻.

Example 44: 5-{1-fluoro-3-hydroxy-7-[2-(methylamino)ethoxy]naphthalen-2-yl}-1λ⁶,2,5-thiadiazolidine-1,1,3-trione (Compound 143)

The title compound was prepared using the methodologies described in Example 46 substituting methanamine for propan-2-amine. $^1$H NMR (500 MHz, DMSO-d$_6$) δ ppm 10.16 (br s, 1H), 8.72 (br s, 2H), 7.72 (d, J=8, Hz, 1H), 7.25 (d, J=2, Hz, 1H), 7.21 (dd, J=8, 2 Hz, 1H), 7.05 (s, 1H), 4.34 (s, 2H), 4.32 (t, J=5 Hz, 2H), 3.47 (m, 2H), 2.62 (m, 3H); MS (ESI⁻) m/z 368 (M−H)⁻.

Example 45: 5-{7-[2-(ethylamino)ethoxy]-1-fluoro-3-hydroxynaphthalen-2-yl}-1λ⁶,2,5-thiadiazolidine-1,1,3-trione (Compound 144)

The title compound was prepared using the methodologies described in Example 46 substituting ethanamine for propan-2-amine. $^1$H NMR (500 MHz, DMSO-d$_6$) δ ppm 9.81 (s, 1H), 8.93 (br s, 2H), 7.74 (d, J=8, Hz, 1H), 7.37 (d, J=2, Hz, 1H), 7.24 (dd, J=8, 2 Hz, 1H), 7.07 (s, 1H), 4.52 (t, J=5 Hz, 2H), 4.21 (s, 2H), 3.45 (m, 2H), 3.06 (m, 2H), 1.23 (t, J=7 Hz, 3H); MS (ESI⁻) m/z 382 (M−H)⁻.

Example 46: 5-(1-fluoro-3-hydroxy-7-{2-[(propan-2-yl)amino]ethoxy}naphthalen-2-yl)-1λ⁶,2,5-thiadiazolidine-1,1,3-trione (Compound 145)

Example 46A: 5-[3-(benzyloxy)-7-(2,2-dimethoxyethoxy)-1-fluoronaphthalen-2-yl]-1λ⁶,2,5-thiadiazolidine-1,1,3-trione A mixture of Example 1H (520 mg, 1.292 mmol), cesium carbonate (1011 mg, 3.10 mmol), and 2-bromo-1,1-dimethoxyethane (437 mg, 2.58 mmol) in N,N-dimethylformamide (3 mL) was stirred at 70° C. for 4 hours. The reaction was cooled to ambient temperature and quenched with 0.2 N HCl aqueous solution (20 mL). The mixture was extracted with ethyl acetate (60 mL×2). The combined organic phases were washed with brine (10 mL×2), dried over sodium sulfate, filtered and concentrated. The residue was purified by flash column chromatography on silica gel (120 g) eluted with ethyl acetate, then ethyl acetate/methanol (10:1) to give the title compound (485 mg, 0.989 mmol, 77% yield). $^1$H NMR (500 MHz, DMSO-d$_6$) δ ppm 7.77 (d, J=8 Hz, 1H), 7.56 (d, J=8 Hz, 2H), 7.37 (t, J=8 Hz, 2H), 7.32 (m, 2H), 7.29 (d, J=2 Hz, 1H), 7.23 (dd, J=8.2 Hz, 1H), 5.22 (s, 2H), 4.75 (t, J=6 Hz, 1H), 4.12 (s, 2H), 4.11 (d, J=6 Hz, 2H), 3.38 (s, 6H); MS (ESI⁻) m/z 489 (M−H)⁻.

Example 46B: {[6-(benzyloxy)-8-fluoro-7-(1,1,4-trioxo-1λ⁶,2,5-thiadiazolidin-2-yl)naphthalen-2-yl]oxy}acetaldehyde A mixture of Example 46A (123 mg, 0.251 mmol) in hydrogen chloride (0.125 mL, 0.50 mmol, 4 N in dioxane) and water (0.05 mL) was stirred at ambient temperature for 15 minutes. The mixture was diluted with ethyl acetate (70 mL). The organic phase was washed with water (15 mL×3) and brine (15 mL), dried over sodium sulfate, filtered and concentrated to give the title compound (112 mg, 0.252 mmol, 100% yield). MS (ESI⁻) m/z 443 (M−H)⁻.

Example 46C: 5-[3-(benzyloxy)-1-fluoro-7-{2-[(propan-2-yl)amino]ethoxy}naphthalen-2-yl]-1λ⁶,2,5-thiadiazolidine-1,1,3-trione A mixture of Example 46B (111 mg, 0.250 mmol), triethylamine (126 mg, 1.249 mmol), propan-2-amine (44.3 mg, 0.749 mmol) and sodium triacetoxyborohydride (212 mg, 0.999 mmol) in acetonitrile/methanol (4:1, 3 mL) was stirred at ambient temperature for 18 hours. Then methanol/water (1:2, 2 mL) was added. The solution was filtered, and the filtrate was purified by preparative HPLC [YMC Tri-Art™ C18 Hybrid 5 μm column, 50×100 mm, flow rate 140 mL/minute, 5-55% gradient of methanol in buffer (0.025 M aqueous ammonium bicarbonate, adjusted to pH 10 with ammonium hydroxide)] to give the title compound (68 mg, 0.139 mmol, 55.8% yield). MS (ESI⁻) m/z 486 (M−H)⁻.

Example 46D: 5-(1-fluoro-3-hydroxy-7-{2-[(propan-2-yl)amino]ethoxy}naphthalen-2-yl)-1λ⁶,2,5-thiadiazolidine-1,1,3-trione To a mixture of 1,2,3,4,5-pentamethylbenzene (64.8 mg, 0.437 mmol) and Example 46C (63 mg, 0.125 mmol) in dichloromethane (3 mL) at −78° C. was added trichloroborane (1.498 mL, 1.498 mmol, 1 M in dichloromethane). The mixture was stirred at −78° C. for 10 minutes, then −20° C. for 30 minutes. The mixture was quenched with ethanol (3 mL) and concentrated. The residue was washed with heptane (4×4 mL) and dichloromethane (4×3 mL) and concentrated to give the title compound (48 mg, 0.121 mmol, 97% yield). $^1$H NMR (500 MHz, DMSO-d$_6$) δ ppm 9.61 (s, 1H), 9.00 (br s, 2H), 7.72 (d, J=8, Hz, 1H), 7.25 (d, J=2, Hz, 1H), 7.21 (dd, J=8, 2 Hz, 1H), 7.07 (s, 1H), 4.39 (t, J=5 Hz, 2H), 4.09 (s, 2H), 3.37 (m, 1H), 2.52 (m, 2H), 1.29 (d, J=7 Hz, 6H); MS (ESI⁻) m/z 396 (M−H)⁻.

Example 47: 5-{7-[3-(diethylphosphoryl)propoxy]-1-fluoro-3-hydroxynaphthalen-2-yl}-1$\lambda^6$,2,5-thiadiazolidine-1,1,3-trione (Compound 146)

Example 47A: 3-(diethylphosphoryl)propan-1-ol

To a mixture of prop-2-en-1-ol (2.487 mL, 36.6 mmol) and 2,2'-azobis(2-methylpropionitrile) (AIBN, 0.150 g, 0.914 mmol) was added diethyl-$\lambda^5$-phosphanone (2 g, 18.28 mmol) dropwise with stirring over 40 minutes at 100° C. under nitrogen. The mixture was stirred for 3 hours at 100° C. Thin-layer chromatography (I$_2$, ethyl acetate:methanol=5:1, R$_f$=0.3) showed the starting material was consumed. Then the mixture was purified by column chromatography on silica gel eluted with petroleum ether/ethyl acetate (0-100%) and methanol/ethyl acetate (0-10%) to give the title compound (1.9 g, 53.8% yield). $^1$H NMR (400 MHz, CDCl$_3$) δ ppm 3.72 (t, J=5.29 Hz, 2H), 1.67-1.99 (m, 8H), 1.10-1.24 (m, 6H).

Example 47B: 3-(diethylphosphoryl)propyl methanesulfonate

To a solution of the compound of Example 47A (2.9 g, 15.01 mmol) in dichloromethane (100 mL) was added triethylamine (4.19 mL, 30.0 mmol) and then methanesulfonyl chloride (1.404 mL, 18.02 mmol) was added dropwise at 0° C. under nitrogen. Then the mixture was stirred for 1 hour at 0° C. Thin-layer chromatography (I$_2$, ethyl acetate/methanol=3:1, R$_f$=0.25) showed the starting material was consumed. Then the mixture was quenched with water (250 mL), and the resulting mixture was extracted with dichloromethane (3×150 mL). The combined organic phases were dried over anhydrous sodium sulfate and concentrated under reduced pressure to give the title compound (1.8 g, 42.1% yield) which was used in the next step without further purification. $^1$H NMR (400 MHz, CDCl$_3$) δ ppm 4.30-4.36 (m, 2H), 3.04 (s, 3H), 2.04-2.15 (m, 2H), 1.68-1.84 (m, 7H), 1.12-1.24 (m, 7H).

Example 47C: 5-{3-(benzyloxy)-7-[3-(diethylphosphoryl)propoxy]-1-fluoronaphthalen-2-yl}-1$\lambda^6$,2,5-thiadiazolidine-1,1,3-trione To a solution of Example 1H (515 mg, 2.125 mmol) in N,N-dimethylformamide (4 mL) was added cesium carbonate (Cs$_2$CO$_3$, 462 mg, 1.417 mmol) and the compound of Example 47B (515 mg, 2.125 mmol) in order at 20° C. Then the mixture was stirred for 4 hours at 80° C. The mixture was quenched with water (50 mL), and the mixture was acidified by adding aqueous 1 M hydrochloric acid dropwise to pH=3. The resulting mixture was extracted with ethyl acetate (3×30 mL). The combined organic phases were washed with brine (3×30 mL), dried over anhydrous sodium sulfate and concentrated under reduced pressure to give the title compound (350 mg, 77% yield) which was used in the next step without further purification. MS (ESI$^-$) m/z 547 (M–H)$^-$.

Example 47D: 5-{7-[3-(diethylphosphoryl)propoxy]-1-fluoro-3-hydroxynaphthalen-2-yl}-1$\lambda^6$,2,5-thiadiazolidine-1,1,3-trione, ammonium salt To a solution of the compound of Example 47C (350 mg, 0.542 mmol) in N,N-dimethylformamide (1 mL) and tetrahydrofuran (30 mL) was added 10% Pd/C (500 mg, 2.349 mmol) at 20° C. under argon. Then the mixture was stirred for 2 hours at 20° C. under a hydrogen balloon (15 psi). The mixture was filtered, and the filtrate was concentrated to remove most of tetrahydrofuran under reduced pressure. The resulting solution was purified by preparative HPLC [Shimadzu LC-8A, Waters Xbridge™ BEH C18 100×25 mm, 5 μm column, flow rate 30 mL/minute, 2-30% gradient of acetonitrile in buffer (10 mM aqueous ammonium bicarbonate, wavelength: 220&254 nm)] and lyophilization to give the title compound as an ammonium salt (53 mg, 20.00% yield). $^1$H NMR (400 MHz, DMSO-d$_6$) δ ppm 9.21-9.64 (m, 1H), 7.66 (d, J=8.88 Hz, 1H), 7.00-7.20 (m, 6H), 4.12 (t, J=6.25 Hz, 2H), 4.08 (s, 2H), 1.89-2.00 (m, 2H), 1.74-1.84 (m, 2H), 1.65 (dq, J=11.88, 7.67 Hz, 4H), 0.98-1.07 (m, 6H); $^1$H NMR (400 MHz, DMSO-d$_6$/D$_2$O) δ ppm 7.67 (d, J=8.88 Hz, 1H), 7.11-7.20 (m, 2H), 4.13 (t, J=6.25 Hz, 2H), 4.09 (s, 2H), 1.88-1.99 (m, 2H), 1.75-1.85 (m, 2H), 1.66 (dq, J=11.90, 7.71 Hz, 4H), 0.98-1.09 (m, 6H); MS (ESI$^-$) m/z 547 (M–H)$^-$.

Example 48: 5-{1-fluoro-3-hydroxy-7-[(3S)-3-hydroxybutoxy]naphthalen-2-yl}-1$\lambda^6$,2,5-thiadiazolidine-1,1,3-trione (Compound 147)

The title compound was prepared using the methodologies described in Example 50 substituting (S)-butane-1,3-diol for (R)-butane-1,3-diol. $^1$H NMR (500 MHz, DMSO-d$_6$) δ ppm 9.36 (br s, 1H), 7.66 (dd, J=8, 2 Hz, 1H), 7.24 (br s, 3H), 7.17 (d, J=2 Hz, 1H), 7.12 (dd, J=8, 2 Hz, 1H), 7.02 (s, 1H), 4.59 (d, J=5 Hz, 1H), 4.13 (m, 2H), 4.09 (s, 2H), 3.85 (m, 1H), 1.81 (m, 2H), 1.14 (d, J=7 Hz, 3H); MS (ESI$^-$) m/z 383 (M–H)$^-$.

Example 49: 5-{1,4-difluoro-3-hydroxy-7-[(3-methylbutyl)amino]naphthalen-2-yl}-1$\lambda^6$,2,5-thiadiazolidine-1,1,3-trione (Compound 148)

To a solution of the product of Example 1G (1.000 g, 2.149 mmol) in dimethylformamide (20 mL) was added 1-chloromethyl-4-fluoro-1,4-diazoniabicyclo[2.2.2]octane bis(tetrafluoroborate) (1.523 g, 4.30 mmol) followed by heating the resulting solution to 60° C. After 3 hours, another portion of 1-chloromethyl-4-fluoro-1,4-diazoniabicyclo[2.2.2]octane bis(tetrafluoroborate) (0.381 g, 1.075 mmol) was added with continued heating. After 2.5 hours, the reaction mixture was cooled to room temperature, quenched with 1 M aqueous sodium thiosulfate (50 mL), and acidified to pH<4 with concentrated hydrochloric acid. The crude aqueous layer was extracted with ethyl acetate (3×50 mL). The organic layers were combined and washed sequentially with saturated aqueous ammonium chloride (2×50 mL), and then a 6:1 mixture of brine and 2 M hydrochloric acid (30 mL). The organic fraction was dried over anhydrous sodium sulfate, then filtered and concentrated under reduced pressure to give 5-[3-(benzyloxy)-7-bromo-1,4-difluoronaphthalen-2-yl]-1$\lambda^6$,2,5-thiadiazolidine-1,1,3-trione which was used for the next reaction without purification. MS (APCI$^-$) m/z 483 [M–H]$^-$.

In a 20 mL pressure release vial, the crude 5-[3-(benzyloxy)-7-bromo-1,4-difluoronaphthalen-2-yl]-1$\lambda^6$,2,5-thiadiazolidine-1,1,3-trione (0.5012 g, 1.037 mmol), cesium carbonate (1.014 g, 3.11 mmol), methanesulfonato(2-dicyclohexylphosphino-3,6-dimethoxy-2',4',6'-tri-1-propyl-1,1'-biphenyl)(2'-amino-1,1'-biphenyl-2-yl)palladium(II) (BrettPhos Pd G3 precatalyst, 0.028 g, 0.031 mmol), and 2-(dicyclohexylphosphino)3,6-dimethoxy-2',4',6'-triisopropyl-1,1'-biphenyl (BrettPhos, 0.017 g, 0.031 mmol) were combined. The solids were placed under vacuum for 5 minutes at ambient temperature, then the vial was filled with nitrogen, followed by tert-amyl alcohol (10 mL) and isoamylamine (0.241 mL, 2.074 mmol). The resulting suspension was degassed by five vacuum/nitrogen backfills, stirred for 10 minutes at ambient temperature and then heated to 100° C. After 33 hours, the reaction mixture was cooled to ambient temperature, then quenched with 1 M hydrochloric acid (5 mL) and diluted with ethyl acetate (5 mL). The aqueous layer was extracted with ethyl acetate (2×5 mL). The combined organic layers were washed with a 4:1 mixture of brine and 1 M hydrochloric acid (2.5 mL), dried over anhydrous sodium sulfate, then filtered and concentrated under reduced pressure to give 5-{3-(benzyloxy)-1,4-difluoro-7-[(3-methylbutyl)amino]naphthalen-2-yl}-1$\lambda^6$,2,5-thiadiazolidine-1,1,3-trione, which was used for the next reaction without purification. MS (APCI$^+$) m/z 490 [M+H]$^+$.

To a suspension of the crude 5-{3-(benzyloxy)-1,4-difluoro-7-[(3-methylbutyl)amino]naphthalen-2-yl}-1$\lambda^6$,2,5-thiadiazolidine-1,1,3-trione (0.508 g, 1.038 mmol) and pentamethylbenzene (0.308 g, 2.075 mmol) in dichloromethane (10 mL) at −78° C. was added a solution of boron trichloride in dichloromethane (7.8 mL, 1 M, 7.8 mmol) slowly along the side of the flask so that the internal temperature remained below −70° C. The resulting solution was stirred for 5 minutes at −78° C., then the cooling bath was removed, and the reaction mixture was allowed to warm to an internal temperature of 0° C. before cooling back to −78° C. The reaction was quenched by addition of ethyl acetate (5 mL) followed by anhydrous ethanol (5 mL). The mixture was warmed to ambient temperature and concentrated under reduced pressure to give a solid. The crude solid was triturated with heptanes (3×5 mL), then acetonitrile (3×5 mL) and methanol (3×5 mL) to give the title compound (0.0056 g, 0.014 mmol, 1.4% yield). $^1$H NMR (400 MHz, DMSO-d$_6$) δ ppm 10.12 (s, 1H), 7.68 (dd, J=9.0, 1.6 Hz, 1H), 7.18 (dd, J=9.2, 2.2 Hz, 1H), 6.75 (s, 1H), 4.49 (s, 2H), 3.12 (t, J=7.3 Hz, 2H), 1.80-1.65 (m, 1H), 1.51 (q, J=7.1 Hz, 2H), 0.93 (d, J=6.6 Hz, 6H); MS (APC$^+$) m/z 400 [M+H]$^+$.

Example 50: 5-{1-fluoro-3-hydroxy-7-[(3R)-3-hydroxybutoxy]naphthalen-2-yl}-1$\lambda^6$,2,5-thiadiazolidine-1,1,3-trione (Compound 149)

Example 50A: (R)-3-hydroxybutyl methanesulfonate

To a mixture of (R)-butane-1,3-diol (160 mg, 1.78 mmol) and triethylamine (270 mg, 2.67 mmol) in dichloromethane (3 mL) at 0° C. was added methanesulfonyl chloride (214 mg, 1.869 mmol) in dichloromethane (1 mL). The mixture was stirred at 0° C. for 1 hour and then at ambient temperature for 1 hour. The mixture was diluted with dichloromethane (40 mL), washed with 0.1 N HCl aqueous solution (10 mL) and water (10 mL). The organic phase was dried over sodium sulfate, filtered and concentrated to give the title compound (275 mg, 1.635 mmol, 92% yield). $^1$H NMR (400 MHz, DMSO-d$_6$) δ ppm 4.63 (d, J=6 Hz, 1H), 4.27 (m, 2H), 3.72 (m, 1H), 3.15 (s, 3H), 1.71 (m, 2H), 1.05 (d, J=7 Hz, 3H).

Example 50B: 5-{3-(benzyloxy)-1-fluoro-7-[(3R)-3-hydroxybutoxy]naphthalen-2-yl}-1$\lambda^6$,2,5-thiadiazolidine-1,1,3-trione A mixture of Example 1H (130 mg, 0.323 mmol), Example 50A (272 mg, 1.615 mmol) and cesium carbonate (421 mg, 1.292 mmol) in N,N-dimethylformamide (1 mL) was stirred at 65° C. for 0.5 hour. The mixture was quenched with 0.2 N HCl aqueous (15 mL) and extracted with ethyl acetate (80 mL). The organic phase was washed with brine (15 mL), dried over sodium sulfate, filtered and concentrated. The residue was purified by preparative HPLC [YMC TriArt™ C18 Hybrid 5 μm column, 50×100 mm, flow rate 140 mL/minute, 5-60% gradient of methanol in buffer (0.025 M aqueous ammonium bicarbonate, adjusted to pH 10 with ammonium hydroxide)] to give the title compound (80 mg, 0.169 mmol, 52.2% yield). MS (ESI$^-$) m/z 473 (M−H)$^-$.

Example 50C: 5-{-fluoro-3-hydroxy-7-[(3R)-3-hydroxybutoxy]naphthalen-2-yl}-$\lambda^6$,2,5-thiadiazolidine-1,1,3-trione To a mixture of 1,2,3,4,5-pentamethylbenzene (58.8 mg, 0.397 mmol) and Example 50B (65 mg, 0.132 mmol) in dichloromethane (4 mL) at −78° C. was added trichloroborane (1.322 mL, 1.322 mmol, 1 M in dichloromethane). The mixture was stirred at −78° C. for 20 minutes and then at −20° C. for 20 minutes. The mixture was quenched with ethanol (3 mL) and concentrated. The residue was washed with heptane (4×4 mL) and concentrated to give the crude product. The crude material was purified by preparative HPLC [YMC TriArt™ C18 Hybrid 5 μm column, 50×100 mm, flow rate 140 mL/minute, 5-50% gradient of methanol in buffer (0.025 M aqueous ammonium bicarbonate, adjusted to pH 10 with ammonium hydroxide)] to give the title compound (36 mg, 0.09 mmol, 67.8% yield). $^1$H NMR (500 MHz, DMSO-d$_6$) δ ppm 7.66 (dd, J=8.2 Hz, 1H), 7.24 (br s, 4H), 7.17 (d, J=2 Hz, 1H), 7.12 (dd, J=8, 2 Hz, 1H), 7.02 (s, 1H), 4.59 (d, J=5 Hz, 1H), 4.13 (m, 2H), 4.09 (s, 2H), 3.85 (m, 1H), 1.81 (m, 2H), 1.14 (d, J=7 Hz, 3H); MS (ESI$^-$) m/z 383 (M−H)$^-$.

Example 51: 5-[7-(2-cyclopropyl-2-hydroxyethoxy)-1-fluoro-3-hydroxynaphthalen-2-yl]-1$\lambda^6$,2,5-thiadiazolidine-1,1,3-trione (Compound 150)

Example 51A: 5-[3-(benzyloxy)-7-(2-{[tert-butyl(dimethyl)silyl]oxy}-2-cyclopropylethoxy)-1-fluoronaphthalen-2-yl]-1$\lambda^6$,2,5-thiadiazolidine-1,1,3-trione A solution of 2-bromo-1-cyclopropylethanol (250 mg, 1.515 mmol) in dichloromethane (2 mL) was added to a stirred solution of tert-butyldimethylchlorosilane (240 mg, 1.591 mmol) and imidazole (113 mg, 1.666 mmol) in dichloromethane (2 mL). The mixture was stirred at ambient temperature for 3 hours. Water (5 mL) was added and the mixture was extracted with dichloromethane (3×5 mL). The organic layers were combined, dried over sodium sulfate, and concentrated under reduced pressure. The (2-bromo-1-cyclopropylethoxy)(tert-butyl)dimethylsilane was subjected to the next step without purification.

To a solution of Example 1H (120 mg, 0.298 mmol) in N,N-dimethylformamide (2 mL), was added cesium carbonate (214 mg, 0.656 mmol) and crude (2-bromo-1-cyclopropylethoxy)(tert-butyl)dimethylsilane (167 mg, 0.596 mmol). The mixture was heated to 80° C. overnight. After cooling, the volatiles were removed under reduced pressure, and the residue was subjected to preparative HPLC [Phenomenex® Luna® C18(2) 5 μm 100 Å AXIA™ column (250 mm×25 mm). 30-100% gradient of acetonitrile (A) and 0.1% trifluoroacetic acid in water (B) over 15 minutes, at a flow rate of 25 mL/minute] to afford the title compound (64 mg, 0.107 mmol, 36% yield). MS (APCI⁻) m/z 599 [M−H]⁻.

Example 51B: 5-[7-(2-cyclopropyl-2-hydroxy-ethoxy)-1-fluoro-3-hydroxynaphthalen-2-yl]-1$\lambda^6$,2,5-thiadiazolidine-1,1,3-trione A 250 mL-round bottom flask was filled with nitrogen, followed by addition of Pd/C (4.34 mg, 0.041 mmol) and tetrahydrofuran (8 mL). A solution of Example 51A (100 mg, 0.166 mmol) in tetrahydrofuran (2 mL) was then added. An adapter fitted with a hydrogen balloon was inserted and the flask was evacuated and refilled with hydrogen (3 times). The reaction was stirred at ambient temperature overnight. The mixture was filtered through a pad of diatomaceous earth under nitrogen gas. The volatiles were removed under reduced pressure, and the crude 5-[7-(2-{[tert-butyl(dimethyl)silyl]oxy}-2-cyclopropylethoxy)-1-fluoro-3-hydroxynaphthalen-2-yl]-1$\lambda^6$,2,5-thiadiazolidine-1,1,3-trione was subjected to the next step without purification. MS (APCI⁻) m/z 509 [M−H]⁻.

To a solution of crude 5-[7-(2-{[tert-butyl(dimethyl)silyl]oxy}-2-cyclopropylethoxy)-1-fluoro-3-hydroxynaphthalen-2-yl]-1$\lambda^6$,2,5-thiadiazolidine-1,1,3-trione (100 mg, 0.196 mmol) in 1,4-dioxane (3 mL) was added 4 M HCl in dioxane (4 mL), and the reaction mixture was stirred at ambient temperature for 6 hours. The volatiles were removed under reduced pressure, and the residue was subjected to preparative HPLC [Phenomenex® Luna® C18(2) 5 μm 100 Å AXIA™ column (250 mm×25 mm). 30-100% gradient of acetonitrile (A) and 0.1% trifluoroacetic acid in water (B) over 15 minutes, at a flow rate of 25 mL/minute] to afford the title compound. ¹H NMR (400 MHz, DMSO-d₆) δ ppm 10.37 (s, 1H), 7.76-7.68 (m, 1H), 7.24-7.17 (m, 2H), 7.07 (d, J=1.3 Hz, 1H), 4.52 (s, 2H), 4.09 (dd, J=9.9, 4.1 Hz, 1H), 4.02 (dd, J=9.9, 6.7 Hz, 1H), 3.34 (td, J=6.8, 4.0 Hz, 1H), 1.04-0.91 (m, 1H), 0.50-0.36 (m, 2H), 0.39-0.24 (m, 2H); MS (APCI⁻) m/z 395 [M−H]⁻.

Example 52: 5-{1-fluoro-3-hydroxy-7-[(4R)-4-hydroxypentyl]naphthalen-2-yl}-1$\lambda^6$,2,5-thiadiazolidine-1,1,3-trione (Compound 151)

The title compound was prepared using the methodologies described in Example 55 substituting (R)-pent-4-en-2-ol for 2-methylpent-4-en-2-ol. ¹H NMR (500 MHz, DMSO-d₆) δ ppm 9.52 (br s, 1H), 7.66 (d, J=8 Hz, 1H), 7.63 (s, 1H), 7.33 (dd, J=8, 2 Hz, 1H), 7.10 (m, 4H), 7.03 (s, J=2 Hz, 1H), 4.35 (d, J=5 Hz, 1H), 4.09 (s, 2H), 3.61 (m, 1H), 2.70 (m, 2H), 1.65 (m, 2H), 1.34 (m, 2H), 1.04 (d, J=7 Hz, 3H); MS (ESI⁻) m/z 381 (M−H)⁻.

Example 53: 5-{1-fluoro-3-hydroxy-7-[(4R)-4-hydroxypentyl]naphthalen-2-yl}-1$\lambda^6$,2,5-thiadiazolidine-1,1,3-trione (Compound 152)

Example 53A: 3-(dimethylphosphoryl)propan-1-ol

A mixture of prop-2-en-1-ol (6.97 mL, 102 mmol) and 2,2'-azobis(2-methylpropionitrile) (AIBN, 0.421 g, 2.56 mmol) was added to dimethyl-$\lambda^5$-phosphanone (4 g, 51.2 mmol) dropwise with stirring over 30 minutes at 100° C. under nitrogen. The mixture was stirred for 5 hours at 100° C. Thin-layer chromatography (I₂, ethyl acetate:methanol=5:1, R_f=0.25) showed starting material was consumed. Then the mixture was purified by column chromatography on silica gel eluted first with petroleum ether/ethyl acetate (0-100%) and then with methanol/ethyl acetate (0-10%) to give the title compound (4 g, 48.7% yield). ¹H NMR (400 MHz, CDCl₃) δ ppm 3.72 (t, J=5.38 Hz, 2H), 1.80-1.98 (m, 4H), 1.53 (d, J=12.63 Hz, 6H).

Example 53B: 3-(dimethylphosphoryl)propyl methanesulfonate

To a solution of the compound of Example 53A (1.5 g, 11.02 mmol) in dichloromethane (15 mL) were added triethylamine (3.07 mL, 22.04 mmol) and then methanesulfonyl chloride (1.030 mL, 13.22 mmol) dropwise at 0° C. under nitrogen. Then the mixture was stirred for 1 hour at 0° C. Thin-layer chromatography (I₂, ethyl acetate:methanol=5:1, R_f=0.3) showed starting material was consumed. The mixture was quenched with water (50 mL) and then extracted with dichloromethane (3×25 mL). The organic layers were dried over anhydrous sodium sulfate and concentrated under reduced pressure to give the title compound (500 mg, 16.95% yield) which was used for the next step without further purification. ¹H NMR (400 MHz, CDCl₃) δ ppm 4.31-4.39 (m, 2H), 3.10-3.23 (m, 2H), 2.98-3.08 (m, 3H), 2.05-2.19 (m, 2H), 1.80-1.94 (m, 3H), 1.47-1.61 (m, 6H), 1.39 (t, J=7.34 Hz, 3H).

Example 53C: 5-{3-(benzyloxy)-7-[3-(dimethylphosphoryl)propoxy]-1-fluoronaphthalen-2-yl}-1$\lambda^6$, 2,5-thiadiazolidine-1,1,3-trione Step 3: To a solution of Example 1H (300 mg, 0.671 mmol) in N,N-dimethylformamide (10 mL) was added cesium carbonate (Cs₂CO₃, 437 mg, 1.342 mmol) and the compound of Example 53B (500 mg, 1.867 mmol) in order at 20° C. Then the mixture was stirred for 4 hours at 80° C. The mixture was quenched with water (50 mL) and adjusted to pH=3 with aqueous hydrochloric acid (1 M). The mixture was extracted with ethyl acetate (3×50 mL). The combined organic layers were washed with brine (4×30 mL), dried over anhydrous sodium sulfate and concentrated under reduced pressure to give the title compound (250 mg, 42.9% yield), which was used for the next step without further purification. MS (ESI⁻) m/z 519 (M−H)⁻.

Example 53D: 5-{-fluoro-3-hydroxy-7-[(4R)-4-hydroxypentyl]naphthalen-2-yl}-1$\lambda^6$,2,5-thiadiazolidine-1,1,3-trione, ammonium salt To a mixture of the compound of Example 53C (100 mg, 0.115 mmol) in N,N-dimethylformamide (2 mL) and tetrahydrofuran (30 mL) was added 10% Pd/C (30 mg, 0.141 mmol) at 20° C. under argon. Then the mixture was stirred for 2 hours at 20° C. under a hydrogen balloon (about 15 psi). Then the mixture was filtered. The resulting filtrate was concentrated to remove most of tetrahydrofuran under reduced pressure (<18° C.) to give crude product with remaining N,N-dimethylformamide. One additional vial on 30 mg scale and one additional vial on 50 mg scale were set up as described above. These three crude reaction mixtures were combined and purified by preparative HPLC [Shimadzu LC-8A, Waters Xbridge™ BEH C18 100×25 mm, 5 μm column, flow rate 30 mL/minute, ²-2³% gradient of acetonitrile in buffer (10 mM aqueous ammonium bicarbonate, wavelength: 220&254 nm)], and lyophilized to give the title compound as an ammonium salt (52 mg, 54.1% yield). ¹H NMR (400 MHz, DMSO-d₆) δ ppm 9.08-9.77 (m, 1H), 7.67 (d, J=9.01 Hz, 1H), 7.00-7.20 (m, 6H), 4.13 (t, J=6.13 Hz, 2H), 4.08 (s, 2H), 1.93-2.03 (m, 2H), 1.77-1.88 (m, 2H), 1.40 (d, J=12.88 Hz, 6H); ¹H NMR (400 MHz, DMSO-d₆/D₂O) δ ppm 7.67 (d, J=9.01 Hz, 1H), 7.11-7.20 (m, 2H), 7.03 (s, 1H), 4.13 (t, J=6.25 Hz, 2H), 4.09 (s, 2H), 1.93-2.04 (m, 2H), 1.77-1.89 (m, 2H), 1.40 (d, J=12.88 Hz, 6H); MS (ESI⁻) m/z 429 (M−H)⁻.

Example 54: 5-{1-fluoro-3-hydroxy-7-[(4S)-4-hydroxypentyl]naphthalen-2-yl}-1λ⁶,2,5-thiadiazolidine-1,1,3-trione (Compound 153)

The title compound was prepared using the methodologies described in Example 55 substituting (S)-pent-4-en-2-ol for 2-methylpent-4-en-2-ol. ¹H NMR (500 MHz, DMSO-d₆) δ ppm 9.52 (br s, 1H), 7.66 (d, J=8 Hz, 1H), 7.63 (s, 1H), 7.33 (dd, J=8, 2 Hz, 1H), 7.10 (m, 4H), 7.03 (s, J=2 Hz, 1H), 4.35 (d, J=5 Hz, 1H), 4.09 (s, 2H), 3.61 (m, 1H), 2.70 (m, 2H), 1.65 (m, 2H), 1.34 (m, 2H), 1.04 (d, J=7 Hz, 3H); MS (ESI⁻) m/z 381 (M−H)⁻.

Example 55: 5-[1-fluoro-3-hydroxy-7-(4-hydroxy-4-methylpentyl)naphthalen-2-yl]-1λ⁶,2,5-thiadiazolidine-1,1,3-trione (Compound 154)

Example 55A: 5-{3-(benzyloxy)-1-fluoro-7-[(1E)-4-hydroxy-4-methylpent-1-en-1-yl]naphthalen-2-yl}-1λ⁶,2,5-thiadiazolidine-1,1,3-trione A mixture of Example 1G (0.120 g, 0.258 mmol), 2-(di-tert-butylphosphino)biphenyl (0.018 g, 0.059 mmol), palladium(II) acetate (0.013 g, 0.059 mmol), 2-methylpent-4-en-2-ol (0.077 g, 0.774 mmol) and triethylamine (0.057 g, 0.567 mmol) in N,N-dimethylformamide (0.8 mL) was placed in a nitrogen atmosphere and then heated to 120° C. for 1 hour. The mixture was cooled to ambient temperature, dissolved in methanol (5 mL), filtered through a glass microfiber frit and purified by preparative HPLC [YMC TriArt™ C18 Hybrid 5 μm column, 50×100 mm, flow rate 140 mL/minute, 5-70% gradient of methanol in buffer (0.025 M aqueous ammonium bicarbonate, adjusted to pH 10 with ammonium hydroxide)] to give the title compound (110 mg, 0.227 mmol, 88% yield). MS (ESI⁻) m/z 483 (M−H)⁻.

Example 55B: 5-[1-fluoro-3-hydroxy-7-(4-hydroxy-4-methylpentyl)naphthalen-2-yl]-1λ⁶,2,5-thiadiazolidine-1,1,3-trione To Example 55A (100 mg, 0.206 mmol) in tetrahydrofuran (4 mL) was added 5 weight % palladium on carbon (100 mg, 0.438 mmol) in a 20 mL Barnstead Hast C reactor. The mixture was stirred under 50 psi of hydrogen at 25° C. for 0.35 hour. Tetrahydrofuran (15 mL) was added, and the mixture was filtered. The filtrate was concentrated, and the residue was purified by preparative HPLC [YMC TriArt™ C18 Hybrid 5 μm column, 50×100 mm, flow rate 140 mL/minute, 5-70% gradient of methanol in buffer (0.025 M aqueous ammonium bicarbonate, adjusted to pH 10 with ammonium hydroxide)] to give the title compound (73 mg, 0.177 mmol, 86% yield). ¹H NMR (500 MHz, DMSO-d₆) δ ppm 7.67 (s, 1H), 7.64 (d, J=8 Hz, 1H), 7.54 (br s, 4H), 7.34 (dd, J=8, 2 Hz, 1H), 7.03 (d, J=2 Hz, 1H),), 4.09 (s, 2H), 4.08 (s, 1H), 2.70 (t, J=7 Hz, 2H), 1.68 (m, 2H), 1.38 (m, 2H), 1.05 (s, 6H); MS (ESI⁻) m/z 395 (M−H)⁻.

Example 56: 5-{1-fluoro-3-hydroxy-7-[(3-oxopentyl)oxy]naphthalen-2-yl}-1λ⁶,2,5-thiadiazolidine-1,1,3-trione (Compound 155)

Example 56A: 2-(J-hydroxycyclopropyl)ethyl 4-methylbenzene-1-sulfonate

To a solution of 1-(2-hydroxyethyl)cyclopropanol (130 mg, 1.273 mmol) in dichloromethane (5 mL) at 0° C. under an atmosphere of nitrogen was added triethylamine (0.355 mL, 2.55 mmol) followed by p-toluenesulfonyl chloride (340 mg, 1.782 mmol). The mixture was stirred at ambient temperature for 5 hours. The reaction mixture was diluted with ethyl acetate and washed with 1 M HCl (10 mL), saturated aqueous NaHCO₃ (10 mL) and brine (15 mL). The combined organic fractions were dried (Na₂SO₄), filtered and concentrated. The residue was purified by flash chromatography [12 g SiO₂, gradient of ethyl acetate in heptanes from 5% to 50% over 15 minutes] to afford the title compound (150 mg, 0.585 mmol, 46.0% yield). ¹H NMR (400 MHz, CDCl₃) δ ppm 7.85-7.77 (m, 2H), 7.39-7.32 (m, 2H), 4.31 (t, J=6.3 Hz, 2H), 2.46 (s, 3H), 1.91 (t, J=6.3 Hz, 2H), 0.85-0.74 (m, 2H), 0.53-0.45 (m, 2H).

Example 56B: 5-{t-fluoro-3-hydroxy-7-[(3-oxopentyl)oxy]naphthalen-2-yl}-1λ⁶,2,5-thiadiazolidine-1,1,3-trione A mixture of the compound of Example 1H (180 mg, 0.447 mmol), 2-(1-hydroxycyclopropyl)ethyl 4-methylbenzene-1-sulfonate (138 mg, 0.537 mmol) and Cs₂CO₃ (518 mg, 1.590 mmol) in N,N-dimethylformamide (5 mL) was stirred at 50° C. for 16 hours. The reaction mixture was treated with 1 mL of 2 M Na₂CO₃ and then extracted with ethyl acetate. The organic layer was discarded, and the aqueous layer was acidified with 2 N HCl to pH=1-2. The acidic aqueous fraction was extracted with ethyl acetate. The organic fraction was washed with water and brine, dried over Na₂SO₄, and concentrated. The residue was purified by chromatography on silica gel eluting with 1-10% methanol in dichloromethane to give 5-{3-(benzyloxy)-1-fluoro-7-[2-(1-hydroxycyclopropyl)ethoxy]naphthalen-2-yl}-1λ⁶,2,5-thiadiazolidine-1,1,3-trione (290 mg, 0.596 mmol, 75.0% yield). MS (APCI⁺) m/z 487.7 (M+H)⁺.

5-{3-(Benzyloxy)-1-fluoro-7-[2-(1-hydroxycyclopropyl)ethoxy]naphthalen-2-yl}-1λ⁶,2,5-thiadiazolidine-1,1,3-trione (200 mg, 0.411 mmol) in tetrahydrofuran (2.0 mL) was added to 5% Pd/C (wet) (60.3 mg, 0.206 mmol) in a 20 mL RS10 reactor with a glass liner. The mixture was stirred under 50 psi of H₂ at 25° C. for 20 hours. The reaction mixture was then filtered, and the filtrate was concentrated. The residue was purified by preparative HPLC on a Phenomenex® C8(2) Luna® 5 μm AXIA™ 150×30 mm column eluted with a gradient of acetonitrile (A) and 0.1% trifluoroacetic acid in water (B) at a flow rate of 50 mL/minute (0-0.5 minute, 5% A, 0.5-8.5 minutes linear gradient 05-100% A, 8.7-10.7 minutes, 100% A, 10.7-11 min linear gradient 100-05% A) to give the title compound (26 mg, 0.066 mmol, 15.96% yield). ¹H NMR (400 MHz, DMSO-d₆) δ ppm 7.66 (dd, J=9.1, 1.6 Hz, 1H), 7.19 (d, J=2.6 Hz, 1H), 7.09 (dd, J=9.0, 2.5 Hz, 1H), 7.03 (d, J=1.4 Hz, 1H), 4.29 (t, J=6.1 Hz, 2H), 4.10 (s, 2H), 2.94 (t, J=6.0 Hz, 2H), 2.58-2.50 (m, 2H), 0.96 (t, J=7.3 Hz, 3H); MS (ESI⁺) m/z 414.2 (M+18)+.

Example 57: 5-[1-fluoro-3-hydroxy-7-(3-hydroxybutoxy)naphthalen-2-yl]-1λ⁶,2,5-thiadiazolidine-1,1,3-trione (Compound 156)

Example 57A: 5-[3-(benzyloxy)-1-fluoro-7-(3-hydroxybutoxy)naphthalen-2-yl]-1λ⁶,2,5-thiadiazolidine-1,1,3-trione The title compound was prepared using the methodologies described in Example 104A substituting 4-bromobutan-2-ol for 2-bromoacetonitrile. MS (ESI⁻) m/z 473 (M–H)⁻.

Example 57B: 5-[1-fluoro-3-hydroxy-7-(3-hydroxybutoxy)naphthalen-2-yl]-1λ⁶,2,5-thiadiazolidine-1,1,3-trione To a mixture of 1,2,3,4,5-pentamethylbenzene (98 mg, 0.664 mmol) and Example 57A (105 mg, 0.221 mmol) in dichloromethane (4 mL) at −78° C. was added trichloroborane (1.77 mL, 1.770 mmol, 1 M in dichloromethane). The mixture was stirred at −78° C. for 1.5 hours. The mixture was quenched with ethanol (3 mL) and concentrated. The residue was washed with heptane (4×4 mL) and concentrated to give the crude product. The crude product was purified by preparative HPLC [YMC TriArt™ C18 Hybrid 5 μm column, 50×100 mm, flow rate 140 mL/minute, 5-50% gradient of methanol in buffer (0.025 M aqueous ammonium bicarbonate, adjusted to pH 10 with ammonium hydroxide)] to give the title compound (45 mg, 0.112 mmol, 50.7% yield). ¹H NMR (500 MHz, DMSO-d₆) δ ppm 7.66 (dd, J=8, 2 Hz, 1H), 7.24 (br s, 4H), 7.17 (d, J=2 Hz, 1H), 7.12 (dd, J=8, 2 Hz, 1H), 7.02 (s, 1H), 4.59 (d, J=5 Hz, 1H), 4.13 (m, 2H), 4.09 (s, 2H), 3.85 (m, 1H), 1.81 (m, 2H), 1.14 (d, J=7 Hz, 3H); MS (ESI⁻) m/z 383 (M–H)⁻.

Example 58: N-[8-fluoro-6-hydroxy-7-(1,1,4-trioxo-1λ⁶,2,5-thiadiazolidin-2-yl)naphthalen-2-yl]-3-methylbutanamide (Compound 157)

Example 58A: N-[6-(benzyloxy)-8-fluoro-7-(1,1,4-trioxo-1λ⁶,2,5-thiadiazolidin-2-yl)naphthalen-2-yl]-3-methylbutanamide A mixture of Example 1G (0.2 g, 0.430 mmol), 3-methylbutanamide (0.078 g, 0.774 mmol), 4,5-bis(diphenylphosphino)-9,9-dimethylxanthene (0.037 g, 0.064 mmol, Xantphos), cesium carbonate (0.280 g, 0.860 mmol) and palladium(II) acetate (9.65 mg, 0.043 mmol) in dioxane (3 mL) was degassed and filled with nitrogen five times, and then heated to 100° C. for 18 hours. The mixture was cooled to ambient temperature and quenched with 0.2 N HCl aqueous solution (10 mL). The mixture was extracted with ethyl acetate (50 mL×2). The combined organic fractions were dried over sodium sulfate, filtered and concentrated. The residue was purified by flash column chromatography on silica gel (40 g) eluted with dichloromethane/methanol (0 to 15%) to give the title compound (130 mg, 0.268 mmol, 62.3% yield). MS (ESI⁻) m/z 484 (M–H)⁻.

Example 58B: N-[8-fluoro-6-hydroxy-7-(1,1,4-trioxo-1λ⁶,2,5-thiadiazolidin-2-yl)naphthalen-2-yl]-3-methylbutanamide To a mixture of 1,2,3,4,5-pentamethylbenzene (78 mg, 0.525 mmol) and Example 58A (85 mg, 0.175 mmol) in dichloromethane (4 mL) at −78° C. was added trichloroborane (1.05 mL, 1.050 mmol, 1 M in dichloromethane). The mixture was stirred at −78° C. for 5 minutes and then warmed to 0° C. for 15 minutes. The mixture was quenched with ethanol (3 mL) and concentrated. The residue was washed with heptane (4×4 mL) and concentrated to give the crude product. The crude product was dissolved in methanol (4 mL), and purified by preparative HPLC [YMC TriArt™ C18 Hybrid 5 μm column, 50×100 mm, flow rate 140 mL/minute, 5-65% gradient of methanol in water (0.1% trifluoroacetic acid)] to give the title compound (40 mg, 0.101 mmol, 57.8% yield). ¹H NMR (500 MHz, DMSO-d₆) δ ppm 10.40 (br s, 1H), 10.08 (s, 1H), 8.32 (d, J=2 Hz, 1H), 7.72 (br d, J=8 Hz, 1H), 7.62 (dd, J=8, 2 Hz, 1H), 7.05 (s, 1H), 4.47 (s, 2H), 2.23 (d, J=7 Hz, 2H), 2.11 (m, 1H), 0.96 (d, J=7 Hz, 6H); MS (ESI⁻) m/z 394 (M–H)⁻.

Example 59: 5-[1-fluoro-3-hydroxy-7-(4,4,4-trifluorobutoxy)naphthalen-2-yl]-1λ⁶,2,5-thiadiazolidine-1,1,3-trione (Compound 158)

Example 59A: 5-[3-(benzyloxy)-1-fluoro-7-(4,4,4-trifluorobutoxy)naphthalen-2-yl]-1λ⁶,2,5-thiadiazolidine-1,1,3-trione The title compound was prepared using the methodologies described in Example 104A substituting 1,1,1-trifluoro-4-iodobutane for 2-bromoacetonitrile. MS (ESI⁻) m/z 511 (M–H)⁻.

Example 59B: 5-[1-fluoro-3-hydroxy-7-(4,4,4-trifluorobutoxy)naphthalen-2-yl]-1λ⁶,2,5-thiadiazolidine-1,1,3-trione The title compound was prepared using the methodologies described in Example 137B substituting Example 59A for Example 137A. ¹H NMR (500 MHz, DMSO-d₆) δ ppm 10.31 (br s, 1H), 7.73 (br d, J=8 Hz, 1H), 7.22 (s, 1H), 7.20 (dd, J=8, 2 Hz, 1H), 7.07 (s, 1H), 4.48 (s, 2H), 4.15 (t, J=8 Hz, 2H), 2.44 (m, 2H), 2.00 (m, 2H); MS (ESI⁻) m/z 421 (M–H)⁻.

Example 60: 1-(2-{[8-fluoro-6-hydroxy-7-(1,1,4-trioxo-1λ⁶,2,5-thiadiazolidin-2-yl)naphthalen-2-yl]oxy}ethyl)cyclopropane-1-carbonitrile (Compound 159)

The title compound was prepared from Example 1H and 1-(2-hydroxyethyl)cyclopropanecarbonitrile using the procedures described for Example 56 in 38% yield. ¹H NMR (400 MHz, DMSO-d₆) δ ppm 10.23 (s, 1H), 7.73 (dd, J=9.1, 1.5 Hz, 1H), 7.26 (d, J=2.5 Hz, 1H), 7.19 (dd, J=9.0, 2.5 Hz, 1H), 7.07 (s, 1H), 4.44 (s, 2H), 4.25 (t, J=6.1 Hz, 2H), 1.99 (t, J=6.1 Hz, 2H), 1.27-1.19 (m, 2H), 1.07-0.99 (m, 2H); MS (APCI⁻) m/z 404.5 (M–H)⁻.

Example 61: 5-(1-fluoro-3-hydroxy-7-{2-[1-(methoxymethyl)cyclopropyl]ethoxy}naphthalen-2-yl)-1λ⁶,2,5-thiadiazolidine-1,1,3-trione (Compound 160)

The title compound was prepared from Example 1H and 2-(1-(methoxymethyl)cyclopropyl)ethanol using the procedures for Example 56 in 24% yield. ¹H NMR (400 MHz, DMSO-d₆) δ ppm 10.33 (s, 1H), 7.71 (dd, J=9.1, 1.5 Hz, 1H), 7.21 (d, J=2.6 Hz, 1H), 7.16 (dd, J=9.0, 2.5 Hz, 1H), 7.07 (d, J=1.4 Hz, 1H), 4.50 (s, 2H), 4.17 (t, J=7.1 Hz, 2H), 3.26 (s, 3H), 3.23 (s, 2H), 1.82 (t, J=7.0 Hz, 2H), 0.49-0.43 (m, 2H), 0.43-0.37 (m, 2H); MS (APCI⁻) m/z 423.5 (M−H)⁻.

Example 62: 5-(7-{[(cyclopropylmethyl)amino] methyl}-1-fluoro-3-hydroxynaphthalen-2-yl)-1λ⁶,2, 5-thiadiazolidine-1,1,3-trione (Compound 161)

Example 62A: 5-[3-(benzyloxy)-7-ethenyl-1-fluoronaphthalen-2-yl]-1λ⁶,2,5-thiadiazolidine-1,1,3-trione To a mixture of Example 1G (2 g, 4.17 mmol), vinylboronic acid pinacol ester (3.21 g, 20.85 mmol) and potassium carbonate (1.152 g, 8.34 mmol) in dioxane (200 mL) and water (20 mL) was added 1,1-bis(diphenylphosphino)ferrocene-palladium(II) dichloride dichloromethane complex (0.681 g, 0.834 mmol) at 20° C. under nitrogen. Then the mixture was stirred at 80° C. for 18 hours under nitrogen. The reaction mixture was acidified with aqueous 2 M HCl to pH=5 and extracted with ethyl acetate (3×60 mL). The combined organic layers were washed with brine (2×60 mL), dried over anhydrous sodium sulfate and concentrated under reduced pressure. The residue was purified by flash column (SiO₂, ethyl acetate:methanol=10:1) to give the title compound (1.63 g, 3.7 mmol, 89% yield). MS (ESI⁻) m/z 411 [M−H]⁻.

Example 62B: 6-(benzyloxy)-8-fluoro-7-(1,1,4-trioxo-1λ⁶,2,5-thiadiazolidin-2-yl)naphthalene-2-carbaldehyde To solution of Example 62A (240 mg, 0.435 mmol) in tetrahydrofuran (5 mL) and water (5.00 mL) was added sodium periodate (186 mg, 0.869 mmol) at 0° C., and then a solution of osmium tetroxide (0.275 mL, 0.022 mmol, 0.079 mol/L in tert-butyl alcohol) was added into the mixture. Then the mixture was stirred at 0° C. for 3 hours. The reaction was quenched by addition of saturated aqueous sodium thiosulfate solution (20 mL). The mixture was acidified with aqueous 2 M hydrochloric acid to pH=3, and then extracted by ethyl acetate (3×20 mL). The aqueous layer was washed with ethyl acetate (2×20 mL). The combined organic layers were purified via reverse phase column [Agela 100 Å SNAP C₁₈ flash column, 330 g, 20×35 μm, flow rate 100 mL/minute, 0-100% gradient of acetonitrile in water] to give the desired aldehyde (380 mg, 0.889 mmol, 28% yield). ¹H NMR (400 MHz, DMSO-d₆) δ ppm 10.12-10.16 (m, 1H), 8.60 (s, 1H), 7.88-8.00 (m, 2H), 7.58 (br d, J=7.28 Hz, 2H), 7.50 (s, 1H), 7.29-7.41 (m, 3H), 5.33 (s, 2H), 4.10 (s, 2H); MS (ESI⁻) m/z 413 [M−H]⁻.

Example 62C: 5-(7-{[(cyclopropylmethyl)amino] methyl}-1-fluoro-3-hydroxynaphthalen-2-yl)-1λ⁶,2, 5-thiadiazolidine-1,1,3-trione A 20 mL microwave vial was charged with Example 62B (100 mg, 0.241 mmol), cyclopropylmethanamine (51.5 mg, 0.724 mmol), N,N-dimethylformamide (3 mL) and acetic acid (0.069 mL, 1.207 mmol). The mixture stirred for 15 minutes at ambient temperature followed by addition of sodium cyanoborohydride (91 mg, 1.448 mmol). The reaction mixture was stirred overnight at ambient temperature and a precipitate was formed. The mixture was filtered, and the collected solid was washed with water to give 5-[3-(benzyloxy)-7-{[(cyclopropylmethyl)amino]methyl}-1-fluoronaphthalen-2-yl]-1λ⁶,2,5-thiadiazolidine-1,1,3-trione, which was used in the next step without purification. MS (APCI⁻) m/z 468 [M−H]⁻

A 250 mL-round bottom flask was filled with nitrogen, followed by addition of Pd/C (80 mg, 0.752 mmol) and tetrahydrofuran (10 mL). A solution of crude 5-[3-(benzyloxy)-7-{[(cyclopropylmethyl)amino]methyl}-1-fluoronaphthalen-2-yl]-1λ⁶,2,5-thiadiazolidine-1,1,3-trione (80 mg, 0.170 mmol) in tetrahydrofuran (2 mL), was then added. An adapter fitted with a hydrogen balloon was inserted, and the flask was evacuated and refilled with hydrogen (3 times). The reaction was stirred at ambient temperature overnight. The mixture was filtered through a pad of diatomaceous earth under nitrogen gas. The volatiles were removed from the filtrate under reduced pressure, and the residue was subjected to preparative HPLC [Phenomenex® Luna® C18 (2) 5 μm 100 Å AXIA™ column (250 mm×25 mm). 30-100% gradient of acetonitrile (A) and 0.1% trifluoroacetic acid in water (B) over 15 minutes, at a flow rate of 25 mL/minute] to afford the title compound (20 mg, 0.053 mmol, 31% yield). ¹H NMR (400 MHz, DMSO-d₆) δ ppm 8.05 (d, J=1.7 Hz, 1H), 7.81 (dd, J=8.6, 1.5 Hz, 1H), 7.53 (dd, J=8.6, 1.7 Hz, 1H), 7.11 (d, J=1.3 Hz, 1H), 4.29 (s, 2H), 4.10 (s, 2H), 2.85 (d, J=7.4 Hz, 2H), 1.06 (tt, J=7.8, 4.8 Hz, 1H), 0.63-0.53 (m, 2H), 0.35 (dt, J=6.3, 4.4 Hz, 2H); MS (APCI⁺) m/z 380 [M+H]⁺.

Example 63: 5-(7-{[(cyclopropylmethyl)amino] methyl}-1-fluoro-3-hydroxynaphthalen-2-yl)-1λ⁶,2, 5-thiadiazolidine-1,1,3-trione (Compound 162)

The title compound was prepared using the methodologies described in Example 78 substituting 2,2-difluoropropan-1-amine for 2-(azetidin-1-yl)ethanamine. ¹H NMR (500 MHz, DMSO-d₆) δ ppm 9.93 (br s, 1H), 7.52 (br d, J=8 Hz, 1H), 7.11 (dd, J=8, 2 Hz, 1H), 6.93 (s, 1H), 6.85 (d, J=2 Hz, 1H), 4.44 (s, 2H), 3.59 (m, 2H), 1.67 (t, J=19 Hz, 3H); MS (ESI⁻) m/z 388 (M−H)⁻.

Example 64: 5-{7-[3,3-dimethyl-4-(methylamino) butoxy]-1-fluoro-3-hydroxynaphthalen-2-yl}-1λ⁶,2, 5-thiadiazolidine-1,1,3-trione (Compound 163)

Example 64A: tert-butyl (4-hydroxy-2,2-dimethylbutyl)(methyl)carbamate

A mixture of 3,3-dimethyl-4-(methylamino)butan-1-ol hydrochloride (100 mg, 0.596 mmol) and di-tert-butyl dicarbonate (137 mg, 0.626 mmol) in ethyl acetate (1 mL) was stirred at ambient temperature for 14 hours. The reaction mixture was diluted with ethyl acetate, washed with water and brine, dried over Na₂SO₄, and concentrated. The title compound was used in the next step without further purification. ¹H NMR (400 MHz, DMSO-d₆) δ ppm 4.27 (s, 1H), 3.51-3.41 (m, 2H), 3.03 (s, 2H), 2.83 (s, 3H), 1.39 (s, 9H), 1.43-1.33 (m, 2H), 0.85 (s, 6H).

Example 64B: 4-((tert-butoxycarbonyl)(methyl) amino)-3,3-dimethylbutyl methanesulfonate To the solution of tert-butyl (4-hydroxy-2,2-dimethylbutyl)(methyl)carbamate (134 mg, 0.579 mmol) in methylene chloride (5 mL) at 0° C. was added methanesulfonyl chloride (133 mg, 1.159 mmol) and pyridine (0.094 mL, 1.159 mmol). The mixture was stirred for 15 minutes at 0° C. and 2 hours at ambient temperature. Water (5 mL) was then added, and the mixture was extracted with methylene chloride (3×5 mL). The organic layers were combined, washed with a saturated solution of copper(II) sulfate (5 mL) and dried with Na$_2$SO$_4$. The volatiles were removed under reduced pressure to afford the title compound, which was subjected to the next step without purification.

Example 64C: tert-butyl (4-{[6-(benzyloxy)-8-fluoro-7-(1,1,4-trioxo-1λ$^6$,2,5-thiadiazolidin-2-yl)naphthalen-2-yl]oxy}-2,2-dimethylbutyl)methylcarbamate To the product of Example 1H (150 mg, 0.373 mmol) in N,N-dimethylformamide (3 mL) was added cesium carbonate (267 mg, 0.820 mmol) and freshly prepared crude 4-((tert-butoxycarbonyl)(methyl)amino)-3,3-dimethylbutyl methanesulfonate (Example 64B, 115 mg, 0.373 mmol). The reaction mixture was stirred overnight at 60° C. and 3 hours at 80° C. After cooling to ambient temperature, methanol (1 mL) was added, and volatiles were removed under reduced pressure. The residue was purified by preparative HPLC [Phenomenex® Luna® C18(2) 5 µm 100 Å AXIA™ column (250 mm×25 mm). 30-100% gradient of acetonitrile (A) and 0.1% ammonium acetate in water (B) over 15 minutes, at a flow rate of 25 mL/minute] to afford the title compound (55 mg, 0.089 mmol, 24% yield over 3 steps). MS (APCI$^-$) m/z 614 [M–H]$^-$.

Example 64D: 5-{7-[3,3-dimethyl-4-(methylamino)butoxy]-1-fluoro-3-hydroxynaphthalen-2-yl}-1λ$^6$,2,5-thiadiazolidine-1,1,3-trione A 250 mL-round bottom flask was filled with nitrogen, followed by addition of Pd/C (35 mg, 0.329 mmol) and tetrahydrofuran (10 mL). A solution of Example 64C (35 mg, 0.057 mmol) in tetrahydrofuran (2 mL), was then added. An adapter fitted with a hydrogen balloon was inserted, and the flask was evacuated and refilled with hydrogen (3 times). The reaction mixture was stirred at ambient temperature overnight. The mixture was filtered through a pad of diatomaceous earth under nitrogen gas. The volatiles were removed under reduced pressure and the crude material was subjected to the next step without purification. MS (APCI$^-$) m/z 524 [M–H]$^-$.

To a 50 mL-round bottom flask was added crude tert-butyl (4-{[8-fluoro-6-hydroxy-7-(1,1,4-trioxo-1λ$^6$,2,5-thiadiazolidin-2-yl)naphthalen-2-yl]oxy}-2,2-dimethylbutyl)methylcarbamate (30 mg, 0.057 mmol), methylene chloride (2 mL), and trifluoroacetic acid (2 mL) at ambient temperature. The reaction mixture was stirred for 30 minutes. The volatiles were removed under reduced pressure, and the residue was subjected to preparative HPLC [Phenomenex® Luna® C18 (2) 5 µm 100 Å AXIA™ column (250 mm×25 mm). 30-100% gradient of acetonitrile (A) and 0.1% trifluoroacetic acid in water (B) over 15 minutes, at a flow rate of 25 mL/minute] to afford the title compound (15 mg, 0.035 mmol, 62% yield over two steps). $^1$H NMR (400 MHz, DMSO-d$_6$) δ ppm 9.43 (s, 1H), 8.06 (s, 2H), 7.61 (dd, J=9.0, 1.5 Hz, 1H), 7.17 (d, J=2.5 Hz, 1H), 7.06 (dd, J=9.0, 2.5 Hz, 1H), 6.97 (d, J=1.3 Hz, 1H), 4.09 (t, J=6.8 Hz, 2H), 4.05 (s, 2H), 2.88-2.80 (m, 2H), 2.55 (t, J=5.1 Hz, 3H), 1.76 (t, J=6.8 Hz, 2H), 0.99 (s, 6H); MS (APCI$^+$) m/z 426 [M+H]$^+$.

Example 65: 5-{1-fluoro-3-hydroxy-7-[(2-phenylethyl)amino]naphthalen-2-yl}-1λ$^6$,2,5-thiadiazolidine-1,1,3-trione (Compound 164)

The title compound was prepared using the methodologies described in Example 80 substituting 2-phenylethanamine for 2-methoxyethanamine. $^1$H NMR (500 MHz, DMSO-d$_6$) δ ppm 9.74 (br s, 1H), 7.53 (br d, J=8 Hz, 1H), 7.31 (m, 4H), 7.21 (m, 1H), 7.05 (dd, J=8, 2 Hz, 1H), 6.92 (s, 1H), 6.72 (d, J=2 Hz, 1H), 4.37 (s, 2H), 3.34 (t, J=8 Hz, 2H), 2.92 (t, J=8 Hz, 2H); MS (ESI$^-$) m/z 414 (M–H)$^-$.

Example 66: 5-[7-(3-amino-3-methylbutoxy)-1-fluoro-3-hydroxynaphthalen-2-yl]-1λ$^6$,2,5-thiadiazolidine-1,1,3-trione (Compound 165)

Example 66A: 3-((tert-butoxycarbonyl)amino)-3-methylbutyl methanesulfonate

To the solution of tert-butyl (4-hydroxy-2-methylbutan-2-yl)carbamate (200 mg, 0.984 mmol) in methylene chloride (5 mL) at 0° C. was added methanesulfonyl chloride (135 mg, 1.181 mmol) and pyridine (0.159 mL, 1.968 mmol). The reaction was stirred for 15 minutes at 0° C. and 2 hours at ambient temperature. Water (5 mL) was then added, and the mixture was extracted with dichloromethane (3×5 mL). The organic layers were combined, washed with a saturated solution of CuSO$_4$ (2 mL), and dried with Na$_2$SO$_4$. The volatiles were removed under reduced pressure to afford crude 3-((tert-butoxycarbonyl)amino)-3-methylbutyl methanesulfonate, which was subjected to the next step without purification.

Example 66B: tert-butyl (4-{[6-(benzyloxy)-8-fluoro-7-(1,1,4-trioxo-1λ$^6$,2,5-thiadiazolidin-2-yl)naphthalen-2-yl]oxy}-2-methylbutan-2-yl)carbamate To the product from Example 1H (150 mg, 0.373 mmol) in N,N-dimethylformamide (3 mL) was added cesium carbonate (267 mg, 0.820 mmol) and freshly prepared 3-((tert-butoxycarbonyl)amino)-3-methylbutyl methanesulfonate (210 mg, 0.746 mmol, Example 66A). The reaction mixture was stirred overnight at 60° C. and 3 hours at 80° C. After cooling to ambient temperature, methanol (1 mL) was added, volatiles were removed under reduced pressure, and the residue was purified by preparative HPLC [Phenomenex® Luna® C18(2) 5 µm 100 Å AXIA™ column (250 mm×25 mm). 30-100% gradient of acetonitrile (A) and 0.1% ammonium acetate in water (B) over 15 minutes, at a flow rate of 25 mL/minute] to afford the title compound (14 mg, 0.024 mmol, 7% yield over two steps). MS (APCI$^-$) m/z 586 [M–H]$^-$.

Example 66C: 5-[7-(3-amino-3-methylbutoxy)-1-fluoro-3-hydroxynaphthalen-2-yl]-1λ$^6$,2,5-thiadiazolidine-1,1,3-trione A 250 mL-round bottom flask was filled with nitrogen, followed by addition of Pd/C (14 mg, 0.132 mmol) and tetrahydrofuran (10 mL). A solution of the product of Example 66B (35 mg, 0.057 mmol) in tetrahydrofuran (2 mL) was then added. An adapter fitted with a hydrogen balloon was inserted, and the flask was evacuated and refilled with hydrogen (3 times). The reaction mixture was stirred at ambient temperature overnight. The mixture was filtered through a pad of diatomaceous earth under nitrogen gas. The volatiles were removed from the filtrate under reduced pressure and the residue was subjected to the next step without purification. MS (APCI$^-$) m/z 496 [M–H]$^-$.

To a 50 mL-round bottom flask was added crude tert-butyl (4-{[8-fluoro-6-hydroxy-7-(1,1,4-trioxo-1λ$^6$,2,5-thiadiazolidin-2-yl)naphthalen-2-yl]oxy}-2-methylbutan-2-yl)carbamate (11.8 mg, 0.024 mmol) in methylene chloride (2 mL). The mixture was treated with trifluoroacetic acid (2 mL) at ambient temperature and stirred for 30 minutes at room temperature. The volatiles were removed under reduced pressure, and the residue was subjected to preparative HPLC [Phenomenex® Luna® C18(2) 5 μm 100 Å AXIA™ column (250 mm×25 mm). 30-100% gradient of acetonitrile (A) and 0.1% trifluoroacetic acid in water (B) over 15 minutes, at a flow rate of 25 mL/minute] to afford the title compound (6 mg, 0.015 mmol, 64% yield over two steps). $^1$H NMR (400 MHz, DMSO-$d_6$) δ ppm 9.48 (s, 1H), 7.83 (s, 2H), 7.69 (dd, J=9.2, 1.5 Hz, 1H), 7.25 (d, J=2.6 Hz, 1H), 7.15 (dd, J=9.0, 2.5 Hz, 1H), 7.04 (d, J=1.4 Hz, 1H), 4.23 (t, J=6.5 Hz, 2H), 4.10 (s, 2H), 2.12-2.04 (m, 2H), 1.34 (s, 6H); MS (APCI$^+$) m/z 398 [M+H]$^+$.

Example 67: 5-{1-fluoro-3-hydroxy-7-[(4,4,4-trifluorobutyl)amino]naphthalen-2-yl}-1λ$^6$,2,5-thiadiazolidine-1,1,3-trione (Compound 166)

The title compound was prepared using the methodologies described in Example 78 substituting 4,4,4-trifluorobutan-1-amine for 2-(azetidin-1-yl)ethanamine. $^1$H NMR (500 MHz, DMSO-$d_6$) δ ppm 9.72 (br s, 1H), 7.51 (br d, J=8 Hz, 1H), 7.01 (dd, J=8, 2 Hz, 1H), 6.93 (s, 1H), 6.67 (d, J=2 Hz, 1H), 4.37 (s, 2H), 3.18 (t, J=8 Hz, 2H), 2.40 (m, 2H), 1.82 (m, 2H); MS (ESI$^-$) m/z 420 (M-H)$^-$.

Example 68: 5-[7-(difluoromethyl)-1-fluoro-3-hydroxynaphthalen-2-yl]-1λ$^6$,2,5-thiadiazolidine-1,1,3-trione (Compound 167)

Example 68A: 5-[3-(benzyloxy)-7-(difluoromethyl)-1-fluoronaphthalen-2-yl]-1λ$^6$,2,5-thiadiazolidine-1,1,3-trione To the solution of 6-(benzyloxy)-8-fluoro-7-(1,1,4-trioxo-1λ$^6$,2,5-thiadiazolidin-2-yl)naphthalene-2-carbaldehyde (70 mg, 0.167 mmol, Example 62B) in dichloromethane (12 mL) was added diethylaminosulfur trifluoride (0.662 mL, 5.01 mmol) at −70° C., then the mixture was stirred for 1 hour at 0° C. and 19 hours at 20° C. The reaction was quenched by addition of saturated ammonium bicarbonate solution (20 mL). Then the mixture was acidified with aqueous hydrochloric acid (1 N) to pH=2. An additional reaction on 0.01 g scale and one reaction on 0.07 g scale were set up and run as described above. The combined reaction mixtures were extracted with ethyl acetate (3×30 mL). The organic layers were combined and washed with water (2×30 mL) and brine (2×30 mL), dried with anhydrous sodium sulfate and filtered. The filtrate was concentrated under reduced pressure to give crude title compound (140 mg, 0.128 mmol, 26.6% yield) which was used in the next step without further purification. MS (ESI$^-$) m/z 435 (M-H)$^-$.

Example 68B: 5-[7-(difluoromethyl)-1-fluoro-3-hydroxynaphthalen-2-yl]-1λ$^6$,2,5-thiadiazolidine-1,1,3-trione To a solution of the compound of Example 68A (130 mg, 0.119 mmol) in dichloromethane (3 mL) was added boron trichloride (1.192 mL, 1.192 mmol) at −70° C., and the mixture was stirred for 15 minutes at −70° C. The reaction was quenched by the addition of methanol (5 mL). An additional reaction on 0.01 g scale was set up and run as described above. The mixtures were combined and concentrated under reduced pressure. Then the residue was purified by preparative HPLC [Nano-Micro UniSil 5-100 C18 ULTRA 5 μm, 100×250 μm, flow rate 25 mL/minute, 10-100% gradient of acetonitrile in water (10 mM ammonium bicarbonate aqueous)] to give the title compound (3.2 mg, 8.62 μmol, 5.53% yield). $^1$H NMR (400 MHz, DMSO-$d_6$) δ ppm 8.10 (s, 1H), 7.87 (d, J=8.80 Hz, 1H), 7.62 (d, J=8.80 Hz, 1H), 7.27 (s, 1H), 7.15 (s, 1H), 7.13 (s, 1H), 6.99 (s, 1H), 4.21 (s, 2H); 19F NMR (377 MHz, DMSO-$d_6$) δ ppm −125.51-125.37 (m, 1 F) −108.36, −108.12 (m, 2 F); MS (ESI$^-$) m/z 345 (M-H)$^-$.

Example 69: 5-{7-[1-(dimethylphosphoryl)-2,5-dihydro-1H-pyrrol-3-yl]-1-fluoro-3-hydroxynaphthalen-2-yl}-1λ$^6$,2,5-thiadiazolidine-1,1,3-trione (Compound 168)

Example 69A: 5-[7-(2,5-dihydro-H-pyrrol-3-yl)-1-fluoro-3-hydroxynaphthalen-2-yl]-1λ$^6$,2,5-thiadiazolidine-1,1,3-trione To a solution of Example 14A (200 mg, 0.343 mmol) in dichloromethane (5 mL) was added boron trichloride (3.43 mL, 3.43 mmol) dropwise at −70° C. The mixture was stirred for 2 hours at −70° C. under nitrogen. The reaction was quenched with methanol (4 mL) at −70° C., and the resulting mixture was concentrated under reduced pressure to give the title compound (130 mg, 0.304 mmol, 89% yield) which was used in the next step without further purification. MS (ESI$^-$) m/z 362 (M-H)$^-$.

Example 69B: 5-{7-[1-(dimethylphosphoryl)-2,5-dihydro-H-pyrrol-3-yl]-1-fluoro-3-hydroxynaphthalen-2-yl}-1λ$^6$,2,5-thiadiazolidine-1,1,3-trione To a solution of Example 69A (100 mg, 0.234 mmol) in N,N-dimethylformamide (3 mL) was added N,N-diisopropylethylamine (0.409 mL, 2.339 mmol) and dimethylphosphinic chloride (105 mg, 0.936 mmol) in order at 0° C. The reaction was stirred for 12 hours at 25° C. The reaction solution was purified by reversed phase chromatography [Agela Claricep™ Flash AQ C18 Column, 20-35 μm, 100 Å, 40 g, flow rate 50 mL/minute, 5-100% gradient of acetonitrile in water] and lyophilization to give crude title compound. The crude title compound was purified by preparative thin-layer chromatography on silica gel (ethyl acetate: methyl alcohol=2:1) to give the title compound (12 mg, 0.027 mmol, 8.98% yield). $^1$H NMR (400 MHz, methanol-$d_4$) δ ppm 7.63-7.66 (m, 1H), 7.47-7.57 (m, 2H), 6.86-6.89 (m, 1H), 6.24-6.28 (m, 1H), 4.39-4.46 (m, 2H), 4.31-4.36 (m, 2H), 4.14-4.20 (m, 2H), 1.50-1.59 (m, 1H); MS (ESI$^-$) m/z 438 (M-H)$^-$.

Example 70: 5-{1-fluoro-3-hydroxy-7-[(3,3,3-trifluoropropyl)amino]naphthalen-2-yl}-1λ$^6$,2,5-thiadiazolidine-1,1,3-trione (Compound 169)

The title compound was prepared using the methodologies described in Example 78 substituting 3,3,3-trifluoropropan-1-amine for 2-(azetidin-1-yl)ethanamine. $^1$H NMR (500 MHz, DMSO-$d_6$) δ ppm 9.81 (br s, 1H), 7.53 (br d, J=8 Hz, 1H), 7.01 (dd, J=8, 2 Hz, 1H), 6.95 (s, 1H), 6.68 (d, J=2 Hz, 1H), 4.40 (s, 2H), 3.37 (t, J=8 Hz, 2H), 2.59 (m, 2H); MS (ESI$^-$) m/z 406 (M-H)$^-$.

Example 71: 5-[1-fluoro-3-hydroxy-7-(3-methoxy-3-methylbutoxy)naphthalen-2-yl]-1λ⁶,2,5-thiadiazolidine-1,1,3-trione (Compound 170)

Example 71A: 3-methoxy-3-methylbutyl methanesulfonate

To a solution of 3-methoxy-3-methylbutan-1-ol (200 mg, 1.692 mmol) in methylene chloride (5 mL) at 0° C. was added methanesulfonyl chloride (388 mg, 3.38 mmol) and triethylamine (0.354 mL, 2.54 mmol). The reaction mixture was stirred at 0° C. for 30 minutes and 2 hours at ambient temperature. Water (5 mL) was then added, and the mixture was extracted with methylene chloride (3×5 mL). The organic layers were combined, washed with brine (2 mL), and dried with $Na_2SO_4$. The volatiles were removed under reduced pressure to afford the title compound, which was subjected to the next step without purification.

Example 71B: 5-[3-(benzyloxy)-1-fluoro-7-(3-methoxy-3-methylbutoxy)naphthalen-2-yl]-1λ⁶,2,5-thiadiazolidine-1,1,3-trione To a solution of Example 1H (150 mg, 0.373 mmol) in N,N-dimethylformamide (3 mL) was slowly added a freshly prepared solution of 3-methoxy-3-methylbutyl methanesulfonate (161 mg, 0.820 mmol, Example 71A) in N,N-dimethylformamide (1 mL). The reaction was stirred overnight at 50° C. and for 3 hours at 80° C. After cooling to ambient temperature, methanol (1 mL) was added, and volatiles were removed under reduced pressure. The residue was purified by preparative HPLC [Phenomenex® Luna® C18(2) 5 μm 100 Å AXIA™ column (250 mm×25 mm). 30-100% gradient of acetonitrile (A) and 0.1% ammonium acetate in water (B) over 15 minutes, at a flow rate of 25 mL/minute] to afford the title compound (49 mg, 0.098 mmol, 26.2% yield). MS (APCI⁻) m/z 501 [M−H]⁻.

Example 71C: 5-[1-fluoro-3-hydroxy-7-(3-methoxy-3-methylbutoxy)naphthalen-2-yl]-1λ⁶,2,5-thiadiazolidine-1,1,3-trione A 250 mL-round bottom flask was filled with nitrogen, followed by addition of Pd/C (40 mg, 0.376 mmol) and tetrahydrofuran (10 mL). A solution of Example 71B (40 mg, 0.080 mmol) in tetrahydrofuran (2 mL), was then added. An adapter fitted with a hydrogen balloon was inserted and the flask was evacuated and refilled with hydrogen (3 times). The reaction mixture was stirred at ambient temperature overnight. The mixture was filtered through a pad of diatomaceous earth under nitrogen gas. The volatiles were removed from the filtrate under reduced pressure, and the residue was subjected to preparative HPLC [Phenomenex® Luna® C18(2) 5 μm 100 Å AXIA™ column (250 mm×25 mm). 30-100% gradient of acetonitrile (A) and 0.1% trifluoroacetic acid in water (B) over 15 minutes, at a flow rate of 25 mL/minute] to afford the title compound (14 mg, 0.034 mmol, 9.03% yield). ¹H NMR (501 MHz, DMSO-d₆) δ ppm 10.34 (s, 1H), 7.71 (dd, J=9.1, 1.4 Hz, 1H), 7.22 (d, J=2.6 Hz, 1H), 7.17 (dd, J=9.0, 2.5 Hz, 1H), 7.07 (d, J=1.3 Hz, 1H), 4.51 (s, 2H), 4.14 (t, J=7.2 Hz, 2H), 3.13 (s, 3H), 1.97 (t, J=7.2 Hz, 2H), 1.19 (s, 6H); MS (APCI⁻) m/z 411 [M−H]⁻.

Example 72: 5-[7-(2-cyclopropylpropoxy)-1-fluoro-3-hydroxynaphthalen-2-yl]-1λ⁶,2,5-thiadiazolidine-1,1,3-trione (Compound 171)

Example 72A: 5-[3-(benzyloxy)-7-(2-cyclopropylpropoxy)-1-fluoronaphthalen-2-yl]-1λ⁶,2,5-thiadiazolidine-1,1,3-trione To a suspension of Example 1H (120 mg, 0.298 mmol) in N,N-dimethylformamide (3 mL), was added cesium carbonate (214 mg, 0.656 mmol) and (1-bromopropan-2-yl)cyclopropane (107 mg, 0.656 mmol). The mixture was heated to 90° C. for 2 hours. After cooling, the mixture was filtered, and the filtrate was concentrated. The residue was subjected to preparative HPLC [Phenomenex® Luna® C18(2) 5 μm 100 Å AXIA™ column (250 mm×25 mm). 30-100% gradient of acetonitrile (A) and 0.1% trifluoroacetic acid in water (B) over 15 minutes, at a flow rate of 25 mL/minute] to the title compound (59 mg, 0.122 mmol, 41% yield). ¹H NMR (400 MHz, DMSO-d₆) δ ppm 7.80 (dd, J=9.8, 1.5 Hz, 1H), 7.56-7.48 (m, 2H), 7.43-7.34 (m, 3H), 7.37-7.29 (m, 1H), 7.33-7.23 (m, 2H), 5.24 (s, 2H), 4.46 (s, 2H), 4.10 (dd, J=9.4, 5.0 Hz, 1H), 3.98 (dd, J=9.4, 7.0 Hz, 1H), 1.31-1.20 (m, 1H), 1.09 (d, J=6.7 Hz, 3H), 0.73 (dtd, J=13.3, 8.6, 4.9 Hz, 1H), 0.50-0.37 (m, 2H), 0.26 (ddd, J=10.4, 4.7, 1.8 Hz, 1H), 0.14 (ddd, J=9.3, 4.8, 1.6 Hz, 1H); MS (APCI⁻) m/z 483 [M−H]⁻.

Example 72B: 5-[7-(2-cyclopropylpropoxy)-1-fluoro-3-hydroxynaphthalen-2-yl]-1λ⁶,2,5-thiadiazolidine-1,1,3-trione A 250 mL-round bottom flask was filled with nitrogen, followed by addition of Pd/C (45 mg, 0.423 mmol) and tetrahydrofuran (10 mL). A solution of Example 72A (45 mg, 0.093 mmol) in tetrahydrofuran (2 mL) was then added. An adapter fitted with a hydrogen balloon was inserted and the flask was evacuated and refilled with hydrogen (3 times). The reaction mixture was stirred at ambient temperature overnight. The mixture was filtered through a pad of diatomaceous earth under nitrogen gas. The filtrate was concentrated under reduced pressure. The residue was subjected to preparative HPLC [Phenomenex® Luna® C18(2) 5 μm 100 Å AXIA™ column (250 mm×25 mm). 30-100% gradient of acetonitrile (A) and 0.1% trifluoroacetic acid in water (B) over 15 minutes, at a flow rate of 25 mL/minute] to afford the title compound (13 mg, 0.033 mmol, 7.79% yield). ¹H NMR (501 MHz, DMSO-d₆) δ ppm 10.33 (s, 1H), 7.71 (dt, J=8.1, 1.4 Hz, 1H), 7.19 (d, J=8.1 Hz, 2H), 7.07 (s, 1H), 4.50 (s, 2H), 4.08 (dd, J=9.3, 5.1 Hz, 1H), 3.95 (dd, J=9.3, 7.1 Hz, 1H), 1.26 (tt, J=9.3, 6.1 Hz, 1H), 1.08 (d, J=6.7 Hz, 3H), 0.78-0.67 (m, 1H), 0.49-0.38 (m, 2H), 0.25 (ddd, J=10.9, 4.8, 2.2 Hz, 1H), 0.13 (ddd, J=9.3, 4.8, 1.7 Hz, 1H); MS (APCI⁻) m/z 393 [M−H]⁻.

Example 73: 5-[1-fluoro-3-hydroxy-7-({2-[(propan-2-yl)oxy]ethyl}amino)naphthalen-2-yl]-1λ⁶,2,5-thiadiazolidine-1,1,3-trione (Compound 172)

The title compound was prepared using the methodologies described in Example 80 substituting 2-isopropoxyethanamine for 2-methoxyethanamine. ¹H NMR (500 MHz, DMSO-d₆) δ ppm 7.46 (br d, J=8 Hz, 1H), 7.01 (dd, J=8, 2 Hz, 1H), 6.89 (s, 1H), 6.66 (d, J=2 Hz, 1H), 5.78 (t, t=6 Hz, 1H),), 4.07 (s, 2H), 3.60 (m, 1H), 3.57 (t, J=8 Hz, 2H), 3.23 (m, 2H), 1.11 (d, J=8 Hz, 6H); MS (ESI⁻) m/z 396 (M−H)⁻.

Example 74: 5-(1-fluoro-3-hydroxy-7-{[1-(methanesulfonyl)pyrrolidin-3-yl]methoxy}naphthalen-2-yl)-1$\lambda^6$,2,5-thiadiazolidine-1,1,3-trione (Compound 173)

The title compound was prepared as described for Example 56B from Example 1H and 3-(bromomethyl)-1-methylsulfonylpyrrolidine in 39.7% yield. $^1$H NMR (400 MHz, DMSO-d$_6$) δ ppm 10.14 (s, 1H), 7.68 (dd, J=9.0, 1.5 Hz, 1H), 7.21 (d, J=2.6 Hz, 1H), 7.16 (dd, J=9.0, 2.5 Hz, 1H), 7.03 (s, 1H), 4.38 (s, 2H), 4.06 (qd, J=9.6, 6.8 Hz, 2H), 3.50-3.41 (m, 2H), 3.28-3.20 (m, 1H), 3.10 (dd, J=10.1, 6.9 Hz, 1H), 2.88 (s, 3H), 2.72 (p, J=7.2 Hz, 1H), 2.07 (m, 1H), 1.77 (m, 1H); MS (APCI$^-$) m/z 472.3 (M–H)$^-$.

Example 75: 4-{[8-fluoro-6-hydroxy-7-(1,1,4-trioxo-1$\lambda^6$,2,5-thiadiazolidin-2-yl)naphthalen-2-yl]amino}butanenitrile (Compound 174)

The title compound was prepared using the methodologies described in Example 78 substituting 4-aminobutanenitrile for 2-(azetidin-1-yl)ethanamine. $^1$H NMR (500 MHz, –d$_6$) δ ppm 10.15 (br s, 1H), 7.96 (br s, 1H), 7.53 (d, J=8 Hz, 1H), 7.07 (dd, J=8, 2 Hz, 1H), 6.95 (br s, 1H), 6.80 (br s, 1H), 4.47 (s, 2H), 3.17 (t, J=8 Hz, 2H), 2.60 (m, 2H), 1.87 (m, 2H); MS (ESI$^-$) m/z 377 (M–H)$^-$.

Example 76: 5-[1-fluoro-3-hydroxy-7-(2-hydroxyethyl)naphthalen-2-yl]-1$\lambda^6$,2,5-thiadiazolidine-1,1,3-trione (Compound 175)

Example 76A: 5-[3-(benzyloxy)-1-fluoro-7-(prop-2-en-1-yl)naphthalen-2-yl]-1$\lambda^6$,2,5-thiadiazolidine-1,1,3-trione To a solution of Example 1G in 1,4-dioxane (5 mL) were added allylboronic acid pinacol ester (280 mg, 1.668 mmol), potassium carbonate (173 mg, 1.251 mmol) and [1,1'-bis(diphenylphosphino)ferrocene]dichloropalladium(II), complex with dichloromethane (Pd (dppf)Cl$_2$.CH$_2$C$_2$, 34.0 mg, 0.042 mmol) at 25° C. under nitrogen, and the reaction mixture was stirred at 80° C. for 16 hours under nitrogen. An additional reaction on 30 mg scale was set up and run as described above. The resulting mixtures were combined and concentrated under reduced pressure. The residue was purified by flash column chromatography on silica gel (elution with methanol/dichloromethane from 0 to 20%) to give the title compound (120 mg, 0.27 mmol, 64.8% yield). $^1$H NMR (400 MHz, DMSO-d$_6$) δ ppm 7.77 (d, J=8.33 Hz, 1H), 7.72 (s, 1H), 7.56 (d, J=7.45 Hz, 2H), 7.34-7.41 (m, 3H), 7.28-7.33 (m, 2H), 5.95-6.13 (m, 1H), 5.22-5.26 (m, 2H), 5.06-5.16 (m, 2H), 4.07-4.09 (m, 2H), 3.51-3.56 (m, 2H), 3.12-3.21 (m, 4H); MS (ESI$^-$) m/z 425 (M–H)$^-$.

Example 76B: [6-(benzyloxy)-8-fluoro-7-(1,1,4-trioxo-1$\lambda^6$,2,5-thiadiazolidin-2-yl)naphthalen-2-yl]acetaldehyde To solution of Example 76A (1 g, 2.345 mmol) in tetrahydrofuran (15 mL) and water (5 mL) was added sodium periodate (1.003 g, 4.69 mmol) at 20° C., and then osmium tetroxide (1 M in tert-butanol, 0.117 mL, 0.117 mmol) was added at 0° C. The mixture was stirred at 0° C. for 3 hours. Then the reaction was quenched with saturated aqueous sodium sulfite (150 mL). The mixture was acidified with aqueous hydrochloric acid (1 M) to pH=5, and then extracted with ethyl acetate (3×100 mL). The aqueous layer was filtered and purified by reversed-phase chromatography [Agela Claricep™ Flash AQ C18 Column, 20-35 μm, 100 Å, 120 g flash column, flow rate 50 mL/minute, 0-100% gradient of acetonitrile in water] to give the title compound (500 mg, 1.167 mmol, 24.8% yield). MS (ESI$^-$) m/z 427 (M–H)$^-$.

Example 76C: 5-[3-(benzyloxy)-1-fluoro-7-(2-hydroxyethyl)naphthalen-2-yl]-1$\lambda^6$,2,5-thiadiazolidine-1,1,3-trione To the solution of Example 76B (200 mg, 0.327 mmol) in tetrahydrofuran (2 mL) was added sodium borohydride (37.1 mg, 0.980 mmol) at 0° C., and the mixture was stirred for 2 hours at 0° C. The reaction was quenched by addition of water (15 mL) at 25° C., and then stirred for 5 minutes. The resulting mixture was extracted with ethyl acetate (3×20 mL). The organic phase was washed with brine, dried over anhydrous sodium sulfate and concentrated under reduced pressure. The residue was was purified by preparative HPLC [Kromasil 150×25 mm, 10 μm, C18 column, flow rate 25 mL/minute, 10-100% gradient of acetonitrile in water (0.04% ammonium hydroxide and ammonium bicarbonate 10 mM)] to afford the title compound (30 mg, 0.063 mmol, 19.41% yield). $^1$H NMR (400 MHz, DMSO-d$_6$) δ ppm 7.70-7.75 (m, 1H), 7.51-7.57 (m, 2H), 7.39-7.44 (m, 1H), 7.32-7.38 (m, 2H), 7.25-7.32 (m, 2H), 7.17-7.21 (m, 1H), 7.06 (s, 1H), 6.91-6.96 (m, 1H), 5.15-5.28 (m, 2H), 4.08 (s, 2H), 3.65 (t, J=6.84 Hz, 1H), 2.79-2.92 (m, 2H); MS (ESI$^+$) m/z 431 (M+H)$^+$.

Example 76D: 5-[1-fluoro-3-hydroxy-7-(2-hydroxyethyl)naphthalen-2-yl]-1$\lambda^6$,2,5-thiadiazolidine-1,1,3-trione, ammonium salt To solution of Example 76C (28 mg, 0.059 mmol) in methanol (15 mL) was added 10% Pd/C (6.30 mg) at 20° C. under argon. The suspension was degassed under vacuum and purged with hydrogen several times, and then the reaction was stirred for 2 hours at 20° C. The reaction mixture was filtered, and the filtrate was concentrated under reduced pressure. The residue was purified by preparative HPLC [Waters Xbridge™ 150×25 μm, 5 μm column, flow rate 50 mL/minute, 25-100% gradient of acetonitrile in aqueous ammonium bicarbonate (10 mM)] to afford the title compound as an ammonium salt (2.3 mg, 6.29 μmol, 9.39% yield). $^1$H NMR (400 MHz, DMSO-d$_6$) δ ppm 9.57-9.67 (m, 1H), 7.61-7.70 (m, 2H), 7.35 (dd, J=8.44, 1.47 Hz, 1H), 7.17-7.26 (m, 1H), 7.08-7.16 (m, 1H), 7.02 (s, 1H), 6.91-7.00 (m, 1H), 4.59-4.70 (m, 1H), 4.06-4.10 (m, 2H), 3.64-3.68 (m, 2H), 3.64-3.64 (m, 1H), 3.16-3.18 (m, 1H), 2.84-2.87 (m, 2H); $^1$H NMR (400 MHz, DMSO-d$_6$/D$_2$O) δ ppm 7.66-7.68 (m, 1H), 7.61-7.65 (m, 1H), 7.33-7.38 (m, 1H), 7.00-7.04 (m, 1H), 4.05-4.13 (m, 2H), 3.65-3.66 (m, 2H), 3.13-3.16 (m, 1H), 2.80-2.88 (m, 2H); MS (ESI$^+$) m/z 341 (M+H)$^+$.

Example 77: 5-[7-(4-amino-3,3-dimethylbutoxy)-1-fluoro-3-hydroxynaphthalen-2-yl]-1$\lambda^6$,2,5-thiadiazolidine-1,1,3-trione (Compound 176)

Example 77A: 4-{[6-(benzyloxy)-8-fluoro-7-(1,1,4-trioxo-1$\lambda^6$,2,5-thiadiazolidin-2-yl)naphthalen-2-yl]oxy}-2,2-dimethylbutanenitrile To a solution of Example 1H (100 mg, 0.249 mmol) in N,N-dimethylformamide (3 mL) was added sodium hydride (21.87 mg, 0.547 mmol) at ambient temperature in three portions. The reaction was stirred for 30 minutes until no evolution of bubbles was observed. A solution of 4-bromo-2,2-dimethylbutanenitrile (96 mg, 0.547 mmol) in N,N-dimethylformamide (2 mL) was slowly added to the reaction mixture. The reaction was stirred overnight at ambient temperature. Methanol (2 mL) was added, the solvents were removed under reduced pressure, and the residue was subjected to column chromatography ($SiO_2$, 10% methanol in dichloromethane) to afford the title compound (65 mg, 0.131 mmol, 53% yield). $^1$H NMR (501 MHz, DMSO-$d_6$) δ ppm 7.77 (dd, J=9.1, 1.4 Hz, 1H), 7.59-7.50 (m, 2H), 7.44-7.26 (m, 5H), 7.20 (dd, J=9.0, 2.5 Hz, 1H), 5.22 (s, 2H), 4.28 (t, J=6.5 Hz, 2H), 4.09 (s, 2H), 3.17 (d, J=5.2 Hz, 1H), 2.12-2.05 (m, 2H), 1.41 (s, 6H); MS (APCI$^-$) m/z 496 (M−H)$^-$.

Example 77B: 5-[7-(4-amino-3,3-dimethylbutoxy)-1-fluoro-3-hydroxynaphthalen-2-yl]-1λ$^6$,2,5-thiadiazolidine-1,1,3-trione Example 77A (26 mg, 0.052 mmol) and acetic acid (1 mL) were added to 10% Pd/C, dry (48 mg, 0.451 mmol) in a 20 mL Barnstead Hast C reactor. The reaction was stirred for 45 hours at ambient temperature under 117 psi hydrogen gas. The reaction was filtered, the volatiles were removed under reduced pressure, and the residue was subjected to preparative HPLC [Phenomenex® Luna® C18(2) 5 μm 100 Å AXIA™ column (250 mm×25 mm). 30-100% gradient of acetonitrile (A) and 0.1% trifluoroacetic acid in water (B) over 15 minutes, at a flow rate of 25 mL/minute] to afford the title compound (9 mg, 0.022 mmol, 4% yield). $^1$H NMR (400 MHz, DMSO-$d_6$) δ ppm 9.50 (s, 1H), 7.75 (d, J=1.4 Hz, 1H), 7.73 (broad, 2H), 7.31 (d, J=2.6 Hz, 1H), 7.19 (dd, J=9.0, 2.5 Hz, 1H), 7.12-7.07 (m, 1H), 4.22 (t, J=6.8 Hz, 2H), 4.15 (s, 2H), 2.85 (s, 2H), 1.88 (t, J=6.8 Hz, 2H), 1.10 (s, 6H); MS (APCI$^+$) m/z 412 [M+H]$^+$.

Example 78: 5-(7-{[2-(azetidin-1-yl)ethyl]amino}-1-fluoro-3-hydroxynaphthalen-2-yl)-1λ$^6$,2,5-thiadiazolidine-1,1,3-trione (Compound 177)

Example 78A: 5-[7-{[2-(azetidin-1-yl)ethyl]amino}-3-(benzyloxy)-1-fluoronaphthalen-2-yl]-1λ$^6$,2,5-thiadiazolidine-1,1,3-trione A mixture of Example 1G (93 mg, 0.2 mmol), BrettPhos Pd G3 (10.88 mg, 0.012 mmol), BrettPhos (6.44 mg, 0.012 mmol), cesium carbonate (195 mg, 0.600 mmol) and 2-(azetidin-1-yl)ethanamine (40.1 mg, 0.400 mmol) in 2-methylbutan-2-ol (2 mL) was degassed and filled with nitrogen five times and then was heated to 105° C. for 3 hours. Dichloromethane/methanol (10:1, 50 mL) was added to the mixture followed by 4 M HCl in dioxane (0.2 mL). The mixture was stirred for 10 minutes and filtered. The filtrate was concentrated, and the residue was purified by flash column chromatography on silica gel (12 g) eluted with dichloromethane/methanol (0 to 65%) to give the title compound (85 mg, 0.175 mmol, 88% yield). MS (ESI$^-$) m/z 483 (M−H)$^-$.

Example 78B: 5-(7-{[2-(azetidin-1-yl)ethyl]amino}-1-fluoro-3-hydroxynaphthalen-2-yl)-1λ$^6$,2,5-thiadiazolidine-1,1,3-trione To a mixture of 1,2,3,4,5-pentamethylbenzene (41.3 mg, 0.279 mmol) and Example 78A (45 mg, 0.093 mmol) in dichloromethane (2.5 mL) at −78° C. was added trichloroborane (1.672 mL, 1.672 mmol, 1 M in dichloromethane). The mixture was stirred at −78° C. for 20 minutes, warmed to 0° C. for 30 minutes, and then quenched with ethanol (4 mL). The mixture was stirred at ambient temperature for 5 minutes and concentrated. The residue was washed with dichloromethane (4×4 mL) and dried to give the title compound (40 mg, 0.093 mmol, 100% yield). $^1$H NMR (500 MHz, DMSO-$d_6$) δ ppm 10.38 (br s, 1H), 10.12 (br s, 1H), 7.55 (br d, J=8 Hz, 1H), 7.03 (dd, J=8, 2 Hz, 1H), 6.97 (s, 1H), 6.75 (d, J=2 Hz, 1H), 4.50 (s, 2H), 4.11 (m, 2H), 4.06 (m, 2H), 3.37 (m, 4H), 2.40 (m, 1H), 2.25 (m, 1H); MS (ESI$^-$) m/z 393 (M−H)$^-$.

Example 79: 5-(7-{[1-(cyclopropanesulfonyl)azetidin-3-yl]oxy}-1-fluoro-3-hydroxynaphthalen-2-yl)-1λ$^6$,2,5-thiadiazolidine-1,1,3-trione (Compound 178)

Example 79A: tert-butyl 3-{[6-(benzyloxy)-8-fluoro-7-(1,1,4-trioxo-1λ$^6$,2,5-thiadiazolidin-2-yl)naphthalen-2-yl]oxy}azetidine-1-carboxylate A mixture of Example 1H (150 mg, 0.373 mmol), $Cs_2CO_3$ (243 mg, 0.746 mmol) and tert-butyl 3-iodoazetidine-1-carboxylate (106 mg, 0.373 mmol) in N,N-dimethylformamide (1 mL) was stirred at ambient temperature for 4 hours. The mixture was heated at 60° C. for 14 hours. After cooling down, a 2 N $Na_2CO_3$ solution (0.5 mL) was added, and the mixture was extracted with 20 mL of ethyl acetate. The organic layer was discarded, and the aqueous layer was acidified with acetic acid (0.25 mL) and extracted with ethyl acetate (2×25 mL). The combined ethyl acetate fractions were washed with brine, dried over $Na_2SO_4$, and concentrated to give the title compound which was used without further purification in the next step. $^1$H NMR (501 MHz, DMSO-$d_6$) δ ppm 7.85 (dd, J=9.1, 1.3 Hz, 1H), 7.55-7.48 (m, 2H), 7.42 (s, 1H), 7.38 (t, J=7.3 Hz, 2H), 7.36-7.30 (m, 1H), 7.26 (dd, J=8.9, 2.5 Hz, 1H), 7.06 (d, J=2.6 Hz, 1H), 5.24 (s, 2H), 5.17 (tt, J=6.4, 3.9 Hz, 1H), 4.43 (d, J=2.7 Hz, 2H), 4.37 (s, 2H), 3.85 (dd, J=10.0, 3.7 Hz, 2H), 1.40 (s, 9H).

Example 79B: 5-{7-[(azetidin-3-yl)oxy]-3-(benzyloxy)-1-fluoronaphthalen-2-yl}-1λ$^6$,2,5-thiadiazolidine-1,1,3-trione A mixture of Example 79A (190 mg, 0.341 mmol) and trifluoroacetic acid (0.5 mL) in $CH_2Cl_2$ (3 mL) was stirred at ambient temperature for 4 hours and then at 60° C. for 14 hours. The mixture was concentrated to give the title compound which was used in the next step without further purification. MS (APCI$^+$) m/z 469.8 (M+H)$^+$.

Example 79C: 5-[3-(benzyloxy)-7-{[1-(cyclopropanesulfonyl)azetidin-3-yl]oxy}-1-fluoronaphthalen-2-yl]-1λ$^6$,2,5-thiadiazolidine-1,1,3-trione To a mixture of Example 79B (60 mg, 0.131 mmol) and triethylamine (39.8 mg, 0.393 mmol) in 1:1 $CH_2Cl_2$—N,N-dimethylformamide (1 mL) was added cyclopropanesulfonyl chloride (23.97 mg, 0.171 mmol). The mixture was stirred at ambient temperature for 14 hours. The mixture was diluted with ethyl acetate, washed with 0.1 N HCl and brine, dried over $Na_2SO_4$, and concentrated to give the title compound which was used in the next step without further purification. $^1$H NMR (400 MHz, DMSO-$d_6$) δ ppm 7.82

(dd, J=9.1, 1.5 Hz, 1H), 7.52-7.46 (m, 2H), 7.39 (s, 1H), 7.38-7.29 (m, 3H), 7.25 (dd, J=9.0, 2.6 Hz, 1H), 7.10 (d, J=2.6 Hz, 1H), 5.21 (m, 3H), 4.44-4.32 (m, 4H), 3.95 (dd, J=9.3, 4.5 Hz, 2H), 2.81-2.74 (m, 1H), 1.06-0.99 (m, 2H), 0.93 (dd, J=4.6, 2.4 Hz, 2H).

Example 79D: 5-(7-{[1-(cyclopropanesulfonyl)azetidin-3-yl]oxy}-1-fluoro-3-hydroxynaphthalen-2-yl)-1$\lambda^6$,2,5-thiadiazolidine-1,1,3-trione The above Example 79C (35 mg, 0.062 mmol) and 20% Pd (OH)$_2$ wet (70 mg, 0.254 mmol) in tetrahydrofuran (2 mL) was stirred under 50 psi of H$_2$ for 50 hours. The mixture was filtered, concentrated and purified by preparative HPLC on a Phenomenex C8(2) Luna 5 μm AXIA™ 150×30 mm column with a gradient of 5-100% acetonitrile (A) in 0.1% trifluoroacetic acid in water (B) at a flow rate of 50 mL/minute to give the title compound (8 mg, 0.017 mmol, 27.2% yield). $^1$H NMR (501 MHz, DMSO-d$_6$) δ ppm 10.22 (s, 1H), 7.76 (dd, J=9.1, 1.4 Hz, 1H), 7.20 (dd, J=9.0, 2.6 Hz, 1H), 7.08 (s, 1H), 7.06 (d, J=2.6 Hz, 1H), 5.22 (tt, J=6.5, 4.7 Hz, 1H), 4.44-4.32 (m, 4H), 3.98 (dd, J=9.3, 4.6 Hz, 2H), 2.82 (tt, J=7.9, 4.8 Hz, 1H), 1.09-0.99 (m, 2H), 1.02-0.93 (m, 2H); MS (APCI$^-$) m/z 469.8 (M–H)$^-$.

Example 80: 5-{1-fluoro-3-hydroxy-7-[(2-methoxyethyl)amino]naphthalen-2-yl}-1$\lambda^6$,2,5-thiadiazolidine-1,1,3-trione (Compound 179)

A mixture of Example 1G (93 mg, 0.2 mmol), BrettPhos Pd G3 (10.88 mg, 0.012 mmol), BrettPhos (6.44 mg, 0.012 mmol), cesium carbonate (195 mg, 0.600 mmol) and 2-methoxyethanamine (30.0 mg, 0.400 mmol) in 2-methylbutan-2-ol (2 mL) was degassed and filled with nitrogen five times and then was heated to 105° C. for 3 hours. Dichloromethane/methanol (10:1, 50 mL) was added to the mixture followed by 4 M HCl in dioxane (0.2 mL). The mixture was stirred for 10 minutes and filtered. The filtrate was concentrated, and the residue was purified by flash column chromatography on silica gel (40 g) eluted with dichloromethane/methanol (0 to 35%) to give the title compound (20 mg, 0.054 mmol, 27.1% yield). $^1$H NMR (500 MHz, DMSO-d$_6$) δ ppm 8.87 (br s, 1H), 7.46 (br d, J=8 Hz, 1H), 7.01 (dd, J=8, 2 Hz, 1H), 6.89 (s, 1H). 6.65 (d, J=2 Hz, 1H), 5.85 (t, J=5 Hz, 1H), 4.07 (s, 2H), 3.53 (m, 2H), 3.28 (s, 3H), 3.26 (m, 1H), 2.97 (m, 1H); MS (ESI$^-$) m/z 368 (M–H)$^-$.

Example 81: 5-[1-fluoro-3-hydroxy-7-(3,3,3-trifluoropropoxy)naphthalen-2-yl]-1$\lambda^6$,2,5-thiadiazolidine-1,1,3-trione (Compound 180)

Example 81A: 5-(3-(benzyloxy)-1-fluoro-7-(3,3,3-trifluoropropoxy)naphthalen-2-yl)-1,2,5-thiadiazolidin-3-one 1,1-dioxide The title compound was prepared using the methodologies described in Example 104A substituting 3,3,3-trifluoropropyl methanesulfonate for 2-bromoacetonitrile. MS (ESI$^-$) m/z 497 (M–H)$^-$.

Example 81B: 5-[1-fluoro-3-hydroxy-7-(3,3,3-trifluoropropoxy)naphthalen-2-yl]-1$\lambda^6$,2,5-thiadiazolidine-1,1,3-trione The title compound was prepared using the methodologies described in Example 137B substituting Example 81A for Example 137A. $^1$H NMR (500 MHz, DMSO-d$_6$) δ ppm 10.20 (br s, 1H), 7.72 (br d, J=8 Hz, 1H), 7.27 (d, J=2 Hz, 1H), 7.18 (dd, J=8, 2 Hz, 1H), 7.09 (s, 1H), 4.40 (s, 2H), 4.33 (t, J=8 Hz, 2H), 2.84 (m, 2H); MS (ESI$^-$) m/z 407 (M–H)$^-$.

Example 82: 1-({[8-fluoro-6-hydroxy-7-(1,1,4-trioxo-1$\lambda^6$,2,5-thiadiazolidin-2-yl)naphthalen-2-yl]amino}methyl)cyclopropane-1-carbonitrile (Compound 181)

In a 20 mL pressure release vial, combined the product of Example 1G (0.605 g, 1.3 mmol), cesium carbonate (1.271 g, 3.90 mmol), methanesulfonato(2-dicyclohexylphosphino-3,6-dimethoxy-2',4',6'-tri-i-propyl-1,1'-biphenyl)(2'-amino-1,1'-biphenyl-2-yl)palladium(II) (BrettPhos Pd G3 precatalyst, 0.035 g, 0.039 mmol), and 2-(dicyclohexylphosphino) 3,6-dimethoxy-2',4',6'-triisopropyl-1,1'-biphenyl (BrettPhos, 0.021 g, 0.039 mmol). The solids were placed under vacuum for 5 minutes at ambient temperature, then the vial was filled with nitrogen, followed by tert-amyl alcohol (12 mL) and 1-(aminomethyl)cyclopropanecarbonitrile (0.25 g, 2.60 mmol). The resulting suspension was degassed by five vacuum/nitrogen backfills, stirred for 10 minutes at ambient temperature and then heated to 90° C. After 73 hours, the reaction mixture was cooled to ambient temperature, then quenched with 1 M hydrochloric acid (6 mL) and diluted with ethyl acetate (6 mL). The aqueous layer was extracted with ethyl acetate (2×6 mL). The combined organic layers were washed with a 4:1 mixture of brine and 1 M hydrochloric acid (3 mL), dried over anhydrous sodium sulfate, then filtered and concentrated under reduced pressure to give 2-[3-(benzyloxy)-7-{[(1-cyanocyclopropyl)methyl]amino}-1-fluoronaphthalen-2-yl]-4-oxo-1$\lambda^4$,2,5-thiadiazolidine-1,1-bis(olate), which was used for the next reaction without purification. MS (APCI$^-$) m/z 479 [M–H]$^-$.

To a suspension of the crude 2-[3-(benzyloxy)-7-{[(1-cyanocyclopropyl)methyl]amino}-1-fluoronaphthalen-2-yl]-4-oxo-1$^4$,2,5-thiadiazolidine-1,1-bis(olate) (0.625 g, 1.301 mmol) and pentamethylbenzene (0.386 g, 2.60 mmol) in dichloromethane (12 mL) at −78° C. was added a solution of boron trichloride in dichloromethane (7.8 mL, 1 M, 7.8 mmol) slowly along the side of the flask so that the internal temperature remained below −70° C. The resulting solution was stirred for 5 minutes at −78° C., then the cooling bath was removed, and the reaction mixture was allowed to warm to an internal temperature of 0° C. before cooling back to −78° C. The reaction was quenched by addition of ethyl acetate (5 mL) followed by anhydrous ethanol (5 mL). The mixture was warmed to ambient temperature and concentrated under reduced pressure to give a solid. The solid was triturated with heptanes (3×5 mL), then dichloromethane (2×3 mL). The triturated product was dissolved in a dimethyl sulfoxide/methanol mixture and was filtered through a glass microfiber frit. The resulting solution was directly purified by preparative HPLC [Waters XBridge™ C18 5 μm OBD column, 50×100 mm, flow rate 100 mL/minute, a gradient of 5-40% methanol in buffer (0.1% trifluoroacetic acid in water by volume)] to give the title compound (0.2446 g, 0.627 mmol, 48.2% yield). $^1$H NMR (501 MHz, DMSO-d$_6$) δ ppm 10.05 (s, 1H), 7.54 (dd, J=9.0, 1.5 Hz, 1H), 7.10 (dd, J=8.9, 2.3 Hz, 1H), 6.94 (s, 1H), 6.79 (d, J=2.3 Hz, 1H), 4.49 (s, 2H), 3.33 (s, 2H), 1.25 (q, J=4.6 Hz, 2H), 1.13-1.04 (m, 2H); MS (ESI$^-$) m/z 389 [M–H]$^-$.

Example 83: 5-[1-fluoro-3-hydroxy-7-(3-hydroxy-3-methylbutoxy)naphthalen-2-yl]-1λ⁶,2,5-thiadiazolidine-1,1,3-trione (Compound 182)

Example 83A: 5-[3-(benzyloxy)-1-fluoro-7-(3-hydroxy-3-methylbutoxy)naphthalen-2-yl]-1λ⁶,2,5-thiadiazolidine-1,1,3-trione A mixture of Example 1H (100 mg, 0.249 mmol), 4-bromo-2-methylbutan-2-ol (49.8 mg, 0.298 mmol) and $Cs_2CO_3$ (162 mg, 0.497 mmol) in N,N-dimethylformamide (1 mL) was stirred at ambient temperature for 14 hours. The mixture was diluted with ethyl acetate and 0.2 N HCl (15 mL). The organic layer was separated, washed with brine, dried over $Na_2SO_4$, and concentrated to give the title compound which was used in the next step without further purification. MS (APCI⁻) m/z 487.5 (M−H)⁻.

Example 83B: 5-[1-fluoro-3-hydroxy-7-(3-hydroxy-3-methylbutoxy)naphthalen-2-yl]-1λ⁶,2,5-thiadiazolidine-1,1,3-trione Example 83A (120 mg, 0.246 mmol) in tetrahydrofuran (6 mL) was added to a 20 mL Barnstead Hast C reactor charged with 5% Pd/C, wet (145 mg, 0.681 mmol). The mixture was stirred under hydrogen at 150 psi pressure for 25 hours at 25° C. The reaction mixture was filtered, the filtrate was concentrated, and the residue was triturated with dichloromethane to give the title compound (65 mg, 0.163 mmol, 66.4% yield). $^1$H NMR (400 MHz, DMSO-d$_6$) δ ppm 10.22 (s, 1H), 7.70 (dd, J=9.1, 1.5 Hz, 1H), 7.22 (d, J=2.5 Hz, 1H), 7.16 (dd, J=9.0, 2.6 Hz, 1H), 7.06 (s, 1H), 4.45 (s, 2H), 4.19 (t, J=7.2 Hz, 2H), 1.90 (t, J=7.2 Hz, 2H), 1.19 (s, 6H); MS (APCI⁻) m/z 397.7 (M−H)⁻.

Example 84: 5-{1-fluoro-3-hydroxy-7-[3-(H-pyrazol-1-yl)propoxy]naphthalen-2-yl}-1λ⁶,2,5-thiadiazolidine-1,1,3-trione (Compound 183)

Example 84A: 5-{3-(benzyloxy)-1-fluoro-7-[3-(H-pyrazol-1-yl)propoxy]naphthalen-2-yl}-1λ⁶,2,5-thiadiazolidine-1,1,3-trione A mixture of the product of Example 1H (125 mg, 0.31 mmol), 1-(3-chloropropyl)-1H-pyrazole (89.8 mg, 0.62 mmol) and cesium carbonate (304 mg, 0.93 mmol) in N,N-dimethylformamide (2 mL) was stirred at 50° C. for 14 hours. The reaction mixture was filtered and purified by reverse-phase preparative HPLC on a Phenomenex® Luna® C8(2) 5 μm 100 Å AXIA™ column (50 mm×30 mm) eluted with a gradient of 5-100% acetonitrile (A) and 0.1% ammonium acetate in water (B) at a flow rate of 40 mL/minute to give the title compound. MS (APCI⁺) m/z 511.1 (M+H)⁺.

Example 84B: 5-{-fluoro-3-hydroxy-7-[3-(H-pyrazol-1-yl)propoxy]naphthalen-2-yl}-1λ⁶,2,5-thiadiazolidine-1,1,3-trione To a solution of Example 84A (101.4 mg, 0.199 mmol) in tetrahydrofuran (2 mL) was added 5% Pd/C (wet JM #9) (200 mg, 0.876 mmol). The mixture was stirred in a 4 mL pressure bottle with hydrogen at 150 psi pressure for 28 hours. The reaction mixture was filtered, the filtrate was concentrated, and the residue was purified by reverse-phase preparative HPLC on a Waters XBridge™ C8 5 μm column (75 mm×30 mm) eluted with a gradient of 5-100% methanol (A) and 25 mM ammonium bicarbonate buffer (pH 10) in water (B) at a flow rate of 40 mL/minute to give the title compound. $^1$H NMR (501 MHz, DMSO-d$_6$) δ ppm 7.75 (d, J=2.1 Hz, 1H), 7.71 (dd, J=9.1, 1.4 Hz, 1H), 7.50 (d, J=1.9 Hz, 1H), 7.28-7.14 (m, 2H), 7.08 (s, 1H), 6.28 (t, J=2.0 Hz, 1H), 4.35 (t, J=6.8 Hz, 2H), 4.17 (s, 2H), 4.05 (t, J=6.2 Hz, 2H), 2.30 (p, J=6.6 Hz, 2H); MS (ESI⁺) m/z 421.3 (M+H)⁺.

Example 85: 5-(7-{1-[(4-aminophenyl)methanesulfonyl]-2,5-dihydro-1H-pyrrol-3-yl}-1-fluoro-3-hydroxynaphthalen-2-yl)-1λ⁶,2,5-thiadiazolidine-1,1,3-trione (Compound 184)

Example 85A: 3-(4,4,5,5-tetramethyl-1,3,2-dioxaborolan-2-yl)-2,5-dihydro-1H-pyrrole hydrochloride To a solution of tert-butyl 3-(4,4,5,5-tetramethyl-1,3,2-dioxaborolan-2-yl)-2,5-dihydro-1H-pyrrole-1-carboxylate (5 g, 16.09 mmol) in ethyl acetate (5 mL) was added a solution of hydrochloric acid in ethyl acetate (20 mL, 80 mmol, 4 M) dropwise at 0° C., and the mixture was stirred for 2 hours at 25° C. The mixture was concentrated under reduced pressure to give the title compound (4 g, 16.09 mmol, 97% yield), which was used in the next step without further purification. $^1$H NMR (400 MHz, DMSO-d$_6$) δ ppm 9.76 (br s, 2H), 6.42 (d, J=1.98 Hz, 1H), 3.96 (br d, J=10.80 Hz, 4H), 1.23 (s, 12H).

Example 85B: 1-[(4-nitrophenyl)methanesulfonyl]-3-(4,4,5,5-tetramethyl-1,3,2-dioxaborolan-2-yl)-2,5-dihydro-1H-pyrrole To a solution of Example 85A (0.983 g, 4.24 mmol) in tetrahydrofuran (20 mL) was added potassium tert-butoxide (9.34 mL, 9.34 mmol, 1 M in tetrahydrofuran) dropwise at 0° C. After stirring for 5 minutes at 0° C., (4-nitrophenyl)methanesulfonyl chloride (1 g, 4.24 mmol) was added to the mixture in portions at 0° C., and then the resulting mixture was stirred for 12 hours at 25° C. Then the mixture was concentrated under reduced pressure, and the crude title compound (2 g, purity was about 40%) was used in the next step without further purification. MS (ESI⁻) m/z 311 (M−83).

Example 85C: 5-[3-(benzyloxy)-1-fluoro-7-{-[(4-nitrophenyl)methanesulfonyl]-2,5-dihydro-1H-pyrrol-3-yl}naphthalen-2-yl]-1λ⁶,2,5-thiadiazolidine-1,1,3-trione To a solution of Example 1G (0.472 g, 1.015 mmol) and Example 85B (2 g, 2.029 mmol, crude) in dioxane (25 mL) was added tetrakis[triphenylphosphine]palladium (0.234 g, 0.203 mmol) and sodium carbonate ($Na_2CO_3$, 0.538 g, 5.07 mmol) under nitrogen, and the resulting mixture was stirred at 80° C. for 12 hours under nitrogen. The mixture was diluted with water (75 mL) and adjusted to pH=3 with HCl (1 M). Then the mixture was extracted with ethyl acetate (3×80 mL). The combined organic layers were washed with brine (150 mL), dried over $Na_2SO_4$ and concentrated. The residue was purified by reversed-phase chromatography [Agela Claricep™ Flash AQ C18 Column, 20-35 μm, 100 Å, 330 g flash column, flow rate 100 mL/minute, 0-100% gradient of acetonitrile in water] to give the title compound (420 mg, 0.525 mmol, yield 25.9%). MS (ESI⁻) m/z 651 (M−H)⁻.

Example 85D: 5-(1-fluoro-3-hydroxy-7-{-[(4-nitrophenyl)methanesulfonyl]-2,5-dihydro-1H-pyrrol-3-yl}naphthalen-2-yl)-1λ⁶,2,5-thiadiazolidine-1,1,3-trione To a solution of Example 85C (420 mg, 0.579 mmol) in dichloromethane (30 mL) was added boron trichloride (5.79 mL, 5.79 mmol, 1 M in dichloromethane) dropwise at −70° C., and the mixture was stirred for 2 hours at 25° C. Then the mixture was quenched with methanol (10 mL), and the mixture was concentrated under reduced pressure to give the title compound (350 mg, 0.498 mmol, 86% yield) which was used in the next step without further purification. MS (ESI⁻) m/z 561 (M−H)⁻.

Example 85E: 5-(7-{-[(4-aminophenyl)methanesulfonyl]-2,5-dihydro-1H-pyrrol-3-yl}-1-fluoro-3-hydroxynaphthalen-2-yl)-1λ⁶,2,5-thiadiazolidine-1,1,3-trione To a solution of Example 85D (350 mg, 0.498 mmol) in ethanol (15 mL), methanol (15 mL) and water (3 mL) was added iron powder (278 mg, 4.98 mmol) and ammonium chloride (266 mg, 4.98 mmol) at 20° C. Then the mixture was stirred for 2 hours at 90° C. Then the mixture was filtered, and the filtrate was concentrated under reduced pressure. The residue was purified by preparative HPLC [Waters Xbridge™ Prep OBD C18 150×40 mm, 10 μm column, flow rate 50 mL/minute, 10-35% gradient of acetonitrile in aqueous ammonium bicarbonate (10 mM)] and lyophilized to give the title compound (42 mg, 0.071 mmol, 14.34% yield). $^1$H NMR (400 MHz, DMSO-d₆) δ ppm 10.00 (br s, 1H), 7.68-7.80 (m, 2H), 7.64 (s, 1H), 7.21 (s, 1H), 7.01-7.14 (m, 4H), 6.95 (s, 1H), 6.49-6.59 (m, 2H), 6.43 (br s, 1H), 4.52 (br s, 2H), 4.38 (s, 2H), 4.13 (s, 4H); $^{19}$F NMR (377 MHz, DMSO-d₆) δ ppm −125.43 (br s, 1F); MS (ESI⁻) m/z 531 (M−H)⁻.

Example 86: 5-[1-fluoro-3-hydroxy-7-(hydroxymethyl)naphthalen-2-yl]-1λ⁶,2,5-thiadiazolidine-1,1,3-trione (Compound 185)

Example 86A: 5-[3-(benzyloxy)-1-fluoro-7-(hydroxymethyl)naphthalen-2-yl]-1λ⁶,2,5-thiadiazolidine-1,1,3-trione To the solution of Example 62B (250 mg, 0.595 mmol) in methanol (10 mL) was added sodium borohydride (NaBH₄, 25 mg, 0.654 mmol) at 20° C., and the mixture was stirred for 30 minutes. The reaction was quenched by addition of aqueous hydrochloric acid (1 N) to pH=5, the mixture was added to 20 mL of brine, and the resulting mixture was extracted with ethyl acetate (2×40 mL). The organic layers were combined, washed with brine (2×40 mL), dried with anhydrous sodium sulfate, and filtered. The filtrate was concentrated under reduced pressure to give the title compound (210 mg, 0.438 mmol, 73.7% yield) which was used in the next step without further purification. $^1$H NMR (400 MHz, DMSO-d₆) δ ppm 7.89-7.93 (m, 1H), 7.82-7.88 (m, 1H), 7.49-7.58 (m, 3H), 7.43-7.47 (m, 1H), 7.30-7.42 (m, 3H), 5.24-5.31 (m, 2H), 4.63-4.71 (m, 2H), 4.51-4.56 (m, 2H); MS (ESI⁻) m/z 415 (M−H)⁻.

Example 86B: 5-[1-fluoro-3-hydroxy-7-(hydroxymethyl)naphthalen-2-yl]-1λ⁶,2,5-thiadiazolidine-1,1,3-trione To the solution of Example 86A (0.05 g, 0.104 mmol) in dichloromethane (1 mL) was added boron trichloride (1.044 mL, 1.044 mmol) at −70° C., and the mixture was stirred for 15 minutes at −70° C. Then the reaction was quenched by addition of 20 mL of methanol. An additional reaction on 0.01 g scale was set up and run as described above. The mixture was concentrated under reduced pressure. Then the residue was purified by preparative HPLC [Xtimate™ C18 5 μm column, 25×150 mm, flow rate 25 mL/minute, 10-100% gradient of acetonitrile in water (10 mM ammonium bicarbonate)] to give the title compound (0.011 g, 0.033 mmol, 26.6% yield). $^1$H NMR (400 MHz, DMSO-d₆) δ ppm 7.75-7.81 (m, 1H), 7.62-7.70 (m, 1H), 7.37-7.44 (m, 1H), 7.01-7.06 (m, 1H), 4.58-4.60 (m, 2H), 4.12 (s, 2H); MS (ESI⁻) m/z 325 (M−H)⁻.

Example 87: 5-{7-[1-(cyclopropanesulfonyl)piperidin-3-yl]-1-fluoro-3-hydroxynaphthalen-2-yl}-1λ⁶,2,5-thiadiazolidine-1,1,3-trione (Compound 186)

In a 4 mL vial were combined NiCl₂ dimethoxyethane adduct (3.97 mg, 0.018 mmol, 0.12 equivalents) and 4,4'-di-tert-butyl-2,2'-dipyridyl (4.85 mg, 0.018 mmol, 0.12 equivalents) in N,N-dimethylacetamide (1.0 mL). Example 1G (70 mg, 0.15 mmol, 1.0 equivalents), potassium (1-(tert-butoxycarbonyl)piperidin-3-yl)trifluoroborate (88 mg, 0.301 mmol, 2.0 equivalents), cesium carbonate (98 mg, 0.30 mmol, 2.0 equivalents) and bis[3,5-difluoro-2-[5-(trifluoromethyl)-2-pyridyl]phenyl]iridium(1+); 2-(2-pyridyl)pyridine; hexafluorophosphate (5.0 mg, 0.005 mmol, 0.03 equivalents) were added, followed by dioxane (1.0 mL). The reaction was irradiated overnight using a 450 nm LED photoreactor.

The reaction was filtered and purified by reverse-phase preparative HPLC on a Waters XBridge™ C8 5 μm column (75 mm×30 mm). A gradient of methanol (A) and 25 mM ammonium bicarbonate buffer (pH 10) in water (B) was used, at a flow rate of 40 mL/minute (0-0.5 minutes 15% A, 0.5-8.0 minutes linear gradient 15-100% A, 8.0-9.0 minutes 100% A, 9.0-9.1 minutes linear gradient 100-15% A, 9.1-10.0 minutes 15% A) to afford the tert-butyl 3-[6-(benzyloxy)-8-fluoro-7-(1,1,4-trioxo-1λ⁶,2,5-thiadiazolidin-2-yl)naphthalen-2-yl]piperidine-1-carboxylate (23.9 mg, 28% yield). The residue was treated with 4 M HCl in dioxane (1 mL). Volatiles were removed under a stream of nitrogen.

In a 4 mL vial, 5-[3-(benzyloxy)-1-fluoro-7-(piperidin-3-yl)naphthalen-2-yl]-1λ⁶,2,5-thiadiazolidine-1,1,3-trione (0.020 g, 0.042 mmol) was treated with N,N-dimethylformamide (0.5 mL). N-Ethyl-N-isopropylpropan-2-amine (0.022 mL, 0.126 mmol) was added, followed by cyclopropanesulfonyl chloride (6.42 μL, 0.063 mmol). The reaction was stirred overnight at ambient temperature. The reaction was filtered and purified by reverse-phase preparative HPLC on a Waters XBridge™ C8 5 μm column (75 mm×30 mm). A gradient of methanol (A) and 25 mM ammonium bicarbonate buffer (pH 10) in water (B) was used, at a flow rate of 40 mL/minute (0-0.5 minutes 5% A, 0.5-8.0 minutes linear gradient 5-100% A, 8.0-9.0 minutes 100% A, 9.0-9.1 minutes linear gradient 100-5% A, 9.1-10.0 minutes 5% A) to give a mixture of the sulfonylated material, 5-{3-(benzyloxy)-7-[1-(cyclopropanesulfonyl)piperidin-3-yl]-1-fluoronaphthalen-2-yl}-1λ⁶,2,5-thiadiazolidine-1,1,3-trione and the free amine. 5-{3-(Benzyloxy)-7-[1-(cyclopropanesulfonyl)piperidin-3-yl]-1-fluoronaphthalen-2-yl}-1λ⁶,2,5-thiadiazolidine-1,1,3-trione (13.1 mg, 0.023 mmol) and tetrahydrofuran (1 mL) were added to 5% Pd/C (wet JM #9) (45 mg, 0.197 mmol) in a 4 mL pressure bottle and stirred for 38 hours at 75 psi hydrogen without external heating. The reaction was filtered, and the filtrate was concentrated under a stream of nitrogen. The reaction was reconstituted in dimethyl sulfoxide/methanol and purified by reverse-phase preparative HPLC on a Waters XBridge™ C8 5 µm column (75 mm×30 mm). A gradient of methanol (A) and 25 mM ammonium bicarbonate buffer (pH 10) in water (B) was used, at a flow rate of 40 mL/minute (0-0.5 minutes 5% A, 0.5-8.0 minutes linear gradient 5-100% A, 8.0-9.0 minutes 100% A, 9.0-9.1 minutes linear gradient 100-5% A, 9.1-10.0 minutes 5% A) to afford the title compound eluted from 4.27-4.66 minutes (10 mg, 91% yield). $^1$H NMR (400 MHz, DMSO-$d_6$) δ ppm 7.78 (s, 1H), 7.71 (d, J=8.4 Hz, 1H), 7.46 (d, J=9.4 Hz, 1H), 7.07 (s, 1H), 4.19 (d, J=40.7 Hz, 3H), 3.00 (dd, J=24.5, 13.4 Hz, 4H), 2.68-2.58 (m, 1H), 2.07-1.53 (m, 4H), 1.33-1.12 (m, 1H), 1.09-0.76 (m, 3H); MS (ESI$^-$) m/z 481.8 (M−H)$^-$.

Example 88: 5-{7-[1-(cyclopropanecarbonyl)pyrrolidin-2-yl]-1-fluoro-3-hydroxynaphthalen-2-yl}-1$\lambda^6$,2,5-thiadiazolidine-1,1,3-trione (Compound 187)

In a 4 mL vial were combined NiCl$_2$ dimethoxyethane adduct (3.97 mg, 0.018 mmol, 0.12 equivalents) and 4,4'-di-tert-butyl-2,2'-dipyridyl (4.85 mg, 0.018 mmol, 0.12 equivalents) in N,N-dimethylacetamide (1.0 mL). Example 1G (70 mg, 0.15 mmol, 1.0 equivalents), potassium (1-(tert-butoxycarbonyl)pyrrolidin-2-yl)trifluoroborate (83 mg, 0.301 mmol, 2.0 equivalents), cesium carbonate (98 mg, 0.30 mmol, 2.0 equivalents) and bis[3,5-difluoro-2-[5-(trifluoromethyl)-2-pyridyl]phenyl]iridium(1+); 2-(2-pyridyl)pyridine; hexafluorophosphate (5.0 mg, 0.005 mmol, 0.03 equivalents) were added, followed by dioxane (1.0 mL). The reaction was irradiated overnight using a 450 nm LED photoreactor.

The reaction was filtered and purified by reverse-phase preparative HPLC on a Waters XBridge™ C8 5 µm column (75 mm×30 mm). A gradient of methanol (A) and 25 mM ammonium bicarbonate buffer (pH 10) in water (B) was used, at a flow rate of 40 mL/minute (0-0.5 minutes 15% A, 0.5-8.0 minutes linear gradient 15-100% A, 8.0-9.0 minutes 100% A, 9.0-9.1 minutes linear gradient 100-15% A, 9.1-10.0 minutes 15% A) to afford tert-butyl 2-[6-(benzyloxy)-8-fluoro-7-(1,1,4-trioxo-1$\lambda^6$,2,5-thiadiazolidin-2-yl)naphthalen-2-yl]pyrrolidine-1-carboxylate (69.2 mg, 83% yield). The residue was treated with 1 mL 4 M HCl in dioxane. Volatiles were removed under a stream of nitrogen.

The residue (28.5 mg, 0.06 mmol) was dissolved in N,N-dimethylformamide (1.0 mL). N-Ethyl-N-isopropylpropan-2-amine (33 µL, 0.19 mmol, 3.0 equivalents) was added, followed by cyclopropanecarbonyl chloride (7.4 µL, 0.08 mmol, 1.3 equivalents). The reaction was stirred overnight at ambient temperature. The reaction was filtered and purified by reverse-phase preparative HPLC on a Waters XBridge™ C8 5 µm column (75 mm×30 mm). A gradient of methanol (A) and 25 mM ammonium bicarbonate buffer (pH 10) in water (B) was used, at a flow rate of 40 mL/minute (0-0.5 minutes 5% A, 0.5-8.0 minutes linear gradient 5-100% A, 8.0-9.0 minutes 100% A, 9.0-9.1 minutes linear gradient 100-5% A, 9.1-10.0 minutes 5% A) to give 5-{3-(benzyloxy)-7-[1-(cyclopropanecarbonyl)pyrrolidin-2-yl]-1-fluoronaphthalen-2-yl}-1$\lambda^6$,2,5-thiadiazolidine-1,1,3-trione (22.5 mg, 69% yield).

To 5-{3-(benzyloxy)-7-[1-(cyclopropanecarbonyl)pyrrolidin-2-yl]-1-fluoronaphthalen-2-yl}-1$\lambda^6$,2,5-thiadiazolidine-1,1,3-trione (22.5 mg, 0.043 mmol) and tetrahydrofuran (1 mL) was added 5% Pd/C (wet JM #9) (38 mg, 0.166 mmol) in a 4 mL pressure bottle. The reaction was stirred for 18 hours at 75 psi hydrogen without external heating. Methanol (2 mL) was added, and the reaction mixture was hydrogenated for ~32 hours. The reaction mixture was filtered and concentrated under a stream of nitrogen. The residue was reconstituted in dimethyl sulfoxide/methanol and purified by reverse-phase preparative HPLC on a Waters XBridge™ C8 5 µm column (75 mm×30 mm). A gradient of methanol (A) and 25 mM ammonium bicarbonate buffer (pH 10) in water (B) was used, at a flow rate of 40 mL/minute (0-0.5 minutes 5% A, 0.5-8.0 minutes linear gradient 5-100% A, 8.0-9.0 minutes 100% A, 9.0-9.1 minutes linear gradient 100-5% A, 9.1-10.0 minutes 5% A) to afford the title compound (11.3 mg, 39% yield). $^1$H NMR (400 MHz, DMSO-$d_6$) δ ppm 7.82-7.51 (m, 2H), 7.34 (d, J=8.7 Hz, 1H), 7.09 (s, 1H), 5.55-4.93 (m, 1H), 4.13 (d, J=1.0 Hz, 2H), 3.93-3.50 (m, 2H), 2.47-2.21 (m, 1H), 2.11-1.30 (m, 4H), 0.81-0.18 (m, 4H); MS (APCI$^+$) m/z 434.3 (M+H)$^+$.

Example 89: 5-{1-fluoro-3-hydroxy-7-[2-(1H-pyrazol-1-yl)ethoxy]naphthalen-2-yl}-1$\lambda^6$,2,5-thiadiazolidine-1,1,3-trione (Compound 188)

The title compound was prepared from Example 1H and 1-(2-bromoethyl)-1H-pyrazole in the same way as described for Example 84. $^1$H NMR (501 MHz, DMSO-$d_6$) δ ppm 7.83 (d, J=2.2 Hz, 1H), 7.69 (dd, J=9.2, 1.4 Hz, 1H), 7.52 (d, J=2.0 Hz, 1H), 7.22 (d, J=2.6 Hz, 1H), 7.13 (dd, J=9.0, 2.6 Hz, 1H), 7.07 (s, 1H), 6.31 (t, J=2.1 Hz, 1H), 4.58 (t, J=5.0 Hz, 2H), 4.47 (t, J=5.1 Hz, 2H), 4.17 (s, 2H); MS (ESI$^+$) m/z 407.6 (M+H)$^+$.

Example 90: 5-{7-[1-(cyclopropanesulfonyl)pyrrolidin-2-yl]-1-fluoro-3-hydroxynaphthalen-2-yl}-1$\lambda^6$,2,5-thiadiazolidine-1,1,3-trione (Compound 189)

5-[3-(Benzyloxy)-1-fluoro-7-(pyrrolidin-2-yl)naphthalen-2-yl]-1$\lambda^6$,2,5-thiadiazolidine-1,1,3-trione was prepared using the photoredox method described in Example 88. The residue (28.5 mg, 0.06 mmol) was dissolved in N,N-dimethylformamide (1.0 mL). N-Ethyl-N-isopropylpropan-2-amine (33 µL, 0.19 mmol, 3.0 equivalents) was added, followed by cyclopropanesulfonyl chloride (8.3 µL, 0.08 mmol, 1.3 equivalents). The reaction was stirred overnight at ambient temperature. The reaction was filtered and purified by reverse-phase preparative HPLC on a Waters XBridge™ C8 5 µm column (75 mm×30 mm). A gradient of methanol (A) and 25 mM ammonium bicarbonate buffer (pH 10) in water (B) was used, at a flow rate of 40 mL/minute (0-0.5 minutes 5% A, 0.5-8.0 minutes linear gradient 5-100% A, 8.0-9.0 minutes 100% A, 9.0-9.1 minutes linear gradient 100-5% A, 9.1-10.0 minutes 5% A) to give 5-{3-(benzyloxy)-7-[1-(cyclopropanesulfonyl)pyrrolidin-2-yl]-1-fluoronaphthalen-2-yl}-1$\lambda^6$,2,5-thiadiazolidine-1,1,3-trione (16.0 mg, 46% yield).

5-{3-(benzyloxy)-7-[1-(cyclopropanesulfonyl)pyrrolidin-2-yl]-1-fluoronaphthalen-2-yl}-1$\lambda^6$,2,5-thiadiazolidine-1,1,3-trione (16 mg, 0.029 mmol) and tetrahydrofuran (1 mL) were added to 5% Pd/C (wet JM #9) (18 mg, 0.079 mmol) in a 4 mL pressure bottle and stirred for 20 hours at 75 psi hydrogen without external heating. The reaction mixture was filtered and concentrated under a stream of nitrogen. The reaction was reconstituted in dimethyl sulfoxide/methanol and purified by reverse-phase preparative HPLC on a Waters XBridge™ C8 5 µm column (75 mm×30 mm). A gradient of methanol (A) and 25 mM ammonium bicarbonate buffer (pH 10) in water (B) was used, at a flow rate of 40 mL/minute (0-0.5 minutes 5% A, 0.5-8.0 minutes linear gradient 5-100% A, 8.0-9.0 minutes 100% A, 9.0-9.1 minutes linear gradient 100-5% A, 9.1-10.0 minutes 5% A) to afford the title compound (3.9 mg, 13% yield). $^1$H NMR (501 MHz, DMSO-d$_6$) δ ppm 7.83 (s, 1H), 7.75 (d, J=8.6 Hz, 1H), 7.51 (dd, J=8.7, 1.8 Hz, 1H), 7.11 (s, 1H), 5.15-5.04 (m, 1H), 4.18 (d, J=1.7 Hz, 2H), 3.70-3.53 (m, 2H), 2.76-2.69 (m, 1H), 2.51-2.44 (m, 1H), 2.09-1.73 (m, 3H), 1.09-0.87 (m, 4H); MS (APCI$^+$) m/z 470.2 (M+H)$^+$.

Example 91: 5-{7-[1-(cyclopropanesulfonyl)pyrrolidin-2-yl]-1-fluoro-3-hydroxynaphthalen-2-yl}-1λ$^6$,2,5-thiadiazolidine-1,1,3-trione (Compound 190)

5-[3-(Benzyloxy)-1-fluoro-7-(oxolan-2-yl)naphthalen-2-yl]-1λ$^6$,2,5-thiadiazolidine-1,1,3-trione was prepared using the photoredox method described in Example 88, using Example 1G (1 equivalent), tetrahydrofuran-2-carboxylic acid (1.5 equivalents), bis[3,5-difluoro-2-[5-(trifluoromethyl)-2-pyridyl]phenyl]iridium(1+); 2-(2-pyridyl)pyridine; hexafluorophosphate (0.02 eq), NiCl$_2$ dimethoxyethane adduct (0.05 eq), 4,4'-di-tert-butyl-2,2'-dipyridyl (0.05 eq), Cs$_2$CO$_3$ (1.5 eq) in N,N-dimethylacetamide (0.025 M). The reaction was irradiated for 72 hours using 450 nm blue LEDs. The reaction was purified by reverse-phase preparative HPLC on a Waters XBridge™ C8 5 μm column (75 mm×30 mm). A gradient of methanol (A) and ammonium acetate in water (B) was used, at a flow rate of 40 mL/minute (0-0.5 minutes 5% A, 0.5-8.0 minutes linear gradient 5-100% A, 8.0-9.0 minutes 100% A, 9.0-9.1 minutes linear gradient 100-5% A, 9.1-10.0 minutes 5% A) to afford 5-[3-(Benzyloxy)-1-fluoro-7-(oxolan-2-yl)naphthalen-2-yl]-1λ$^6$,2,5-thiadiazolidine-1,1,3-trione (4.0 mg). 5-[3-(Benzyloxy)-1-fluoro-7-(oxolan-2-yl)naphthalen-2-yl]-1λ$^6$,2,5-thiadiazolidine-1,1,3-trione (4 mg, 8.76 μmol) and tetrahydrofuran (1 mL) were added to 5% Pd/C (wet JM #9) (10 mg, 0.044 mmol) in a 4 mL pressure bottle and stirred for 20 hours at 75 psi hydrogen and 25° C. The reaction mixture was filtered, and the solvent was removed under a stream of nitrogen. The residue was dissolved in methanol and purified by reverse-phase preparative HPLC on a Waters XBridge™ C8 5 μm column (75 mm×30 mm). A gradient of methanol (A) and 25 mM ammonium bicarbonate buffer (pH 10) in water (B) was used, at a flow rate of 40 mL/minute (0-0.5 minutes 5% A, 0.5-8.0 minutes linear gradient 5-100% A, 8.0-9.0 minutes 100% A, 9.0-9.1 minutes linear gradient 100-5% A, 9.1-10.0 minutes 5% A) to afford the title compound (1.1 mg, 34% yield). $^1$H NMR (400 MHz, DMSO-d$_6$) δ ppm 7.79 (s, 1H), 7.71 (d, J=8.6 Hz, 1H), 7.44 (d, J=8.5 Hz, 1H), 7.08 (s, 1H), 4.95 (t, J=7.2 Hz, 1H), 4.14 (s, 2H), 4.04 (q, J=7.1 Hz, 1H), 3.86 (d, J=7.4 Hz, 1H), 2.04-1.92 (m, 3H), 1.72 (dd, J=12.3, 7.9 Hz, 1H); MS (ESI$^-$) m/z 365.1 (M–H)$^+$.

Example 92: 5-[1-fluoro-3-hydroxy-7-(piperidin-3-yl)naphthalen-2-yl]-1λ$^6$,2,5-thiadiazolidine-1,1,3-trione (Compound 191)

The title compound was isolated during the preparation of Example 87, having resulted in incomplete sulfonylation (1.5 mg) and eluted from 3.80-4.15 minutes. $^1$H NMR (501 MHz, DMSO-d$_6$) δ ppm 7.87-7.63 (m, 2H), 7.44 (d, J=9.5 Hz, 1H), 7.08 (s, 1H), 4.14 (s, 2H), 3.35-3.18 (m, 2H), 3.04-2.99 (m, 2H), 2.90-2.82 (m, 1H), 2.01-1.87 (m, 2H), 1.84-1.68 (m, 2H); MS (ESI$^-$) m/z 378.1 (M–H)$^+$.

Example 93: 5-{7-[2-(2,2-difluorocyclopropyl)ethoxy]-1-fluoro-3-hydroxynaphthalen-2-yl}-1λ$^6$,2,5-thiadiazolidine-1,1,3-trione (Compound 192)

Example 93A: 5-{3-(benzyloxy)-7-[2-(2,2-difluorocyclopropyl)ethoxy]-1-fluoronaphthalen-2-yl}-1λ$^6$,2,5-thiadiazolidine-1,1,3-trione To a solution of 5-[3-(benzyloxy)-1-fluoro-7-hydroxynaphthalen-2-yl]-1λ$^6$,2,5-thiadiazolidine-1,1,3-trione, ammonium salt, the product of Example 1H (200 mg, 0.497 mmol), in N,N-dimethylformamide was added cesium carbonate (356 mg, 1.093 mmol) and 2-(2-bromoethyl)-1,1-difluorocyclopropane (202 mg, 1.093 mmol). The mixture was heated to 80° C. for 2 hours. After cooling, the reaction mixture was filtered, the volatiles were removed, and the residue was subjected to column chromatography (SiO$_2$, dry load with diatomaceous earth, 5% methanol in dichloromethane) to give the title compound (115 mg, 0.227 mmol, 46% yield). $^1$H NMR (400 MHz, DMSO-d$_6$) δ ppm 7.76 (dd, J=9.1, 1.5 Hz, 1H), 7.60-7.48 (m, 2H), 7.45-7.32 (m, 2H), 7.36-7.26 (m, 2H), 7.26 (d, J=2.5 Hz, 1H), 7.21 (dd, J=8.9, 2.5 Hz, 1H), 5.22 (s, 2H), 4.25-4.15 (m, 1H), 4.20-4.01 (m, 1H), 4.08 (s, 2H), 2.01 (q, J=9.9, 8.5 Hz, 1H), 1.93-1.72 (m, 2H), 1.65-1.51 (m, 1H), 1.25 (dtd, J=14.9, 7.3, 3.5 Hz, 1H); MS (APCI$^-$) m/z 505 [M–H]$^-$.

Example 93B: 5-{7-[2-(2,2-difluorocyclopropyl)ethoxy]-1-fluoro-3-hydroxynaphthalen-2-yl}-1λ$^6$,2,5-thiadiazolidine-1,1,3-trione A 250 mL-round bottom flask was filled with nitrogen, followed by addition of Pd/C (8.40 mg, 0.079 mmol) and tetrahydrofuran (10 mL). A solution of Example 93A (40 mg, 0.079 mmol) in tetrahydrofuran (2 mL), was then added. An adapter fitted with a hydrogen balloon was inserted and the flask was evacuated and refilled with hydrogen (3 times). The reaction was stirred at ambient temperature overnight. The mixture was filtered through a pad of diatomaceous earth under nitrogen gas. The volatiles were removed under reduced pressure, and the residue was subjected to preparative HPLC [Phenomenex® Luna® C18(2) 5 μm 100 Å AXIA™ column (250 mm×25 mm). 30-100% gradient of acetonitrile (A) and 0.1% trifluoroacetic acid in water (B) over 15 minutes, at a flow rate of 25 mL/minute] to give the title compound (12 mg, 0.029 mmol, 37% yield). $^1$H NMR (501 MHz, DMSO-d$_6$) δ ppm 7.72 (dd, J=9.1, 1.4 Hz, 1H), 7.22 (d, J=2.6 Hz, 1H), 7.19 (dd, J=8.9, 2.5 Hz, 1H), 7.07 (s, 1H), 4.45 (s, 2H), 4.22-4.11 (m, 2H), 2.03-1.95 (m, 1H), 1.88-1.79 (m, 2H), 1.63-1.52 (m, 1H), 1.29-1.22 (m, 1H); MS (APCI$^-$) m/z 415 [M–H]$^-$.

Example 94: 5-{1-fluoro-3-hydroxy-7-[2-(1-methylcyclopropyl)ethoxy]naphthalen-2-yl}-1λ$^6$,2,5-thiadiazolidine-1,1,3-trione (Compound 193)

Example 94A: 5-{3-(benzyloxy)-1-fluoro-7-[2-(1-methylcyclopropyl)ethoxy]naphthalen-2-yl}-1λ$^6$,2,5-thiadiazolidine-1,1,3-trione To a solution of Example 1H (130 mg, 0.323 mmol) in N,N-dimethylformamide (3 mL), was added cesium carbonate (232 mg, 0.711 mmol) and 1-(2-bromoethyl)-1-methylcyclopropane (105 mg, 0.646 mmol). The mixture was heated to 80° C. for 2 hours. After cooling, the reaction mixture was filtered, and the filtrate was concentrated under reduced pressure, and the residue was subjected to column chromatography (SiO$_2$, dry load with diatomaceous earth, 10% methanol in dichloromethane) to give the title compound (107 mg, 0.221 mmol, 68% yield). $^1$H NMR (501 MHz, DMSO-d$_6$) δ ppm 7.75 (dd, J=9.0, 1.4 Hz, 1H), 7.59-7.53 (m, 2H), 7.45-7.27 (m, 4H), 7.26 (d, J=2.5 Hz, 1H), 7.18 (dd, J=9.0, 2.5 Hz, 1H), 5.22 (s, 2H), 4.19 (t, J=6.9 Hz, 2H), 4.11 (s, 2H), 1.74 (t, J=6.9 Hz, 2H), 1.12 (s, 3H), 0.43-0.37 (m, 2H), 0.30-0.23 (m, 2H); MS (APCI$^-$) m/z 483 [M−H]$^-$.

Example 94B: 5-{1-fluoro-3-hydroxy-7-[2-(1-methylcyclopropyl)ethoxy]naphthalen-2-yl}-1λ$^6$,2,5-thiadiazolidine-1,1,3-trione A 250 mL-round bottom flask was filled with nitrogen, followed by addition of 5% Pd/C (8.79 mg, 0.083 mmol) and tetrahydrofuran (10 mL). A solution of Example 94A (40 mg, 0.083 mmol) in tetrahydrofuran (2 mL), was then added. An adapter fitted with a hydrogen balloon was inserted and the flask was evacuated and refilled with hydrogen (3 times). The reaction mixture was stirred at ambient temperature overnight. The mixture was filtered through a pad of diatomaceous earth under nitrogen gas. The volatiles were removed under reduced pressure, and the residue was subjected to preparative HPLC [Phenomenex® Luna® C18(2) 5 μm 100 Å AXIA™ column (250 mm×25 mm). 30-100% gradient of acetonitrile (A) and 0.1% trifluoroacetic acid in water (B) over 15 minutes, at a flow rate of 25 mL/minute] to give the title compound (11 mg, 0.028 mmol, 34% yield). $^1$H NMR (400 MHz, DMSO-d$_6$) δ ppm 7.70 (dd, J=9.0, 1.5 Hz, 1H), 7.22 (d, J=2.6 Hz, 1H), 7.17 (dd, J=9.0, 2.5 Hz, 1H), 7.06 (s, 1H), 4.46 (s, 2H), 4.17 (t, J=6.9 Hz, 2H), 1.73 (t, J=6.9 Hz, 2H), 1.11 (s, 3H), 0.43-0.33 (m, 2H), 0.33-0.24 (m, 2H); MS (APCI$^-$) m/z 393 [M−H]$^-$.

Example 95: 5-(7-{1-[(3-aminophenyl)methanesulfonyl]-2,5-dihydro-1H-pyrrol-3-yl}-1-fluoro-3-hydroxynaphthalen-2-yl)-1λ$^6$,2,5-thiadiazolidine-1,1,3-trione (Compound 194)

Example 95A: 1-[(3-nitrophenyl)methanesulfonyl]-3-(4,4,5,5-tetramethyl-1,3,2-dioxaborolan-2-yl)-2,5-dihydro-1H-pyrrole To a solution of 3-(4,4,5,5-tetramethyl-1,3,2-dioxaborolan-2-yl)-2,5-dihydro-1H-pyrrole hydrochloride (1 g, 4.10 mmol) in tetrahydrofuran (10 mL) was added potassium tert-butoxide (9.03 mL, 1 M in tetrahydrofuran) at 0° C., after stirring for 5 minutes, (3-nitrophenyl)methanesulfonyl chloride (0.967 g, 4.10 mmol) was added to the mixture dropwise at 0° C. The resulting mixture was stirred for 12 hours at 25° C. Then the mixture was concentrated under reduced pressure to give the title compound (2 g, 2.029 mmol, 49.5% yield) which was used for the next step without further purification. MS (ESI$^-$) m/z 311 (M−83)$^-$.

Example 95B: 5-[3-(benzyloxy)-1-fluoro-7-{-[(3-nitrophenyl)methanesulfonyl]-2,5-dihydro-1H-pyrrol-3-yl}naphthalen-2-yl]-1λ$^6$,2,5-thiadiazolidine-1,1,3-trione To a solution of Example 1G (0.472 g, 1.015 mmol) and Example 95A (2 g, 2.029 mmol) in dioxane (25 mL) was added sodium carbonate (Na$_2$CO$_3$, 0.538 g, 5.07 mmol) and tetrakis[triphenylphosphine]palladium (0.234 g, 0.203 mmol) under nitrogen in order, and the resulting mixture was heated to 80° C. for 12 hours under nitrogen. One additional vial on 400 mg scale was set up and run as described above. The mixtures were combined and diluted with water (100 mL). The mixture was adjusted to pH=3 with aqueous hydrochloric acid (1 M), and the mixture was extracted with ethyl acetate (3×80 mL). The combined organic phase was washed with brine (3×50 mL), dried over anhydrous sodium sulfate and concentrated under reduced pressure. The residue was purified by reversed-phase chromatography [Agela Claricep™ Flash AQ C18 20-35 μm, 100 Å, 330 g flash column, flow rate 100 mL/minute, 10-100% gradient of acetonitrile in water] to afford the title compound (280 mg, 0.331 mmol, purity 80%) and the title compound (120 mg, 0.16 mmol, purity 90%). MS (ESI$^-$) m/z 651 (M−H)$^-$.

Example 95C: 5-(1-fluoro-3-hydroxy-7-{t-[(3-nitrophenyl)methanesulfonyl]-2,5-dihydro-1H-pyrrol-3-yl}naphthalen-2-yl)-1λ$^6$,2,5-thiadiazolidine-1,1,3-trione To a solution of Example 95B (50 mg, 0.054 mmol) in dichloromethane (30 mL) was added boron trichloride (0.536 mL, 0.536 mmol, 1 M in dichloromethane) dropwise at −70° C., and the mixture was stirred for 2 hours at 25° C. One additional vial on 280 mg scale was set up and run as described above. Then each mixture was concentrated under reduced pressure. The residues were combined and purified by preparative HPLC [Waters Xbridge™ Prep OBD C18 150×40 mm, 10 μm column, flow rate 50 mL/minute, 20-40% gradient of acetonitrile in aqueous ammonium bicarbonate (10 mM)] to give the title compound (180 mg, 0.176 mmol, 72.5% yield). MS (ESI$^-$) m/z 561 (M−H)$^-$.

Example 95D: 5-(7-{t-[(3-aminophenyl)methanesulfonyl]-2,5-dihydro-1H-pyrrol-3-yl}-1-fluoro-3-hydroxynaphthalen-2-yl)-1λ$^6$,2,5-thiadiazolidine-1,1,3-trione To a solution of Example 95C (180 mg, 0.304 mmol) in ethanol (20 mL), methanol (20 mL) and water (5 mL) was added iron powder (170 mg, 3.04 mmol) and ammonium chloride (163 mg, 3.04 mmol) at 20° C. in order. Then the mixture was stirred for 2 hours at 90° C. The mixture was filtered, and the filtrate was concentrated under reduced pressure. The residue was purified by preparative HPLC [Waters Xbridge™ Prep OBD C18 150×25 mm, 5 μm column, flow rate 25 mL/minute, 10-40% gradient of acetonitrile in aqueous ammonium bicarbonate (10 mM)] and lyophilized to give the title compound (55 mg, 0.095 mmol, 31.4% yield, ammonium salt). $^1$H NMR (400 MHz, DMSO-d$_6$) δ ppm 7.71 (br s, 2H), 7.60 (s, 1H), 7.07 (s, 1H), 6.95 (br t, J=7.76 Hz, 1H), 6.67 (br s, 1H), 6.50-6.62 (m, 2H), 6.41 (br s, 1H), 4.49 (br s, 2H), 4.38 (s, 2H), 4.21 (br s, 2H), 4.12 (s, 2H); $^{19}$F NMR (377 MHz, DMSO-d$_6$) δ ppm −125.50 (br s, 1F); MS (ESI$^-$) m/z 531 (M−H)$^-$.

Example 96: 5-(7-{1-[(2-aminophenyl)methanesulfonyl]-2,5-dihydro-1H-pyrrol-3-yl}-1-fluoro-3-hydroxynaphthalen-2-yl)-1λ$^6$,2,5-thiadiazolidine-1,1,3-trione (Compound 195)

Example 96A: 1-[(2-nitrophenyl)methanesulfonyl]-3-(4,4,5,5-tetramethyl-1,3,2-dioxaborolan-2-yl)-2,5-dihydro-1H-pyrrole To a solution of Example 85A (1 g, 4.10 mmol) in tetrahydrofuran (10 mL) was added potassium tert-butoxide (9.03 mL, 9.03 mmol, 1 M in tetrahydrofuran) at 0° C., and after stirring for 5 minutes, (2-nitrophenyl)methanesulfonyl chloride (0.967 g, 4.10 mmol) was added to the mixture dropwise at 0° C. The resulting mixture was stirred for 12 hours at 25° C., and then the mixture was concentrated under reduced pressure to give the title compound (2 g, 2.029 mmol, 49.5% yield), which was used in the next step without further purification. MS (ESI$^-$) m/z 311 (M−83)$^-$.

Example 96B: 5-[3-(benzyloxy)-1-fluoro-7-{-[(2-nitrophenyl)methanesulfonyl]-2,5-dihydro-1H-pyrrol-3-yl}naphthalen-2-yl]-1$\lambda^6$,2,5-thiadiazolidine-1,1,3-trione To a solution of Example 1G (0.472 g, 1.015 mmol) and Example 96A (2 g, 2.029 mmol) in dioxane (25 mL) was added sodium carbonate (Na$_2$CO$_3$, 0.538 g, 5.07 mmol) and tetrakis[triphenylphosphine]palladium (0.234 g, 0.203 mmol) in order under nitrogen, and the mixture was stirred at 80° C. for 12 hours under nitrogen. One additional vial on 400 mg scale was setup as described above. The mixtures were combined and diluted with water (100 mL). The mixture was adjusted to pH=3 with aqueous hydrochloric acid (1 M), and the mixture was extracted with ethyl acetate (3×80 mL). The combined organic phase was washed with brine (3×50 mL), dried over anhydrous sodium sulfate and concentrated. The residue was purified by reversed-phase chromatography [Agela Claricep™ Flash AQ C18 20-35 μm, 100 Å, 330 g flash column, flow rate 100 mL/minute, 0-100% gradient of acetonitrile in water] to afford the title compound (320 mg, purity 85%) and the title compound (90 mg, purity 95%). MS (ESI$^-$) m/z 651 (M−H)$^-$ Example 96C: 5-(1-fluoro-3-hydroxy-7-{1-[(2-nitrophenyl)methanesulfonyl]-2,5-dihydro-H-pyrrol-3-yl}naphthalen-2-yl)-1$\lambda^6$,2,5-thiadiazolidine-1,1,3-trione To a solution of Example 96B (50 mg, 0.054 mmol) in dichloromethane (30 mL) was added boron trichloride (0.536 mL, 0.536 mmol, 1 M in dichloromethane) dropwise at −70° C., and the mixture was stirred for 2 hours at 25° C. One additional vial on 320 mg scale was set up and run as described above. Then the mixtures were concentrated under reduced pressure to give residues which were combined and purified by preparative HPLC [Waters Xbridge™ Prep OBD C18, 150×40 mm, 10 μm column, flow rate 50 mL/minute, 10-40% gradient of acetonitrile in aqueous ammonium bicarbonate (10 mM)] to give the title compound (180 mg, 0.176 mmol, 37.4% yield). MS (ESI$^-$) m/z 561 (M−H)$^-$.

Example 96D: 5-(7-{-[(2-aminophenyl)methanesulfonyl]-2,5-dihydro-1H-pyrrol-3-yl}-1-fluoro-3-hydroxynaphthalen-2-yl)-1$\lambda^6$,2,5-thiadiazolidine-1,1,3-trione, ammonium salt To a solution of Example 96C (180 mg, 0.304 mmol) in ethanol (20 mL), methanol (20 mL) and water (4.00 mL) was added iron powder (170 mg, 3.04 mmol) and ammonium chloride (163 mg, 3.04 mmol) at 20° C. in order. Then the mixture was stirred for 2 hours at 90° C. The mixture was filtered, and the filtrate was concentrated under reduced pressure. The residue was purified by preparative HPLC [Waters Xbridge™ Prep OBD C18, 150×25 mm, 5 μm column, flow rate 25 mL/minute, 10-40% gradient of acetonitrile in aqueous ammonium bicarbonate (10 mM)] and lyophilized to give the title compound (42 mg, 0.074 mmol, 24.41% yield, ammonium salt). $^1$H NMR (400 MHz, DMSO-d$_6$) δ ppm 10.04 (s, 1H), 7.69-7.78 (m, 2H), 7.62 (s, 1H), 7.21 (s, 1H), 7.12 (d, J=7.45 Hz, 1H), 7.05-7.09 (m, 2H), 6.97-7.03 (m, 1H), 6.96 (s, 1H), 6.66 (d, J 10=7.45 Hz, 1H), 6.50 (t, J=7.45 Hz, 1H), 6.45 (br s, 1H), 5.19 (br s, 1H), 4.61 (br s, 2H), 4.49 (s, 2H), 4.25 (br s, 2H), 4.12 (s, 2H); $^{19}$F NMR (377 MHz, DMSO-d$_6$) δ ppm −125.55 (br s, 1F); MS (ESI$^-$) m/z 531 (M−H)$^-$.

Example 97: 5-[7-(2,2-difluoroethyl)-1-fluoro-3-hydroxynaphthalen-2-yl]-1$\lambda^6$,2,5-thiadiazolidine-1,1,3-trione (Compound 196)

Example 97A: 5-[3-(benzyloxy)-1-fluoro-7-(4,4,5,5-tetramethyl-1,3,2-dioxaborolan-2-yl)naphthalen-2-yl]-1$\lambda^6$,2,5-thiadiazolidine-1,1,3-trione To a solution of Example 1G (500 mg, 1.042 mmol) in dioxane (20 mL), was added bis(pinacolato)diboron (662 mg, 2.61 mmol), potassium acetate (307 mg, 3.13 mmol) and [1,1'-bis(diphenylphosphino)ferrocene]dichloropalladium(II), complex with dichloromethane (76 mg, 0.104 mmol) in order under nitrogen. The reaction mixture was stirred at 80° C. for 3 hours under nitrogen. The resulting mixture was concentrated under reduced pressure. The residue was purified by flash column chromatography on silica gel in a gradient elution of methanol in dichloromethane (0 to 20%) to give the title compound (460 mg, 0.718 mmol, 68.9% yield). MS (ESI$^-$) m/z 511 (M−H)$^-$.

Example 97B: 5-[3-(benzyloxy)-7-(2,2-difluoroethyl)-1-fluoronaphthalen-2-yl]-1$\lambda^6$,2,5-thiadiazolidine-1,1,3-trione To a solution of Example 97A (20 mg, 0.031 mmol) in N-methyl-2-pyrrolidinone (0.5 mL), were added 1,1-difluoro-2-iodoethane (25 mg, 0.120 mmol), a solution of potassium phosphate (21.8 mg, 0.100 mmol) in water (0.12 mL) and chloro(2-dicyclohexylphosphino-2,4,6-triisopropyl-1,1-biphenyl)[2-(2-amino-1,1-biphenyl)]palladium(II) (XPhos Pd G2, 3 mg, 3.5 μmol) at 25° C. under nitrogen, and the reaction mixture was heated to 80° C. and stirred for 18 hours at 80° C. under nitrogen. An additional fourteen reactions on 0.5 g scale were set up and run as described above. The combined reaction mixtures were diluted with water (150 mL). The resulting mixture was extracted with ethyl acetate (3×150 mL). The combined organic phases were washed with brine (200 mL), dried over anhydrous sodium sulfate and concentrated under reduced pressure. The residue was purified by preparative HPLC [Waters Xbridge™ Prep OBD C18, 150×25 mm, 5 μm column, flow rate 25 mL/minute, 25-100% gradient of acetonitrile in aqueous ammonium bicarbonate (10 mM)] to give the title compound (7 mg, 0.015 mmol, 3.25% yield). $^1$H NMR (400 MHz, methanol-d$_4$) δ ppm 7.91 (s, 1H), 7.75-7.80 (m, 1H), 7.54-7.59 (m, 2H), 7.44-7.48 (m, 1H), 7.34-7.41 (m, 2H), 7.21-7.32 (m, 2H), 5.91-6.26 (m, 1H), 5.21-5.28 (m, 2H), 4.36-4.42 (m, 2H), 3.31 (s, 3H); MS (ESI$^-$) m/z 449 (M−H)$^-$.

Example 97C: 5-[7-(2,2-difluoroethyl)-1-fluoro-3-hydroxynaphthalen-2-yl]-1$\lambda^6$,2,5-thiadiazolidine-1,1,3-trione To a solution of Example 97B (5 mg, 10.88 μmol) in dichloromethane (1.5 mL) was added boron trichloride (1 M in dichloromethane, 0.033 mL, 0.03 mmol) at −70° C. The reaction mixture was stirred at −70° C. for 2 hours. The reaction was quenched by addition of methanol (1.5 mL) at −78° C. An additional reaction on 2 mg scale was set up and run as described above. The resulting mixtures of the above two reactions were combined and concentrated under reduced pressure. The residue was purified by preparative HPLC [Kromasil 150×25 mm, 10 μm, C18 column, flow rate 25 mL/minute, 25-100% gradient of acetonitrile in aqueous ammonium bicarbonate (10 mM)] to afford the title compound (1.8 mg, 4.68 μmol 30.1% yield). $^1$H NMR (400 MHz, methanol-d$_4$) δ ppm 7.81-7.89 (m, 1H), 7.61-7.70 (m, 1H), 7.35-7.45 (m, 1H), 7.02-7.09 (m, 1H), 5.89-6.23 (m, 1H), 4.36-4.42 (m, 2H), 3.22-3.30 (m, 2H); MS (ESI$^-$) m/z 359 (M−H)$^-$.

Example 98: 5-[1-fluoro-3-hydroxy-7-(2,2,2-trifluoroethoxy)naphthalen-2-yl]-1λ$^6$,2,5-thiadiazolidine-1,1,3-trione (Compound 197)

Example 98A: 5-[3-(benzyloxy)-1-fluoro-7-(2,2,2-trifluoroethoxy)naphthalen-2-yl]-1λ$^6$,2,5-thiadiazolidine-1,1,3-trione The title compound was prepared using the methodologies described in Example 104A substituting 2,2,2-trifluoroethyl methanesulfonate for 2-bromoacetonitrile. MS (ESI$^-$) m/z 483 (M−H)$^-$.

Example 98B: 5-[1-fluoro-3-hydroxy-7-(2,2,2-trifluoroethoxy)naphthalen-2-yl]-1λ$^6$,2,5-thiadiazolidine-1,1,3-trione The title compound was prepared using the methodologies described in Example 137B substituting Example 98A for Example 137A. $^1$H NMR (500 MHz, DMSO-d$_6$) δ ppm 10.68 (br s, 1H), 7.78 (br d, J=8 Hz, 1H), 7.41 (d, J=2 Hz, 1H), 7.29 (dd, J=8, 2 Hz, 1H), 7.16 (s, 1H), 4.91 (m, 2H), 4.55 (s, 2H); MS (ESI$^-$) m/z 483 (M−H)$^-$.

Example 99: 5-[1-fluoro-7-(2-fluoroethoxy)-3-hydroxynaphthalen-2-yl]-1λ$^6$,2,5-thiadiazolidine-1,1,3-trione (Compound 198)

Example 99A: 5-[3-(benzyloxy)-1-fluoro-7-(2-fluoroethoxy)naphthalen-2-yl]-1λ$^6$,2,5-thiadiazolidine-1,1,3-trione The title compound was prepared using the methodologies described in Example 104A substituting 2-fluoroethyl 4-methylbenzenesulfonate for 2-bromoacetonitrile. MS (ESI$^-$) m/z 447 (M−H)$^-$.

Example 99B: 5-[I-fluoro-7-(2-fluoroethoxy)-3-hydroxynaphthalen-2-yl]-1λ$^6$,2,5-thiadiazolidine-1,1,3-trione The title compound was prepared using the methodologies described in Example 137B substituting Example 99A for Example 137A. $^1$H NMR (500 MHz, DMSO-d$_6$) δ ppm 10.38 (br s, 1H), 7.73 (br d, J=8 Hz, 1H), 7.25 (d, J=2 Hz, 1H), 7.23 (dd, J=8, 2 Hz, 1H), 7.10 (s, 1H), 4.86 (m, 1H), 4.74 (m, 1H), 4.47 (s, 2H), 4.39 (m, 1H), 4.32 (m, 1H); MS (ESI$^-$) m/z 357 (M−H)$^-$.

Example 100: 1-({[8-fluoro-6-hydroxy-7-(1,1,4-trioxo-1λ$^6$,2,5-thiadiazolidin-2-yl)naphthalen-2-yl]oxy}methyl)cyclopropane-1-carbonitrile (Compound 199)

Example 100A: 1-({[6-(benzyloxy)-8-fluoro-7-(1,1,4-trioxo-1λ$^6$,2,5-thiadiazolidin-2-yl)naphthalen-2-yl]oxy}methyl)cyclopropane-1-carbonitrile The title compound was prepared using the methodologies described in Example 104A substituting 1-(bromomethyl)cyclopropanecarbonitrile for 2-bromoacetonitrile. MS (ESI$^-$) m/z 480 (M−H)$^-$.

Example 100B: 1-({[8-fluoro-6-hydroxy-7-(1,1,4-trioxo-1λ$^6$,2,5-thiadiazolidin-2-yl)naphthalen-2-yl]oxy}methyl)cyclopropane-1-carbonitrile The title compound was prepared using the methodologies described in Example 137B substituting Example 100A for Example 137A. $^1$H NMR (500 MHz, DMSO-d$_6$) δ ppm 10.13 (br s, 1H), 7.68 (br d, J=8 Hz, 1H), 7.38 (d, J=2 Hz, 1H), 7.23 (dd, J=8, 2 Hz, 1H), 7.07 (s, 1H), 4.30 (s, 2H), 4.11 (s, 2H), 1.35 (t, J=8 Hz, 2H), 1.17 (m, 2H, t, J=8 Hz, 2H); MS (ESI$^-$) m/z 390 (M−H)$^-$.

Example 101: 5-{1-fluoro-3-hydroxy-7-[(3-methylbutyl)amino]naphthalen-2-yl}-1λ$^6$,2,5-thiadiazolidine-1,1,3-trione (Compound 200)

In a 20 mL pressure release vial, the product of Example 1G (0.5 g, 1.075 mmol), cesium carbonate (1.05 g, 3.22 mmol), methanesulfonato(2-dicyclohexylphosphino-3,6-dimethoxy-2',4',6'-tri-i-propyl-1,1'-biphenyl)(2'-amino-1,1'-biphenyl-2-yl)palladium(II) (BrettPhos Pd G3 precatalyst, 0.029 g, 0.032 mmol), and 2-(dicyclohexylphosphino)3,6-dimethoxy-2',4',6'-triisopropyl-1,1'-biphenyl (BrettPhos, 0.017 g, 0.032 mmol) were combined. The solids were placed under vacuum for 5 minutes at ambient temperature, then the vial was filled with nitrogen, followed by tert-amyl alcohol (10 mL) and isoamylamine (0.25 mL, 2.15 mmol). The resulting suspension was degassed by five vacuum/nitrogen backfills, stirred for 10 minutes at ambient temperature and then heated to 100° C. After 31 hours, the reaction mixture was cooled to ambient temperature, then quenched with 1 M hydrochloric acid (5 mL) and diluted with ethyl acetate (5 mL). The aqueous layer was extracted with ethyl acetate (2×5 mL). The combined organic layers were washed with a 4:1 mixture of brine and 1 M hydrochloric acid (3 mL), dried over anhydrous sodium sulfate, then filtered and concentrated under reduced pressure to give 5-{3-(benzyloxy)-1-fluoro-7-[(3-methylbutyl)amino]naphthalen-2-yl}-1λ$^6$,2,5-thiadiazolidine-1,1,3-trione, which was used for the next reaction without purification. MS (APCI$^-$) m/z 470 [M−H]$^-$.

To a suspension of the crude 5-{3-(benzyoxy)-1-fluoro-7-[(3-methylbutyl)amino]naphthalen-2-yl}-1λ$^6$,2,5-thiadiazolidine-1,1,3-trione (0.507 g, 1.075 mmol) and pentamethylbenzene (0.319 g, 2.150 mmol) in dichloromethane (10 mL) at −78° C. was added a solution of boron trichloride in dichloromethane (6.45 mL, 1 M, 6.45 mmol) slowly along the side of the flask so that the internal temperature remained below −70° C. The resulting solution was stirred for 5 minutes at −78° C., then the cooling bath was removed, and the reaction mixture was allowed to warm to an internal temperature of 0° C. before cooling back to −78° C. The reaction was quenched by addition of ethyl acetate (5 mL)

followed by anhydrous ethanol (5 mL). The mixture was warmed to ambient temperature and concentrated under reduced pressure to give a solid. The crude solid was triturated with heptanes (3×5 mL), then dichloromethane (2×3 mL). The triturated product was dissolved in a dimethyl sulfoxide/methanol mixture and was filtered through a glass microfiber frit. The resulting solution was directly purified by preparative HPLC [Waters XBridge™ C18 5 μm OBD column, 50×100 mm, flow rate 100 mL/minute, a gradient of 5-40% methanol in buffer (0.1% trifluoroacetic acid in water by volume)] in two portions to give the title compound (0.1243 g, 0.326 mmol, 30.3% yield). $^1$H NMR (400 MHz, $-d_6$) δ ppm 9.86 (s, 1H), 7.53 (d, J=8.9 Hz, 1H), 7.08 (dd, J=8.9, 2.3 Hz, 1H), 6.94 (s, 1H), 6.78 (s, 1H), 4.39 (s, 2H), 3.16-3.07 (m, 2H), 1.72 (dq, J=13.3, 6.7 Hz, 1H), 1.51 (q, J=7.1 Hz, 2H), 0.93 (d, J=6.6 Hz, 6H); MS (ESI$^-$) m/z 380 [M–H]$^-$.

Example 102: 5-{1-fluoro-3-hydroxy-7-[(2-methylpropyl)amino]naphthalen-2-yl}-1λ$^6$,2,5-thiadiazolidine-1,1,3-trione (Compound 201)

In a 20 mL pressure release vial, the product of Example 1G (0.5 g, 1.075 mmol), cesium carbonate (1.05 g, 3.22 mmol), methanesulfonato(2-dicyclohexylphosphino-3,6-dimethoxy-2',4',6'-tri-i-propyl-1,1'-biphenyl)(2'-amino-1,1'-biphenyl-2-yl)palladium(II) (BrettPhos Pd G3 precatalyst, 0.029 g, 0.032 mmol), and 2-(dicyclohexylphosphino)3,6-dimethoxy-2',4',6'-triisopropyl-1,1'-biphenyl (BrettPhos, 0.017 g, 0.032 mmol) were combined. The solids were placed under vacuum for 5 minutes at ambient temperature, then the vial was filled with nitrogen, followed by tert-amyl alcohol (10 mL) and isobutylamine (0.214 mL, 2.15 mmol). The resulting suspension was degassed by five vacuum/nitrogen backfills, stirred for 10 minutes at ambient temperature and then heated to 100° C. After 31 hours, the reaction mixture was cooled to ambient temperature, then quenched with 1 M hydrochloric acid (5 mL) and diluted with ethyl acetate (5 mL). The aqueous layer was extracted with ethyl acetate (2×5 mL). The combined organic layers were washed with a 4:1 mixture of brine and 1 M hydrochloric acid (3 mL), dried over anhydrous sodium sulfate, then filtered and concentrated under reduced pressure to give 5-{3-(benzyloxy)-1-fluoro-7-[(2-methylpropyl)amino]naphthalen-2-yl}-1λ$^6$,2,5-thiadiazolidine-1,1,3-trione, which was used for the next reaction without purification. MS (APCI$^-$) m/z 456 [M–H]$^-$.

To a suspension of the crude 5-{3-(benzyoxy)-1-fluoro-7-[(2-methylpropyl)amino]naphthalen-2-yl}-1λ$^6$,2,5-thiadiazolidine-1,1,3-trione (0.492 g, 1.075 mmol) and pentamethylbenzene (0.319 g, 2.150 mmol) in dichloromethane (10 mL) at −78° C. was added a solution of boron trichloride in dichloromethane (6.45 mL, 1 M, 6.45 mmol) slowly along the side of the flask so that the internal temperature remained below −70° C. The resulting solution was stirred for 5 minutes at −78° C., then the cooling bath was removed, and the reaction mixture was allowed to warm to an internal temperature of 0° C. before cooling back to −78° C. The reaction was quenched by addition of ethyl acetate (5 mL) followed by anhydrous ethanol (5 mL). The mixture was warmed to ambient temperature and concentrated under reduced pressure to give a solid. The crude solid was triturated with heptanes (3×5 mL), then dichloromethane (2×3 mL). The triturated product was dissolved in a dimethyl sulfoxide/methanol mixture and was filtered through a glass microfiber frit. The resulting solution was directly purified by preparative HPLC [Waters XBridge™ C18 5 μm OBD column, 50×100 mm, flow rate 100 mL/minute, a gradient of 5-40% acetonitrile in buffer (0.1% trifluoroacetic acid in water by volume)] in three portions to give the title compound (0.0648 g, 0.176 mmol, 16.4% yield). $^1$H NMR (400 MHz, DMSO-d$_6$) δ ppm 9.87 (s, 1H), 7.50 (dd, J=9.0, 1.6 Hz, 1H), 7.08 (dd, J=9.0, 2.3 Hz, 1H), 6.92 (s, 1H), 6.68 (d, J=2.2 Hz, 1H), 4.42 (s, 2H), 2.91 (d, J=6.8 Hz, 2H), 1.97-1.84 (m, 1H), 0.97 (d, J=6.6 Hz, 6H); MS (ESI$^-$) m/z 366 [M–H]$^-$.

Example 103: 5-{7-[(cyclopropylmethyl)amino]-1-fluoro-3-hydroxynaphthalen-2-yl}-1λ$^6$,2,5-thiadiazolidine-1,1,3-trione (Compound 202)

In a 20 mL pressure release vial, the product of Example 1G (0.5 g, 1.075 mmol), cesium carbonate (1.05 g, 3.22 mmol), methanesulfonato(2-dicyclohexylphosphino-3,6-dimethoxy-2',4',6'-tri-i-propyl-1,1'-biphenyl)(2'-amino-1,1'-biphenyl-2-yl)palladium(II) (BrettPhos Pd G3 precatalyst, 0.029 g, 0.032 mmol), and 2-(dicyclohexylphosphino)3,6-dimethoxy-2',4',6'-triisopropyl-1,1'-biphenyl (BrettPhos, 0.017 g, 0.032 mmol) were combined. The solids were placed under vacuum for 5 minutes at ambient temperature, then the vial was filled with nitrogen, followed by tert-amyl alcohol (10 mL) and cyclopropylmethylamine (0.186 mL, 2.15 mmol). The resulting suspension was degassed by five vacuum/nitrogen backfills, stirred for 10 minutes at ambient temperature and then heated to 100° C. After 31 hours, the reaction mixture was cooled to ambient temperature, then quenched with 1 M hydrochloric acid (5 mL) and diluted with ethyl acetate (5 mL). The aqueous layer was extracted with ethyl acetate (2×5 mL). The combined organic layers were washed with a 4:1 mixture of brine and 1 M hydrochloric acid (3 mL), dried over anhydrous sodium sulfate, then filtered and concentrated under reduced pressure to give 5-{3-(benzyloxy)-7-[(cyclopropylmethyl)amino]-1-fluoronaphthalen-2-yl}-1λ$^6$,2,5-thiadiazolidine-1,1,3-trione, which was used for the next reaction without purification. MS (APCI$^-$) m/z 454 [M–H]$^-$.

To a suspension of the crude 5-{3-(benzyloxy)-7-[(cyclopropylmethyl)amino]-1-fluoronaphthalen-2-yl}-1λ$^6$,2,5-thiadiazolidine-1,1,3-trione (0.490 g, 1.075 mmol) and pentamethylbenzene (0.319 g, 2.150 mmol) in dichloromethane (10 mL) at −78° C. was added a solution of boron trichloride in dichloromethane (6.45 mL, 1 M, 6.45 mmol) slowly along the side of the flask so that the internal temperature remained below −70° C. The resulting solution was stirred for 5 minutes at −78° C., then the cooling bath was removed, and the reaction mixture was allowed to warm to an internal temperature of 0° C. before cooling back to −78° C. The reaction was quenched by addition of ethyl acetate (5 mL) followed by anhydrous ethanol (5 mL). The mixture was warmed to ambient temperature and concentrated under reduced pressure to give a solid. The crude solid was triturated with heptanes (3×5 mL), then dichloromethane (2×3 mL). The triturated product was dissolved in a dimethyl sulfoxide/methanol mixture and was filtered through a glass microfiber frit. The resulting solution was directly purified by preparative HPLC [Waters XBridge™ C18 5 μm OBD column, 50×100 mm, flow rate 100 mL/minute, a gradient of 5-40% methanol in buffer (0.1% trifluoroacetic acid in water by volume)] in three portions to give the title compound (0.1252 g, 0.343 mmol, 31.9% yield). $^1$H NMR (400 MHz, $-d_6$) δ ppm 10.04 (s, 1H), 7.60 (d, J=8.9 Hz, 1H), 7.18 (dd, J=8.9, 2.2 Hz, 1H), 6.97 (s, 1H), 6.95 (br s, 1H), 4.42 (s, 2H), 3.05 (d, J=6.8 Hz, 2H), 1.12-1.04 (m, 1H), 0.56-0.45 (m, 2H), 0.32-0.24 (m, 2H); MS (ESI⁻) m/z 364 [M−H]⁻.

Example 104: {[8-fluoro-6-hydroxy-7-(1,1,4-trioxo-1λ⁶,2,5-thiadiazolidin-2-yl)naphthalen-2-yl]oxy}acetonitrile (Compound 203)

Example 104A: 2-((6-(benzyloxy)-7-(1,1-dioxido-4-oxo-1,2,5-thiadiazolidin-2-yl)-8-fluoronaphthalen-2-yl)oxy)acetonitrile A mixture of Example 1H (80 mg, 0.2 mmol), 2-bromoacetonitrile (52.8 mg, 0.440 mmol) and cesium carbonate (143 mg, 0.440 mmol) in N,N-dimethylformamide (0.8 mL) was stirred at 75° C. for 30 minutes. The mixture was cooled to ambient temperature and filtered. The resulting filtrate was purified by flash column chromatography on silica gel (80 g) eluted with ethyl acetate, then ethyl acetate/methanol (10:1) to give the title compound (50 mg, 0.113 mmol, 56.6% yield). MS (ESI⁻) m/z 440 (M−H)⁻.

Example 104B: {[8-fluoro-6-hydroxy-7-(1,1,4-trioxo-1λ⁶,2,5-thiadiazolidin-2-yl)naphthalen-2-yl]oxy}acetonitrile The title compound was prepared using the methodologies described in Example 137B substituting Example 104A for Example 137A. ¹H NMR (500 MHz, DMSO-d₆) δ ppm 10.52 (br s, 1H), 7.79 (br d, J=8 Hz, 1H), 7.41 (d, J=2 Hz, 1H), 7.27 (dd, J=8, 2 Hz, 1H), 7.15 (s, 1H), 5.32 (s, 2H), 4.48 (s, 2H); MS (ESI⁻) m/z 350 (M−H)⁻.

Example 105: 5-[1-fluoro-3-hydroxy-7-(3-methylbutoxy)naphthalen-2-yl]-1λ⁶,2,5-thiadiazolidine-1,1,3-trione (Compound 204)

The title compound was prepared from Example 1H and 1-bromo-3-methylbutane using the procedures described for Example 83. ¹H NMR (500 MHz, DMSO-d₆) δ ppm 9.47 (s, 1H), 7.65 (d, J=9.0 Hz, 1H), 7.18 (d, J=2.5 Hz, 1H), 7.12 (dd, J=9.0, 2.5 Hz, 1H), 7.02 (s, 1H), 4.09 (d, J=7.1 Hz, 4H), 1.81 (dq, J=13.1, 6.5 Hz, 1H), 1.67 (q, J=6.7 Hz, 2H), 0.95 (d, J=6.6 Hz, 6H); MS (APCI⁻) m/z 381.3 (M−H)⁻.

Example 106: 5-(1,8-difluoro-3-hydroxy-7-methoxynaphthalen-2-yl)-1λ⁶,2,5-thiadiazolidine-1,1,3-trione (Compound 205)

Example 106A: benzyl 3-hydroxy-7-methoxynaphthalene-2-carboxylate

To a solution of 3-hydroxy-7-methoxynaphthalene-2-carboxylic acid (5 g, 22.91 mmol) in N,N-dimethylformamide (50 mL) was added sodium bicarbonate (3.85 g, 45.8 mmol) and benzyl bromide (4.09 mL, 34.4 mmol) in order at 25° C. The mixture was heated to 60° C. and stirred for 12 hours at 60° C. The reaction was quenched with water (100 mL). The mixture was extracted with ethyl acetate (3×150 mL). The combined organic layers were washed with brine (3×100 mL), dried over anhydrous sodium sulfate and concentrated under reduced pressure to give the title compound (7 g, 20.43 mmol, 89% yield). ¹H NMR (400 MHz, DMSO-d₆) δ ppm 10.10 (s, 1H), 8.40 (s, 1H), 7.68 (s, 1H), 7.54 (s, 2H), 7.43 (br d, J=7.50 Hz, 4H), 7.31 (s, 1H), 7.19-7.24 (m, 1H), 5.44 (s, 2H), 3.82 (s, 1H); MS (ESI⁺) m/z 309 (M+H)⁺.

Example 106B: benzyl 3-(acetyloxy)-7-methoxynaphthalene-2-carboxylate

To a solution of Example 106A (7 g, 20.43 mmol) in dichloromethane (70 mL) was added triethylamine (8.54 mL, 61.3 mmol) and acetyl chloride (4.36 mL, 61.3 mmol) in order at 0° C. The mixture was stirred for 2 hours at 25° C. The reaction was quenched with water (80 mL). The mixture was extracted with dichloromethane (3×200 mL). The combined organic layers were washed with brine (300 mL), dried over sodium sulfate and concentrated under reduced pressure to give the title compound (8 g, 20.09 mmol, 98% yield). ¹H NMR (400 MHz, DMSO-d₆) δ ppm 8.55 (s, 1H), 7.88 (d, J=9.04 Hz, 1H), 7.67 (s, 1H), 7.60 (d, J=2.43 Hz, 1H), 7.47-7.52 (m, 2H), 7.31-7.46 (m, 4H), 5.34 (s, 2H), 3.88 (s, 3H), 2.08-2.16 (m, 1H); MS (ESI⁺) m/z 351 (M+H)⁺, 373 (M+Na)⁺.

Example 106C: benzyl 3-(acetyloxy)-8-fluoro-7-methoxynaphthalene-2-carboxylate

To a solution of Example 106B (2 g, 5.02 mmol) in N,N-dimethylformamide (20 mL) was added Selectfluor® (2.135 g, 6.03 mmol) at 0° C. The mixture was stirred for 12 hours at 25° C. The reaction was quenched with saturated aqueous sodium thiosulfate (100 mL, 1 M). The mixture was extracted with ethyl acetate (3×200 mL). The combined organic layers were washed with brine (500 mL), dried over sodium sulfate and concentrated under reduced pressure. The residue was purified by chromatography on silica gel (petroleum ether: ethyl acetate=5:1) to give the title compound (1 g, 2.308 mmol, 45.9% yield). ¹H NMR (400 MHz, DMSO-d₆) δ ppm 8.56 (s, 1H), 7.75-7.87 (m, 3H), 7.39-7.51 (m, 6H), 5.36 (s, 2H), 4.00 (s, 3H), 2.13 (s, 1H).

Example 106D: 8-fluoro-3-hydroxy-7-methoxynaphthalene-2-carboxylic acid

To a solution of Example 106C (2 g, 4.89 mmol) in tetrahydrofuran (10 mL), methanol (10 mL) and water (5 mL) was added sodium hydroxide (0.586 g, 14.66 mmol) at 25° C. The mixture was heated to 70° C. and stirred for 3 hours at 70° C. The mixture was stirred at 70° C. for addition 3 hours. One additional vial on 770 mg scale was set up and run as described above. The reaction mixtures were combined and concentrated under reduced pressure to remove most of tetrahydrofuran and methanol. Then the residue was diluted with water, the resulting mixture was acidified with aqueous hydrochloric acid (1 M) to pH=3. A solid was precipitated and collected by filtration. The solid was dried under high vacuum to give the title compound (1.4 g, 5.33 mmol, 81.2% yield). MS (ESI⁻) m/z 235 (M−H)⁻.

Example 106E: benzyl 3-(benzyloxy)-8-fluoro-7-methoxynaphthalene-2-carboxylate

To a solution of Example 106D (1.4 g, 5.33 mmol) in N,N-dimethylformamide (15 mL) was added cesium carbonate (Cs₂CO₃, 5.21 g, 16.00 mmol) at 25° C., and the mixture was stirred for 5 minutes at 25° C. Benzyl bromide (1.396 mL, 11.74 mmol) was added to the mixture at 25° C. The reaction was heated to 70° C. and stirred for 12 hours at 70° C. Then the mixture was poured into ice-water (100 mL) and stirred for 30 minutes. A solid precipitated. The solid was collected by filtration and dried under high vacuum to give the title compound (2.3 g, 4.69 mmol, 88% yield). ¹H NMR (400 MHz, DMSO-d₆) δ ppm 8.25 (s, 1H), 7.70 (s, 1H), 7.59-7.67 (m, 2H), 7.46-7.51 (m, 2H), 7.34 (br d, J=2.20 Hz, 8H), 5.34-5.39 (m, 2H), 5.26 (s, 2H), 3.89-4.00 (m, 1H); MS (ESI$^+$) m/z 417, 439 (M+H, M+Na)$^+$.

Example 106F: 3-(benzyloxy)-8-fluoro-7-methoxynaphthalene-2-carboxylic acid

To a solution of Example 106E (2.3 g, 4.69 mmol) in tetrahydrofuran (10 mL), methanol (10 mL) and water (5 mL) was added sodium hydroxide (0.376 g, 9.39 mmol) at 25° C. The mixture was heated to 60° C. and stirred for 3 hours at 60° C. The reaction mixture was concentrated under reduced pressure to remove most of tetrahydrofuran and methanol. The residue was diluted with water (30 mL), and the resulting mixture was acidified with aqueous hydrochloric acid (1 M) to pH=3. A solid was precipitated. The mixture was filtered, and the solid was collected and dried under high vacuum to give the title compound (1.8 g, 4.69 mmol, 100% yield). $^1$H NMR (400 MHz, DMSO-d$_6$) δ ppm 8.03 (s, 1H), 7.63 (s, 1H), 7.48-7.58 (m, 4H), 7.40 (s, 2H), 7.32 (s, 1H), 5.24 (s, 2H), 3.90-3.98 (m, 1H); MS (ESI$^-$) m/z 325 (M–H)$^-$.

Example 106G: tert-butyl[3-(benzyloxy)-8-fluoro-7-methoxynaphthalen-2-yl]carbamate To a solution of Example 106F (1.8 g, 4.69 mmol) in toluene (10 mL) and t-butanol (10 mL) were added diphenylphosphoryl azide (1.935 g, 7.03 mmol) and triethylamine (1.307 mL, 9.38 mmol) at 25° C., and the mixture was heated to 110° C. and stirred for 3 hours at 110° C. under nitrogen. The reaction mixture was concentrated under reduced pressure. The residue was purified by silica gel column chromatography (petroleum ether: ethyl acetate=5:1) to give the title compound (1.4 g, 3.17 mmol, 67.6% yield). $^1$H NMR (400 MHz, DMSO-d$_6$) δ ppm 8.33 (s, 1H), 8.10 (s, 1H), 7.52-7.59 (m, 3H), 7.32-7.48 (m, 5H), 5.28 (s, 2H), 3.91 (s, 1H), 1.49 (s, 9H); MS (ESI$^+$) m/z 298, 342 (M–99, M–55)$^-$.

Example 106H: 3-(benzyloxy)-8-fluoro-7-methoxynaphthalen-2-amine

To a solution of Example 106G (1.4 g, 3.17 mmol) in dichloromethane (12 mL) was added trifluoroacetic acid (3 mL) dropwise at 0° C. The mixture was stirred for 30 minutes at 25° C. The reaction mixture was concentrated under reduced pressure, and the residue was diluted with ethyl acetate (5 mL). The mixture was adjusted to pH=8 with saturated aqueous sodium bicarbonate and extracted with ethyl acetate (3×100 mL). The combined organic layers were washed with brine (500 mL), dried over anhydrous sodium sulfate and concentrated under reduced pressure to give the title compound (1 g, 3.03 mmol, 95% yield) which was used in the next step without further purification. $^1$H NMR (400 MHz, DMSO-d$_6$) δ ppm 7.54 (s, 2H), 7.31-7.44 (m, 4H), 7.26 (s, 1H), 7.02-7.08 (m, 1H), 6.96 (s, 1H), 5.42 (s, 2H), 5.22 (s, 2H), 3.86 (s, 1H); MS (ESI$^+$) m/z 298 (M+H)$^+$.

Example 106I: methyl {[3-(benzyloxy)-8-fluoro-7-methoxynaphthalen-2-yl]amino}acetate To a solution of Example 106H (1 g, 3.03 mmol) in N,N-dimethylformamide (10 mL) was added methyl bromoacetate (0.418 mL, 4.54 mmol) and potassium carbonate (K$_2$CO$_3$, 0.837 g, 6.05 mmol) at 25° C. in order. The mixture was heated to 65° C. and stirred for 4 hours at 65° C. More methyl bromoacetate (0.279 mL, 3.03 mmol) and potassium carbonate (K$_2$CO$_3$, 0.418 g, 3.03 mmol) were added at 65° C., and the mixture was stirred for additional 4 hours at 65° C. Then the mixture was poured into ice-water (50 mL) and stirred for 30 minutes. The mixture was extracted with ethyl acetate (3×100 mL). The combined organic layers were washed with brine (500 mL), dried over anhydrous sodium sulfate and concentrated under reduced pressure. The residue was purified by column chromatography on silica gel (petroleum ether: ethyl acetate=5:1) to give the title compound (900 mg, 2.071 mmol, 68.4% yield). $^1$H NMR (400 MHz, DMSO-d$_6$) δ ppm 7.56 (d, J=7.02 Hz, 2H), 7.40-7.46 (m, 3H), 7.32 (d, J=1.32 Hz, 2H), 7.11 (s, 1H), 6.56 (s, 1H), 5.93 (s, 1H), 5.27 (s, 2H), 4.12 (d, J=6.14 Hz, 2H), 3.88 (s, 3H), 3.68 (s, 1H); MS (ESI$^+$) m/z 370 (M+H)$^+$.

Example 106J: methyl {[3-(benzyloxy)-1,8-difluoro-7-methoxynaphthalen-2-yl]amino}acetate To a solution of Example 106I (900 mg, 2.071 mmol) in N,N-dimethylformamide (10 mL) was added a solution of 1-(chloromethyl)-4-fluoro-1,4-diazoniabicyclo[2.2.2]octane; ditetrafluoroborate (Selectfluor®, 807 mg, 2.278 mmol) in N,N-dimethylformamide (2 mL) dropwise at 0° C. The mixture was stirred for 5 minutes at 0° C. The reaction was quenched with aqueous sodium thiosulfate (50 mL, 1 M) and stirred for 10 minutes at 25° C. The mixture was extracted with ethyl acetate (3×100 mL). The combined organic layers were washed with brine (500 mL), dried over anhydrous sodium sulfate and concentrated under reduced pressure. The crude product was purified by column chromatography on silica gel (petroleum ether: ethyl acetate=5:1) to give the title compound (320 mg, 0.743 mmol, 35.9% yield). $^1$H NMR (400 MHz, DMSO-d$_6$) δ ppm 7.47-7.56 (m, 3H), 7.40-7.46 (m, 2H), 7.36 (s, 1H), 7.20-7.26 (m, 2H), 5.56 (br s, 1H), 5.26 (s, 2H), 4.21 (br d, J=2.69 Hz, 2H), 3.89 (s, 3H), 3.63 (s, 1H); MS (ESI$^+$) m/z 388 (M+H)$^+$.

Example 106K: methyl {[3-(benzyloxy)-1,8-difluoro-7-methoxynaphthalen-2-yl][(tert-butoxycarbonyl)sulfamoyl]amino}acetate To the solution of chlorosulfonyl isocyanate (141 mg, 0.999 mmol) in dichloromethane (10 mL) was added a solution of tert-butanol (0.096 mL, 0.999 mmol) in dichloromethane (3 mL) dropwise at 25° C., and the mixture was stirred for 30 minutes at 25° C. Then the above mixture was added to a solution of Example 106J (215 mg, 0.500 mmol) and triethylamine (0.209 mL, 1.499 mmol) in dichloromethane (10 mL) dropwise at 25° C., and the resulting mixture was stirred for 1 hour at 25° C. The reaction was quenched with water (20 mL). The mixture was extracted with methylene dichloride (3×100 mL). The combined organic layers were washed with brine (300 mL), dried over anhydrous sodium sulfate and concentrated under reduced pressure to give the title compound (300 mg) which was used for the next step without further purification. MS (ESI$^+$) m/z 467, 511, 589 (M–99, M–55, M+Na)+.

Example 106L: methyl {[3-(benzyloxy)-1,8-difluoro-7-methoxynaphthalen-2-yl](sulfamoyl)amino}acetate To a solution of Example 106K (300 mg, 0.477 mmol) in dichloromethane (3 mL) was added trifluoroacetic acid (1 mL) at 0° C. The mixture was stirred for 30 minutes at 25°

C. The reaction mixture was concentrated under reduced pressure. Then the reaction residue was diluted with ethyl acetate (1 mL), and the resulting mixture was basified with saturated sodium bicarbonate solution to pH=8. The mixture was extracted with ethyl acetate (3×100 mL). The combined organic layers were washed with brine (200 mL), dried over sodium sulfate and concentrated under reduced pressure to give the title compound (220 mg, 0.401 mmol, 84% yield). $^1$H NMR (400 MHz, DMSO-$d_6$) δ ppm 7.65-7.70 (m, 1H), 7.57 (br d, J=7.89 Hz, 3H), 7.32-7.45 (m, 4H), 7.08 (s, 2H), 5.24 (s, 2H), 4.44-4.51 (m, 1H), 4.29-4.35 (m, 1H), 3.94 (s, 1H), 3.56 (s, 3H), 1.23 (s, 2H); MS (ESI$^+$) m/z 467, 489 (M+H, M+Na)$^+$.

Example 106M: 5-[3-(benzyloxy)-1,8-difluoro-7-methoxynaphthalen-2-yl]-1$\lambda^6$,2,5-thiadiazolidine-1,1,3-trione To the solution of Example 106L (50 mg, 0.086 mmol) in tetrahydrofuran (2 mL) was added sodium methoxide (49.2 mg, 0.273 mmol) at 25° C., and the mixture was stirred for 2 hours at 25° C. One additional vial on 20 mg scale and one additional vial on 150 mg scale were set up and run as described above. All the mixtures were acidified with aqueous hydrochloric acid (1M) to pH=3 and combined. The resulting mixture was extracted with ethyl acetate (3×200 mL). The combined organic layers were washed with brine (200 mL), dried over sodium sulfate and concentrated under reduced pressure to give the title compound (280 mg, 0.516 mmol, 90% yield) which was used for the next step without further purification. MS (ESI$^-$) m/z 433 (M−H)$^-$.

Example 106N: 5-(1,8-difluoro-3-hydroxy-7-methoxynaphthalen-2-yl)-1$\lambda^6$,2,5-thiadiazolidine-1,1,3-trione To a solution of Example 106M (250 mg, 0.460 mmol) in methylene chloride (3 mL) was added boron trichloride (2.302 mL, 2.302 mmol, 1 M in dichloromethane) at −70° C., and then the mixture was stirred for 4 hours at −70° C. The reaction was quenched with methyl alcohol (5 mL) and concentrated under reduced pressure. The residue was purified by preparative HPLC [HuaPu C8 Extreme BDS 150×30 mm, 5 μm column, flow rate 25 mL/minute, 20-40% gradient of acetonitrile in aqueous ammonium bicarbonate (10 mM)] and lyophilized to give the title compound (85 mg, 0.237 mmol, 51.5% yield). $^1$H NMR (400 MHz, DMSO-$d_6$) δ ppm 9.77-9.92 (m, 1H), 7.55 (s, 1H), 7.50 (d, J=7.95 Hz, 1H), 7.06 (s, 1H), 7.01-7.10 (m, 1H), 4.08 (s, 2H), 3.92 (s, 1H); $^{19}$F NMR (376 MHz, CDCl$_3$) δ ppm−121.53, 112.68 (1F), 143.3, 143.4 (1 F); MS (ESI$^-$) m/z 343 (M−H)$^-$.

Example 107: 5-{7-[1-(cyclopropanesulfonyl)azetidin-3-yl]-1-fluoro-3-hydroxynaphthalen-2-yl}-1$\lambda^6$,2,5-thiadiazolidine-1,1,3-trione (Compound 206)

Example 1G (100 mg, 0.215 mmol, 1.0 equivalents) and SPhos Pd G4 (8.54 mg, 10.75 μmol, 0.05 equivalents) were combined in N,N-dimethylacetamide (2 mL). (1-(tert-Butoxycarbonyl)azetidin-3-yl)zinc(II) iodide (74.9 mg, 0.215 mmol, 1.0 equivalents, 0.18 M in tetrahydrofuran) was added, the reaction purged with N$_2$, capped and heated to 65° C. overnight.

The reaction mixture was purified by reverse-phase preparative HPLC on a Waters XBridge™ C8 5 μm column (75 mm×30 mm). A gradient of methanol (A) and 25 mM ammonium bicarbonate buffer (pH 10) in water (B) was used, at a flow rate of 40 mL/minute (0-0.5 minutes 15% A, 0.5-8.0 minutes linear gradient 15-100% A, 8.0-9.0 minutes 100% A, 9.0-9.1 minutes linear gradient 100-15% A, 9.1-10.0 minutes 15% A) to yield tert-butyl 3-[6-(benzyloxy)-8-fluoro-7-(1,1,4-trioxo-1$\lambda^6$,2,5-thiadiazolidin-2-yl)naphthalen-2-yl]azetidine-1-carboxylate (80 mg, 69% yield). $^1$H NMR (500 MHz, DMSO-$d_6$) δ ppm 7.88-7.81 (m, 2H), 7.60-7.54 (m, 3H), 7.41-7.28 (m, 4H), 5.26 (s, 2H), 4.33-4.30 (m, 2H), 4.10 (s, 2H), 4.04-3.95 (m, 1H), 3.93-3.90 (m, 2H), 1.42 (s, 9H); MS (ESI$^-$) m/z 540.1 (M−H)$^+$.

The residue was dissolved in 1 dichloromethane (1 mL) and trifluoroacetic acid (100 μL) was added and stirred until complete removal of the tert-butoxycarbonyl group. Volatiles were removed under a stream of nitrogen to give 5-[7-(azetidin-3-yl)-3-(benzyloxy)-1-fluoronaphthalen-2-yl]-1$\lambda^6$,2,5-thiadiazolidine-1,1,3-trione trifluoroacetate used directly in the next step.

5-[7-(Azetidin-3-yl)-3-(benzyloxy)-1-fluoronaphthalen-2-yl]-1$\lambda^6$,2,5-thiadiazolidine-1,1,3-trione trifluoroacetate (50 mg, 0.11 mmol, 1.0 equivalents) was dissolved in N,N-dimethylformamide (1.0 mL). N-Ethyl-N-isopropylpropan-2-amine (59 μL, 0.34 mmol, 3.0 equivalents) was added, followed by cyclopropanesulfonyl chloride (14 μL, 0.14 mmol, 1.3 equivalents). The reaction mixture was stirred overnight at ambient temperature. The reaction was filtered and purified by reverse-phase preparative HPLC on a Waters XBridge™ C8 5 μm column (75 mm×30 mm). A gradient of methanol (A) and 25 mM ammonium bicarbonate buffer (pH 10) in water (B) was used, at a flow rate of 40 mL/minute (0-0.5 minutes 5% A, 0.5-8.0 minutes linear gradient 5-100% A, 8.0-9.0 minutes 100% A, 9.0-9.1 minutes linear gradient 100-5% A, 9.1-10.0 minutes 5% A) to give 5-{3-(benzyloxy)-7-[1-(cyclopropanesulfonyl)azetidin-3-yl]-1-fluoronaphthalen-2-yl}-1$\lambda^6$,2,5-thiadiazolidine-1,1,3-trione (31.7 mg, 51% yield).

5-{3-(Benzyloxy)-7-[1-(cyclopropanesulfonyl)azetidin-3-yl]-1-fluoronaphthalen-2-yl}-1$\lambda^6$,2,5-thiadiazolidine-1,1,3-trione (31.7 mg, 0.058 mmol) and tetrahydrofuran (2 mL) were added to 5% Pd/C (wet JM #9) (13.27 mg, 0.058 mmol) in a 20 mL Barnstead Hast C reactor and stirred for 60.1 hours at 60 psi of hydrogen and 25° C. The reaction mixture was filtered, and the solvent was removed under a stream of nitrogen. The mixture was purified by reverse-phase preparative HPLC on a Waters XBridge™ C8 5 μm column (75 mm×30 mm). A gradient of methanol (A) and 25 mM ammonium bicarbonate buffer (pH 10) in water (B) was used, at a flow rate of 40 mL/minute (0-0.5 minutes 5% A, 0.5-8.0 minutes linear gradient 5-100% A, 8.0-9.0 minutes 100% A, 9.0-9.1 minutes linear gradient 100-5% A, 9.1-10.0 minutes 5% A) to yield the title compound (16.5 mg, 62% yield). $^1$H NMR (400 MHz, DMSO-$d_6$) δ ppm 7.90-7.85 (m, 1H), 7.84-7.77 (m, 1H), 7.58 (dd, J=8.7, 1.8 Hz, 1H), 7.13 (s, 1H), 4.38-4.29 (m, 2H), 4.18 (s, 2H), 4.12-4.07 (m, 3H), 2.92-2.81 (m, 1H), 1.22-1.08 (m, 2H), 1.08-0.99 (m, 2H); MS (APCI$^+$) m/z 473.2 (M+H$_2$O)+.

Example 108: 5-{7-[1-(cyclopropanecarbonyl)azetidin-3-yl]-1-fluoro-3-hydroxynaphthalen-2-yl}-1$\lambda^6$,2,5-thiadiazolidine-1,1,3-trione (Compound 207)

Example 108 was prepared using the procedure described in Example 107, replacing cyclopropylcarbonyl chloride for cyclopropansulfonyl chloride, yielding 5-{3-(benzyloxy)-7-[1-(cyclopropanecarbonyl)azetidin-3-yl]-1-fluoronaphthalen-2-yl}-1$\lambda^6$,2,5-thiadiazolidine-1,1,3-trione (35.6 mg, 62% yield).

5-{3-(Benzyloxy)-7-[1-(cyclopropanecarbonyl)azetidin-3-yl]-1-fluoronaphthalen-2-yl}-1$\lambda^6$,2,5-thiadiazolidine-1,1,3-trione (35.6 mg, 0.070 mmol) and tetrahydrofuran (2 mL) were added to 5% Pd/C (wet JM #9) (15.96 mg, 0.070 mmol) in a 20 mL Barnstead Hast C reactor and stirred for 33 hours at 50 psi hydrogen and 25° C. The reaction mixture was filtered, and the solvent was removed under a stream of nitrogen. The residue was purified by reverse-phase preparative HPLC on a Waters XBridge™ C8 5 µm column (75 mm×30 mm). A gradient of methanol (A) and 25 mM ammonium bicarbonate buffer (pH 10) in water (B) was used, at a flow rate of 40 mL/minute (0-0.5 minutes 5% A, 0.5-8.0 minutes linear gradient 5-100% A, 8.0-9.0 minutes 100% A, 9.0-9.1 minutes linear gradient 100-5% A, 9.1-10.0 minutes 5% A) to yield the title compound (15.9 mg, 54% yield). $^1$H NMR (400 MHz, DMSO-$d_6$) δ ppm 7.85 (s, 1H), 7.84-7.76 (m, 1H), 7.57 (dd, J=8.6, 1.8 Hz, 1H), 7.13 (s, 1H), 4.76 (t, J=8.7 Hz, 1H), 4.41-4.33 (m, 2H), 4.18 (s, 2H), 4.14-4.05 (m, 1H), 3.96 (dd, J=9.6, 6.1 Hz, 1H), 1.73-1.60 (m, 1H), 0.87-0.74 (m, 4H); MS (APCI$^+$) m/z 420.2 (M+H)$^+$.

Example 109: (2E)-3-[8-fluoro-6-hydroxy-7-(1,1,4-trioxo-1$\lambda^6$,2,5-thiadiazolidin-2-yl)naphthalen-2-yl]prop-2-enenitrile (Compound 208)

Example 109A: 3-(6-(benzyloxy)-7-(1,1-dioxido-4-oxo-1,2,5-thiadiazolidin-2-yl)-8-fluoronaphthalen-2-yl)acrylonitrile A mixture of Example 1G (233 mg, 0.5 mmol), acrylonitrile (133 mg, 2.500 mmol), 2-dicyclohexylphosphino-2',6'-dimethoxybiphenyl (45.2 mg, 0.110 mmol), potassium carbonate (207 mg, 1.500 mmol) and palladium(II) acetate (12.35 mg, 0.055 mmol) in N,N-dimethylformamide (0.6 mL) was charged with $N_2$ and heated to 130° C. for 40 minutes. The mixture was diluted with ethyl acetate (50 mL) and washed with 0.5 N HCl aqueous solution (10 mL×2) and brine (10 mL). The organic phase was dried over sodium sulfate, filtered and concentrated. The residue was purified by flash column chromatography on silica gel (80 g) eluted with ethyl acetate/methanol (0 to 10%) to give the title compound (140 mg, 0.32 mmol, 64% yield). MS (ESI$^-$) m/z 436 (M−H)$^-$.

Example 109B: (2E)-3-[8-fluoro-6-hydroxy-7-(1,1,4-trioxo-1$\lambda^6$,2,5-thiadiazolidin-2-yl)naphthalen-2-yl]prop-2-enenitrile The title compound was prepared using the methodologies described in Example 137B substituting Example 109A for Example 137A. $^1$H NMR (500 MHz, DMSO-$d_6$) δ ppm 11.02 (br s, 1H), 8.36 (d, J=2 Hz, 1H), 8.02 (dd, J=8, 2, 1H), 7.89 (br d, J=8 Hz, 1H), 7.56 (d, J=12 Hz, 1H), 7.19 (s, 1H), 5.92 (d, J=12 Hz, 1H), 4.46 (s, 2H); MS (ESI$^-$) m/z 348 (M−H)$^-$.

Example 110: 5-[7-(2-cyclopropylethyl)-1-fluoro-3-hydroxynaphthalen-2-yl]-1$\lambda^6$,2,5-thiadiazolidine-1,1,3-trione (Compound 209)

The product of Example 140 (0.048 g, 0.132 mmol) and trifluoroethanol (2 mL) were added to 10% Pd/C, dry (0.014 g, 0.132 mmol) in a 20 mL Barnstead Hastelloy C reactor. The mixture was allowed to stir for 86 hours under hydrogen (158 psi) at 25° C. The reaction mixture was filtered, and the filter-cake was washed with methanol. The filtrate was concentrated to yield crude title compound which was purified by reverse phase HPLC (Phenomenex® C8(2) Luna® 5 µm AXIA™ 150×30 mm column, 3-100% gradient of acetonitrile (A) and 10 mM ammonium acetate in water (B) over 17 minutes at a flow rate of 50 mL/minute) to give the title compound (0.013 g, 27% yield). $^1$H NMR (400 MHz, DMSO-$d_6$) δ ppm 6.37 (s, 1H), 3.89 (s, 2H), 2.76-2.55 (m, 3H), 2.06-1.95 (m, 1H), 1.83-1.75 (m, 1H), 1.66-1.47 (m, 1H), 1.39 (q, J=7.0 Hz, 2H), 1.30-1.18 (m, 3H), 0.64 (pd, J=7.3, 3.7 Hz, 1H), 0.40-0.30 (m, 2H), −0.07 (d, J=4.5 Hz, 2H); MS (APCI$^-$) m/z 367 [M−H]$^-$.

Example 111: 5-{7-[(2,2-difluorocyclopropyl)methoxy]-1-fluoro-3-hydroxynaphthalen-2-yl}-1$\lambda^6$,2,5-thiadiazolidine-1,1,3-trione (Compound 210)

The title compound was prepared from Example 1H and 2-(bromomethyl)-1,1-difluoropropane using the procedures described for Example 83. $^1$H NMR (400 MHz, DMSO-$d_6$) δ ppm 7.65 (dd, J=9.0, 1.5 Hz, 1H), 7.20-7.06 (m, 2H), 7.00 (d, J=1.4 Hz, 1H), 4.24 (ddd, J=10.0, 6.4, 3.2 Hz, 1H), 4.05 (s, 2H), 4.09-3.99 (m, 1H), 2.23 (dtt, J=15.8, 8.2, 5.2 Hz, 1H), 1.77-1.63 (m, 1H), 1.49 (dtd, J=13.6, 7.7, 4.2 Hz, 1H); MS (APCI$^-$) m/z 401.3 (M−H)$^-$.

Example 112: 5-[7-(2-cyclopropylethoxy)-1-fluoro-3-hydroxynaphthalen-2-yl]-1$\lambda^6$,2,5-thiadiazolidine-1,1,3-trione (Compound 211)

Example 112A: 5-[3-(benzyloxy)-7-(2-cyclopropylethoxy)-1-fluoronaphthalen-2-yl]-1$\lambda^6$,2,5-thiadiazolidine-1,1,3-trione A mixture of the product of Example 1H (95 mg, 0.24 mmol), 2-bromoethylcyclopropane (70 mg, 0.47 mmol) and cesium carbonate (64 mg, 0.35 mmol) in N,N-dimethylformamide (1 mL) was stirred at ambient temperature for 14 hours. The reaction mixture was concentrated, and the residue was purified by reverse-phase preparative HPLC on a Phenomenex® Luna® C8(2) 5 µm 100 Å AXIA™ column (50 mm×30 mm) with a gradient of acetonitrile (A) and 0.1% ammonium acetate in water (B) at a flow rate of 40 mL/minute (0-0.5 minute 5% A, 0.5-8.0 minutes linear gradient 5-100% A, 8.0-9.0 minutes 100% A, 9.0-9.1 minutes linear gradient 100-5% A, 9.1-10.0 minutes 5% A) to give the title compound. MS (APCI$^+$) m/z 488.1 (M+NH$_4$)$^+$.

Example 112B: 5-[7-(2-cyclopropylethoxy)-1-fluoro-3-hydroxynaphthalen-2-yl]-1$\lambda^6$,2,5-thiadiazolidine-1,1,3-trione To a solution of Example 112A (93 mg, 0.20 mmol) in tetrahydrofuran (2 mL) was added 5% Pd/C (wet JM #9) (29.4 mg, 0.129 mmol). The mixture was stirred in a 2 mL pressure vial with hydrogen at 150 psi pressure for 18 hours. The reaction mixture was concentrated, and the residue was purified by reverse-phase preparative HPLC on a Waters XBridge™ C8 5 µm column (75 mm×30 mm) with a gradient of methanol (A) and 25 mM ammonium bicarbonate buffer (pH 10) in water (B) (0-0.5 minute 15% A, 0.5-8.0 minutes linear gradient 15-100% A, 8.0-9.0 minutes 100% A, 9.0-9.1 minutes linear gradient 100-15% A, 9.1-10.0 minutes 15% A) at a flow rate of 40 mL/minute to give the title compound. $^1$H NMR (400 MHz, DMSO-$d_6$) δ ppm 7.67-7.60 (m, 1H), 7.19-7.09 (m, 2H), 7.02 (s, 1H), 4.14-

4.06 (m, 4H), 1.65 (q, J=6.6 Hz, 2H), 0.90-0.79 (m, 1H), 0.47-0.37 (m, 2H), 0.21-0.06 (m, 2H); MS (ESI⁻) m/z 379.0 (M–H)⁻.

Example 113: 5-{7-[2-(cyclopropylmethoxy)ethoxy]-1-fluoro-3-hydroxynaphthalen-2-yl}-1λ⁶,2,5-thiadiazolidine-1,1,3-trione (Compound 212)

The title compound was prepared from Example 1H and ((2-bromoethoxy)methyl)cyclopropane using the methods described for Example 112. ¹H NMR (501 MHz, DMSO-d₆) δ ppm 7.65 (dd, J=9.1, 1.4 Hz, 1H), 7.19 (d, J=2.6 Hz, 1H), 7.15 (dd, J=9.0, 2.6 Hz, 1H), 7.02 (s, 1H), 4.19-4.14 (m, 2H), 4.12 (s, 2H), 3.30 (d, J=6.8 Hz, 2H), 1.04-0.94 (m, 1H), 0.49-0.41 (m, 2H), 0.19-0.12 (m, 2H); MS (ESI⁻) m/z 409.0 (M–H)⁻.

Example 114: 5-{1-fluoro-3-hydroxy-7-[2-(oxolan-2-yl)ethoxy]naphthalen-2-yl}-1λ⁶,2,5-thiadiazolidine-1,1,3-trione (Compound 213)

The title compound was prepared from Example 1H and 2-(2-bromoethyl)oxolane using the methods described for Example 112. ¹H NMR (501 MHz, DMSO-d₆) δ ppm 7.70 (dd, J=9.0, 1.4 Hz, 1H), 7.24-7.15 (m, 2H), 7.08 (s, 1H), 4.18 (m, 4H), 4.00 (m, 1H), 3.68 (m, 1H), 2.10-1.80 (m, 5H), 1.55 (m, 1H).); MS (ESI⁺) m/z 411.3 (M+H)⁺.

Example 115: 5-{7-[2-(cyclobutyloxy)ethoxy]-1-fluoro-3-hydroxynaphthalen-2-yl}-1λ⁶,2,5-thiadiazolidine-1,1,3-trione (Compound 214)

The title compound was prepared from Example 1H and (2-bromoethoxy)cyclobutane using the methods described for Example 112. ¹H NMR (400 MHz, DMSO-d₆) δ ppm 7.65 (dd, J=9.0, 1.5 Hz, 1H), 7.24-7.08 (m, 2H), 7.02 (d, J=1.3 Hz, 1H), 4.24-4.08 (m, 4H), 4.03-3.88 (m, 1H), 3.68-3.59 (m, 2H), 2.14 (m, 2H), 1.99-1.74 (m, 2H), 1.61 (m, 1H), 1.52-1.23 (m, 1H); MS (ESI⁻) m/z 408.8 (M–H)⁻.

Example 116: 5-(1-fluoro-3-hydroxy-7-{2-[(propan-2-yl)oxy]ethoxy}naphthalen-2-yl)-1λ⁶,2,5-thiadiazolidine-1,1,3-trione (Compound 215)

The title compound was prepared from Example 1H and 2-(2-bromoethoxy)propane using the methods described for Example 112. ¹H NMR (501 MHz, DMSO-d₆) δ ppm 7.70 (dd, J=9.1, 1.4 Hz, 1H), 7.24 (d, J=2.6 Hz, 1H), 7.20 (dd, J=9.0, 2.6 Hz, 1H), 7.08 (s, 1H), 4.19 (m, 4H), 3.79-3.75 (m, 2H), 3.73-3.63 (m, 1H), 1.16 (d, J=6.1 Hz, 6H); MS (ESI⁻) m/z 397.0 (M–H)⁻.

Example 117: 5-[7-(3-ethoxypropoxy)-1-fluoro-3-hydroxynaphthalen-2-yl]-1λ⁶,2,5-thiadiazolidine-1,1,3-trione (Compound 216)

The title compound was prepared from Example 1H and 1-bromo-3-ethoxypropane using the methods described for Example 112. ¹H NMR (501 MHz, DMSO-d₆) δ ppm 7.70 (dd, J=9.0, 1.4 Hz, 1H), 7.22 (d, J=2.6 Hz, 1H), 7.19 (dd, J=9.0, 2.5 Hz, 1H), 7.08 (s, 1H), 4.22-4.09 (m, 4H), 3.58 (t, J=6.3 Hz, 2H), 3.48 (q, J=7.0 Hz, 2H), 2.03 (t, J=6.3 Hz, 2H), 1.15 (t, J=7.0 Hz, 3H); MS (ESI⁻) m/z 396.9 (M–H)⁻.

Example 118: 5-[7-(2-tert-butoxyethoxy)-1-fluoro-3-hydroxynaphthalen-2-yl]-1λ⁶,2,5-thiadiazolidine-1,1,3-trione (Compound 217)

The title compound was prepared from Example 1H and 2-(2-bromoethoxy)-2-methylpropane using the methods described for Example 112. ¹H NMR (400 MHz, DMSO-d₆) δ ppm 7.70 (dd, J=8.9, 1.4 Hz, 1H), 7.25 (d, J=2.5 Hz, 1H), 7.19 (dd, J=9.0, 2.5 Hz, 1H), 7.08 (s, 1H), 4.17 (m, 4H), 3.76-3.65 (m, 2H), 1.21 (s, 9H); MS (ESI⁻) m/z 410.9 (M–H)⁻.

Example 119: 5-(7-{[rac-(1R,2R)-2-ethylcyclopropyl]methoxy}-1-fluoro-3-hydroxynaphthalen-2-yl)-1λ⁶,2,5-thiadiazolidine-1,1,3-trione (Compound 218)

The title compound was prepared from Example 1H and rac-(1R,2R)-1-(bromomethyl)-2-ethylcyclopropane using the methods described for Example 112. ¹H NMR (501 MHz, DMSO-d₆) δ ppm 7.76-7.65 (m, 1H), 7.24-7.12 (m, 2H), 7.07 (s, 1H), 4.17 (s, 2H), 3.96 (dd, J=7.0, 3.5 Hz, 2H), 1.40-1.21 (m, 2H), 1.03 (dt, J=8.2, 4.5 Hz, 1H), 0.96 (t, J=7.3 Hz, 3H), 0.79 (dt, J=8.1, 5.0 Hz, 1H), 0.55 (dt, J=8.8, 4.6 Hz, 1H), 0.43 (dt, J=8.2, 4.8 Hz, 1H); MS (ESI⁻) m/z 410.9 (M–H)⁻.

Example 120: 5-[1-fluoro-3-hydroxy-7-(4-methylpentyl)naphthalen-2-yl]-1λ⁶,2,5-thiadiazolidine-1,1,3-trione (Compound 219)

The product of Example 141 (0.0506 g, 0.134 mmol) and trifluoroethanol (2 mL) were added to 10% Pd/C, dry (0.0145 g, 0.134 mmol) in a 20 mL Barnstead Hastelloy C reactor. The mixture was allowed to stir for 86 hours under hydrogen (158 psi) at 25° C. The reaction mixture was filtered, and the filter-cake was washed with methanol. The filtrate was concentrated to yield crude title compound which was purified by reverse phase HPLC (Phenomenex® C8(2) Luna® 5 µm AXIA™ 150×30 mm column, 3-100% gradient of acetonitrile (A) and 10 mM ammonium acetate in water (B) over 17 minutes at a flow rate of 50 mL/minute to give the title compound as an ammonium salt (0.0154 g, 30%). ¹H NMR (400 MHz, DMSO-d₆) δ ppm 9.64 (s, 1H), 7.69-7.60 (m, 2H), 7.34 (dd, J=8.4, 1.7 Hz, 1H), 7.21 (s, 1H), 7.09 (s, 1H), 7.03 (d, J=1.4 Hz, 1H), 6.96 (s, 1H), 4.10 (s, 2H), 2.70 (t, J=7.6 Hz, 2H), 1.69-1.59 (m, 2H), 1.55 (dq, J=13.2, 6.8 Hz, 1H), 1.26-1.14 (m, 2H), 0.85 (d, J=6.6 Hz, 6H); MS (APCI⁻) m/z 379 [M–H]⁻.

Example 121: 5-{7-[3-(2,2-dimethylpropyl)pyrrolidin-1-yl]-1-fluoro-3-hydroxynaphthalen-2-yl}-1λ⁶,2,5-thiadiazolidine-1,1,3-trione (Compound 220)

In a 4 mL vial, combined the product of Example 1G (0.100 g, 0.215 mmol), cesium carbonate (0.210 g, 0.645 mmol), (2-dicyclohexylphosphino-2',6'-diisopropoxy-1,1'-biphenyl)[2-(2'-amino-1,1'-biphenyl)]palladium(II) methanesulfonate (RuPhos Pd G3 precatalyst, 0.0054 g, 0.0065 mmol), and 2-dicyclohexylphosphino-2',6'-diisopropoxybiphenyl (RuPhos, 0.003 g, 0.0065 mmol). The solids were placed under vacuum for 5 minutes at ambient temperature, then the vial was filled with nitrogen, followed by tert-amyl alcohol (2 mL) and 3-(2,2-dimethylpropyl)pyrrolidine (0.74 mL, 0.43 mmol). The resulting suspension was degassed by five vacuum/nitrogen backfills, stirred for 10 minutes at ambient temperature and then heated to 100° C. After 16 hours, the reaction mixture was cooled to ambient temperature, then quenched with 1 M hydrochloric acid (2 mL) and diluted with ethyl acetate (2 mL). The aqueous layer was extracted with ethyl acetate (2×2 mL). The combined organic layers were washed with a 4:1 mixture of brine and 1 M hydrochloric acid (1 mL), dried over anhydrous sodium sulfate, then filtered and concentrated under reduced pressure to give 5-{3-(benzyloxy)-7-[3-(2,2-dimethylpropyl)pyrrolidin-1-yl]-1-fluoronaphthalen-2-yl}-1λ$^6$,2,5-thiadiazolidine-1,1,3-trione, which was used for the next reaction without purification. MS (APCI$^-$) m/z 524 [M−H]$^-$.

To a suspension of the crude 5-{3-(benzyloxy)-7-[3-(2,2-dimethylpropyl)pyrrolidin-1-yl]-1-fluoronaphthalen-2-yl}-1λ$^6$,2,5-thiadiazolidine-1,1,3-trione (0.113 g, 0.215 mmol) and pentamethylbenzene (0.064 g, 0.430 mmol) in dichloromethane (2 mL) at −78° C. was added a solution of boron trichloride in dichloromethane (1.29 mL, 1 M, 1.29 mmol) slowly along the side of the flask so that the internal temperature remained below −70° C. The resulting solution was stirred for 5 minutes at −78° C., then the cooling bath was removed and the reaction mixture was allowed to warm to an internal temperature of 0° C. before cooling back to −78° C. The reaction was quenched by addition of ethyl acetate (1 mL) followed by anhydrous ethanol (1 mL). The mixture was warmed to ambient temperature and concentrated under reduced pressure to give a solid. The crude solid was triturated with heptanes (3×3 mL) then dissolved in a dimethyl sulfoxide/methanol mixture and filtered through a glass microfiber frit. The resulting solution was directly purified by preparative HPLC on a Phenomenex® Luna® C8(2) 5 μm 100 Å AXIA™ column (30 mm×75 mm) with a gradient of acetonitrile (A) and 10 mM ammonium acetate in water (B) at a flow rate of 50 mL/minute (0-1.0 minute 5% A, 1.0-8.5 minutes linear gradient 5-100% A, 8.5-11.5 minutes 100% A, 11.5-12.0 minutes linear gradient 95-5% A) to give the title compound as an ammonium salt (0.0434 g, 0.0096 mmol, 44.6% yield). $^1$H NMR (400 MHz, DMSO-d$_6$) δ ppm 7.57 (dd, J=9.1, 1.7 Hz, 1H), 7.00 (dd, J=9.1, 2.4 Hz, 1H), 6.92 (d, J=1.3 Hz, 1H), 6.59 (d, J=2.4 Hz, 1H), 4.08 (s, 2H), 3.60-3.51 (m, 2H), 3.42-3.25 (m, 2H), 2.89 (t, J=9.1 Hz, 1H), 2.41-2.28 (m, 1H), 2.24-2.12 (m, 1H), 1.63 (dq, J=11.6, 9.1 Hz, 1H), 1.43 (d, J=6.1 Hz, 2H), 0.95 (s, 9H); MS (ESI$^-$) m/z 434 [M−H]$^-$.

Example 122: 5-[7-(1-chloro-3-hydroxypropan-2-yl)-1-fluoro-3-hydroxynaphthalen-2-yl]-1λ$^6$,2,5-thiadiazolidine-1,1,3-trione (Compound 221)

Example 122A: 5-[3-(benzyloxy)-1-fluoro-7-(4,4,5,5-tetramethyl-1,3,2-dioxaborolan-2-yl)naphthalen-2-yl]-1λ$^6$,2,5-thiadiazolidine-1,1,3-trione A mixture of Example 1G (326 mg, 0.7 mmol), 1,1'-bis(diphenylphosphino)ferrocene]dichloropalladium(II) dichloromethane complex (28.6 mg, 0.035 mmol), 4,4,4',4',5,5,5',5'-octamethyl-2,2'-bi(1,3,2-dioxaborolane) (284 mg, 1.120 mmol) and potassium acetate (206 mg, 2.100 mmol) in N,N-dimethylformamide (3.5 mL) was sparged with nitrogen for 5 minutes and then was heated to 100° C. for 3 hours. The mixture was cooled to ambient temperature and diluted with dichloromethane (50 mL). The organic phase was washed with 0.1 N HCl aqueous solution (15 mL), dried over sodium sulfate, filtered and concentrated. The resulting residue was purified by flash column chromatography on silica gel (40 g) eluted with dichloromethane/methanol (0 to 10%) to give the title compound (250 mg, 0.488 mmol, 69.7% yield). $^1$H NMR (500 MHz, DMSO-d$_6$) δ ppm 8.26 (s, 1H), 7.82 (br d, J=8 Hz, 1H), 7.74 (m, 1H), 7.57 (m, 2H), 7.37 (m, 3H), 7.32 (m, 1H), 5.28 (s, 2H), 4.10 (s, 2H), 1.34 (s, 12H); MS (ESI$^-$) m/z 511 (M−H)$^-$.

Example 122B: 5-[3-(benzyloxy)-1-fluoro-7-(oxetan-3-yl)naphthalen-2-yl]-1λ$^6$,2,5-thiadiazolidine-1,1,3-trione A mixture of Example 122A (208 mg, 0.405 mmol), sodium bis(trimethylsilyl)amide (89 mg, 0.486 mmol), trans-2-aminocyclohexanol hydrochloride (6.14 mg, 0.041 mmol), and nickel(II) iodide (12.66 mg, 0.041 mmol) in isopropanol (1 mL) was sparged with nitrogen for 25 minutes, then 3-iodooxetane (49.7 mg, 0.27 mmol) in isopropanol (0.5 mL) was added. The mixture was heated to 120° C. for 1.5 hours, then cooled to ambient temperature, diluted with dichloromethane (50 mL), and washed with 0.1 N HCl aqueous solution (15 mL). The organic phase was dried over sodium sulfate, filtered and concentrated. The resulting residue was purified by flash column chromatography on silica gel (80 g) eluted with ethyl acetate/methanol (0 to 10%) to give the title compound (30 mg, 0.068 mmol, 25.1% yield). $^1$H NMR (500 MHz, DMSO-d$_6$) δ ppm 7.88 (br s, 1H), 7.86 (br d, J=8 Hz, 1H), 7.65 (dd, J=8, 2 Hz, 1H), 7.56 (m, 2H), 7.35 (m, 4H), 5.26 (s, 2H), 5.01 (dd, J=8, 14 Hz, 2H)), 4.77 (dd, J=8, 14 Hz, 2H)), 4.44 (m, 1H), 4.09 (s, 2H); MS (ESI$^-$) m/z 441 (M−H)$^-$.

Example 122C: 5-[7-(1-chloro-3-hydroxypropan-2-yl)-1-fluoro-3-hydroxynaphthalen-2-yl]-1λ$^6$,2,5-thiadiazolidine-1,1,3-trione To a mixture of Example 122B (20 mg, 0.045 mmol) and 1,2,3,4,5-pentamethylbenzene (20.10 mg, 0.136 mmol) in dichloromethane (2 mL) at −78° C. was added trichloroborane (0.678 mL, 0.678 mmol, 1 M in dichloromethane). The mixture was stirred at −78° C. for 1 hour and then at 0° C. for 30 minutes. The mixture was quenched with ethanol (3 mL), stirred at 0° C. for 5 minutes, and concentrated. The solid was washed heptane (4×2 mL) and dichloromethane (4×2 mL) and concentrated to give the title compound (17 mg, 0.044 mmol, 97% yield). $^1$H NMR (500 MHz, DMSO-d$_6$) δ ppm 10.58 (br s, 1H), 7.78 (s, 1H), 7.73 (br d, J=8, 1H), 7.48 (dd, J=8, 2, 1H), 7.11 (s, 1H), 4.47 (s, 2H), 4.05 (m, 1H), 3.97 (m, 1H), 3.71 (d, J=8, 2H), 3.23 (m, 1H); MS (ESI$^-$) m/z 387 (M−H)$^-$.

Example 123: 5-{7-[1-(cyclopropylmethyl)pyrrolidin-3-yl]-1-fluoro-3-hydroxynaphthalen-2-yl}-1λ$^6$,2,5-thiadiazolidine-1,1,3-trione (Compound 222)

Example 123A: tert-butyl 3-[6-(benzyloxy)-8-fluoro-7-(1,1,4-trioxo-1λ$^6$,2,5-thiadiazolidin-2-yl)naphthalen-2-yl]-2,5-dihydro-1H-pyrrole-1-carboxylate A microwave tube was charged with Example 1G (4 g, 8.60 mmol), tert-butyl 3-(4,4,5,5-tetramethyl-1,3,2-dioxaborolan-2-yl)-2,5-dihydro-1H-pyrrole-1-carboxylate (3.05 g, 10.32 mmol), tetrakis(triphenylphosphine)palladium(0) (497 mg, 0.43 mmol), and sodium carbonate (1 M, 12.90 mL, 25.8 mmol). 1,4-Dioxane (4 mL) was subsequently added, and the reaction mixture was flushed with nitrogen for 5 minutes and then heated at 90° C. overnight. After cooling, the mixture was partitioned between water (5 mL) and ethyl acetate (5 mL), and the aqueous layer was further extracted with ethyl acetate. The combined organic fractions were concentrated under reduced pressure, and the residue was subjected to column chromatography (SiO$_2$, dry load with diatomaceous earth, 10% methanol in dichloromethane) to afford the title compound (3.75 g, 6.77 mmol, 79% yield). ¹H NMR (501 MHz, DMSO-d₆) δ ppm 7.86-7.78 (m, 2H), 7.78-7.71 (m, 1H), 7.59-7.53 (m, 2H), 7.41-7.33 (m, 3H), 7.35-7.28 (m, 1H), 6.54 (dt, J=15.2, 2.1 Hz, 1H), 5.27 (s, 2H), 4.53 (dd, J=9.3, 4.7 Hz, 2H), 4.26 (d, J=11.7 Hz, 2H), 4.10 (s, 2H), 1.47 (d, J=10.7 Hz, 9H); MS (APCI⁻) m/z 552 [M−H]⁻.

Example 123B: tert-butyl 3-[8-fluoro-6-hydroxy-7-(1,1,4-trioxo-1λ⁶,2,5-thiadiazolidin-2-yl)naphthalen-2-yl]pyrrolidine-1-carboxylate Example 123A (2.76 g, 4.99 mmol) and tetrahydrofuran (10 mL) were added to 5% Pd/C (wet) (2.8 g, 12.26 mmol) in a 20 mL Barnstead Hast C reactor and was stirred at 25° C. for 68 hours under 61 psi of hydrogen gas. After filtration on diatomaceous earth, the filtrate was concentrated under the reduced pressure, and the residue was subjected to preparative HPLC [Phenomenex® Luna® C18(2) 5 μm 100 Å AXIA™ column (250 mm×25 mm). 30-100% gradient of acetonitrile (A) and 0.1% trifluoroacetic acid in water (B) over 15 minutes, at a flow rate of 25 mL/minute] to afford the title compound (1.7 g, 3.65 mmol, 73% yield). ¹H NMR (400 MHz, DMSO-d₆) δ ppm 7.74-7.67 (m, 2H), 7.44 (dd, J=8.6, 1.7 Hz, 1H), 7.05 (d, J=1.3 Hz, 1H), 4.10 (s, 2H), 3.75 (dd, J=10.4, 7.5 Hz, 1H), 3.55-3.44 (m, 2H), 3.37-3.21 (m, 2H), 2.25 (s, 1H), 2.02 (s, 1H), 1.42 (d, J=4.3 Hz, 9H); MS (APCI⁻) m/z 464 [M−H]⁻.

Example 123C: 5-{7-[1-(cyclopropylmethyl)pyrrolidin-3-yl]-1-fluoro-3-hydroxynaphthalen-2-yl}-1λ⁶,2,5-thiadiazolidine-1,1,3-trione To a 50 mL-round bottom flask was added product from Example 123B (100 mg, 0.21 mmol), methylene chloride (2 mL) and trifluoroacetic acid (2 mL) at ambient temperature. The reaction mixture was stirred for 30 minutes at ambient temperature. The volatiles were removed under reduced pressure, and the residue was subjected to the next step without purification. MS (APCI⁺) m/z 366 [M+H]⁺.

A 20 mL microwave vial was charged with trifluoroacetic acid salt of crude 5-[1-fluoro-3-hydroxy-7-(pyrrolidin-3-yl)naphthalen-2-yl]-1λ⁶,2,5-thiadiazolidine-1,1,3-trione and sodium carbonate (58.0 mg, 0.547 mmol). N,N-Dimethylformamide (3 mL) was then added, and the mixture was stirred at ambient temperature for 5 minutes. Subsequently, cyclopropanecarbaldehyde (57.5 mg, 0.821 mmol) and acetic acid (0.078 mL, 1.368 mmol) were added, and the mixture was for stirred 5 minutes at room temperature. Sodium cyanoborohydride (103 mg, 1.642 mmol) was then added. The mixture was stirred at ambient temperature for two hours. The reaction was partitioned between water (5 mL) and ethyl acetate (5 mL). The aqueous layer was extracted with more ethyl acetate (2×3 mL). The combined organic layers were washed with saturated aqueous ammonium chloride (5 mL) and dried over sodium sulfate. The volatiles were removed under reduced pressure, and the residue was subjected to preparative HPLC [Phenomenex® Luna® C18(2) 5 μm 100 Å AXIA™ column (250 mm×25 mm). 30-100% gradient of acetonitrile (A) and 0.1% trifluoroacetic acid in water (B) over 15 minutes, at a flow rate of 25 mL/minute] to afford the title compound (15 mg, 0.036 mmol, 17% yield over two steps). ¹H NMR (400 MHz, DMSO-d₆) δ ppm 9.75 (s, 1H), 7.76 (d, J=1.7 Hz, 1H), 7.69 (d, J=8.5 Hz, 1H), 7.43 (dd, J=8.6, 1.8 Hz, 1H), 7.00 (s, 1H), 4.04 (s, 2H), 3.84-3.71 (m, 1H), 3.70-3.57 (m, J=9.4 Hz, 1H), 3.49 (s, 2H), 3.53-3.35 (m, 3H), 3.06 (dd, J=7.3, 2.6 Hz, 2H), 2.42-2.35 (m, 1H), 2.12-2.01 (m, 1H), 1.10-0.99 (m, 1H), 0.61-0.50 (m, 2H), 0.37-0.25 (m, 2H); MS (APCI⁻) m/z 418 [M−H]⁻.

Example 124: 5-[7-(cyclopropyloxy)-1-fluoro-3-hydroxynaphthalen-2-yl]-1λ⁶,2,5-thiadiazolidine-1,1,3-trione (Compound 223)

Example 124A: 5-[3-(benzyloxy)-7-(cyclopropyloxy)-1-fluoronaphthalen-2-yl]-1λ⁶,2,5-thiadiazolidine-1,1,3-trione To the product of Example 1H (300 mg, 0.746 mmol) in N,N-dimethylformamide (2 mL), was added cesium carbonate (534 mg, 1.640 mmol) and bromocyclopropane (1.2 mL, 14.91 mmol). The mixture was heated to 130° C. overnight. After cooling, the reaction mixture was filtered, and the residue was subjected to preparative HPLC [Phenomenex® Luna® C18(2) 5 μm 100 Å AXIA™ column (250 mm×25 mm). 30-100% gradient of acetonitrile (A) and 0.1% trifluoroacetic acid in water (B) over 15 minutes, at a flow rate of 25 mL/minute] to afford the title compound (40 mg, 0.090 mmol, 12% yield). MS (APCI⁻) m/z 441 [M−H]⁻.

Example 124B: 5-[7-(cyclopropyloxy)-1-fluoro-3-hydroxynaphthalen-2-yl]-1λ⁶,2,5-thiadiazolidine-1,1,3-trione A 250 mL-round bottom flask was filled with nitrogen, followed by addition of 5% Pd/C (35 mg, 0.329 mmol) and tetrahydrofuran (10 mL). A solution of Example 124A (40 mg, 0.083 mmol) in tetrahydrofuran (2 mL), was then added. An adapter fitted with a hydrogen balloon was inserted and the flask was evacuated and refilled with hydrogen (3 times). The reaction mixture was stirred at ambient temperature overnight. The mixture was filtered through a pad of diatomaceous earth under nitrogen gas. The filtrate was concentrated under reduced pressure, and the residue was subjected to preparative HPLC [Phenomenex® Luna® C18(2) 5 μm 100 Å AXIA™ column (250 mm×25 mm). 30-100% gradient of acetonitrile (A) and 0.1% trifluoroacetic acid in water (B) over 15 minutes, at a flow rate of 25 mL/minute] to afford the title compound (12 mg, 0.034 mmol, 10.36% yield). ¹H NMR (500 MHz, DMSO-d₆) δ ppm 7.60 (dd, J=9.0, 1.4 Hz, 1H), 7.38 (d, J=2.5 Hz, 1H), 7.06 (dd, J=9.0, 2.5 Hz, 1H), 6.97 (s, 1H), 4.05 (s, 2H), 3.89 (tt, J=6.0, 2.9 Hz, 1H), 0.78 (dt, J=7.3, 5.6 Hz, 2H), 0.67-0.60 (m, 2H); MS (APCI⁻) m/z 351 [M−H]⁻.

Example 125: 5-{7-[(2-cyclopropylethyl)amino]-1-fluoro-3-hydroxynaphthalen-2-yl}-1λ⁶,2,5-thiadiazolidine-1,1,3-trione (Compound 224)

In a 4 mL vial, combined the product of Example 1G (0.150 g, 0.322 mmol), cesium carbonate (0.315 g, 0.967 mmol), methanesulfonato(2-dicyclohexylphosphino-3,6-dimethoxy-2',4',6'-tri-i-propyl-1,1'-biphenyl)(2'-amino-1,1'-biphenyl-2-yl)palladium(II) (BrettPhos Pd G3 precatalyst, 8.8 mg, 9.7 μmol), and 2-(dicyclohexylphosphino)3,6-dimethoxy-2',4',6'-triisopropyl-1,1'-biphenyl (BrettPhos, 5.2 mg, 9.7 μmol). The solids were placed under vacuum for 5 minutes at ambient temperature, then the vial was filled with nitrogen, followed by tert-amyl alcohol (3 mL) and 2-cyclopropylethylamine (0.061 mL, 0.65 mmol). The resulting suspension was degassed by five vacuum/nitrogen backfills, stirred for 10 minutes at ambient temperature and then heated to 100° C. After 16 hours, the reaction mixture was cooled to ambient temperature, then quenched with 1 M hydrochloric acid (3 mL) and diluted with ethyl acetate (3 mL). The aqueous layer was extracted with ethyl acetate (2×3 mL). The combined organic layers were washed with a 4:1 mixture of brine and 1 M hydrochloric acid (3 mL), dried over anhydrous sodium sulfate, then filtered and concentrated under reduced pressure to give 5-{3-(benzyloxy)-7-[(2-cyclopropylethyl)amino]-1-fluoronaphthalen-2-yl}-1$\lambda^6$,2,5-thiadiazolidine-1,1,3-trione, which was used for the next reaction without purification. MS (APCI$^-$) m/z 468 [M−H]$^-$.

To a suspension of the crude 5-{3-(benzyloxy)-7-[(2-cyclopropylethyl)amino]-1-fluoronaphthalen-2-yl}-1$\lambda^6$,2,5-thiadiazolidine-1,1,3-trione (0.151 g, 0.322 mmol) and pentamethylbenzene (0.064 g, 0.430 mmol) in dichloromethane (2 mL) at −78° C. was added a solution of boron trichloride in dichloromethane (1.29 mL, 1 M, 1.29 mmol) slowly along the side of the flask so that the internal temperature remained below −70° C. The resulting solution was stirred for 5 minutes at −78° C., then the cooling bath was removed and the reaction mixture was allowed to warm to an internal temperature of 0° C. before cooling back to −78° C. The reaction was quenched by addition of ethyl acetate (1 mL) followed by anhydrous ethanol (1 mL). The mixture was warmed to ambient temperature and concentrated under reduced pressure to give a solid. The crude solid was triturated with heptanes (3×3 mL) then dissolved in a dimethyl sulfoxide/methanol mixture and filtered through a glass microfiber frit. The resulting solution was directly purified by preparative HPLC on a Phenomenex® Luna® C8(2) 5 μm 100 Å AXIA™ column (30 mm×75 mm) with gradient of acetonitrile (A) and 10 mM ammonium acetate in water (B) at a flow rate of 50 mL/minute (0-1.0 minute 5% A, 1.0-8.5 minutes linear gradient 5-100% A, 8.5-11.5 minutes 100% A, 11.5-12.0 minutes linear gradient 95-5% A) to give the title compound as an ammonium salt (0.0178 g, 0.045 mmol, 13.9% yield). $^1$H NMR (400 MHz, DMSO-d$_6$) δ ppm 7.45 (dd, J=8.9, 1.6 Hz, 1H), 6.97 (dd, J=8.9, 2.3 Hz, 1H), 6.88 (d, J=1.4 Hz, 1H), 6.61 (d, J=2.2 Hz, 1H), 5.82 (t, J=5.5 Hz, 1H), 4.07 (s, 2H), 3.14 (td, J=7.0, 4.2 Hz, 2H), 1.51 (q, J=7.0 Hz, 2H), 0.89-0.78 (m, 1H), 0.50-0.37 (m, 2H), 0.14-0.06 (m, 2H); MS (ESI$^-$) m/z 378 [M−H]$^-$.

Example 126: 5-[1-fluoro-3-hydroxy-7-(4-methyl-1H-imidazol-2-yl)naphthalen-2-yl]-1$\lambda^6$,2,5-thiadiazolidine-1,1,3-trione (Compound 225)

Example 126A: 5-[3-(benzyloxy)-1-fluoro-7-(4,4,5,5-tetramethyl-1,3,2-dioxaborolan-2-yl)naphthalen-2-yl]-1$\lambda^6$,2,5-thiadiazolidine-1,1,3-trione To a 100 mL flask were added the product of Example 1G (2.50 g, 5.37 mmol), [1,1'-bis(diphenylphosphino)ferrocene]dichloropalladium(II), complex with dichloromethane (0.219 g, 0.269 mmol), 4,4,4',4',5,5,5',5'-octamethyl-2,2'-bi(1,3,2-dioxaborolane) (2.18 g, 8.60 mmol), and potassium acetate (1.58 g, 16.1 mmol). The flask was capped, evacuated, and refilled with nitrogen. The evacuation/refill cycle was repeated three additional times. Next, 1,4-dioxane (27 mL)—which had been degassed using the same evacuation/refill process described above—was added. The flask was then heated to 80° C. for 18 hours. The mixture was cooled to ambient temperature and filtered over diatomaceous earth with the aid of ethyl acetate. The filter cake was washed with ethyl acetate (2×100 mL). The filtrate was washed with 0.1 M hydrochloric acid (200 mL). The aqueous phase was extracted with ethyl acetate (2×50 mL). The combined organic phases were washed with brine (3×100 mL), dried over sodium sulfate, and concentrated under reduced pressure. The residual solid was triturated with dichloromethane and collected via filtration. The collected material was washed with dichloromethane and then tert-butyl methyl ether, and finally dried under vacuum to give the title compound (1.93 g, 3.77 mmol, 70% yield). $^1$H NMR (500 MHz, DMSO-d$_6$) δ ppm 8.30 (s, 1H), 7.87 (d, J=8.3 Hz, 1H), 7.79 (dd, J=8.1, 1.2 Hz, 1H), 7.53 (dd, J=8.1, 1.7 Hz, 2H), 7.47 (s, 1H), 7.41-7.36 (m, 2H), 7.36-7.31 (m, 1H), 5.29 (s, 2H), 4.46 (s, 2H), 1.33 (s, 12H); MS (APCI$^+$) m/z 530.4 [M+NH$_4$]$^+$.

Example 126B: 5-[3-(benzyloxy)-1-fluoro-7-(4-methyl-H-imidazol-2-yl)naphthalen-2-yl]-1$\lambda^6$,2,5-thiadiazolidine-1,1,3-trione, hydrochloric acid To a microwave vial were added the product of Example 126A (0.025 g, 0.049 mmol), 2-bromo-4-methyl-1H-imidazole (0.016 g, 0.098 mmol), potassium carbonate (0.020 g, 0.15 mmol), and [(1,3,5,7-tetramethyl-6-phenyl-2,4,6-trioxa-6-phosphaadamantane)-2-(2'-amino-1,1'-biphenyl)]palladium(II) methanesulfonate (meCgPPh Pd G3, 3.23 mg, 4.88 μmol). The vial was sealed, evacuated, and refilled with nitrogen. The evacuation/refill cycle was repeated three additional times. Next, a mixture of 1,4-dioxane (0.20 mL) and water (0.049 mL)—which had been degassed using the same evacuation/refill process described above—was added. The vial was then heated to 125° C. for 5 hours. The vial was cooled to ambient temperature. Next, acetonitrile (2 mL) was added, followed by 1 M hydrochloric acid (6 mL). The resulting mixture was stirred for 5 minutes, and then the precipitate was collected by filtration. The solid was washed with acetonitrile (2 mL) and ethyl acetate (2 mL) and then dried to give the title compound (0.017 g, 0.034 mmol, 69% yield). $^1$H NMR (500 MHz, DMSO-d$_6$) δ ppm 14.56 (br s, 2H), 8.68 (d, J=1.6 Hz, 1H), 8.11-8.03 (m, 2H), 7.59-7.53 (m, 3H), 7.48 (s, 1H), 7.40-7.36 (m, 2H), 7.34-7.29 (m, 1H), 5.32 (s, 2H), 4.20 (s, 2H), 2.37 (s, 3H); MS (APCI$^+$) m/z 467.3 [M+H]$^+$.

Example 126C: 5-[1-fluoro-3-hydroxy-7-(4-methyl-H-imidazol-2-yl)naphthalen-2-yl]-1$\lambda^6$,2,5-thiadiazolidine-1,1,3-trione A flask containing a suspension of the product of Example 126B (0.084 g, 0.17 mmol) and 1,2,3,4,5-pentamethylbenzene (0.074 g, 0.50 mmol) in dichloromethane (1.7 mL) was cooled to −78° C. with stirring under an atmosphere of nitrogen. Next, trichloroborane (1.0 M in dichloromethane) (1.34 mL, 1.34 mmol) was added slowly along the side of the flask. The resulting mixture was stirred at −78° C. for 10 minutes, and then the dry ice/acetone bath was replaced with an ice/water bath. After 10 minutes, the mixture was recooled to −78° C. and quenched with ethyl acetate (2 mL) followed by ethanol (2 mL). The mixture was then allowed to warm to ambient temperature and stirred for 15 minutes. The mixture was concentrated under reduced pressure, and then the residue was treated with ethanol (2×5 mL) and concentrated again under reduced pressure. Next, heptanes (6 mL) was added, the flask was sonicated, and the solid was collected by filtration. The solid was then washed with heptanes (2×6 mL), heptanes/ethyl acetate (1:1 v/v) (2×6 mL), dichloromethane (2×6 mL), and acetonitrile (2×6 mL) to give 5-[1-fluoro-3-hydroxy-7-(4-methyl-1H-imidazol-2-yl)naphthalen-2-yl]-1$\lambda^6$,2,5-thiadiazolidine-1,1,3-trione, hydrochloric acid as a solid, along with a small impurity.

This solid was dissolved in methanol, loaded onto diatomaceous earth, concentrated under reduced pressure, and purified using reversed-phase chromatography (30 g Biotage® Sfar C18 Duo 100 Å 30 m column, 10 to 100% methanol in water [buffered with 0.025 M aqueous ammonium bicarbonate, adjusted to pH 7 with dry ice]) to give the title compound (0.012 g, 0.032 mmol, 19% yield). $^1$H NMR (400 MHz, DMSO-$d_6$) δ ppm 10.44 (s, 1H), 8.59 (s, 1H), 7.97 (s, 2H), 7.47 (s, 1H), 7.16 (s, 1H), 4.13 (s, 2H), 2.36 (s, 3H); MS (APCI$^+$) m/z 377.4 [M+H]$^+$.

Example 127: 5-[7-(azetidin-3-yl)-1-fluoro-3-hydroxynaphthalen-2-yl]-1$\lambda^6$,2,5-thiadiazolidine-1,1,3-trione (Compound 226)

Example 127A: 5-{7-bromo-1-fluoro-3-[(2-methoxyethoxy)methoxy]naphthalen-2-yl}-2-[(2-methoxyethoxy)methyl]-1$\lambda^6$,2,5-thiadiazolidine-1,1,3-trione To a suspension of 5-(7-bromo-1-fluoro-3-hydroxynaphthalen-2-yl)-1$\lambda^6$,2,5-thiadiazolidine-1,1,3-trione (Example 128A, 1.41 g, 3.76 mmol) in dichloromethane (14 mL) under an atmosphere of nitrogen was added Hunig's Base (N,N-diisopropylethylamine) (1.97 mL, 11.3 mmol), and a homogeneous solution resulted. Thereafter, 2-methoxyethoxymethyl chloride (0.804 mL, 7.89 mmol) was added slowly over 2 minutes, and the reaction mixture was stirred at room temperature. After 30 minutes, the mixture was diluted with dichloromethane (20 mL), quenched with saturated aqueous NaHCO$_3$ (10 mL), and the layers were separated. The organic layer was dried over sodium sulfate, filtered, and concentrated. The crude solid was dissolved in ethyl acetate (50 mL), washed with water (3×30 mL) and brine (1×30 mL), dried over sodium sulfate, filtered, and concentrated to afford the title compound (1.76 g, 3.19 mmol, 85% yield). MS (APCI$^+$) m/z 553 [M+H]$^+$.

Example 127B: tert-butyl 3-{8-fluoro-6-[(2-methoxyethoxy)methoxy]-7-(1,1,4-trioxo-1$\lambda^6$,2,5-thiadiazolidin-2-yl)naphthalen-2-yl}azetidine-1-carboxylate In a 4 mL vial were combined 5-{7-bromo-1-fluoro-3-[(2-methoxyethoxy)methoxy]naphthalen-2-yl}-2-[(2-methoxyethoxy)methyl]-1$\lambda^6$,2,5-thiadiazolidine-1,1,3-trione (Example 127A, 120 mg, 0.218 mmol, 1.0 equivalents) and Pd SPhos G4 (8.64 mg, 10.88 μmol, 0.05 equivalents) in N,N-dimethylacetamide (2 mL). (1-(tert-Butoxycarbonyl)azetidin-3-yl)zinc(II) iodide (4.35 mL, 0.435 mmol, 2.0 equivalents, 0.11 M in tetrahydrofuran) was added. The vial was purged with N$_2$, capped and heated to 65° C. overnight. The reaction mixture was purified by reverse-phase preparative HPLC on a Waters XBridge™ C8 5 μm column (75 mm×30 mm). A gradient of methanol (A) and 25 mM ammonium bicarbonate buffer (pH 10) in water (B) was used, at a flow rate of 40 mL/minute (0-0.5 minutes 25% A, 0.5-8.0 minutes linear gradient 25-100% A, 8.0-9.0 minutes 100% A, 9.0-9.1 minutes linear gradient 100-25% A, 9.1-10.0 minutes 25% A) to yield the title compound (65 mg, 55% yield). $^1$H NMR (500 MHz, DMSO-$d_6$) δ ppm 7.87 (dd, J=8.6, 1.5 Hz, 1H), 7.85-7.81 (m, 1H), 7.57 (dd, J=8.5, 1.8 Hz, 1H), 7.37 (s, 1H), 5.36 (s, 2H), 4.33-4.30 (m, 2H), 4.07 (s, 2H), 3.99 (tt, J=8.5, 5.9 Hz, 1H), 3.91 (s, 2H), 3.83-3.77 (m, 2H), 3.50-3.45 (m, 2H), 3.23 (s, 3H), 1.42 (s, 9H); MS (ESI$^-$) m/z 538.1 (M−H)$^+$.

Example 127C: 5-[7-(azetidin-3-yl)-1-fluoro-3-hydroxynaphthalen-2-yl]-1$\lambda^6$,2,5-thiadiazolidine-1,1,3-trione tert-Butyl 3-{8-fluoro-6-[(2-methoxyethoxy)methoxy]-7-(1,1,4-trioxo-1$\lambda^6$,2,5-thiadiazolidin-2-yl)naphthalen-2-yl}azetidine-1-carboxylate was dissolved in 4 M HCl in dioxane (1 mL) and stirred until complete consumption of starting material. The reaction mixture was purified by reverse-phase preparative HPLC on a Waters XBridge™ C8 5 μm column (75 mm×30 mm). A gradient of methanol (A) and 25 mM ammonium bicarbonate buffer (pH 10) in water (B) was used, at a flow rate of 40 mL/minute (0-0.5 minutes 5% A, 0.5-8.0 minutes linear gradient 5-100% A, 8.0-9.0 minutes 100% A, 9.0-9.1 minutes linear gradient 100-5% A, 9.1-10.0 minutes 5% A) to yield the title compound (7.8 mg, 18% yield). $^1$H NMR (501 MHz, DMSO-$d_6$) δ ppm 7.90 (d, J=1.7 Hz, 1H), 7.77 (d, J=8.5 Hz, 1H), 7.51 (dd, J=8.6, 1.9 Hz, 1H), 7.09 (s, 1H), 4.31-4.25 (m, 2H), 4.15-4.11 (m, 3H); MS (ESI$^+$) m/z 352.2 (M+H)$^+$.

Example 128: 5-[1-fluoro-3-hydroxy-7-(5-methoxythiophen-2-yl)naphthalen-2-yl]-1$\lambda^6$,2,5-thiadiazolidine-1,1,3-trione (Compound 227)

Example 128A: 5-(7-bromo-1-fluoro-3-hydroxynaphthalen-2-yl)-1$\lambda^6$,2,5-thiadiazolidine-1,1,3-trione A dry 250 mL round-bottom flask was charged with 5-[3-(benzyloxy)-7-bromo-1-fluoronaphthalen-2-yl]-1$\lambda^6$,2,5-thiadiazolidine-1,1,3-trione (2.5 g, 5.37 mmol, Example 1G) and pentamethylbenzene (1.593 g, 10.75 mmol). The vessel was purged with dry nitrogen for 5 minutes and then charged with dichloromethane (50 mL). The mixture was cooled to −78° C. Subsequently, a 1 M solution of BCl$_3$ (16.12 mL, 16.12 mmol) in dichloromethane was added dropwise over 15 minutes. After an additional 30 minutes, the reaction was quenched at −78° C. with ethyl acetate (20 mL) followed by rapid addition of methanol (5.22 mL, 129 mmol) and then slowly warmed to room temperature over 20 minutes under nitrogen. The volatiles were removed under reduced pressure to afford a solid. The solid was slurried with ethyl acetate/heptanes (1:1, 20 mL), stirred for 5 minutes, then isolated by filtration on a fritted funnel. The product was washed/slurried with additional ethyl acetate/heptanes (1:1, 2×5 mL), then heptanes (2×5 mL) and dried to afford the title compound (1.55 g, 4.13 mmol, 77% yield). $^1$H NMR (501 MHz, DMSO-$d_6$) δ ppm 10.89 (s, 1H), 8.09 (d, J=2.0 Hz, 1H), 7.78 (dd, J=9.0, 1.3 Hz, 1H), 7.64 (dd, J=8.8, 2.0 Hz, 1H), 7.15 (s, 1H), 4.50 (s, 2H); MS (APCI$^-$) m/z 372.8 (M−H)$^-$.

Example 128B: 5-[1-fluoro-3-hydroxy-7-(5-methoxythiophen-2-yl)naphthalen-2-yl]-1$\lambda^6$,2,5-thiadiazolidine-1,1,3-trione A microwave tube was charged with Example 128A (60 mg, 0.160 mmol), (4-methoxy-thiophen-2-yl)boronic acid (30.3 mg, 0.192 mmol), and K$_2$CO$_3$ (66.3 mg, 0.480 mmol). A solution of dioxane (1 mL) in water (0.333 mL) was added. The mixture was bubbled with N$_2$ for 5 minutes before 1,1'-bis(di-tert-butylphosphino)ferrocene palladium dichloride (10.42 mg, 0.016 mmol) was added. The mixture was then heated at 60° C. for 30 minutes. The reaction mixture was cooled to ambient temperature, filtered and purified by preparative HPLC on Phenomenex® Luna® 10

µm C18 columns (30 mm×250 mm) eluted with a gradient of acetonitrile (A) with 0.1% trifluoroacetic acid and water (B) 0.1% with trifluoroacetic acid at a flow rate of 50 mL/minute (0-1 minutes 10% A, 1-20 minutes linear gradient 10-100%) to afford the title compound (28 mg, 0.069 mmol, 42.9% yield). $^1$H NMR (501 MHz, DMSO-d$_6$) δ ppm 10.60 (s, 1H), 8.02 (d, J=1.6 Hz, 1H), 7.84-7.71 (m, 2H), 7.35 (d, J=1.7 Hz, 1H), 7.09 (s, 1H), 6.60 (d, J=1.6 Hz, 1H), 4.40 (s, 2H), 3.77 (s, 3H); MS (APCI$^+$) m/z 308.8 (M+H)$^+$.

Example 129: [8-fluoro-6-hydroxy-7-(1,1,4-trioxo-1λ$^6$,2,5-thiadiazolidin-2-yl)naphthalen-2-yl]acetonitrile (Compound 228)

Example 129A: [6-(benzyloxy)-8-fluoro-7-(1,1,4-trioxo-1λ$^6$,2,5-thiadiazolidin-2-yl)naphthalen-2-yl]acetonitrile A mixture of Example 1G (168 mg, 0.36 mmol), 1,1'-bis(di-tert-butylphosphino)ferrocene]palladium(II) dichloride (23.46 mg, 0.036 mmol), isoxazol-4-ylboronic acid (85 mg, 0.756 mmol) and cesium carbonate (328 mg, 1.008 mmol) in tetrahydrofuran (2.5 mL) and water (0.25 mL) was degassed and filled with nitrogen five times. The mixture was heated to 115° C. for 4 hours, cooled to ambient temperature, and diluted with dichloromethane (50 mL). The organic phase was washed with 0.1N HCl aqueous solution (15 mL), dried over sodium sulfate, filtered and concentrated. The resulting residue was purified by flash column chromatography on silica gel (12 g) eluted with dichloromethane/methanol (0 to 10%) to give the title compound (85 mg, 0.20 mmol, 55.5% yield). $^1$H NMR (500 MHz, DMSO-d$_6$) δ ppm 7.92 (s, 1H), 7.88 (br d, J=8 Hz, 1H), 7.54 (d, J=8 Hz, 2H), 7.51 (dd, J=8, 2 Hz, 1H), 7.35 (m, 4H), 5.27 (s, 2H), 4.22 (s, 2H), 4.09 (s, 2H); MS (ESI$^-$) m/z 424 (M−H)$^-$.

Example 129B: [8-fluoro-6-hydroxy-7-(1,1,4-trioxo-1λ$^6$,2,5-thiadiazolidin-2-yl)naphthalen-2-yl]acetonitrile The title compound was prepared using the methodologies described in Example 137B substituting Example 129A for Example 137A. $^1$H NMR (500 MHz, DMSO-d$_6$) δ ppm 10.62 (br s, 1H), 7.89 (s, 1H), 7.79 (br d, J=8, Hz 1H), 7.48 (dd, J=8, 2 Hz, 1H), 7.15 (s, 1H), 4.42 (s, 2H), 4.19 (s, 2H); MS (ESI$^-$) m/z 334 (M−H)$^-$.

Example 130: 5-[1-fluoro-3-hydroxy-7-(methoxymethyl)naphthalen-2-yl]-1λ$^6$,2,5-thiadiazolidine-1,1,3-trione (Compound 229)

In a 4 mL vial were combined NiCl$_2$ dimethoxyethane adduct (3.4 mg, 0.015 mmol, 0.12 equivalents) and 4,4'-di-tert-butyl-2,2'-dipyridyl (4.15 mg, 0.015 mmol, 0.12 equivalents) in N,N-dimethylacetamide (1.0 mL). Example 1G (60 mg, 0.13 mmol, 1.0 equivalents), potassium trifluoro(methoxymethyl)borate (58 mg, 0.39 mmol, 3.0 equivalents), cesium carbonate (105 mg, 0.32 mmol, 2.5 equivalents) and bis[3,5-difluoro-2-[5-(trifluoromethyl)-2-pyridyl]phenyl]iridium(1+); 2-(2-pyridyl)pyridine; hexafluorophosphate (4.3 mg, 0.004 mmol, 0.03 equivalents) were added, followed by dioxane (1.0 mL). The reaction was irradiated overnight using a 450 nm LED photoreactor.

The reaction was filtered and purified by reverse-phase preparative HPLC on a Waters XBridge™ C8 5 µm column (75 mm×30 mm). A gradient of methanol (A) and 25 mM ammonium bicarbonate buffer (pH 10) in water (B) was used, at a flow rate of 40 mL/minute (0-0.5 minutes 15% A, 0.5-8.0 minutes linear gradient 15-100% A, 8.0-9.0 minutes 100% A, 9.0-9.1 minutes linear gradient 100-15% A, 9.1-10.0 minutes 15% A) to afford 5-[3-(benzyloxy)-1-fluoro-7-(methoxymethyl)naphthalen-2-yl]-1λ$^6$,2,5-thiadiazolidine-1,1,3-trione (52.4 mg, 94% yield).

5-[3-(Benzyloxy)-1-fluoro-7-(methoxymethyl)naphthalen-2-yl]-1λ$^6$,2,5-thiadiazolidine-1,1,3-trione (52.4 mg, 0.122 mmol) and tetrahydrofuran (2 mL) were added to 5% Pd/C (wet JM #9) (27 mg, 0.118 mmol) in a 20 mL Barnstead Hast C reactor and stirred for 41.6 hours at 70 psi hydrogen and 25° C. Methanol and 5% Pd/C (wet JM #9) (27.8 mg, 0.122 mmol) were added and the reaction mixture was hydrogenated for 3.5 hours. The reaction mixture was filtered and concentrated under a stream of nitrogen. The residue was dissolved in dimethyl sulfoxide/methanol and purified by reverse-phase preparative HPLC on a Waters XBridge™ C8 5 µm column (75 mm×30 mm). A gradient of methanol (A) and 25 mM ammonium bicarbonate buffer (pH 10) in water (B) was used, at a flow rate of 40 mL/minute (0-0.5 minutes 15% A, 0.5-8.0 minutes linear gradient 15-100% A, 8.0-9.0 minutes 100% A, 9.0-9.1 minutes linear gradient 100-15% A, 9.1-10.0 minutes 15% A) to afford the title compound (9 mg, 22% yield). $^1$H NMR (400 MHz, DMSO-d$_6$) δ ppm 7.84 (s, 1H), 7.76 (dd, J=8.6, 1.5 Hz, 1H), 7.47 (dd, J=8.6, 1.6 Hz, 1H), 7.12 (s, 1H), 4.57 (s, 2H), 4.18 (s, 2H), 3.34 (s, 3H).

Example 131: 5-{1-fluoro-3-hydroxy-7-[(3-methyloxetan-3-yl)methoxy]naphthalen-2-yl}-1λ$^6$,2,5-thiadiazolidine-1,1,3-trione (Compound 230)

Example 131A: 5-{3-(benzyloxy)-1-fluoro-7-[(3-methyloxetan-3-yl)methoxy]naphthalen-2-yl}-1λ$^6$,2,5-thiadiazolidine-1,1,3-trione To a solution of product of Example 1H (140 mg, 0.348 mmol) in N,N-dimethylformamide (2 mL) was added (3-methyloxetan-3-yl)methyl 4-methylbenzenesulfonate (196 mg, 0.765 mmol) and cesium carbonate (249 mg, 0.765 mmol). The reaction mixture was heated to 40° C. overnight. The mixture was then cooled down to ambient temperature and filtered. The volatiles were removed under reduced pressure and the residue was subjected to preparative HPLC [Phenomenex® Luna® C18(2) 5 µm 100 Å AXIA™ column (250 mm×25 mm). 30-100% gradient of acetonitrile (A) and 0.1% trifluoroacetic acid in water (B) over 15 minutes, at a flow rate of 25 mL/minute] to afford the title compound (120 mg, 0.247 mmol, 71% yield). $^1$H NMR (501 MHz, DMSO-d$_6$) δ ppm 7.77 (dd, J=8.9, 1.4 Hz, 1H), 7.59-7.50 (m, 2H), 7.45-7.34 (m, 2H), 7.31 (q, J=2.6 Hz, 3H), 7.24 (dd, J=9.0, 2.6 Hz, 1H), 5.22 (s, 2H), 4.56 (d, J=5.8 Hz, 2H), 4.33 (d, J=5.8 Hz, 2H), 4.19 (s, 2H), 4.09 (s, 2H), 1.91 (s, 1H), 1.41 (s, 3H); MS (APCI$^-$) m/z 485 [M−H]$^-$.

Example 131B: 5-{-fluoro-3-hydroxy-7-[(3-methyloxetan-3-yl)methoxy]naphthalen-2-yl}-1λ$^6$,2,5-thiadiazolidine-1,1,3-trione A 250 mL-round bottom flask was filled with nitrogen, followed by addition of 5% Pd/C (100 mg, 0.940 mmol) and tetrahydrofuran (10 mL). A solution of product 131A (40 mg, 0.083 mmol) in tetrahydrofuran (2 mL), was then added. An adapter fitted with a hydrogen balloon was inserted and the flask was evacuated and refilled with hydrogen (3 times).

The reaction was stirred at ambient temperature overnight. The mixture was filtered through a pad of diatomaceous earth under nitrogen gas. The filtrate was concentrated under reduced pressure, and the residue was subjected to preparative HPLC [Phenomenex® Luna® C18(2) 5 μm 100 Å AXIA™ column (250 mm×25 mm). 30-100% gradient of acetonitrile (A) and 0.1% trifluoroacetic acid in water (B) over 15 minutes, at a flow rate of 25 mL/minute] to afford the title compound (12 mg, 0.030 mmol, 15% yield). $^1$H NMR (400 MHz, DMSO-$d_6$) δ ppm 7.73 (d, J=9.0 Hz, 1H), 7.28 (d, J=2.6 Hz, 1H), 7.23 (dd, J=9.0, 2.5 Hz, 1H), 7.08 (s, 1H), 4.54 (d, J=5.8 Hz, 2H), 4.48 (s, 3H), 4.33 (d, J=5.8 Hz, 2H), 4.17 (s, 2H), 1.40 (s, 3H); MS (APCI$^-$) m/z 395 [M−H]$^-$.

Examples 132A and Example 132B: 5-{4-bromo-7-[1-(cyclopropanesulfonyl)-2,5-dihydro-1H-pyrrol-3-yl]-1-fluoro-3-hydroxynaphthalen-2-yl}-1λ$^6$,2,5-thiadiazolidine-1,1,3-trione (Product A, Compound 231A) and 5-{4-bromo-7-[1-(cyclopropanesulfonyl)-1H-pyrrol-3-yl]-1-fluoro-3-hydroxynaphthalen-2-yl}-1λ$^6$,2,5-thiadiazolidine-1,1,3-trione (Product B, Compound 231B)

To a solution of Example 14 (20 mg, 0.043 mmol) in N,N-dimethylformamide (0.5 mL) was added N-bromosuccinimide (7.61 mg, 0.043 mmol), and the mixture was stirred at ambient temperature for 1 hour. The reaction mixture was combined with another same reaction with 10 mg of Example 14 and 3.8 mg of N-bromosuccinimide, and purified by preparative HPLC on a Phenomenex® Luna® 10 μm, C18 column (30 mm×250 mm) eluted with a gradient of acetonitrile (A) with 0.1% trifluoroacetic acid and water (B) 0.1% with trifluoroacetic acid at a flow rate of 50 mL/minute (0-1 minutes 10% A, 1-20 minutes linear gradient 10-100%) to give title compounds 5-{4-bromo-7-[1-(cyclopropanesulfonyl)-2,5-dihydro-1H-pyrrol-3-yl]-1-fluoro-3-hydroxynaphthalen-2-yl}-1λ$^6$,2,5-thiadiazolidine-1,1,3-trione (17 mg, 0.031 mmol, 48.5% yield) (product A) and 5-{4-bromo-7-[1-(cyclopropanesulfonyl)-1H-pyrrol-3-yl]-1-fluoro-3-hydroxynaphthalen-2-yl}-1λ$^6$,2,5-thiadiazolidine-1,1,3-trione (5 mg, 9.18 μmol, 14% yield) (product B).

Product A: $^1$H NMR (400 MHz, DMSO-$d_6$) δ ppm 10.25 (s, 1H), 8.08-8.01 (m, 1H), 7.98 (dd, J=9.0, 1.8 Hz, 1H), 7.85 (d, J=1.7 Hz, 1H), 6.65-6.59 (m, 1H), 4.71-4.64 (m, 2H), 4.38 (q, J=3.7, 3.2 Hz, 2H), 4.25 (s, 2H), 2.87-2.79 (m, 1H), 1.05 (m, 2H), 1.03-0.93 (m, 2H); MS (APCI$^+$) m/z 545.8 (M+H)$^+$.

Product B: $^1$H NMR (501 MHz, DMSO-$d_6$) δ ppm 9.97 (s, 1H), 8.21 (d, J=1.6 Hz, 1H), 8.09-8.01 (m, 2H), 7.95 (t, J=2.0 Hz, 1H), 7.36 (dd, J=3.3, 2.2 Hz, 1H), 7.05 (dd, J=3.3, 1.7 Hz, 1H), 4.18 (s, 2H), 1.31 (m, 2H), 1.21-1.13 (m, 2H); MS (APCI$^-$) m/z 543.7 (M−H)$^-$.

Example 133: 5-{1-fluoro-3-hydroxy-7-[(3S)-pyrrolidin-3-yl]naphthalen-2-yl}-1λ$^6$,2,5-thiadiazolidine-1,1,3-trione (Compound 232)

Example 133A: tert-butyl (3S)-3-[6-(benzyloxy)-8-fluoro-7-(1,1,4-trioxo-1λ$^6$, 2,5-thiadiazolidin-2-yl) naphthalen-2-yl]pyrrolidine-1-carboxylate To a solution of Example 14A (3 g, 4.61 mmol) in methanol (50 mL) and tetrahydrofuran (50 mL) was added tris(triphenylphosphine)rhodium(I) chloride (0.426 g, 0.461 mmol) at 20° C., and the mixture was stirred for 24 hours at 25° C. under H$_2$ (50 psi). One additional vial on 3 g scale was set up and run as described above. All the mixture was combined and concentrated under reduced pressure. The residue was purified by reversed-phase MPLC (Agela 20-35 um 100 Å 330 g flash column, flow rate 100 mL/minute, 10-100% gradient of acetonitrile in water) to give crude title compound (4 g). The crude title compound was separated by chiral SFC (Waters prep-SFC 80Q; Column: CHIRALPAK® IC-H, 250×30 mm i.d., 5 μm; Mobile phase: A for CO$_2$ and B for ethanol:acetonitrile=4:1(0.1% of ammonium hydroxide); Gradient: B %=50%; Flow rate: 70 g/minute; Column temperature: 40° C.; System back pressure: 100 bar) to give the title compound, tert-butyl (3S)-3-[6-(benzyloxy)-8-fluoro-7-(1,1,4-trioxo-1λ$^6$,2,5-thiadiazolidin-2-yl)naphthalen-2-yl]pyrrolidine-1-carboxylate (680 mg, yield 12.62%, peak 1, first eluted compound, stereochemistry arbitrarily assigned, product A) and tert-butyl (3R)-3-[6-(benzyloxy)-8-fluoro-7-(1,1,4-trioxo-1λ$^6$,2,5-thiadiazolidin-2-yl)naphthalen-2-yl]pyrrolidine-1-carboxylate (480 mg, yield 8.91%, peak 2, second eluted compound, stereochemistry arbitrarily assigned, product B). Product A: $^1$H NMR (400 MHz, DMSO-$d_6$) δ ppm 1.43 (br d, J=3.55 Hz, 10H), 2.03-2.11 (m, 1H), 2.19-2.32 (m, 1H), 3.20-3.27 (m, 2H), 3.43-3.59 (m, 2H), 3.77 (dd, J 10.27, 7.70 Hz, 1H), 4.08 (s, 2H), 5.26 (s, 2H), 6.93-7.24 (m, 4H), 7.27-7.42 (m, 4H), 7.48-7.60 (m, 3H), 7.75-7.83 (m, 2H); Product B: $^1$H NMR (400 MHz, DMSO-$d_6$) δ ppm 1.42 (d, J 5.14 Hz, 9H), 2.05 (br d, J=10.03 Hz, 1H), 2.26 (br s, 1H), 3.21-3.31 (m, 2H), 3.44-3.59 (m, 2H), 3.76 (dd, J=10.27, 7.70 Hz, 1H), 4.07 (s, 2H), 5.25 (s, 2H), 6.92-7.24 (m, 1H), 7.27-7.40 (m, 4H), 7.47-7.60 (m, 3H), 7.74-7.84 (m, 2H).

Example 133B: tert-butyl (3S)-3-[8-fluoro-6-hydroxy-7-(1,1,4-trioxo-1λ$^6$, 2,5-thiadiazolidin-2-yl) naphthalen-2-yl]pyrrolidine-1-carboxylate To a mixture of 10% Pd/C (50 mg, 0.470 mmol) in methanol (10 mL) was added Example 133A, Product A (50 mg, 0.090 mmol) at 25° C., and the mixture was stirred for 2 hours at 25° C. under H$_2$ (15 psi). Then the mixture was concentrated under reduced pressure. The residue was purified by preparative HPLC on Xtimate™ C18 150×25 mm, 5 μm column eluted with 20-100% acetonitrile in H$_2$O containing 10 mM NH$_4$HCO$_3$ for 20 minutes at a flow rate 25 mL/minute to give the title compound (25 mg, yield 56.7%). MS (ESI$^-$) m/z 464 (M−H)$^-$ Example 133C: 5-{t-fluoro-3-hydroxy-7-[(3S)-pyrrolidin-3-yl]naphthalen-2-yl}-1λ$^6$,2,5-thiadiazolidine-1,1,3-trione To a solution of Example 133B (25 mg, 0.051 mmol) in ethyl acetate (1 mL) was added HCl/ethyl acetate (5 mL, 165 mmol) at 25° C., and the mixture was stirred for 2 hours at 25° C.

Then the mixture was concentrated under reduced pressure. The residue was purified by preparative HPLC (Xtimate™ C18 150×25 mm, 5 μm column eluted with acetonitrile in H$_2$O containing 10 mM NH$_4$HCO$_3$ [0.0-10 minutes, 10-40% B; 10-10.1 minutes, 40% B; 10.1-10.2 minutes; 40-100% B; 10.2-16.2 minutes, 100% B; 16.2-16.3 minutes, 100-10% B; 16.3-17.5 minutes, 10% B, minutes] at a flow rate 25 mL/minute monitored at 220 and 254 nm) to give the title compound (10 mg, yield 53.3%). $^1$HNMR (400 MHz, DMSO-$d_6$) δ ppm 1.93-2.10 (m, 1H), 2.35-2.42 (m, 1H), 3.11-3.24 (m, 2H), 3.45-3.50 (m, 1H), 3.54-3.73 (m, 2H), 4.09 (s, 2H), 7.06 (s, 1H), 7.46 (dd, J=8.68, 1.59 Hz, 1H), 7.75 (d, J=8.44 Hz, 1H), 7.80 (s, 1H), 8.58-9.34 (m, 1H); MS (ESI⁻) m/z 364 (M−H)⁻.

Example 134: 5-{1-fluoro-3-hydroxy-7-[(3R)-pyrrolidin-3-yl]naphthalen-2-yl}-1$\lambda^6$,2,5-thiadiazolidine-1,1,3-trione (Compound 233)

The title compound was prepared from Example 133A, product B using the methods described for Examples 133B and Example 133C. ¹HNMR (400 MHz, DMSO-d₆) δ ppm 2.03 (dq, J=12.73, 9.33 Hz, 1H), 2.35-2.42 (m, 1H), 3.11-3.27 (m, 1H), 3.43-3.50 (m, 1H), 3.54-3.74 (m, 2H), 4.09 (s, 2H), 7.06 (s, 1H), 7.46 (dd, J=8.56, 1.59 Hz, 1H), 7.75 (d, J=8.56 Hz, 1H), 7.80 (s, 1H), 8.34-9.87 (m, 2H); MS (ESI⁻) m/z364 (M−H)⁻.

Example 135: 5-(8-chloro-1-fluoro-3-hydroxy-7-methoxynaphthalen-2-yl)-1$\lambda^6$,2,5-thiadiazolidine-1,1,3-trione (Compound 234)

Example 135A: benzyl 3-(benzyloxy)-8-chloro-7-methoxynaphthalene-2-carboxylate

To a solution of Example 25A (3.3 g, 7.87 mmol) in dichloromethane (30 mL) was added zirconium(IV) chloride (0.275 g, 1.180 mmol) and 1-chloropyrrolidine-2,5-dione (1.051 g, 7.87 mmol) in order at 20° C. The mixture was stirred at 40° C. for 2 hours. The mixture was concentrated under reduced pressure. The residue was purified by flash chromatography (petroleum ether: ethyl acetate=20:1) to give the title compound (2.53 g, 5.73 mmol, 72.8% yield). ¹H NMR (400 MHz, DMSO-d₆) δ ppm 8.41 (s, 1H), 7.91 (d, J=9.04 Hz, 1H), 7.70 (s, 1H), 7.65 (d, J=9.26 Hz, 1H), 7.45-7.52 (m, 2H), 7.31-7.44 (m, 8H), 5.37 (s, 2H), 5.27 (s, 2H), 3.98 (s, 3H); MS (ESI⁺) m/z 433 (M+H)⁺.

Example 135B: 3-(benzyloxy)-8-chloro-7-methoxynaphthalene-2-carboxylic acid

To a solution of Example 135A (2.53 g, 5.73 mmol) in methanol (20 mL), tetrahydrofuran (20 mL) and water (10 mL) was added a solution of sodium hydroxide (0.229 g, 5.73 mmol) in water (2 mL) at 20° C. The mixture was reflux at 60° C. for 3 hours. The mixture was extracted with ethyl acetate (30 mL). The aqueous phase was adjusted to pH=3 with aqueous hydrochloric acid (1 M). A solid precipitated. Then solid was collected by filtration, and the solid was dried under high vacuum to give the title compound (1.67 g, 4.77 mmol, 83% yield). ¹H NMR (400 MHz, DMSO-d₆) δ ppm 8.31-8.35 (m, 1H), 7.86-7.92 (m, 1H), 7.59-7.66 (m, 2H), 7.52-7.57 (m, 2H), 7.38-7.44 (m, 2H), 7.30-7.36 (m, 1H), 5.28 (s, 2H), 3.98 (s, 3H); MS (ESI⁺) m/z 343 (M+H)⁺.

Example 135C: tert-butyl[3-(benzyloxy)-8-chloro-7-methoxynaphthalen-2-yl]carbamate To a solution of Example 135B (1.45 g, 4.15 mmol) in toluene (15 mL) was added triethylamine (1.733 mL, 12.44 mmol), t-butanol (15 mL) and diphenylphosphoryl azide (2.282 g, 8.29 mmol) in order at 20° C. The mixture was stirred at 110° C. for 3 hours under nitrogen. One additional vial on 100 mg scale was set up and run as described above. The mixtures were combined and concentrated under reduced pressure. The crude product was purified by flash chromatography (petroleum ether: ethyl acetate=5:1) to give the title compound (2.2 g, 4.643 mmol, 97.2% yield). ¹H NMR (400 MHz, DMSO-d₆) δ ppm 8.50-8.59 (m, 1H), 8.08 (s, 1H), 7.72-7.77 (m, 1H), 7.53-7.60 (m, 2H), 7.47-7.53 (m, 1H), 7.34-7.45 (m, 4H), 5.29 (s, 2H), 3.94 (s, 3H), 1.49 (s, 9H); MS (ESI⁺) m/z 314, 358, 414 (M−99, M−55, M+H)⁺.

Example 135D: 3-(benzyloxy)-8-chloro-7-methoxynaphthalen-2-amine

To a solution of Example 135C (996 mg, 2.222 mmol) in dichloromethane (15 mL) was added trifluoroacetic acid (5 mL, 64.9 mmol) dropwise at 0° C. The mixture was stirred at 20° C. for 1 hour. The mixture was concentrated under reduced pressure. The residue was diluted with water (20 mL) and saturated aqueous sodium bicarbonate was added to adjust the pH to 9. The mixture was extracted with ethyl acetate (3×30 mL). The combined organic phases were washed with brine (50 mL), dried over anhydrous sodium sulfate and concentrated under reduced pressure to give the title compound (996 mg, 2.22 mmol, 92% yield). ¹H NMR (400 MHz, DMSO-d₆) δ ppm 7.53-7.60 (m, 4H), 7.39-7.44 (m, 3H), 7.14 (s, 1H), 0.06-7.10 (m, 1H), 5.50 (s, 2H), 5.23 (s, 2H), 3.88 (s, 3H); MS (ESI⁺) m/z 313 (M+H)⁺.

Example 135E: methyl {[3-(benzyloxy)-8-chloro-7-methoxynaphthalen-2-yl]amino}acetate To a solution of Example 135D (1.1 g, 3.51 mmol) in N,N-dimethylformamide (10 mL) was added potassium carbonate (0.969 g, 7.01 mmol) at 20° C., and the mixture was stirred for 5 minutes. Then methyl bromoacetate (0.485 mL, 5.26 mmol) was added. The mixture was stirred at 70° C. for 3 hours. The solution was diluted with water (50 mL), and the resulting mixture was extracted with ethyl acetate (3×30 mL). The combined organic layers were washed with brine (3×25 mL), dried over anhydrous sodium sulfate, and concentrated under reduced pressure. The residue was purified by preparative HPLC [Phenomenex® Luna® C18 100× 30 mm, 5 µm column, flow rate 25 mL/minute, 50-80% gradient of acetonitrile in water (10 mM trifluoroacetic acid solution)] and lyophilized to give the title compound (610 mg, 1.265 mmol, 36.1% yield). MS (ESI⁺) m/z 386 (M+H)⁺.

Example 135F: methyl{[3-(benzyloxy)-8-chloro-1-fluoro-7-methoxynaphthalen-2-yl]amino}acetate To a solution of Example 135E (500 mg, 1.037 mmol) in N,N-dimethylformamide (6 mL) was added 1-(chloromethyl)-4-fluoro-1,4-diazoniabicyclo[2.2.2]octane bis(tetrafluoroborate) (Selectfluor®, 441 mg, 1.244 mmol) at 0° C., and the mixture was stirred for 5 minutes. Then the mixture was quenched with saturated aqueous sodium thiosulfate (20 mL). The mixture was extracted with ethyl acetate (3×30 mL). The combined organic layers were washed with brine (70 mL), dried over anhydrous sodium sulfate, and concentrated under reduced pressure. The residue was purified by flash column (petroleum ether/ethyl acetate=5:1) to give the title compound (300 mg, 0.706 mmol, 68.1% yield). ¹H NMR (400 MHz, DMSO-d₆) δ ppm 7.68 (dd, J=8.93, 1.43 Hz, 1H), 7.54 (d, J=7.28 Hz, 2H), 7.39-7.46 (m, 2H), 7.33-7.39 (m, 1H), 7.21-7.29 (m, 2H), 5.54-5.61 (m, 1H), 5.25 (s, 2H), 4.20 (dd, J=6.50, 3.64 Hz, 2H), 3.90 (s, 3H), 3.61 (s, 3H); MS (ESI⁺) m/z 404 (M+H)⁺.

Example 135G: methyl {[3-(benzyloxy)-8-chloro-1-fluoro-7-methoxynaphthalen-2-yl][(tert-butoxycarbonyl)sulfamoyl]amino}acetate To the solution of sulfurisocyanatidic chloride (200 mg, 1.411 mmol) in dichloromethane (6 mL) was added a solution of tert-butanol (0.135 mL, 1.411 mmol) in dichloromethane (6 mL) dropwise at 20° C., and the mixture was stirred for 30 minutes at 20° C. Then the mixture was added to a solution of Example 135F (300 mg, 0.706 mmol) and triethylamine (0.393 mL, 2.82 mmol) in dichloromethane (6 mL) dropwise at 20° C., and the resulting mixture was stirred for 60 minutes at 20° C. The mixture was concentrated under reduced pressure to give the title compound (880 mg, crude) which was used for the next step without further purification. MS (ESI⁺) m/z 605 (M+Na)⁺.

Example 135H: methyl {[3-(benzyloxy)-8-chloro-1-fluoro-7-methoxynaphthalen-2-yl](sulfamoyl) amino}acetate To the solution of Example 135G (880 mg, crude) in dichloromethane (9 mL) was added trifluoroacetic acid (3 mL, 38.9 mmol) dropwise at 0° C., and the mixture was stirred for 2 hours at 20° C. The reaction mixture was concentrated under reduced pressure. The mixture was diluted with water (20 mL) and the pH was adjusted to pH=9 with saturated aqueous sodium bicarbonate. The mixture was extracted with ethyl acetate (3×30 mL). The combined organic phases were dried over anhydrous sodium sulfate and concentrated under reduced pressure to give the title compound (390 mg, 0.646 mmol, 89% yield). MS (ESI⁺) m/z 505 (M+Na)⁺.

Example 135I: 5-[3-(benzyloxy)-8-chloro-1-fluoro-7-methoxynaphthalen-2-yl]-1,2,5-thiadiazolidine-1, 1,3-trione To a solution of Example 135H (390 mg, 0.646 mmol) in tetrahydrofuran (3 mL) was added sodium methoxide (175 mg, 0.969 mmol, 30% in methanol) at 20° C. under nitrogen, and the mixture was stirred for 2 hours at 20° C. The pH of the mixture was adjusted to pH=4 with aqueous hydrochloric acid (1 M). The mixture was extracted with ethyl acetate (3×30 mL). The combined organic phases were dried over anhydrous sodium sulfate and concentrated under reduced pressure to give the title compound (200 mg, 0.399 mmol, 61.8% yield) which was used for the next step without further purification. MS (ESI⁻) m/z 449 (M–H)⁻.

Example 135J: 5-(8-chloro-1-fluoro-3-hydroxy-7-methoxynaphthalen-2-yl)-1$\lambda^6$,2,5-thiadiazolidine-1, 1,3-trione To a solution of Example 135I (120 mg, 0.240 mmol) in dichloromethane (3 mL) was added boron trichloride (1.198 mL, 1.198 mmol) at −65° C., and the mixture was stirred for 1 hour at −65° C. One additional vial on 10 mg scale was set up and run as described above. The reaction mixture was quenched by the addition of methanol (3 mL). The reaction mixtures were combined and concentrated under reduced pressure. The residue was purified by preparative HPLC [Xtimate™ C18, 150×25 mm, 5 μm column, flow rate 25 mL/minute, 15-40% gradient of acetonitrile in water (10 mM ammonium bicarbonate solution)] and lyophilized to give the title compound (17 mg, 0.043 mmol, 16.5% yield). $^1$H NMR (400 MHz, DMSO-d$_6$) δ ppm 7.73-7.78 (m, 1H), 7.48 (d, J=9.21 Hz, 1H), 7.09 (s, 2H), 4.06 (s, 2H), 3.94 (s, 3H); $^{19}$F NMR (377 MHz, DMSO-d$_6$) δ ppm-118.23 (s, 1F); MS (ESI⁻) m/z 359 (M–H)⁻.

Example 136: 5-{7-[(3,3-difluorocyclobutyl) methoxy]-1-fluoro-3-hydroxynaphthalen-2-yl}-1$\lambda^6$, 2,5-thiadiazolidine-1,1,3-trione (Compound 235)

In a 20 mL vial were combined Example 1H (511 mg, 1.270 mmol, 1.0 equivalents), 3-(bromomethyl)-1,1-difluorocyclobutane (470 mg, 2.54 mmol, 2.0 equivalents), and cesium carbonate (1241 mg, 3.81 mmol, 3.0 equivalents) in N,N-dimethylformamide (5 mL). The reaction mixture was heated overnight at 50° C. The material was diluted with aqueous 1 M HCl and extracted with ethyl acetate. The organic fraction was washed with NH$_4$Cl (2×) and brine. The organic layer was dried over Na$_2$SO$_4$, filtered, and concentrated in vacuo. The residue was purified using silica gel chromatography (0-10% methanol in dichloromethane) to give 5-{3-(benzyloxy)-7-[(3,3-difluorocyclobutyl) methoxy]-1-fluoronaphthalen-2-yl}-1$\lambda^6$,2,5-thiadiazolidine-1,1,3-trione (409 mg, 64% yield). $^1$H NMR (400 MHz, DMSO-d$_6$) δ ppm 7.79 (dd, J=9.0, 1.5 Hz, 1H), 7.55-7.45 (m, 2H), 7.43-7.19 (m, 6H), 5.20 (s, 2H), 4.47 (s, 2H), 4.14 (d, J=6.3 Hz, 2H), 2.81-2.49 (m, 5H).

5-{3-(Benzyloxy)-7-[(3,3-difluorocyclobutyl)methoxy]-1-fluoronaphthalen-2-yl}-1$\lambda^6$,2,5-thiadiazolidine-1,1,3-trione (406 mg, 0.802 mmol) in tetrahydrofuran (4.0 mL) was added to 5% Pd/C (wet JM #9) (108 mg, 0.451 mmol) in a 20 mL RS10 Hast C reactor. The reactor was purged with argon. The mixture was stirred at 1200 RPM under 65 psi of hydrogen at 25° C. After 16.3 hours, the reactor was vented. The mixture was filtered through a filter funnel with a polyethylene frit packed with diatomaceous earth as a tetrahydrofuran (4.0 mL) solution. The catalyst was washed successive with methanol (2×) and again with tetrahydrofuran. The combined filtrate and washes were concentrated by rotary evaporation to afford a film. Upon placing the film under house vacuum for 10 minutes a foam resulted. The material was triturated with dichloromethane/heptanes to afford the title compound as a solid (267 mg, 80% yield). $^1$H NMR (400 MHz, DMSO-d$_6$) δ ppm 7.68 (dd, J=9.0, 1.5 Hz, 1H), 7.24-7.13 (m, 2H), 7.03 (s, 1H), 4.43 (s, 2H), 4.11 (d, J=6.3 Hz, 2H), 2.80-2.48 (m, 5H); MS (ESI⁻) m/z 414.9 [M–H]⁻.

Example 137: 5-(7-cyclopropyl-1-fluoro-3-hydroxynaphthalen-2-yl)-1$\lambda^6$,2,5-thiadiazolidine-1,1,3-trione (Compound 236)

Example 137A: 5-[3-(benzyloxy)-7-cyclopropyl-1-fluoronaphthalen-2-yl]-1$\lambda^6$,2,5-thiadiazolidine-1,1,3-trione A mixture of Example 1G (140 mg, 0.3 mmol), 1,1'-bis (di-tert-butylphosphino)ferrocene]palladium(II) dichloride (29.3 mg, 0.045 mmol), 2-cyclopropyl-4,4,5,5-tetramethyl-1,3,2-dioxaborolane (136 mg, 0.810 mmol) and cesium carbonate (293 mg, 0.900 mmol) in tetrahydrofuran (2.5 mL) and water (0.23 mL) was degassed and filled with nitrogen five times, then the mixture was heated to 115° C. for 3 hours. The mixture was cooled to ambient temperature and diluted with dichloromethane (50 mL). The organic phase was washed with 0.1 N HCl aqueous solution (15 mL), dried over sodium sulfate, filtered and concentrated. The resulting residue was purified by flash column chromatography on silica gel (40 g) eluted with dichloromethane/methanol (0 to 10%) to give title compound (85 mg, 0.199 mmol, 66.4% yield). $^1$H NMR (500 MHz, DMSO-d$_6$) δ ppm 7.72 (br d, J=8 Hz, 1H), 7.61 (d, J=2 Hz, 1H), 7.56 (m, 2H), 7.35 (m, 3H), 7.26 (m, 2H), 5.23 (s, 2H), 4.09 (s, 2H), 2.11 (m, 1H), 1.01 (m, 2H), 0.79 (m, 2H); MS (ESI⁻) m/z 425 (M–H)⁻.

Example 137B: 5-(7-cyclopropyl-1-fluoro-3-hydroxynaphthalen-2-yl)-1$\lambda^6$,2,5-thiadiazolidine-1,1,3-trione To a mixture of 1,2,3,4,5-pentamethylbenzene (73.0 mg, 0.492 mmol) and Example 137A (70 mg, 0.164 mmol) in dichloromethane (3 mL) at −78° C. was added trichloroborane (0.985 mL, 0.985 mmol, 1 M in dichloromethane). The mixture was stirred at −78° C. for 20 minutes and then quenched with ethanol (3 mL). The mixture was stirred at 0° C. for 5 minutes and then concentrated. The resulting solid was washed with heptane (4×2 mL) and dichloromethane (4×2 mL) and concentrated to give the title compound (46 mg, 0.137 mmol, 83% yield). $^1$H NMR (500 MHz, DMSO-d$_6$) δ ppm 10.41 (br s, 1H), 7.67 (br d, J=8 Hz, 1H), 7.58 (d, J=2 Hz, 1H), 7.23 (dd, J=8, 2 Hz, 1H), 7.07 (s, 1H), 4.44 (s, 2H), 2.09 (m, 1H), 1.00 (m, 2H), 0.77 (m, 2H); MS (ESI$^−$) m/z 335 (M−H)$^−$.

Example 138: 5-{7-[1-(cyclopropanecarbonyl)-2,5-dihydro-1H-pyrrol-3-yl]-1-fluoro-3-hydroxynaphthalen-2-yl}-1λ$^6$,2,5-thiadiazolidine-1,1,3-trione (Compound 237)

Example 138A: 3-(4,4,5,5-tetramethyl-1,3,2-dioxaborolan-2-yl)-2,5-dihydro-1H-pyrrole To a solution of tert-butyl 3-(4,4,5,5-tetramethyl-1,3,2-dioxaborolan-2-yl)-2,5-dihydro-1H-pyrrole-1-carboxylate (250 mg, 0.847 mmol) in methylene chloride (2 mL) was added trifluoroacetic acid (2 mL). The reaction was stirred at ambient temperature for 2 hours. The volatiles were then removed under reduced pressure and the residue was used for the next step without further purification.

Example 138B: cyclopropyl(3-(4,4,5,5-tetramethyl-1,3,2-dioxaborolan-2-yl)-2,5-dihydro-1H-pyrrol-1-yl)methanone To a solution of crude 3-(4,4,5,5-tetramethyl-1,3,2-dioxaborolan-2-yl)-2,5-dihydro-1H-pyrrole (250 mg, 1.282 mmol) and cyclopropanecarbonyl chloride (147 mg, 1.410 mmol) in tetrahydrofuran (2 mL) was added triethylamine (0.876 mL, 6.41 mmol). The mixture was allowed to stir at ambient temperature for 14 hours. The mixture was diluted with water and then extracted with ethyl acetate. The combined organic fractions were washed with water and brine. The organic fraction was dried over anhydrous sodium sulfate, filtered and concentrated under reduced pressure to provide the title compound which was used for the next step without further purification. MS (APCI$^+$) m/z 264 [M+H]$^+$.

Example 138C: 5-{7-[1-(cyclopropanecarbonyl)-2,5-dihydro-H-pyrrol-3-yl]-1-fluoro-3-hydroxynaphthalen-2-yl}-1λ$^6$,2,5-thiadiazolidine-1,1,3-trione A microwave tube was charged with product of Example 128A (250 mg, 0.666 mmol), crude cyclopropyl(3-(4,4,5,5-tetramethyl-1,3,2-dioxaborolan-2-yl)-2,5-dihydro-1H-pyrrol-1-yl)methanone (Example 138B, 263 mg, 1 mmol), potassium carbonate (276 mg, 1.999 mmol), and 1,1'-bis(di-tert-butylphosphino)ferrocene palladium dichloride (8.69 mg, 0.013 mmol). 1,4-Dioxane (2 mL) and water (1 mL) were subsequently added. The reaction mixture was flushed with N$_2$ for 5 minutes and then heated to 70° C. After 1.5 hours, the reaction was cooled down to ambient temperature, the volatiles were removed under reduced pressure, and the residue was subjected to preparative HPLC [Phenomenex® Luna® C18(2) 5 μm 100 Å AXIA™ column (250 mm×25 mm). 30-100% gradient of acetonitrile (A) and 0.1% ammonium acetate in water (B) over 15 minutes, at a flow rate of 25 mL/minute] to give the title compound (30 mg, 0.070 mmol, 11% yield over three steps). $^1$H NMR (400 MHz, DMSO-d$_6$) δ ppm 9.99 (s, 1H), 7.78-7.63 (m, 3H), 7.15 (s, 1H, NH$_3$), 7.03 (s, 1H, NH$_3$), 7.02 (s, 1H), 6.90 (s, 1H, NH$_3$), 6.51 (dt, J=9.6, 2.0 Hz, 1H), 4.89 (td, J=3.8, 1.8 Hz, 1H), 4.60 (p, J=2.3 Hz, 1H), 4.51 (d, J=3.0 Hz, 1H), 4.23 (q, J=3.3 Hz, 1H), 4.09 (s, 2H), 1.96 (h, J=5.9, 5.4 Hz, 1H), 0.79-0.67 (m, 4H); MS (APCI$^−$) m/z 430 [M−H]$^−$.

Example 139: 5-(4-chloro-1-fluoro-3-hydroxy-7-methoxynaphthalen-2-yl)-1λ$^6$,2,5-thiadiazolidine-1,1,3-trione (Compound 238)

To a solution of 5-(1-fluoro-3-hydroxy-7-methoxynaphthalen-2-yl)-1λ$^6$,2,5-thiadiazolidine-1,1,3-trione (30 mg, 0.092 mmol, Example 25) in N,N-dimethylformamide ( ) (0.5 mL) was added N-chlorosuccinimide (12.28 mg, 0.092 mmol), and the mixture was stirred at ambient temperature for 1 hour. The reaction mixture was purified on preparative HPLC on a Phenomenex® Luna® 10 μm, C$_{18}$ column (30 mm×250 mm) eluted with a gradient of acetonitrile (A) with 0.1% trifluoroacetic acid and water (B) 0.1% with trifluoroacetic acid at a flow rate of 50 mL/minute (0-1 minutes 10% A, 1-20 minutes linear gradient 10-100%) to give the title compound (12 mg). $^1$H NMR (400 MHz, DMSO-d$_6$) δ ppm 10.16 (s, 1H), 7.99 (dd, J=9.2, 1.4 Hz, 1H), 7.38 (dd, J=9.2, 2.6 Hz, 1H), 7.32 (d, J=2.6 Hz, 1H), 4.39 (s, 2H), 3.90 (s, 3H); MS (APCI$^−$) m/z 358.7 (M−H)$^−$.

Example 140: 5-{7-[(E)-2-cyclopropylethenyl]-1-fluoro-3-hydroxynaphthalen-2-yl}-1λ$^6$,2,5-thiadiazolidine-1,1,3-trione (Compound 239)

To a solution of the product of Example 128A (0.134 g, 0.36 mmol) was added dioxane:water (3:1, 4 mL) followed by (E)-2-(2-cyclopropylvinyl)-4,4,5,5-tetramethyl-1,3,2-dioxaborolane (0.139 g, 0.714 mmol) and potassium carbonate (0.166 g, 1.199 mmol). This suspension was sparged with N$_2$ for 10 minutes, and then 1,1'-bis(di-tert-butylphosphino)ferrocene palladium dichloride (0.00261 g, 0.004 mmol) was added. Sparging was continued for 5 minutes, and then the biphasic suspension was heated at 80° C. for 12 hours. The mixture was allowed to cool to ambient temperature, and the volatiles were removed under reduced pressure. The resulting residue was purified over SiO$_2$(0-25% methanol in ethyl acetate) to yield the title compound (0.048 g, 0.132 mmol, 37% yield). $^1$H NMR (501 MHz, DMSO-d$_6$) δ ppm 9.76 (s, 1H), 7.69-7.62 (m, 2H), 7.58 (dd, J=8.7, 1.7 Hz, 1H), 7.03 (d, J=1.2 Hz, 1H), 6.62 (d, J=15.8 Hz, 1H), 5.95 (dd, J=15.8, 9.1 Hz, 1H), 4.10 (s, 2H), 1.66-1.56 (m, 1H), 0.86-0.76 (m, 2H), 0.58-0.52 (m, 2H); MS (APCI$^−$) m/z 361 [M−H]$^−$.

Example 141: 5-{1-fluoro-3-hydroxy-7-[(1E)-4-methylpent-1-en-1-yl]naphthalen-2-yl}-1λ$^6$,2,5-thiadiazolidine-1,1,3-trione (Compound 240)

To a solution of the product of Example 128A (0.15 g, 0.4 mmol) was added dioxane:water (3:1, 4 mL, 0.1 M) followed by (E)-(4-methylpent-1-en-1-yl)boronic acid (0.102 g, 0.8 mmol) and potassium carbonate (0.166 g, 1.199 mmol). This suspension was sparged with N$_2$ for 10 minutes, and then 1,1'-bis(di-tert-butylphosphino)ferrocene palladium dichloride (0.00261 g, 0.004 mmol) was added. Sparging was continued for 5 minutes, and then the biphasic suspension was heated at 80° C. for 12 hours. The mixture was allowed to cool to ambient temperature, and the volatiles were removed under reduced pressure to yield crude title compound which was purified by reverse phase HPLC (Phenomenex® C8(2) Luna® 5 μm AXIA™ 150×30 mm column, 3-100% gradient of acetonitrile (A) and 10 mM ammonium acetate in water (B) over 17 minutes at a flow rate of 50 mL/minute to give the title compound (0.0783 g, 0.207 mmol, 52% yield). $^1$H NMR (400 MHz, DMSO-d$_6$) δ ppm 7.68 (s, 1H), 7.62 (d, J=2.1 Hz, 2H), 7.00 (s, 1H), 6.52 (d, J=15.8 Hz, 1H), 6.41-6.26 (m, 1H), 4.05 (s, 2H), 2.08 (t, J=6.9 Hz, 2H), 1.70 (dq, J=13.3, 6.7 Hz, 1H), 0.90 (d, J=6.6 Hz, 6H); MS (APCI$^-$) m/z 377 [M−H]$^-$.

Example 142: 5-{1-fluoro-3-hydroxy-7-[1-(pentamethylphenyl)ethenyl]naphthalen-2-yl}-1λ$^6$,2,5-thiadiazolidine-1,1,3-trione (Compound 241)

Example 142A: 5-{3-(benzyloxy)-1-fluoro-7-[(trimethylsilyl)ethynyl]naphthalen-2-yl}-1λ$^6$,2,5-thiadiazolidine-1,1,3-trione A mixture of Example 1G (186 mg, 0.4 mmol), bis(triphenylphosphine)palladium(II) dichloride (25.3 mg, 0.036 mmol), copper(I) iodide (11.43 mg, 0.060 mmol) and ethynyltrimethylsilane (130 mg, 1.320 mmol) in triethylamine (0.7 g) and tetrahydrofuran (3.5 mL) was heated to 125° C. for 60 minutes. The mixture was diluted with ethyl acetate (70 mL). The organic phase was washed with brine (3×15 mL), dried over sodium sulfate, filtered and concentrated to give the title compound (190 mg, 0.414 mmol, 98% yield). MS (ESI$^-$) m/z 481 (M−H)$^-$.

Example 142B: 5-[3-(benzyloxy)-7-ethynyl-1-fluoronaphthalen-2-yl]-1λ$^6$,2,5-thiadiazolidine-1,1,3-trione To Example 142A (190 mg, 0.4 mmol) in methanol (2.5 mL) and was added potassium carbonate (193 mg, 1.400 mmol). The mixture was stirred at 25° C. for 1 hour. The mixture was diluted with dichloromethane (5 mL) and filtered. The filtrate was concentrated. The resulting residue was purified by flash column chromatography on silica gel (40 g) eluted with ethyl acetate/methanol (0 to 10%) to give the title compound (110 mg, 0.268 mmol, 67% yield). MS (ESI$^-$) m/z 409 (M−H)$^-$.

Example 142C: 5-{-fluoro-3-hydroxy-7-[1-(pentamethylphenyl)ethenyl]naphthalen-2-yl}-1λ$^6$,2,5-thiadiazolidine-1,1,3-trione To a mixture of 1,2,3,4,5-pentamethylbenzene (108 mg, 0.731 mmol) and Example 142B (100 mg, 0.244 mmol) in dichloromethane (5 mL) at −78° C. was added trichloroborane (0.975 mL, 0.975 mmol, 1 M in dichloromethane). The mixture was stirred at −78° C. for 30 minutes and then at 0° C. for 30 minutes. The mixture was quenched with ethanol (2 mL), stirred at 0° C. for 5 minutes, and then concentrated. The resulting residue was purified by flash column chromatography on silica gel (40 g) eluted with 0-100% ethyl acetate/heptane to give the title compound (67 mg, 0.143 mmol, 58.7% yield). $^1$H NMR (500 MHz, DMSO-d$_6$) δ ppm 10.54 (br s, 1H), 7.76 (s, 2H), 7.37 (s, 1H), 7.09 (s, 1H), 6.18 (s, 1H), 5.05 (s, 1H), 4.39 (s, 2H), 2.24 (s, 3H), 2.19 (s, 6H), 2.02 (s, 6H); MS (ESI$^-$) m/z 469 (M+H)$^+$.

Example 143: 5-{7-[1-(cyclopropylmethyl)-2,5-dihydro-1H-pyrrol-3-yl]-1-fluoro-3-hydroxynaphthalen-2-yl}-1λ$^6$,2,5-thiadiazolidine-1,1,3-trione (Compound 242)

Example 143A: 5-[3-(benzyloxy)-7-(2,5-dihydro-H-pyrrol-3-yl)-1-fluoronaphthalen-2-yl]-1λ$^6$,2,5-thiadiazolidine-1,1,3-trione To a solution of product from Example 123A (800 mg, 1.44 mmol) in dichloromethane (5 mL) was added trifluoroacetic acid (2 mL). The mixture was stirred at ambient temperature for 30 minutes. The volatiles were removed under reduced pressure, and the residue was subjected to preparative HPLC [Phenomenex® Luna® C18(2) 5 μm 100 Å AXIA™ column (250 mm×25 mm). 30-100% gradient of acetonitrile (A) and 0.1% ammonium acetate in water (B) over 15 minutes, at a flow rate of 25 mL/minute] to afford the title compound (474 mg, 1.05 mmol, 73% yield). $^1$H NMR (400 MHz, DMSO-d$_6$) δ ppm 7.86 (d, J=3.7 Hz, 2H), 7.60-7.48 (m, 2H), 7.46-7.27 (m, 5H), 6.60 (t, J=2.2 Hz, 1H), 5.28 (s, 2H), 4.50 (q, J=2.3 Hz, 2H), 4.19 (dt, J=5.0, 2.5 Hz, 2H), 4.10 (s, 2H); MS (APCI$^-$) m/z 452 [M−H]$^-$.

Example 143B: 5-{7-[1-(cyclopropylmethyl)-2,5-dihydro-H-pyrrol-3-yl]-1-fluoro-3-hydroxynaphthalen-2-yl}-1λ$^6$,2,5-thiadiazolidine-1,1,3-trione A 20 mL microwave vial was charged with the product from Example 143A (200 mg, 0.441 mmol) and N,N-dimethylformamide. Subsequently, cyclopropanecarbaldehyde (93 mg, 1.323 mmol) and acetic acid (0.126 mL, 2.205 mmol) were added, and the mixture was stirred for 5 minutes at ambient temperature. Sodium cyanoborohydride (166 mg, 2.65 mmol) was then added. The mixture was stirred at ambient temperature overnight. The reaction mixture was partitioned between water (5 mL) and ethyl acetate (5 mL). The aqueous layer was further extracted with ethyl acetate (2×3 mL), and the combined organic layers were washed with saturated aqueous ammonium chloride (5 mL) and dried over sodium sulfate. The volatiles were removed under reduced pressure and the residue was subjected to preparative HPLC [Phenomenex® Luna® C18(2) 5 μm 100 Å AXIA™ column (250 mm×25 mm). 30-100% gradient of acetonitrile (A) and 0.1% trifluoroacetic acid in water (B) over 15 minutes, at a flow rate of 25 mL/minute] to afford 5-{3-(benzyloxy)-7-[1-(cyclopropylmethyl)-2,5-dihydro-1H-pyrrol-3-yl]-1-fluoronaphthalen-2-yl}-1λ$^6$,2,5-thiadiazolidine-1,1,3-trione (70 mg, 0.138 mmol, 31% yield). MS (APCI$^-$) m/z 506 [M−H]$^-$.

A 50 mL round bottom flask was charged with 5-{3-(benzyloxy)-7-[1-(cyclopropylmethyl)-2,5-dihydro-1H-pyrrol-3-yl]-1-fluoronaphthalen-2-yl}-1λ$^6$,2,5-thiadiazolidine-1,1,3-trione (68 mg, 0.134 mmol),1,2,3,4,5-pentamethylbenzene (59.6 mg, 0.402 mmol) and methylene chloride (3 mL). The mixture was flushed with nitrogen for 5 minutes. The heterogeneous suspension was cooled to −78° C. and equilibrated for 5 minutes. Subsequently, a 1 M solution of trichloroborane (0.670 mL, 0.670 mmol) in dichloromethane was added dropwise over 5 minutes. The reaction was stirred at −78° C. for 30 minutes. Ethyl acetate (1 mL) and methanol (0.2 mL) were added and the reaction was warmed to ambient temperature. The volatiles were removed under reduced pressure and the residue was subjected to preparative HPLC [Phenomenex® Luna® C18(2) 5 μm 100 Å AXIA™ column (250 mm×25 mm). 30-100% gradient of acetonitrile (A) and 0.1% trifluoroacetic acid in water (B) over 15 minutes, at a flow rate of 25 mL/minute] to afford the title compound (22 mg, 0.053 mmol, 39% yield). $^1$H NMR (400 MHz, DMSO-d$_6$) δ ppm 10.05 (s, 1H), 7.79 (d, J=3.6 Hz, 3H), 7.10 (d, J=1.3 Hz, 1H), 6.58 (t, J=2.1 Hz, 1H), 4.63 (s, 2H), 4.30 (s, 2H), 4.10 (s, 2H), 3.26-3.19 (m, 2H), 1.21-1.14 (m, 1H), 0.71-0.60 (m, 2H), 0.48-0.40 (m, 2H); MS (APCI$^-$) 416 m/z [M–H]$^-$.

Example 144: 5-(4-bromo-1-fluoro-3-hydroxy-7-methoxynaphthalen-2-yl)-1λ$^6$,2,5-thiadiazolidine-1,1,3-trione (Compound 243)

To a solution of 5-(1-fluoro-3-hydroxy-7-methoxynaphthalen-2-yl)-1λ$^6$,2,5-thiadiazolidine-1,1,3-trione (20 mg, 0.061 mmol, Example 25) in N,N-dimethylformamide (0.5 mL) was added N-bromosuccinimide (10.91 mg, 0.061 mmol), and the mixture was stirred at ambient temperature for 1 hour. The mixture was purified by preparative HPLC on a Phenomenex® Luna® 10 μm, C18 column (30 mm×250 mm) eluted with a gradient of acetonitrile (A) with 0.1% trifluoroacetic acid and water (B) 0.1% with trifluoroacetic acid at a flow rate of 50 mL/minute (0-1 minutes 10% A, 1-20 minutes linear gradient 10-100%) to give the title compound (22 mg, 89% yield). $^1$H NMR (400 MHz, DMSO-d$_6$) δ ppm 9.97 (s, 1H), 7.99 (dd, J=9.2, 1.4 Hz, 1H), 7.37 (dd, J=9.3, 2.6 Hz, 1H), 7.31 (d, J=2.6 Hz, 1H), 4.34 (s, 2H), 3.90 (s, 3H); MS (APCI$^-$) m/z 404.6 (M–H)$^-$.

Example 145: 5-{7-[1-(2-cyclopropylethyl)-2,5-dihydro-1H-pyrrol-3-yl]-1-fluoro-3-hydroxynaphthalen-2-yl}-1λ$^6$,2,5-thiadiazolidine-1,1,3-trione (Compound 244)

Example 145A: 5-{3-(benzyloxy)-7-[1-(2-cyclopropylethyl)-2,5-dihydro-1H-pyrrol-3-yl]-1-fluoronaphthalen-2-yl}-1λ$^6$,2,5-thiadiazolidine-1,1,3-trione A 20 mL microwave vial was charged with product of Example 143A (200 mg, 0.441 mmol) and N,N-dimethylformamide (3 mL). Subsequently, 2-cyclopropylacetaldehyde and acetic acid (0.126 mL, 2.205 mmol) were added, and the reaction was stirred for 5 minutes at ambient temperature. Sodium cyanoborohydride (166 mg, 2.65 mmol) was then added. The mixture was stirred at ambient temperature overnight. The mixture was partitioned between water (5 mL) and ethyl acetate (5 mL). The aqueous layer was extracted with ethyl acetate (2×3 mL). The combined organic layers were washed with saturated aqueous ammonium chloride (5 mL) and dried over sodium sulfate. The volatiles were removed under reduced pressure and the residue was subjected to preparative HPLC [Phenomenex® Luna® C18(2) 5 μm 100 Å AXIA™ column (250 mm×25 mm). 30-100% gradient of acetonitrile (A) and 0.1% trifluoroacetic acid in water (B) over 15 minutes, at a flow rate of 25 mL/minute] to afford the title compound (23 mg, 0.044 mmol, 10% yield). MS (APCI$^-$) m/z 520 [M–H]$^-$.

Example 145B: 5-{7-[1-(2-cyclopropylethyl)-2,5-dihydro-H-pyrrol-3-yl]-1-fluoro-3-hydroxynaphthalen-2-yl}-1λ$^6$,2,5-thiadiazolidine-1,1,3-trione A 50 mL round bottom flask was charged with the product of Example 145A (20 mg, 0.038 mmol),1,2,3,4,5-pentamethylbenzene (17.05 mg, 0.115 mmol) and methylene chloride (3 mL). The reaction mixture was flushed with nitrogen for 5 minutes. The heterogeneous suspension was cooled to −78° C. and equilibrated for 5 minutes. Subsequently, a 1 M solution of trichloroborane (0.192 mL, 0.192 mmol) in dichloromethane was added dropwise over 5 minutes. The reaction mixture was stirred at −78° C. for 30 minutes. Ethyl acetate (1 mL) and methanol (0.2 mL) were added and the reaction mixture was warmed to ambient temperature. The volatiles were removed under reduced pressure and the residue was subjected to preparative HPLC [Phenomenex® Luna® C18(2) 5 μm 100 Å AXIA™ column (250 mm×25 mm). 30-100% gradient of acetonitrile (A) and 0.1% trifluoroacetic acid in water (B) over 15 minutes, at a flow rate of 25 mL/minute] to give the title compound (2 mg, 0.046 mmol, 12% yield). $^1$H NMR (400 MHz, DMSO-d$_6$) δ ppm 10.01 (s, 1H), 7.76 (s, 3H), 7.09 (s, 1H), 6.53 (d, J=12.7 Hz, 1H), 4.49 (s, 2H), 4.18 (s, 2H), 4.10 (s, 2H), 3.32-3.25 (m, 2H), 1.59 (q, J=7.7, 7.3 Hz, 2H), 0.77 (dd, J=8.8, 4.3 Hz, 1H), 0.51-0.42 (m, 2H), 0.19-0.11 (m, 2H); MS (APCI$^-$) m/z 430 [M–H]$^-$.

Example 146: 5-{1-fluoro-3-hydroxy-7-[(1E)-3-methoxyprop-1-en-1-yl]naphthalen-2-yl}-1λ$^6$,2,5-thiadiazolidine-1,1,3-trione (Compound 245)

To a solution of the product of Example 128A (0.170 g, 0.453 mmol) was added dioxane:water (3:1, 4.5 mL, 0.1 M) followed by (E)-2-(3-methoxyprop-1-en-1-yl)-4,4,5,5-tetramethyl-1,3,2-dioxaborolane (0.179 g, 0.906 mmol) and potassium carbonate (0.188 g, 1.359 mmol). This suspension was sparged with N$_2$ for 10 minutes, and then 1,1'-bis(di-tert-butylphosphino)ferrocene palladium dichloride (0.00295 g, 0.00453 mmol) was added. Sparging was continued for 5 minutes, and then the biphasic suspension was heated at 80° C. for 12 hours. The mixture was allowed to cool to ambient temperature, and the volatiles were removed under reduced pressure to yield crude title compound which was purified by reverse phase HPLC (Phenomenex® C8(2) Luna® 5 μm AXIA™ 150×30 mm column, 3-100% gradient of acetonitrile (A) and 10 mM ammonium acetate in water (B) over 17 minutes at a flow rate of 50 mL/minute to give the title compound (0.137 g, 0.374 mmol, 83%). $^1$H NMR (501 MHz, DMSO-d$_6$) δ ppm 7.80 (s, 1H), 7.69 (d, J=1.4 Hz, 2H), 7.05 (d, J=1.2 Hz, 1H), 6.77 (d, J=16.0 Hz, 1H), 6.44 (dt, J=16.0, 5.8 Hz, 1H), 4.08 (d, J=5.9 Hz, 4H), 3.30 (s, 3H); MS (APCI$^-$) m/z 365 [M–H]$^-$.

Example 147: 5-[7-(2-ethoxyethoxy)-1-fluoro-3-hydroxynaphthalen-2-yl]-1λ$^6$,2,5-thiadiazolidine-1,1,3-trione (Compound 246)

The title compound was prepared from Example 1H and 1-bromo-2-ethoxyethane using the methods described for Example 83. $^1$H NMR (501 MHz, DMSO-d$_6$) δ ppm 10.31 (s, 1H), 7.71 (d, J=9.0 Hz, 1H), 7.24-7.17 (m, 2H), 7.07 (s, 1H), 4.48 (s, 2H), 4.22-4.17 (m, 2H), 3.78-3.72 (m, 2H), 3.52 (q, J=7.0 Hz, 2H), 1.14 (t, J=7.0 Hz, 3H); MS (APCI$^-$) m/z 382.8 (M–H)$^-$.

Example 148: 5-[1-fluoro-3-hydroxy-7-(3-methoxypropoxy)naphthalen-2-yl]-1λ$^6$,2,5-thiadiazolidine-1,1,3-trione (Compound 247)

The title compound was prepared from Example 1H and 1-bromo-3-methoxypropane using the methods described for Example 83. $^1$H NMR (400 MHz, DMSO-d$_6$) δ ppm 10.20 (s, 1H), 7.74-7.67 (m, 1H), 7.23-7.14 (m, 2H), 7.06 (s, 1H), 4.43 (s, 2H), 4.12 (t, J=6.4 Hz, 2H), 3.51 (t, J=6.3 Hz, 2H), 3.26 (s, 2H), 2.00 (p, J=6.4 Hz, 2H); MS (APCI$^-$) m/z 382.9 (M–H)$^-$.

Example 149: 5-[7-(1,1-dioxo-1λ⁶-thian-4-yl)-1-fluoro-3-hydroxynaphthalen-2-yl]-1λ⁶,2,5-thiadiazolidine-1,1,3-trione (Compound 248)

Example 149A: 5-[3-(benzyloxy)-7-(1,1-dioxo-1,2,3,6-tetrahydro-1λ⁶-thiopyran-4-yl)-1-fluoronaphthalen-2-yl]-1λ⁶,2,5-thiadiazolidine-1,1,3-trione To the product of Example 1G (180 mg, 0.698 mmol) in a 20 mL microwave vial was added dioxane (2 mL), a 2 M aqueous solution of sodium carbonate (0.806 mL, 1.612 mmol), and tetrakis(triphenylphosphine)palladium(0) (62.1 mg, 0.054 mmol). The mixture was bubbled with $N_2$ for 5 minutes and heated at 100° C. overnight. The reaction mixture was cooled down to ambient temperature and the volatiles were removed under reduced pressure. The residue was subjected to preparative HPLC [Phenomenex® Luna® C18(2) 5 μm 100 Å AXIA™ column (250 mm×25 mm). 30-100% gradient of acetonitrile (A) and 0.1% trifluoroacetic acid in water (B) over 15 minutes, at a flow rate of 25 mL/minute] to give the title compound (156 mg, 0.302 mmol, 56% yield). $^1$H NMR (400 MHz, DMSO-$d_6$) δ ppm 7.91 (d, J=2.0 Hz, 1H), 7.84 (dd, J=8.8, 1.6 Hz, 1H), 7.72 (dd, J=8.7, 2.0 Hz, 1H), 7.52-7.45 (m, 2H), 7.42 (s, 1H), 7.39-7.30 (m, 2H), 7.34-7.25 (m, 1H), 6.20-6.13 (m, 1H), 5.24 (s, 2H), 4.44 (s, 2H), 3.90 (d, J=4.9 Hz, 2H), 3.50-3.47 (m, 1H), 3.35 (s, 1H), 3.13 (d, J=6.4 Hz, 2H); MS (APCI⁻) m/z 515 [M–H]⁻.

Example 149B: 5-[7-(1,1-dioxo-1λ⁶-thian-4-yl)-1-fluoro-3-hydroxynaphthalen-2-yl]-1λ⁶,2,5-thiadiazolidine-1,1,3-trione The product of Example 149A (55 mg, 0.106 mmol) and 1,4-dioxane (2 mL) were added to 5% Pd/C (wet, 57 mg, 0.250 mmol) in a 20 mL Barnstead Hast C reactor and the mixture was stirred at 25° C. for 37 hours under 74 psi of hydrogen gas. The mixture was filtered under nitrogen, and the filtrate was concentrated under reduced pressure. The residue was subjected to preparative HPLC [Phenomenex® Luna® C18(2) 5 μm 100 Å AXIA™ column (250 mm×25 mm). 30-100% gradient of acetonitrile (A) and 0.1% ammonium acetate in water (B) over 15 minutes, at a flow rate of 25 mL/minute] to give the title compound (14 mg, 0.033 mmol, 31% yield). $^1$H NMR (400 MHz, DMSO-$d_6$) δ ppm 7.78-7.69 (m, 2H), 7.48 (dd, J=8.6, 1.7 Hz, 1H), 7.10 (d, J=1.3 Hz, 1H), 4.55 (s, 2H), 3.89 (ddd, J=11.0, 4.1, 1.8 Hz, 2H), 3.48-3.36 (m, 2H), 2.94 (tt, J=10.7, 3.9 Hz, 1H), 2.03-1.94 (m, 1H), 1.90-1.76 (m, 1H), 1.68 (tq, J=8.1, 4.0 Hz, 2H); MS (APCI⁻) m/z 427 [M–H]⁻.

Example 150: 5-[1-fluoro-3-hydroxy-7-(oxan-3-yl)naphthalen-2-yl]-1λ⁶,2,5-thiadiazolidine-1,1,3-trione (Compound 249)

Example 150A: 5-[3-(benzyloxy)-7-(5,6-dihydro-2H-pyran-3-yl)-1-fluoronaphthalen-2-yl]-1λ⁶,2,5-thiadiazolidine-1,1,3-trione To the product of Example 1G (250 mg, 0.537 mmol) was added 1,4-dioxane (2 mL), 2-(5,6-dihydro-2H-pyran-3-yl)-4,4,5,5-tetramethyl-1,3,2-dioxaborolane (147 mg, 0.698 mmol) and a 2M aqueous solution of sodium carbonate (0.806 mL, 1.612 mmol). Tetrakis(triphenylphosphine)palladium(0) (62.1 mg, 0.054 mmol) was added and the reaction mixture was bubbled with $N_2$ for 5 minutes. The mixture was heated to 90° C. and was stirred overnight. The mixture was cooled down to ambient temperature and the volatiles were removed under reduced pressure. The residue was subjected to preparative HPLC [Phenomenex® Luna® C18(2) 5 μm 100 Å AXIA™ column (250 mm×25 mm). 30-100% gradient of acetonitrile (A) and 0.1% ammonium acetate in water (B) over 15 minutes, at a flow rate of 25 mL/minute] to give the title compound (146 mg, 0.312 mmol, 58% yield). MS (APCI⁻) m/z 467 [M–H]⁻

Example 150B: 5-[1-fluoro-3-hydroxy-7-(oxan-3-yl)naphthalen-2-yl]-1λ⁶,2,5-thiadiazolidine-1,1,3-trione The product of Example 150A (55 mg, 0.117 mmol) and tetrahydrofuran (2 mL) were added to 5% Pd/C (wet, 54 mg, 0.236 mmol) in a 20 mL Barnstead Hast C reactor and the mixture was stirred at 25° C. for 37 hours under 58 psi of hydrogen gas. The mixture was filtered under $N_2$, and the filtrate was concentrated under reduced pressure. The residue was subjected to preparative HPLC [Phenomenex® Luna® C18(2) 5 μm 100 Å AXIA™ column (250 mm×25 mm). 30-100% gradient of acetonitrile (A) and 0.1% ammonium acetate in water (B) over 15 minutes, at a flow rate of 25 mL/minute] to give the title compound (12 mg, 0.032 mmol, 23% yield). $^1$H NMR (400 MHz, DMSO-$d_6$) δ ppm 7.79-7.70 (m, 2H), 7.47 (dd, J=8.6, 1.8 Hz, 1H), 7.10 (d, J=1.3 Hz, 1H), 4.52 (s, 2H), 3.42-3.30 (m, 2H), 3.20-3.05 (m, 3H), 2.27-2.13 (m, 4H); MS (APCI⁻) m/z 379 [M–H]⁻.

Example 151: 5-[7-(cyclopropylmethoxy)-1-fluoro-3-hydroxynaphthalen-2-yl]-1λ⁶,2,5-thiadiazolidine-1,1,3-trione (Compound 250)

The title compound was prepared from Example 1H and (bromomethyl)cyclopropane using the methods described for Example 83. $^1$H NMR (501 MHz, DMSO-$d_6$) δ ppm 10.36 (s, 1H), 7.71 (d, J=9.1 Hz, 1H), 7.20 (dd, J=9.0, 2.6 Hz, 1H), 7.17 (d, J=2.5 Hz, 1H), 7.07 (s, 1H), 4.50 (s, 2H), 3.92 (d, J=7.0 Hz, 2H), 1.27 (ddd, J=12.4, 7.6, 4.8 Hz, 1H), 0.64-0.54 (m, 2H), 0.40-0.32 (m, 2H); MS (APCI⁻) m/z 365 (M–H)⁻.

Example 152: 5-(1-fluoro-3-hydroxy-7-{[1-(2,2,2-trifluoroethyl)pyrrolidin-3-yl]methyl}naphthalen-2-yl)-1λ⁶,2,5-thiadiazolidine-1,1,3-trione (Compound 251)

In a 4 mL vial were combined 5-{7-bromo-1-fluoro-3-[(2-methoxyethoxy)methoxy]naphthalen-2-yl}-2-[(2-methoxyethoxy)methyl]-1λ⁶,2,5-thiadiazolidine-1,1,3-trione (Example 127A, 100 mg, 0.181 mmol, 1.0 equivalents) and Pd SPhos G4 (7.20 mg, 9.07 μmol, 0.05 equivalents) in N,N-dimethylacetamide (2 mL). ((1-(tert-Butoxycarbonyl)pyrrolidin-3-yl)methyl)zinc(II) iodide (3.30 mL, 0.363 mmol, 2.0 equivalents, 0.11 M in tetrahydrofuran) was added. The vial was purged with $N_2$, capped and heated to 65° C. overnight.

The residue was purified by reverse-phase preparative HPLC on a Waters XBridgem C8 5 μm column (75 mm×30 mm). A gradient of methanol (A) and 25 mM ammonium bicarbonate buffer (pH 10) in water (B) was used, at a flow rate of 40 mL/minute (0-0.5 minutes 25% A, 0.5-8.0 minutes linear gradient 25-100% A, 8.0-9.0 minutes 100% A, 9.0-9.1 minutes linear gradient 100-25% A, 9.1-10.0 minutes 5% A) to give tert-butyl 3-[(8-fluoro-6-[(2-methoxyethoxy)methoxy]-7-{5-[(2-methoxyethoxy)methyl]-1,1,4-trioxo-1λ⁶,2,5-thiadiazolidin-2-yl}naphthalen-2-yl)methyl]pyrrolidine-1-carboxylate (42.1 mg, 41% yield).

The tert-butyl 3-[(8-fluoro-6-[(2-methoxyethoxy)methoxy]-7-{5-[(2-methoxyethoxy)methyl]-1,1,4-trioxo-1λ⁶,2,5-thiadiazolidin-2-yl}naphthalen-2-yl)methyl]pyrrolidine-1-carboxylate was suspended in 4 M HCl in dioxane (1 mL), stirred for 10 minutes and dried under a stream of nitrogen to give 5-{1-fluoro-3-hydroxy-7-[(pyrrolidin-3-yl)methyl]naphthalen-2-yl}-1λ⁶,2,5-thiadiazolidine-1,1,3-trione. ¹H NMR (400 MHz, DMSO-d₆) δ ppm 7.79-7.56 (m, 2H), 7.38 (dd, J=8.5, 1.7 Hz, 1H), 7.05 (s, 1H), 4.13 (s, 2H), 3.26-3.01 (m, 3H), 2.86-2.72 (m, 3H), 2.58-2.52 (m, 1H), 2.05-1.84 (m, 1H), 1.67-1.48 (m, 1H); MS (ESI⁺) m/z 380.3 (M+H)⁺.

5-{1-Fluoro-3-hydroxy-7-[(pyrrolidin-3-yl)methyl]naphthalen-2-yl}-1λ⁶,2,5-thiadiazolidine-1,1,3-trione (25 mg, 0.07 mmol, 1.0 equivalents) was dissolved in N,N-dimethylformamide (1.0 mL). N-Ethyl-N-isopropylpropan-2-amine (34 μL, 0.20 mmol, 3.0 equivalents) was added, followed by trifluoroethyl trifluoromethanesulfonate (11 μL, 0.08 mmol, 1.2 equivalents). The reaction mixture was stirred overnight at ambient temperature. The reaction was purified by reverse-phase preparative HPLC on a Phenomenex® Luna® C8(2) 5 μm 100 Å AXIA™ column (50 mm×30 mm). A gradient of acetonitrile (A) and 0.1% ammonium acetate in water (B) was used, at a flow rate of 40 mL/minute (0-0.5 minutes 5% A, 0.5-8.0 minutes linear gradient 5-100% A, 8.0-9.0 minutes 100% A, 9.0-9.1 minutes linear gradient 100-5% A, 9.1-10.0 minutes 5% A) to afford the title compound (1.1 mg, 4% yield). ¹H NMR (400 MHz, DMSO-d₆) δ ppm 7.74-7.68 (m, 2H), 7.41 (dd, J=8.6, 1.6 Hz, 1H), 7.09 (s, 1H), 4.18 (s, 2H), 3.56-3.33 (m, 2H), 2.87 (dd, J=31.7, 8.3 Hz, 6H), 1.99-1.89 (m, 1H), 1.62-1.53 (m, 1H), 1.33-1.23 (m, 1H); MS (APCI⁺) m/z 462.1 [M+H]⁺.

Example 153: 5-(1-fluoro-3-hydroxy-7-{[1-(2,2,2-trifluoroethyl)piperidin-4-yl]methyl}naphthalen-2-yl)-1λ⁶,2,5-thiadiazolidine-1,1,3-trione (Compound 252)

In a 4 mL vial were combined Example 1G (91 mg, 0.196 mmol, 1.0 equivalents) and SPhos Pd G4 (7.7 mg, 9.78 μmol, 0.05 equivalents) in N,N-dimethylacetamide (2 mL). ((1-(tert-Butoxycarbonyl)piperidin-4-yl)methyl)zinc(II) iodide (2.445 mL, 0.391 mmol, 2.0 equivalents) (0.16 M in tetrahydrofuran) was added. The vial was purged with N₂, capped and heated to 65° C. overnight.

The reaction mixture was concentrated, and the residue was purified by reverse-phase preparative HPLC on a Waters XBridge™ C8 5 μm column (75 mm×30 mm). A gradient of methanol (A) and 25 mM ammonium bicarbonate buffer (pH 10) in water (B) was used, at a flow rate of 40 mL/minute (0-0.5 minutes 35% A, 0.5-8.0 minutes linear gradient 35-100% A, 8.0-9.0 minutes 100% A, 9.0-9.1 minutes linear gradient 100-35% A, 9.1-10.0 minutes 35% A) to afford the tert-butyl 4-{[6-(benzyloxy)-8-fluoro-7-(1,1,4-trioxo-1λ⁶,2,5-thiadiazolidin-2-yl)naphthalen-2-yl]methyl}piperidine-1-carboxylate (95.7 mg, 84% yield); MS (APCI⁺) m/z 601.4 [M+H₂O]⁺.

tert-Butyl 4-{[6-(benzyloxy)-8-fluoro-7-(1,1,4-trioxo-1λ⁶,2,5-thiadiazolidin-2-yl)naphthalen-2-yl]methyl}piperidine-1-carboxylate was dissolved in dichloromethane (1 mL) and trifluoroacetic acid (100 μL) was added. The reaction was stirred at ambient temperature until the reaction was complete by HPLC/MS (Column: Phenomenex® Luna® 5 μm, C8(2) 100 Å, 50×2.00 mm. A gradient of acetonitrile (A) in 0.1% ammonium acetate in water (B) was used, at a flow rate of 2 mL/minute (0-2.5 minutes linear gradient 0-100% A, 2.5-2.9 minutes linear gradient 100-0% A, 2.9-3.0 minutes 0% A). Retention time 1.376 minutes.). Volatiles were removed under a stream of nitrogen and the solid material was dried in vacuo to give 5-{3-(benzyloxy)-1-fluoro-7-[(piperidin-4-yl)methyl]naphthalen-2-yl}-1λ⁶,2,5-thiadiazolidine-1,1,3-trione.

5-{3-(Benzyloxy)-1-fluoro-7-[(piperidin-4-yl)methyl]naphthalen-2-yl}-1λ⁶,2,5-thiadiazolidine-1,1,3-trione (50 mg, 0.10 mmol, 1.0 equivalents) was dissolved in N,N-dimethylformamide (1.0 mL). N-Ethyl-N-isopropylpropan-2-amine (54 μL, 0.31 mmol, 3.0 equivalents) was added, followed by 2,2,2-trifluoroethyl trifluoromethanesulfonate (18 μL, 0.12 mmol, 1.2 equivalents). The reaction was stirred overnight at ambient temperature. The reaction was purified by reverse-phase preparative HPLC on a Phenomenex® Luna® C8(2) 5 μm 100 Å AXIA™ column (50 mm×30 mm). A gradient of acetonitrile (A) and 0.1% ammonium acetate in water (B) was used, at a flow rate of 40 mL/minute (0-0.5 minutes 15% A, 0.5-8.0 minutes linear gradient 15-100% A, 8.0-9.0 minutes 100% A, 9.0-9.1 minutes linear gradient 100-15% A, 9.1-10.0 minutes 15% A) to afford 5-[3-(benzyloxy)-1-fluoro-7-{[1-(2,2,2-trifluoroethyl)piperidin-4-yl]methyl}naphthalen-2-yl]-1λ⁶,2,5-thiadiazolidine-1,1,3-trione (11.4 mg, 20% yield); MS (APCI⁺) m/z 566.1 [M+H]⁺.

5-[3-(Benzyloxy)-1-fluoro-7-{[1-(2,2,2-trifluoroethyl)piperidin-4-yl]methyl}naphthalen-2-yl]-1λ⁶,2,5-thiadiazolidine-1,1,3-trione (11.4 mg, 0.020 mmol) and tetrahydrofuran (2 mL) were added to 5% Pd/C wet JM #9) (6 mg, 0.026 mmol) in a 20 mL Barnstead Hast C reactor and the mixture was stirred for 1.2 hours at 50 psi hydrogen and 25° C. for 60 hours. The reaction was filtered, and solvent was removed under a stream of nitrogen. The residue was purified by reverse-phase preparative HPLC on a Phenomenex® Luna® C8(2) 5 μm 100 Å AXIA™ column (50 mm×30 mm). A gradient of acetonitrile (A) and 0.1% ammonium acetate in water (B) was used, at a flow rate of 40 mL/minute (0-0.5 minutes 5% A, 0.5-8.0 minutes linear gradient 5-100% A, 8.0-9.0 minutes 100% A, 9.0-9.1 minutes linear gradient 100-5% A, 9.1-10.0 minutes 5% A) to give the title compound. ¹H NMR (400 MHz, DMSO-d₆) δ ppm 7.69-7.55 (m, 2H), 7.32 (dd, J=8.4, 1.7 Hz, 1H), 7.04 (s, 1H), 4.12 (s, 2H), 3.05 (q, J=10.2 Hz, 2H), 2.85 (d, J=11.4 Hz, 2H), 2.63 (d, J=6.7 Hz, 2H), 2.23 (dd, J=12.7, 10.4 Hz, 2H), 1.64-1.43 (m, 3H), 1.31-1.06 (m, 2H); MS (APCI⁺) m/z 476.1 [M+H]⁺.

Example 154: 5-(1-fluoro-3-hydroxy-7-{2-[methyl(2-methylpropyl)amino]ethoxy}naphthalen-2-yl)-1λ⁶,2,5-thiadiazolidine-1,1,3-trione (Compound 253)

Example 154A: 5-[3-(benzyloxy)-7-(2,2-dimethoxyethoxy)-1-fluoronaphthalen-2-yl]-1λ⁶,2,5-thiadiazolidine-1,1,3-trione To a mixture of Example 1H (2 g, 4.47 mmol) in N,N-dimethyl formamide (40 mL) was added cesium carbonate ($Cs_2CO_3$, 4.367 g, 13.42 mmol) and 2-bromo-1,1-dimethoxyethane (2.268 g, 13.42 mmol) in order at 20° C. Then the mixture was stirred for 12 hours at 50° C. under nitrogen. The reaction was quenched with water (20 mL) and acidified with HCl (1 N, aqueous) to pH=4. The resulting mixture was extracted with ethyl acetate (3×200 mL). The organic layer was washed with brine (700 mL), dried over sodium sulfate, and concentrated under reduced pressure. The residue was triturated with methyl tert-butyl ether (100 mL) and filtered.

The cake was collected and dried under high vacuum to give the title compound (2.3 g, 4.22 mmol, 90% yield). $^1$H NMR (400 MHz, DMSO-$d_6$) δ ppm 7.95 (s, 1H), 7.82 (d, J=8.80 Hz, 1H), 7.52 (br d, J=6.85 Hz, 2H), 7.27-7.46 (m, 6H), 5.24 (s, 1H), 4.75 (s, 1H), 4.52 (s, 1H), 4.13 (d, J=5.01 Hz, 2H), 3.38 (s, 5H); MS (ESI$^-$) m/z 489 (M−H)$^-$.

Example 154B: 5-[7-(2,2-dimethoxyethoxy)-1-fluoro-3-hydroxynaphthalen-2-yl]-1λ$^6$,2,5-thiadiazolidine-1,1,3-trione To a mixture of 10% Pd—C (0.859 g, 8.07 mmol) in methanol (100 mL) was added Example 154A (2.2 g, 4.04 mmol) at 25° C., and then the mixture was stirred for 1 hour at 25° C. under a hydrogen balloon (15 psi). The mixture was filtered through a pad of diatomaceous earth, and the filtrate was concentrated under reduced pressure to give the title compound (1.5 g, 3.18 mmol, 79% yield) which was used in the next step without further purification. MS (ESI$^-$) m/z 399 (M−H)$^-$.

Example 154C: {[8-fluoro-6-hydroxy-7-(1,1,4-trioxo-1λ$^6$, 2,5-thiadiazolidin-2-yl)naphthalen-2-yl]oxy}acetaldehyde To a solution of Example 154B (1.5 g, 3.18 mmol) in acetone (10 mL) was added hydrochloric acid (6 N, aqueous) (10 mL, 60.0 mmol) dropwise at 20° C. The reaction mixture was then heated at 60° C. for 30 minutes. The reaction mixture was then concentrated under reduced pressure. The residue was purified by preparative HPLC: Phenomenex® Luna® C18 10 μm column, 50×250 mm, flow rate 80 mL/minute, 30-100% gradient of acetonitrile in water (0.048 M aqueous HCl)] and lyophilized to give the title compound (182 mg, 0.478 mmol, 15% yield). $^1$H NMR (400 MHz, DMSO-$d_6$) δ ppm 10.31-10.52 (m, 1H), 9.73 (s, 1H), 7.75 (d, J=9.13 Hz, 1H), 7.16-7.30 (m, 2H), 7.09 (s, 1H), 5.01 (s, 2H), 4.51 (s, 1H); MS (ESI$^-$) m/z 353 (M−H)$^-$.

Example 154D: 5-(1-fluoro-3-hydroxy-7-{2-[methyl(2-methylpropyl)amino]ethoxy}naphthalen-2-yl)-1λ$^6$,2,5-thiadiazolidine-1,1,3-trione Example 154C (10 mg, 0.028 mmol) was dissolved in methanol (0.2 mL), then N,2-dimethylpropan-1-amine (4.92 mg, 0.056 mmol) and acetic acid (8.47 mg, 0.141 mmol) were added, and the resultant mixture was stirred 30 minutes at room temperature. NaBH$_3$CN (3.55 mg, 0.056 mmol) was then added. The mixture was stirred for 2 hours. The reaction mixture was purified by preparative HPLC on Phenomenex® Luna® 10 μm C18 column (30 mm×250 mm) eluted with a gradient of acetonitrile (A) and water (B) 0.1% with trifluoroacetic acid at a flow rate of 50 mL/minute (0-1 minute 0% A, 1-20 minutes linear gradient 20-100%) to give the title compound (6 mg, 34% yield). $^1$H NMR (500 MHz, DMSO-$d_6$) δ ppm 9.75 (s, 1H), 9.00 (s, 1H), 7.74 (dd, J=9.1, 1.4 Hz, 1H), 7.30 (d, J=2.6 Hz, 1H), 7.19 (dd, J=9.0, 2.5 Hz, 1H), 7.07 (s, 1H), 4.48 (t, J=5.1 Hz, 2H), 4.18 (s, 2H), 3.64 (m, 1H), 3.55 (m, 1H), 3.12 (m, 1H), 2.98 (m, 1H), 2.91 (d, J=4.7 Hz, 3H), 2.11 (m, 1H), 0.97 (dd, J=6.6, 4.1 Hz, 6H); MS (APCI$^+$) m/z 426.0 (M+H)$^+$.

Example 155: 5-{1-fluoro-3-hydroxy-7-[(oxolan-2-yl)methoxy]naphthalen-2-yl}-1λ$^6$,2,5-thiadiazolidine-1,1,3-trione (Compound 254)

Example 155A: 5-{3-(benzyloxy)-1-fluoro-7-[(oxolan-2-yl)methoxy]naphthalen-2-yl}-1λ$^6$,2,5-thiadiazolidine-1,1,3-trione To a solution of product Example 1H (100 mg, 0.249 mmol) in N,N-dimethylformamide (2 mL) was added 2-(bromomethyl)tetrahydrofuran (90 mg, 0.547 mmol) and cesium carbonate (178 mg, 0.547 mmol). The reaction mixture was heated to 65° C. overnight. The reaction mixture was then cooled down to ambient temperature and partitioned between water (5 mL) and ethyl acetate (5 mL). The aqueous layer was further extracted with ethyl acetate (2×3 mL), and the combined organic layers were washed with saturated aqueous ammonium chloride (5 mL) and dried over sodium sulfate. The volatiles were removed under reduced pressure and the residue was subjected to column chromatography (SiO$_2$, 10% methanol in dichloromethane) to afford the title compound (35 mg, 0.072 mmol, 29% yield). MS (APCI$^-$) m/z 485 [M−H]$^-$.

Example 155B: 5-{-fluoro-3-hydroxy-7-[(oxolan-2-yl)methoxy]naphthalen-2-yl}-1λ$^6$,2,5-thiadiazolidine-1,1,3-trione The product of Example 155A (55 mg, 0.117 mmol) and tetrahydrofuran (2 mL) were added to 5% Pd/C (wet, 54 mg, 0.236 mmol) in a 20 mL Barnstead Hast C reactor and the mixture was stirred at 25° C. for 37 hours under 58 psi of hydrogen gas. The mixture was filtered, and the filtrate was concentrated under reduced pressure. The residue was subjected to preparative HPLC [Phenomenex® Luna® C18(2) 5 μm 100 Å AXIA™ column (250 mm×25 mm). 30-100% gradient of acetonitrile (A) and 0.1% ammonium acetate in water (B) over 15 minutes, at a flow rate of 25 mL/minute] to afford the title compound (12 mg, 0.032 mmol, 23% yield). $^1$H NMR (400 MHz, DMSO-$d_6$) δ ppm 7.79-7.70 (m, 2H), 7.47 (dd, J=8.6, 1.8 Hz, 1H), 7.10 (d, J=1.3 Hz, 1H), 4.52 (s, 2H), 3.42-3.30 (m, 2H), 3.20-3.05 (m, 3H), 2.27-2.13 (m, 4H); MS (APCI$^-$) m/z 379 [M−H]$^-$.

Example 156: 5-[1-fluoro-3-hydroxy-7-(oxolan-3-yl)naphthalen-2-yl]-1λ$^6$,2,5-thiadiazolidine-1,1,3-trione (Compound 255)

Example 156A: 5-[3-(benzyloxy)-7-(2,5-dihydrofuran-3-yl)-1-fluoronaphthalen-2-yl]-1λ$^6$,2,5-thiadiazolidine-1,1,3-trione To the product from Example 1G (120 mg, 0.258 mmol) was added 2-(2,5-dihydrofuran-3-yl)-4,4,5,5-tetramethyl-1,3,2-dioxaborolane (65.7 mg, 0.335 mmol) and a 2 M aqueous solution of sodium carbonate (0.387 ml, 0.774 mmol). Tetrakis(triphenylphosphine)palladium(0) (29.8 mg, 0.026 mmol) was added and the reaction mixture was bubbled with N$_2$ for 5 minutes. The mixture was heated to 100° C. and was stirred overnight. The reaction mixture was cooled down to ambient temperature and the volatiles were removed under reduced pressure. The residue was subjected to column chromatography (SiO$_2$, dry load on diatomaceous earth, 5% methanol in dichloromethane) to afford the title compound (35 mg, 0.077 mmol, 30% yield). MS (APCI$^+$) m/z 455 [M+H]$^-$ Example 156B: 5-[1-fluoro-3-hydroxy-7-(oxolan-3-yl)naphthalen-2-yl]-1λ$^6$,2,5-thiadiazolidine-1,1,3-trione A 50 mL-round bottom flask was filled with nitrogen, followed by addition of 5% Pd/C (23.18 mg, 0.218 mmol) and tetrahydrofuran (5 mL). A solution of product 156A (40 mg, 0.083 mmol) in tetrahydrofuran (2 mL), was then added. An adapter fitted with a hydrogen balloon was inserted and the flask was evacuated and refilled with hydrogen (3 times).

The reaction was stirred at ambient temperature overnight. The mixture was filtered through a pad of diatomaceous earth under nitrogen gas. The filtrate was concentrated under reduced pressure, and the residue was subjected to preparative HPL [Phenomenex® Luna® C18(2) 5 µm 100 Å AXIA™ column (250 mm×25 mm). 30-100% gradient of acetonitrile (A) and 0.1% trifluoroacetic acid in water (B) over 15 minutes, at a flow rate of 25 mL/minute] to give the title compound (8 mg, 0.022 mmol, 30% yield). $^1$H NMR (400 MHz, DMSO-$d_6$) δ ppm 7.74 (dd, J=8.5, 1.6 Hz, 2H), 7.47 (dd, J=8.6, 1.8 Hz, 1H), 7.08 (s, 1H), 4.45 (s, 2H), 4.07 (t, J=7.7 Hz, 1H), 3.99 (td, J=8.3, 4.6 Hz, 1H), 3.83 (q, J=7.8 Hz, 1H), 3.67-3.59 (m, 1H), 3.56 (d, J=7.5 Hz, 1H), 2.36 (dtd, J=12.2, 7.6, 4.5 Hz, 1H), 2.09-1.92 (m, 1H); MS (APCI$^-$) m/z 365 [M−H]$^-$.

Example 157: 5-(7-{[1-(cyclopropanesulfonyl)azetidin-3-yl]methyl}-1-fluoro-3-hydroxynaphthalen-2-yl)-1λ$^6$,2,5-thiadiazolidine-1,1,3-trione (Compound 256)

In a 4 mL vial were combined Example 1G (78 mg, 0.16 mmol, 1.0 equivalents) and SPhos Pd G4 (6.6 mg, 8.38 µmol, 0.05 equivalents) in N,N-dimethylacetamide (2 mL). ((1-(tert-Butoxycarbonyl)azetidin-3-yl)methyl)zinc(II) iodide (1.86 mL, 0.33 mmol, 2.0 equivalents) (0.18 M in tetrahydrofuran) was added. The vial was purged with $N_2$, capped and heated to 65° C. overnight.

The reaction mixture was concentrated, and the residue was purified by reverse-phase preparative HPLC on a Waters XBridge™ C8 5 µm column (75 mm×30 mm). A gradient of methanol (A) and 25 mM ammonium bicarbonate buffer (pH 10) in water (B) was used, at a flow rate of 40 mL/minute (0-0.5 minutes 15% A, 0.5-8.0 minutes linear gradient 15-100% A, 8.0-9.0 minutes 100% A, 9.0-9.1 minutes linear gradient 100-15% A, 9.1-10.0 minutes 15% A) to afford tert-butyl 3-{[6-(benzyloxy)-8-fluoro-7-(1,1,4-trioxo-1λ$^6$,2,5-thiadiazolidin-2-yl)naphthalen-2-yl]methyl}azetidine-1-carboxylate (61.1 mg, 66% yield).

The residue was dissolved in dichloromethane (1 mL) and trifluoroacetic acid (100 µL) was added. The reaction was stirred at ambient temperature until the reaction was complete by HPLC/MS (Column: Phenomenex® Luna® 5 µm, C8(2) 100 Å, 50×2.00 mm. A gradient of acetonitrile (A) in 0.1% ammonium acetate in water (B) was used, at a flow rate of 2 mL/minute (0-2.5 minutes linear gradient 0-100% A, 2.5-2.9 minutes linear gradient 100-0% A, 2.9-3.0 minutes 0% A). Retention time 1.304 minutes.). Volatiles were removed under a stream of nitrogen and 5-{7-[(azetidin-3-yl)methyl]-3-(benzyloxy)-1-fluoronaphthalen-2-yl}-1λ$^6$,2,5-thiadiazolidine-1,1,3-trione was dried in vacuo.

5-{7-[(Azetidin-3-yl)methyl]-3-(benzyloxy)-1-fluoronaphthalen-2-yl}-1λ$^6$,2,5-thiadiazolidine-1,1,3-trione (31.9 mg, 0.07 mmol, 1.0 equivalents) was dissolved in N,N-dimethylformamide (0.5 mL). N-Ethyl-N-isopropylpropan-2-amine (34 µL, 0.20 mmol, 3.0 equivalents) was added, followed by cyclopropylsulfonyl chloride (8 µL, 0.08 mmol, 1.2 equivalents). The reaction was stirred overnight at ambient temperature. The reaction was purified by reverse-phase preparative HPLC on a Phenomenex® Luna® C8(2) 5 µm 100 Å AXIA™ column (50 mm×30 mm). A gradient of acetonitrile (A) and 0.1% ammonium acetate in water (B) was used, at a flow rate of 40 mL/minute (0-0.5 minutes 15% A, 0.5-8.0 minutes linear gradient 15-100% A, 8.0-9.0 minutes 100% A, 9.0-9.1 minutes linear gradient 100-15% A, 9.1-10.0 minutes 15% A) to 5-[3-(benzyloxy)-7-{[1-(cyclopropanesulfonyl)azetidin-3-yl]methyl}-1-fluoronaphthalen-2-yl]-1λ$^6$,2,5-thiadiazolidine-1,1,3-trione (19.7 mg, 50% yield). H NMR (500 MHz, DMSO-$d_6$) δ ppm 7.80-7.69 (m, 2H), 7.56-7.53 (m, 2H), 7.44-7.25 (m, 5H), 5.23 (s, 2H), 4.12 (s, 2H), 3.95-3.88 (m, 2H), 3.72-3.65 (m, 2H), 3.08-3.02 (m, 2H), 3.01-2.92 (m, 1H), 2.74-2.67 (m, 1H), 1.07-0.94 (m, 2H), 0.94-0.85 (m, 2H).

5-[3-(Benzyloxy)-7-{[1-(cyclopropanesulfonyl)azetidin-3-yl]methyl}-1-fluoronaphthalen-2-yl]-1λ$^6$,2,5-thiadiazolidine-1,1,3-trione (20 mg, 0.036 mmol) and a solvent mixture of tetrahydrofuran (2 mL), methanol (1 mL), and dichloromethane (0.2 mL) were added to 5% Pd/C, wet (20 mg, 0.094 mmol) in a 20 mL Barnstead Hast C reactor and the mixture was stirred for 17 hours at 50 psi hydrogen and 25° C. HPLC analysis indicated incomplete conversion (Column: Supelco Ascentis® Express C18, 2.7 µm fused core silica, 4.6×150 mm. A gradient of acetonitrile (A) in 0.1% HClO$_4$ in water (B) was used, at a flow rate of 1.5 mL/minute (0-8 minutes linear gradient 10-90% A, 8-13 minutes 90% A. Retention time 4.1 minutes.), and the hydrogenation was continued hydrogenation for an additional 14 hours. HPLC indicated complete consumption of the starting material. The reaction mixture was filtered and concentrated under a stream of nitrogen. The residue was dissolved in dimethyl sulfoxide/methanol and purified by reverse-phase preparative HPLC on a Waters XBridge™ C8 5 µm column (75 mm×30 mm). A gradient of methanol (A) and 25 mM ammonium bicarbonate buffer (pH 10) in water (B) was used, at a flow rate of 40 mL/minute (0-0.5 minutes 15% A, 0.5-8.0 minutes linear gradient 15-100% A, 8.0-9.0 minutes 100% A, 9.0-9.1 minutes linear gradient 100-15% A, 9.1-10.0 minutes 15% A) to afford the title compound (10.4 mg, 61% yield). $^1$H NMR (400 MHz, DMSO-$d_6$) δ ppm 7.74-7.60 (m, 2H), 7.36 (dd, J=8.4, 1.7 Hz, 1H), 7.05 (s, 1H), 4.12 (s, 2H), 3.91 (s, 2H), 3.73-3.63 (m, 2H), 3.10-2.91 (m, 3H), 2.75-2.67 (m, 1H), 1.11-0.99 (m, 2H), 0.95-0.80 (m, 2H); MS (ESI$^+$) m/z 470.5 [M+H]$^+$.

Example 158: 5-(7-{[1-(cyclopropanesulfonyl)piperidin-4-yl]methyl}-1-fluoro-3-hydroxynaphthalen-2-yl)-1λ$^6$,2,5-thiadiazolidine-1,1,3-trione (Compound 257)

In a 4 mL vial were combined Example 1G (91 mg, 0.196 mmol, 1.0 equivalents) and SPhos Pd G4 (7.7 mg, 9.78 µmol, 0.05 equivalents) in N,N-dimethylacetamide (2 mL). ((1-(tert-Butoxycarbonyl)piperidin-4-yl)methyl)zinc(II) iodide (2.445 mL, 0.391 mmol, 2.0 equivalents) (0.16 M in tetrahydrofuran) was added. The vial was purged with $N_2$, capped and heated to 65° C. overnight.

The reaction mixture was concentrated, and the residue was purified by reverse-phase preparative HPLC on a Waters XBridge™ C8 5 µm column (75 mm×30 mm). A gradient of methanol (A) and 25 mM ammonium bicarbonate buffer (pH 10) in water (B) was used, at a flow rate of 40 mL/minute (0-0.5 minutes 35% A, 0.5-8.0 minutes linear gradient 35-100% A, 8.0-9.0 minutes 100% A, 9.0-9.1 minutes linear gradient 100-35% A, 9.1-10.0 minutes 35% A) to afford tert-butyl 4-{[6-(benzyloxy)-8-fluoro-7-(1,1,4-trioxo-1λ$^6$,2,5-thiadiazolidin-2-yl)naphthalen-2-yl]methyl}piperidine-1-carboxylate (95.7 mg, 84% yield). MS (APCI$^+$) m/z 601.4 [M+H$_2$O].

tert-Butyl 4-{[6-(benzyloxy)-8-fluoro-7-(1,1,4-trioxo-1λ$^6$,2,5-thiadiazolidin-2-yl)naphthalen-2-yl]methyl}piperidine-1-carboxylate was dissolved in dichloromethane (1 mL) and trifluoroacetic acid (100 µL) was added. The reaction was stirred at ambient temperature until the reaction was complete by HPLC/MS (Column: Phenomenex® Luna® 5 µm, C8(2) 100 Å, 50×2.00 mm. A gradient of acetonitrile (A) in 0.1% ammonium acetate in water (B) was used, at a flow rate of 2 mL/minute (0-2.5 minutes linear gradient 0-100% A, 2.5-2.9 minutes linear gradient 100-0% A, 2.9-3.0 minutes 0% A). Retention time 1.376 minutes.). Volatiles were removed under a stream of nitrogen and 5-{3-(benzyloxy)-1-fluoro-7-[(piperidin-4-yl)methyl]naphthalen-2-yl}-1$\lambda^6$,2,5-thiadiazolidine-1,1,3-trione was dried in vacuo.

5-{3-(Benzyloxy)-1-fluoro-7-[(piperidin-4-yl)methyl]naphthalen-2-yl}-1$\lambda^6$,2,5-thiadiazolidine-1,1,3-trione (31.9 mg, 0.07 mmol, 1.0 equivalents) was dissolved in N,N-dimethylformamide (0.5 mL). N-Ethyl-N-isopropylpropan-2-amine (34 µL, 0.20 mmol, 3.0 equivalents) was added, followed by cyclopropylsulfonyl chloride (8 µL, 0.08 mmol, 1.2 equivalents). The reaction was stirred overnight at ambient temperature. The reaction was purified by reverse-phase preparative HPLC on a Phenomenex® Luna® C8(2) 5 µm 100 Å AXIA™ column (50 mm×30 mm). A gradient of acetonitrile (A) and 0.1% ammonium acetate in water (B) was used, at a flow rate of 40 mL/minute (0-0.5 minutes 15% A, 0.5-8.0 minutes linear gradient 15-100% A, 8.0-9.0 minutes 100% A, 9.0-9.1 minutes linear gradient 100-15% A, 9.1-10.0 minutes 15% A) to afford 5-[3-(benzyloxy)-7-{[1-(cyclopropanesulfonyl)piperidin-4-yl]methyl}-1-fluoronaphthalen-2-yl]-1$\lambda^6$,2,5-thiadiazolidine-1,1,3-trione (19.2 mg, 50% yield).

Pentamethylbenzene (10.1 mg, 0.07 mmol, 2.0 equivalents) was added neat to a reaction vial containing 5-[3-(benzyloxy)-7-{[1-(cyclopropanesulfonyl)piperidin-4-yl]methyl}-1-fluoronaphthalen-2-yl]-1$\lambda^6$,2,5-thiadiazolidine-1,1,3-trione. Dichloromethane (1 mL) was added, and the vial capped and cooled to −78° C. BCl$_3$ (1 M in dichloromethane, 100 µL, 0.1 mmol, 3.0 equivalents) was added dropwise. The reaction mixture was stirred at −78° C. for 1 hour. 100 µL of a 1:1 methanol/dichloromethane mixture added. The mixture was dried down under a stream of nitrogen and reconstituted in dimethyl sulfoxide/methanol and purified by reverse-phase preparative HPLC on a Waters XBridge™ C8 5 µm column (75 mm×30 mm). A gradient of methanol (A) and 25 mM ammonium bicarbonate buffer (pH 10) in water (B) was used, at a flow rate of 40 mL/minute (0-0.5 minutes 15% A, 0.5-8.0 minutes linear gradient 15-100% A, 8.0-9.0 minutes 100% A, 9.0-9.1 minutes linear gradient 100-15% A, 9.1-10.0 minutes 15% A) to afford the title compound (8.8 mg, 52% yield). $^1$H NMR (501 MHz, DMSO-d$_6$) δ ppm 7.73-7.68 (m, 2H), 7.39 (dd, J=8.4, 1.7 Hz, 1H), 7.09 (s, 1H), 4.17 (s, 2H), 3.65-3.55 (m, 2H), 2.84-2.76 (m, 2H), 2.72 (d, J=7.1 Hz, 2H), 1.73-1.67 (m, 2H), 1.33-1.25 (m, 2H), 1.03-0.96 (m, 2H), 0.96-0.89 (m, 2H).

Example 159: 5-[1-fluoro-3-hydroxy-7-(pyrrolidin-2-yl)naphthalen-2-yl]-1$\lambda^6$,2,5-thiadiazolidine-1,1,3-trione (Compound 258)

In a 4 mL vial were combined NiCl$_2$ dimethoxyethane adduct (1.44 mg, 0.006 mmol, 0.12 equivalents) and 4,4'-di-tert-butyl-2,2'-dipyridyl (1.75 mg, 0.006 mmol, 0.12 equivalents) in N,N-dimethylacetamide (0.5 mL). 5-{7-Bromo-1-fluoro-3-[(2-methoxyethoxy)methoxy]naphthalen-2-yl}-2-[(2-methoxyethoxy)methyl]-1$\lambda^6$,2,5-thiadiazolidine-1,1,3-trione (Example 127A, 30 mg, 0.05 mmol, 1.0 equivalents), potassium (1-(tert-butoxycarbonyl)pyrrolidin-2-yl)trifluoroborate (22.6 mg, 0.08 mmol, 2.0 equivalents), and bis[3,5-difluoro-2-[5-(trifluoromethyl)-2-pyridyl]phenyl]iridium(1+); 2-(2-pyridyl)pyridine; hexafluorophosphate (5.0 mg, 0.005 mmol, 0.03 equivalents) were added, followed by dioxane (0.5 mL). 2,6-Dimethylpyridine (10 µL, 0.087 mmol, 1.6 equivalents) was added, and the reaction mixture was irradiated overnight using a 450 nm LED photoreactor.

The reaction was filtered and purified by reverse-phase preparative HPLC on a Waters XBridge™ C8 5 µm column (75 mm×30 mm). A gradient of methanol (A) and 25 mM ammonium bicarbonate buffer (pH 10) in water (B) was used, at a flow rate of 40 mL/minute (0-0.5 minutes 35% A, 0.5-8.0 minutes linear gradient 35-100% A, 8.0-9.0 minutes 100% A, 9.0-9.1 minutes linear gradient 100-35% A, 9.1-10.0 minutes 35% A) to afford tert-butyl 2-{8-fluoro-6-[(2-methoxyethoxy)methoxy]-7-(1,1,4-trioxo-1$\lambda^6$,2,5-thiadiazolidin-2-yl)naphthalen-2-yl}pyrrolidine-1-carboxylate.

tert-Butyl 2-{8-fluoro-6-[(2-methoxyethoxy)methoxy]-7-(1,1,4-trioxo-1$\lambda^6$,2,5-thiadiazolidin-2-yl)naphthalen-2-yl}pyrrolidine-1-carboxylate was treated with 1 4 M HCl in dioxane (1 mL) and stirred until complete by HPLC/MS (Column: Phenomenex® Luna® 5 µm, C8(2) 100 Å, 50×2.00 mm. A gradient of acetonitrile (A) in 0.1% ammonium acetate in water (B) was used, at a flow rate of 2 mL/minute (0-2.5 minutes linear gradient 0-100% A, 2.5-2.9 minutes linear gradient 100-0% A, 2.9-3.0 minutes 0% A). Retention time 0.93 minutes). The reaction was purified by reverse-phase preparative HPLC on a Waters XBridge™ C8 5 µm column (75 mm×30 mm). A gradient of methanol (A) and 25 mM ammonium bicarbonate buffer (pH 10) in water (B) was used, at a flow rate of 40 mL/minute (0-0.5 minutes 5% A, 0.5-8.0 minutes linear gradient 5-100% A, 8.0-9.0 minutes 100% A, 9.0-9.1 minutes linear gradient 100-5% A, 9.1-10.0 minutes 5% A) to afford the title compound (4 mg, 20% yield). $^1$H NMR (501 MHz, DMSO-d$_6$) δ ppm 7.99-7.91 (m, 1H), 7.80 (d, J=8.6 Hz, 1H), 7.55 (dd, J=8.7, 1.8 Hz, 1H), 7.18-6.98 (m, 1H), 4.63-4.55 (m, 1H), 4.15 (s, 2H), 3.39-3.20 (m, 2H), 2.46-2.31 (m, 1H), 2.20-1.95 (m, 3H); MS (ESI$^-$) m/z 364.0 (M−H)$^+$.

Example 160: 5-(7-{[1-(cyclopropanesulfonyl)piperidin-3-yl]methyl}-1-fluoro-3-hydroxynaphthalen-2-yl)-1$\lambda^6$,2,5-thiadiazolidine-1,1,3-trione (Compound 259)

In a 4 mL vial were combined Example 1G (98 mg, 0.21 mmol, 1.0 equivalents) and SPhos Pd G4 (7.2 mg, 10.5 µmol, 0.05 equivalents) in N,N-dimethylacetamide (1 mL). ((1-(tert-Butoxycarbonyl)piperidin-3-yl)methyl)zinc(II) iodide (2.81 mL, 0.42 mmol, 2.0 equivalents) (0.15 M in tetrahydrofuran) was added. The vial was purged with N$_2$, capped and heated to 65° C. overnight. The reaction mixture was concentrated, and the residue was purified by reverse-phase preparative HPLC on a Waters XBridge™ C8 5 µm column (75 mm×30 mm). A gradient of methanol (A) and 25 mM ammonium bicarbonate buffer (pH 10) in water (B) was used, at a flow rate of 40 mL/minute (0-0.5 minutes 35% A, 0.5-8.0 minutes linear gradient 35-100% A, 8.0-9.0 minutes 100% A, 9.0-9.1 minutes linear gradient 100-35% A, 9.1-10.0 minutes 35% A) to afford tert-butyl 3-{[6-(benzyloxy)-8-fluoro-7-(1,1,4-trioxo-1$\lambda^6$,2,5-thiadiazolidin-2-yl)naphthalen-2-yl]methyl}piperidine-1-carboxylate (62.1 mg, 51% yield).

The tert-butyl 3-{[6-(benzyloxy)-8-fluoro-7-(1,1,4-trioxo-1$\lambda^6$,2,5-thiadiazolidin-2-yl)naphthalen-2-yl]methyl}piperidine-1-carboxylate was dissolved in dichloromethane (1 mL) and trifluoroacetic acid (100 µL) was added. The reaction mixture was stirred at ambient temperature until the reaction was complete by HPLC/MS (Column:

Phenomenex® Luna® 5 μm, C8(2) 100 Å, 50×2.00 mm. A gradient of acetonitrile (A) in 0.1% ammonium acetate in water (B) was used, at a flow rate of 2 mL/minute (0-2.5 minutes linear gradient 0-100% A, 2.5-2.9 minutes linear gradient 100-0% A, 2.9-3.0 minutes 0% A). Retention time 1.391 minutes.). Volatiles were removed under a stream of nitrogen and 5-{3-(benzyloxy)-1-fluoro-7-[(piperidin-3-yl) methyl]naphthalen-2-yl}-1$\lambda^6$,2,5-thiadiazolidine-1,1,3-trione was dried in vacuo.

5-{3-(Benzyloxy)-1-fluoro-7-[(piperidin-3-yl)methyl] naphthalen-2-yl}-1$\lambda^6$,2,5-thiadiazolidine-1,1,3-trione (31.9 mg, 0.07 mmol, 1.0 equivalents) was dissolved in N,N-dimethylformamide (0.5 mL). N-Ethyl-N-isopropylpropan-2-amine (34 μL, 0.20 mmol, 3.0 equivalents) was added, followed by cyclopropylsulfonyl chloride (8 μL, 0.08 mmol, 1.2 equivalents). The reaction was stirred overnight at ambient temperature. The reaction was purified by reverse-phase preparative HPLC on a Phenomenex® Luna® C8(2) 5 μm 100 Å AXIA™ column (50 mm×30 mm). A gradient of acetonitrile (A) and 0.1% ammonium acetate in water (B) was used, at a flow rate of 40 mL/minute (0-0.5 minutes 15% A, 0.5-8.0 minutes linear gradient 15-100% A, 8.0-9.0 minutes 100% A, 9.0-9.1 minutes linear gradient 100-15% A, 9.1-10.0 minutes 15% A) to afford 5-[3-(benzyloxy)-7-{[1-(cyclopropanesulfonyl)piperidin-3-yl]methyl}-1-fluoronaphthalen-2-yl]-1$\lambda^6$,2,5-thiadiazolidine-1,1,3-trione (18.2 mg, 47% yield). $^1$H NMR (500 MHz, DMSO-d$_6$) δ ppm 7.81-7.68 (m, 2H), 7.59-7.49 (m, 2H), 7.48-7.25 (m, 5H), 5.23 (s, 2H), 4.12 (d, J=3.4 Hz, 2H), 3.40 (d, J=11.4 Hz, 2H), 2.86-2.55 (m, 5H), 1.90-1.81 (m, 1H), 1.75-1.60 (m, 2H), 1.46-1.37 (m, 1H), 1.26-1.05 (m, 1H), 0.99-0.92 (m, 2H), 0.87-0.77 (m, 2H).

Pentamethylbenzene (10.1 mg, 0.07 mmol, 2.0 equivalents) was added neat to a reaction vial containing 5-[3-(benzyloxy)-7-{[1-(cyclopropanesulfonyl)piperidin-3-yl] methyl}-1-fluoronaphthalen-2-yl]-1$\lambda^6$,2,5-thiadiazolidine-1,1,3-trione. Dichloromethane (1 mL) was added, and the vial was capped and cooled to −78° C. BCl$_3$ (1 M in dichloromethane, 100 μL, 0.1 mmol, 3.0 equivalents) was added dropwise. The reaction mixture was stirred at −78° C. for 1 hour. 100 μL of a 1:1 methanol/dichloromethane mixture was added. The mixture was dried down under a stream of nitrogen and reconstituted in dimethyl sulfoxide/methanol and purified by reverse-phase preparative HPLC on a Waters XBridgem C8 5 μm column (75 mm×30 mm). A gradient of methanol (A) and 25 mM ammonium bicarbonate buffer (pH 10) in water (B) was used, at a flow rate of 40 mL/minute (0-0.5 minutes 15% A, 0.5-8.0 minutes linear gradient 15-100% A, 8.0-9.0 minutes 100% A, 9.0-9.1 minutes linear gradient 100-15% A, 9.1-10.0 minutes 15% A) to afford the title compound (8.8 mg, 52% yield). $^1$H NMR (400 MHz, DMSO-d$_6$) δ ppm 7.75-7.68 (m, 2H), 7.41 (dd, J=8.5, 1.8 Hz, 1H), 7.10 (s, 1H), 4.17 (s, 2H), 3.49 (t, J=14.0 Hz, 2H), 2.91-2.81 (m, 1H), 2.75-2.58 (m, 2H), 1.94-1.89 (m, 1H), 1.81-1.70 (m, 1H), 1.52-1.45 (m, 1H), 1.22-1.15 (m, 1H), 1.05-0.95 (m, 2H), 0.91-0.85 (m, 2H).

Example 161: 5-[7-(difluoromethoxy)-1-fluoro-3-hydroxynaphthalen-2-yl]-1$\lambda^6$,2,5-thiadiazolidine-1, 1,3-trione (Compound 260)

To a slurry of Example 1H (200 mg, 0.497 mmol) in acetonitrile (1.2 mL) was added a solution of potassium hydroxide (558 mg, 9.94 mmol) in water (1.2 mL). Thereafter, the mixture was cooled to −78° C., and diethyl (bromodifluoromethyl)phosphonate (177 μl, 0.994 mmol) was added in one portion to the frozen solution. After warming to ambient temperature, the reaction was stirred 15 minutes, diluted with ethyl acetate (10 mL), and quenched with 1 M HCl (20 mL). The resulting layers were separated. The organic layer was washed with brine (2×10 mL), dried over sodium sulfate, filtered, and concentrated in vacuo (14 mbar, 36° C.) to afford 191 mg of 5-[3-(benzyloxy)-7-(difluoromethoxy)-1-fluoronaphthalen-2-yl]-1$\lambda^6$,2,5-thiadiazolidine-1,1,3-trione that was suspended with 1,2,3,4,5-pentamethylbenzene (188 mg, 1.27 mmol) in dichloromethane (2.1 mL) and cooled to −78° C. A solution of boron trichloride (844 μL, 0.844 mmol, 1.0 M in dichloromethane) was added dropwise over 5 minutes. After 15 minutes, the reaction was quenched with anhydrous methanol (205 μL, 5.07 mmol), and the mixture was warmed to ambient temperature under nitrogen. The volatiles were removed to afford a residue that was dissolved in dimethyl sulfoxide:methanol (1:1, 3 mL) and purified by reverse-phase HPLC [Phenomenex® Luna® 10 M C18(2) 100 Å, AX (00G-4253-U0-AX) column, 250×30 mm, 50 mL/minute, 1 injection, 5%-95% acetonitrile/water (with 0.1% trifluoroacetic acid) over 15 minutes, monitored/collected at 205 nm] to afford the title compound (51.8 mg, 0.143 mmol, 34% yield). $^1$H NMR (400 MHz, CD$_3$OD) ppm 7.73 (dd, J=9.3, 1.2 Hz, 1H), 7.60 (d, J=2.2 Hz, 1H), 7.30 (dd, J=9.3, 2.5 Hz, 1H), 7.09 (s, 1H), 6.91 (t, J$_{H-F}$=74.4 Hz, 1H), 4.55 (s, 2H); MS (ESI$^-$) m/z 361 [M−H]$^-$.

Example 162: 5-(7-{[1-(cyclopropanesulfonyl)pyrrolidin-3-yl]methyl}-1-fluoro-3-hydroxynaphthalen-2-yl)-1$\lambda^6$,2,5-thiadiazolidine-1,1,3-trione (Compound 261)

In a 4 mL vial were combined 5-{7-bromo-1-fluoro-3-[(2-methoxyethoxy)methoxy]naphthalen-2-yl}-2-[(2-methoxyethoxy)methyl]-1$\lambda^6$,2,5-thiadiazolidine-1,1,3-trione (Example 127A, 100 mg, 0.181 mmol, 1.0 equivalents) and Pd SPhos G4 (7.20 mg, 9.07 μmol, 0.05 equivalents) in N,N-dimethylacetamide (2 mL). ((1-(tert-Butoxycarbonyl) pyrrolidin-3-yl)methyl)zinc(II) iodide (3.30 mL, 0.363 mmol, 2.0 equivalents, 0.11 M in tetrahydrofuran) was added. The vial was purged with N$_2$, capped and heated to 65° C. overnight. The residue was purified by reverse-phase preparative HPLC on a Waters XBridge™ C8 5 μm column (75 mm×30 mm). A gradient of methanol (A) and 25 mM ammonium bicarbonate buffer (pH 10) in water (B) was used, at a flow rate of 40 mL/minute (0-0.5 minutes 25% A, 0.5-8.0 minutes linear gradient 25-100% A, 8.0-9.0 minutes 100% A, 9.0-9.1 minutes linear gradient 100-25% A, 9.1-10.0 minutes 5% A) to give tert-butyl 3-({8-fluoro-6-[(2-methoxyethoxy)methyl]-7-(1,1,4-trioxo-1$\lambda^6$,2,5-thiadiazolidin-2-yl)naphthalen-2-yl}methyl)pyrrolidine-1-carboxylate (42.1 mg, 41% yield).

tert-butyl 3-({8-fluoro-6-[(2-methoxyethoxy)methoxy]-7-(1,1,4-trioxo-1$\lambda^6$,2,5-thiadiazolidin-2-yl)naphthalen-2-yl}methyl)pyrrolidine-1-carboxylate was suspended in 4 M HCl in dioxane (1 mL), stirred for 10 minutes and dried under a stream of nitrogen to give 5-{1-fluoro-3-hydroxy-7-[(pyrrolidin-3-yl)methyl]naphthalen-2-yl}-1$\lambda^6$,2,5-thiadiazolidine-1,1,3-trione. $^1$H NMR (400 MHz, DMSO-d$_6$) δ ppm 7.79-7.56 (m, 2H), 7.38 (dd, J=8.5, 1.7 Hz, 1H), 7.05 (s, 1H), 4.13 (s, 2H), 3.26-3.01 (m, 3H), 2.86-2.72 (m, 3H), 2.58-2.52 (m, 1H), 2.05-1.84 (m, 1H), 1.67-1.48 (m, 1H); MS (ESI$^+$) m/z 380.3 (M+H)$^+$.

5-{1-Fluoro-3-hydroxy-7-[(pyrrolidin-3-yl)methyl]naphthalen-2-yl}-1$\lambda^6$,2,5-thiadiazolidine-1,1,3-trione (32 mg, 0.08 mmol, 1.0 equivalents) was dissolved in N,N-dimethylformamide (1.0 mL). N-Ethyl-N-isopropylpropan-2- amine (44 μL, 0.25 mmol, 3.0 equivalents) was added, followed by cyclopropylsulfonyl chloride (10 μL, 0.10 mmol, 1.2 equivalents). The reaction was stirred overnight at ambient temperature. The reaction was purified by reverse-phase preparative HPLC on a Phenomenex® Luna® C8(2) 5 μm 100 Å AXIA™ column (50 mm×30 mm). A gradient of acetonitrile (A) and 0.1% ammonium acetate in water (B) was used, at a flow rate of 40 mL/minute (0-0.5 minutes 5% A, 0.5-8.0 minutes linear gradient 5-100% A, 8.0-9.0 minutes 100% A, 9.0-9.1 minutes linear gradient 100-5% A, 9.1-10.0 minutes 5% A) to afford the title compound (4.6 mg, 11% yield). $^1$H NMR (500 MHz, DMSO-$d_6$) δ ppm 7.71-7.64 (m, 2H), 7.38 (d, J=7.6 Hz, 1H), 7.04 (s, 1H), 4.12 (s, 2H), 3.49-3.19 (m, 4H), 3.02-2.95 (m, 1H), 2.87-2.78 (m, 1H), 1.67-1.55 (m, 1H), 1.16 (d, J=17.7 Hz, 4H), 0.97-0.87 (m, 3H); MS (ESI$^-$) m/z 483.0 [M−H]$^+$.

Example 163: 5-{1-fluoro-3-hydroxy-7-[(pyrrolidin-3-yl)methyl]naphthalen-2-yl}-1$\lambda^6$,2,5-thiadiazolidine-1,1,3-trione (Compound 262)

In a 4 mL vial were combined 5-{7-bromo-1-fluoro-3-[(2-methoxyethoxy)methoxy]naphthalen-2-yl}-2-[(2-methoxyethoxy)methyl]-1$\lambda^6$,2,5-thiadiazolidine-1,1,3-trione (Example 127A, 100 mg, 0.181 mmol, 1.0 equivalents) and Pd SPhos G4 (7.20 mg, 9.07 μmol, 0.05 equivalents) in N,N-dimethylacetamide (2 mL). ((1-(tert-Butoxycarbonyl)pyrrolidin-3-yl)methyl)zinc(II) iodide (3.30 mL, 0.363 mmol, 2.0 equivalents, 0.11 M in tetrahydrofuran) was added. The vial was purged with $N_2$, capped and heated to 65° C. overnight. The residue was purified by reverse-phase preparative HPLC on a Waters XBridge™ C8 5 μm column (75 mm×30 mm). A gradient of methanol (A) and 25 mM ammonium bicarbonate buffer (pH 10) in water (B) was used, at a flow rate of 40 mL/minute (0-0.5 minutes 25% A, 0.5-8.0 minutes linear gradient 25-100% A, 8.0-9.0 minutes 100% A, 9.0-9.1 minutes linear gradient 100-25% A, 9.1-10.0 minutes 5% A) to give tert-butyl 3-[(8-fluoro-6-[(2-methoxyethoxy)methoxy]-7-{5-[(2-methoxyethoxy)methyl]-1,1,4-trioxo-1$\lambda^6$,2,5-thiadiazolidin-2-yl}naphthalen-2-yl)methyl]pyrrolidine-1-carboxylate.

A sample of the tert-butyl 3-[(8-fluoro-6-[(2-methoxyethoxy)methoxy]-7-{5-[(2-methoxyethoxy)methyl]-1,1,4-trioxo-1$\lambda^6$,2,5-thiadiazolidin-2-yl}naphthalen-2-yl)methyl]pyrrolidine-1-carboxylate was suspended in 4 M HCl in dioxane (1 mL), stirred for 10 minutes and dried under a stream of nitrogen. The residue was purified by reverse-phase preparative HPLC on a Waters XBridge™ C8 5 μm column (75 mm×30 mm). A gradient of methanol (A) and 25 mM ammonium bicarbonate buffer (pH 10) in water (B) was used, at a flow rate of 40 mL/minute (0-0.5 minutes 5% A, 0.5-8.0 minutes linear gradient 5-100% A, 8.0-9.0 minutes 100% A, 9.0-9.1 minutes linear gradient 100-5% A, 9.1-10.0 minutes 5% A) to afford the title compound (2.1 mg). $^1$H NMR (400 MHz, DMSO-$d_6$) δ ppm 7.79-7.56 (m, 2H), 7.38 (dd, J=8.5, 1.7 Hz, 1H), 7.05 (s, 1H), 4.13 (s, 2H), 3.26-3.01 (m, 3H), 2.86-2.72 (m, 3H), 2.58-2.52 (m, 1H), 2.05-1.84 (m, 1H), 1.67-1.48 (m, 1H); MS (ESI$^+$) m/z 380.3 (M+H)$^+$.

Example 164: 5-[7-(2,5-dihydrofuran-3-yl)-1-fluoro-3-hydroxynaphthalen-2-yl]-1$\lambda^6$,2,5-thiadiazolidine-1,1,3-trione (Compound 263)

A microwave tube was charged with the product of Example 128A (80 mg, 0.213 mmol), 2-(2,5-dihydrofuran-3-yl)-4,4,5,5-tetramethyl-1,3,2-dioxaborolane (54.3 mg, 0.277 mmol), 1,1'-bis(di-tert-butylphosphino)ferrocene palladium dichloride (2.085 mg, 3.20 μmol), and potassium carbonate (88 mg, 0.640 mmol). 1,4-Dioxane (2 mL) and water (1 mL) were subsequently added. The reaction mixture was flushed with $N_2$ for 5 minutes and stirred at 60° C. overnight. The reaction was then cooled down to ambient temperature and partitioned between water (5 mL) and ethyl acetate (5 mL). The aqueous layer was extracted with ethyl acetate (2×3 mL), the combined organic layers were washed with saturated aqueous ammonium chloride (5 mL) and dried over sodium sulfate. The volatiles were removed under reduced pressure, and the residue was subjected to preparative HPLC [Phenomenex® Luna® C18(2) 5 μm 100 Å AXIA™ column (250 mm×25 mm). 30-100% gradient of acetonitrile (A) and 0.1% trifluoroacetic acid in water (B) over 15 minutes, at a flow rate of 25 mL/minute] to afford the title compound (40 mg, 0.110 mmol, 52% yield). $^1$H NMR (500 MHz, DMSO-$d_6$) δ ppm 10.76 (s, 1H), 7.79 (s, 2H), 7.64 (s, 1H), 7.12 (s, 1H), 6.65 (t, J=2.1 Hz, 1H), 5.01 (td, J=4.7, 2.0 Hz, 2H), 4.77 (td, J=4.7, 1.9 Hz, 2H), 4.50 (s, 2H); MS (APCI$^-$) m/z 363 [M−H]$^-$.

Example 165: 5-[7-(3,6-dihydro-2H-pyran-4-yl)-1-fluoro-3-hydroxynaphthalen-2-yl]-1$\lambda^6$,2,5-thiadiazolidine-1,1,3-trione (Compound 264)

A microwave tube was charged with product of Example 128A (80 mg, 0.213 mmol), 2-(3,6-dihydro-2H-pyran-4-yl)-4,4,5,5-tetramethyl-1,3,2-dioxaborolane (58.2 mg, 0.277 mmol), potassium carbonate (88 mg, 0.640 mmol), and 1,1'-bis(di-tert-butylphosphino)ferrocene palladium dichloride (2.085 mg, 3.20 μmol). 1,4-Dioxane (2 mL) and water (1 mL) were subsequently added, and the reaction mixture was flushed with $N_2$ for 5 minutes and stirred at 60° C. overnight. The mixture was then cooled down to ambient temperature and partitioned between water (5 mL) and ethyl acetate (5 mL). The aqueous layer was extracted with ethyl acetate (2×3 mL). The combined organic layers were washed with saturated aqueous ammonium chloride (5 mL) and dried over sodium sulfate. The volatiles were removed under reduced pressure and the residue was subjected to preparative HPLC [Phenomenex® Luna® C18(2) 5 μm 100 Å AXIA™ column (250 mm×25 mm). 30-100% gradient of acetonitrile (A) and 0.1% trifluoroacetic acid in water (B) over 15 minutes, at a flow rate of 25 mL/minute] to afford the title compound (37 mg, 0.098 mmol, 46% yield). $^1$H NMR (500 MHz, DMSO-$d_6$) δ ppm 10.65 (s, 1H), 7.82 (s, 1H), 7.79-7.71 (m, 2H), 7.10 (s, 1H), 6.45 (dq, J=2.9, 1.4 Hz, 1H), 4.49 (s, 2H), 4.27 (q, J=2.8 Hz, 2H), 3.87 (t, J=5.5 Hz, 2H), 2.56 (ddd, J=8.9, 5.7, 2.9 Hz, 2H); MS (APCI$^-$) m/z 377 [M−H]$^-$.

Example 166: 5-[7-(2,5-dihydro-1H-pyrrol-3-yl)-1-fluoro-3-hydroxynaphthalen-2-yl]-1$\lambda^6$,2,5-thiadiazolidine-1,1,3-trione (Compound 265)

The product of Example 123A (75 mg, 0.135 mmol) and 1,2,3,4,5-pentamethylbenzene (60.3 mg, 0.406 mmol) in a 50 mL round bottom flask was flushed with nitrogen for 5 minutes. Dichloromethane (2 mL) was then added, and the heterogeneous suspension was cooled to −78° C. and equilibrated for 5 minutes. Subsequently, a 1 M solution of trichloroborane (0.406 mL, 0.406 mmol) in dichloromethane was added dropwise over 5 minutes. Consequently, the reaction was quenched at −78° C. with ethanol (0.1 mL) and dichloromethane (0.9 mL) and then slowly warmed to ambient temperature. The volatiles were removed under reduced pressure, and the residue was subjected to preparative HPLC [Phenomenex® Luna® C18(2) 5 µm 100 Å AXIA™ column (250 mm×25 mm). 30-100% gradient of acetonitrile (A) and 0.1% ammonium acetate in water (B) over 15 minutes, at a flow rate of 25 mL/minute] to afford the title compound (8 mg, 0.022 mmol, 16% yield). $^1$H NMR (400 MHz, DMSO-d$_6$) δ ppm 7.78 (broad, 3H), 7.09 (d, J=1.3 Hz, 1H), 6.56 (t, J=2.1 Hz, 1H), 4.49 (q, J=2.4 Hz, 2H), 4.19 (q, J=2.4 Hz, 2H), 4.10 (s, 2H); MS (APCI$^+$) m/z 364 [M+H]$^+$.

Example 167: 5-[1-fluoro-3-hydroxy-7-(pyridin-3-yl)naphthalen-2-yl]-1λ$^6$,2,5-thiadiazolidine-1,1,3-trione (Compound 266)

A microwave tube was charged with product of Example 128A (80 mg, 0.213 mmol), 3-(4,4,5,5-tetramethyl-1,3,2-dioxaborolan-2-yl)pyridine (56.8 mg, 0.277 mmol), potassium carbonate (88 mg, 0.640 mmol), and 1,1'-bis(di-tert-butylphosphino)ferrocene palladium dichloride (2.085 mg, 3.20 µmol). 1,4-Dioxane (2 mL) and water (1 mL) were subsequently added. The reaction mixture was flushed with N$_2$ for 5 minutes and stirred at 60° C. overnight. The reaction was then cooled down to ambient temperature and partitioned between water (5 mL) and ethyl acetate (5 mL). The aqueous layer was extracted with ethyl acetate (2×3 mL). The combined organic layers were washed with saturated aqueous ammonium chloride (5 mL) and dried over sodium sulfate. The volatiles were removed under reduced pressure and the residue was subjected to preparative HPLC [Phenomenex® Luna® C18(2) 5 µm 100 Å AXIA™ column (250 mm×25 mm). 30-100% gradient of acetonitrile (A) and 0.1% trifluoroacetic acid in water (B) over 15 minutes, at a flow rate of 25 mL/minute] to give the title compound (26 mg, 0.07 mmol, 33%). $^1$H NMR (500 MHz, DMSO-d$_6$) δ ppm 10.53 (s, 1H), 9.20 (s, 1H), 8.73 (d, J=5.1 Hz, 1H), 8.60-8.55 (m, 1H), 8.31 (s, 1H), 7.97-7.92 (m, 1H), 7.80 (dd, J=8.1, 5.1 Hz, 1H), 7.17 (s, 1H), 4.33 (s, 2H); MS (APCI$^-$) m/z 372 [M–H]$^-$.

Example 168: 5-{7-[(azetidin-3-yl)methyl]-1-fluoro-3-hydroxynaphthalen-2-yl}-1λ$^6$,2,5-thiadiazolidine-1,1,3-trione (Compound 267)

In a 4 mL vial were combined 5-(7-bromo-1-fluoro-3-hydroxynaphthalen-2-yl)-1λ$^6$,2,5-thiadiazolidine-1,1,3-trione (50 mg, 0.133 mmol, 1.0 equivalents, Example 128A) and Pd SPhos G4 (5.29 mg, 6.66 µmol, 0.05 equivalents) in N,N-dimethylacetamide (1 mL). ((1-(tert-Butoxycarbonyl)azetidin-3-yl)methyl)zinc(II) iodide (1.481 mL, 0.267 mmol, 2.0 equivalents) (0.18 M in tetrahydrofuran) was added. The reaction was purged with N$_2$, capped and heated to 65° C. overnight. The residue was purified by reverse-phase preparative HPLC on a Waters XBridge™ C8 5 µm column (75 mm×30 mm). A gradient of methanol (A) and 25 mM ammonium bicarbonate buffer (pH 10) in water (B) was used, at a flow rate of 40 mL/minute (0-0.5 minutes 5% A, 0.5-8.0 minutes linear gradient 5-100% A, 8.0-9.0 minutes 100% A, 9.0-9.1 minutes linear gradient 100-5% A, 9.1-10.0 minutes 5% A) to tert-butyl 3-{[8-fluoro-6-hydroxy-7-(1,1,4-trioxo-1λ$^6$,2,5-thiadiazolidin-2-yl)naphthalen-2-yl]methyl}azetidine-1-carboxylate.

The residue was dissolved in 1 mL dichloromethane and 100 µL trifluoroacetic acid was added. The reaction was stirred for 10 minutes at ambient temperature. Volatiles were removed under a stream of nitrogen. The residue was reconstituted in dimethyl sulfoxide/methanol and purified by reverse-phase preparative HPLC on a Waters XBridge™ C8 5 µm column (75 mm×30 mm). A gradient of methanol (A) and 25 mM ammonium bicarbonate buffer (pH 10) in water (B) was used, at a flow rate of 40 mL/minute (0-0.5 minutes 5% A, 0.5-8.0 minutes linear gradient 5-100% A, 8.0-9.0 minutes 100% A, 9.0-9.1 minutes linear gradient 100-5% A, 9.1-10.0 minutes 5% A) to afford the title compound (7 mg, 14% yield). $^1$H NMR (400 MHz, DMSO-d$_6$) δ ppm 7.73-7.62 (m, 2H), 7.32 (dd, J=8.5, 1.7 Hz, 1H), 7.08 (d, J=1.5 Hz, 1H), 4.14 (s, 2H), 4.02-3.94 (m, 2H), 3.80-3.64 (m, 2H), 3.21-3.14 (m, 1H), 3.06 (d, J=7.8 Hz, 2H); MS (ESI$^+$) m/z 366.3 (M+H)$^+$.

Example 169: N-(2-cyclopropylethyl)-2-{[8-fluoro-6-hydroxy-7-(1,1,4-trioxo-1λ$^6$,2,5-thiadiazolidin-2-yl)naphthalen-2-yl]amino}acetamide (Compound 268)

To a solution of the product of Example 181 (0.033 g, 0.089 mmol) and 2-cyclopropylethanamine hydrochloride (0.013 g, 0.107 mmol) in dimethylformamide (0.6 mL) was added 1-[bis(dimethylamino)methylene]-1H-1,2,3-triazolo[4,5-b]pyridinium 3-oxid hexafluorophosphate (0.048 g, 0.125 mmol), followed by N,N-diisopropylethylamine (0.062 mL, 0.357 mmol). After 5 minutes, the reaction mixture was quenched with methanol (0.5 mL) and then filtered through a glass microfiber frit. The resulting solution was directly purified by preparative HPLC [Waters XBridge™ C18 5 µm OBD column, 30×100 mm, flow rate 40 mL/minute, a gradient of 3-30% methanol in buffer (0.025 M aqueous ammonium bicarbonate, adjusted to pH 10 with ammonium hydroxide)] to give the title compound as an ammonium salt (0.028 g, 0.062 mmol, 69.1% yield). $^1$H NMR (400 MHz, –d$_6$) δ ppm 7.95 (t, J=5.8 Hz, 1H), 7.47 (dd, J=8.9, 1.6 Hz, 1H), 7.00 (dd, J=8.9, 2.3 Hz, 1H), 6.90 (d, J=1.2 Hz, 1H), 6.55 (d, J=2.4 Hz, 1H), 4.08 (s, 2H), 3.68 (s, 2H), 3.19-3.09 (m, 2H), 1.25 (q, J=7.0 Hz, 2H), 0.66-0.51 (m, 1H), 0.35-0.23 (m, 2H), –0.04--0.09 (m, 2H); MS (ESI$^-$) m/z 435 [M–H]$^-$.

Example 170: 4-{[8-fluoro-6-hydroxy-7-(1,1,4-trioxo-1λ$^6$,2,5-thiadiazolidin-2-yl)naphthalen-2-yl]oxy}-N-methylbutanamide (Compound 269)

To a suspension of the product of Example 1H (0.200 g, 0.497 mmol) and cesium carbonate (0.486 g, 1.491 mmol) in dimethylformamide (2 mL) was added tert-butyl 4-bromobutanoate (0.176 mL, 0.994 mmol) and the resulting mixture was heated to 60° C. After 2 hours, the reaction mixture was cooled to ambient temperature, quenched with 1 M hydrochloric acid (2 mL) and diluted with ethyl acetate (2 mL). The aqueous layer was extracted with ethyl acetate (2×2 mL). The organic layers were combined and washed with saturated aqueous ammonium chloride (4×1 mL) followed by a 4:1 mixture of brine and 1 M hydrochloric acid, dried over anhydrous sodium sulfate, then filtered and concentrated under reduced pressure to give tert-butyl 4-{[6-(benzyloxy)-8-fluoro-7-(1,1,4-trioxo-1λ$^6$,2,5-thiadiazolidin-2-yl)naphthalen-2-yl]oxy}butanoate, which was used without purification for the next reaction. MS (APCI$^-$) m/z 543 [M–H]$^-$.

To a solution of the crude tert-butyl 4-{[6-(benzyloxy)-8-fluoro-7-(1,1,4-trioxo-1λ$^6$,2,5-thiadiazolidin-2-yl)naphthalen-2-yl]oxy}butanoate (0.271 g, 0.497 mmol) and pentamethylbenzene (0.147 g, 0.994 mmol) in dichloromethane (5.4 mL) at −78° C. was added a solution of boron trichloride in dichloromethane (2.98 mL, 1 M, 2.98 mmol) slowly along the side of the flask so that the internal temperature remained below −70° C. The resulting solution was stirred for 5 minutes at −78° C., then the cooling bath was removed, and the reaction mixture was allowed to warm to an internal temperature of 0° C. before cooling back to −78° C. The reaction was quenched by addition of ethyl acetate (2 mL) followed by water (2 mL), warmed to ambient temperature and concentrated under reduced pressure to give a solid. The crude solid was triturated with heptanes (3×3 mL). The solid was rinsed with ethyl acetate (3×3 mL), and the filtrate was concentrated under reduced pressure to give a solid. The new solid was triturated with acetonitrile (2×2 mL), and the filtrate was concentrated under reduced pressure to give 4-{[8-fluoro-6-hydroxy-7-(1,1,4-trioxo-1λ$^6$,2,5-thiadiazolidin-2-yl)naphthalen-2-yl]oxy}butanoic acid as a solid, which was used for the next reaction without purification. MS (APCI$^-$) m/z 397 [M−H]$^-$.

To a solution of the product of the crude 4-{[8-fluoro-6-hydroxy-7-(1,1,4-trioxo-1λ$^6$,2,5-thiadiazolidin-2-yl)naphthalen-2-yl]oxy}butanoic acid (1 mL, 0.249 mmol) in dimethylformamide (1 mL) was added a solution of methylamine in tetrahydrofuran (0.746 mL, 2 M, 1.49 mmol), followed by 1-[bis(dimethylamino)methylene]-1H-1,2,3-triazolo[4,5-b]pyridinium 3-oxid hexafluorophosphate (0.132 g, 0.348 mmol). After 5 minutes, the reaction mixture was quenched with methanol (0.5 mL), then the resulting solution was filtered through a glass microfiber frit. The resulting solution was directly purified by preparative HPLC [Waters XBridge™ C18 5 μm OBD column, 30×100 mm, flow rate 40 mL/minute, a gradient of 5-35% acetonitrile in buffer (0.025 M aqueous ammonium bicarbonate, adjusted to pH 10 with ammonium hydroxide)] to give the title compound as an ammonium salt (0.0146 g, 0.034 mmol, 13.8% yield). $^1$H NMR (501 MHz, DMSO-d$_6$) δ ppm 7.64 (dd, J=9.1, 1.4 Hz, 1H), 7.15 (d, J=2.6 Hz, 1H), 7.15-7.08 (m, 1H), 7.01 (s, 1H), 4.11 (s, 2H), 4.06 (t, J=6.3 Hz, 2H), 3.59 (s, 2H), 2.48 (t, J=7.2 Hz, 2H), 2.00 (p, J=6.8 Hz, 2H); MS (ESI$^-$) m/z 410 [M−H]$^-$.

Example 171: N-ethyl-N'-(2-{[8-fluoro-6-hydroxy-7-(1,1,4-trioxo-1λ$^6$,2,5-thiadiazolidin-2-yl)naphthalen-2-yl]oxy}ethyl)urea (Compound 270)

To Example 210 (30 mg, 0.084 mmol) in dimethyl sulfoxide (1 mL) was added isocyanatoethane (10.80 mg, 0.152 mmol) in N,N-dimethylformamide (0.2 mL) and sodium carbonate (26.8 mg, 0.253 mmol). The mixture was stirred at ambient temperature for 30 minutes, filtered through a glass microfiber frit and purified by preparative HPLC [YMC TriArt™ C18 Hybrid 5 μm column, 50×100 mm, flow rate 140 mL/minute, 5-100% gradient of methanol in buffer (0.025 M aqueous ammonium bicarbonate, adjusted to pH 10 with ammonium hydroxide)] to give the title compound (10 mg, 0.023 mmol, 27.8% yield). $^1$H NMR (400 MHz, DMSO-d$_6$) δ ppm 9.74 (br s, 1H), 8.50 (s, 1H), 7.67 (d, J=8 Hz, 1H), 7.19 (d, J=2 Hz, 1H), 7.14 (dd, J=8, 2 Hz, 1H), 7.04 (s, 1H), 6.12 (t, J=8 Hz, 1H), 5.99 (t, J=8 Hz, 1H), 4.10 (s, 2H), 4.05 (t, J=8 Hz, 2H), 3.43 (m, 2H), 3.02 (q, J=8 Hz, 2H), 0.98 (t, J=8 Hz, 3H), MS (ESI$^-$) m/z 425 (M−H)$^-$.

Example 172: 5-{1-fluoro-3-hydroxy-7-[(oxan-3-yl)methoxy]naphthalen-2-yl}-1λ$^6$,2,5-thiadiazolidine-1,1,3-trione (Compound 271)

Example 172A: 5-{3-(benzyloxy)-1-fluoro-7-[(oxan-3-yl)methoxy]naphthalen-2-yl}-1λ$^6$,2,5-thiadiazolidine-1,1,3-trione To a solution of product of Example 1H (120 mg, 0.298 mmol) in N,N-dimethylformamide (2 mL) was added 3-(bromomethyl)tetrahydro-2H-pyran (117 mg, 0.656 mmol) and cesium carbonate (214 mg, 0.656 mmol). The reaction was heated to 80° C. for 3 hours. The reaction was then cooled down to ambient temperature and partitioned between water (5 mL) and ethyl acetate (5 mL). The aqueous layer was further extracted with ethyl acetate (2×3 mL). The combined organic layers were washed with saturated aqueous ammonium chloride (5 mL) and dried over sodium sulfate. The volatiles were removed under reduced pressure, and the residue was subjected to column chromatography (SiO$_2$, 10% methanol in dichloromethane) to give afford the title compound (89 mg, 0.178 mmol, 60% yield). $^1$H NMR (501 MHz, DMSO-d$_6$) δ ppm 7.75 (dd, J=8.9, 1.4 Hz, 1H), 7.59-7.53 (m, 2H), 7.39-7.34 (m, 2H), 7.33-7.29 (m, 2H), 7.25-7.18 (m, 3H), 5.22 (s, 2H), 4.09 (s, 2H), 3.98 (dd, J=6.6, 3.8 Hz, 2H), 3.95-3.90 (m, 1H), 3.34-3.28 (m, 2H), 3.79-3.72 (m, 1H), 3.31 (dd, J=11.1, 9.1 Hz, 1H), 2.09-2.01 (m, 1H), 1.89 (dd, J=12.9, 4.3 Hz, 1H), 1.63 (dt, J=13.0, 3.9 Hz, 1H), 1.59-1.48 (m, 1H), 1.48-1.38 (m, 1H); MS (APCI$^-$) m/z 499 [M−H]$^-$.

Example 172B: 5-{1-fluoro-3-hydroxy-7-[(oxan-3-yl)methoxy]naphthalen-2-yl}-1λ$^6$,2,5-thiadiazolidine-1,1,3-trione The product of Example 172A (87 mg, 0.174 mmol) and pentamethylbenzene (51.5 mg, 0.348 mmol) in a 250 mL round bottom flask was flushed with nitrogen for 5 minutes. Dichloromethane (50 mL) was then added and the heterogeneous suspension was cooled to −78° C. and equilibrated for 5 minutes. Subsequently, a 1 M solution of boron trichloride (0.695 mL, 0.695 mmol) in dichloromethane was added dropwise over 5 minutes. After stirring for 30 minutes, the reaction was quenched at −78° C. with ethyl acetate (20 mL) followed by methanol (4 mL), then slowly warmed to ambient temperature over 20 minutes under nitrogen. The volatiles were removed under reduced pressure and the residue was subjected to preparative HPLC [Phenomenex® Luna® C18(2) 5 μm 100 Å AXIA™ column (250 mm×25 mm). 30-100% gradient of acetonitrile (A) and 0.1% ammonium acetate in water (B) over 15 minutes, at a flow rate of 25 mL/minute] to afford the title compound (34 mg, 0.083 mmol, 47.7% yield). $^1$H NMR (400 MHz, DMSO-d$_6$) δ ppm 10.40 (s, 1H), 7.71 (d, J=8.8 Hz, 1H), 7.23-7.17 (m, 2H), 7.07 (s, 1H), 4.52 (s, 2H), 4.02-3.88 (m, 3H), 3.75 (dd, J=9.6, 5.7 Hz, 1H), 3.42-3.26 (m, 2H), 2.05 (dqd, J=9.9, 6.3, 2.9 Hz, 1H), 1.92-1.84 (m, 1H), 1.63 (dt, J=12.3, 3.9 Hz, 1H), 1.62-1.36 (m, 2H); MS (APCI$^-$) m/z 409 [M−H]$^-$.

Example 173: 5-{7-[(1-chloro-3-hydroxypropan-2-yl)oxy]-1-fluoro-3-hydroxynaphthalen-2-yl}-1λ$^6$,2,5-thiadiazolidine-1,1,3-trione (Compound 272)

To a suspension of the product of Example 1H (0.100 g, 0.249 mmol) and cesium carbonate (0.324 g, 0.994 mmol) in dimethylformamide (1 mL) was added oxetan-3-yl-4-methylbenzenesulfonate (0.170 g, 0.746 mmol) and the resulting mixture was heated to 60° C. After 2 hours, the reaction mixture was cooled to ambient temperature, quenched with 1 M hydrochloric acid (2 mL) and diluted with ethyl acetate (2 mL). The aqueous layer was extracted with ethyl acetate (2×2 mL). The organic layers were combined and washed with saturated aqueous ammonium chloride (4×1 mL) followed by a 4:1 mixture of brine and 1 M hydrochloric acid, dried over anhydrous sodium sulfate, then filtered and concentrated under reduced pressure to give 5-{3-(benzyloxy)-1-fluoro-7-[(oxetan-3-yl)oxy]naphthalen-2-yl}-1λ$^6$,2, 5-thiadiazolidine-1,1,3-trione, which was used without purification for the next reaction. MS (ESI⁻) m/z 457 [M–H]⁻.

To a suspension of the crude 5-{3-(benzyloxy)-1-fluoro-7-[(oxetan-3-yl)oxy]naphthalen-2-yl}-1λ$^6$,2,5-thiadiazolidine-1,1,3-trione (0.114 g, 0.249 mmol) and pentamethylbenzene (0.074 g, 0.498 mmol) in dichloromethane (2.3 mL) at −78° C. was added a solution of boron trichloride in dichloromethane (1.29 mL, 1 M, 1.29 mmol) slowly along the side of the flask so that the internal temperature remained below −70° C. The resulting solution was stirred for 5 minutes at −78° C., then the cooling bath was removed, and the reaction mixture was allowed to warm to an internal temperature of 0° C. before cooling back to −78° C. The reaction was quenched by addition of ethyl acetate (2 mL), followed by anhydrous ethanol (2 mL), warmed to ambient temperature and concentrated under reduced pressure. The crude product was then dissolved in a dimethyl sulfoxide/methanol mixture and was filtered through a glass microfiber frit. The resulting solution was directly purified by preparative HPLC [Waters XBridge™ C18 5 μm OBD column, 30×100 mm, flow rate 40 mL/minute, a gradient of 5-40% methanol in buffer (0.025 M aqueous ammonium bicarbonate, adjusted to pH 10 with ammonium hydroxide)] to give the title compound as an ammonium salt (0.0231 g, 0.055 mmol, 22% yield). $^1$H NMR (400 MHz, DMSO-d$_6$) δ ppm 7.69 (dd, J=9.1, 1.5 Hz, 1H), 7.32 (d, J=2.6 Hz, 1H), 7.19 (dd, J=9.0, 2.5 Hz, 1H), 7.03 (s, 1H), 5.12 (t, J=5.8 Hz, 1H), 4.65 (p, J=5.1 Hz, 1H), 4.09 (s, 2H), 3.95 (dd, J=11.7, 4.0 Hz, 1H), 3.85 (dd, J=11.9, 5.5 Hz, 1H), 3.72-3.63 (m, 2H); MS (ESI⁻) m/z 403 [M–H]⁻.

Example 174: 5-{1-fluoro-3-hydroxy-7-[(oxan-4-yl)methoxy]naphthalen-2-yl}-1λ$^6$,2,5-thiadiazolidine-1,1,3-trione (Compound 273)

Example 174A: 5-{3-(benzyloxy)-1-fluoro-7-[(oxan-4-yl)methoxy]naphthalen-2-yl}-1λ$^6$,2,5-thiadiazolidine-1,1,3-trione To a solution of the product of Example 1H (120 mg, 0.298 mmol) in N,N-dimethylformamide (2 mL) was added 4-(bromomethyl)tetrahydro-2H-pyran (117 mg, 0.656 mmol) and cesium carbonate (214 mg, 0.656 mmol). The reaction was heated to 80° C. for 3 hours. The reaction was then cooled down to ambient temperature and partitioned between water (5 mL) and ethyl acetate (5 mL). The aqueous layer was further extracted with ethyl acetate (2×3 mL), and the combined organic layers were washed with saturated aqueous ammonium chloride (5 mL) and dried over sodium sulfate. The volatiles were removed under reduced pressure and the residue was subjected to column chromatography (SiO$_2$, 10% methanol in dichloromethane) to afford the title compound (60 mg, 0.120 mmol, 40% yield). $^1$H NMR (501 MHz, DMSO-d$_6$) δ ppm 7.75 (dd, J=9.0, 1.3 Hz, 1H), 7.59-7.53 (m, 2H), 7.40-7.33 (m, 2H), 7.37-7.27 (m, 2H), 7.24 (d, J=2.6 Hz, 1H), 7.20 (dd, J=8.9, 2.5 Hz, 1H), 5.22 (s, 2H), 4.09 (s, 2H), 3.97 (d, J=6.4 Hz, 2H), 3.89 (ddd, J=11.3, 4.4, 1.9 Hz, 2H), 2.13-1.99 (m, 1H), 1.72 (ddd, J=12.7, 4.4, 2.1 Hz, 2H), 1.44-1.32 (m, 2H); MS (APCI⁻) m/z 499 [M–H]⁻.

Example 174B: 5-{-fluoro-3-hydroxy-7-[(oxan-4-yl)methoxy]naphthalen-2-yl}-1λ$^6$,2,5-thiadiazolidine-1,1,3-trione Example 174A (57 mg, 0.114 mmol) and pentamethylbenzene (33.8 mg, 0.228 mmol) in a 250 mL round bottom flask was flushed with nitrogen for 5 minutes. Dichloromethane (5 mL) was then added and the heterogeneous suspension was cooled to −78° C. and equilibrated for 5 minutes. Subsequently, a 1 M solution of boron trichloride (0.456 mL, 0.456 mmol) in dichloromethane was added dropwise over 5 minutes. After stirring for 30 minutes, the reaction was quenched at −78° C. with ethyl acetate (20 mL) followed by methanol (4 mL), then slowly warmed to ambient temperature over 20 minutes under nitrogen. The volatiles were removed under reduced pressure to give a solid. Heptanes (5 mL) were added, the slurry was filtered using fritted funnel, and the collected solid was further washed with heptanes (5 mL) to afford the titled compound (25 mg, 0.061 mmol, 54% yield). $^1$H NMR (400 MHz, DMSO-d$_6$) δ ppm 10.15 (s, 1H), 7.70 (d, J=8.8 Hz, 1H), 7.22-7.15 (m, 2H), 7.06 (s, 1H), 4.41 (s, 2H), 3.98-3.84 (m, 4H), 3.42-3.26 (m, 2H), 2.09-2.01 (m, 1H), 1.76-1.67 (m, 2H), 1.37 (qd, J=12.1, 4.4 Hz, 2H); MS (APCI⁻) m/z 409 [M–H]⁻.

Example 175: 5-{1-fluoro-3-hydroxy-7-[(oxetan-3-yl)oxy]naphthalen-2-yl}-1λ$^6$,2,5-thiadiazolidine-1,1,3-trione (Compound 274)

To a suspension of the product of Example 1H (0.100 g, 0.249 mmol) and cesium carbonate (0.324 g, 746 mmol) in dimethylformamide (1 mL) was added oxetan-3-yl-4-methylbenzenesulfonate (0.113 g, 0.497 mmol) and the resulting mixture was heated to 60° C. After 2 hours, the reaction mixture was cooled to ambient temperature, quenched with 1 M hydrochloric acid (2 mL) and diluted with ethyl acetate (2 mL). The aqueous layer was extracted with ethyl acetate (2×2 mL). The organic layers were combined and washed with saturated aqueous ammonium chloride (4×1 mL) followed by a 4:1 mixture of brine and 1 M hydrochloric acid, dried over anhydrous sodium sulfate, then filtered and concentrated under reduced pressure to give 5-{3-(benzyloxy)-1-fluoro-7-[(oxetan-3-yl)oxy]naphthalen-2-yl}-1λ$^6$,2,5-thiadiazolidine-1,1,3-trione, which was used without purification for the next reaction. MS (ESI⁻) m/z 457 [M–H]⁻.

To a solution of the crude 5-{3-(benzyloxy)-1-fluoro-7-[(oxetan-3-yl)oxy]naphthalen-2-yl}-1λ$^6$,2,5-thiadiazolidine-1,1,3-trione (0.114 g, 0.249 mmol) in tetrahydrofuran (5 mL) in a 20 mL Barnstead STEM RS10 pressure reactor was added wet 5% palladium on carbon (0.2 g, 0.044 mmol). The reactor was purged with nitrogen, then filled with hydrogen gas (50 psi) and stirred for 1.4 hours at 25° C. The reactor was vented and purged with nitrogen, and the crude reaction mixture was filtered, and the solid washed with methanol (3×5 mL). The filtrate was concentrated to give a solid, which was then dissolved in a dimethyl sulfoxide/methanol mixture and was filtered through a glass microfiber frit. The resulting solution was directly purified by preparative HPLC [Waters XBridge™ C18 5 μm OBD column, 30×100 mm, flow rate 40 mL/minute, a gradient of 5-45% methanol in buffer (0.025 M aqueous ammonium bicarbonate, adjusted to pH 10 with ammonium hydroxide)] to give the title compound as an ammonium salt (0.0281 g, 0.073 mmol, 29.3% yield). $^1$H NMR (501 MHz, DMSO-d$_6$) δ ppm 7.71 (dd, J=9.0, 1.4 Hz, 1H), 7.14 (dd, J=9.0, 2.5 Hz, 1H), 7.04 (d, J=1.3 Hz, 1H), 6.86 (d, J=2.6 Hz, 1H), 5.46-5.38 (m, 1H), 4.99 (br t, J=7.9 Hz, 2H), 4.59 (br dd, J=7.7, 4.9 Hz, 2H), 4.08 (s, 2H); MS (ESI⁻) m/z 367 [M–H]⁻.

Example 176: 5-{1-fluoro-3-hydroxy-7-[1-(2,2,2-trifluoroethyl)-1,2,3,6-tetrahydropyridin-4-yl]naphthalen-2-yl}-1λ⁶,2,5-thiadiazolidine-1,1,3-trione (Compound 275)

Example 176A: tert-butyl 4-(6-(benzyloxy)-7-(1,1-dioxido-4-oxo-1,2,5-thiadiazolidin-2-yl)-8-fluoronaphthalen-2-yl)-3,6-dihydropyridine-1(2H)-carboxylate To the product of Example 1G (400 mg, 0.860 mmol) in 1,4-dioxane (5 mL) was added tert-butyl 4-(4,4,5,5-tetramethyl-1,3,2-dioxaborolan-2-yl)-5,6-dihydropyridine-1(2H)-carboxylate (399 mg, 1.290 mmol) and sodium carbonate (1.290 mL, 2.58 mmol). Tetrakis(triphenylphosphine)palladium(0) (99 mg, 0.086 mmol) was added, and the reaction mixture was bubbled with $N_2$ for 5 minutes. The mixture was heated at 90° C. overnight. The reaction was cooled down to ambient temperature and the volatiles were removed under reduced pressure. The residue was subjected to column chromatography ($SiO_2$, dry load, 5% methanol in dichloromethane) to afford the title compound (304 mg, 0.536 mmol, 62% yield). $^1$H NMR (400 MHz, DMSO-$d_6$) δ ppm 7.88-7.70 (m, 3H), 7.59-7.55 (m, 2H), 7.40-7.28 (m, 4H), 6.36 (s, 1H), 5.26 (s, 2H), 4.11 (s, 2H), 4.08-4.03 (m, 2H), 3.59 (t, J=5.7 Hz, 2H), 2.63-2.54 (m, 2H), 1.44 (s, 9H); MS (APCI⁻) m/z 566 [M−H]⁻.

Example 176B: 5-{-fluoro-3-hydroxy-7-[1-(2,2,2-trifluoroethyl)-1,2,3,6-tetrahydropyridin-4-yl]naphthalen-2-yl}-1λ⁶,2,5-thiadiazolidine-1,1,3-trione To a solution of product of Example 176A (200 mg, 0.352 mmol) in dichloromethane (2 mL) was added trifluoroacetic acid (2 mL). The resulting solution was stirred at ambient temperature for 30 minutes. The volatiles were removed under reduced pressure, methylene chloride (5 mL) was added and the volatiles were removed under reduced pressure (twice). The residue was subjected to the next reaction without purification. MS (APCI⁺) m/z 468 [M+H]⁺.

To a solution of crude 5-[3-(benzyloxy)-1-fluoro-7-(1,2,3,6-tetrahydropyridin-4-yl)naphthalen-2-yl]-1λ⁶,2,5-thiadiazolidine-1,1,3-trione in dichloromethane (2 mL) was added 2,2,2-trifluoroethyl trifluoromethanesulfonate (49.6 mg, 0.214 mmol) and N-ethyl-N-isopropylpropan-2-amine (27.6 mg, 0.214 mmol). The reaction was stirred at ambient temperature for 30 minutes. The volatiles were removed under reduced pressure, methylene chloride (5 mL) was added and the volatiles were removed under reduced pressure (twice). The residue was subjected to the next reaction without purification. MS (APCI⁻) m/z 548 [M−H]⁻.

The crude 5-{3-(benzyloxy)-1-fluoro-7-[1-(2,2,2-trifluoroethyl)-1,2,3,6-tetrahydropyridin-4-yl]naphthalen-2-yl}-1λ⁶,2,5-thiadiazolidine-1,1,3-trione and 1,2,3,4,5-pentamethylbenzene (81 mg, 0.546 mmol) in a 50 mL round bottom flask was flushed with nitrogen for 5 minutes. Dichloromethane (2 mL) was then added and the heterogeneous suspension was cooled to −78° C. and equilibrated for 5 minutes. Subsequently, a 1 M solution of trichloroborane (64.0 mg, 0.546 mmol) in dichloromethane was added dropwise over 5 minutes. Consequently, the reaction was quenched at −78° C. with ethyl acetate (0.9 mL) and ethanol (0.1 mL) and then slowly warmed to ambient temperature. The volatiles were removed under reduced pressure and the residue was subjected to preparative HPLC [Phenomenex® Luna® $C_{18}$(2) 5 μm 100 Å AXIA™ column (250 mm×25 mm). 30-100% gradient of acetonitrile (A) and 0.1% ammonium acetate in water (B) over 15 minutes, at a flow rate of 25 mL/minute] to afford the title compound (4 mg, 8.71 μmol, 4.78% yield over three steps). $^1$H NMR (501 MHz, DMSO-$d_6$) δ ppm 10.22 (s, 1H), 7.80 (d, J=1.8 Hz, 1H), 7.75-7.66 (m, 2H), 7.07 (s, 1H), 6.33 (t, J=3.7 Hz, 1H), 4.28 (s, 2H), 2.96 (s, 1H), 2.62 (s, 2H), 2.54 (s, 4H); MS (APCI⁻) m/z 458 [M−H]⁻.

Example 177: 5-(1-fluoro-3,7-dihydroxynaphthalen-2-yl)-1λ⁶,2,5-thiadiazolidine-1,1,3-trione (Compound 276)

To a mixture of 5-[3-(benzyloxy)-7-(cyclopropylmethoxy)-1-fluoronaphthalen-2-yl]-1λ⁶,2,5-thiadiazolidine-1,1,3-trione (60 mg, 0.131 mmol) (the intermediate from the first step in the preparation of Example 151) and pentamethylbenzene (97 mg, 0.657 mmol) in dichloromethane (3 mL) cooled to −78° C. was added a solution of $BCl_3$ (0.789 mL, 0.789 mmol) in dichloromethane dropwise over 5 minutes. After 30 minutes, the reaction was quenched with 0.5 N HCl (2 mL), diluted with ethyl acetate, washed with brine, and dried over $Na_2SO_4$, and concentrated. The residue was triturated with dichloromethane to give the title compound (30 mg, 0.096 mmol, 73.1% yield). $^1$H NMR (501 MHz, DMSO-$d_6$) δ ppm 10.22 (s, 1H), 9.82 (s, 1H), 7.64 (d, J=8.6 Hz, 1H), 7.13-7.08 (m, 2H), 7.02 (s, 1H), 4.48 (s, 2H); MS (APCI⁻) m/z 311.3 (M−H)⁻.

Example 178: 5-[1-fluoro-3-hydroxy-7-(2-hydroxyethoxy)naphthalen-2-yl]-1λ⁶,2,5-thiadiazolidine-1,1,3-trione (Compound 277)

Example 178A: 5-{3-(benzyloxy)-7-[2-(benzyloxy)ethoxy]-1-fluoronaphthalen-2-yl}-1,2,5-thiadiazolidine-1,1,3-trione A mixture of Example 1H (121 mg, 0.3 mmol), ((2-bromoethoxy)methyl)benzene (161 mg, 0.750 mmol) and cesium carbonate (293 mg, 0.900 mmol) in N,N-dimethylformamide (1 mL) was stirred at 70° C. for 1 hour. The mixture was cooled to ambient temperature. The solution was filtered. The filtrate was purified by flash column chromatography on silica gel (10 g) eluted with dichloromethane, then dichloromethane/methanol (7:1) to give the title compound (100 mg, 0.186 mmol, 62.1% yield). MS (ESI⁻) m/z 535 (M−H)⁻.

Example 178B: 5-[1-fluoro-3-hydroxy-7-(2-hydroxyethoxy)naphthalen-2-yl]-1λ⁶,2,5-thiadiazolidine-1,1,3-trione To Example 178A (91 mg, 0.17 mmol) and 1,2,3,4,5-pentamethylbenzene (76 mg, 0.510 mmol) in dichloromethane (3 mL) at −78° C. was added trichloroborane (1.36 mL, 1.36 mmol, 1 M in dichloromethane). The mixture was stirred at −78° C. for 5 minutes and then at 0° C. for 15 minutes before being quenched with ethanol (3 mL). The mixture was stirred at ambient temperature for 5 minutes and then concentrated. The resulting solid was washed with heptane (3×5 mL), dichloromethane (4×5 mL), 2% methanol in dichloromethane (2×5 mL) and concentrated to give the title compound (45 mg, 0.126 mmol, 74.3% yield). $^1$H NMR (400 MHz, DMSO-$d_6$) δ ppm 10.31 (br s, 1H), 7.71 (d, J=8 Hz, 1H), 7.20 (d, J=2 Hz, 1H), 7.18 (dd, J=8, 2 Hz, 1H), 7.09 (s, 1H), 4.46 (s, 2H), 4.09 (t, J=8 Hz, 2H), 3.77 (m, 2H); MS (ESI⁻) m/z 355 (M−H)⁻.

Example 179: 5-(1-fluoro-3-hydroxy-7-propoxynaphthalen-2-yl)-1λ$^6$,2,5-thiadiazolidine-1,1,3-trione (Compound 278)

The title compound was prepared from Example 1H and 1-bromopropane using the methods described for Example 30 in 35.8% overall yield. $^1$H NMR (501 MHz, DMSO-d$_6$) δ ppm 10.18 (s, 1H), 7.73-7.67 (m, 1H), 7.18 (d, J=8.1 Hz, 2H), 7.06 (s, 1H), 4.43 (s, 2H), 4.03 (t, J=6.5 Hz, 2H), 1.78 (h, J=7.1 Hz, 2H), 1.01 (t, J=7.4 Hz, 3H); MS (APCI$^-$) m/z 352.8 (M–H)$^-$.

Example 180: 5-{1-fluoro-3-hydroxy-7-[(propan-2-yl)oxy]naphthalen-2-yl}-1λ$^6$,2,5-thiadiazolidine-1,1,3-trione (Compound 279)

The title compound was prepared from Example 1H and 2-iodopropane using the methods described for Example 30. $^1$H NMR (501 MHz, DMSO-d$_6$) δ ppm 10.27 (s, 1H), 7.70 (dd, J=9.0, 1.4 Hz, 1H), 7.20 (d, J=2.6 Hz, 1H), 7.16 (dd, J=9.0, 2.5 Hz, 1H), 7.06 (s, 1H), 4.75 (p, J=6.0 Hz, 1H), 4.47 (s, 2H), 1.32 (d, J=6.0 Hz, 6H); MS (APCI$^-$) m/z 352.9 (M–H)$^-$.

Example 181: {[8-fluoro-6-hydroxy-7-(1,1,4-trioxo-1λ$^6$,2,5-thiadiazolidin-2-yl)naphthalen-2-yl]amino}acetic acid (Compound 280)

In a 20 mL pressure release vial, glycine tert-butyl ester hydrochloride (0.144 g, 0.860 mmol), the product of Example 1G (0.2 g, 0.430 mmol), sodium tert-butoxide (0.207 g, 2.15 mmol), methanesulfonato(2-dicyclohexylphosphino-3,6-dimethoxy-2',4',6'-tri-i-propyl-1,1'-biphenyl)(2'-amino-1,1'-biphenyl-2-yl)palladium(II) (BrettPhos Pd G3 precatalyst, 12 mg, 13 μmol), and 2-(dicyclohexylphosphino)3,6-dimethoxy-2',4',6'-triisopropyl-1,1'-biphenyl (BrettPhos, 7 mg, 13 μmol) were combined. The solids were placed under vacuum for 5 minutes with stirring, then the vial was filled with nitrogen followed by 1,4-dioxane (4 mL). The resulting suspension was degassed by five vacuum/nitrogen backfills, stirred for 10 minutes at ambient temperature, and then was heated to 100° C. After 30 minutes at 100° C., the reaction mixture was cooled to ambient temperature, then quenched with 1 M hydrochloric acid (4 mL) and diluted with ethyl acetate (4 mL). The aqueous layer was extracted with ethyl acetate (2×2 mL). The combined organic layers were washed with a 4:1 mixture of brine and 1 M hydrochloric acid (1 mL), dried over anhydrous sodium sulfate, then filtered and concentrated under reduced pressure to give tert-butyl {[6-(benzyloxy)-8-fluoro-7-(1,1,4-trioxo-1λ$^6$,2,5-thiadiazolidin-2-yl)naphthalen-2-yl]amino}acetate, which was used for the next reaction without purification. MS (APCI$^-$) m/z 514 [M–H]$^-$.

To a suspension of the crude tert-butyl {[6-(benzyloxy)-8-fluoro-7-(1,1,4-trioxo-1λ$^6$,2,5-thiadiazolidin-2-yl)naphthalen-2-yl]amino}acetate (0.222 g, 0.43 mmol) and pentamethylbenzene (0.127 g, 0.860 mmol) in dichloromethane (4.4 mL) at −78° C. was added a solution of boron trichloride in dichloromethane (2.58 mL, 1 M, 2.58 mmol) slowly along the side of the flask so that the internal temperature remained below −70° C. The resulting solution was stirred for 5 minutes at −78° C., then the cooling bath was removed, and the reaction mixture was allowed to warm to an internal temperature of 0° C. before cooling back to −78° C. The reaction was quenched by addition of ethyl acetate (2 mL), followed by water (2 mL), warmed to ambient temperature and concentrated under reduced pressure to give a solid. The crude solid was triturated with heptanes (3×4 mL), ethyl acetate (2×2 mL), and then water (2×2 mL) to give the title compound (0.0388 g, 0.105 mmol, 24.4% yield). $^1$H NMR (400 MHz, DMSO-d$_6$) δ ppm 9.98 (br s, 1H), 7.52 (d, J=8.9 Hz, 1H), 7.09 (dd, J=8.9, 2.3 Hz, 1H), 6.94 (s, 1H), 6.59 (d, J=2.3 Hz, 1H), 4.47 (s, 2H), 3.89 (s, 2H); MS (ESI$^-$) m/z 368 [M–H]$^-$.

Example 182: N-(2-cyclopropylethyl)-2-{[8-fluoro-6-hydroxy-7-(1,1,4-trioxo-1λ$^6$,2,5-thiadiazolidin-2-yl)naphthalen-2-yl]oxy}acetamide (Compound 281)

To a suspension of the product of Example 1H (0.200 g, 0.477 mmol) and cesium carbonate (0.466 g, 1.431 mmol) in dimethylformamide (2 mL) was added tert-butyl bromoacetate (0.155 mL, 1.05 mmol) and the resulting mixture was heated to 60° C. After 2 hours, the reaction mixture was cooled to ambient temperature, quenched with 1 M hydrochloric acid (2 mL) and diluted with ethyl acetate (2 mL). The aqueous layer was extracted with ethyl acetate (2×2 mL). The organic layers were combined and washed with saturated aqueous ammonium chloride (4×1 mL) followed by a 4:1 mixture of brine and 1 M hydrochloric acid, dried over anhydrous sodium sulfate, then filtered and concentrated under reduced pressure to give tert-butyl {[6-(benzyloxy)-8-fluoro-7-(1,1,4-trioxo-1λ$^6$,2,5-thiadiazolidin-2-yl)naphthalen-2-yl]oxy}acetate, which was used without purification for the next reaction. MS (ESI$^-$) m/z 515 [M–H]$^-$.

To a solution of the crude tert-butyl {[6-(benzyloxy)-8-fluoro-7-(1,1,4-trioxo-1λ$^6$,2,5-thiadiazolidin-2-yl)naphthalen-2-yl]oxy}acetate (0.246 g, 0.476 mmol) and pentamethylbenzene (0.141 g, 0.952 mmol) in dichloromethane (5 mL) at −78° C. was added a solution of boron trichloride in dichloromethane (2.86 mL, 1 M, 2.86 mmol) slowly along the side of the flask so that the internal temperature remained below −70° C. The resulting solution was stirred for 5 minutes at −78° C., then the cooling bath was removed, and the reaction mixture was allowed to warm to an internal temperature of 0° C. before cooling back to −78° C. The reaction was quenched by addition of ethyl acetate (2 mL), followed by anhydrous ethanol (2 mL), warmed to ambient temperature and concentrated under reduced pressure to give a solid. The crude solid was triturated with heptanes (3×3 mL) to give ethyl {[8-fluoro-6-hydroxy-7-(1,1,4-trioxo-1λ$^6$,2,5-thiadiazolidin-2-yl)naphthalen-2-yl]oxy}acetate, which was used for the next reaction without purification. MS (ESI$^-$) m/z 397 [M–H]$^-$.

To a solution of the crude ethyl {[8-fluoro-6-hydroxy-7-(1,1,4-trioxo-1λ$^6$,2,5-thiadiazolidin-2-yl)naphthalen-2-yl]oxy}acetate (0.190 g, 0.476 mmol) in a mixture of tetrahydrofuran (1.9 mL) and methanol (1.9 mL), was added 1 M aqueous sodium hydroxide (1.9 mL, 1.9 mmol). After 5 minutes the reaction mixture was concentrated under reduced pressure to give a residue that was dissolved in dimethylformamide and acidified with a solution of hydrogen chloride in 1,4-dioxane (0.476 mL, 4 M, 1.0 mmol). The solution was partially concentrated under reduced pressure to give a stock solution of 2-[7-(carboxymethoxy)-1-fluoro-3-hydroxynaphthalen-2-yl]-4-oxo-1λ$^4$,2,5-thiadiazolidine-1,1-bis(olate) in dimethylformamide, which was assumed to be 0.053 M based on a theoretical 100% yield. MS (APCI$^-$) m/z 369 [M–H].

To a solution of 2-[7-(carboxymethoxy)-1-fluoro-3-hydroxynaphthalen-2-yl]-4-oxo-1λ$^4$,2,5-thiadiazolidine-1,1-bis(olate) in dimethylformamide (3 mL, 0.053 M, 0.159 mmol) was added (1-[bis(dimethylamino)methylene]-1H-1, 2,3-triazolo[4,5-b]pyridinium 3-oxid hexafluorophosphate) (0.085 g, 0.223 mmol) and diethylamine (0.020 mL, 0.191 mmol), followed by N,N-diisopropylethylamine (0.111 mL, 0.636 mmol). After 5 minutes, the reaction mixture was quenched with 1 M hydrochloric acid (3 mL) and diluted with ethyl acetate (3 mL). The aqueous layer was extracted with ethyl acetate (2×2 mL). The organic layers were combined, washed with a 4:1 mixture of brine and 1 M hydrochloric acid (1 mL), dried over anhydrous sodium sulfate, then filtered and concentrated under reduced pressure. The crude product was then dissolved in a dimethyl sulfoxide/methanol mixture and was filtered through a glass microfiber frit. The resulting solution was directly purified by preparative HPLC [Waters XBridge™ C18 5 μm OBD column, 30×100 mm, flow rate 40 mL/minute, a gradient of 5-45% acetonitrile in buffer (0.025 M aqueous ammonium bicarbonate, adjusted to pH 10 with ammonium hydroxide)] to give the title compound as an ammonium salt (0.0224 g, 0.049 mmol, 31% yield). $^1$H NMR (500 MHz, DMSO-$d_6$) δ ppm 10.02 (s, 1H), 8.16 (t, J=5.8 Hz, 1H), 7.72 (dd, J=9.2, 1.4 Hz, 1H), 7.25 (dd, J=9.0, 2.6 Hz, 1H), 7.18 (d, J=2.6 Hz, 1H), 7.06 (s, 1H), 4.57 (s, 2H), 4.30 (s, 2H), 3.21 (dt, J=7.6, 6.0 Hz, 2H), 1.34 (q, J=7.1 Hz, 2H), 0.72-0.60 (m, 1H), 0.41-0.32 (m, 2H), 0.07-0.08 (m, 2H); MS (ESI$^-$) m/z 436 [M−H]$^-$.

Example 183: N,N-diethyl-2-{[8-fluoro-6-hydroxy-7-(1,1,4-trioxo-1$\lambda^6$,2,5-thiadiazolidin-2-yl)naphthalen-2-yl]oxy}acetamide (Compound 282)

To a solution of {[8-fluoro-6-hydroxy-7-(1,1,4-trioxo-1$\lambda^6$,2,5-thiadiazolidin-2-yl)naphthalen-2-yl]oxy}acetic acid in dimethylformamide (3 mL, 0.053 M, 0.159 mmol) from Example 182 was added (1-[bis(dimethylamino)methylene]-1H-1,2,3-triazolo[4,5-b]pyridinium 3-oxid hexafluorophosphate) (0.085 g, 0.223 mmol) and diethylamine (0.020 mL, 0.191 mmol), followed by N,N-diisopropylethylamine (0.111 mL, 0.636 mmol). After 5 minutes, the reaction mixture was quenched with 1 M hydrochloric acid (3 mL) and diluted with ethyl acetate (3 mL). The aqueous layer was extracted with ethyl acetate (2×2 mL). The organic layers were combined, washed with a 4:1 mixture of brine and 1 M hydrochloric acid (1 mL), dried over anhydrous sodium sulfate, then filtered and concentrated. The crude product was then dissolved in a dimethyl sulfoxide/methanol mixture and was filtered through a glass microfiber frit. The resulting solution was directly purified by preparative HPLC [Waters XBridge™ C18 5 μm OBD column, 30×100 mm, flow rate 40 mL/minute, a gradient of 5-45% acetonitrile in buffer (0.025 M aqueous ammonium bicarbonate, adjusted to pH 10 with ammonium hydroxide)] to give the title compound as an ammonium salt (0.0123 g, 0.028 mmol, 17.5% yield). $^1$H NMR (500 MHz, DMSO-$d_6$) δ ppm 7.67 (dd, J=9.1, 1.4 Hz, 1H), 7.16 (dd, J=9.0, 2.6 Hz, 1H), 7.12 (d, J=2.6 Hz, 1H), 7.02 (s, 1H), 4.87 (s, 2H), 4.08 (s, 2H), 3.38 (q, J=7.1 Hz, 2H), 3.30 (q, J=7.1 Hz, 2H), 1.18 (t, J=7.1 Hz, 3H), 1.04 (t, J=7.1 Hz, 3H); MS (ESI$^-$) m/z 425 [M−H]$^-$.

Example 184: 5-{1-fluoro-3-hydroxy-7-[2-oxo-2-(pyrrolidin-1-yl)ethoxy]naphthalen-2-yl}-1$\lambda^6$,2,5-thiadiazolidine-1,1,3-trione (Compound 283)

To a solution of {[8-fluoro-6-hydroxy-7-(1,1,4-trioxo-1$\lambda^6$,2,5-thiadiazolidin-2-yl)naphthalen-2-yl]oxy}acetic acid in dimethylformamide (3 mL, 0.053 M, 0.159 mmol) from Example 182 was added (1-[bis(dimethylamino)methylene]-1H-1,2,3-triazolo[4,5-b]pyridinium 3-oxid hexafluorophosphate) (0.085 g, 0.223 mmol) and pyrrolidine (0.020 mL, 0.242 mmol), followed by N,N-diisopropylethylamine (0.111 mL, 0.636 mmol). After 5 minutes, the reaction mixture was quenched with 1 M hydrochloric acid (3 mL) and diluted with ethyl acetate (3 mL). The aqueous layer was extracted with ethyl acetate (2×2 mL). The organic layers were combined, washed with a 4:1 mixture of brine and 1 M hydrochloric acid (1 mL), dried over anhydrous sodium sulfate, then filtered and concentrated. The crude product was then dissolved in a dimethyl sulfoxide/methanol mixture and was filtered through a glass microfiber frit. The resulting solution was directly purified by preparative HPLC [Waters XBridge™ C18 5 μm OBD column, 30×100 mm, flow rate 40 mL/minute, a gradient of 5-45% acetonitrile in buffer (0.025 M aqueous ammonium bicarbonate, adjusted to pH 10 with ammonium hydroxide)] to give the title compound as an ammonium salt (0.0105 g, 0.024 mmol, 15.0% yield). $^1$H NMR (400 MHz, DMSO-$d_6$) δ ppm 9.46 (s, 1H), 7.67 (d, J=8.6 Hz, 1H), 7.19-7.14 (m, 2H), 7.03 (s, 1H), 4.82 (s, 2H), 4.08 (s, 2H), 3.51 (t, J=6.8 Hz, 2H), 3.36-3.32 (m, 2H), 1.91 (p, J=6.8 Hz, 2H), 1.78 (p, J=6.9 Hz, 2H); MS (ESI$^-$) m/z 422 [M−H]$^-$.

Example 185: 5-(1-fluoro-3-hydroxy-7-{[1-(methanesulfonyl)piperidin-4-yl]oxy}naphthalen-2-yl)-1$\lambda^6$,2,5-thiadiazolidine-1,1,3-trione (Compound 284)

To a solution of the product of Example 1H (0.100 g, 0.249 mmol) and 1-(methylsulfonyl)piperidin-4-ol (0.128 g, 0.715 mmol) in tetrahydrofuran (3 mL) at 0° C. was added tri-n-butylphosphine (0.194 mL, 0.787 mmol), followed by 1,1'-(azodicarbonyl)dipiperidine (0.186 g, 0.739 mmol), The resulting suspension was stirred for 30 minutes and then heated to 60° C. After 24 hours, the reaction mixture was cooled to ambient temperature and additional portions of 1-(methylsulfonyl)piperidin-4-ol (0.043 g, 0.238 mmol), tri-n-butylphosphine (0.088 mL, 0.358 mmol) and 1,1'-(azodicarbonyl)dipiperidine (0.90 g, 0.358 mmol) were added followed by resumed heating. After 3 days, the reaction mixture was cooled to ambient temperature, then diluted with a 1:1 mixture of acetonitrile and methanol (5 mL), then silica (2 g) was added and the mixture was concentrated under reduced pressure. The crude product was dry loaded onto a Teledyne Isco 12 g gold column and purified by column chromatography with a gradient of 0-12% methanol in dichloromethane to give 5-[3-(benzyloxy)-1-fluoro-7-{[1-(methanesulfonyl)piperidin-4-yl]oxy}naphthalen-2-yl]-1$\lambda^6$,2,5-thiadiazolidine-1,1,3-trione (0.0472 g, 0.084 mmol, 33.7% yield). MS (ESI$^-$) m/z 562 [M−H]$^-$.

To a suspension of 5-[3-(benzyloxy)-1-fluoro-7-{[1-(methanesulfonyl)piperidin-4-yl]oxy}naphthalen-2-yl]-1$\lambda^6$,2,5-thiadiazolidine-1,1,3-trione (0.0472 g, 0.084 mmol) and pentamethylbenzene (0.025 g, 0.167 mmol) in dichloromethane (2.3 mL) at −78° C. was added a solution of boron trichloride in dichloromethane (0.840 mL, 1 M, 0.840 mmol) slowly along the side of the flask so that the internal temperature remained below −70° C. The resulting solution was stirred for 5 minutes at −78° C., then the cooling bath was removed, and the reaction mixture was allowed to warm to an internal temperature of 0° C. before cooling back to −78° C. The reaction was quenched by addition of ethyl acetate (1 mL), followed by anhydrous ethanol (1 mL), warmed to ambient temperature and concentrated under reduced pressure to give a solid.

The crude solid was triturated with heptanes (3×3 mL), then dissolved in a dimethyl sulfoxide/methanol mixture and filtered through a glass microfiber frit. The resulting solution was directly purified by preparative HPLC [Waters XBridge™ C18 5 μm OBD column, 30×100 mm, flow rate 40 mL/minute, a gradient of 5-20% methanol in buffer (0.025 M aqueous ammonium bicarbonate, adjusted to pH 10 with ammonium hydroxide)] to give the title compound as an ammonium salt (0.0111 g, 0.0226 mmol, 27.1% yield). $^1$H NMR (400 MHz, DMSO-$d_6$) δ ppm 7.66 (d, J=9.0 Hz, 1H), 7.26 (d, J=2.5 Hz, 1H), 7.17 (dd, J=9.0, 2.5 Hz, 1H), 7.02 (s, 1H), 4.68 (p, J=3.8 Hz, 1H), 4.11 (s, 2H), 3.34 (dd, J=7.4, 3.9 Hz, 2H), 3.13 (ddd, J=11.9, 8.1, 3.6 Hz, 2H), 2.87 (s, 3H), 2.09-1.99 (m, 2H), 1.82-1.69 (m, 2H); MS (ESI$^-$) m/z 472 [M−H]$^-$.

Example 186: 5-{1-fluoro-3-hydroxy-7-[1-(oxolane-3-sulfonyl)-2,5-dihydro-1H-pyrrol-3-yl]naphthalen-2-yl}-1λ$^6$,2,5-thiadiazolidine-1,1,3-trione (Compound 285)

The product of Example 166 (44 mg, 0.12 mmol, 1.0 equivalent) was dissolved in N,N-dimethylformamide (1 mL), and neat diisopropylethylamine (63 uL, 0.36 mmol, 3.0 equivalents) was added. Tetrahydrofuran-3-sulfonyl chloride (0.4 M in tetrahydrofuran, 363 μL, 0.15 mmol, 1.2 equivalents) was added and the reaction mixture was stirred overnight at room temperature. The reaction mixture was concentrated, and the residue was purified by reverse-phase preparative HPLC on a Waters XBridge™ C8 5 μm column (75 mm×30 mm). A gradient of methanol (A) and 25 mM ammonium bicarbonate buffer (pH 10) in water (B) was used, at a flow rate of 40 mL/minute (0-0.5 minutes 15% A, 0.5-8.0 minutes linear gradient 15-100% A, 8.0-9.0 minutes 100% A, 9.0-9.1 minutes linear gradient 100-15% A, 9.1-10.0 minutes 15% A) to yield the title compound (4.2 mg, 0.008 mmol, 7% yield). $^1$H NMR (501 MHz, DMSO-$d_6$) δ ppm 7.75 (s, 1H), 7.72 (s, 1H), 7.08 (s, 2H), 6.58-6.50 (m, 1H), 4.67 (td, J=4.6, 1.9 Hz, 2H), 4.38 (dt, J=6.4, 2.9 Hz, 2H), 4.26 (qd, J=7.8, 5.8 Hz, 1H), 4.09 (s, 2H), 4.02-3.92 (m, 2H), 3.85 (dt, J=8.4, 6.6 Hz, 1H), 3.69 (dt, J=8.4, 7.0 Hz, 1H), 2.24 (q, J=7.0 Hz, 2H); MS (ESI$^+$) m/z 498 [M+H]$^+$.

Example 187: 5-{1-fluoro-3-hydroxy-7-[1-(2-methoxyethanesulfonyl)-2,5-dihydro-1H-pyrrol-3-yl]naphthalen-2-yl}-1λ$^6$,2,5-thiadiazolidine-1,1,3-trione (Compound 286)

The title compound was prepared using the procedure described in Example 186 substituting 2-methoxyethane-1-sulfonyl chloride for tetrahydrofuran-3-sulfonyl chloride. $^1$H NMR (501 MHz, DMSO-$d_6$) δ ppm 7.74 (s, 2H), 7.70 (s, 1H), 7.08 (s, 1H), 6.49 (t, J=2.1 Hz, 1H), 4.65-4.59 (m, 2H), 4.33 (dd, J=5.3, 2.6 Hz, 2H), 4.09 (s, 2H), 3.71 (t, J=5.9 Hz, 2H), 3.50 (t, J=5.9 Hz, 2H), 3.23 (s, 3H); MS (ESI$^+$) m/z 486 [M+H]$^+$.

Example 188: 5-{1-fluoro-3-hydroxy-7-[1-(3,3,3-trifluoropropane-1-sulfonyl)-2,5-dihydro-1H-pyrrol-3-yl]naphthalen-2-yl}-1λ$^6$,2,5-thiadiazolidine-1,1,3-trione (Compound 287)

The title compound was prepared using the procedure described in Example 186 substituting 3,3,3-trifluoropropane-1-sulfonyl chloride for tetrahydrofuran-3-sulfonyl chloride. $^1$H NMR (501 MHz, DMSO-$d_6$) δ ppm 9.93 (s, 1H), 7.75 (2, 2H), 7.71 (s, 1H), 6.51 (t, J=2.2 Hz, 1H), 4.70 (q, J=3.1, 1.8 Hz, 2H), 4.41-4.38 (m, 2H), 4.10 (s, 2H), 3.55-3.48 (m, 2H), 2.82-2.68 (m, 2H); MS (ESI$^+$) m/z 541 [M+NH$_4$]$^+$.

Example 189: 5-{1-fluoro-3-hydroxy-7-[1-(3,3,3-trifluoropropane-1-sulfonyl)-2,5-dihydro-1H-pyrrol-3-yl]naphthalen-2-yl}-1λ$^6$,2,5-thiadiazolidine-1,1,3-trione (Compound 288)

The title compound was prepared using the procedure described in Example 186 substituting propane-1-sulfonyl chloride for tetrahydrofuran-3-sulfonyl chloride. $^1$H NMR (501 MHz, DMSO-$d_6$) δ ppm 9.93 (s, 1H), 7.75 (s, 2H), 7.71 (s, 1H), 6.51 (t, J=2.1 Hz, 1H), 4.63 (td, J=5.1, 4.6, 1.8 Hz, 2H), 4.33 (q, J=3.9, 3.0 Hz, 2H), 4.10 (s, 2H), 3.22-3.16 (m, 2H), 1.79-1.68 (m, 2H), 1.00 (t, J=7.4 Hz, 3H); MS (ESI$^+$) m/z 470 [M+H]$^+$.

Example 190: 5-(1-fluoro-3-hydroxy-7-{1-[(oxan-2-yl)methanesulfonyl]-2,5-dihydro-1H-pyrrol-3-yl}naphthalen-2-yl)-1λ$^6$,2,5-thiadiazolidine-1,1,3-trione (Compound 289)

The title compound was prepared using the procedure described in Example 186 substituting (tetrahydro-2H-pyran-2-yl)methanesulfonyl chloride for tetrahydrofuran-3-sulfonyl chloride. $^1$H NMR (501 MHz, DMSO-$d_6$) δ ppm 7.74 (d, J=1.2 Hz, 2H), 7.68 (s, 1H), 7.07 (d, J=1.2 Hz, 1H), 6.47 (t, J=2.1 Hz, 1H), 4.63-4.57 (m, 2H), 4.30 (q, J=2.9 Hz, 2H), 4.09 (s, 2H), 3.82-3.68 (m, 2H), 3.47 (dd, J=14.7, 8.4 Hz, 1H), 3.25 (dd, J=14.7, 3.2 Hz, 1H), 1.74 (d, J=13.1 Hz, 1H), 1.70-1.63 (m, 1H), 1.55-1.44 (m, 1H), 1.43-1.37 (m, 2H), 1.31-1.23 (m, 2H); MS (ESI$^+$) m/z 526 [M+H]$^+$.

Example 191: 5-{1-fluoro-3-hydroxy-7-[1-(4,4,4-trifluorobutane-1-sulfonyl)-2,5-dihydro-1H-pyrrol-3-yl]naphthalen-2-yl}-1λ$^6$,2,5-thiadiazolidine-1,1,3-trione (Compound 290)

The title compound was prepared using the procedure described in Example 186 substituting 4,4,4-trifluorobutane-1-sulfonyl chloride for tetrahydrofuran-3-sulfonyl chloride. $^1$H NMR (501 MHz, DMSO-$d_6$) δ ppm 9.93 (s, 1H), 7.75 (s, 2H), 7.71 (s, 1H), 6.52 (t, J=2.1 Hz, 1H), 4.67-4.61 (m, 2H), 4.35 (dd, J=4.8, 2.6 Hz, 2H), 4.09 (s, 2H), 2.48-2.37 (m, 2H), 1.98-1.88 (m, 2H); MS (ESI$^+$) m/z 538 [M+H]$^+$.

Example 192: 5-{7-[1-(butane-1-sulfonyl)-2,5-dihydro-1H-pyrrol-3-yl]-1-fluoro-3-hydroxynaphthalen-2-yl}-1λ$^6$,2,5-thiadiazolidine-1,1,3-trione (Compound 291)

The title compound was prepared using the procedure described in Example 186 substituting butane-1-sulfonyl chloride for tetrahydrofuran-3-sulfonyl chloride. $^1$H NMR (501 MHz, DMSO-$d_6$) δ ppm 9.93 (s, 1H), 7.75 (d, J=1.5 Hz, 2H), 7.71 (s, 1H), 7.08 (s, 1H), 6.51 (t, J=2.1 Hz, 1H), 4.66-4.60 (m, 2H), 4.35-4.31 (m, 2H), 4.09 (s, 2H), 3.24-3.17 (m, 2H), 1.69 (tt, J=7.8, 6.4 Hz, 2H), 1.41 (h, J=7.3 Hz, 2H), 1.25 (d, J=7.2 Hz, 1H), 0.90 (t, J=7.4 Hz, 3H); MS (ESI$^+$) m/z 484 [M+H]$^+$.

Example 193: 5-(7-{1-[(1,4-dioxan-2-yl)methanesulfonyl]-2,5-dihydro-1H-pyrrol-3-yl}-1-fluoro-3-hydroxynaphthalen-2-yl)-1λ$^6$,2,5-thiadiazolidine-1,1,3-trione (Compound 292)

The title compound was prepared using the procedure described in Example 186 substituting (1,4-dioxan-2-yl)

methanesulfonyl chloride for tetrahydrofuran-3-sulfonyl chloride. $^1$H NMR (501 MHz, DMSO-$d_6$) δ ppm 7.74 (s, 2H), 7.70 (s, 1H), 7.07 (s, 2H), 6.48 (t, J=2.1 Hz, 1H), 4.65-4.60 (m, 2H), 4.33 (q, J=5.9, 5.1 Hz, 2H), 4.09 (s, 2H), 3.97 (t, J=8.6 Hz, 1H), 3.76 (dd, J=11.5, 2.7 Hz, 1H), 3.69-3.54 (m, 3H), 3.49-3.41 (m, 2H), 3.30-3.25 (m, 2H); MS (ESI$^+$) m/z 528 [M+H]$^+$.

Example 194: 5-{3-[8-fluoro-6-hydroxy-7-(1,1,4-trioxo-1λ$^6$,2,5-thiadiazolidin-2-yl)naphthalen-2-yl]-2,5-dihydro-1H-pyrrole-1-sulfonyl}pentanenitrile (Compound 293)

The title compound was prepared using the procedure described in Example 186 substituting 4-cyanobutane-1-sulfonyl chloride for tetrahydrofuran-3-sulfonyl chloride. $^1$H NMR (501 MHz, DMSO-$d_6$) δ ppm 7.75 (s, 2H), 7.71 (s, 1H), 7.07 (s, 1H), 6.51 (t, J=2.1 Hz, 1H), 4.63 (s, 2H), 4.33 (s, 2H), 4.09 (d, J=1.8 Hz, 2H), 3.25-3.18 (m, 2H), 2.08 (t, J=7.2 Hz, 2H), 1.73-1.67 (m, 2H), 1.63-1.58 (m, 2H); MS (ESI$^+$) m/z 527 [M+NH$_4$]$^+$.

Example 195: 5-{1-fluoro-3-hydroxy-7-[1-(pentane-2-sulfonyl)-2,5-dihydro-1H-pyrrol-3-yl]naphthalen-2-yl}-1λ$^6$,2,5-thiadiazolidine-1,1,3-trione (Compound 294)

The title compound was prepared using the procedure described in Example 186 substituting pentane-2-sulfonyl chloride for tetrahydrofuran-3-sulfonyl chloride and was purified by reverse-phase preparative HPLC on a Waters XBridgem C8 5 µm column (75 mm×30 mm). A gradient of methanol (A) and 25 mM ammonium bicarbonate buffer (pH 10) in water (B) was used, at a flow rate of 40 mL/minute (0-0.5 minutes 5% A, 0.5-8.0 minutes linear gradient 5-100% A, 8.0-9.0 minutes 100% A, 9.0-9.1 minutes linear gradient 100-5% A, 9.1-10.0 minutes 5% A). $^1$H NMR (501 MHz, DMSO-$d_6$) δ ppm 7.75 (s, 2H), 7.70 (s, 1H), 7.07 (s, 2H), 6.55-6.51 (m, 1H), 4.65 (s, 1H), 4.37 (s, 2H), 4.09 (s, 2H), 1.84-1.80 (m, 1H), 1.48 (s, 1H), 1.53-1.43 (m, 2H), 1.37-1.29 (m, 2H), 1.27 (d, J=6.8 Hz, 3H), 0.90 (t, J=7.2 Hz, 3H); MS (ESI$^+$) m/z 498 [M+H]$^+$.

Example 196: 5-{7-[1-(ethanesulfonyl)-2,5-dihydro-1H-pyrrol-3-yl]-1-fluoro-3-hydroxynaphthalen-2-yl}-1λ$^6$,2,5-thiadiazolidine-1,1,3-trione (Compound 295)

The title compound was prepared using the procedure described in Example 186 substituting ethanesulfonyl chloride for tetrahydrofuran-3-sulfonyl chloride. $^1$H NMR (501 MHz, DMSO-$d_6$) δ ppm 7.75 (d, J=1.5 Hz, 2H), 7.71-7.70 (m, 1H), 7.08 (d, J=1.3 Hz, 1H), 6.51 (t, J=2.1 Hz, 1H), 4.66-4.60 (m, 2H), 4.34 (td, J=4.5, 4.1, 2.3 Hz, 2H), 4.09 (s, 2H), 3.23 (q, J=7.4 Hz, 2H), 1.25 (t, J=7.3 Hz, 3H); MS (ESI$^+$) m/z 456 [M+H]$^+$.

Example 197: 5-{1-fluoro-3-hydroxy-7-[1-(propane-2-sulfonyl)-2,5-dihydro-1H-pyrrol-3-yl]naphthalen-2-yl}-1λ$^6$,2,5-thiadiazolidine-1,1,3-trione (Compound 296)

The title compound was prepared using the procedure described in Example 186 substituting propane-2-sulfonyl chloride for tetrahydrofuran-3-sulfonyl chloride. $^1$H NMR (501 MHz, DMSO-$d_6$) δ ppm 7.75 (d, J=1.6 Hz, 2H), 7.70 (d, J=1.4 Hz, 1H), 7.08 (d, J=1.2 Hz, 1H), 6.53 (t, J=2.1 Hz, 1H), 4.66 (td, J=5.3, 4.7, 1.9 Hz, 2H), 4.38 (td, J=4.5, 4.0, 2.2 Hz, 2H), 4.09 (s, 2H), 3.61 (hept, J=6.8 Hz, 1H), 1.28 (s, 3H), 1.29 (s, 3H); MS (ESI$^+$) m/z 470 [M+H]$^+$.

Example 198: 5-{7-[1-(cyclopropanesulfonyl)-1,2,3,6-tetrahydropyridin-4-yl]-1-fluoro-3-hydroxynaphthalen-2-yl}-1λ$^6$,2,5-thiadiazolidine-1,1,3-trione (Compound 297)

To a solution of product of Example 176A (200 mg, 0.352 mmol) in dichloromethane (2 mL) was added trifluoroacetic acid (2 mL). The resulting reaction was stirred at ambient temperature for 30 minutes. The volatiles were removed under reduced pressure, methylene chloride (5 mL) was added and the volatiles were removed under reduced pressure (twice). The residue was subjected to the next reaction without purification. MS (APCI$^+$) m/z 468 [M+H]$^+$.

To a solution of crude 5-[3-(benzyloxy)-1-fluoro-7-(1,2,3,6-tetrahydropyridin-4-yl)naphthalen-2-yl]-1λ$^6$,2,5-thiadiazolidine-1,1,3-trione in dichloromethane (2 mL) was added cyclopropanesulfonyl chloride (45.1 mg, 0.321 mmol) and Hunig's base (0.187 mL, 1.069 mmol). The reaction was stirred at ambient temperature for 30 minutes. Volatiles were removed under reduced pressure, methylene chloride (5 mL) was added and the volatiles were removed under reduced pressure (twice). The residue was subjected to the next reaction without purification. MS (APCI$^-$) m/z 570 [M-H]$^-$.

The crude 5-{3-(benzyloxy)-7-[1-(cyclopropanesulfonyl)-1,2,3,6-tetrahydropyridin-4-yl]-1-fluoronaphthalen-2-yl}-1λ$^6$,2,5-thiadiazolidine-1,1,3-trione (100 mg, 0.175 mmol) and 1,2,3,4,5-pentamethylbenzene (78 mg, 0.525 mmol) in a 50 mL round bottom flask was flushed with nitrogen for 5 minutes. Dichloromethane (2 mL) was then added and the heterogeneous suspension was cooled to −78° C. and equilibrated for 5 minutes. Subsequently, a 1 M solution of trichloroborane (61.5 mg, 0.525 mmol) in dichloromethane was added dropwise over 5 minutes. Consequently, the reaction was quenched at −78° C. with ethyl acetate (0.9 mL) and ethanol (0.1 mL) and then slowly warmed up to ambient temperature. The volatiles were removed under reduced pressure and the residue was subjected to preparative HPLC [Phenomenex® Luna® C$_{18}$(2) 5 µm 100 Å AXIA™ column (250 mm×25 mm). 30-100% gradient of acetonitrile (A) and 0.1% ammonium acetate in water (B) over 15 minutes, at a flow rate of 25 mL/minute] to afford the title compound (7 mg, 0.015 mmol, 8% yield over three steps). $^1$H NMR (400 MHz, DMSO-$d_6$) δ ppm 7.82 (d, J=1.9 Hz, 1H), 7.72 (dd, J=8.8, 1.5 Hz, 1H), 7.70-7.59 (m, 1H), 7.06 (s, 1H), 6.41-6.34 (m, 1H), 4.09 (s, 2H), 3.98 (t, J=3.1 Hz, 2H), 3.50 (m, 2H), 2.72 (t, J=4.4 Hz, 2H), 2.71-2.62 (m, 1H), 1.05-0.95 (m, 4H); MS (APCI$^-$) m/z 480 [M-H]$^-$.

Example 199: N-(2-{[8-fluoro-6-hydroxy-7-(1,1,4-trioxo-1λ$^6$,2,5-thiadiazolidin-2-yl)naphthalen-2-yl]oxy}ethyl)oxetane-3-sulfonamide (Compound 298)

To Example 210 (40 mg, 0.113 mmol) and triethylamine (46 mg, 0.45 mmol) in N,N-dimethylformamide (1 mL) was added oxetane-3-sulfonyl chloride (19.4 mg, 0.124 mmol) in N,N-dimethylformamide (0.3 mL). The mixture was stirred for 1 hour at ambient temperature and then diluted with N,N-dimethylformamide (1 mL). The mixture was filtered through a glass microfiber frit, and the filtrate was purified by preparative HPLC [YMC TriArt™ C18 Hybrid 5 [m column, 50×100 mm, flow rate 140 mL/minute, 5-100% gradient of methanol in buffer (0.025 M aqueous ammonium bicarbonate, adjusted to pH 10 with ammonium hydroxide)] to give the title compound (15 mg, 0.032 mmol, 28% yield). $^1$H NMR (400 MHz, DMSO-$d_6$) δ ppm 9.53 (s, 1H), 7.69 (d, J=8 Hz, 1H), 7.20 (d, J=2 Hz, 1H), 7.18 (dd, J=8, 2 Hz, 1H), 7.11 (br s, 1H), 7.04 (s, 1H), 4.78 (m, 2H), 4.68 (m, 3H), 4.11 (s, 2H), 4.10 (t, J=8 Hz, 2H), 3.41 (m, 2H); MS (ESI$^-$) m/z 474 (M–H)$^-$.

Example 200: 5-[1-fluoro-3-hydroxy-7-(piperidin-4-yl)naphthalen-2-yl]-1λ$^6$,2,5-thiadiazolidine-1,1,3-trione (Compound 299)

A 250 mL-round bottom flask was filled with nitrogen, followed by addition of 5% Pd/C (50 mg, 0.470 mmol) and tetrahydrofuran (10 mL). A solution of the product of Example 176A (40 mg, 0.080 mmol) in tetrahydrofuran (2 mL), was then added. An adapter fitted with a hydrogen balloon was inserted and the flask was evacuated and refilled with hydrogen (3 times). The reaction was stirred at ambient temperature overnight. The mixture was filtered through a pad of diatomaceous earth under nitrogen gas. The filtrate was concentrated under reduced pressure, and the residue was subjected to the next step without purification. MS (APCI$^-$) m/z 478 [M–H]$^-$.

To the solution of crude tert-butyl 4-[8-fluoro-6-hydroxy-7-(1,1,4-trioxo-1λ$^6$,2,5-thiadiazolidin-2-yl)naphthalen-2-yl]piperidine-1-carboxylate in dichloromethane (2 mL) was added trifluoroacetic acid (2 mL). The resulting mixture was stirred at ambient temperature for 30 minutes. The volatiles were removed under reduced pressure, methylene chloride (5 mL) was added and the volatiles were removed under reduced pressure (twice). The residue was then subjected to preparative HPLC [Phenomenex® Luna® C18(2) 5 μm 100 Å AXIA™ column (250 mm×25 mm). 30-100% gradient of acetonitrile (A) and 0.1% ammonium acetate in water (B) over 15 minutes, at a flow rate of 25 mL/minute] to afford the title compound (24 mg, 0.063 mmol, 30% yield over two steps). $^1$H NMR (501 MHz, DMSO-$d_6$) δ ppm 7.72 (d, J=8.5 Hz, 1H), 7.66 (d, J=1.7 Hz, 1H), 7.38 (dd, J=8.6, 1.8 Hz, 1H), 7.05 (s, 1H), 4.10 (s, 2H), 3.39-3.37 (m, 2H), 3.06-2.94 (m, 3H), 2.01 (dd, J=14.5, 3.6 Hz, 2H), 1.89-1.76 (m, 2H); MS (APCI$^-$) m/z 378 [M–H]$^-$.

Example 201: 5-{1-fluoro-3-hydroxy-7-[1-(2-methylpropane-1-sulfonyl)-2,5-dihydro-1H-pyrrol-3-yl]naphthalen-2-yl}-1λ$^6$,2,5-thiadiazolidine-1,1,3-trione (Compound 300)

5-[7-(2,5-Dihydro-1H-pyrrol-3-yl)-1-fluoro-3-hydroxynaphthalen-2-yl]-1λ$^6$,2,5-thiadiazolidine-1,1,3-trione (44 mg, 0.12 mmol, 1.0 equivalents, Example 166) was dissolved in N,N-dimethylformamide (1 mL), and neat diisopropylethylamine (63 μL, 0.36 mmol, 3.0 equivalents) was added. Isobutylsulfonyl chloride (0.4 M in tetrahydrofuran, 363 μL, 0.15 mmol, 1.2 equivalents) was added and the reaction was stirred overnight at ambient temperature. The reaction was purified by reverse-phase preparative HPLC on a Phenomenex® Luna® C8(2) 5 μm 100 Å AXIA™ column (50 mm×30 mm). A gradient of acetonitrile (A) and 0.1% ammonium acetate in water (B) was used, at a flow rate of 40 mL/minute (0-0.5 minutes 5% A, 0.5-8.0 minutes linear gradient 5-100% A, 8.0-9.0 minutes 100% A, 9.0-9.1 minutes linear gradient 100-5% A, 9.1-10.0 minutes 5% A). Following purification, a number of impurities were present, and the residue was redissolved in dimethyl sulfoxide/methanol and reverse-phase preparative HPLC on a Waters XBridge™ C8 5 μm column (75 mm×30 mm). A gradient of methanol (A) and 25 mM ammonium bicarbonate buffer (pH 10) in water (B) was used, at a flow rate of 40 mL/minute (0-0.5 minutes 5% A, 0.5-8.0 minutes linear gradient 5-100% A, 8.0-9.0 minutes 100% A, 9.0-9.1 minutes linear gradient 100-5% A, 9.1-10.0 minutes 5% A) to afford the title compound (4.0 mg, 7% yield). $^1$H NMR (400 MHz, DMSO-$d_6$) δ ppm 7.77-7.67 (m, 3H), 7.09 (s, 1H), 6.50-6.43 (m, 1H), 4.64-4.54 (m, 2H), 4.37-4.29 (m, 2H), 4.13 (s, 3H), 3.06 (d, J=6.6 Hz, 2H), 2.19-2.05 (m, 1H), 1.04 (d, J=6.7 Hz, 6H); MS (ESI$^+$) m/z 484.3 (M+H)$^+$.

Example 202: 5-(7-ethoxy-1-fluoro-3-hydroxynaphthalen-2-yl)-1λ$^6$,2,5-thiadiazolidine-1,1,3-trione (Compound 301)

The title compound was prepared from Example 1H and bromoethane in 79% yield (combined yield for 2 steps) using the methods described for Example 12. $^1$H NMR (400 MHz, DMSO-$d_6$) δ ppm 10.26 (s, 1H), 7.70 (d, J=8.8 Hz, 1H), 7.17 (d, J=8.3 Hz, 2H), 7.06 (s, 1H), 4.46 (s, 2H), 4.13 (q, J=6.9 Hz, 2H), 1.38 (t, J=6.9 Hz, 3H).

Example 203: 5-[7-(2,2-difluoroethoxy)-1-fluoro-3-hydroxynaphthalen-2-yl]-1λ$^6$,2,5-thiadiazolidine-1,1,3-trione (Compound 302)

The title compound was prepared from Example 1H and 2-bromo-1,1-difluoroethane in 84% yield (combined yield for 2 steps) using the methods described for Example 12. $^1$H NMR (400 MHz, DMSO-$d_6$) δ ppm 10.49 (s, 1H), 7.76 (d, J=9.1 Hz, 1H), 7.33 (d, J=2.6 Hz, 1H), 7.26 (dd, J=9.0, 2.6 Hz, 1H), 7.10 (s, 1H), 6.44 (tt, J=54.5, 3.5 Hz, 1H), 4.52 (s, 2H), 4.45 (td, J=14.7, 3.5 Hz, 2H); MS (APCI$^-$) m/z 375.2 (M–H)$^-$.

Example 204: 5-{7-[1-(cyclopropanesulfonyl)-1H-pyrazol-4-yl]-1-fluoro-3-hydroxynaphthalen-2-yl}-1λ$^6$,2,5-thiadiazolidine-1,1,3-trione (Compound 303)

Example 204A: 5-[3-(benzyloxy)-1-fluoro-7-(H-pyrazol-4-yl)naphthalen-2-yl]-1λ$^6$,2,5-thiadiazolidine-1,1,3-trione To the product of Example 1G (120 mg, 0.258 mmol) in 1,4-dioxane (5 mL) was added tert-butyl 4-(4,4,5,5-tetramethyl-1,3,2-dioxaborolan-2-yl)-1H-pyrazole-1-carboxylate (114 mg, 0.387 mmol), and sodium carbonate (0.387 mL, 0.774 mmol). Tetrakis(triphenylphosphine)palladium(0) (29.8 mg, 0.026 mmol) was added, and the reaction mixture was bubbled with N$_2$ for 5 minutes. The mixture was heated at 90° C. for 14 hours. The reaction was cooled down to ambient temperature and the volatiles were removed under reduced pressure. The residue was subjected to column chromatography (SiO$_2$, dry load with diatomaceous earth, 5% methanol in dichloromethane) to afford the title compound (63 mg, 0.139 mmol, 54% yield). MS (APCI$^-$) m/z 451 [M–H]$^-$.

Example 204B: 5-{7-[1-(cyclopropanesulfonyl)-H-pyrazol-4-yl]-1-fluoro-3-hydroxynaphthalen-2-yl}-1λ$^6$,2,5-thiadiazolidine-1,1,3-trione To a solution of the product of Example 204A (48 mg, 0.106 mmol) in dioxane (5 mL) was added cyclopropanesulfonyl chloride (0.022 mL, 0.212 mmol) at ambient temperature followed by N-ethyl-N-isopropylpropan-2-amine (0.148 mL, 0.849 mmol). The reaction mixture was stirred overnight at ambient temperature. Water (5 mL) was added, and the reaction was extracted with ethyl acetate (2×3 mL). The combined organic layers were mixed and dried over sodium sulfate. The volatiles were removed under reduced pressure and the residue was subjected to the next step without purification. MS (APCI⁻) m/z 555 [M−H]⁻

The crude 5-{3-(benzyloxy)-7-[1-(cyclopropanesulfonyl)-1H-pyrazol-4-yl]-1-fluoronaphthalen-2-yl}-1$\lambda^6$,2,5-thiadiazolidine-1,1,3-trione (38 mg, 0.084 mmol) and 1,2,3,4,5-pentamethylbenzene (37.4 mg, 0.252 mmol) in a 50 mL round bottom flask was flushed with nitrogen for 5 minutes. Methylene chloride (5 mL) was then added and the heterogeneous suspension was cooled to −78° C. and equilibrated for 5 minutes. Subsequently, a 1 M solution of trichloroborane (0.252 mL, 0.252 mmol) in dichloromethane was added dropwise over 5 minutes. Consequently, the reaction was quenched at −78° C. with ethyl acetate (0.9 mL) and ethanol (0.1 mL) and then slowly warmed to ambient temperature. The solvents were removed under reduced pressure and the residue was subjected to preparative HPLC [Phenomenex® Luna® C18(2) 5 μm 100 Å AXIA™ column (250 mm×25 mm). 30-100% gradient of acetonitrile (A) and 0.1% ammonium acetate in water (B) over 15 minutes, at a flow rate of 25 mL/minute] to afford the title compound (18 mg, 0.039 mmol, 37% yield over two steps). $^1$H NMR (400 MHz, DMSO-d$_6$) δ ppm 8.92 (s, 1H), 8.63 (s, 1H), 8.26 (d, J=1.8 Hz, 1H), 7.89 (dd, J=8.7, 1.8 Hz, 1H), 7.79 (dd, J=8.7, 1.5 Hz, 1H), 7.08 (s, 1H), 4.11 (s, 2H), 3.21-3.12 (m, 1H), 1.37-1.17 (m, 5H); MS (APCI⁻) m/z 465 [M−H]⁻.

Example 205: 5-(1-fluoro-3-hydroxy-7-{[(3R)-1-(methanesulfonyl)pyrrolidin-3-yl]amino}naphthalen-2-yl)-1$\lambda^6$,2,5-thiadiazolidine-1,1,3-trione (Compound 304)

In a 4 mL vial, combined (3R)-1-methanesulfonylpyrrolidin-3-amine hydrochloride (0.086 g, 0.430 mmol), the product of Example 1G (0.1 g, 0.215 mmol), sodium tert-butoxide (0.124 g, 1.29 mmol), methanesulfonato(2-dicyclohexylphosphino-3,6-dimethoxy-2',4',6'-tri-i-propyl-1,1'-biphenyl)(2'-amino-1,1'-biphenyl-2-yl)palladium(II) (BrettPhos Pd G3 precatalyst, 5.8 mg, 6.5 μmol), and 2-(dicyclohexylphosphino)3,6-dimethoxy-2',4',6'-triisopropyl-1,1'-biphenyl (BrettPhos, 3.5 mg, 6.5 μmol). The solids were placed under vacuum for 5 minutes with stirring, then the vial was filled with nitrogen followed by 1,4-dioxane (2 mL). The resulting suspension was degassed by five vacuum/nitrogen backfills, stirred for 10 minutes at ambient temperature, and then was heated to 100° C. After 30 minutes at 100° C., the reaction mixture was cooled to ambient temperature, then quenched with 1 M hydrochloric acid (2 mL) and diluted with ethyl acetate (2 mL). The aqueous layer was extracted with ethyl acetate (2×2 mL). The combined organic layers were washed with a 4:1 mixture of brine and 1 M hydrochloric acid (1 mL), dried over anhydrous sodium sulfate, then filtered and concentrated under reduced pressure to give 5-[3-(benzyloxy)-1-fluoro-7-{[(3R)-1-(methanesulfonyl)pyrrolidin-3-yl]amino}naphthalen-2-yl]-1$\lambda^6$,2,5-thiadiazolidine-1,1,3-trione, which was used for the next reaction without purification. MS (APCI⁻) m/z 547 [M−H]⁻.

To a suspension of the crude 5-[3-(benzyloxy)-1-fluoro-7-{[(3R)-1-(methanesulfonyl)pyrrolidin-3-yl]amino}naphthalen-2-yl]-1$\lambda^6$,2,5-thiadiazolidine-1,1,3-trione (0.118 g, 0.215 mmol) and pentamethylbenzene (0.064 g, 0.430 mmol) in dichloromethane (2.4 mL) at −78° C. was added a solution of boron trichloride in dichloromethane (2.15 mL, 1 M, 2.15 mmol) slowly along the side of the flask so that the internal temperature remained below −70° C. The resulting solution was stirred for 5 minutes at −78° C., then the cooling bath was removed, and the reaction mixture was allowed to warm to an internal temperature of 0° C. before cooling back to −78° C. The reaction was quenched by addition of ethyl acetate (1 mL), followed by anhydrous ethanol (1 mL), warmed to ambient temperature and concentrated under reduced pressure to give a solid. The crude solid was triturated with heptanes (3×3 mL) to give a sticky solid, which was dissolved in a dimethyl sulfoxide/methanol mixture and filtered through a glass microfiber frit. The resulting solution was directly purified by preparative HPLC [Waters XBridge™ C18 5 μm OBD column, 30×100 mm, flow rate 40 mL/minute, a gradient of 4-20% methanol in buffer (0.025 M aqueous ammonium bicarbonate, adjusted to pH 10 with ammonium hydroxide)] to give the title compound as an ammonium salt (0.0208 g, 0.044 mmol, 20.4% yield). $^1$H NMR (400 MHz, DMSO-d$_6$) δ ppm 7.48 (dd, J=9.0, 1.6 Hz, 1H), 6.98 (dd, J=8.9, 2.3 Hz, 1H), 6.90 (s, 1H), 6.67 (d, J=2.4 Hz, 1H), 4.21-4.05 (m, 1H), 4.10 (s, 2H), 3.55 (dd, J=10.3, 5.7 Hz, 1H), 3.45-3.30 (m, 2H), 3.15 (dd, J=10.3, 3.7 Hz, 1H), 2.84 (s, 3H), 2.26 (dq, J=13.9, 7.5 Hz, 1H), 1.96-1.84 (m, 1H); MS (ESI⁻) m/z 457 [M−H]⁻.

Example 206: 5-(1-fluoro-3-hydroxy-7-{[1-(methanesulfonyl)piperidin-4-yl]amino}naphthalen-2-yl)-1$\lambda^6$,2,5-thiadiazolidine-1,1,3-trione (Compound 305)

In a 4 mL vial, combined 1-(methanesulfonyl)piperidin-4-amine (0.077 g, 0.430 mmol), the product of Example 1G (0.1 g, 0.215 mmol), sodium tert-butoxide (0.062 g, 0.645 mmol), methanesulfonato(2-dicyclohexylphosphino-3,6-dimethoxy-2',4',6'-tri-i-propyl-1,1'-biphenyl)(2'-amino-1,1'-biphenyl-2-yl)palladium(II) (BrettPhos Pd G3 precatalyst, 5.8 mg, 6.5 μmol), and 2-(dicyclohexylphosphino)3,6-dimethoxy-2',4',6'-triisopropyl-1,1'-biphenyl (BrettPhos, 3.5 mg, 6.5 μmol). The solids were placed under vacuum for 5 minutes with stirring, then the vial was filled with nitrogen followed by 1,4-dioxane (2 mL). The resulting suspension was degassed by five vacuum/nitrogen backfills, stirred for 10 minutes at ambient temperature, and then was heated to 100° C. After 30 minutes at 100° C., the reaction mixture was cooled to ambient temperature, then additional portions of 1-(methanesulfonyl)piperidin-4-amine (0.077 g, 0.430 mmol), sodium tert-butoxide (0.062 g, 0.645 mmol), methanesulfonato(2-dicyclohexylphosphino-3,6-dimethoxy-2',4',6'-tri-i-propyl-1,1'-biphenyl)(2'-amino-1,1'-biphenyl-2-yl)palladium(II) (BrettPhos Pd G3 precatalyst, 5.8 mg, 6.5 μmol), and 2-(dicyclohexylphosphino)3,6-dimethoxy-2',4',6'-triisopropyl-1,1'-biphenyl (BrettPhos, 3.5 mg, 6.5 μmol) were added, the reaction mixture was degassed by three vacuum/nitrogen backfills, stirred for 10 minutes at ambient temperature and then was heated to 100° C. After 30 minutes at 100° C., the reaction mixture was cooled to ambient temperature, then quenched with 1 M hydrochloric acid (2 mL) and diluted with ethyl acetate (2 mL). The aqueous layer was extracted with ethyl acetate (2×2 mL). The combined organic layers were washed with a 4:1 mixture of brine and 1 M hydrochloric acid (mL), dried over anhydrous sodium sulfate, then filtered and concentrated under reduced pressure to give 5-[3-(benzyloxy)-1-fluoro-7-{[1-(methanesulfonyl)piperidin-4-yl]amino}naphthalen-2-yl]-1$\lambda^6$,2,5- thiadiazolidine-1,1,3-trione (0.121 g, 0.215 mmol), which was used for the next reaction without purification. MS (APCI⁻) m/z 561 [M–H]⁻.

To a suspension of the crude 5-[3-(benzyloxy)-1-fluoro-7-{[1-(methanesulfonyl)piperidin-4-yl]amino}naphthalen-2-yl]-1λ⁶,2,5-thiadiazolidine-1,1,3-trione (0.121 g, 0.215 mmol) and pentamethylbenzene (0.064 g, 0.430 mmol) in dichloromethane (2.4 mL) at −78° C. was added a solution of boron trichloride in dichloromethane (2.15 mL, 1 M, 2.15 mmol) slowly along the side of the flask so that the internal temperature remained below −70° C. The resulting solution was stirred for 5 minutes at −78° C., then the cooling bath was removed, and the reaction mixture was allowed to warm to an internal temperature of 0° C. before cooling back to −78° C. The reaction was quenched by addition of ethyl acetate (1 mL), followed by anhydrous ethanol (1 mL), warmed to ambient temperature and concentrated under reduced pressure to give a solid. The crude solid was triturated with heptanes (3×3 mL) to give a sticky solid, which was dissolved in a dimethyl sulfoxide/methanol mixture and filtered through a glass microfiber frit. The resulting solution was directly purified by preparative HPLC [Waters XBridge™ C18 5 μm OBD column, 30×100 mm, flow rate 40 mL/minute, a gradient of 5-20% methanol in buffer (0.025 M aqueous ammonium bicarbonate, adjusted to pH 10 with ammonium hydroxide)] to give the title compound as an ammonium salt (0.0161 g, 0.033 mmol, 15.3% yield). ¹H NMR (400 MHz, DMSO-d₆) δ ppm 7.55-7.44 (m, 1H), 6.99 (dd, J=8.9, 2.3 Hz, 1H), 6.90 (s, 1H), 6.73 (d, J=2.3 Hz, 1H), 4.11 (s, 2H), 3.56-3.42 (m, 2H), 3.00-2.90 (m, 2H), 2.88-2.84 (m, 4H), 2.10-2.01 (m, 2H), 1.51-1.38 (m, 2H); MS (ESI⁻) m/z 471 [M–H]⁻.

Example 207: 5-(7-{[1-(cyclopropanesulfonyl)pyrrolidin-3-yl]amino}-1-fluoro-3-hydroxynaphthalen-2-yl)-1λ⁶,2,5-thiadiazolidine-1,1,3-trione (Compound 306)

In a 4 mL vial, combined 1-(cylopropylsulfonyl)pyrrolidin-3-amine (0.082 g, 0.430 mmol), the product of Example 1G (0.1 g, 0.215 mmol), sodium tert-butoxide (0.062 g, 0.645 mmol), methanesulfonato(2-dicyclohexylphosphino-3,6-dimethoxy-2',4',6'-tri-i-propyl-1,1'-biphenyl)(2'-amino-1,1'-biphenyl-2-yl)palladium(II) (BrettPhos Pd G3 precatalyst, 5.8 mg, 6.5 μmol), and 2-(dicyclohexylphosphino)3,6-dimethoxy-2',4',6'-triisopropyl-1,1'-biphenyl (BrettPhos, 3.5 mg, 6.5 μmol). The solids were placed under vacuum for 5 minutes with stirring, then the vial was filled with nitrogen followed by 1,4-dioxane (2 mL). The resulting suspension was degassed by five vacuum/nitrogen backfills, stirred for 10 minutes at ambient temperature, and then was heated to 100° C. After 30 minutes at 100° C., the reaction mixture was cooled to ambient temperature, then quenched with 1 M hydrochloric acid (2 mL) and diluted with ethyl acetate (2 mL). The aqueous layer was extracted with ethyl acetate (2×2 mL). The combined organic layers were washed with a 4:1 mixture of brine and 1 M hydrochloric acid (1 mL), dried over anhydrous sodium sulfate, then filtered and concentrated under reduced pressure to give 5-[3-(benzyloxy)-7-{[1-(cyclopropanesulfonyl)pyrrolidin-3-yl]amino}-1-fluoronaphthalen-2-yl]-1λ⁶,2,5-thiadiazolidine-1,1,3-trione, which was used for the next reaction without purification. MS (APCI⁻) m/z 573 [M–H]⁻.

To a suspension of the crude 5-[3-(benzyloxy)-7-{[1-(cyclopropanesulfonyl)pyrrolidin-3-yl]amino}-1-fluoronaphthalen-2-yl]-1λ⁶,2,5-thiadiazolidine-1,1,3-trione (0.124 g, 0.215 mmol) and pentamethylbenzene (0.064 g, 0.430 mmol) in dichloromethane (2.5 mL) at −78° C. was added a solution of boron trichloride in dichloromethane (2.15 mL, 1 M, 2.15 mmol) slowly along the side of the flask so that the internal temperature remained below −70° C. The resulting solution was stirred for 5 minutes at −78° C., then the cooling bath was removed, and the reaction mixture was allowed to warm to an internal temperature of 0° C. before cooling back to −78° C. The reaction was quenched by addition of ethyl acetate (1 mL), followed by anhydrous ethanol (1 mL), warmed to ambient temperature and concentrated under reduced pressure to give a solid. The crude solid was triturated with heptanes (3×3 mL) to give a sticky solid, which was dissolved in a dimethyl sulfoxide/methanol mixture and filtered through a glass microfiber frit. The resulting solution was directly purified by preparative HPLC [Waters XBridge™ C18 5 μm OBD column, 30×100 mm, flow rate 40 mL/minute, a gradient of 5-25% methanol in buffer (0.025 M aqueous ammonium bicarbonate, adjusted to pH 10 with ammonium hydroxide)] to give the title compound as an ammonium salt (0.0142 g, 0.028 mmol, 13.2% yield). ¹H NMR (400 MHz, DMSO-d₆) δ ppm 7.48 (dd, J=9.0, 1.6 Hz, 1H), 6.98 (dd, J=8.9, 2.3 Hz, 1H), 6.90 (d, J=1.3 Hz, 1H), 6.66 (d, J=2.3 Hz, 1H), 4.14-4.09 (m, 1H), 4.10 (s, 2H), 3.63 (dd, J=10.2, 5.8 Hz, 1H), 3.51-3.35 (m, 2H), 3.18 (dd, J=10.2, 4.1 Hz, 1H), 2.69-2.57 (m, 1H), 2.28 (dt, J=14.0, 7.0 Hz, 1H), 1.96-1.84 (m, 1H), 1.03-0.79 (m, 4H).; MS (ESI⁻) m/z 483 [M–H]⁻.

Example 208: 5-(1-fluoro-7-{[3-fluoro-1-(methanesulfonyl)pyrrolidin-3-yl]methoxy}-3-hydroxynaphthalen-2-yl)-1λ⁶,2,5-thiadiazolidine-1,1,3-trione (Compound 307)

Example 208A: 5-[3-(benzyloxy)-1-fluoro-7-{[3-fluoro-1-(methanesulfonyl)pyrrolidin-3-yl]methoxy}naphthalen-2-yl]-1λ⁶,2,5-thiadiazolidine-1,1,3-trione To a solution of the product of Example 1H (150 mg, 0.373 mmol) and (3-fluoro-1-(methylsulfonyl)pyrrolidin-3-yl)methanol (22 mg, 0.037 mmol) in tetrahydrofuran (5 mL) at 0° C. was added (E)-diazene-1,2-diylbis(piperidin-1-yl-methanone) (329 mg, 1.305 mmol). The reaction mixture was flushed with N₂ at 0° C. for 5 minutes followed by addition of tri-n-butylphosphine (0.322 mL, 1.305 mmol). The reaction mixture was stirred at 60° C. for 14 hours. After cooling to ambient temperature, the volatiles were removed under reduced pressure, and the residue was subjected to preparative HPLC [Phenomenex® Luna® C18(2) 5 μm 100 Å AXIA™ column (250 mm×25 mm). 30-100% gradient of acetonitrile (A) and 0.1% ammonium acetate in water (B) over 15 minutes, at a flow rate of 25 mL/minute] to afford the title compound (34 mg, 0.058 mmol, 16% yield). MS (APCI⁻) m/z 580 [M–H]⁻.

Example 208B: 5-(1-fluoro-7-{[3-fluoro-1-(methanesulfonyl)pyrrolidin-3-yl]methoxy}-3-hydroxynaphthalen-2-yl)-1λ⁶,2,5-thiadiazolidine-1,1,3-trione The product of Example 208A (32 mg, 0.055 mmol) and 1,2,3,4,5-pentamethylbenzene (24.47 mg, 0.165 mmol) in a 50 mL round bottom flask was flushed with nitrogen for 5 minutes. Methylene chloride (5 mL) was then added, and the heterogeneous suspension was cooled to −78° C. and equilibrated for 5 minutes. Subsequently, a 1 M solution of trichloroborane (0.165 mL, 0.165 mmol) in dichloromethane was added dropwise over 5 minutes. Consequently, the reaction was quenched at −78° C. with ethyl acetate (0.9 mL) and ethanol (0.1 mL) and then slowly warmed to ambient temperature. The solvents were removed under reduced pressure and the residue was subjected to preparative HPLC [Phenomenex® Luna® C18(2) 5 μm 100 Å AXIA™ column (250 mm×25 mm). 30-100% gradient of acetonitrile (A) and 0.1% ammonium acetate in water (B) over 15 minutes, at a flow rate of 25 mL/minute] to afford the title compound (12 mg, 0.026 mmol, 48%). $^1$H NMR (400 MHz, DMSO-$d_6$) δ ppm 7.70 (dd, J=9.0, 1.5 Hz, 1H), 7.25 (d, J=2.6 Hz, 1H), 7.19 (dd, J=9.0, 2.5 Hz, 1H), 7.05 (d, J=1.4 Hz, 1H), 4.52-4.44 (m, 1H), 4.44-4.34 (m, 1H), 4.11 (s, 2H), 3.68 (s, 1H), 3.67-3.48 (m, 2H), 3.46 (td, J=9.8, 7.5 Hz, 1H), 2.96 (s, 3H), 2.36-2.15 (m, 2H); MS (APCI$^-$) m/z 490 [M−H]$^-$.

Example 209: 5-{1-fluoro-3-hydroxy-7-[1-(propane-2-sulfonyl)pyrrolidin-3-yl]naphthalen-2-yl}-1$\lambda^6$,2,5-thiadiazolidine-1,1,3-trione (Compound 308)

To a solution of Example 143A (50 mg, 0.110 mmol) in methylene chloride (5 mL) was added propane-2-sulfonyl chloride (0.025 mL, 0.221 mmol) at ambient temperature followed by N-ethyl-N-isopropylpropan-2-amine (0.193 mL, 1.103 mmol). The reaction mixture was stirred at ambient temperature for 5 hours. Water (5 mL) was added, and the mixture was extracted with ethyl acetate (3×3 mL). The organic layers were combined, dried over Na$_2$SO$_4$, and concentrated under reduced pressure. The residue was subjected to the next reaction without purification. MS (APCI$^-$) m/z 558 [M−H]$^-$.

A 250 mL-round bottom flask was filled with nitrogen, followed by addition of 5% Pd/C (25 mg, 0.235 mmol) and tetrahydrofuran (10 mL). A solution of crude 5-{3-(benzyloxy)-1-fluoro-7-[1-(propane-2-sulfonyl)-2,5-dihydro-1H-pyrrol-3-yl]naphthalen-2-yl}-1$\lambda^6$,2,5-thiadiazolidine-1,1,3-trione in tetrahydrofuran (2 mL), was then added. An adapter fitted with a hydrogen balloon was inserted and the flask was evacuated and refilled with hydrogen (3 times). The reaction mixture was stirred at ambient temperature overnight. The mixture was filtered through a pad of diatomaceous earth under nitrogen gas. The volatiles were removed under reduced pressure, and the residue was subjected to preparative HPLC [Phenomenex® Luna® C18(2) 5 μm 100 Å AXIA™ column (250 mm×25 mm). 30-100% gradient of acetonitrile (A) and 0.1% trifluoroacetic acid in water (B) over 15 minutes, at a flow rate of 25 mL/minute] to afford the title compound (5 mg, 0.01 mmol, 9.6%). $^1$H NMR (400 MHz, −$d_6$) δ ppm 9.78 (s, 1H), 7.77 (d, J=1.6 Hz, 1H), 7.72 (dd, J=8.6, 1.6 Hz, 1H), 7.46 (dd, J=8.7, 1.8 Hz, 1H), 7.05 (d, J=1.3 Hz, 1H), 4.11 (s, 2H), 3.81 (dd, J=9.2, 7.4 Hz, 1H), 3.65-3.42 (m, 5H), 2.41-2.29 (m, 1H), 2.11 (dq, J=12.1, 9.0 Hz, 1H), 1.27 (d, J=6.9 Hz, 6H); MS (APCI$^-$) m/z 470 [M−H]$^-$.

Example 210: 5-[7-(2-aminoethoxy)-1-fluoro-3-hydroxynaphthalen-2-yl]-1$\lambda^6$,2,5-thiadiazolidine-1,1,3-trione (Compound 309)

Example 210A: 2-((tert-butoxycarbonyl)amino)ethyl methanesulfonate

To a mixture of tert-butyl (2-hydroxyethyl)carbamate (572 mg, 3.55 mmol), and triethylamine (1078 mg, 10.65 mmol) in dichloromethane (12 mL) was added methanesulfonyl chloride (427 mg, 3.73 mmol) in dichloromethane (3 mL) at 0° C. The mixture was stirred at ambient temperature for 40 minutes and then diluted with dichloromethane (50 mL). The organic phase was washed with water (20 mL) and brine (20 mL), dried over sodium sulfate, and concentrated at 0° C. to give the title compound (756 mg, 3.16 mmol, 89% yield) which was used in the next step without further purification. $^1$H NMR (400 MHz, CDCl$_3$) δ ppm 4.92 (m, 1H), 4.29 (t, J=8 Hz, 2H), 3.48 (m, 2H), 3.04 (s, 3H), 1.45 (s, 9H).

Example 210B: tert-butyl (2-{[6-(benzyloxy)-8-fluoro-7-(1,1,4-trioxo-1$\lambda^6$, 2,5-thiadiazolidin-2-yl) naphthalen-2-yl]oxy}ethyl)carbamate A mixture of Example 1H, Example 210A (605 mg, 2.53 mmol) and cesium carbonate (1124 mg, 3.45 mmol) in N,N-dimethylformamide (2 mL) was stirred at 65° C. for 1 hour. The mixture was cooled to ambient temperature and diluted with ethyl acetate (50 mL). The organic phase was washed with water (20 mL) and brine (20 mL), dried over sodium sulfate, filtered and concentrated. The resulting residue was purified by flash column chromatography on silica gel (40 g) eluted with dichloromethane, then dichloromethane/methanol (10:1) to give the title compound (380 mg, 0.697 mmol, 60.6% yield). $^1$H NMR (400 MHz, DMSO-$d_6$) δ ppm 8.95 (br s, 1H), 7.77 (br d, J=8 Hz, 1H), 7.56 (br d, J=8 Hz, 2H), 7.29-7.39 (m, 4H), 7.25 (d, J=2 Hz, 1H), 7.20 (dd, J=8, 2 Hz, 1H), 7.03 (m, 1H), 5.22 (s, 2H), 4.12 (s, 2H), 4.10 (t, J=8 Hz, 2H), 3.36 (m, 2H), 1.39 (s 9H); MS (ESI$^-$) m/z 544 (M−H)$^-$.

Example 210C: 5-[7-(2-aminoethoxy)-3-(benzyloxy)-1-fluoronaphthalen-2-yl]-1$\lambda^6$,2,5-thiadiazolidine-1,1,3-trione, trifluoroacetic acid salt A mixture of Example 210B (370 mg, 0.678 mmol) and trifluoroacetic acid (1.933 g, 16.95 mmol) in dichloromethane (2 mL) was stirred at room temperature for 20 minutes. The mixture was concentrated to give the title compound (611 mg, 0.678 mmol, 100% yield). MS (ESI$^+$) m/z 446 (M+H)$^+$.

Example 210D: 5-[7-(2-aminoethoxy)-1-fluoro-3-hydroxynaphthalen-2-yl]-1$\lambda^6$,2,5-thiadiazolidine-1,1,3-trione To Example 210C (610 mg, 0.677 mmol) and 1,2,3,4,5-pentamethylbenzene (301 mg, 2.030 mmol) in dichloromethane (3 mL) at −78° C. was added trichloroborane (8.12 mL, 8.12 mmol, 1 M in dichloromethane). The mixture was stirred at −78° C. for 10 minutes and then at 0° C. for 40 minutes. The mixture was quenched with ethanol (10 mL), stirred for 40 minutes at ambient temperature, and then concentrated. The resulting solid was washed with heptane (5×10 mL), heptane/dichloromethane (1:1, 5×8 mL), and concentrated to give the title compound (220 mg, 0.619 mmol, 92% yield). $^1$H NMR (400 MHz, DMSO-$d_6$) δ ppm 10.37 (br s, 1H), 8.18 (br s, 3H), 7.75 (d, J=8 Hz, 1H), 7.26 (d, J=2 Hz, 1H), 7.19 (dd, J=8, 2 Hz, 1H), 7.01 (s, 1H), 4.44 (s, 2H), 4.30 (t, J=8 Hz, 2H), 3.27 (m, 2H); MS (ESI$^-$) m/z 354 (M−H)$^-$.

Example 211: 5-{7-[1-(1,3-dimethyl-1H-pyrazole-4-sulfonyl)-2,5-dihydro-1H-pyrrol-3-yl]-1-fluoro-3-hydroxynaphthalen-2-yl}-1$\lambda^6$,2,5-thiadiazolidine-1,1,3-trione (Compound 310)

The product of Example 166 (44 mg, 0.12 mmol, 1.0 equivalent) was dissolved in N,N-dimethylformamide (1 mL), and neat diisopropylethylamine (63 µL, 0.36 mmol, 3.0 equivalents) was added. 1,3-Dimethyl-1H-pyrazole-4-sulfonyl chloride (0.4 M in tetrahydrofuran, 363 µL, 0.15 mmol, 1.2 equivalents) was added and the reaction mixture was stirred overnight at room temperature. The reaction mixture was concentrated, and the residue was purified by reverse-phase preparative HPLC on a Phenomenex® Luna® C8(2) 5 µm 100 Å AXIA™ column (50 mm×30 mm). A gradient of acetonitrile (A) and 0.1% ammonium acetate in water (B) was used, at a flow rate of 40 mL/minute (0-0.5 minutes 5% A, 0.5-8.0 minutes linear gradient 5-100% A, 8.0-9.0 minutes 100% A, 9.0-9.1 minutes linear gradient 100-5% A, 9.1-10.0 minutes 5% A) to yield the title compound (6 mg, 0.0115 mmol, 10% yield). $^1$H NMR (400 MHz, DMSO-$d_6$) δ ppm 8.36 (s, 1H), 7.79-7.69 (m, 3H), 7.12 (s, 1H), 6.44 (t, J=2.1 Hz, 1H), 4.53 (s, 2H), 4.25 (s, 2H), 4.18 (s, 2H), 2.40 (s, 3H), 1.88 (s, 3H); MS (APCI$^+$) m/z 522 [M+H]$^+$.

Example 212: N-(2-{[8-fluoro-6-hydroxy-7-(1,1,4-trioxo-1$\lambda^6$,2,5-thiadiazolidin-2-yl)naphthalen-2-yl]oxy}ethyl)ethanesulfonamide (Compound 311)

The title compound was prepared using the methodologies described in Example 199 substituting ethanesulfonyl chloride for oxetane-3-sulfonyl chloride. $^1$H NMR (400 MHz, DMSO-$d_6$) δ ppm 9.55 (s, 1H), 7.69 (d, J=8 Hz, 1H), 7.35 (t, J=8 Hz, 1H), 7.20 (d, J=2 Hz, 1H), 7.16 (dd, J=8, 2 Hz, 1H), 7.04 (s, 1H), 4.13 (t, J=8 Hz, 2H), 4.11 (s, 2H), 3.41 (m, 2H), 3.07 (q, J=8 Hz, 2H), 1.20 (t, J=8 Hz, 3H); MS (ESI$^-$) m/z 446 (M−H)$^-$.

Example 213: 5-{1-fluoro-7-[1-(furan-3-sulfonyl)-2,5-dihydro-1H-pyrrol-3-yl]-3-hydroxynaphthalen-2-yl}-1$\lambda^6$,2,5-thiadiazolidine-1,1,3-trione (Compound 312)

The title compound was prepared using the procedure described in Example 211 substituting furan-3-sulfonyl chloride for 1,3-dimethyl-1H-pyrazole-4-sulfonyl chloride. $^1$H NMR (501 MHz, DMSO-$d_6$) δ ppm 8.45-8.44 (m, 1H), 7.86 (t, J=1.8 Hz, 1H), 7.71-7.69 (m, 3H), 7.08 (s, 1H), 6.98 (dd, J=2.0, 0.8 Hz, 1H), 6.40 (t, J=2.1 Hz, 1H), 4.57 (s, 2H), 4.27 (s, 2H), 4.15 (s, 2H); MS (APCI$^+$) m/z 494 [M+H]$^+$.

Example 214: 5-{1-fluoro-3-hydroxy-7-[1-(3-methylbutane-1-sulfonyl)-2,5-dihydro-1H-pyrrol-3-yl]naphthalen-2-yl}-1$\lambda^6$,2,5-thiadiazolidine-1,1,3-trione (Compound 313)

The title compound was prepared using the procedure described in Example 211 substituting 3-methylbutane-1-sulfonyl chloride for 1,3-dimethyl-1H-pyrazole-4-sulfonyl chloride. $^1$H NMR (501 MHz, DMSO-$d_6$) δ ppm 7.79 (t, J=1.5 Hz, 2H), 7.76-7.75 (m, 1H), 7.13 (s, 1H), 6.54 (t, J=2.2 Hz, 1H), 4.67 (d, J=4.6 Hz, 2H), 4.38 (s, 2H), 4.18 (s, 2H), 3.26-3.20 (m, 2H), 1.71 (dt, J=13.0, 6.6 Hz, 1H), 1.67-1.60 (m, 2H), 0.94 (s, 3H), 0.92 (s, 3H); MS (APCI$^+$) m/z 498 [M+H]$^+$.

Example 215: 5-{1-fluoro-3-hydroxy-7-[1-(thiophene-3-sulfonyl)-2,5-dihydro-1H-pyrrol-3-yl]naphthalen-2-yl}-1$\lambda^6$,2,5-thiadiazolidine-1,1,3-trione (Compound 314)

The title compound was prepared using the procedure described in Example 211 substituting thiophene-3-sulfonyl chloride for 1,3-dimethyl-1H-pyrazole-4-sulfonyl chloride. $^1$H NMR (400 MHz, DMSO-$d_6$) δ ppm 8.40 (dd, J=3.0, 1.4 Hz, 1H), 7.80 (dd, J=5.1, 3.0 Hz, 1H), 7.74-7.70 (m, 2H), 7.56 (dd, J=5.2, 1.4 Hz, 1H), 7.11 (s, 1H), 6.41-6.39 (m, 1H), 4.61 (s, 2H), 4.29 (d, J=8.9 Hz, 2H), 4.18 (s, 2H), 1.20 (s, 2H); MS (APCI$^+$) m/z 510 [M+H]$^+$.

Example 216: 5-{7-[1-(benzenesulfonyl)-2,5-dihydro-1H-pyrrol-3-yl]-1-fluoro-3-hydroxynaphthalen-2-yl}-1$\lambda^6$,2,5-thiadiazolidine-1,1,3-trione (Compound 315)

The title compound was prepared using the procedure described in Example 211 substituting benzenesulfonyl chloride for 1,3-dimethyl-1H-pyrazole-4-sulfonyl chloride. $^1$H NMR (400 MHz, DMSO-$d_6$) δ ppm 7.96-7.87 (m, 2H), 7.73-7.56 (m, 6H), 7.05 (s, 1H), 6.37-6.32 (m, 1H), 4.55 (d, J=4.4 Hz, 2H), 4.24 (d, J=8.7 Hz, 2H), 4.13 (s, 2H); MS (APCI$^+$) m/z 504 [M+H]$^+$.

Example 217: 5-{7-[1-(cyclobutanesulfonyl)-2,5-dihydro-1H-pyrrol-3-yl]-1-fluoro-3-hydroxynaphthalen-2-yl}-1$\lambda^6$,2,5-thiadiazolidine-1,1,3-trione (Compound 316)

In a 4 mL vial were combined 5-[7-(2,5-dihydro-1H-pyrrol-3-yl)-1-fluoro-3-hydroxynaphthalen-2-yl]-1$\lambda^6$,2,5-thiadiazolidine-1,1,3-trione (38 mg, 0.105 mmol, Example 166) in N,N-dimethylformamide (1 mL). N-Ethyl-N-isopropylpropan-2-amine (0.055 mL, 0.314 mmol) was added neat, followed by cyclobutanesulfonyl chloride (0.288 mL, 0.115 mmol, 0.4 M in tetrahydrofuran). The reaction was stirred overnight at ambient temperature. The reaction was purified by reverse-phase preparative HPLC on a Phenomenex® Luna® C8(2) 5 µm 100 Å AXIA™ column (50 mm×30 mm). A gradient of acetonitrile (A) and 0.1% ammonium acetate in water (B) was used, at a flow rate of 40 mL/minute (0-0.5 minutes 5% A, 0.5-8.0 minutes linear gradient 5-100% A, 8.0-9.0 minutes 100% A, 9.0-9.1 minutes linear gradient 100-5% A, 9.1-10.0 minutes 5% A) to afford the title compound (32.5 mg, 64% yield). $^1$H NMR (501 MHz, DMSO-$d_6$) δ ppm 7.74 (s, 2H), 7.70 (s, 1H), 7.10 (s, 1H), 6.50 (t, J=2.2 Hz, 1H), 4.61-4.55 (m, 2H), 4.35-4.29 (m, 2H), 4.28-4.18 (m, 1H), 4.15 (s, 2H), 2.50-2.37 (m, 2H), 2.29-2.19 (m, 2H), 2.07-1.86 (m, 2H); MS (ESI$^+$) m/z 481.9 (M+H)$^+$.

Example 218: methyl (2S)-2-amino-4-{[8-fluoro-6-hydroxy-7-(1,1,4-trioxo-1$\lambda^6$,2,5-thiadiazolidin-2-yl)naphthalen-2-yl]oxy}butanoate (Compound 317)

Example 218A: methyl (2S)-4-{[6-(benzyloxy)-8-fluoro-7-(1,1,4-trioxo-1$\lambda^6$, 2,5-thiadiazolidin-2-yl)naphthalen-2-yl]oxy}-2-[(tert-butoxycarbonyl)amino]butanoate To a solution of Example 1H (120 mg, 0.298 mmol) in N,N-dimethylformamide (2 mL), was added cesium carbonate (214 mg, 0.656 mmol) and methyl (2S)-4-bromo-2-[(tert-butoxycarbonyl)amino]butanoate (177 mg, 0.596 mmol). The mixture was heated to 80° C. overnight. After cooling to ambient temperature, the volatiles were removed under reduced pressure, and the residue was subjected to preparative HPLC [Phenomenex® Luna® C18(2) 5 µm 100 Å AXIA™ column (250 mm×25 mm). 30-100% gradient of acetonitrile (A) and 0.1% trifluoroacetic acid in water (B)

over 15 minutes, at a flow rate of 25 mL/minute] to afford the title compound (120 mg, 0.194 mmol, 65% yield). MS (APCI⁻) m/z 616 [M−H]⁻.

Example 218B: methyl (2S)-2-amino-4-{[8-fluoro-6-hydroxy-7-(1,1,4-trioxo-1λ⁶, 2,5-thiadiazolidin-2-yl)naphthalen-2-yl]oxy}butanoate A 250 mL-round bottom flask was filled with nitrogen, followed by addition of 5% Pd/C (18 mg, 0.166 mmol) and tetrahydrofuran (8 mL). A solution of Example 218A (100 mg, 0.166 mmol) in tetrahydrofuran (2 mL) was then added. An adapter fitted with a hydrogen balloon was inserted and the flask was evacuated and refilled with hydrogen (3 times). The reaction was stirred at ambient temperature overnight. The mixture was filtered through a pad of diatomaceous earth under nitrogen gas. The volatiles were removed under reduced pressure, and the crude material was subjected to the next step without purification. MS (APCI⁻) m/z 526 [M−H]⁻.

To a solution of crude methyl (2S)-2-[(tert-butoxycarbonyl)amino]-4-{[8-fluoro-6-hydroxy-7-(1,1,4-trioxo-1λ⁶,2,5-thiadiazolidin-2-yl)naphthalen-2-yl]oxy}butanoate (50 mg, 0.95 mmol) in dichloromethane (2 mL) was added trifluoroacetic acid (2 mL). The resulting reaction mixture was stirred at ambient temperature for 30 minutes. The volatiles were removed under reduced pressure and the residue was subjected to preparative HPLC [Phenomenex® Luna® C18(2) 5 µm 100 Å AXIA™ column (250 mm×25 mm). 30-100% gradient of acetonitrile (A) and 0.1% trifluoroacetic acid in water (B) over 15 minutes, at a flow rate of 25 mL/minute] to give the title compound (31 mg, 0.057 mmol, 60% yield). ¹H NMR (600 MHz, DMSO-d₆) δ ppm 9.56 (s, 1H), 8.44 (s, 3H), 7.69 (dd, J=9.2, 1.3 Hz, 1H), 7.19 (d, J=2.6 Hz, 1H), 7.11 (dd, J=9.0, 2.6 Hz, 1H), 7.04 (s, 1H), 4.29 (t, J=6.1 Hz, 1H), 4.26-4.20 (m, 2H), 4.11 (s, 2H), 3.79 (s, 3H), 2.37-2.29 (m, 2H); MS (APCI⁺) m/z 428 [M+H]⁺.

Example 219: 5-{7-[(3,5-dimethyl-1H-pyrazol-4-yl)methoxy]-1-fluoro-3-hydroxynaphthalen-2-yl}-1λ⁶,2,5-thiadiazolidine-1,1,3-trione (Compound 318)

The title compound was prepared using the methodologies described in Example 34 substituting tert-butyl 4-(hydroxymethyl)-3,5-dimethyl-1H-pyrazole-1-carboxylate for tert-butyl 4-(hydroxymethyl)-1H-pyrazole-1-carboxylate. ¹H NMR (500 MHz, DMSO-d₆) δ ppm 10.08 (br s, 1H), 7.66 (dd, J=8, 2 Hz, 1H), 7.33 (d, J=2 Hz, 1H), 7.16 (dd, J=8, 2 Hz, 1H), 7.10 (m, 1H), 7.06 (s, 1H), 5.10 (s, 2H), 4.39 (s, 2H), 2.22 (s, 6H); MS (ESI⁻) m/z 419 (M−H)⁻.

Example 220: 5-[7-(3,5-dimethyl-1H-pyrazol-4-yl)-1-fluoro-3-hydroxynaphthalen-2-yl]-1λ⁶,2,5-thiadiazolidine-1,1,3-trione (Compound 319)

Example 220A: 5-[3-(benzyloxy)-7-(3,5-dimethyl-H-pyrazol-4-yl)-1-fluoronaphthalen-2-yl]-1λ⁶,2,5-thiadiazolidine-1,1,3-trione To a microwave vial were added the product of Example 1G (0.200 g, 0.430 mmol), [1,1′-bis(diphenylphosphino)ferrocene]dichloropalladium(II), complex with dichloromethane (0.053 g, 0.064 mmol), tert-butyl 3,5-dimethyl-4-(4,4,5,5-tetramethyl-1,3,2-dioxaborolan-2-yl)-1H-pyrazole-1-carboxylate (0.277 g, 0.860 mmol), and potassium carbonate (0.178 g, 1.29 mmol). The vial was sealed, evacuated, and refilled with nitrogen. The evacuation/refill cycle was repeated three additional times. Next, a mixture of dimethylacetamide (1.9 mL) and water (0.24 mL)—which had been degassed using the same evacuation/refill process described above—was added. The vial was then heated to 85° C. for 14 hours. The mixture was cooled to ambient temperature and partitioned between ethyl acetate (15 mL) and 0.1 M hydrochloric acid (25 mL). The layers were separated, and the aqueous phase was extracted with ethyl acetate (2×10 mL). The organic phases were combined, washed with brine, dried over sodium sulfate, and concentrated under reduced pressure. The residue was loaded onto diatomaceous earth and purified using silica gel chromatography (24 g column, 0 to 30% methanol in dichloromethane) to give the title compound (0.077 g, 0.16 mmol, 37% yield). ¹H NMR (400 MHz, DMSO-d₆) δ ppm 7.92 (d, J=8.5 Hz, 1H), 7.80 (d, J=1.6 Hz, 1H), 7.61-7.51 (m, 3H), 7.47 (s, 1H), 7.39 (t, J=7.3 Hz, 2H), 7.33 (dd, J=8.4, 6.0 Hz, 1H), 5.29 (s, 2H), 4.46 (s, 2H), 2.27 (s, 6H); MS (APCI⁺) m/z 481.3 [M+H]⁺.

Example 220B: 5-[7-(3,5-dimethyl-H-pyrazol-4-yl)-1-fluoro-3-hydroxynaphthalen-2-yl]-1λ⁴ 2,5-thiadiazolidine-1,1,3-trione, ammonium salt The product of Example 220A (0.067 g, 0.14 mmol) was suspended in tetrahydrofuran (4 mL) and added to a 20 mL Barnstead Hast C reactor containing 10% palladium hydroxide on carbon (0.067 g, 0.24 mmol). The resulting mixture was stirred at ambient temperature for 24 hours under an atmosphere of hydrogen (65 psi). The catalyst was then removed by filtration and washed with methanol. The filtrate was concentrated under reduced pressure. The residue was loaded onto diatomaceous earth and purified using reversed-phase chromatography (30 g Biotage® Sfar C18 Duo 100 Å 30 m column, 10 to 100% methanol in water [buffered with 0.025 M aqueous ammonium bicarbonate, adjusted to pH 7 with dry ice]) to give the title compound (0.022 g, 0.054 mmol, 39% yield). ¹H NMR (400 MHz, DMSO-d₆) δ ppm 12.33 (br s, 1H), 9.77 (s, 1H), 7.76 (dd, J=8.6, 1.5 Hz, 1H), 7.67 (d, J=1.7 Hz, 1H), 7.43 (dd, J=8.6, 1.7 Hz, 1H), 7.12 (br s, 3H), 7.08 (s, 1H), 4.11 (s, 2H), 2.23 (s, 6H); MS (APCI⁺) m/z 391.4 [M+H]⁺.

Example 221: 5-[7-(2-cyclohexylethoxy)-1-fluoro-3-hydroxynaphthalen-2-yl]-1λ⁶,2,5-thiadiazolidine-1,1,3-trione (Compound 320)

Example 22JA: 5-[3-(benzyloxy)-7-(2-cyclohexylethoxy)-1-fluoronaphthalen-2-yl]-1λ⁶,2,5-thiadiazolidine-1,1,3-trione To a vial were added the product of Example 1H (0.150 g, 0.373 mmol), (2-bromoethyl)cyclohexane (0.142 g, 0.746 mmol), cesium carbonate (0.364 g, 1.12 mmol), and N,N-dimethylformamide (1.5 mL). The resulting mixture was stirred at ambient temperature. After 13 hours, the reaction mixture was partitioned between 1 M hydrochloric acid (25 mL) and ethyl acetate (15 mL). The layers were separated, and the aqueous phase was extracted with ethyl acetate (2×10 mL). The organic layers were combined and washed with saturated aqueous ammonium chloride (3×15 mL). The ammonium chloride washes were combined and back extracted with ethyl acetate (15 mL). The organic layers were combined, washed with brine/1 M hydrochloric acid (4:1 v/v) (15 mL), dried over sodium sulfate, filtered, and concentrated under reduced pressure to give the title compound, which was used in the next reaction without further purification. MS (APCI⁺) m/z 513.4 [M+H]⁺.

Example 221B: 5-[7-(2-cyclohexylethoxy)-1-fluoro-3-hydroxynaphthalen-2-yl]-1$\lambda^6$,2,5-thiadiazolidine-1,1,3-trione, ammonium salt A vial containing a suspension of the product of Example 221A and 1,2,3,4,5-pentamethylbenzene (0.111 g, 0.746 mmol) in dichloromethane (3.7 mL) was cooled to −78° C. with stirring under an atmosphere of nitrogen. Next, trichloroborane (1.0 M in dichloromethane) (2.24 mL, 2.24 mmol) was added slowly along the side of the vial. The resulting mixture was stirred at −78° C. for 10 minutes, and then the dry ice/acetone bath was replaced with an ice/water bath. After 10 minutes, the mixture was recooled to −78° C. and quenched with ethyl acetate (2 mL) followed by ethanol (2 mL). The mixture was then allowed to warm to ambient temperature and stirred for 15 minutes. The mixture was then concentrated under reduced pressure, and then the residue was treated with ethanol (2×5 mL) and concentrated. The residue was dissolved in methanol, loaded onto diatomaceous earth, concentrated under reduced pressure, and purified using reversed-phase chromatography (30 g Biotage® Sfar C18 Duo 100 Å 30 m column, 10 to 100% methanol in water [buffered with 0.025 M aqueous ammonium bicarbonate, adjusted to pH 7 with dry ice]) to give the title compound as an ammonium salt (0.055 g, 0.13 mmol, 34% yield over two steps). ¹H NMR (400 MHz, DMSO-d₆) δ ppm 9.42 (br s, 1H), 7.65 (dd, J=9.0, 1.6 Hz, 1H), 7.17 (d, J=2.6 Hz, 1H), 7.11 (dd, J=9.0, 2.5 Hz, 1H), 7.09 (br s, 3H), 7.02 (s, 1H), 4.11-4.08 (m, 2H), 4.10 (s, 2H), 1.81-1.72 (m, 2H), 1.71-1.57 (m, 5H), 1.57-1.43 (m, 1H), 1.29-1.11 (m, 3H), 0.97 (qd, J=12.1, 3.2 Hz, 2H); MS (APCI⁻) m/z 421.3 [M−H]⁻.

Example 222: 2-[8-fluoro-6-hydroxy-7-(1,1,4-trioxo-1$\lambda^6$,2,5-thiadiazolidin-2-yl)naphthalen-2-yl]-1H-imidazole-4-carbonitrile (Compound 321)

Example 222A: 2-[6-(benzyloxy)-8-fluoro-7-(1,1,4-trioxo-1$\lambda^6$,2,5-thiadiazolidin-2-yl)naphthalen-2-yl]-1-{[2-(trimethylsilyl)ethoxy]methyl}-1H-imidazole-4-carbonitrile To a microwave vial were added the product of Example 126A (0.150 g, 0.293 mmol), 2-bromo-1-((2-(trimethylsilyl)ethoxy)methyl)-1H-imidazole-4-carbonitrile (0.177 g, 0.586 mmol), potassium carbonate (0.121 g, 0.878 mmol), and [(1,3,5,7-tetramethyl-6-phenyl-2,4,6-trioxa-6-phosphaadamantane)-2-(2'-amino-1,1'-biphenyl)]palladium(II) methanesulfonate (0.019 g, 0.029 mmol). The vial was sealed, evacuated, and refilled with nitrogen. The evacuation/refill cycle was repeated three additional times. Next, a mixture of 1,4-dioxane (1.2 mL) and water (0.29 mL)—which had been degassed using the same evacuation/refill process described above—was added. The vial was then heated to 125° C. for 2 hours. The vial was cooled to ambient temperature. Next, acetonitrile (4 mL) was added, followed by 1 M hydrochloric acid (12 mL). The resulting mixture was stirred for 5 minutes, and then the precipitate was collected by filtration. The solid was washed with acetonitrile (4 mL) and ethyl acetate (4 mL) and then dried under vacuum to give the title compound (0.155 g, 0.255 mmol, 87% yield). ¹H NMR (500 MHz, DMSO-d₆) δ ppm 8.54 (s, 1H), 8.48 (d, J=1.6 Hz, 1H), 8.04-7.98 (m, 2H), 7.58-7.51 (m, 3H), 7.42-7.37 (m, 2H), 7.37-7.31 (m, 1H), 5.49 (s, 2H), 5.32 (s, 2H), 4.50 (s, 2H), 3.69-3.60 (m, 2H), 1.01-0.82 (m, 2H), −0.04 (s, 9H); MS (APCI⁺) m/z 608.4 [M+H]⁺.

Example 222B: 2-(7-(1,1-dioxido-4-oxo-1,2,5-thiadiazolidin-2-yl)-8-fluoro-6-hydroxynaphthalen-2-yl)-1H-imidazole-4-carbonitrile, ammonium salt A flask containing a suspension of the product of Example 222A (0.144 g, 0.237 mmol) and 1,2,3,4,5-pentamethylbenzene (0.105 g, 0.711 mmol) in dichloromethane (2.4 mL) was cooled to −78° C. with stirring under an atmosphere of nitrogen. Next, trichloroborane (1.0 M in dichloromethane) (2.13 mL, 2.13 mmol) was added slowly along the side of the flask. The resulting mixture was stirred at −78° C. for 10 minutes, and then the dry ice/acetone bath was replaced with an ice/water bath. After 10 minutes, the mixture was recooled to −78° C. and quenched with ethyl acetate (3 mL) followed by ethanol (3 mL). The mixture was then allowed to warm to ambient temperature and stirred for 15 minutes. The mixture was concentrated under reduced pressure, and then the residue was treated with ethanol (2×5 mL) and concentrated.

The residue was dissolved in methanol, loaded onto diatomaceous earth, concentrated under reduced pressure, and purified using reversed-phase chromatography (100 g Isco RediSep Rf Gold C18 column, 5 to 75% methanol in water [buffered with 0.025 M aqueous ammonium bicarbonate, adjusted to pH 7 with carbon dioxide]) to give the title compound (0.053 g, 0.13 mmol, 55% yield). ¹H NMR (400 MHz, DMSO-d₆) δ ppm 13.60 (s, 1H), 10.12 (s, 1H), 8.50 (s, 1H), 8.28 (s, 1H), 8.06 (dd, J=8.7, 1.8 Hz, 1H), 7.85 (dd, J=8.8, 1.5 Hz, 1H), 7.15 (br t, J=50.3 Hz, 4H), 7.12 (s, 1H), 4.12 (s, 2H); MS (APCI⁺) m/z 388.3 [M+H]⁺.

Biological Assays

Abbreviations

BSA for bovine serum albumin; DMEM for Dulbecco's modified Eagle's medium; DMSO for dimethyl sulfoxide; DTT for dithiothreitol; D5W for 5% dextrose in water; EDTA for ethylenediaminetetraacetic acid; EGTA for ethylene glycol-bis(2-aminoethylether)-N,N,N',N'-tetraacetic acid; FBS for fetal bovine serum; HEPES for 4-(2-hydroxyethyl)piperazine-1-ethanesulfonic acid; IFNγ for interferon gamma; PBS for phosphate-buffered saline; PEG-400 for polyethylene glycol 400; RPMI 1640 for Roswell Park Memorial Institute 1640 medium; S-MEM for Minimum Essential Medium Eagle, Spinner Modification; TNFα for tumor necrosis factor alpha; and Tween® 20 for polyethylene glycol sorbitan monolaurate.

Example 223: Mobility Shift Assay Used to Determine Potency of PTPN2 Inhibitors

Compound activity was determined using in house His tagged PTPN2 (TC45) protein (SEQ ID NO: 1) in an in vitro enzymatic reaction. The enzymatic assay used to determine activity was a mobility shift assay using a LabChip EZ Reader by Caliper Life Sciences. The enzymatic reaction was carried out in assay buffer (50 mM HEPES pH 7.5, 1 mM EGTA, 10 mM EDTA, 0.01% Tween® 20, and 2 mM DTT). The compounds were dispensed on a white 384 well ProxiPlate™ (PerkinElmer Catalog #6008289) plate using the Labcyte Echo at varying concentrations (12 point, 1:3 dilution). The enzyme (at 0.5 nM) was incubated with compound for 10 minutes at room temperature. Then the substrate (phosphorylated insulin receptor probe sequence: ((OG488)-(NH—CH$_2$—CH$_2$—O—CH$_2$—CH$_2$—O—CH$_2$—CO)-T-R-D-I-(PY)-E-T-D-Y—Y-R-K-K-NH$_2$) (SEQ ID NO: 2) was added at 2 M to the plates and incubated for another 10 minutes at room temperature. Finally, a quench solution (water and 4-bromo-3-(2-oxo-2-propoxyethoxy)-5-(3-{[1-(phenylmethanesulfonyl)piperidin-4-yl]amino}phenyl)thiophene-2-carboxylic acid) was added to the plates, which were then run on the EZ Reader (excitation 488 nm, emission 530 nm) to measure % conversion (the amount of phosphorylated substrate which was de-phosphorylated by PTPN2). Each plate had a 100% control (inhibitor: 4-bromo-3-(2-oxo-2-propoxyethoxy)-5-(3-{[1-(phenylmethanesulfonyl)piperidin-4-yl]amino}phenyl)thiophene-2-carboxylic acid) and 0% control (DMSO), which were used to calculate % inhibition. The % inhibition was then used to calculate the IC$_{50}$ values.

Example 224: Mobility Shift Assay (MSA) Used to Determine Potency of PTP1B Inhibitors Compound activity was determined using in house His tagged full-length PTP1B protein (SEQ ID NO: 3) in an in vitro enzymatic reaction. The enzymatic assay used to determine activity is a mobility shift assay using a LabChip EZ Reader by Caliper Life Sciences. The enzymatic reaction was carried out in assay buffer (50 mM HEPES pH 7.5, 1 mM EGTA, 10 mM EDTA, 0.01% Tween® 20, and 2 mM DTT). The compounds were dispensed on a white 384 well ProxiPlate™ (PerkinElmer Cat #6008289) plate using a Labcyte Echo® liquid handler at varying concentrations (12 point, 1:3 dilution). The enzyme (at 0.5 nM) was incubated with compound for 10 minutes at room temperature. Then the substrate (phosphorylated insulin receptor probe sequence: ((OG488)-(NH—CH$_2$—CH$_2$—CH$_2$—CH$_2$—O—CH$_2$—CO)-T-R-D-I-(PY)-E-T-D-Y—Y-R-K—K—NH$_2$) (SEQ ID NO: 2) was added at 2 M to the plates and incubated for another 10 minutes at room temperature. Finally, a quench solution (water and 4-bromo-3-(2-oxo-2-propoxyethoxy)-5-(3-{[1-(phenylmethanesulfonyl)piperidin-4-yl]amino}phenyl)thiophene-2-carboxylic acid) was added to the plates, which were then run on the EZ Reader (excitation 488 1-nm, emission 530 nm) to measure % conversion (the amount of phosphorylated substrate which was de-phosphorylated by PTPB). Each plate had a 100% control (inhibitor: 4-bromo-3-(2-oxo-2-propoxyethoxy)-5-(3-{[1-(phenylmethanesulfonyl)piperidin-4-yl]amino}phenyl)thiophene-2-carboxylic acid) and 0% control (DMSO), which were used to calculate % inhibition. The % inhibition was then used to calculate the IC$_{50}$ values.

Table 2 below summarizes the IC$_{50}$ data obtained using the PTPN2 MSA assay and the PTP1B MSA assay for exemplary compounds of the disclosure. In this table, "A" represents an IC$_{50}$ of less than 1 nM; "B" an IC$_{50}$ of between 1 nM and 10 nM; "C" an IC$_{50}$ of greater than 10 nM to 100 nM; and "D" an IC$_{50}$ of greater than 100 nM.

TABLE 2

IC$_{50}$ values of exemplary compounds of the disclosure in the PTPN2 and PTP1B Mobility Shift Assays (MSA).

| Compound No. | PTPN2 MSA IC$_{50}$ (nM) | PTP1B MSA IC$_{50}$ (nM) |
|---|---|---|
| 100 | B | C |
| 101 | A | B |
| 102 | B | C |
| 103 | B | C |
| 104 | B | C |
| 105 | B | B |
| 106 | B | B |
| 107 | C | D |
| 108 | B | B |
| 109 | B | C |
| 110 | B | C |
| 111 | A | B |
| 112 | C | C |
| 113 | A | A |
| 114 | B | B |
| 115 | A | B |
| 116 | B | C |
| 117 | B | B |
| 118 | B | B |
| 119 | B | B |
| 120 | A | A |
| 121 | B | B |
| 122 | C | C |
| 123 | B | B |
| 124 | B | B |
| 125 | B | C |
| 126 | B | B |
| 127 | A | B |
| 128 | B | B |
| 129 | A | A |
| 130 | A | B |
| 131 | B | C |
| 132 | A | A |
| 133 | B | B |
| 134 | D | |
| 135 | B | C |
| 136 | B | C |
| 137 | B | B |
| 138 | B | C |
| 139 | B | C |
| 140 | B | C |
| 141 | A | B |
| 142 | B | C |
| 143 | B | C |
| 144 | B | C |
| 145 | C | C |
| 146 | B | B |
| 147 | A | B |
| 148 | B | D |
| 149 | B | B |
| 150 | B | B |
| 151 | B | B |
| 152 | B | B |
| 153 | B | B |
| 154 | A | B |
| 155 | A | B |
| 156 | A | B |
| 157 | B | C |
| 158 | B | B |
| 159 | A | B |
| 160 | B | B |
| 161 | C | C |
| 162 | B | C |
| 163 | A | D |
| 164 | A | D |
| 165 | B | B |
| 166 | B | D |
| 167 | C | D |
| 168 | A | B |
| 169 | B | C |
| 170 | A | B |
| 171 | A | C |
| 172 | B | D |
| 173 | A | C |

TABLE 2-continued

IC$_{50}$ values of exemplary compounds of the disclosure in the PTPN2 and PTP1B Mobility Shift Assays (MSA).

| Compound No. | PTPN2 MSA IC$_{50}$ (nM) | PTP1B MSA IC$_{50}$ (nM) |
|---|---|---|
| 174 | B | D |
| 175 | C | C |
| 176 | B | B |
| 177 | B | D |
| 178 | B | C |
| 179 | C | D |
| 180 | B | C |
| 181 | B | B |
| 182 | A | A |
| 183 | B | B |
| 184 | A | B |
| 185 | B | C |
| 186 | B | C |
| 187 | B | C |
| 188 | B | B |
| 189 | B | C |
| 190 | B | |
| 191 | B | |
| 192 | A | A |
| 193 | A | C |
| 194 | A | B |
| 195 | A | B |
| 196 | B | |
| 197 | B | D |
| 198 | B | C |
| 199 | B | D |
| 200 | B | A |
| 201 | B | B |
| 202 | B | C |
| 203 | B | D |
| 204 | A | A |
| 205 | C | C |
| 206 | B | B |
| 207 | B | B |
| 208 | B | D |
| 209 | B | C |
| 210 | A | B |
| 211 | A | A |
| 212 | B | B |
| 213 | A | B |
| 214 | B | B |
| 215 | B | B |
| 216 | B | B |
| 217 | B | B |
| 218 | B | B |
| 219 | B | C |
| 220 | C | D |
| 221 | C | D |
| 222 | D | C |
| 223 | B | B |
| 224 | B | B |
| 225 | C | |
| 226 | B | C |
| 227 | B | D |
| 228 | B | C |
| 229 | C | C |
| 230 | B | D |
| 231A | B | |
| 231B | B | B |
| 232 | B | C |
| 233 | B | C |
| 234 | C | C |
| 235 | B | A |
| 236 | B | D |
| 237 | B | A |
| 238 | C | D |
| 239 | B | C |
| 240 | B | B |
| 241 | D | D |
| 242 | B | B |
| 243 | C | D |
| 244 | C | |
| 245 | B | B |
| 246 | B | D |
| 247 | B | B |
| 248 | B | D |
| 249 | B | D |
| 250 | B | B |
| 251 | B | |
| 252 | B | B |
| 253 | B | |
| 254 | B | D |
| 255 | B | D |
| 256 | A | B |
| 257 | B | C |
| 258 | B | C |
| 259 | B | B |
| 260 | B | C |
| 261 | B | B |
| 262 | B | C |
| 263 | A | D |
| 264 | B | C |
| 265 | B | B |
| 266 | B | D |
| 267 | C | C |
| 268 | B | C |
| 269 | B | B |
| 270 | B | B |
| 271 | A | D |
| 272 | B | C |
| 273 | B | D |
| 274 | B | B |
| 275 | B | C |
| 276 | B | D |
| 277 | B | D |
| 278 | B | C |
| 279 | B | D |
| 280 | C | D |
| 281 | B | C |
| 282 | B | C |
| 283 | B | C |
| 284 | B | B |
| 285 | A | B |
| 286 | A | A |
| 287 | A | B |
| 288 | A | A |
| 289 | A | A |
| 290 | A | A |
| 291 | A | A |
| 292 | A | A |
| 293 | A | A |
| 294 | A | A |
| 295 | A | A |
| 296 | A | A |
| 297 | B | B |
| 298 | A | A |
| 299 | B | C |
| 300 | A | A |
| 301 | B | D |
| 302 | B | C |
| 303 | A | B |
| 304 | B | C |
| 305 | C | D |
| 306 | B | C |
| 307 | B | B |
| 308 | A | B |
| 309 | B | |
| 310 | A | B |
| 311 | A | B |
| 312 | A | A |
| 313 | A | A |
| 314 | A | A |
| 315 | A | A |
| 316 | A | A |
| 317 | B | |
| 318 | B | |

TABLE 2-continued

IC$_{50}$ values of exemplary compounds of the disclosure in the PTPN2 and PTP1B Mobility Shift Assays (MSA).

| Compound No. | PTPN2 MSA IC$_{50}$ (nM) | PTP1B MSA IC$_{50}$ (nM) |
|---|---|---|
| 319 | B | |
| 320 | A | |
| 321 | B | |

Example 225: B16F10 IFNγ-Induced Cellular Growth Inhibition Assay

B16F10 mouse melanoma cells (ATCC Cat #CRL-6475, Manassas, Va.) were seeded at a density of 500 cells per well in a 384-well clear bottom plate (Corning Cat #3765, Corning, N.Y.) in 25 μL total volume of DMEM+10% FBS (Sigma Cat #D6429 and Sigma Cat #4135, St. Louis, Mo.). Cells were allowed to adhere overnight at 37° C.+5% CO$_2$. On the following day, 12.5 μL of mouse IFNγ (RD systems Cat #485-MI/CF, Minneapolis, Minn.) was added to half of the plate (columns 13-24) at a concentration of 2 ng/mL for a final assay concentration of 0.5 ng/mL of IFNγ. Media only (12.5 μL of DMEM+10% FBS) was added to the remainder of the plate (columns 1-12). Next, compounds resuspended in DMSO (Sigma Cat #D2650) at 100 mM were diluted in semi-log dilutions in DMSO ranging from 100 mM to 0.001 mM and DMSO only controls were included. The compound/DMSO dilutions were further diluted 1:250 in DMEM+10% FBS, and 12.5 μL of these dilutions were added in triplicates to cells of both treatment arms (with and without IFNγ). Final compound concentrations ranged from 100 μM to 0.001 μM with a final DMSO concentration of 0.1%. Compounds were only dosed in the inner 240 wells, avoiding the outer 2-well perimeter of the plate to minimize edge effects. Finally, the plate was loaded into an IncuCyte® S3 Live Cell Analysis System (Essen Bioscience-Sartorius, Ann Arbor, Mich.) maintained in a 37° C.+5% CO$_2$ incubator, allowed to equilibrate for 2 hours, and imaged every 6 hours for 5 days. Confluence over time for compound dilutions in the presence and absence of IFNγ was measured. Growth inhibition values were obtained when the "DMSO/no IFNγ" control reached confluence >95%. At these time points, the percent growth inhibition of each compound at the indicated concentration was calculated relative to the "DMSO/with IFNγ" control.

Finding novel strategies to inhibit tumor growth is an active field of research in oncology drug discovery. The growth of certain cancer types can be suppressed by IFNγ, a cytokine produced by cells of the immune system like T cells or NK cells. Ablation of IFN signaling promotes tumor growth. In contrast, enhancing IFNγ signaling amplifies tumor growth inhibition. Thus, since PTPN2 is a negative regulator of IFNγ signaling, a potent PTPN2 inhibitor should promote tumor growth arrest in the presence of IFNγ.

Compounds of the present disclosure amplify B16F10 melanoma growth inhibition in the presence of IFNγ. Tumor growth inhibition in Table 3 is expressed as the % inhibition of compound relative to the DMSO control. Importantly, no tumor growth inhibition is observed in the absence of IFNγ indicating an on-target mechanism of the compounds.

Table 3 below summarizes the percent growth inhibition data obtained using the B16F10 growth inhibition assay with and without IFNγ for exemplary compounds of the disclosure. In this table, "A" represents a percent growth inhibition of >90%; "B" a percent growth inhibition of 60-90%; "C" a percent growth inhibition of 2559 and "D" a percent growth inhibition of <25%.

TABLE 3

Percent growth inhibition values of exemplary compounds of the disclosure in the B16F10 growth inhibition assay

| Compound No. | % B16F10 growth inhibition (+0.5 ng/mL IFNγ) @ 33 μM | % B16F10 growth inhibition (no IFNγ) @ 33 μM |
|---|---|---|
| 100 | A | D |
| 101 | B | D |
| 102 | B | D |
| 103 | B | D |
| 104 | C | D |
| 105 | B | D |
| 106 | B | D |
| 107 | B | D |
| 108 | C | D |
| 109 | D | D |
| 110 | B | D |
| 111 | B | D |
| 112 | C | D |
| 113 | A | D |
| 114 | B | D |
| 115 | B | D |
| 116 | A | D |
| 117 | C | D |
| 118 | B | D |
| 119 | B | D |
| 120 | B | D |
| 121 | B | D |
| 122 | B | D |
| 123 | B | D |
| 124 | B | D |
| 125 | B | D |
| 126 | B | D |
| 127 | B | D |
| 128 | A | D |
| 129 | A | D |
| 130 | B | D |
| 131 | A | D |
| 132 | B | D |
| 141 | B | D |
| 147 | A | D |
| 150 | A | D |
| 154 | B | D |
| 155 | B | B |
| 156 | B | D |
| 157 | B | D |
| 158 | B | D |
| 159 | A | D |
| 163 | A | D |
| 164 | A | D |
| 165 | A | D |
| 166 | A | D |
| 167 | B | D |
| 168 | A | D |
| 169 | A | D |
| 170 | B | D |
| 174 | A | D |
| 176 | A | D |
| 177 | A | D |
| 178 | B | D |
| 179 | A | D |
| 180 | B | D |
| 181 | B | D |
| 182 | B | D |
| 184 | C | D |
| 192 | B | D |
| 193 | C | D |
| 195 | B | D |
| 198 | B | D |
| 200 | A | D |
| 201 | B | D |
| 203 | B | D |

TABLE 3-continued

Percent growth inhibition values of exemplary compounds of the disclosure in the Bl6F10 growth inhibition assay

| Compound No. | % B16F10 growth inhibition (+0.5 ng/mL IFNγ) @ 33 μM | % B16F10 growth inhibition (no IFNγ) @ 33 μM |
|---|---|---|
| 204 | B | D |
| 205 | C | D |
| 206 | B | D |
| 207 | C | D |
| 208 | D | D |
| 209 | B | D |
| 210 | A | D |
| 211 | B | D |
| 212 | B | D |
| 213 | B | D |
| 214 | B | D |
| 215 | B | D |
| 216 | C | D |
| 217 | C | D |
| 218 | C | D |
| 223 | B | D |
| 224 | A | D |
| 226 | B | D |
| 227 | B | D |
| 235 | B | D |
| 237 | A | D |
| 238 | D | D |
| 239 | B | D |
| 240 | C | D |
| 242 | B | D |
| 243 | C | D |
| 245 | B | D |
| 246 | B | D |
| 247 | B | D |
| 248 | B | D |
| 249 | B | D |
| 250 | B | D |
| 252 | C | D |
| 254 | B | D |
| 255 | B | D |
| 256 | C | D |
| 257 | C | D |
| 259 | D | D |
| 260 | C | D |
| 261 | C | D |
| 263 | B | D |
| 264 | B | D |
| 271 | B | D |
| 273 | B | D |
| 274 | B | D |
| 276 | C | D |
| 277 | B | D |
| 278 | B | D |
| 279 | B | D |
| 281 | C | D |
| 282 | C | D |
| 283 | C | D |
| 295 | A | D |
| 296 | A | D |
| 297 | C | D |
| 298 | A | D |
| 299 | A | D |
| 300 | B | D |
| 301 | B | D |
| 302 | B | D |
| 303 | B | D |
| 304 | A | D |
| 305 | B | D |
| 306 | B | D |
| 307 | C | D |
| 309 | B | D |
| 310 | A | D |
| 311 | B | D |
| 313 | B | D |

TABLE 4

Comparison of $IC_{50}$ values of Compound 124 and Compound X

Compound X

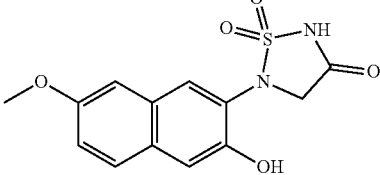

in PTPN2 Mobility Shift Assays (MSA) and percent growth inhibition values of exemplary compounds of the disclosure in the B16F10 growth inhibition assay.

| Compound No. | PTPN2 MSA $IC_{50}$ (nM) | % B16F10 growth inhibition (+ 0.05 ng/mL IFNγ) @33 μM | % B16F10 growth inhibition (no IFNγ) @33 μM |
|---|---|---|---|
| 124 | B | B | D |
| X* | C | D | D |

*Compound X (Na-salt) PTP1B activity reported to be between 5 and 300 nM (International Patent Publication WO2008148744A1)

For $IC_{50}$ data obtained using the PTPN2 MSA assay, "A" represents an $IC_{50}$ of less than 1 nM; "B" an $IC_{50}$ of between 1 nM and 10 nM; "C" an $IC_{50}$ of greater than 10 nM to 100 nM; and "D" an $IC_{50}$ of greater than 100 nM. Percent growth inhibition data obtained using the B16F10 growth inhibition assay with and without IFNγ for exemplary compounds of the disclosure. In this table, "A" represents a percent growth inhibition of >90%; "B" a percent growth inhibition of 60-90%; "C" a percent growth inhibition of 25-59%; and "D" a percent growth inhibition of <25%.

Table 4 shows a comparison of reported Compound X and Compound 124. Compound X has been reported to exhibited biochemical $IC_{50}$ between 5 and 300 nM at PTP1B. The PTPN2 $IC_{50}$ of Compound X was found to be 69 nM while Compound 124 exhibited an $IC_{50}$ at PTPN2 of 4.4 nM. At 33 μM, in the B16F10 IFNγ induced cellular growth inhibition assay described above, Compound 124 exhibited 60-90% growth inhibition while Compound X exhibited <25% growth inhibition in the presence of IFNγ compared to DMSO controls. These data demonstrate significant increase in both biochemical and cellular activity for fluoronaphthyl Compound 124 versus the corresponding des-fluoronaphthyl Compound X. The activity of Compound 124 is IFNγ dependent as demonstrated by no observed growth inhibition in the absence of IFNγ.

Example 226: T Cell Activation and Function Assays

Pan T cells were isolated from C57BL6 splenocytes using a MACS Pan T cell isolation kit II (Miltenyi Biotec, Auburn, Calif.) according to the manufacturer's instructions. Isolated T cells (200,000 cells/well in a 96 well flat-bottom plate) were cultured in RPMI 1640 supplemented with 10% FBS, 50 nM 2-mercatoethanol, 100 U/mL penicillin, and 100 μg/mL streptomycin, and incubated with the indicated concentration of compound or DMSO in duplicates. After 1 hour, mouse T cell activator CD3/CD28 Dynabeads (ThermoFisher Scientific, Waltham, Mass.) were added at a 1:5 beads to cells ratio to stimulate the T cells for 2 or 3 days as outlined below. T cells with or without compound were incubated in the absence of T cell activator beads (media only) as control.

After 2 days of stimulation, activation status of T cells was assessed by flow cytometry. T cells were first subjected to Zombie Violet™ Fixable Viability dye (BioLegend, San Diego, Calif.) for dead cell exclusion, washed and then stained with BUV805 labeled anti-CD8, APC-R700 labeled anti-$CD_{25}$ (both from BD Biosciences, San Jose, Calif.) and PE labeled anti-CD69 (BioLegend, San Diego, Calif.) antibodies. After staining, cells were fixed with 2% paraformaldehyde and acquired on a BD LSRFortessa™ X-20 flow cytometer (BD Biosciences, San Jose, Calif.) using BD FACSDiva™ software. Data was analyzed using FlowJo V10 (Flow Jo LLC, Ashland, Oreg.). Dead cells were excluded and frequencies of activated CD8 T cells was reported as the frequency of CD25+ or CD69+ cells within the CD8+ population. The expression level of CD25 and CD69 indicates the activation status of cells on a per cell basis and was evaluated by the mean fluorescence intensities (MFI) of CD25 and CD69.

After 3 days of stimulation, supernatants were collected and IFNγ and TNFα in supernatants were assessed using an MSD V-plex assay (Meso Scale Discovery, Rockville, Md.).

The increase of T cell activation and most importantly T cell function is a main strategy for novel immune oncology approaches to promote tumor immunity. In vitro assays using primary T cells are commonly used to assess the impact of compound on T cell activation and function.

The expression of CD25 (IL2 receptor alpha chain) and CD69 (very early antigen) on T cells upon TCR (T cell receptor) stimulation is an indicator of T cell activation and can be analyzed by, for example, flow cytometry. An immune stimulatory compound is expected to increase the frequency of T cells expressing CD25 and CD69 and potentially elevate the expression level of CD25 and CD69 on a per cell basis expressed as the MFI.

A read out for T cell function important for tumor immunity is the production of pro-inflammatory, anti-tumorigenic cytokines like IFNγ and TNFα. This can be assessed through the detection of cytokines in the supernatants of in vitro stimulated T cells. An immune stimulatory compound is expected to increase the production of IFNγ and TNFα.

The representative compounds, Compound 124, Compound 113, Compound 182, and Compound 260 increased both T cell activation and T cell function (Table 5). Importantly, none of the compounds activated T cells in the absence of TCR stimulation indicating that these compounds can promote the activity and function of activated T cells (like tumor-specific T cells) but do not promote unspecific activation of T cells (i.e. naïve T cells).

Tables 5-A, 5-B, 5-C and 5-D: Flow cytometry data from the T cell activation and function assays. (All values are means of duplicates.)

TABLE 5-A

|  | Compound 113 (μM) | no TCR stimulation | Mouse T cell activator anti-CD3/ anti-CD28 Dynabeads (1:5 beads:cells) |
| --- | --- | --- | --- |
| CD25 MFI | 0 | 48.85 | 373 |
|  | 30 | 51.7 | 1265 |
| CD69 MFI | 0 | 31.75 | 436 |
|  | 30 | 28.8 | 1891 |
| % CD25 within CD8+ | 0 | 0.43% | 16.20% |
|  | 30 | 0.49% | 44.55% |
| % CD69 within CD8+ | 0 | 0.25% | 24.05% |
|  | 30 | 0.24% | 73.95% |

TABLE 5-B

|  | Compound 124 (μM) | no TCR stimulation | Mouse T cell activator anti-CD3/ anti-CD28 Dynabeads (1:5 beads:cells) |
| --- | --- | --- | --- |
| CD25 MFI | 0 | 54 | 363 |
|  | 30 | 57.05 | 846.5 |
| CD69 MFI | 0 | 32.65 | 460.5 |
|  | 30 | 28.1 | 1421.5 |
| % CD25 within CD8+ | 0 | 0.34% | 16.00% |
|  | 30 | 0.39% | 32.55% |
| % CD69 within CD8+ | 0 | 0.22% | 25.70% |
|  | 30 | 0.23% | 61.90% |

TABLE 5-C

|  | Compound 182 (μM) | no TCR stimulation | Mouse T cell activator anti-CD3/ anti-CD28 Dynabeads (1:5 beads:cells) |
| --- | --- | --- | --- |
| CD25 MFI | 0 | 46.9 | 262 |
|  | 30 | 72.4 | 741 |
| CD69 MFI | 0 | 16.5 | 486.5 |
|  | 30 | 18.3 | 1601.5 |
| % CD25 within CD8+ | 0 | 0.36% | 10% |
|  | 30 | 1.17% | 29.20% |
| % CD69 within CD8+ | 0 | 0.80% | 22.90% |
|  | 30 | 0.45% | 61.90% |

TABLE 5-D

|  | Compound 260 (μM) | no TCR stimulation | Mouse T cell activator anti-CD3/ anti-CD28 Dynabeads (1:5 beads:cells) |
| --- | --- | --- | --- |
| CD25 MFI | 0 | 26.6 | 554 |
|  | 30 | 28.3 | 1085 |
| CD69 MFI | 0 | 11.6 | 204.5 |
|  | 30 | 10.2 | 464.5 |
| % CD25 within CD8+ | 0 | 0.52% | 25.95% |
|  | 30 | 0.29% | 39.60% |
| % CD69 within CD8+ | 0 | 0.24% | 36.40% |
|  | 30 | 0.17% | 61.65% |

Tables 5-E, 5-F, 5-G, and 5-H: Cytokine data from the T cell activation and function assays.

TABLE 5-E

|  | Compound 113 (μM) | no TCR stimulation | Mouse T cell activator anti-CD3/ anti-CD28 Dynabeads (1:5 beads:cells) |
| --- | --- | --- | --- |
| IFNγ (ng/mL) | 0 | 1.2 | 70 |
|  | 30 | 1.2 | 356 |
| TNFα (ng/mL) | 0 | 1.2 | 92 |
|  | 30 | 1.5 | 208 |

TABLE 5-F

|  | Compound 124 (μM) | no TCR stimulation | Mouse T cell activator anti-CD3/ anti-CD28 Dynabeads (1:5 beads:cells) |
| --- | --- | --- | --- |
| IFNγ (ng/mL) | 0 | 1.2 | 118 |
|  | 30 | 1.2 | 435 |

TABLE 5-F-continued

| Compound 124 (μM) | no TCR stimulation | Mouse T cell activator anti-CD3/anti-CD28 Dynabeads (1:5 beads:cells) |
|---|---|---|
| TNFα (ng/mL) 0 | 1.4 | 101 |
| 30 | 1.4 | 195 |

TABLE 5-G

| Compound 182 (μM) | no TCR stimulation | Mouse T cell activator anti-CD3/anti-CD28 Dynabeads (1:5 beads:cells) |
|---|---|---|
| IFNγ (ng/mL) 0 | | 25 |
| 30 | | 189 |
| TNFα (ng/mL) 0 | | 92 |
| 30 | | 135 |

TABLE 5-H

| Compound 260 (μM) | no TCR stimulation | Mouse T cell activator anti-CD3/anti-CD28 Dynabeads (1:5 beads:cells) |
|---|---|---|
| IFNγ (ng/mL) 0 | 3.8 | 139 |
| 30 | 3.8 | 752 |
| TNFα (ng/mL) 0 | 2.0 | 113 |
| 30 | 2.1 | 207 |

Example 227. In Vivo Efficacy of PTPN2 Inhibitors in MC38 Tumor Model and Impact on Pharmacodynamic Markers Mice.

All experiments were conducted in compliance with AbbVie's Institutional Animal Care and Use Committee and the National Institutes of Health Guide for Care and Use of Laboratory Animals guidelines in a facility accredited by the Association for the Assessment and Accreditation of Laboratory Animal Care. C57Bl/6 female mice were obtained from Charles River (Wilmington, Mass.). The mice were group-housed 10 per cage. Food and water were available ad libitum. Animals were acclimated to the animal facilities for a period of at least one week prior to commencement of experiments. Animals were tested in the light phase of a 12-hour light:12-hour dark schedule (lights on 0600 hours).

Tumor Cell Inoculation and Treatments.

Cells were grown to passage 3 in vitro. A total of $1 \times 10^5$ viable MC-38 cells were inoculated subcutaneously into the right flank of female C57Bl/6 mice (7-12 weeks old) on Day 0. The injection volume was 0.1 mL and was composed of a 1:1 mixture of S-MEM and Matrigel® (Corning, N.Y., USA). Tumors were size matched on Day 14 and the mice had a mean body weight of ~21 g. The mean tumor volume (TV) at size match was approximately 116 8 mm³. Following size match, treatments were initiated on the same day. Dosing of mice was conducted orally, twice a day (BID) at 7 am and 5 pm for 21 days. Mice were dosed (300 mg/kg/dose) with either compound 124, 182 or vehicle controls (n=10-15 mice/group). Compound 124 was formulated in 5% DMSO, 5% Tween 80 (Polysorbate 80), 20% PEG-400 and 70% D5W (5% dextrose in water) and was dosed at 10 mL/kg. Compound 182 was formulated in 10% ethanol, 30% PEG-400 and 60% Phosal 50 PG and was dosed at 10 mL/kg. Tumor volume was calculated three times weekly. Measurements of the length (L) and width (W) of the tumor were taken via electronic caliper and the volume was calculated according to the following equation: $V = L \times W^2/2$ using Study Director Version 3.1.399.22 (Studylog Systems, Inc, CA, USA). Mice were euthanized when tumor volume was ≤3000 mm³ or skin ulcerations occurred. Tumor growth inhibition (TGI) was calculated as TGI=1-(Mean $TV_{Timepoint\ (Treatment)}$/Mean $TV_{Timepoint\ (Vehicle)}$) for each timepoint that tumor volumes were measured. Reported $TGI_{Max}$ is the largest TGI value for any timepoint that tumors volumes were collected for that treatment group.

pSTAT5 Flow Cytometry Assay in Mouse Whole Blood.

Whole blood was drawn into EDTA powder coated tubes by cardiac puncture from mice on day 8 of dosing with indicated PTPN2/1B inhibitor (2 hours after the $1_6$th dose). 100 μL of whole blood were stimulated with 100 ng/mL murine IL-2 (R&D Systems, Minneapolis, Minn., cat #402-ML) for 20 minutes at 37° C., 5% $CO_2$. After stimulation, 1.8 mL of prewarmed BD Phosflow Lyse/Fix Buffer (BD Biosciences, San Jose, Calif.) was added for 20 minutes at 37° C. Cells were washed twice in FACS buffer (Dulbecco's PBS with 0.2% BSA) and incubated for 30 minutes on ice in cold Perm Buffer III (BD Biosciences, San Jose, Calif.). Cells were washed with FACS buffer and resuspended in 50 L of FACS buffer with antibodies and stained for 3 hours at room temperature with gentle shaking. The antibodies added were a combination of the following: anti-CD3-AF647, clone 145-2C11 (Biolegend, Cat #564279); anti-CD4-FITC, clone GK1.5 (Biolegend, San Diego, Calif., Cat #100406); anti-pSTAT5 (pY694)-PE, clone 47 (BD Biosciences, San Jose, Calif., Cat #562077); anti-CD45-BUV395, clone 30-F11 (BD Biosciences, San Jose, Calif., cat #564279). After staining, cells were washed twice with FACS buffer, and the samples were acquired on a BD LSRFortessa™ X20 flow cytometers (BD Biosciences, San Jose, Calif.) and analyzed with FLowJo V10 software (FlowJo, Ashland, Oreg.). The mean fluorescence intensity (MFI) of pSTAT5 as a measure of the amount of phosphorylated STAT5 in the CD3+ T cell population was reported as fold-change of compound treated over vehicle treated animal groups.

Granzyme B Staining of CD8 T Cells Flow Cytometry Assay in Mouse Spleen.

Mice were sacrificed on day 8 of dosing with indicated PTPN2/1B inhibitor (2 hours after the $16^{th}$ dose) and spleens were excised. Spleens were dissociated with a gentleMACS dissociator (Miltenyi Biotec, Bergisch Gladbach, Germany), red blood cells lysed, and single cell suspensions were prepared. Splenocytes were stained with Zombie UV™ Fixable Viability kit (Biolegend, San Diego, Calif.) diluted in Dulbecco's PBS for 10 minutes at room temperature to exclude dead cells followed by staining for surface markers for 45 minutes on ice using the following flow cytometry antibodies diluted in autoMACS Running Buffer (Miltenyi Biotec, Bergisch Gladbach, Germany): Brilliant Violet 510-labeled anti-CD45, Brilliant Ultraviolet 395-labeled anti-CD3, Brilliant Violet 786-labeled anti-CD4, APC/Cy7-labeled anti-CD8. Cells were washed twice with autoMACS Running Buffer, permeabilized with Fixation/Permeabilization buffer (FoxP3/Transcription Factor Staining Buffer Set; eBioscience) and stained intracellularly with PE-labeled anti-Granzyme B antibody diluted in Permeabilization buffer (FoxP3/Transcription Factor Staining Buffer Set; eBioscience, San Diego, Calif.) for 1 hour on ice. After staining, cells were washed twice with autoMACS Running Buffer, and the samples were acquired on a BD LSRFortessa™ X20 flow cytometers (BD Biosciences, San Jose, Calif.) and analyzed with FLowJo V10 software (FlowJo, Ashland, Oreg.). Fold-changes in the frequency of Granzyme B+cells within the CD8+ T cell population of compound treated over the vehicle control group were reported.

Cytokine Measurement in Mouse Plasma.

Whole blood was drawn into sodium heparin by cardiac puncture from mice on day 8 of dosing with indicated PTPN2/1B inhibitor (2 hours after the $16^{th}$ dose) and plasma was prepared by centrifugation. Cytokines in plasma were measured using the Th1/Th2 Cytokine & Chemokine 20-Plex Mouse ProcartaPlex™ Panel 1 (Invitrogen, Carlsbad, Calif.). IP10 levels were expressed as fold-changes over the vehicle control animal group.

Results

Expression within tumor cells of the phosphatases PTPN2 and its highly homologous counterpart, PTP1B, were recently described to be negative regulators of tumor-directed immune responses. The functional activity of PTPN2 to inhibit signaling cascades of extrinsic factors within tumor cells, particularly de-phosphorylation of STAT molecules downstream of the IFN receptor was defined as a significant contributor to the ability of tumor cells to evade or suppress anti-tumor immune responses. To confirm these claims, specific inhibitors of PTPN2/1B were created and tested for their ability to inhibit tumor growth and elicit anti-tumor inflammation in an in vivo syngeneic mouse tumor model. Mice were inoculated on their hind flank with the murine colon adenocarcinoma, MC-38. Following two weeks of tumor cell growth, mice began oral BID treatment for 21 days with either the vehicle or the formulated Compound 124 or Compound 182. Both Compound 124 and Compound 182 were well tolerated, without obvious adverse health events. However, within 7-10 days of treatment, apparent tumor stasis and shrinkage was observed in animals dosed with either Compound 124 or Compound 182. Eventually, 50% of mice treated with either Compound 124 or Compound 182 achieved complete cures, and an overall $TGI_{Max}$ of 75% and 94%, respectively (Table 6). Significant tumor efficacy observed with Compound 124 and Compound 182 was followed by further examination of direct target engagement of the compounds in vivo as well as their effects on anti-tumor immune responses.

IL2 signaling in T cells promotes T cell homeostasis and proliferation. STAT5 is a signaling molecule in the IL2 pathway and a direct target of PTPN2 and PTPN1 which serve as negative regulators of IL2 signaling. A PTPN2/1B inhibitor is expected to increase the phosphorylation of STAT5 upon stimulation with IL2. To demonstrate in vivo target engagement, we measured pSTAT5 levels in T cells from whole blood of PTPN2/1B inhibitor dosed animals after in vitro stimulation of whole blood with IL2. In mice treated with Compound 124 or Compound 182, pSTAT5 in whole blood T cells was increased by 2.3 and 2.1-fold, respectively, over vehicle control treated mice (Table 6).

One desirable effect of immunotherapy is the induction of functional cytotoxic T cells which can improve tumor immunity. In Compound 124 or Compound 182 treated mice, the frequency of functional, granzyme B (GzB) producing cells within the cytotoxic CD8+T population in the spleen was 2.9 and 1.8-fold, respectively, increased over vehicle control treated animals (Table 6).

Because a PTPN2/1B inhibitor promotes IFNγ signaling by increasing the phosphorylation of JAK and STAT signaling molecules and IP10 is an IFNγ induced protein, a PTPN2/1B inhibitor is expected to increase the production of IP10. IP10 levels in plasma of Compound 124 or Compound 182 treated mice, were 2.5 and 1.5-fold, respectively, increased over vehicle control treated animals (Table 6).

TABLE 6

Impact of oral BID dosing with indicated compounds on tumor growth and PD marker movement in the MC-38 syngeneic tumor model. $TGI_{Max}$ was determined over the entirety of the study. PD markers were evaluated on day 8 of dosing (2 hours post $16^{th}$ dose). Data are represented as fold-changes of compound treated over vehicle control animals.

| Compound | Tumor Growth Inhibition (Max) compared to vehicle [%] | % GzB+ cells within splenic CD8+ T cells [fold change over vehicle] | pSTAT5 level in CD3+ T cells from IL2 stimulated whole blood [fold increase over vehicle] | IP10 in plasma [fold increase over vehicle] |
|---|---|---|---|---|
| 124 | 75 | 2.9 | 2.3 | 2.5 |
| 182 | 94 | 1.8 | 2.1 | 1.5 |

EQUIVALENTS AND SCOPE

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the disclosure, or aspects of the disclosure, is/are referred to as comprising particular elements and/or features, certain embodiments of the disclosure or aspects of the disclosure consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the disclosure, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

The invention claimed is:

1. A compound, wherein the compound is

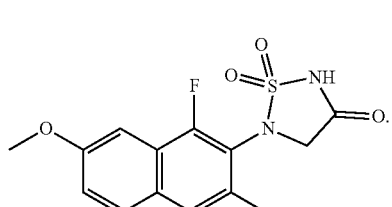

2. A compound, wherein the compound is

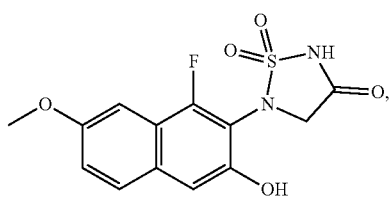 [SMILES: COc1ccc2cc(O)c(N3CC(=O)NS3(=O)=O)c(F)c2c1]

or a pharmaceutically acceptable salt thereof.

3. The compound of claim 2, wherein the compound is a pharmaceutically acceptable salt of
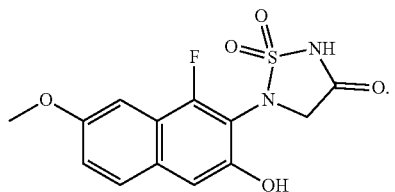 [SMILES: COc1ccc2cc(O)c(N3CC(=O)NS3(=O)=O)c(F)c2c1]
4. The compound of claim 2, wherein the compound is a sodium salt of
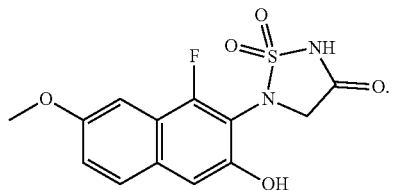 [SMILES: COc1ccc2cc(O)c(N3CC(=O)NS3(=O)=O)c(F)c2c1]
* * * * *